United States Patent
Washburn et al.

(10) Patent No.: US 9,499,482 B2
(45) Date of Patent: Nov. 22, 2016

(54) PYRROLONE OR PYRROLIDINONE MELANIN CONCENTRATING HORMONE RECEPTOR-1 ANTAGONISTS

(71) Applicant: BRISTOL-MYERS SQUIBB COMPANY, Princeton, NJ (US)

(72) Inventors: William N. Washburn, Titusville, NJ (US); Murugaiah Andappan Murugaiah Subbaiah, Hosur (IN); Saleem Ahmad, Wall, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/425,165

(22) PCT Filed: Sep. 3, 2013

(86) PCT No.: PCT/US2013/057767
§ 371 (c)(1),
(2) Date: Mar. 2, 2015

(87) PCT Pub. No.: WO2014/039412
PCT Pub. Date: Mar. 13, 2014

(65) Prior Publication Data
US 2015/0218092 A1    Aug. 6, 2015

Related U.S. Application Data

(60) Provisional application No. 61/697,004, filed on Sep. 5, 2012.

(51) Int. Cl.

| | | |
|---|---|---|
| *A61K 31/5377* | (2006.01) | |
| *A61K 31/4025* | (2006.01) | |
| *A61K 31/496* | (2006.01) | |
| *A61K 31/445* | (2006.01) | |
| *A61K 31/506* | (2006.01) | |
| *A61K 31/435* | (2006.01) | |
| *A61K 31/422* | (2006.01) | |
| *A61K 31/4178* | (2006.01) | |
| *C07D 207/273* | (2006.01) | |
| *C07D 403/12* | (2006.01) | |
| *C07D 401/14* | (2006.01) | |
| *C07D 401/12* | (2006.01) | |
| *C07D 403/14* | (2006.01) | |
| *C07D 405/12* | (2006.01) | |
| *C07D 413/12* | (2006.01) | |
| *C07D 417/12* | (2006.01) | |
| *C07D 491/10* | (2006.01) | |
| *C07D 295/096* | (2006.01) | |
| *C07D 295/135* | (2006.01) | |
| *C07D 491/107* | (2006.01) | |

(52) U.S. Cl.
CPC ....... *C07D 207/273* (2013.01); *A61K 31/4025* (2013.01); *A61K 31/4178* (2013.01); *A61K 31/422* (2013.01); *A61K 31/435* (2013.01); *A61K 31/445* (2013.01); *A61K 31/496* (2013.01); *A61K 31/506* (2013.01); *A61K 31/5377* (2013.01); *C07D 295/096* (2013.01); *C07D 295/135* (2013.01); *C07D 401/12* (2013.01); *C07D 401/14* (2013.01); *C07D 403/12* (2013.01); *C07D 403/14* (2013.01); *C07D 405/12* (2013.01); *C07D 413/12* (2013.01); *C07D 417/12* (2013.01); *C07D 491/10* (2013.01); *C07D 491/107* (2013.01)

(58) Field of Classification Search
None
See application file for complete search history.

(56) References Cited

U.S. PATENT DOCUMENTS

| | | |
|---|---|---|
| 3,674,836 A | 7/1972 | Creger |
| 4,027,009 A | 5/1977 | Grier et al. |
| 4,379,785 A | 4/1983 | Weyer et al. |
| 4,639,436 A | 1/1987 | Junge et al. |
| 4,759,923 A | 7/1988 | Buntin et al. |
| 4,904,769 A | 2/1990 | Rauenbusch |
| 5,447,954 A | 9/1995 | Gribble et al. |

(Continued)

FOREIGN PATENT DOCUMENTS

| | | |
|---|---|---|
| DE | 196 22 222 A1 | 12/1997 |
| EP | 0 675 714 B1 | 10/1995 |

(Continued)

OTHER PUBLICATIONS

Borowsky, B. et al., "Antidepressant, anxiolytic and anorectic effects of a melanin-concentrating hormone-1 receptor antagonist", Nature Medicine, vol. 8, No. 8, pp. 825-830 (2002) and vol. 8, No. 9, p. 639 (2002) (corrigenda).

(Continued)

*Primary Examiner* — Samantha Shterengarts
(74) *Attorney, Agent, or Firm* — Barry H. Jacobsen; Yong Lu

(57) ABSTRACT

The present invention provides compounds of Formula (I): as defined in the specification and compositions comprising any of such novel compounds. These compounds are melanin concentrating hormone receptor-1 (MCHR1) antagonists which may be used as medicaments.

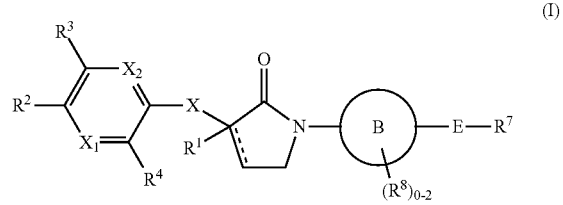

(I)

13 Claims, No Drawings

(56) References Cited

U.S. PATENT DOCUMENTS

| | | | |
|---|---|---|---|
| 5,488,064 A | 1/1996 | Sher | |
| 5,491,134 A | 2/1996 | Sher et al. | |
| 5,541,204 A | 7/1996 | Sher et al. | |
| 5,594,016 A | 1/1997 | Ueno et al. | |
| 5,612,359 A | 3/1997 | Murugesan | |
| 5,698,527 A | 12/1997 | Kim | |
| 5,770,615 A | 6/1998 | Cheng et al. | |
| 5,776,983 A | 7/1998 | Washburn et al. | |
| 6,043,265 A | 3/2000 | Murugesan et al. | |
| 6,414,002 B1 | 7/2002 | Cheng et al. | |
| 6,414,126 B1 | 7/2002 | Ellsworth et al. | |
| 7,101,885 B2 * | 9/2006 | Lowe, III | C07D 207/273 514/253.09 |
| 2014/0256756 A1 * | 9/2014 | Aicher | C07D 413/14 514/272 |

FOREIGN PATENT DOCUMENTS

| | | |
|---|---|---|
| EP | 0 818 448 A1 | 1/1998 |
| EP | 0 992 496 A1 | 4/2000 |
| EP | 1 022 272 A1 | 7/2000 |
| GB | 2 304 106 A | 3/1997 |
| WO | WO 94/15592 | 7/1994 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/39077 | 7/2000 |
| WO | WO 00/50574 | 8/2000 |
| WO | WO 2004/047755 | 6/2004 |
| WO | WO 2005/072740 | 8/2005 |
| WO | WO 2006/019020 | 2/2006 |
| WO | WO 2006/044775 | 4/2006 |
| WO | WO 2006/082010 | 8/2006 |
| WO | WO 2006/134317 | 12/2006 |
| WO | WO 2010/042674 | 4/2010 |
| WO | WO 2010/047956 | 4/2010 |
| WO | WO 2010/104830 | 9/2010 |
| WO | WO 2011/146335 | 11/2011 |
| WO | WO 2013/066869 | 5/2013 |

OTHER PUBLICATIONS

Bundgaard, H., Chapter 5: "Design and Application of Prodrugs", A Textbook of Drug Design and Development, pp. 113-191, Krogsgaard-Larsen, P. et al., eds., Harwood Academic Publishers, publ. (1991).

Bundgaard, H., ed., Design of Prodrugs, Elsevier Science Publishers B.V., publ. (1985).

Bundgaard, H., "Prodrugs as a means to improve the delivery of peptide drugs", Advanced Drug Delivery Reviews, vol. 8, pp. 1-38 (1992).

Gehlert, D.R. et al., "Preclinical Evaluation of Melanin-Concentrating Hormone Receptor 1 Antagonism for the Treatment of Obesity and Depression", The Journal of Pharmacology and Experimental Therapeutics, vol. 329, No. 2, pp. 429-438 (2009).

Gennaro, A.R., ed., Remington's Pharmaceutical Sciences, 18th Edition, pp. xv-xvi, Mack Publishing Company, publ. (1990).

Greene, T.W. et al., Protective Groups in Organic Synthesis, Second Edition, pp. ix-x, John Wiley & Sons, Inc., publ. (1991).

Hara, S., "Ileal $Na^+$/bile acid cotransporter inhibitors", Drugs of the Future, vol. 24, No. 4, pp. 425-430 (1999).

Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).

Kokkotou, E. et al., "Melanin-concentrating hormone as a mediator of intestinal inflammation", Proc. Natl. Acad. Sci., vol. 105, No. 30, pp. 10613-10618 (2008).

Kowalski, T.J. et al., "Melanin-concentrating hormone-1 receptor antagonism decreases feeding by reducing meal size", European Journal of Pharmacology, vol. 497, pp. 41-47 (2004).

Lewis, Sr., R.J., Hawley's Condensed Chemical Dictionary, Thirteenth Edition, John Wiley & Sons, Inc., publ. (1997).

Ljung, B. et al., "AZ 242, a novel PPARα/β agonist with beneficial effects on insulin resistance and carbohydrate and lipid metabolism in ob/ob mice and obese Zucker rats", Journal of Lipid Research, vol. 43, pp. 1855-1863 (2002).

Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", Journal of Medicinal Chemistry, vol. 41, No. 6, pp. 973-980 (1998).

Salisbury, B.G., "Hypocholesterolemic activity of a novel inhibitor of cholesterol absorption, SCH 48461", Atherosclerosis, vol. 115, pp. 45-63 (1995).

Takekawa, S. et al., "T-226296: a novel, orally active and selective melanin-concentrating hormone receptor antagonist", European Journal of Pharmacology, vol. 438, pp. 129-135 (2002).

Testa, B. et al., Hydrolysis in Drug and Prodrug Metabolism: Chemistry, Biochemistry, and Enzymology, pp. xi-xx, Wiley-VCH GmbH & Co., publ. (2003).

Widder, K.J. et al., eds., Section III: "Prodrugs", Methods in Enzymology, vol. 112, pp. 309-396, Academic Press, Inc., publ. (1985).

Yajima, K. et al., "Combination therapy with $PPAR_\gamma$ and $PPAR_\alpha$ agonists increases glucose-stimulated insulin secretion in db/db mice", Am. J. Physiol. Endocrinol. Metab., vol. 284, pp. E966-E971 (2003) and vol. 285, p. E926 (2003) (corrigenda).

* cited by examiner

PYRROLONE OR PYRROLIDINONE MELANIN CONCENTRATING HORMONE RECEPTOR-1 ANTAGONISTS

The present application is a 371 of International Application No. PCT/US2013/057767 filed on Sep. 3, 2013, which claims priority benefit of U.S. provisional application Ser. No. 61/697,004, filed Sep. 5, 2012; each of which is fully incorporated by reference herein.

FIELD OF THE INVENTION

The present invention relates to novel pyrrolone or pyrrolidinone melanin concentrating hormone receptor-1 (MCHR1) antagonists, pharmaceutical compositions, processes of preparing, and therapeutic and prophylactic uses thereof. Diseases treated and/or prevented include obesity, diabetes and related diseases ameliorated by antagonizing MCHR1 receptor.

BACKGROUND OF THE INVENTION

Several lines of pharmacological and genetic evidence support the role of melanin concentrating hormone receptor-1 (hereafter "MCHR1") as a modulator of food intake and body weight. Central administration of melanin concentrating hormone (MCH) increases food intake and body weight in both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; Takekawa, S. et al., *Eur. J. Pharmacol.*, 438:129-135 (2002); Borowsky, B. et al., *Nat. Med.*, 8:825-830 (2002); Kowalski, T. J. et al., *Eur. J. Pharmacol.*, 497:41-47 (2004).

MCHR1 has also been reported to play a key role in the pathogenesis of acute experimental colitis and possibly human IBD (inflammatory bowel disease). It has been shown that immunoneutralization is an effective treatment for TNBS-induced colitis. Kokkotou, E. et al., "Melanin-concentrating hormone as a mediator of intestinal inflammation", *PNAS*, 105(30):10613-10618 (2008).

In addition, MCH and MCHR1 have also been reported to play a role in the endocrine and behavioral responses to stress. Treatment of rats and mice with MCHR antagonists produces a robust anti-depressant and anti-anxiolytic effect (Gehlert, D. R. et al., *JPET*, 329(2):429-438 (2009)).

Non-peptide MCHR1 antagonists have been disclosed, but none of the MCHR1 publications disclosed pyrrolone or pyrrolidinone containing compounds as described in the present invention. In accordance with the present invention, there is provided a series of novel pyrrolone or pyrrolidinone MCHR1 antagonists.

SUMMARY OF THE INVENTION

The present invention provides pyrrolone or pyrrolidinone compounds, and their analogues thereof, which are useful as MCHR1 antagonists, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with MCHR1 antagonists, such as obesity, diabetes, anxiety or depression.

The compounds of the invention may be used in therapy.

The compounds of the invention may be used for the manufacture of a medicament for the treatment and/or prophylaxis of multiple diseases or disorders associated with MCHR1.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

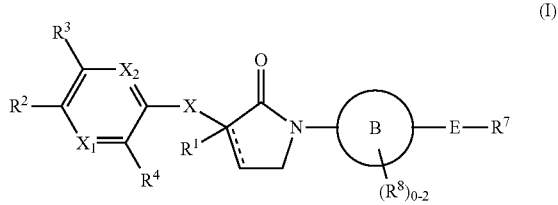

or a stereoisomer, a tautomer, a pharmaceutically acceptable salt, or a solvate thereof, wherein:

=== is independently a single or double bond; provided that when === is a single bond, $R^1$ is H or $C_{1-4}$ alkyl; and when === is a double bond $R^1$ is absent;

X is independently O or S;

$X_1$ is independently N or $CR^5$;

$X_2$ is independently N or $CR^6$;

ring B is independently $C_{3-6}$ carbocycle or a 5- to 10-membered heterocycle containing carbon atoms and 1-4 heteroatoms selected from the group consisting of N, $NR^e$, O, and $S(O)_p$;

E is independently selected from: a bond, O and $CH_2$;

$R^2$, at each occurrence, is independently at selected from: H, halogen, OH, CN, $NO_2$, $C_{1-6}$ alkyl, $C_{1-6}$ alkoxy, $C_{1-6}$ alkylthio, $C_{1-6}$ haloalkyl, $C_{1-6}$ haloalkoxy, $C_{1-6}$ haloalkylthio, $R^9$, and —O—$R^9$;

$R^3$, $R^4$, $R^5$ and $R^6$, at each occurrence, are independently selected from: H, halogen, OH, CN, $NO_2$, $C_{1-6}$ alkyl, $C_{1-6}$ alkoxy, $C_{1-6}$ alkylthio, $C_{1-6}$ haloalkyl, $C_{1-6}$ haloalkoxy, and $C_{1-6}$ haloalkylthio;

$R^7$ is independently $-(CH_2)_n-NR^{12}R^{13}$ or

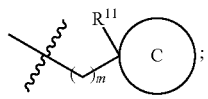

ring C is independently a 3- to 6-membered heterocycle containing carbon atoms and 1-4 heteroatoms selected from the group consisting of N, $NR^e$, O, and $S(O)_p$; wherein said heterocycle is substituted with 0-3 $R^c$ and contains at least one nitrogen atom;

$R^8$, at each occurrence, is independently selected from: H, $C_{1-6}$ alkyl, $C_{1-6}$ alkoxy, halogen, $C_{1-6}$ alkylthio, $C_{1-6}$ haloalkyl, $C_{1-6}$ haloalkoxy, $C_{1-6}$ haloalkylthio, CN, $C_{3-6}$ cycloalkyl, and $-O-C_{3-6}$ cycloalkyl;

$R^9$, at each occurrence, is independently a $C_{3-6}$ carbocycle or a 3- to 6-membered heterocycle containing carbon atoms and 1-4 heteroatoms selected from the group consisting of N, $NR^e$, O, and $S(O)_p$; wherein said carbocycle and heterocycle are each substituted with 0-3 $R^b$;

$R^{11}$, at each occurrence, is independently H or $OR^d$;

$R^{12}$ is independently selected from: H, $C_{1-8}$ alkyl substituted with 0-3 $R^a$, $C_{1-4}$ haloalkyl, $CO(C_{1-4}$ alkyl, $COCH_2O$ $(C_{1-4}$ alkyl), $CO_2(C_{1-4}$ alkyl), $SO_2R^f$, $-(CH_2)_s-(C_{3-6}$ carbocycle substituted with 0-2 $R^b$),

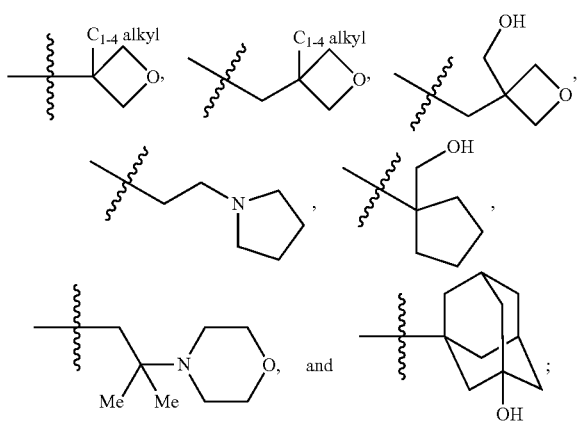

$R^{13}$ is independently H or $C_{1-4}$ alkyl;

alternatively, $R^{12}$ and $R^{13}$ are combined, together with the nitrogen atom they are attached to, form a 4- to 10-membered heterocycle containing carbon atoms and additional 1-2 heteroatoms selected from the group consisting of N, $NR^e$, O, and $S(O)_p$; wherein said heterocycle is substituted with 0-3 $R^c$ and may form a spiro ring;

$R^a$, at each occurrence, is independently selected from: halogen, $OR^d$, $CH_2OR^d$, CN, $C_{1-4}$ alkyl, $C_{1-4}$ alkoxy, $C_{1-4}$ haloalkyl, $C_{3-6}$ cycloalkyl, $-O-C_{3-6}$ cycloalkyl, $C(O)C_{1-4}$ alkyl, $CO_2H$, $CO_2C_{1-4}$ alkyl, $SO(C_{1-4}$ alkyl), and $SO_2(C_{1-4}$ alkyl);

$R^b$, at each occurrence, is independently selected from: halogen, OH, CN, $CH_2OH$, $C_{1-4}$ alkyl, $C_{1-4}$ alkoxy, $C_{1-4}$ haloalkyl, $C_{1-4}$ haloalkoxy, $C_{3-6}$ cycloalkyl, and $-O-C_{3-6}$ cycloalkyl;

$R^c$, at each occurrence, is independently selected from: $=O$, halogen, $OR^d$, $CH_2OR^d$, CN, $C_{1-4}$ alkyl, $C_{1-4}$ alkoxy, $C_{1-4}$ haloalkyl, $NH_2$, $N(C_{1-4}$ alkyl$)_2$, $CH_2C_{1-4}$ alkoxy, $C_{1-4}$ haloalkoxy, $CONH_2$, $CO_2(C_{1-4}$ alkyl), $CO_2Bn$, $SO_2C_{1-4}$ alkyl, $NHCOC_{1-4}$ alkyl, $NHCOC_{1-4}$ haloalkyl, $NHCO_2C_{1-4}$ alkyl, $NHCO_2Ph$, $NHCO_2Bn$, $C_{3-6}$ cycloalkyl, pyrrolidinyl, and morpholinyl; and $R^d$, at each occurrence, is independently selected from: H, $C(O)C_{1-4}$ alkyl, $C(O)(Ph)$, $C(O)CH_2NH_2$, $-C(O)CH(C_{1-4}$ alkyl$)NH_2$, $-C(O)CH_2CO_2H$, $-C(O)(CH_2)_2CO_2H$, and $P(O)(OH)_2$;

$R^e$, at each occurrence, is independently H, $C_{1-4}$ alkyl, $C(O)C_{1-4}$ alkyl, $CO_2(C_{1-4}$ alkyl), $CO_2Bn$, pyrimidinyl and pyrazinyl;

$R^f$ is independently selected from: $C_{1-4}$ alkyl, $C_{1-4}$ haloalkyl, $C_{3-6}$ cycloalkyl, Ph,

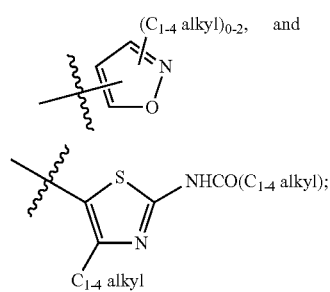

m, at each occurrence, is independently 0, 1, 2, or 3;
n, at each occurrence, is independently 1, 2, and 3;
p, at each occurrence, is independently 0, 1 or 2; and
s, at each occurrence, is independently 0, 1, or 2.

In a second aspect, the present invention includes compounds of Formula (II):

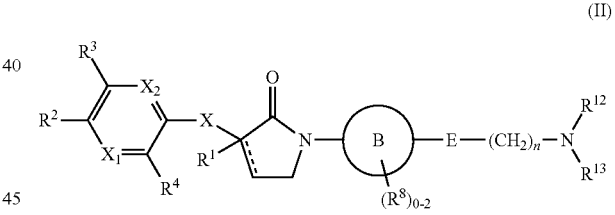

or a stereoisomer, a tautomer, a pharmaceutically acceptable salt, or a solvate thereof, within the scope of the first aspect.

In a third aspect, the present invention includes compounds of Formula (I) or (II), or a stereoisomer, a tautomer, a pharmaceutically acceptable salt, or a solvate thereof, within the scope of the first or second aspect wherein:

$---$ is independently a single or double bond; provided that when $---$ is a single bond, $R^1$ is H or $C_{1-2}$ alkyl; and when $---$ is a double bond $R^1$ is absent;

$X_1$ is independently N or $CR^5$;

$X_2$ is independently N or $CR^6$;

provided that $X_1$ and $X_2$ are not both N;

$R^2$, at each occurrence, is independently at selected from: $C_{1-6}$ alkyl, $C_{1-6}$ alkoxy, $C_{1-6}$ alkylthio, $C_{1-6}$ haloalkyl, $C_{1-6}$ haloalkoxy, $C_{1-6}$ haloalkylthio, $R^9$, and $-O-R^9$; and $R^3$, $R^4$, $R^5$ and $R^6$, at each occurrence, are independently selected from: H, halogen, OH, CN, $C_{1-4}$ alkyl, $C_{1-4}$ alkoxy, $C_{1-2}$ haloalkyl, and $C_{1-2}$ haloalkoxy.

In a fourth aspect, the present invention includes compounds of Formula (III):

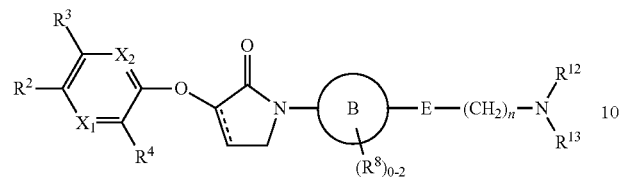

(III)

or a stereoisomer, a tautomer, a pharmaceutically acceptable salt, or a solvate thereof, within the scope of the first, second or third aspect.

In a fifth aspect, the present invention includes a compound of Formula (IIIa):

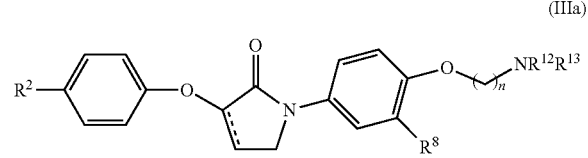

(IIIa)

or a stereoisomer, a tautomer, a pharmaceutically acceptable salt, or a solvate thereof, within the scope of any of the first, second, third and fourth aspects, wherein:

--- is a single or double bond;

$R^2$ is independently $C_{3-6}$ cycloalkyl or phenyl substituted with 0-2 $R^b$;

$R^8$ is independently selected from: halogen, $C_{1-4}$ alkyl, $C_{1-4}$ alkoxy, $C_{1-4}$ haloalkoxy, and $C_{3-6}$ cycloalkyl;

$R^{12}$ is independently at selected from: H, $C_{1-6}$ alkyl, $CH_2CH_2OH$, $CH_2CH_2(C_{1-4}$ alkoxy), $CH_2CN$, $C_{1-4}$ haloalkyl, $CO(C_{1-4}$ alkyl, $COCH_2O(C_{1-4}$ alkyl), $CO_2(C_{1-4}$ alkyl), $SO_2(C_{1-4}$ alkyl), $SO_2CH_2CF_3$, $SO_2(C_{3-6}$ cycloalkyl), $SO_2Ph$, $C_{3-6}$ cycloalkyl,

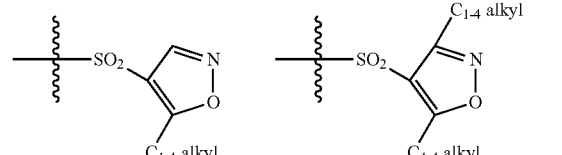

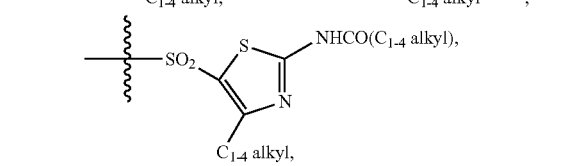

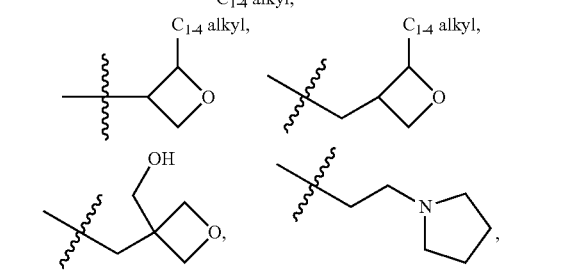

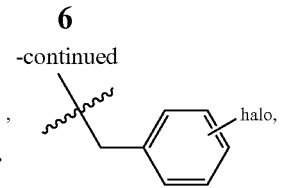

$R^{13}$ is independently H or $C_{1-4}$ alkyl;

alternatively, $R^{12}$ and $R^{13}$ are combined, together with the nitrogen atom they are attached to, form a heterocycle substituted with 0-3 $R^c$; wherein said heterocycle is independently at selected from:

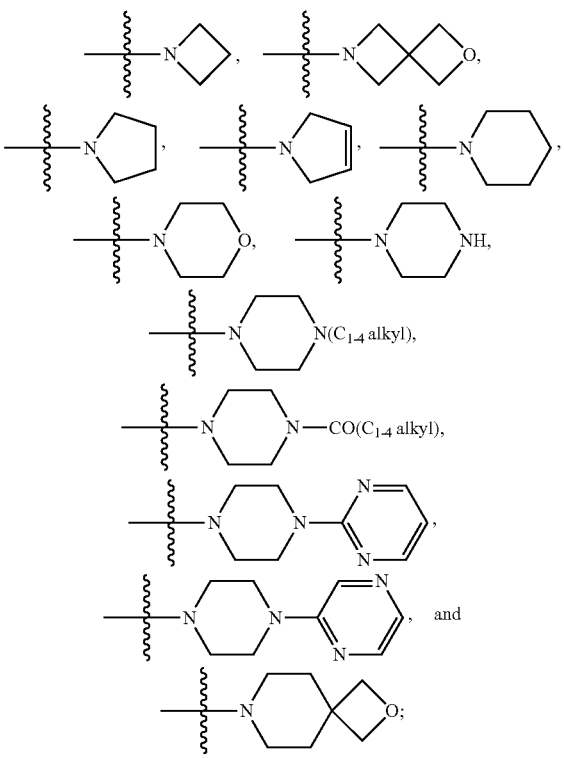

$R^b$, at each occurrence, is independently selected from: halogen, $C_{1-4}$ alkyl, $C_{1-4}$ alkoxy, $C_{1-4}$ haloalkyl, and $C_{1-4}$ haloalkoxy;

$R^c$, at each occurrence, is independently selected from: =O, halogen, OH, $CH_2OH$, CN, $NH_2$, $N(C_{1-4}$ alkyl)$_2$, $C_{1-4}$ alkyl, $C_{1-4}$ alkoxy, $CH_2C_{1-4}$ alkoxy, $C_{1-4}$ haloalkyl, $C_{1-4}$ haloalkoxy, $CONH_2$, $SO_2C_{1-4}$ alkyl, $NHCOC_{1-4}$ alkyl, $NHCOC_{1-4}$ haloalkyl, $NHCO_2C_{1-4}$ alkyl, $NHCO_2Bn$, $C_{3-6}$ cycloalkyl, pyrrolidinyl, and morpholinyl; and n, at each occurrence, is independently 1, or 2.

In a sixth aspect, the present invention includes a compound of Formula (IIIb):

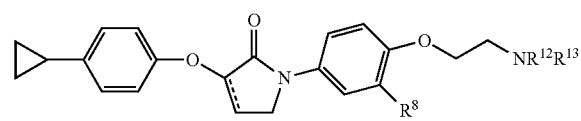

or a stereoisomer, a tautomer, a pharmaceutically acceptable salt, or a solvate thereof, within the scope of any of the above aspects, wherein:

=== is a single or double bond;

$NR^{12}R^{13}$ is independently at selected from: $NH_2$, $NH(C_{1-6}$ alkyl), $N(C_{1-4}$ alkyl$)_2$, $NH(CH_2CH_2OH)$, $NH(CH_2CH_2(C_{1-4}$ alkoxy$))$, $NH(CH_2CN)$, $NH(C_{1-4}$ haloalkyl), $N(C_{1-2}$ alkyl$)(CH_2CH_2OH)$, $NH(CO(C_{1-4}$ alkyl$))$, $N(C_{1-2}$ alkyl$)(CO(C_{1-4}$ alkyl$))$, $N(C_{1-2}$ alkyl$)(COCH_2O(C_{1-4}$ alkyl$))$, $N(C_{1-2}$ alkyl$)(CO_2(C_{1-4}$ alkyl$))$, $NH(SO_2(C_{1-4}$ alkyl$))$, $N(C_{1-2}$ alkyl$)(SO_2(C_{1-4}$ alkyl$))$, $N(C_{1-2}$ alkyl$)(SO_2CH_2CF_3)$, $N(C_{1-2}$ alkyl$)(SO_2Ph)$,

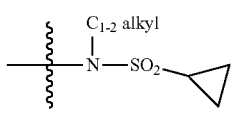, 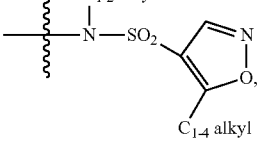

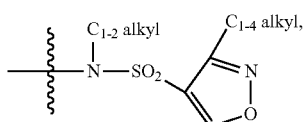

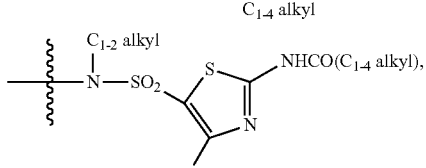

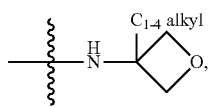, 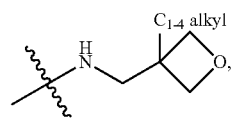

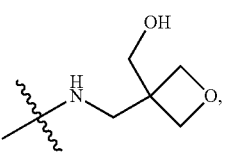 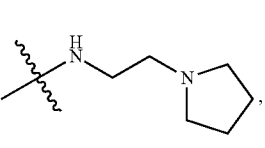

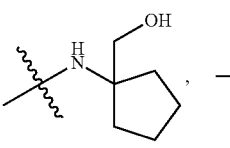, 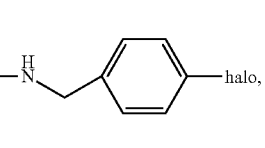

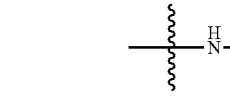 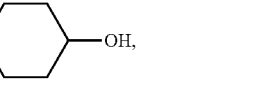

-continued

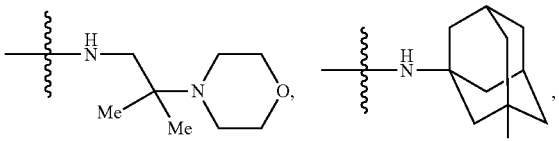

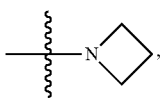

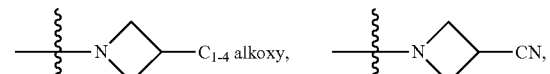

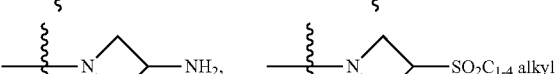

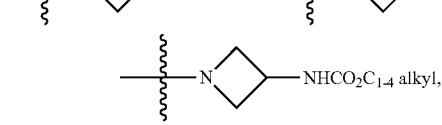

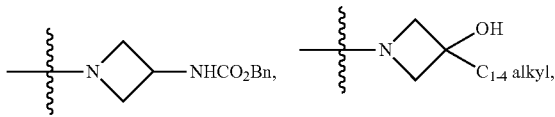

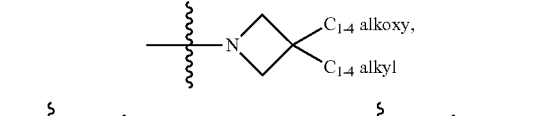

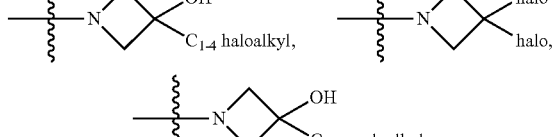

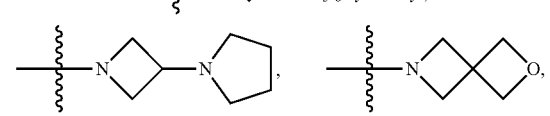

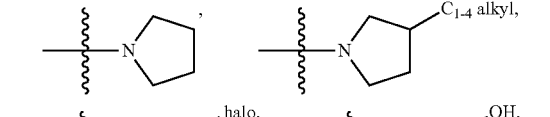

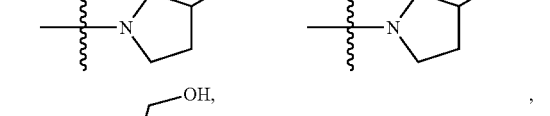

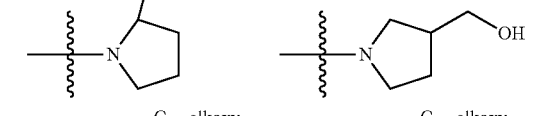

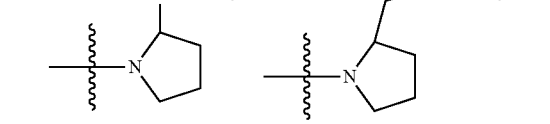

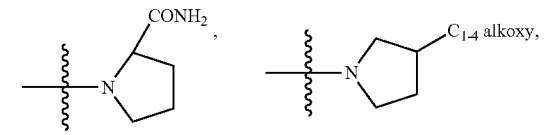

-continued

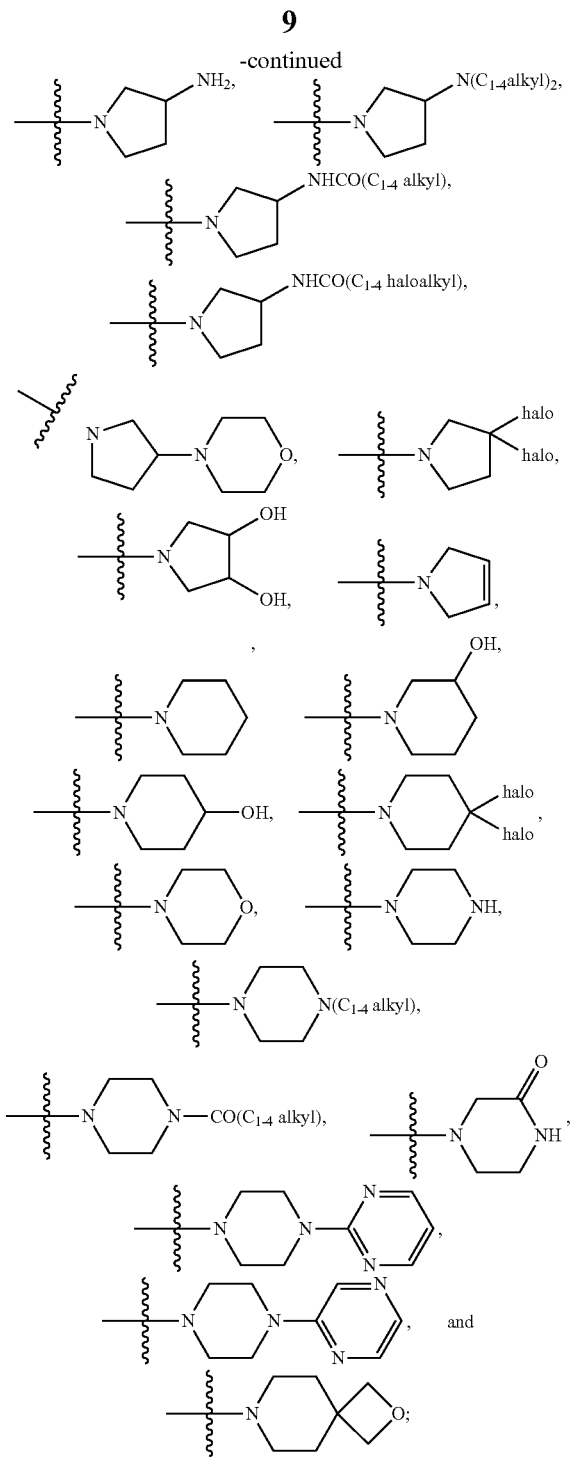

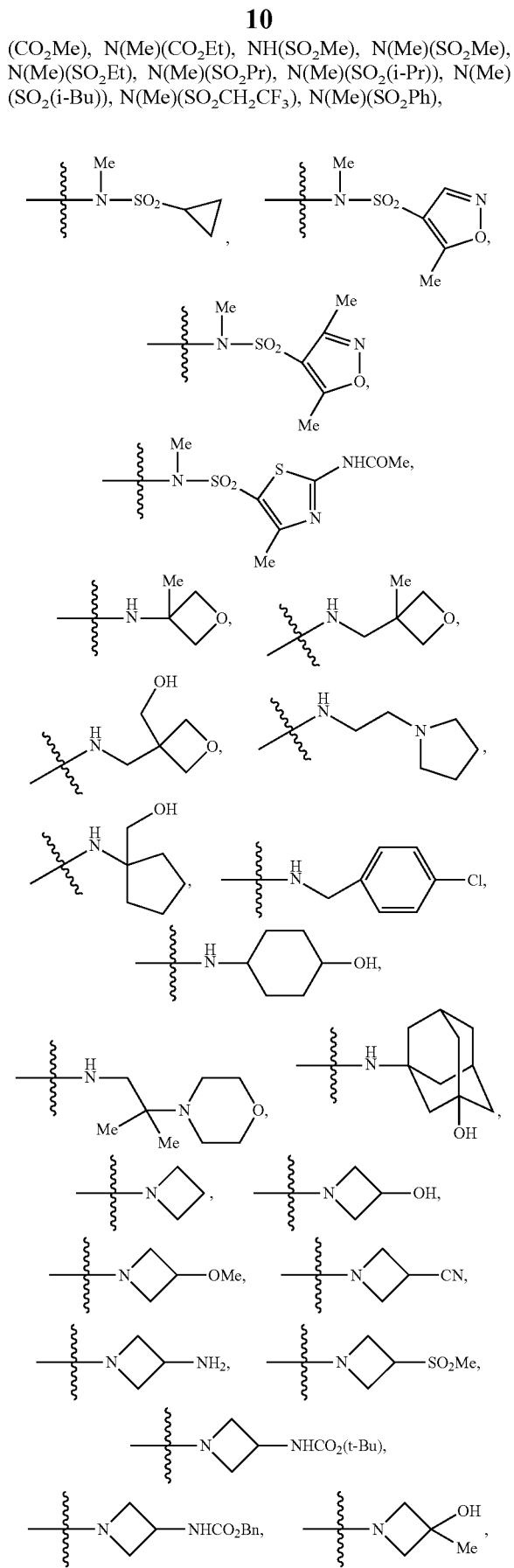

and

R[8] is independently selected from: halogen, $C_{1-4}$ alkyl, $C_{1-4}$ alkoxy, $C_{1-4}$ haloalkoxy, and cyclopropyl.

In a seventh aspect, the present invention includes a compound of Formula (IIIb) or a stereoisomer, a tautomer, a pharmaceutically acceptable salt, or a solvate thereof, within the scope of within the scope of any of the above aspects, wherein:

$NR^{12}R^{13}$ is independently at selected from: $NH_2$, NHMe, NH(t-Bu), $NMe_2$, $NH(CH_2CH_2OH)$, $NH(CH_2CH_2OMe)$, $NH(CH_2CN)$, $NH(CH_2CF_3)$, $N(Me)(CH_2CH_2OH)$, NH(COMe), N(Me)(COMe), $N(Me)(COCH_2OMe)$, N(Me)($CO_2Me$), N(Me)($CO_2Et$), $NH(SO_2Me)$, $N(Me)(SO_2Me)$, $N(Me)(SO_2Et)$, $N(Me)(SO_2Pr)$, $N(Me)(SO_2(i\text{-Pr}))$, $N(Me)(SO_2(i\text{-Bu}))$, $N(Me)(SO_2CH_2CF_3)$, $N(Me)(SO_2Ph)$, -continued

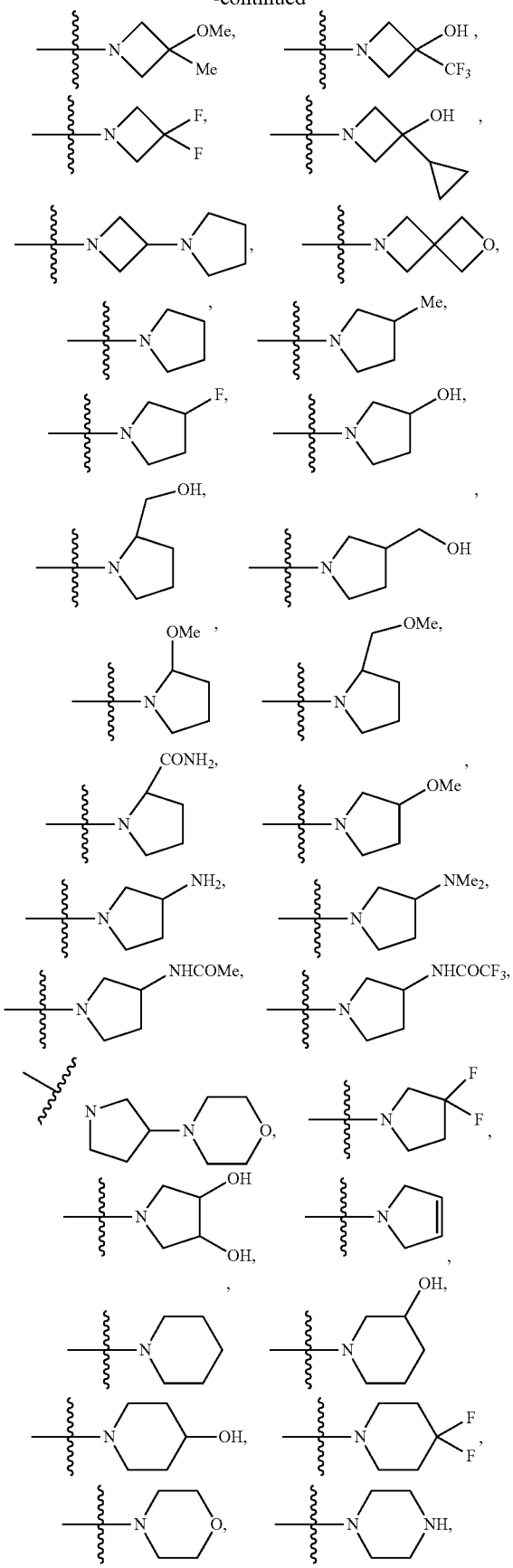

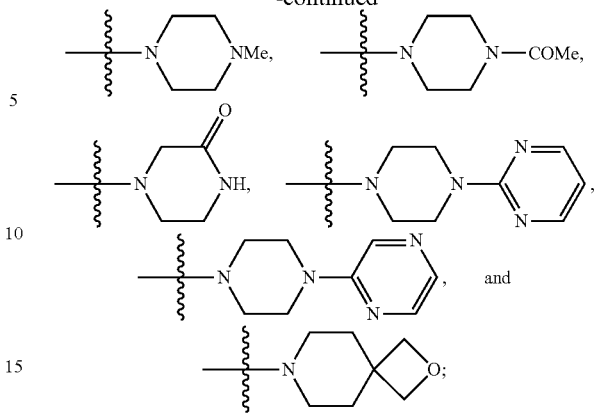

and
R[8] is independently selected from: Cl, Br, Me, Et, OMe, OCF$_2$, and cyclopropyl.

In an eighth aspect, the present invention includes a compound of Formula (IIIc):

(IIIc)

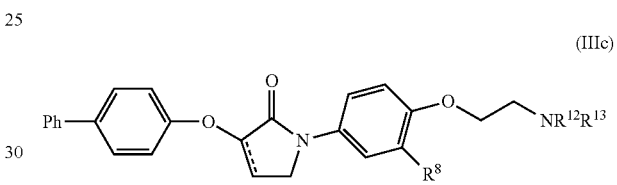

or a stereoisomer, a tautomer, a pharmaceutically acceptable salt, or a solvate thereof, within the scope of any of the first to fifth aspects, wherein:
=== is a single or double bond;
NR$^{12}$R$^{13}$ is independently at selected from:

-continued

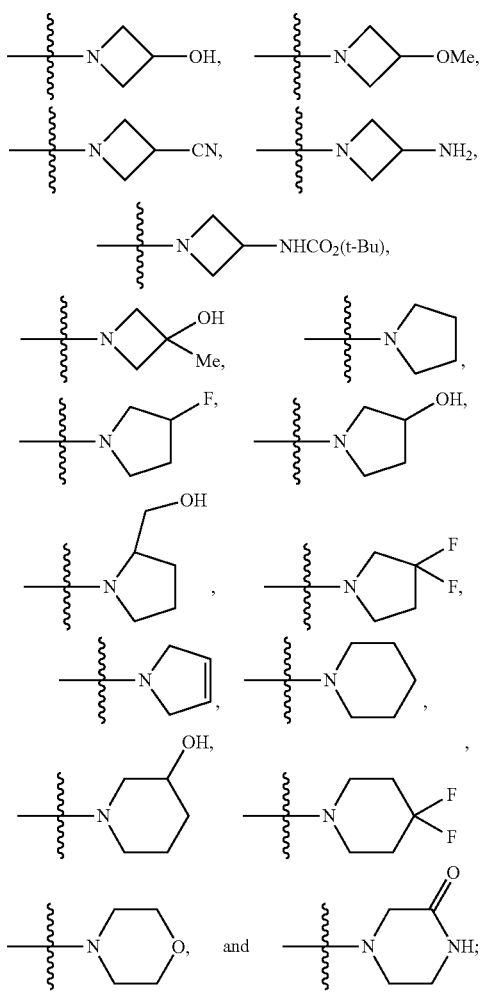

and

R[8] is independently selected from: halogen, $C_{1-4}$ alkyl and $C_{1-4}$ alkoxy.

In a ninth aspect, the present invention includes a compound of Formula (IIIc) or a stereoisomer, a tautomer, a pharmaceutically acceptable salt, or a solvate thereof, within the scope of any of the first to fifth and eighth aspects, wherein:

$NR^{12}R^{13}$ is independently at selected from:

and

R[8] is independently selected from: Cl, Me, Et, and OMe.

In a tenth aspect, the present invention includes a compound of Formula (IIId):

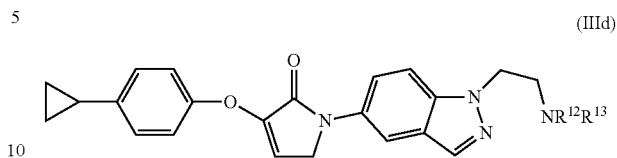

(IIId)

or a stereoisomer, a tautomer, a pharmaceutically acceptable salt, or a solvate thereof, within the scope of any of the first to fifth aspects, wherein:

$NR^{12}R^{13}$ is independently at selected from:

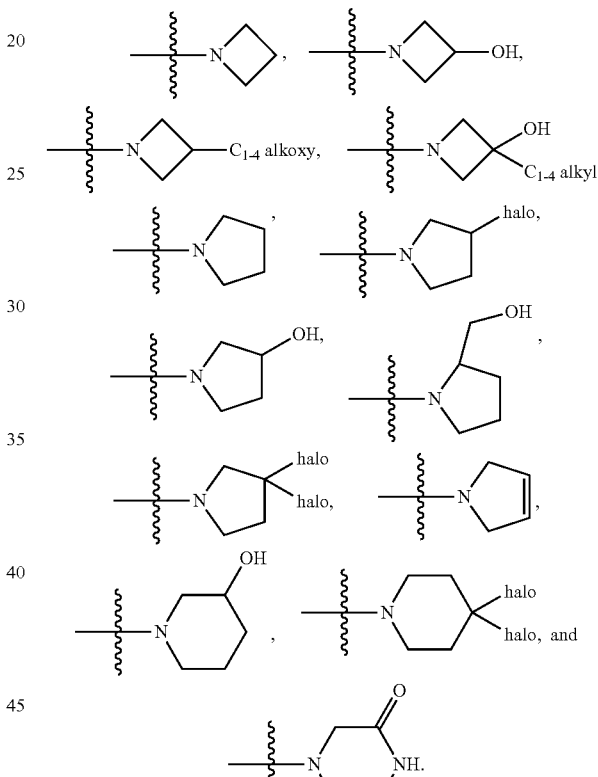

In an eleventh aspect, the present invention includes a compound of Formula (IIId) or a stereoisomer, a tautomer, a pharmaceutically acceptable salt, or a solvate thereof, within the scope of any of the first to fifth and tenth aspects, wherein:

$NR^{12}R^{13}$ is independently at selected from:

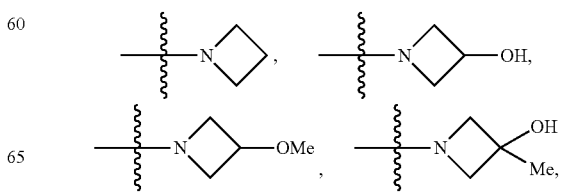

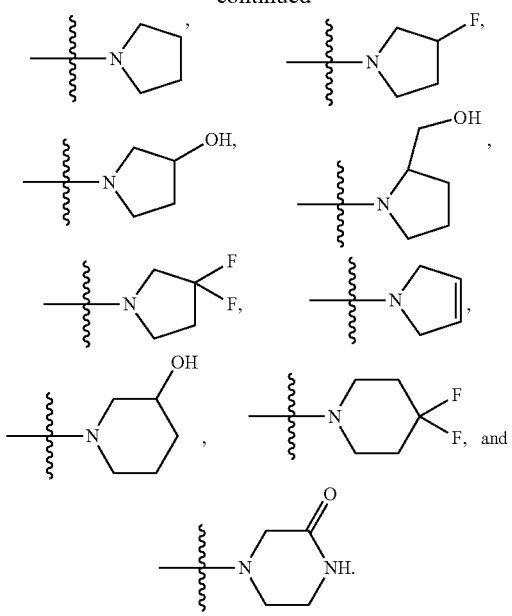

In another embodiment, X is O.

In another embodiment, R² is independently cyclopropyl or phenyl.

In a twelfth aspect, the present invention provides a compound selected from the exemplified examples or a stereoisomer, a tautomer, a pharmaceutically acceptable salt, or a solvate thereof.

In another aspect, the present invention provides a compound selected from any subset list of the exemplified examples or any one of the exemplified examples or a stereoisomer, a tautomer, a pharmaceutically acceptable salt, or a solvate thereof, within the scope of the twelfth aspect.

In another embodiment, the compounds of the present invention have hMCHR1 Ki values ≤10 μM, preferably, Ki values 5 μM, more preferably, Ki values ≤1 μM, even more preferably, Ki values ≤0.5 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). In a preferred embodiment, the present invention provides pharmaceutical composition, wherein the additional therapeutic agent is, for example, a dipeptidyl peptidase-IV (DPP4) inhibitor (for example a member selected from saxagliptin, sitagliptin, vildagliptin and alogliptin).

In another embodiment, the present invention provides a method for the treatment and/or prophylaxis of multiple diseases or disorders associated with MCHR1, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the MCHR1 that can be prevented, modulated, or treated according to the present invention include, but are not limited to, metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; psychiatric disorders, such as depression, anxiety, schizophrenia, substance abuse, cognition-enhancement and Parkinson's disease; and inflammatory diseases such as inflammatory bowel disease, colitis and/or Crohn's disease.

In another embodiment, the present invention provides a method for the treatment and/or prophylaxis of obesity, diabetes, anxiety or depression, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of obesity or diabetes, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with MCHR1.

In another embodiment, the present invention also provides the use of a compound of the present invention for the manufacture of a medicament for the treatment and/or prophylaxis of multiple diseases or disorders associated with MCHR1.

In another embodiment, the present invention provides a method for the treatment and/or prophylaxis of multiple diseases or disorders associated with MCHR1, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with MCHR1.

Where desired, the compound of the present invention may be used in combination with one or more other types of therapeutic agents which may be administered orally in the same dosage form, in a separate oral dosage form or by injection. The other types of therapeutic agent that may be optionally employed in combination with the MCHR1 antagonist of the present invention may be one, two, three or more therapeutic agents which may be administered orally in the same dosage form, in a separate oral dosage form, or by injection to produce an additional pharmacological benefit.

Examples of other types of therapeutic agents include, e.g., anti-obesity agents; anti-diabetic agents, appetite suppressants; cholesterol/lipid-lowering agents, and high-density lipoprotein (HDL)-raising agents. Preferably, the anti-diabetic agent, for example, is dipeptidyl peptidase-IV (DPP4) inhibitor (for example a member selected from saxagliptin, sitagliptin, vildagliptin and alogliptin).

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 13th Edition, John Wiley & Sons, New York (1997). "$C_{6-10}$ aryl" refers to phenyl and naphthyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Greene et al., *Protective Groups in Organic Synthesis*, John Wiley & Sons, New York (1991) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I)

is a prodrug within the scope and spirit of the invention. Various forms of prodrugs are well known in the art. For examples of such prodrug derivatives, see:

a) Bundgaard, H., ed., Design of Prodrugs, Elsevier (1985), and Widder, K. et al., eds., *Methods in Enzymology*, 112:309-396, Academic Press (1985);
b) Bundgaard, H., Chapter 5, "Design and Application of Prodrugs", *A Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988); and
e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "meq" for milliequivalent or milliequivalents, "g" for gram or grams, "mg" for milligram or milligrams, "L" for liter or liters, "mL" for milliliter or milliliters, "μL" for microliter or microliters, "N" for normal, "M" for molar, "mol" for mole or moles, "mmol" for millimole or millimoles, "min" for minute or min, "h" for hour or h, "rt" for room temperature, "$t_R$" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
Boc tert-butyloxycarbonyl
MeOH methanol
EtOH ethanol
i-PrOH or IPA isopropanol
KOH potassium hydroxide
NaOH sodium hydroxide
LiOH lithium hydroxide
n-BuLi n-butyllithium
CDCl$_3$ deutero-chloroform
CHCl$_3$ chloroform
CH$_2$Cl$_2$ dichloromethane
CH$_3$CN or ACN acetonitrile
cDNA complimentary DNA
CsF cesium fluoride
DCE dichloroethane
DCM dichloromethane
DEAD diethyl azodicarboxylate
DIAD diisopropyl azodicarboxylate
DIC 2-dimethylaminoisopropyl chloride HCl
DIPEA diisopropylethylamine
DMF dimethyl formamide
DMSO dimethyl sulfoxide
DMAP 4-dimethylaminopyridine
EDC 1-(3-dimethylaminopropyl)-3-ethylcarbodiimide HCl
EDCI 1-ethyl-3-(3-dimethylaminopropyl)carbodiimide
EtOAc ethyl acetate
Et$_2$O diethyl ether
HCl hydrochloric acid
HOAc or AcOH acetic acid HOBT hydroxybenzotriazole
$H_2SO_4$ sulfuric acid
$H_2O_2$ hydrogen peroxide
$K_2CO_3$ potassium carbonate
LHMDS lithium hexamethyldisilazide
mCPBA or m-CPBA meta-chloroperbenzoic acid
$MgSO_4$ magnesium sulfate
$N_2$ nitrogen
$NaBH_4$ sodium borohydride
$NaH_2PO_4.H_2O$ sodium dihydrogen phosphate hydrate
NaCl sodium chloride
NaH sodium hydride
$NaHCO_3$ sodium bicarbonate
$NaHSO_3$ sodium bisulfite
$Na_2SO_3$ sodium sulfite
$Na_2S_2O_3$ sodium thiosulfate
$Na_2SO_4$ sodium sulfate
$NEt_3$ triethylamine
$NH_3$ ammonia
$NH_4Cl$ ammonium chloride
$NH_4OH$ ammonium hydroxide
NMO 4-methylmorpholine N-oxide
$OSO_4$ osmium tetroxide
Pd/C palladium on carbon
$Pd(PPh_3)_4$ palladium tetrakis(triphenylphosphine)
$PPh_3$ triphenylphosphine
SEM 2-(trimethylsilyl)ethoxymethyl
SEM-Cl 2-(trimethylsilyl)ethoxymethyl chloride
$SiO_2$ silica oxide
$SOCl_2$ thionyl chloride
TBAB tetrabutylammonium bromide
TBS tert-butyldimethylsilyl
TEA triethylamine
Tf triflate
TFA trifluoroacetic acid
THF tetrahydrofuran
LG leaving group
PG Protecting group The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula (I) falling into a given class may be compatible with some of the reaction conditions required in some of the methods described. Restrictions to the substituents that are compatible with the reaction conditions will be readily apparent to one skilled in the art and alternate methods must then be used.

Synthesis

The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula (I) may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula (I) falling into a given class may be compatible with some of the reaction conditions required in some of the methods described. Such restrictions to the substituents, which are compatible with the reaction conditions, will be readily apparent to one skilled in the art and alternate methods must be used.

It will be understood that $R^7$ may be present in its final form throughout the synthesis or can be introduced at any point in the following synthetic sequences particularly if $R^7$ contains a hydroxyl. Specifically, $R^7$ may be carried along as a truncated moiety $R^{7'}$ such as EH that may be protected as a SEM ether, SEM thioether, BOC amine, or etc. and then elongated whenever appropriate. Likewise compounds of Formula I for which $R^7$ contains —$CH_2CH_2SO(C_{1-2}$ alkyl), —$CH_2CH_2SO_2(C_{1-2}$ alkyl), —$CH_2CH(OH)CH_2SO_2(C_{1-2}$ alkyl), or —$CH_2CH_2SO_2(CH_2C(C_{1-2}$ alkyl)$_2$OH) can be prepared by treatment of precursors containing —$CH_2CH_2S(C_{1-2}$ alkyl), —$CH_2CH(OH)CH_2S(C_{1-2}$ alkyl), or —$CH_2CH_2S(CH_2C(C_{1-2}$ alkyl)$_2$OH) with one or two equivalents respectively of an oxidant such as m-chloroperbenzoic acid in a solvent such as $CH_2Cl_2$.

Compounds of Formula (II) containing a saturated pyrrolidinone for which m is 2 can be prepared as shown in Scheme 1. Substituted nitrated SEM protected phenols of Formula A can be hydrogenated with Pd/C to give anilines of Formula B. In a one pot reaction compounds of Formula B can be sequentially reacted with 2,4-dibromobutanoyl chloride and a base, e.g., $NEt_3$ followed by addition an additional base such as KOH with TBAB or AMBERLITE® IRA-400 and an phenol of Formula C to generate compounds of Formula D. After removal of the protecting group with HCl in ether to generate compounds of Formula E, Compounds of Formula F can be prepared upon treatment of compounds of Formula E with 2-bromoethanol in the presence of a base such as $Et_3N$. Compounds of Formula F can be converted to compounds of Formula I by sequential treatment with mesyl chloride and a base e.g., $Et_3N$ followed by treatment with an amine of Formula G.

Scheme 1

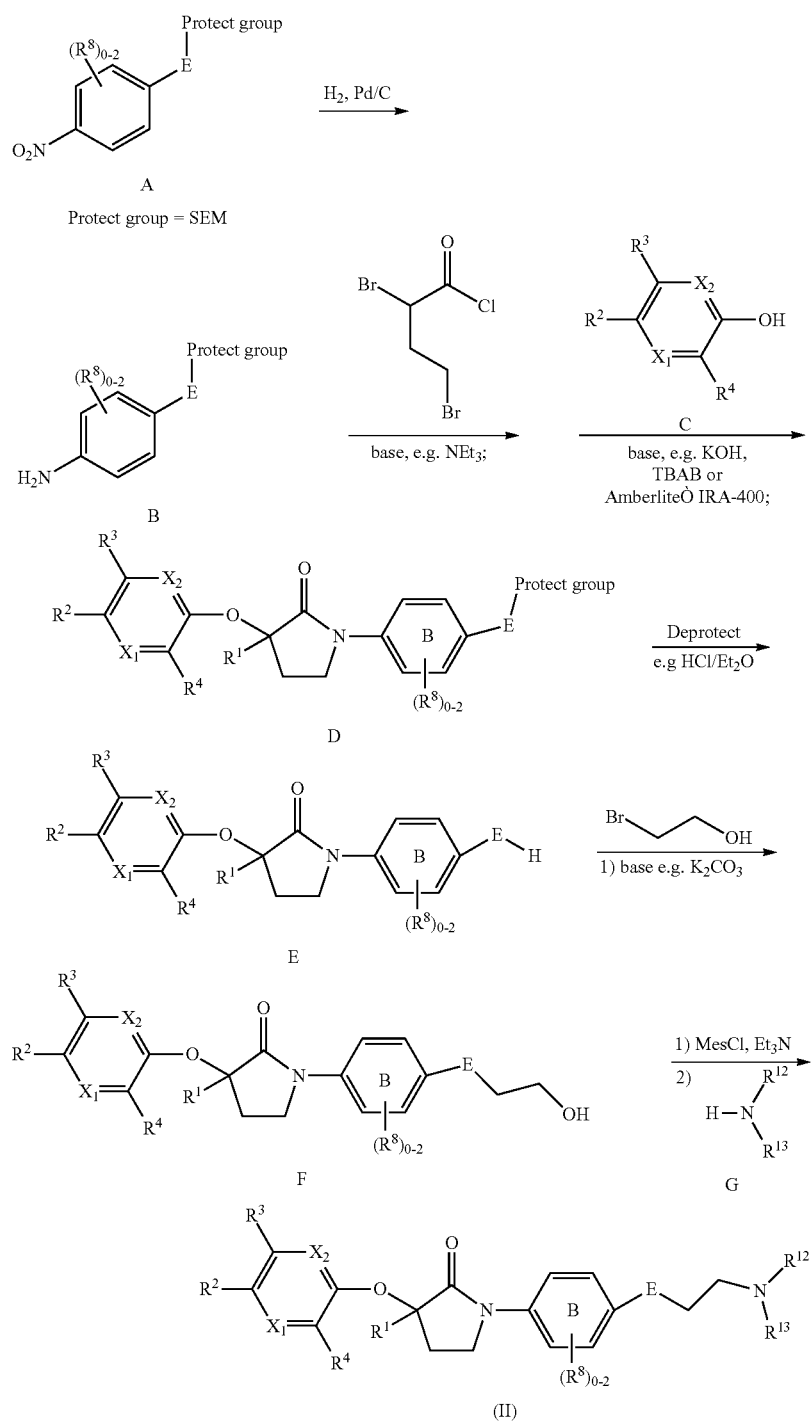

where
X = O, R$^1$ = H, n = 2
----- is a single bond

Compounds of Formula (II) containing an unsaturated pyrrolidone for which E is oxygen and n is 2 can be prepared as shown in Scheme 2. Compounds of Formula H can be prepared by sequential treatment of compound D, prepared as described in Scheme 1, with a strong base such as lithium hexamethyldisilazide followed by phenyl selenyl chloride.

Compounds of Formula J can be obtained upon hydrogen peroxide mediated oxidation of compounds of Formula H to generate the pyrrolone moiety followed by deprotection of the phenol. Compounds of Formula J can be converted to compounds of Formula K by sequential alkylation with 2-bromoethanol in the presence of a base such as $K_2CO_3$. Conversion of compounds of Formula K to compounds if Formula (I) can be achieved by treatment with mesyl chloride followed by reaction with the appropriate amine of Formula G by employing a set reaction conditions described for Scheme 1.

with Compounds of Formula B in the presence of a reagent such as EDC. Compounds of Formula N can be prepared following sequential treatment of Compounds of Formula M with a strong base such as NaH followed by allyl bromide. Conversion of Compounds of Formula N to Compounds of Formula O can be achieved by gentle heating in the presence of a Grubbs metathesis catalyst such as tricyclohexylphosphine[1,3-bis(2,4,6-trimethylphenyl)-4,5-dihydroimidazol-2-ylidene][benzylidine]ruthenium (IV) dichloride. Compounds of Formula O can be converted to compounds of Formula (II) by sequential alkylation with 2-bromoethanol,

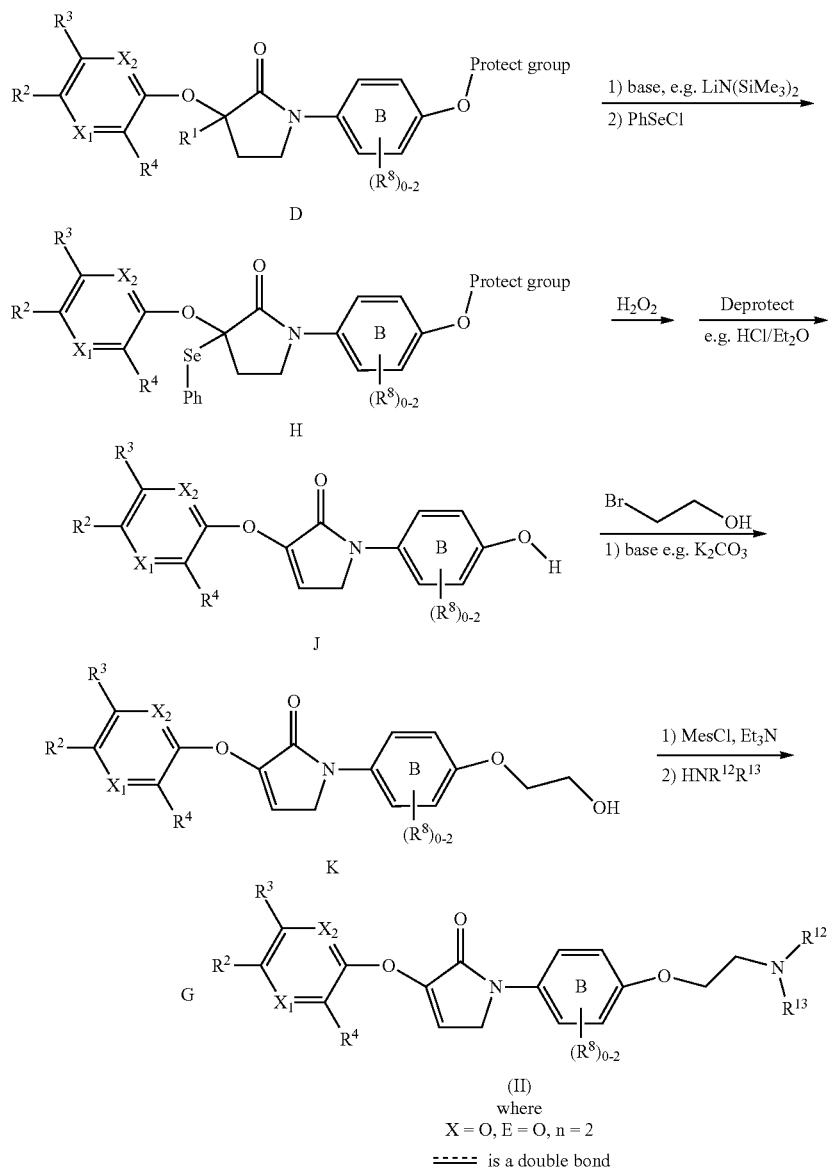

An alternative route for preparation of compounds of Formula (II) containing a pyrrolone core is outlined in Scheme 3. Compounds of Formula L can be prepared by a base promoted condensation of compounds of Formula C with methyl 2-bromo-2-butenoate Compounds of Formula M can be prepared by reaction of compounds of Formula L treatment with mesyl chloride and reaction with an appropriate amine of Formula G by employing a set reaction conditions described for Scheme 1. It should be noted that hydrogenation of compounds of Formula 1 containing an unsaturated pyrrolidone ring will generate compounds of Formula 1 containing an saturated pyrrolidinone ring.

Scheme 3

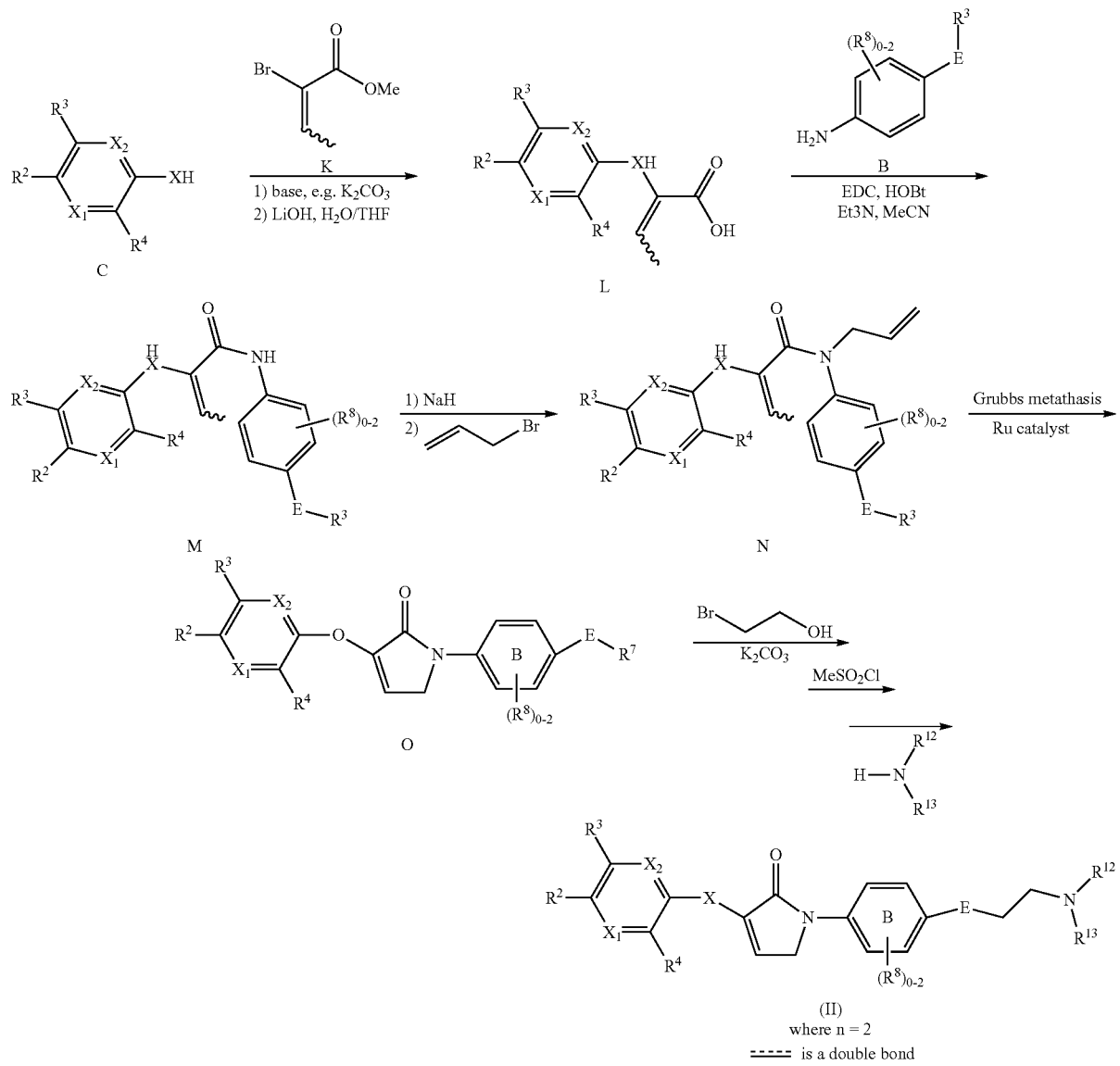

Compounds of Formula (II) for which E is a bond and n=1, can be obtained by NaBH₄ reduction of nitrobenzaldehydes of Formula P to the corresponding alcohol and subsequent conversion to the t-butyldimethylsilyl ether of compounds of Formula Q. Compounds of Formula R, obtained by ammonium formate/Pd(OH)₂ mediated reduction of compounds of Formula Q, were subsequently converted to Compounds of Formula S by sequential coupling with Compounds of Formula L, allylation and cyclization as previously discussed in Scheme 3. Compounds of Formula T can be prepared from compounds of Formula S by deprotection with aq. HCl followed by oxidation with Dess-Martin Periodinane. Compounds of Formula (II) where n=1 and E is a bond can be formed upon reductive amination with amines of Formula G and sodium triacetoxyborohydride.

Scheme 4

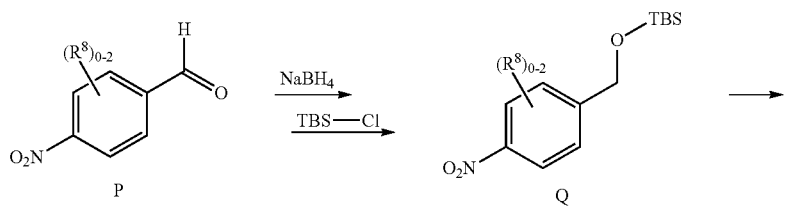

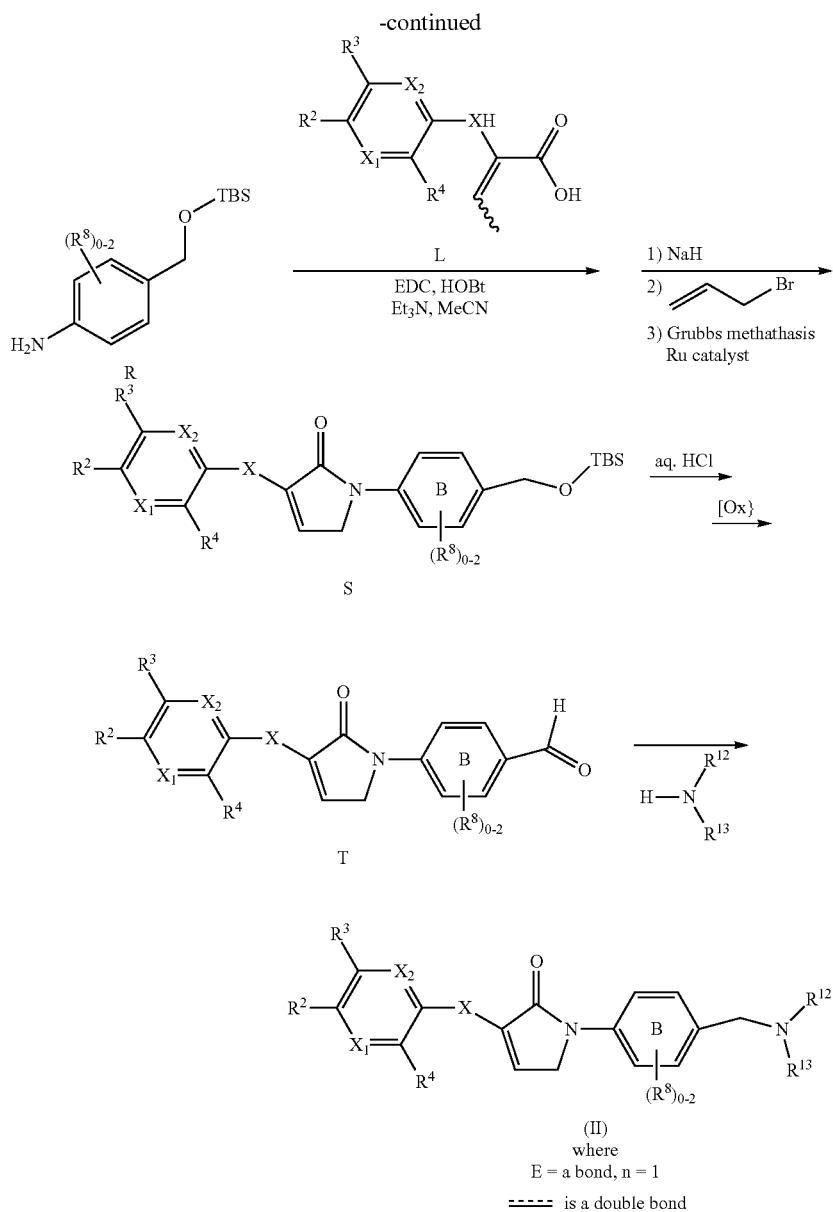

Alternatively, compounds of Formula (Ia) for which B is a heterocycle, E is a bond and n=2 is exemplified in Scheme 5. Compounds of Formula V can be generated by alkylation of compounds of Formula U with 2-(2-bromoethoxyl)tetrahydropyran followed by reduction over Pd/C with hydrogen. Compounds for Formula W can be prepared by sequential coupling of compounds of Formula V with Compounds of Formula L, allylation and cyclization as previously discussed in Scheme 3. Conversion of compounds of Formula W to compounds of Formula (Ia) can be achieved by sequential aq HCl deprotection, reaction with mesyl chloride and treatment with an appropriate amine of Formula G.

Scheme 5

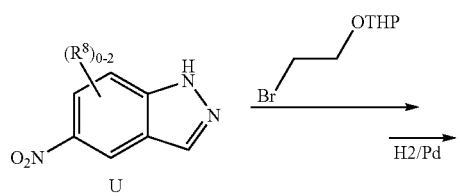

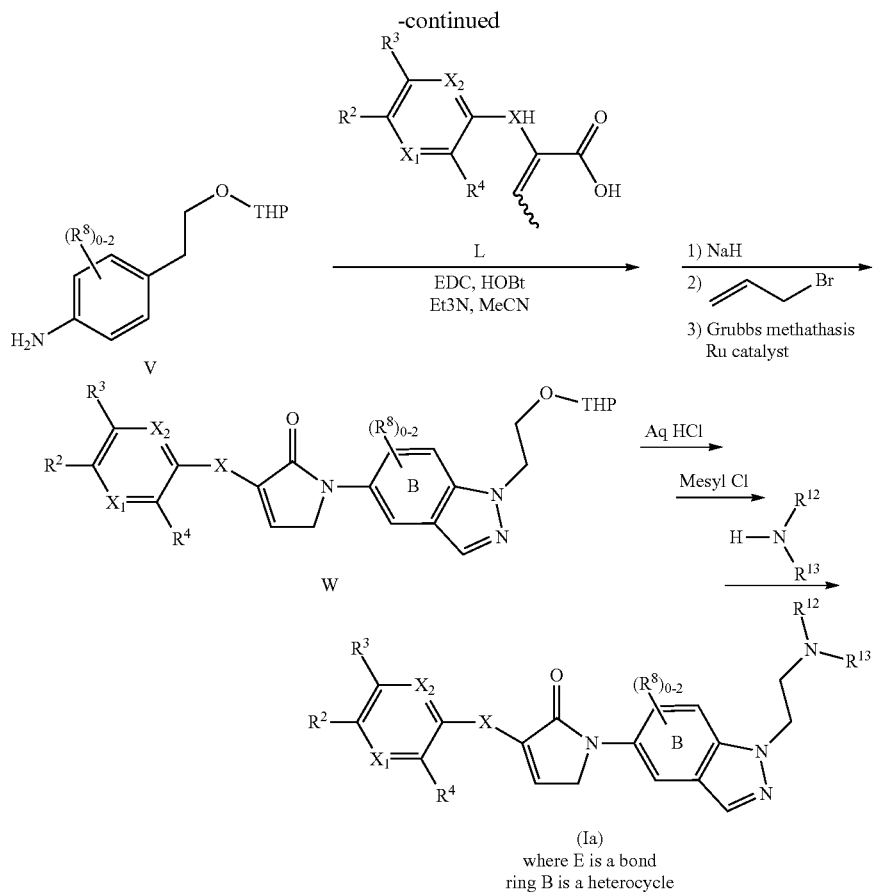

Scheme 6 illustrates the preparation of compounds of Formula (Ib) where u and v are both greater than 1 by treatment of compounds of Formula E or of Formula J with cyclic hydroxyl substituted amines of Formula X in the presence of triphenylphosphine and DEAD.

Scheme 7 illustrates the preparation of compounds of Formula (II) for which E is a bond and $R^7$ is $NR^{12}R^{13}$. Treatment of compounds of Formula A with an amine of Formula W generates compounds of Formula Y. Hydrogenation of compounds of Formula Y generates compounds of

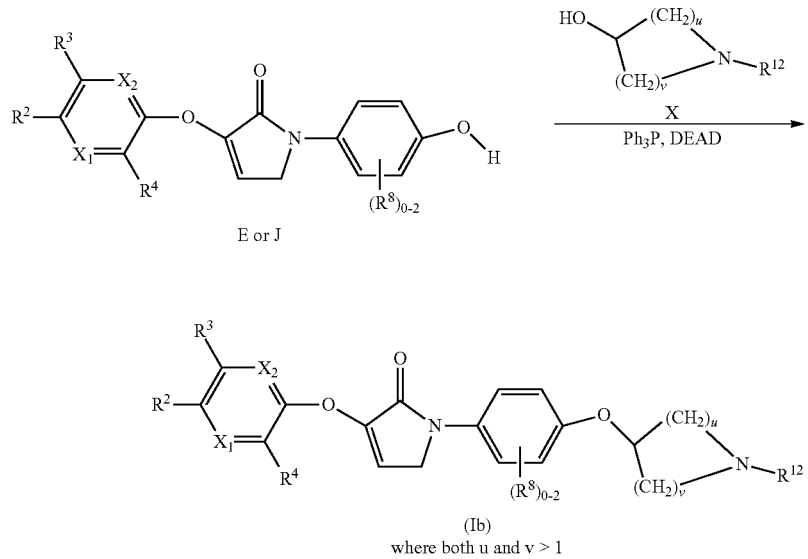

Formula Z. Compounds of Formula Z can be sequentially reacted with 2,4-dibromobutanoyl chloride and a base, e.g., $NEt_3$ followed by addition an additional base such as KOH with TBAB or AMBERLITE® IRA-400 and an phenol of Formula C to generate compounds of Formula (II).

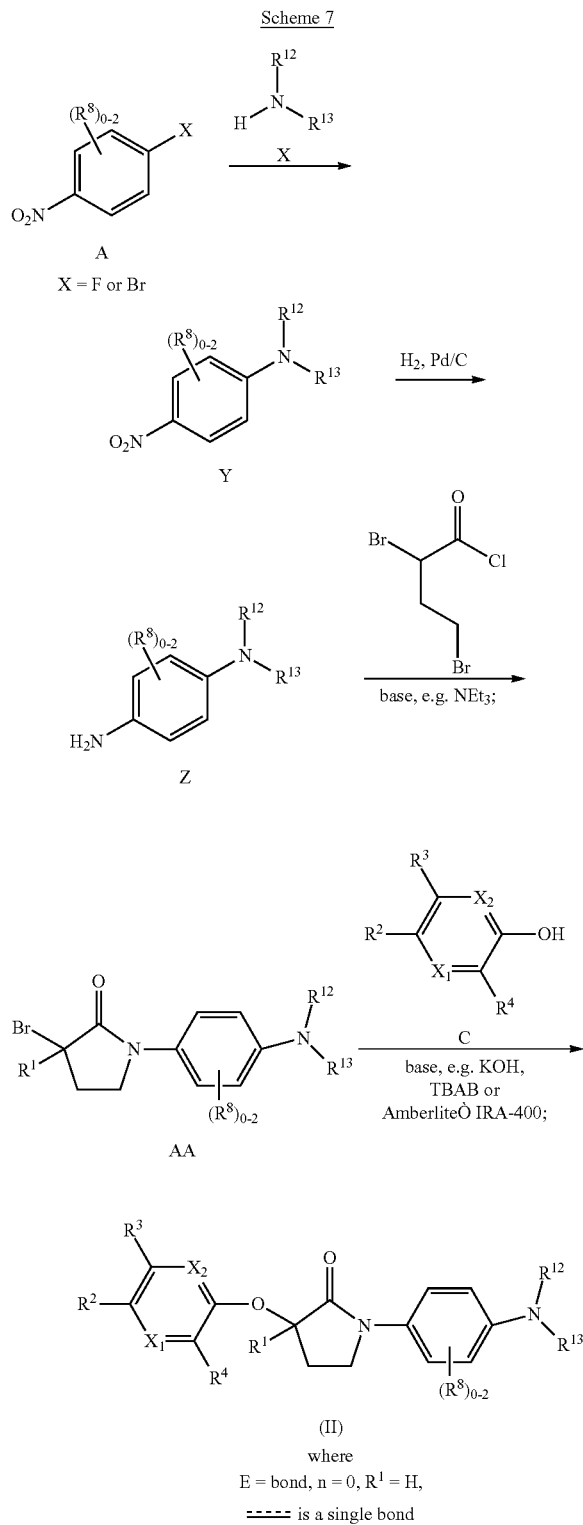

IV. Biological Assays and Evaluation

Radioligand Binding Assay for Assessment of MCHR1 Activity

An in vitro binding assay was used to determine the compound Ki value or ability to antagonize binding of a peptide agonist to the human melanin concentrating hormone receptor (MCHR1). Membranes from stably transfected HEK-293 cells expressing a mutated (E4Q, A5T) hMCHR1 receptor were prepared by dounce homogenization and differential centrifugation. Binding experiments were carried out with 0.5-1.0 ug of membrane protein incubated in a total of 0.2 mL in 25 mM HEPES (pH 7.4) with 10 mM $MgCl_2$, 2 mM EGTA, and 0.1% BSA (Binding Buffer) for 90 min. For competition binding assays, reactions were carried out in the presence of with 0.06-0.1 nM [$Phe^{13}$, [$^{125}I$]$Tyr^{19}$]-MCH and increasing concentrations of unlabeled test molecules. Reactions were terminated by rapid vacuum filtration over 96 well-GFC UNIFILTER® plates pre-coated with 0.075 mL binding buffer containing 1% BSA, and washed 3 times with 0.4 mL of Phosphobuffered Saline (pH 7.4) containing 0.01% TX-100. Filters were dried, 0.05 mL MicroScint 20 was added to each well and radioactivity was subsequently quantified by scintillation counting on a TOPCOUNT® microplate scintillation counter (Packard). Inhibitory constants were determined by nonlinear least squares analysis using a four parameter logistic equation.

The following representative in vitro biological data was measured in a binding assay for Compound Ia and the six Comparator Compounds above:

V. Utilities, Pharmaceutical Compositions and Combinations

The compounds of the present invention can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease; and inflammatory diseases such as inflammatory bowel disease, colitis and/or Crohn's disease.

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and neurotropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

According to one embodiment of the present invention, methods are provided for treating obesity in a patient in need of such treatment, comprising administering a therapeutically effective amount of at least Compound I (including a prodrug, a polymorph or a pharmaceutical acceptable salt) according to the present invention alone or in combination with one or more additional antiobesity agents, wherein the obesity agent is selected from those described herein.

According to one embodiment of the present invention, methods are provided for treating diabetes, especially Type II diabetes, in a patient in need of such treatment, comprising administering a therapeutically effective amount of at least Compound I (including a prodrug, a polymorph or a pharmaceutical acceptable salt), according to the present invention alone or in combination with one or more additional antidiabetic agents, wherein the diabetic agent is described herein.

According to one embodiment of the present invention, methods for treating depression and/or anxiety in a patient are provided, comprising administering a therapeutically effective amount of at least Compound I, or a prodrug, a polymorph or a pharmaceutical acceptable salt thereof, according to the present invention.

According to one embodiment of the present invention, methods are provided for treating inflammatory bowel disease, comprising administering a therapeutically effective amount of at least Compound I, or a prodrug, a polymorph or a pharmaceutical acceptable salt thereof.

According to some embodiments of the present invention, pharmaceutical compositions are provided, comprising at least Compound I, or a prodrug, a polymorph or a pharmaceutical acceptable salt thereof, as described herein, and at least one pharmaceutically acceptable diluent or carrier. The pharmaceutical compositions of the present invention may optionally include at least one additional therapeutic agent selected from the group consisting of anti-obesity agent, anti-diabetic agent, anti-depressant agent, anti-anxiety agent, anti-inflammatory agent, appetite suppressant, cholesterol/lipid-lowering agent, and HDL-raising agent, and other therapeutic agents as defined herein.

The present invention is also directed to pharmaceutical combinations, comprising at least Compound I, or a prodrug, a polymorph or a pharmaceutical acceptable salt thereof, and at least one additional therapeutic agent, selected from the group consisting of anti-obesity agent, anti-diabetic agent, anti-depressant agent, anti-anxiety agent, anti-inflammatory agent, appetite suppressant, cholesterol/lipid-lowering agent, and HDL-raising agent, and other therapeutic agents as defined herein.

According to one embodiment of the present invention, the anti-diabetic agent is selected from the group consisting of insulin secretagogues, insulin sensitizers, glucokinase inhibitors, glucocorticoid antagonist, fructose 1,6-bis phosphatase inhibitors, AMP kinase activators, incretin modulators glucosidase inhibitors, aldose reductase inhibitors PPAR γ agonists, PPAR α agonists, PPAR δ antagonists or agonists, PPAR α/γ dual agonists, 11-β-HSD-1 inhibitors, dipeptidyl peptidase IV (DP4) inhibitors, SGLT2 inhibitors, such as dapagliflozin, insulin, glucagon-like peptide-1 (GLP-1), GLP-1 agonists, and PTP-1B inhibitors.

According to one embodiment of the present invention, the additional therapeutic agent is an antiobesity agent.

Examples of suitable anti-obesity agents for use in combination with the compounds of the present invention include melanocortin receptor (MC4R) agonists, cannabinoid receptor modulators, endocannabinoid synthesis modulators, GPR119 agonists, inhibitors of fat absorption, growth hormone secretagogue receptor (GHSR) antagonists, galanin receptor modulators, orexin antagonists, SGLT2 inhibitors, DPP4 inhibitors, triple monoamine reuptake inhibitors, CCK agonists, GLP-1 agonists, and other Pre-proglucagon-derived peptides; NPY1 or NPY5 antagonist, NPY2 and NPY4 modulators, corticotropin releasing factor modulators, histamine receptor-3 (H3) modulators, aP2 inhibitors, PPAR gamma modulators, PPAR delta modulators, acetyl-CoA carboxylase (ACC) inhibitors, steroyl Co-A desaturase-1 (SCD-1) inhibitors, 11-β-HSD-1 inhibitors, adiponectin receptor modulators; beta 3 adrenergic agonists, thyroid receptor beta modulators, lipase inhibitors, serotonin receptor agonists, monoamine reuptake inhibitors or releasing agents, anorectic agents, CNTF (ciliary neurotrophic factor), BDNF (brain-derived neurotrophic factor), leptin and leptin receptor modulators, cannabinoid-1 receptor inverse agonists/neutral antagonists, DGAT inhibitors, opiate antagonists, and amylin receptor modulators.

Preferred antiobesity agents include SGLT2 inhibitors, such as those disclosed in U.S. Pat. No. 6,414,126. Most preferred anti-obesity agents include dapagliflozin and lipase inhibitors, such as orlistat, or monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

The compounds of the present invention can be administered in oral dosage form. The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 30 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight). The other active component or components having different modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

The present invention includes within its scope pharmaceutical compositions including, as an active ingredient, a therapeutically effective amount of at least one of the compounds of the invention, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the melanin-concentrating hormone receptor (MCHR) antagonists in accordance with the invention.

Examples of suitable anti-obesity agents for use in combination with the compounds of the present invention include melanocortin receptor (MC4R) agonists, cannabinoid receptor modulators, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adiponectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists (e.g., BVT-933 (Biovitrum) or lorcaserin (Arena)), 5HT6 antagonists, monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, tesofensine, dexamphetamine, phentermine, phenylpropanolamine or mazindol, anorectic agents such as topiramate (Johnson & Johnson), CNTF (ciliary neurotrophic factor)/AXOKINE® (Regeneron), BDNF (brain-derived neurotrophic factor), leptin and leptin receptor modulators, or cannabinoid-1 receptor inverse agonists/neutral antagonists, such as SR-141716 (Sanofi) or SLV-319 (Solvay), DGAT inhibitors such as those described in WO 2006/134317 (A1) (Astra Zeneca), WO 2006/044775 (A2) (Bayer), WO 2006/019020 (A1) (Sankyo), WO 2006/082010 (A1) (Roche), WO 2004/047755 (A2) (Japan Tobacco, Tularik), and WO 2005/0727401 (A2) (Amgen, Japan Tobacco) and combination agents such as Qnexa and Contrave.

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors including saxagliptin, vildagliptin and sitagliptin, SGLT2 inhibitors including dapagliflozin and canaglifozin, glycogen phosphorylase inhibitors, and/or meglitinides, as well as insulin, and/or glucagon-like peptide-1 (GLP-1), GLP-1 agonists and other incretins, SIRT activators (resveratrol) and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer), isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPAR α/γ dual agonist such as MK-767/KRP-297 (Merck/Kyorin; as described in Yajima, K. et al., *Am. J. Physiol. Endocrinol. Metab.*, 284:E966-E971 (2003)), AZ-242 (tesaglitazar; Astra-Zeneca; as described in Ljung, B. et al., *J. Lipid Res.*, 43:1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to lovastatin, pravastatin, simvastatin, fluvastatin, atorvastatin, pitavastatin, or rosuvastatin.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX®, Policexide) and cholestagel (Sankyo/Geltex), as well as LIPOSTABIL® (Rhone-Poulenc), EISAI® E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277, 082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis*, 115:45-63 (1995) and *J. Med. Chem.*, 41:973 (1998).

The other lipid agent or lipid-modulating agent may be a cholesteryl transfer protein inhibitor (CETP) such as Pfizer's CP-529,414 as well as those disclosed in WO 00/38722 and in EP 818448 (Bayer) and EP 992496, and Pharmacia's SC-744 and SC-795, CETi-1, JTT-705 and anacetrapib.

The hypolipidemic agent may be an ileal Na+/bile acid cotransporter inhibitor such as disclosed in *Drugs of the Future*, 24:425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 00/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 00/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin, rosuvastatin, and ezetimibe as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

MCHR1 antagonists could be useful in treating other diseases associated with obesity, including sleep disorders. Therefore, the compounds described in accordance with the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of MCHR1 receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in accordance with the present invention may be used alone or in combination with anti-anxiety agents or anti-depressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpha-adrenoreceptor antagonists, and atypical anti-depressants (bupropion, lithium, nefazodone, trazodone and viloxazine).

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS, Preparatory/Analytical HPLC, and Chiral Separation Methods Employed in Characterization or Purification of Examples Analytical HPLC Method 1: Sunfire C18 [150×4.6 mm] column; 0.05% trifluoroacetic acid in water with pH 2.5 as buffer; Mobile Phase A=buffer: MeCN [95:5]; Mobile Phase B: MeCN:buffer [95:5]; 10% B to 100% B; 23 min; Flow rate: 1.0 mL/min Analytical HPLC Method 2: XBridge Phenyl C18 [150× 4.6 mm] column; 0.05% trifluoroacetic acid in water pH 2.5 as buffer; Mobile Phase A=buffer: MeCN [95:5]; Mobile Phase B: MeCN:buffer [95:5]; 10% B to 100% B; 23 min; Flow rate: 1.0 mL/min Chiral HPLC Method 3: CHIRALPAK® AS-H column [250×4.6 mm], 5μ; Mobile Phase: 0.2% DEA in n-hexane: ethanol[70:30]; Flow rate: 1.0 mL/min Chiral HPLC Method 4: CHIRALCEL® OD-H column [250×4.6 mm], 5μ; Mobile Phase: 0.2% DEA in n-hexane: ethanol[50:50 or 60:40 as required]; Flow rate: 1.0 mL/min NMR Employed in Characterization of Examples $^1$H NMR spectra were obtained with Bruker or JEOL Fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Procedure-A1

Examples 1 and 2

Enantiomers of 3-(4-cyclopropylphenoxy)-1-(3-methoxy-4-(2-(pyrrolidin-1-yl)ethoxy)phenyl)pyrrolidin-2-one

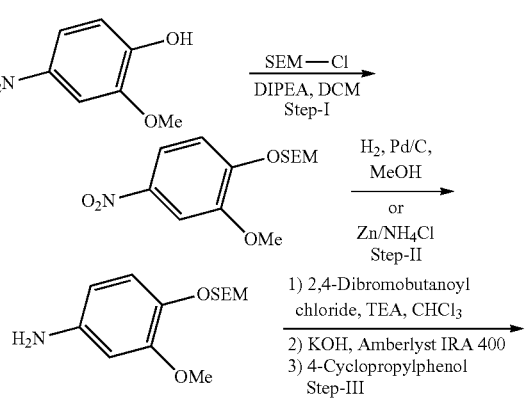

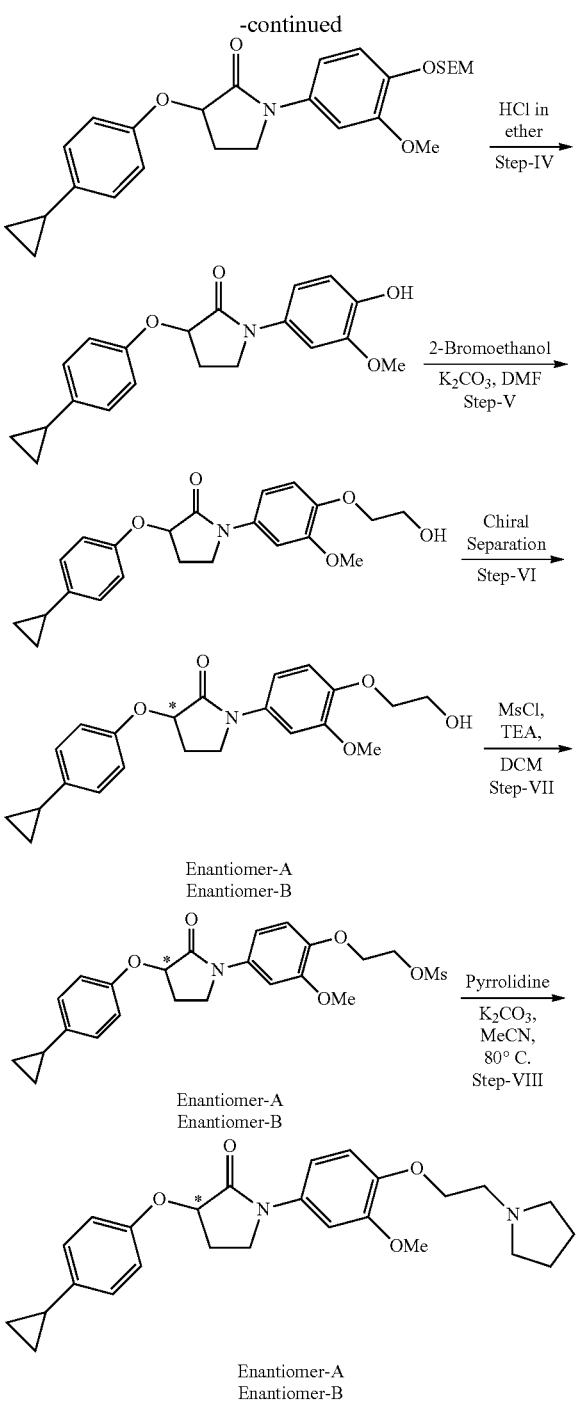

Enantiomer-A
Enantiomer-B

Step-I: (2-((2-Methoxy-4-nitrophenoxy)methoxy)ethyl)trimethylsilane (intermediate A1-1)

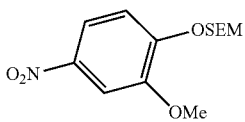

To a solution of 2-methoxy-4-nitrophenol (4.0 g, 23.65 mmol) in DCM (60.0 mL) at 0° C. under nitrogen atmosphere, was added N,N-diisopropylethylamine (10.33 mL, 59.1 mmol) and subsequently 2-(trimethylsilyl)ethoxymethyl chloride (6.29 mL, 35.5 mmol) dropwise. The reaction mixture was gradually warmed to room temperature and stirred for 6.0 h. The solvent was removed in vacuo and the residue purified by CombiFlash instrument (120 g silica gel column, 15% ethyl acetate in hexane) to afford the product as a colorless oil (7.0 g, 99%). $^1$H NMR (400 MHz, chloroform-d) δ=7.90-7.86 (m, 1H), 7.79-7.76 (m, 1H), 7.26-7.23 (m, 1H), 5.37 (s, 2H), 3.97 (s, 3H), 3.83-3.77 (m, 2H), 0.98-0.93 (m, 2H), 0.00 (s, 9H); MS (ES): m/z 356.5 [M+2H]$^+$.

Step-II: 3-Methoxy-4-((2-(trimethylsilyl)ethoxy)methoxy)aniline (intermediate A1-2)

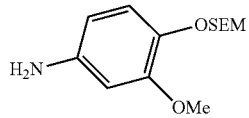

To a solution of (2-((2-methoxy-4-nitrophenoxy)methoxy)ethyl)trimethylsilane (14.0 g, 46.8 mmol) in ethyl acetate (140 mL), was added palladium on carbon (1.4 g, 1.316 mmol). The reaction was flushed with hydrogen gas followed by degassing (3×) under vacuum. The mixture was then stirred at ambient temperature under hydrogen bladder for 24.0 h. The catalyst was filtered and rinsed with ethyl acetate. The filtrate was concentrated in vacuo. The crude product was obtained as a dark-brownish oil (11.50 g, 91% yield) and used as such in the next reaction. $^1$H NMR (400 MHz, chloroform-d) δ 6.89-7.02 (m, 1H), 6.26-6.33 (m, 1H), 6.16-6.24 (m, 1H), 5.14 (s, 2H), 3.82 (s, 5H), 3.43-3.56 (m, 2H), 0.91-1.01 (m, 2H), −0.05-0.05 (m, 9H); MS (ES): m/z 270.2 [M+H]$^+$.

Step-III: (+/−)-3-(4-Cyclopropylphenoxy)-1-(3-methoxy-4-((2-(trimethylsilyl)ethoxy)methoxy)phenyl)pyrrolidin-2-one (intermediate A1-3)

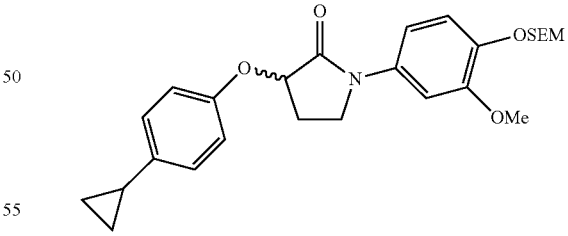

To a solution of 3-methoxy-4-((2-(trimethylsilyl)ethoxy)methoxy)aniline (7.4 g, 27.5 mmol) and triethylamine (5.74 mL, 41.2 mmol) in CHCl$_3$ (70 mL), was added 2,4-dibromobutanoyl chloride (4.36 mL, 33.0 mmol) at 0° C. under nitrogen atmosphere. The mixture was stirred for 2.0 h at ambient temperature. An aqueous solution of potassium hydroxide (6.16 g, 110 mmol), dissolved in 70.0 mL of water, was added dropwise. AMBERLYST® IR-400 (7.0 g, 27.5 mmol) was then added. Subsequently, the mixture was stirred for 12.0 h. Lithium phenoxide dihydrate (4.84 g, 27.5 mmol) was then added as one lot. The reaction mixture was heated to 55° C. and stirred for 12 h. The mixture was partitioned between water and chloroform. The organic layer was washed with water, dried over anhydrous sodium sulfate, and concentrated in vacuo. The crude product was purified using CombiFlash instrument (120 g silica gel column; 25% ethyl acetate in petroleum ether) to afford the product as a colorless solid (5.7 g, 44%). $^1$H NMR (400 MHz, chloroform-d) δ=7.86-7.72 (m, 1H), 7.15 (s, 1H), 7.00 (d, J=8.0 Hz, 4H), 6.85-6.74 (m, 1H), 5.25 (s, 2H), 5.04-4.91 (m, 1H), 3.89 (s, 7H), 2.73-2.60 (m, 1H), 2.35-2.21 (m, 1H), 1.92-1.80 (m, 1H), 1.02-0.85 (m, 4H), 0.69-0.54 (m, 2H), 0.01 (s, 9H); MS (ES): m/z 470.2 [M+H]$^+$.

Step-IV: (+/−)-3-(4-Cyclopropylphenoxy)-1-(4-hydroxy-3-methoxyphenyl)pyrrolidin-2-one (intermediate A1-4)

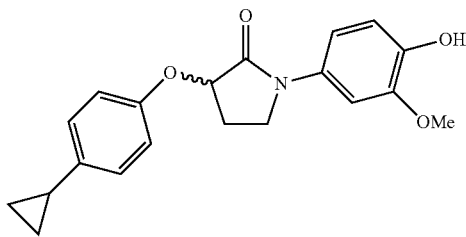 [SMILES: COc1cc(N2CCC(Oc3ccc(C4CC4)cc3)C2=O)ccc1O]

To a solution of (+/−)-3-(4-cyclopropylphenoxy)-1-(3-methoxy-4-((2-(trimethylsilyl)ethoxy)methoxy)phenyl)pyrrolidin-2-one (5.6 g, 11.92 mmol) in CH$_2$Cl$_2$ (25.0 mL) at 0° C. under nitrogen atmosphere, was added etheral solution of hydrogen chloride gas (2.0 M solution in diethyl ether) (5.96 mL, 119 mmol). The mixture was gradually warmed to room temperature and stirred for 4.0 h. Petroleum ether (300.0 mL) was added. The precipitated solid was filtered and dried under vacuum. The product was obtained as a colorless solid (3.3 g, 82%). The product was used as such in the next step. $^1$H NMR (400 MHz, chloroform-d) δ=7.77 (d, J=2.3 Hz, 1H), 7.07-6.96 (m, 4H), 6.90 (d, J=8.8 Hz, 1H), 6.79-6.69 (m, 1H), 5.53 (s, 1H), 5.05-4.93 (m, 1H), 3.96-3.75 (m, 5H), 2.73-2.57 (m, 1H), 2.34-2.19 (m, 1H), 1.92-1.80 (m, 1H), 0.90 (dd, J=1.9, 8.4 Hz, 2H), 0.62 (dd, J=1.6, 5.1 Hz, 2H); MS (ES): m/z 340.2 [M+H]$^+$.

Step-V: (+/−)-3-(4-Cyclopropylphenoxy)-1-(4-(2-hydroxyethoxy)-3-methoxyphenyl)pyrrolidin-2-one (intermediate A1-5)

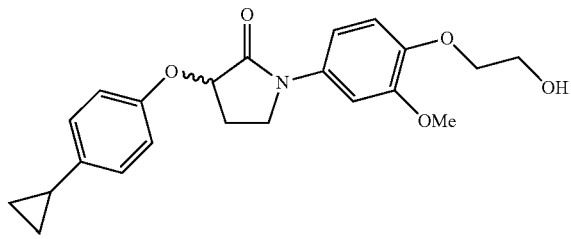 [SMILES: COc1cc(N2CCC(Oc3ccc(C4CC4)cc3)C2=O)ccc1OCCO]

To a solution of (+/−)-3-(4-cyclopropylphenoxy)-1-(4-hydroxy-3-methoxyphenyl)pyrrolidin-2-one (3.25 g, 9.58 mmol) in N,N-dimethylformamide (30.0 mL), were added potassium carbonate (7.94 g, 57.5 mmol) and 2-bromoethanol (3.38 mL, 47.9 mmol). The mixture was heated to 80° C. for 12 h. The mixture was partitioned between water and ethyl acetate. The organic layer was washed with water and brine, dried over anhydrous sodium sulfate, and concentrated in vacuo. The crude product was purified using CombiFlash instrument (120 g silica gel column; 80% ethyl acetate in petroleum ether) to afford the product as a colorless solid (3.0 g, 82%). $^1$H NMR (400 MHz, chloroform-d) δ=7.74 (d, J=2.5 Hz, 1H), 7.07-6.90 (m, 5H), 6.89-6.81 (m, 1H), 4.98 (t, J=7.5 Hz, 1H), 4.18-4.10 (m, 2H), 4.05-3.60 (m, 8H), 2.72-2.61 (m, 1H), 2.35-2.26 (m, 1H), 1.86 (s, 1H), 0.94-0.87 (m, 2H), 0.62 (dd, J=1.8, 5.0 Hz, 2H); MS (ES): m/z 384.2 [M+H]$^+$.

Step-VI: Chiral separation of (+/−)-3-(4-cyclopropylphenoxy)-1-(4-(2-hydroxyethoxy)-3-methoxyphenyl)pyrrolidin-2-one The racemic mixture, (+/−)-3-(4-cyclopropylphenoxy)-1-(4-hydroxy-3-methoxyphenyl)pyrrolidin-2-one (3.0 g), was separated under chiral SFC conditions [Column: CHIRALCEL® OD-H; CO$_2$: 60%; Co-solvent: 40% of MeOH with 0.5% DEA; Column Temperature: 32.2; CO$_2$ Flow rate: 1.8; Co-solvent Flow rate: 1.2; Co-solvent %: 40; Total Flow: 3; Back pressure: 104] to provide intermediate A1-6a (enantiomer A, 1.2 g, 40% yield; chiral purity: 99.3%) and intermediate A1-6b (enantiomer B, 1.3 g, 43% yield; chiral purity: 98.01%) as colorless solids.

Intermediate A1-6a: $^1$H NMR (400 MHz, chloroform-d) δ=7.74 (d, J=2.5 Hz, 1H), 7.08-6.90 (m, 5H), 6.85 (d, J=2.5 Hz, 1H), 4.98 (s, 1H), 4.17-4.10 (m, 2H), 3.99-3.73 (m, 8H), 2.72-2.60 (m, 1H), 2.35-2.23 (m, 1H), 1.91-1.80 (m, 1H), 0.94-0.88 (m, 2H), 0.67-0.58 (m, 2H); MS (ES): m/z 384.2 [M+H]$^+$; HPLC-RT: 9.87 min (Analytical HPLC Method A); Chiral HPLC-RT: 13.56 min (CHIRALCEL® OD-H column [250×4.6 mm], 5μ; Mobile Phase: 0.2% DEA in n-hexane:ethanol[70:30]; Flow rate: 1.0 mL/min).

Intermediate A1-6b: $^1$H NMR (400 MHz, chloroform-d) δ=7.74 (d, J=2.5 Hz, 1H), 7.07-6.90 (m, 5H), 6.88-6.79 (m, 1H), 4.98 (t, J=7.7 Hz, 1H), 4.17-4.08 (m, 2H), 4.00-3.69 (m, 8H), 2.75-2.59 (m, 1H), 2.34-2.26 (m, 1H), 1.86 (s, 1H), 0.94-0.88 (m, 2H), 0.66-0.59 (m, 2H); MS (ES): m/z 384.2 [M+H]$^+$; HPLC-RT: 9.86 min (Analytical HPLC Method A); Chiral HPLC-RT: 21.33 min (CHIRALCEL® OD-H column [250×4.6 mm], 5μ; Mobile Phase: 0.2% DEA in n-hexane:ethanol[70:30]; Flow rate: 1.0 mL/min).

Step-VIIa: 2-(4-(3-(4-Cyclopropylphenoxy)-2-oxopyrrolidin-1-yl)-2-methoxyphenoxy)ethyl methanesulfonate (intermediate A1-7a)

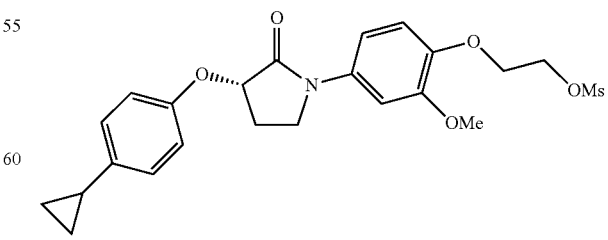

To a solution of 3-(4-cyclopropylphenoxy)-1-(4-(2-hydroxyethoxy)-3-methoxyphenyl)pyrrolidin-2-one (0.2 g, 0.522 mmol; intermediate A1-6a) in DCM (3.0 mL), was added triethylamine (0.182 mL, 1.304 mmol) and subsequently methanesulfonyl chloride (0.049 mL, 0.626 mmol). After being stirred for 6.0 h, the mixture was concentrated and the residue purified by CombiFlash instrument (50% ethyl acetate in hexane; 48 g neutral alumina column) to afford the product as a colorless solid (0.1 g, 42% yield). $^1$H NMR (400 MHz, DMSO-d$_6$) δ=7.53 (d, J=2.5 Hz, 1H), 7.12-6.95 (m, 6H), 5.15 (s, 1H), 4.59-4.49 (m, 2H), 4.28-4.20 (m, 2H), 3.78 (s, 5H), 3.25 (s, 3H), 2.72-2.62 (m, 1H), 2.12-1.97 (m, 1H), 1.93-1.81 (m, 1H), 0.89 (d, J=6.3 Hz, 2H), 0.60 (dd, J=2.0, 5.3 Hz, 2H); MS (ES): m/z 462.2 [M+H]$^+$; Chiral HPLC-RT: 10.95 min (CHIRALCEL® OD-H column [250×4.6 mm], 5μ; Mobile Phase: n-hexane:ethanol[70:30]; Flow rate: 1.0 mL/min)

Step-VIII a: S-3-(4-Cyclopropylphenoxy)-1-(3-methoxy-4-(2-(pyrrolidin-1-yl)ethoxy)phenyl)pyrrolidin-2-one Example 1

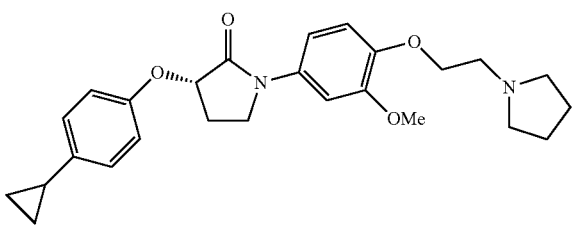 [SMILES: COc1cc(N2CC[C@H](Oc3ccc(C4CC4)cc3)C2=O)ccc1OCCN1CCCC1]

To a solution of 2-(4-(3-(4-cyclopropylphenoxy)-2-oxopyrrolidin-1-yl)-2-methoxyphenoxy)ethyl methanesulfonate (50 mg, 0.108 mmol; intermediate A1-7a) in acetonitrile (2.0 mL), were added pyrrolidine (0.018 mL, 0.217 mmol), potassium iodide (17.98 mg, 0.108 mmol), and potassium carbonate (29.9 mg, 0.217 mmol) sequentially. The reaction mixture was stirred at 80° C. for 12.0 h. The reaction mixture was gradually cooled to room temperature. Ice crystals were added. The precipitated solid was filtered, washed with ether, and dried under vacuum to afford the product as a colorless solid (30.7 mg, 65%).

Step-VIIb: R2-(4-(3-(4-Cyclopropylphenoxy)-2-oxopyrrolidin-1-yl)-2-methoxyphenoxy)ethyl methanesulfonate (intermediate A1-7b)

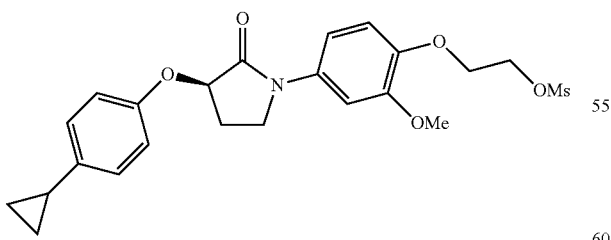

To a solution of 3-(4-cyclopropylphenoxy)-1-(4-(2-hydroxyethoxy)-3-methoxyphenyl)pyrrolidin-2-one (0.2 g, 0.522 mmol (intermediate A1-6b) in DCM (3.0 mL), was added triethylamine (0.182 mL, 1.304 mmol) and subsequently methanesulfonyl chloride (0.049 mL, 0.626 mmol). After being stirred for 6.0 h, the mixture was concentrated and the residue purified by CombiFlash instrument (50% ethyl acetate in hexane; 48 g neutral alumina column) to afford the product as a colorless solid (0.12 g, 50% yield). $^1$H NMR (400 MHz, DMSO-d$_6$) δ=7.54 (d, J=2.3 Hz, 1H), 7.08 (d, J=2.3 Hz, 1H), 7.06-7.00 (m, 3H), 6.99-6.91 (m, 2H), 5.15 (s, 1H), 4.53 (td, J=2.3, 4.0 Hz, 2H), 4.23 (td, J=2.3, 4.0 Hz, 2H), 3.90-3.74 (m, 5H), 3.25 (s, 3H), 2.73-2.62 (m, 1H), 2.12-1.98 (m, 1H), 1.92-1.81 (m, 1H), 0.89 (dd, J=2.0, 8.3 Hz, 2H), 0.63-0.57 (m, 2H); MS (ES): m/z 462.2 [M+H]$^+$; Chiral HPLC-RT: 16.74 min (CHIRALCEL® OD-H column [250×4.6 mm], 5μ; Mobile Phase: n-hexane:ethanol [70:30]; Flow rate: 1.0 mL/min).

Step-VIIIb: 3-(4-Cyclopropylphenoxy)-1-(3-methoxy-4-(2-(pyrrolidin-1-yl)ethoxy)phenyl)pyrrolidin-2-one Example 2

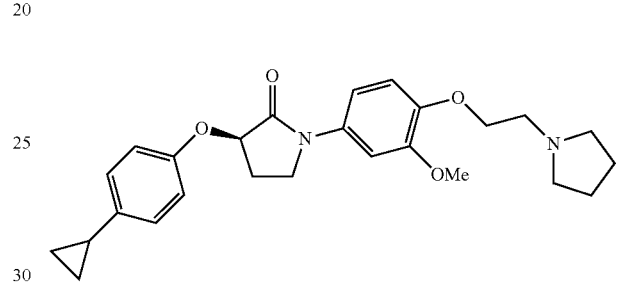

To a solution of 2-(4-(3-(4-cyclopropylphenoxy)-2-oxopyrrolidin-1-yl)-2-methoxyphenoxy)ethyl methanesulfonate (50 mg, 0.108 mmol; intermediate A1-7b) in acetonitrile (2.0 mL), were added pyrrolidine (0.018 mL, 0.217 mmol), potassium iodide (17.98 mg, 0.108 mmol), and potassium carbonate (29.9 mg, 0.217 mmol) sequentially. The reaction mixture was stirred at 80° C. for 12.0 h. The reaction mixture was gradually cooled to room temperature. Ice crystals were added. The precipitated solid was filtered, washed with ether, and dried under vacuum to afford the product as a colorless solid (32.2 mg, 68%).

Examples 3 to 40 contained in Table A by were prepared by coupling intermediate A1-7a with an appropriate amine as described in Procedure A1.

Procedure-A2

Examples 41 and 42

Enantiomers of 3-(4-cyclopropylphenoxy)-1-(3-ethyl-4-(2-(pyrrolidin-1-yl)ethoxy)phenyl)pyrrolidin-2-one

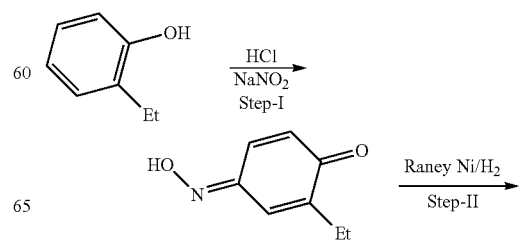

-continued

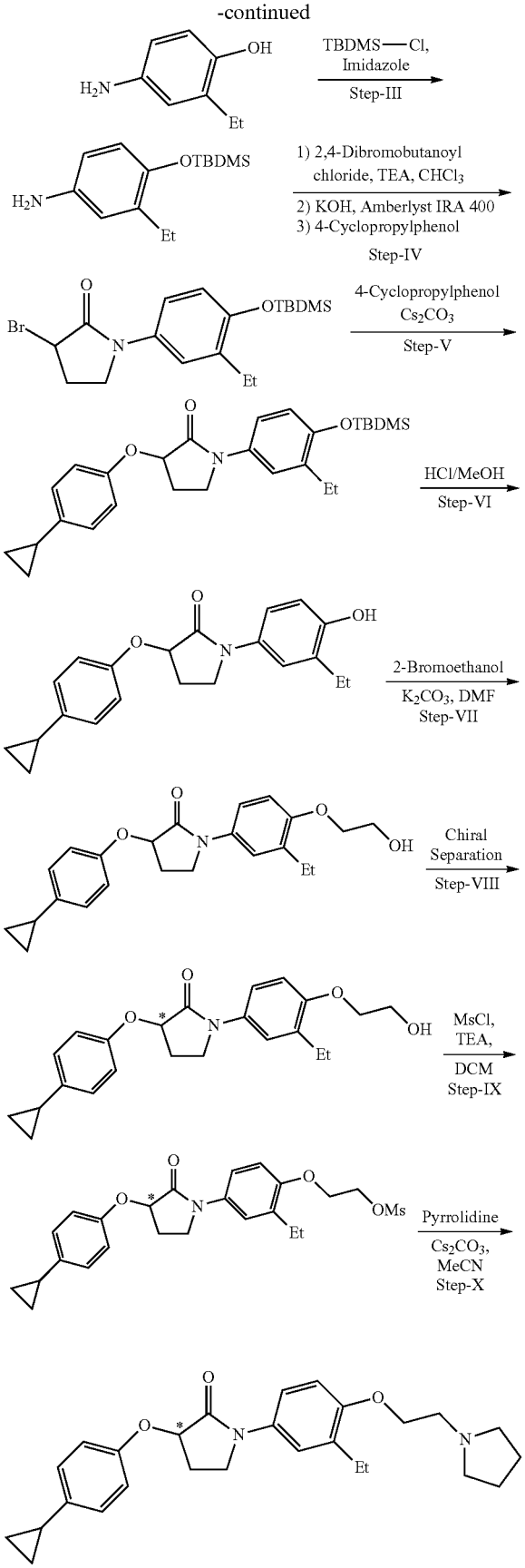

Step-I: 2-Ethyl-4-(hydroxyimino)cyclohexa-2,5-dienone (intermediate A2-1)

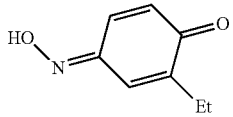

To a solution of 2-ethylphenol (25 g, 205 mmol) in ethanol (200 mL), was added concentrated aqueous hydrochloric acid (37%, 200 mL, 205 mmol) followed by sodium nitrite (21.18 g, 307 mmol) portion wise at −5° C. Then the reaction mixture was stirred for 2.0 h at 0° C. The reaction mixture was poured into ice cold water. The brownish solid, which was precipitated, was filtered through a filter paper and washed with water. The crude product (brown solid) was directly taken to next step (30.1 g, 96.1%); $^1$H NMR (400 MHz, DMSO-$d_6$) δ 13.34-13.66 (m, 1H), 7.48-7.84 (m, 1H), 7.03-7.39 (m, 1H), 6.36-6.56 (m, 1H), 2.27-2.45 (m, 2H), 0.93-1.18 (m, 3H); MS (ES): m/z 152.2 [M+H]$^+$.

Step-II: 4-Amino-2-ethylphenol (intermediate A2-2)

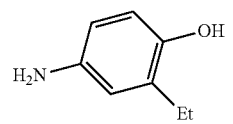

To a degassed solution of 2-ethyl-4-(hydroxyimino)cyclohexa-2,5-dienone (20 g, 132 mmol) in MeOH (250 mL), was added Raney Ni (2 g, 13.23 mmol). The reaction mixture was again degassed. Then the reaction mixture was stirred at room temperature under hydrogen pressure (3 Kg/cm$^2$) in an autoclave for 4.0 h. The reaction mixture was filtered through a Celite® bed and rinsed with methanol. The filtrate was concentrated in vacuo. The residue was washed thrice with petroleum ether to remove the non-polar impurities to afford the crude product as a brownish oil, which was used as such in the next reaction (16 g, 88%). $^1$H NMR (400 MHz, DMSO-$d_6$) δ 8.13 (s, 1H), 6.47 (d, J=8.28 Hz, 1H), 6.34 (d, J=2.76 Hz, 1H), 6.24 (dd, J=2.76, 8.28 Hz, 1H), 4.29 (s, 2H), 2.42 (q, J=7.53 Hz, 2H), 1.08 (t, J=7.53 Hz, 3H); MS (ES): m/z 137.6 [M+H]$^+$.

Step-III: 4-(tert-Butyldimethylsilyloxy)-3-ethylaniline (intermediate A2-3)

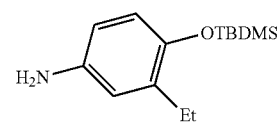

To a solution of 1H-imidazole (16.38 g, 241 mmol) in THF (150 mL), was added TBDMS-chloride (24.19 g, 156 mmol) with rapid stirring at room temperature. The reaction mixture was allowed to stir at room temperature for 4 h. The reaction mixture was diluted with water and extracted with methyl t-butyl ether thrice. The organic layers were combined, dried over sodium sulfate and concentrated in vacuo to get a blackish oil. The crude product was purified by CombiFlash instrument (120 g REDISEP® column; 20% ethyl acetate in petroleum ether) to afford the title product as a colorless liquid (28 g, 93%). $^1$H NMR (400 MHz, DMSO-d$_6$) δ 6.48 (s, 1H), 6.36-6.42 (m, 1H), 6.25-6.33 (m, 1H), 4.54 (s, 2H), 2.43 (d, J=7.53 Hz, 2H), 1.08 (t, J=7.53 Hz, 3H), 0.93-1.01 (m, 9H), 0.14 (s, 6H); MS (ES): m/z 251.7 [M+H]$^+$.

Step-IV: (+/−)-3-Bromo-1-(4-(tert-butyldimethylsilyloxy)-3-ethylphenyl)pyrrolidin-2-one (intermediate A2-4)

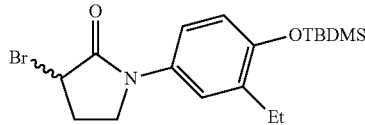 [SMILES: CCc1cc(N2CCC(Br)C2=O)ccc1O[Si](C)(C)C(C)(C)C]

To a solution of 4-((tert-butyldimethylsilyl)oxy)-3-ethylaniline (10 g, 39.8 mmol) and triethylamine (16.63 mL, 119 mmol) in 1,2-dichloroethane (550 mL) was added 2,4-dibromobutanoyl chloride (6.83 mL, 51.7 mmol) dropwise over a period of 10 min. The mixture was stirred at room temperature for 30 min. Then 30% aqueous potassium hydroxide (11.16 g, 199 mmol) solution and AMBERLITE® IR-400 (5 g, 39.8 mmol) were added and the reaction was allowed to stir at room temperature for 16 h. The reaction mixture was diluted with water and extracted with dichloromethane twice. The organic layers were dried over sodium sulfate and concentrated. The crude was purified by CombiFlash instrument (120 g REDISEP® column; 20% ethyl acetate in petroleum ether) to afford the title product as a blackish oil (13 g, 82%). MS (ES): m/z 400.45 [M+H]$^+$.

Step-V: (+/−)-1-(4-(tert-Butyldimethylsilyloxy)-3-ethylphenyl)-3-(4-cyclopropylphenoxyl)pyrrolidin-2-one (intermediate A2-5)

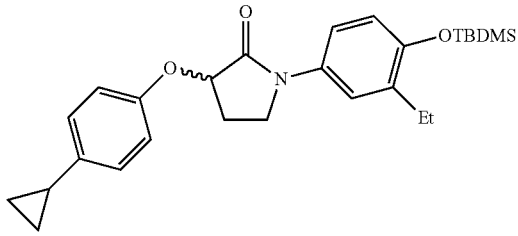 [SMILES: CCc1cc(N2CCC(Oc3ccc(C4CC4)cc3)C2=O)ccc1O[Si](C)(C)C(C)(C)C]

To a solution of 3-bromo-1-(4-((tert-butyldimethylsilyl)oxy)-3-ethylphenyl)pyrrolidin-2-one (12 g, 30.1 mmol) in 1,2-dichloroethane (500 mL), were added cesium carbonate (29.4 g, 90 mmol) and 4-cyclopropylphenol (4.85 g, 36.1 mmol). The reaction mixture was allowed to stir at 60° C. for 16 h. The reaction mixture was diluted with water and extracted with DCM twice. The organic layers were dried over anhydrous sodium sulfate and concentrated in vacuo. The crude was purified by CombiFlash instrument (120 g REDISEP® column; 20% ethyl acetate in petroleum ether) to afford the title product as a white solid. (13 g, 88%); $^1$H NMR (400 MHz, DMSO-d$_6$) δ 7.48-7.54 (m, 1H), 7.35-7.43 (m, 1H), 6.91-7.06 (m, 4H), 6.80-6.88 (m, 1H), 5.06-5.16 (m, 1H), 3.72-3.89 (m, 2H), 2.56-2.70 (m, 3H), 1.98-2.10 (m, 1H), 1.81-1.93 (m, 1H), 1.14 (t, J=7.53 Hz, 3H), 0.96-1.03 (m, 9H), 0.84-0.92 (m, 2H), 0.54-0.64 (m, 2H), 0.22 (s, 6H); MS (ES): m/z 452.4 [M+H]$^+$.

Step-VI: (+/−)-3-(4-Cyclopropylphenoxy)-1-(3-ethyl-4-hydroxyphenyl)pyrrolidin-2-one (intermediate A2-6)

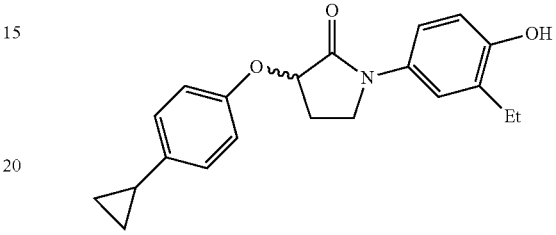

To a solution of 1-(4-((tert-butyldimethylsilyl)oxy)-3-ethylphenyl)-3-(4-cyclopropylphenoxyl)pyrrolidin-2-one (12 g, 26.6 mmol) in MeOH (120 mL), was added concentrated aqueous hydrochloric acid (12 mL) at 0° C. The reaction mixture was stirred at room temperature for 16 h. The reaction mixture was filtered through a filter paper. The filtered solid was washed with petroleum ether thrice and dried under vacuum to afford the title product as a white solid (8.1 g, 90%). $^1$H NMR (400 MHz, DMSO-d$_6$) δ 9.21-9.36 (m, 1H), 7.39 (d, J=2.76 Hz, 1H), 7.22-7.31 (m, 1H), 6.90-7.07 (m, 4H), 6.79 (d, J=8.78 Hz, 1H), 5.10 (s, 1H), 3.77 (s, 2H), 2.60-2.72 (m, 1H), 2.54 (d, J=7.53 Hz, 2H), 1.97-2.08 (m, 1H), 1.80-1.92 (m, 1H), 1.13 (t, J=7.53 Hz, 3H), 0.89 (dd, J=2.01, 8.53 Hz, 2H), 0.56-0.65 (m, 2H); MS (ES): m/z 452.4 [M+H]$^+$.

Step-VII: (+/−)-3-(4-Cyclopropylphenoxy)-1-(3-ethyl-4-(2-hydroxyethoxyl)phenyl)pyrrolidin-2-one (intermediate A2-7)

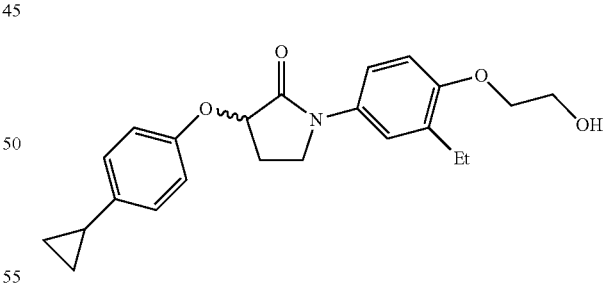

To a solution of 3-(4-cyclopropylphenoxy)-1-(3-ethyl-4-hydroxyphenyl)pyrrolidin-2-one (8 g, 23.71 mmol) in DMF (150 mL), were added potassium carbonate (19.66 g, 142 mmol) and 2-bromoethanol (8.42 mL, 119 mmol). The mixture was heated to 80° C. for 12 h. The mixture was partitioned between water and ethyl acetate. The organic layer was washed with water and brine, dried over anhydrous sodium sulfate, and concentrated in vacuo. The crude product was purified using CombiFlash instrument (120 g silica gel column; 2% methanol in chloroform) to afford the product as a white solid (2.6 g, 28.74%). $^1$H NMR (400

MHz, DMSO-$d_6$) δ 7.50 (d, J=2.76 Hz, 1H), 7.36-7.46 (m, 1H), 6.90-7.06 (m, 5H), 5.12 (s, 1H), 4.73-4.86 (m, 1H), 3.95-4.06 (m, 2H), 3.73 (d, J=5.02 Hz, 4H), 2.61 (d, J=7.53 Hz, 3H), 1.96-2.12 (m, 1H), 1.82-1.93 (m, 1H), 1.15 (t, J=7.40 Hz, 3H), 0.89 (dd, J=2.13, 8.41 Hz, 2H), 0.59 (dd, J=2.01, 5.02 Hz, 2H); MS (ES): m/z 382.2 [M+H]$^+$; HPLC-RT: 10.57 min (Analytical HPLC Method A).

Step-VIII: Chiral separation of (+/−)-3-(4-cyclopropylphenoxy)-1-(3-ethyl-4-(2-hydroxyethoxyl)phenyl)pyrrolidin-2-one The racemic mixture was separated under chiral SFC conditions [Column: CHIRALCEL® OD-H; Co-solvent: 0.5% DEA; CO$_2$ flow rate: 1.8; Co-solvent flow rate: 1.2; Co-solvent %: 40; Total flow: 3; Back pressure: 102] to provide intermediate A2-8a (enantiomer A, 1.3 g, 14.37% yield; chiral purity: 99.3%) and intermediate A2-8b (enantiomer B, 1.3 g, 14.37% yield; chiral purity: 98.01%) as colorless solids.

Intermediate A2-8a: $^1$H NMR (400 MHz, DMSO-$d_6$) δ 7.50 (d, J=2.76 Hz, 1H), 7.41 (dd, J=2.76, 8.78 Hz, 1H), 6.91-7.07 (m, 5H), 5.12 (t, J=7.91 Hz, 1H), 4.81 (t, J=5.52 Hz, 1H), 4.00 (t, J=5.02 Hz, 2H), 3.69-3.86 (m, 4H), 2.56-2.71 (m, 3H), 1.98-2.12 (m, 1H), 1.87 (s, 1H), 1.15 (t, J=7.53 Hz, 3H), 0.82-0.93 (m, 2H), 0.59 (dd, J=2.01, 5.02 Hz, 2H); MS (ES): m/z 382.2 [M+H]$^+$; HPLC-RT: 18.02 min (Analytical HPLC Method A); Chiral HPLC-RT: 8.81 min (CHIRALCEL® OD-H column [250×4.6 mm], 5µ; Mobile Phase: 0.2% DEA in n-hexane:ethanol[70:30]; Flow rate: 1.0 mL/min).

Intermediate A2-8b: $^1$H NMR (400 MHz, DMSO-$d_6$) δ 7.50 (d, J=2.76 Hz, 1H), 7.41 (dd, J=2.76, 8.78 Hz, 1H), 6.91-7.07 (m, 5H), 5.12 (t, J=7.91 Hz, 1H), 4.81 (t, J=5.52 Hz, 1H), 4.00 (t, J=5.02 Hz, 2H), 3.69-3.86 (m, 4H), 2.56-2.71 (m, 3H), 1.98-2.12 (m, 1H), 1.87 (s, 1H), 1.15 (t, J=7.53 Hz, 3H), 0.82-0.93 (m, 2H), 0.59 (dd, J=2.01, 5.02 Hz, 2H); MS (ES): m/z 382.2 [M+H]$^+$; HPLC-RT: 18.03 min (Analytical HPLC Method A); Chiral HPLC-RT: 16.69 min (CHIRALCEL® OD-H column [250×4.6 mm], 5µ; Mobile Phase: 0.2% DEA in n-hexane:ethanol[70:30]; Flow rate: 1.0 mL/min).

Step-IXa: S-2-(4-(3-(4-Cyclopropylphenoxy)-2-oxopyrrolidin-1-yl)-2-ethylphenoxy)ethyl methanesulfonate (intermediate A2-9a)

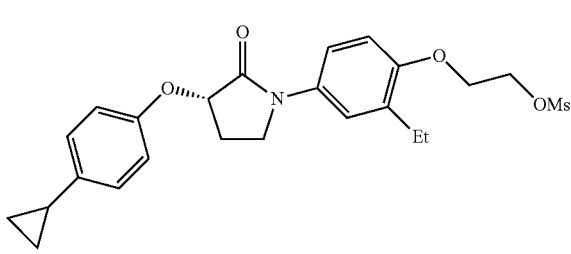 [SMILES: CCc1cc(N2CC[C@H](Oc3ccc(C4CC4)cc3)C2=O)ccc1OCCOS(C)(=O)=O]

To a solution of 3-(4-cyclopropylphenoxy)-1-(3-ethyl-4-(2-hydroxyethoxyl)phenyl)pyrrolidin-2-one (0.100 g, 0.262 mmol (intermediate A2-8a) in DCM (2 mL), was added triethylamine (0.036 mL, 0.262 mmol) and subsequently methanesulfonyl chloride (0.020 mL, 0.262 mmol). The reaction mixture was stirred at room temperature for 16 h. The mixture was partitioned between water and DCM. The organic layer was washed with water and brine, dried over anhydrous sodium sulfate, and concentrated in vacuo to afford the product as a colorless solid (0.11 g, 91% yield). $^1$H NMR (400 MHz, DMSO-$d_6$) δ 7.51-7.59 (m, 1H), 7.41-7.49 (m, 1H), 6.90-7.07 (m, 5H), 5.09-5.19 (m, 1H), 4.50-4.60 (m, 2H), 4.22-4.32 (m, 2H), 3.74-3.87 (m, 2H), 3.23 (s, 3H), 2.57-2.72 (m, 3H), 1.98-2.11 (m, 1H), 1.83-1.93 (m, 1H), 1.14-1.18 (m, 3H), 0.83-0.94 (m, 2H), 0.54-0.66 (m, 2H); MS (ES): m/z 460.0 [M+H]$^+$.

Step-Xa: S-3-(4-Cyclopropylphenoxy)-1-(3-ethyl-4-(2-(pyrrolidin-1-yl)ethoxy)phenyl)pyrrolidin-2-one Example 41

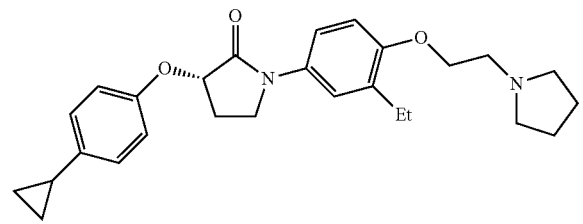 [SMILES: CCc1cc(N2CC[C@H](Oc3ccc(C4CC4)cc3)C2=O)ccc1OCCN1CCCC1]

To a solution of 2-(4-(3-(4-cyclopropylphenoxy)-2-oxopyrrolidin-1-yl)-2-ethylphenoxy)ethyl methanesulfonate (intermediate A2-9a) (0.1 g, 0.218 mmol) in acetonitrile (3 mL), were added pyrrolidine (0.023 g, 0.326 mmol), potassium iodide (0.036 g, 0.218 mmol), and potassium carbonate (0.090 g, 0.653 mmol) sequentially. The mixture was stirred at 80° C. for 16.0 h under nitrogen atmosphere. The mixture was partitioned between water and ethyl acetate. The organic layer was washed with water and brine, dried over anhydrous sodium sulfate, and concentrated in vacuo. The crude product was purified using CombiFlash instrument (12 g silica gel column; 2% MeOH and 0.01% aqueous ammonia in CHCl$_3$) to afford the product as a colorless solid (0.021 g, 21.43%).

Step-IXb: R-2-(4-(3-(4-Cyclopropylphenoxy)-2-oxopyrrolidin-1-yl)-2-ethylphenoxy)ethyl methanesulfonate (intermediate A2-9b)

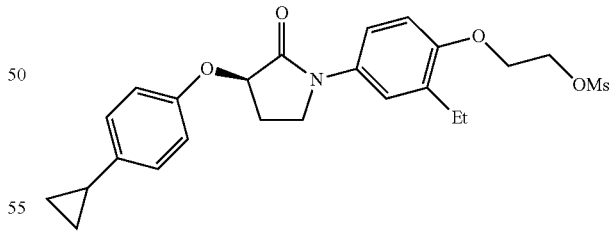

To a solution of 3-(4-cyclopropylphenoxy)-1-(3-ethyl-4-(2-hydroxyethoxyl)phenyl)pyrrolidin-2-one (0.100 g, 0.262 mmol; intermediate A2-8b) in DCM (2 mL), was added triethylamine (0.036 mL, 0.262 mmol) and subsequently methanesulfonyl chloride (0.020 mL, 0.262 mmol). The reaction mixture was stirred at room temperature for 16 h. The mixture was partitioned between water and DCM. The organic layer was washed with water and brine, dried over anhydrous sodium sulfate, and concentrated in vacuo to afford the product as a colorless solid (0.1 g, 83% yield). $^1$H NMR (400 MHz, DMSO-d$_6$) δ 7.53 (d, J=2.76 Hz, 1H), 7.41-7.49 (m, 1H), 6.90-7.07 (m, 5H), 5.13 (s, 1H), 4.54 (td, J=2.26, 4.02 Hz, 2H), 4.23-4.32 (m, 2H), 3.75-3.87 (m, 2H), 2.61 (d, J=7.53 Hz, 3H), 2.37 (s, 3H), 1.98-2.11 (m, 1H), 1.81-1.94 (m, 1H), 1.15 (t, J=7.40 Hz, 3H), 0.89 (dd, J=2.13, 8.41 Hz, 2H), 0.55-0.64 (m, 2H); MS (ES): m/z 460.0 [M+H]$^+$.

Step-Xb: 3-(4-Cyclopropylphenoxy)-1-(3-ethyl-4-(2-(pyrrolidin-1-yl)ethoxy)phenyl)pyrrolidin-2-one Example 42

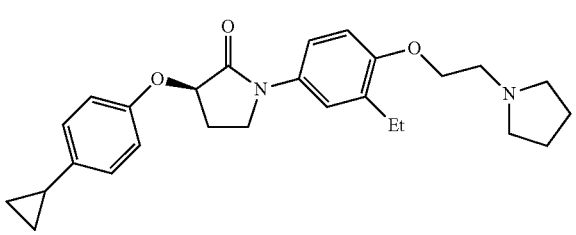 [SMILES: CCc1cc(N2CC[C@@H](Oc3ccc(C4CC4)cc3)C2=O)ccc1OCCN1CCCC1]

To a solution of 2-(4-(3-(4-cyclopropylphenoxy)-2-oxopyrrolidin-1-yl)-2-ethylphenoxy)ethyl methanesulfonate (0.1 g, 0.218 mmol; intermediate A2-9b) in acetonitrile (3 mL), were added pyrrolidine (0.023 g, 0.326 mmol), potassium iodide (0.036 g, 0.218 mmol), and potassium carbonate (0.090 g, 0.653 mmol) sequentially. The mixture was stirred at 80° C. for 16.0 h under nitrogen atmosphere. The mixture was partitioned between water and ethyl acetate. The organic layer was washed with water and brine, dried over anhydrous sodium sulfate, and concentrated in vacuo. The crude product was purified using CombiFlash instrument (12 g silica gel column; 2% MeOH and 0.01% aqueous ammonia in CHCl$_3$) to afford the product as a colorless solid (0.015 g, 15.08%).

Examples 43 to 62 contained in Table A were prepared by coupling intermediate A2-9a with an appropriate amine.

Procedure-A3

Examples 63 and 64

Enantiomers of 3-(4-cyclopropylphenoxy)-1-(3-methyl-4-(2-(pyrrolidin-1-yl)ethoxy)phenyl)pyrrolidin-2-one

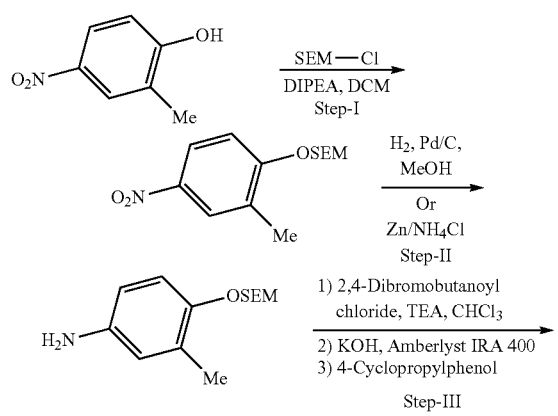

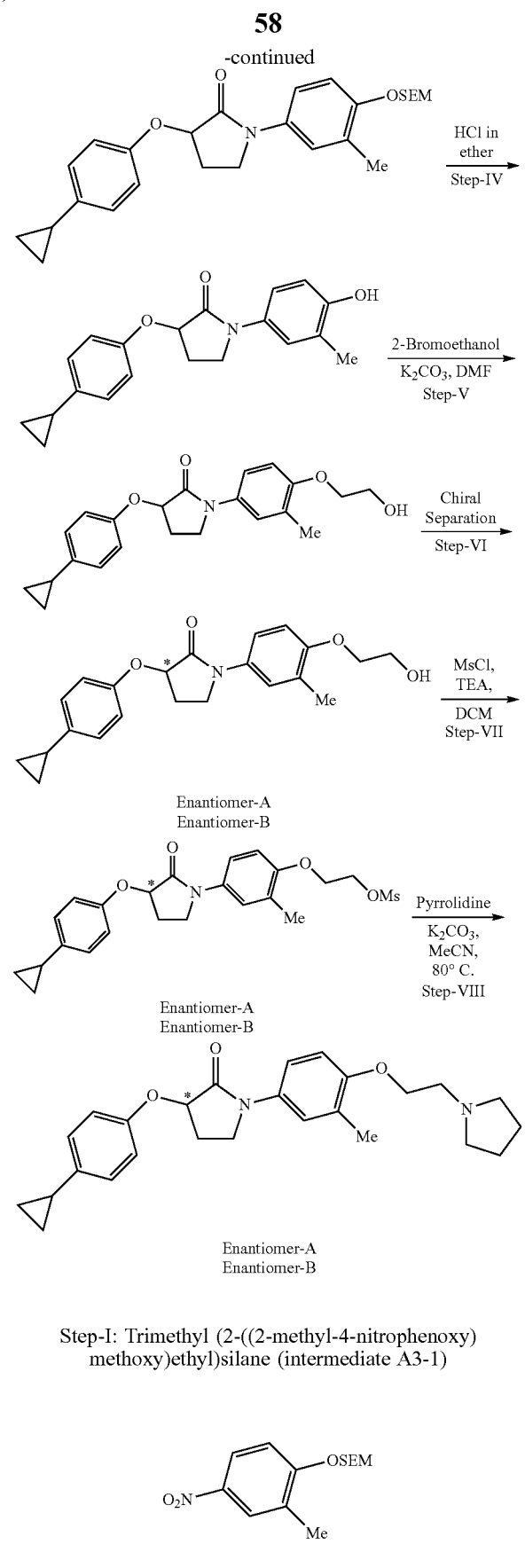

Step-I: Trimethyl (2-((2-methyl-4-nitrophenoxy)methoxy)ethyl)silane (intermediate A3-1)

The title compound was prepared from 2-methyl-4-nitrophenol by following the procedure for the intermediate A1-1

(18.0 g, 97%, off-white solid). $^1$H NMR (400 MHz, chloroform-d) δ 8.02-8.11 (m, 2H), 7.07-7.19 (m, 1H), 5.33 (s, 2H), 3.70-3.83 (m, 2H), 2.29 (s, 3H), 0.89-1.01 (m, 2H), 0.00 (s, 9H); MS (ES): m/z 152 [M-SEM]$^+$.

Step-II: 3-Methyl-4-((2-(trimethylsilyl)ethoxy)methoxy)aniline (intermediate A3-2)

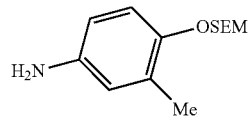

The title compound was prepared from the intermediate A3-1 by following the procedure for the intermediate A1-2 (16.0 g, 85%, dark brownish liquid). $^1$H NMR (400 MHz, DMSO-d$_6$) δ 6.67-6.79 (m, 1H), 6.29-6.42 (m, 2H), 5.03 (s, 2H), 4.58 (s, 2H), 3.64-3.74 (m, 2H), 2.05 (s, 3H), 0.81-0.95 (m, 2H), −0.05-0.04 (m, 9H); MS (ES): m/z 254.2[M+H]$^+$.

Step-III: (+/−)-3-(4-Cyclopropylphenoxy)-1-(3-methyl-4-((2-(trimethylsilyl)ethoxy)methoxy)phenyl)pyrrolidin-2-one (intermediate A3-3)

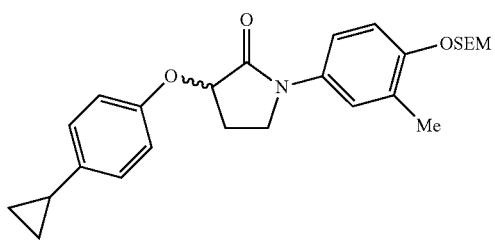

The title compound was prepared from the intermediate A3-2 by following the procedure for the intermediate A1-3 (4.4 g, 39.4%, colorless liquid). $^1$H NMR (400 MHz, chloroform-d) δ 7.47-7.56 (m, 1H), 7.32-7.39 (m, 1H), 7.00 (d, J=6.00 Hz, 5H), 5.22 (s, 2H), 4.90-5.00 (m, 1H), 3.70-3.91 (m, 4H), 2.56-2.69 (m, 1H), 2.25 (s, 4H), 1.79-1.90 (m, 1H), 0.84-1.01 (m, 4H), 0.56-0.68 (m, 2H), 0.00 (d, J=2.00 Hz, 9H); MS (ES): m/z 454.0 [M+H]$^+$.

Step-IV: (+/−)-3-(4-Cyclopropylphenoxy)-1-(4-hydroxy-3-methylphenyl)pyrrolidin-2-one (intermediate A3-4)

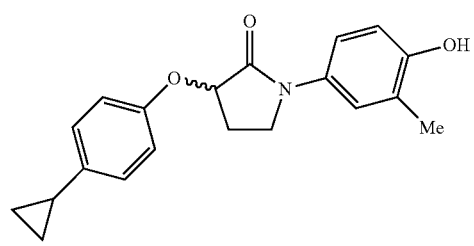 [SMILES: Cc1cc(N2CCC(Oc3ccc(C4CC4)cc3)C2=O)ccc1O]

The title compound was prepared from the intermediate A3-3 by following the procedure for the intermediate A1-4 (3.0 g, 96%, off-white solid). $^1$H NMR (400 MHz, DMSO-d$_6$) δ 9.23-9.34 (m, 1H), 7.21-7.42 (m, 2H), 6.89-7.08 (m, 4H), 6.70-6.84 (m, 1H), 5.00-5.16 (m, 1H), 3.68-3.83 (m, 2H), 2.59-2.73 (m, 1H), 2.13 (s, 3H), 1.95-2.08 (m, 1H), 1.80-1.91 (m, 1H), 0.83-0.95 (m, 2H), 0.54-0.64 (m, 2H); MS (ES): m/z 324.0[M+H]$^+$.

Step-V: (+/−)-3-(4-Cyclopropylphenoxy)-1-(4-(2-hydroxyethoxy)-3-methylphenyl)pyrrolidin-2-one (intermediate A3-5)

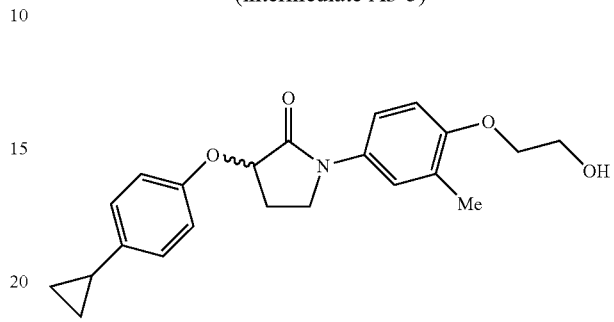

The title compound was prepared from the intermediate A3-4 by following the procedure for the intermediate A1-5 (1.7 g, 50%, off-white solid). $^1$H NMR (400 MHz, DMSO-d$_6$) δ 7.40-7.52 (m, 2H), 6.89-7.06 (m, 5H), 5.04-5.17 (m, 1H), 3.99 (t, J=5.14 Hz, 2H), 3.69-3.87 (m, 4H), 2.58-2.73 (m, 1H), 2.19 (s, 3H), 1.98-2.11 (m, 1H), 1.87 (s, 1H), 0.83-0.94 (m, 2H), 0.54-0.64 (m, 2H); MS (ES): m/z 368.0 [M+H]$^+$.

Step-VI: Chiral separation of (+/−)-3-(4-cyclopropylphenoxy)-1-(4-(2-hydroxyethoxy)-3-methylphenyl)pyrrolidin-2-one

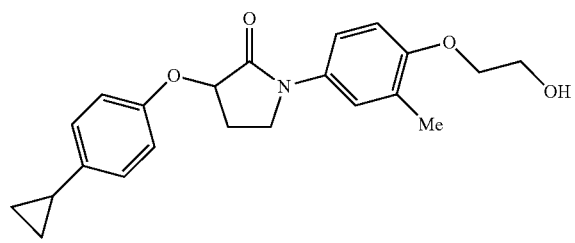 [SMILES: Cc1cc(N2CCC(Oc3ccc(C4CC4)cc3)C2=O)ccc1OCCO]

The racemic mixture (2.8 g), (+/−)-3-(4-cyclopropylphenoxy)-1-(4-hydroxy-3-methylphenyl)pyrrolidin-2-one was separated under chiral SFC conditions to provide the intermediate A3-6a (enantiomer A, 1.0 g) and intermediate A3-6b (enantiomer B, 1.16 g) as colorless solids.

Intermediate A3-6a: $^1$H NMR (400 MHz, chloroform-d) δ 7.38-7.50 (m, 2H), 6.94-7.07 (m, 4H), 6.78-6.88 (m, 1H), 4.88-5.02 (m, 1H), 4.06-4.13 (m, 2H), 3.93-4.02 (m, 2H), 3.76-3.92 (m, 2H), 2.59-2.68 (m, 1H), 2.26 (s, 4H), 1.91-2.00 (m, 1H), 1.79-1.90 (m, 1H), 0.86-0.95 (m, 2H), 0.57-0.66 (m, 2H); MS (ES): m/z 368.0 [M+H]$^+$; HPLC-RT: (a) 17.09 min (Analytical HPLC Method A) (b) 10.06 (Analytical HPLC Method B); Chiral HPLC-RT: 12.07 min (CHIRALCEL® OD-H column [250×4.6 mm], 5μ; Mobile Phase: 0.2% DEA in n-hexane:ethanol[70:30]; Flow rate: 1.0 mL/min).

Intermediate A3-6b: $^1$H NMR (400 MHz, chloroform-d) δ 7.38-7.51 (m, 2H), 7.00 (d, J=6.02 Hz, 4H), 6.78-6.88 (m, 1H), 4.89-5.02 (m, 1H), 4.05-4.17 (m, 2H), 3.94-4.02 (m, 2H), 3.75-3.90 (m, 2H), 2.58-2.70 (m, 1H), 2.26 (s, 4H), 1.93-2.02 (m, 1H), 1.79-1.90 (m, 1H), 0.85-0.96 (m, 2H), 0.51-0.67 (m, 2H); MS (ES): m/z 368.0 [M+H]+; HPLC-RT: (a) 16.9 min (Analytical HPLC Method A) (b) 10.07 (Analytical HPLC Method B); Chiral HPLC-RT: 24.9 min (CHIRALCEL® OD-H column [250×4.6 mm], 5μ; Mobile Phase: 0.2% DEA in n-hexane:ethanol[70:30]; Flow rate: 1.0 mL/min).

Step-VIIa: S-2-(4-(3-(4-Cyclopropylphenoxy)-2-oxopyrrolidin-1-yl)-2-methylphenoxy)ethyl methanesulfonate (intermediate A3-7a)

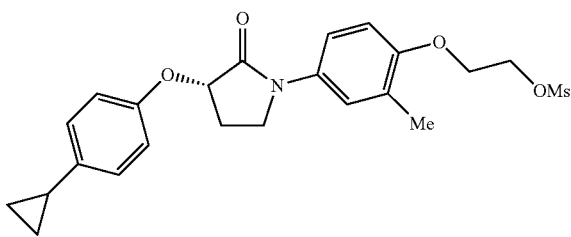

The title compound was prepared from the intermediate A3-6a by following the procedure for the intermediate A1-7a (0.12 g, 99%, light pinkish solid). ¹H NMR (400 MHz, chloroform-d) δ 7.39-7.51 (m, 2H), 7.00 (d, J=7.28 Hz, 4H), 6.73-6.86 (m, 1H), 4.89-5.02 (m, 1H), 4.51-4.65 (m, 2H), 4.21-4.30 (m, 2H), 3.74-3.94 (m, 2H), 3.08 (s, 3H), 2.58-2.71 (m, 1H), 2.25 (s, 4H), 1.80-1.91 (m, 1H), 0.82-0.95 (m, 2H), 0.55-0.67 (m, 2H); MS (ES): m/z 446.0 [M+H]+.

Step-VIIIa: S-3-(4-Cyclopropylphenoxy)-1-(3-methyl-4-(2-(pyrrolidin-1-yl)ethoxy)phenyl)pyrrolidin-2-one Example 63

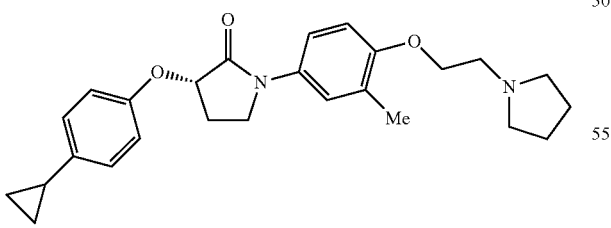

The title compound was prepared from the intermediate A3-7a by following the procedure for the intermediate A1-9a (56 mg, 49.6%, off-white solid).

Step-VIIb: R-2-(4-(3-(4-Cyclopropylphenoxy)-2-oxopyrrolidin-1-yl)-2-methylphenoxy)ethyl methanesulfonate (intermediate A3-7b)

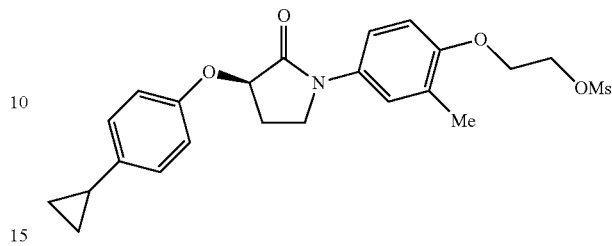

The title compound was prepared from the intermediate A3-6b by following the procedure for the intermediate A1-7b (120 mg, 99%, light pinkish solid). ¹H NMR (400 MHz, chloroform-d) δ 7.40-7.52 (m, 2H), 6.99 (d, J=7.25 Hz, 4H), 6.76-6.86 (m, 1H), 4.87-5.02 (m, 1H), 4.54-4.63 (m, 2H), 4.20-4.29 (m, 2H), 3.76-3.94 (m, 2H), 3.07 (s, 3H), 2.56-2.70 (m, 1H), 2.25 (s, 4H), 1.81-1.91 (m, 1H), 0.84-0.95 (m, 2H), 0.57-0.67 (m, 2H); MS (ES): m/z 446.0[M+H]+.

Step-VIIIb: R-3-(4-Cyclopropylphenoxy)-1-(3-methyl-4-(2-(pyrrolidin-1-yl)ethoxy)phenyl)pyrrolidin-2-one Example 64

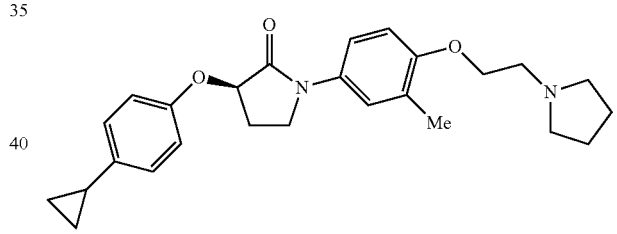

The title compound was prepared from the intermediate A3-7b by following the procedure for the intermediate A1-8b (58.3 mg, 52%, off-white solid).

Examples 65 to 91 contained in Table A were prepared by coupling intermediate A3-7a with an appropriate amine.

Procedure-A4

Examples 92 and 93

Enantiomers of 3-(4-cyclopropylphenoxy)-1-(3-chloro-4-(2-(pyrrolidin-1-yl)ethoxy)phenyl)pyrrolidin-2-one

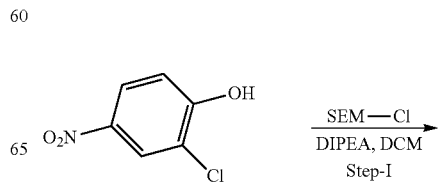

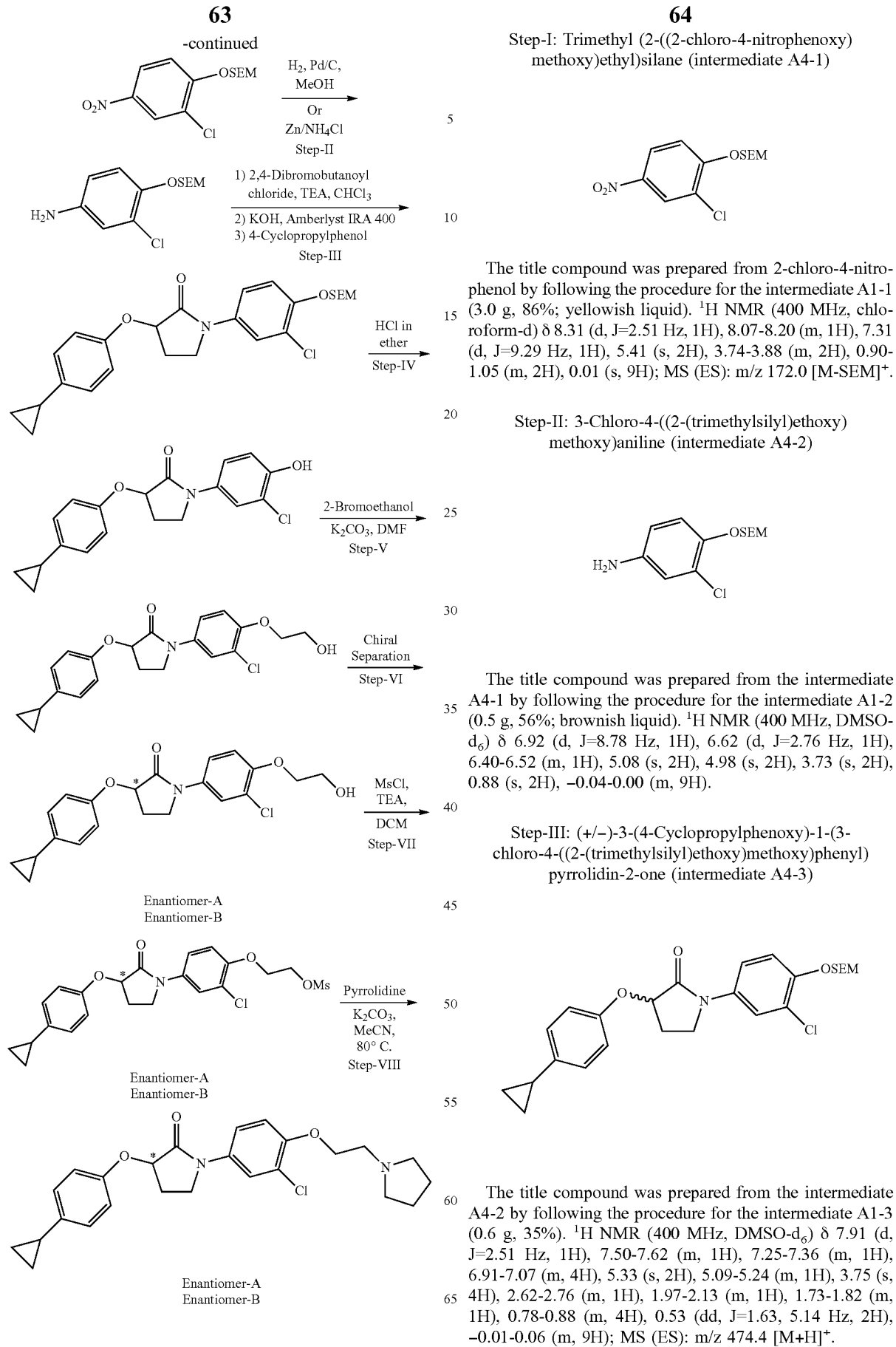

Step-I: Trimethyl (2-((2-chloro-4-nitrophenoxy)methoxy)ethyl)silane (intermediate A4-1)

The title compound was prepared from 2-chloro-4-nitrophenol by following the procedure for the intermediate A1-1 (3.0 g, 86%; yellowish liquid). $^1$H NMR (400 MHz, chloroform-d) δ 8.31 (d, J=2.51 Hz, 1H), 8.07-8.20 (m, 1H), 7.31 (d, J=9.29 Hz, 1H), 5.41 (s, 2H), 3.74-3.88 (m, 2H), 0.90-1.05 (m, 2H), 0.01 (s, 9H); MS (ES): m/z 172.0 [M-SEM]$^+$.

Step-II: 3-Chloro-4-((2-(trimethylsilyl)ethoxy)methoxy)aniline (intermediate A4-2)

The title compound was prepared from the intermediate A4-1 by following the procedure for the intermediate A1-2 (0.5 g, 56%; brownish liquid). $^1$H NMR (400 MHz, DMSO-d$_6$) δ 6.92 (d, J=8.78 Hz, 1H), 6.62 (d, J=2.76 Hz, 1H), 6.40-6.52 (m, 1H), 5.08 (s, 2H), 4.98 (s, 2H), 3.73 (s, 2H), 0.88 (s, 2H), −0.04-0.00 (m, 9H).

Step-III: (+/−)-3-(4-Cyclopropylphenoxy)-1-(3-chloro-4-((2-(trimethylsilyl)ethoxy)methoxy)phenyl)pyrrolidin-2-one (intermediate A4-3)

The title compound was prepared from the intermediate A4-2 by following the procedure for the intermediate A1-3 (0.6 g, 35%). $^1$H NMR (400 MHz, DMSO-d$_6$) δ 7.91 (d, J=2.51 Hz, 1H), 7.50-7.62 (m, 1H), 7.25-7.36 (m, 1H), 6.91-7.07 (m, 4H), 5.33 (s, 2H), 5.09-5.24 (m, 1H), 3.75 (s, 4H), 2.62-2.76 (m, 1H), 1.97-2.13 (m, 1H), 1.73-1.82 (m, 1H), 0.78-0.88 (m, 4H), 0.53 (dd, J=1.63, 5.14 Hz, 2H), −0.01-0.06 (m, 9H); MS (ES): m/z 474.4 [M+H]$^+$.

Step-IV: (+/−)-3-(4-Cyclopropylphenoxy)-1-(4-hydroxy-3-chlorophenyl)pyrrolidin-2-one (intermediate A4-4)

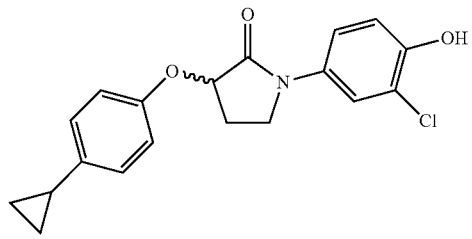 [SMILES: O=C1C(Oc2ccc(C3CC3)cc2)CCN1c1ccc(O)c(Cl)c1]

The title compound was prepared from the intermediate A4-3 by following the procedure for the intermediate A1-4 (4.0 g, 92%, colorless solid). $^1$H NMR (400 MHz, DMSO-$d_6$) δ 10.14 (br. s., 1H), 7.77 (d, J=2.51 Hz, 1H), 7.42 (dd, J=2.76, 8.78 Hz, 1H), 6.87-7.09 (m, 5H), 5.12 (t, J=7.91 Hz, 1H), 3.68-3.89 (m, 2H), 2.58-2.72 (m, 1H), 1.95-2.10 (m, 1H), 1.79-1.93 (m, 1H), 0.82-0.95 (m, 2H), 0.53-0.66 (m, 2H); MS (ES): m/z 344.1 [M+H]$^+$.

Step-V: (+/−)-3-(4-Cyclopropylphenoxy)-1-(4-(2-hydroxyethoxy)-3-chlorophenyl)pyrrolidin-2-one (intermediate A4-5)

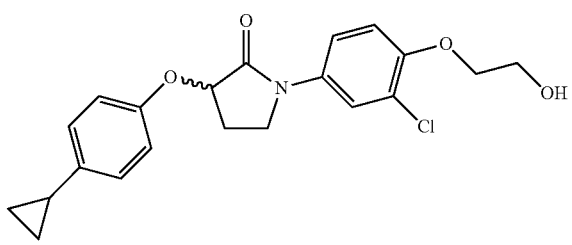 [SMILES: O=C1C(Oc2ccc(C3CC3)cc2)CCN1c1ccc(OCCO)c(Cl)c1]

The title compound was prepared from the intermediate A4-4 by following the procedure for the intermediate A1-5 (1.3 g, 89%; colorless solid). MS (ES): m/z 388.1[M+H]$^+$.

Step-VI: Chiral separation of (+/−)-3-(4-cyclopropylphenoxy)-1-(4-(2-hydroxyethoxy)-3-chlorophenyl)pyrrolidin-2-one

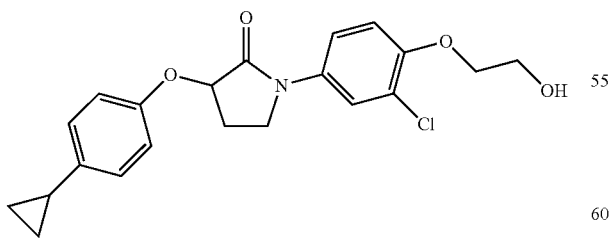

The racemic mixture, (+/−)-3-(4-cyclopropylphenoxy)-1-(4-hydroxy-3-chlorophenyl)pyrrolidin-2-one, was separated under chiral SFC condition to provide the intermediate A4-6a [enantiomer A] and intermediate A4-6b [enantiomer B].

Intermediate A4-6a: $^1$H NMR (400 MHz, DMSO-$d_6$) δ 7.83-7.93 (m, 1H), 7.50-7.60 (m, 1H), 7.18-7.27 (m, 1H), 6.90-7.07 (m, 4H), 5.10-5.21 (m, 1H), 4.82-4.94 (m, 1H), 4.02-4.14 (m, 2H), 3.70-3.89 (m, 4H), 2.41-2.46 (m, 1H), 2.00-2.11 (m, 1H), 1.79-1.93 (m, 1H), 0.84-0.94 (m, 2H), 0.51-0.65 (m, 2H) MS (ES): m/z 388.1 [M+H]$^+$; HPLC-RT (a): 17.4 min (Analytical HPLC Method A) (b): 10.3 (Analytical HPLC Method B); Chiral HPLC-RT: 12.4 min (CHIRALCEL® OD-H column [250×4.6 mm], 5μ; Mobile Phase: 0.2% DEA in n-hexane:ethanol[70:30]; Flow rate: 1.0 mL/min).

Intermediate A4-6b: $^1$H NMR (400 MHz, DMSO-$d_6$) δ 7.83-7.93 (m, 1H), 7.50-7.61 (m, 1H), 7.16-7.28 (m, 1H), 6.86-7.08 (m, 4H), 5.09-5.21 (m, 1H), 4.81-4.92 (m, 1H), 4.08 (s, 2H), 3.67-3.90 (m, 4H), 2.62-2.72 (m, 1H), 1.98-2.12 (m, 1H), 1.81-1.93 (m, 1H), 0.84-0.94 (m, 2H), 0.55-0.66 (m, 2H); MS (ES): m/z 388.1 [M+H]$^+$; MS (ES): m/z 388.1 [M+H]$^+$; HPLC-RT (a): 17.4 min (Analytical HPLC Method A) (b): 10.3 (Analytical HPLC Method B); Chiral HPLC-RT: 20.8 min (CHIRALCEL® OD-H column [250×4.6 mm], 5μ; Mobile Phase: 0.2% DEA in n-hexane:ethanol [70:30]; Flow rate: 1.0 mL/min).

Step-VII: S-2-(4-(3-(4-Cyclopropylphenoxy)-2-oxopyrrolidin-1-yl)-2-chlorophenoxy)ethyl methanesulfonate (intermediate A4-7a)

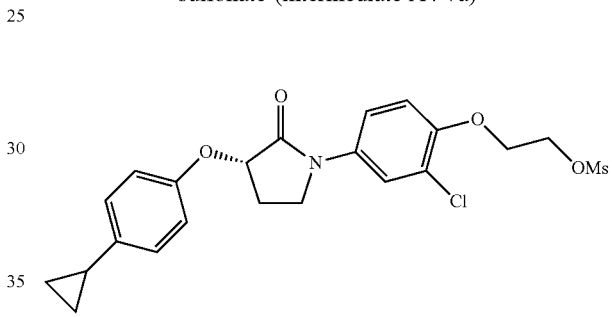

The title compound was prepared from the intermediate A4-6a by following the procedure for the intermediate A1-6a (0.1 g, 83%; colorless solid). $^1$H NMR (400 MHz, DMSO-$d_6$) δ 7.87-7.97 (m, 1H), 7.53-7.64 (m, 1H), 7.17-7.29 (m, 1H), 6.88-7.07 (m, 4H), 5.10-5.22 (m, 1H), 4.51-4.62 (m, 2H), 4.31-4.41 (m, 2H), 3.74-3.91 (m, 2H), 3.25 (s, 3H), 2.62-2.75 (m, 1H), 1.98-2.10 (m, 1H), 1.82-1.92 (m, 1H), 0.83-0.94 (m, 2H), 0.53-0.64 (m, 2H); MS (ES): m/z 466.0 [M+H]$^+$.

Step-VIIIa: S-3-(4-Cyclopropylphenoxy)-1-(3-chloro-4-(2-(pyrrolidin-1-yl)ethoxy)phenyl)pyrrolidin-2-one Example-92

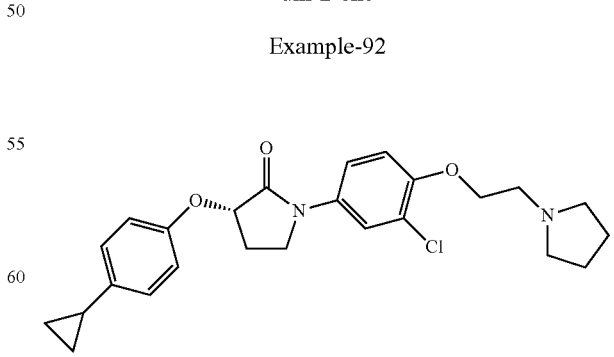

The title compound was prepared from the intermediate A4-7a by following the procedure for A4a (0.2 g, 21%; colorless solid).

Step-VIIb: R-2-(4-(3-(4-Cyclopropylphenoxy)-2-oxopyrrolidin-1-yl)-2-chlorophenoxy)ethyl methanesulfonate (intermediate A4-7b)

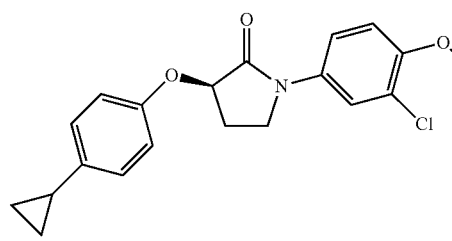

The title compound was prepared from the intermediate A4-6b by following the procedure for the intermediate A1-6b (0.55 g, 92%; colorless solid). $^1$H NMR (400 MHz, DMSO-$d_6$) δ 7.92 (d, J=2.51 Hz, 1H), 7.55-7.65 (m, 1H), 7.25 (d, J=9.29 Hz, 1H), 6.88-7.09 (m, 4H), 5.16 (s, 1H), 4.57 (d, J=4.52 Hz, 2H), 4.37 (d, J=4.27 Hz, 2H), 3.75-3.85 (m, 2H), 3.26 (s, 3H), 2.61-2.73 (m, 1H), 1.99-2.12 (m, 1H), 1.83-1.95 (m, 1H), 0.89 (dd, J=2.01, 8.28 Hz, 2H), 0.60 (dd, J=2.01, 5.02 Hz, 2H); MS (ES): m/z 466.0[M+H]$^+$.

Step-VIIIb: R-3-(4-Cyclopropylphenoxy)-1-(3-chloro-4-(2-(pyrrolidin-1-yl)ethoxy)phenyl)pyrrolidin-2-one Example 93

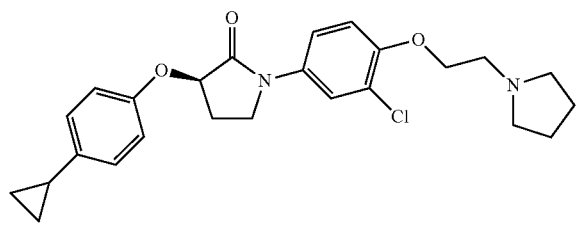 [SMILES: O=C1[C@H](Oc2ccc(C3CC3)cc2)CCN1c1ccc(OCCN2CCCC2)c(Cl)c1]

The title compound was prepared from the intermediate A4-7b by following the procedure for A4b (0.2 g, 42%; colorless solid).

Examples 94 to 107 contained in Table A were prepared in an analogous manner by coupling intermediate A4-7a with an appropriate amine.

Procedure-A5

Examples 108 and 109

Enantiomers of 3-(biphenyl-4-yloxy)-1-(3-methoxy-4-(2-(pyrrolidin-1-yl)ethoxy)phenyl)pyrrolidin-2-one

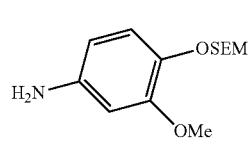

1) 2,4-Dibromo butanoyl chloride, TEA, DCE
2) KOH, Amberlite IRA 400
Step-I

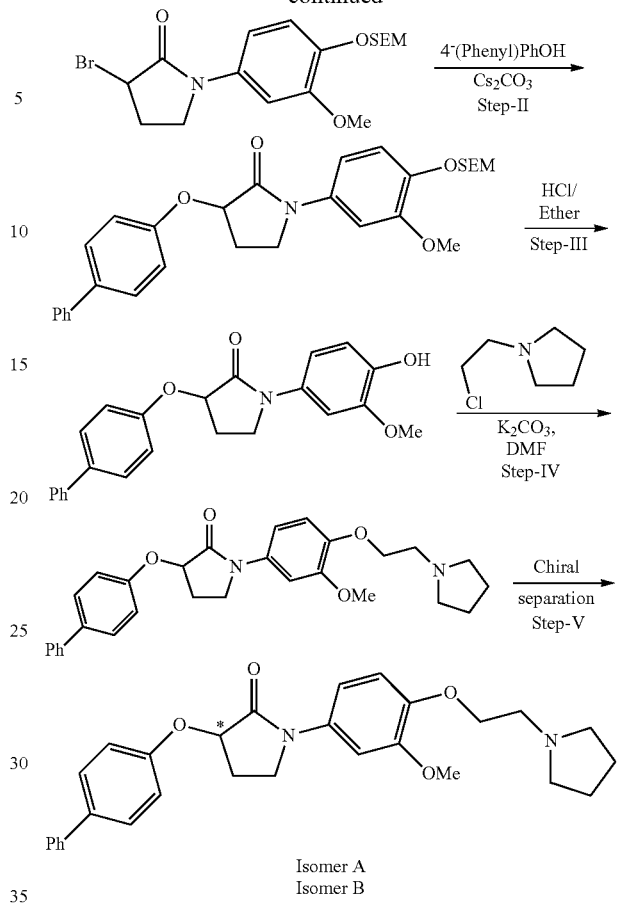

Isomer A
Isomer B

Step-I: (+/−)-3-Bromo-1-(3-methoxy-4-((2-(trimethylsilyl)ethoxy)methoxy)phenyl)pyrrolidin-2-one (intermediate A5-1)

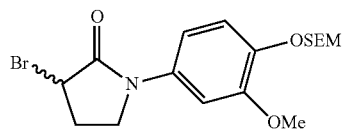

To a solution of 3-methoxy-4-((2-(trimethylsilyl)ethoxy)methoxy)aniline (3 g, 11.14 mmol; intermediate A1-2) and triethylamine (4.66 mL, 33.4 mmol) in 1,2-dichloroethane (50 mL), was added 2,4-dibromobutanoyl chloride (1.913 mL, 14.48 mmol) dropwise over a period of 10 min. The mixture was allowed to stir at room temperature for 30 min. Then 30% aqueous potassium hydroxide (10.4 mL, 55.7 mmol) solution and AMBERLITE® IR-400 resin (5 g, 11.14 mmol) were added and the reaction mixture was allowed to stir at room temperature for 16 h. The mixture was partitioned between water and dichloromethane. The organic layer was washed with water and brine, dried over anhydrous sodium sulfate, and concentrated in vacuo. The crude product was purified using CombiFlash instrument (120 g silica gel column; 20% ethyl acetate in petroleum ether) to afford the product as a brownish semi-solid (4.5 g, 97%). $^1$H NMR (400 MHz, DMSO-$d_6$) δ 7.41-7.51 (m, 1H), 7.05-7.12

(m, 2H), 5.15-5.20 (m, 2H), 4.84-4.91 (m, 1H), 3.91 (s, 5H), 3.68-3.74 (m, 2H), 2.69-2.82 (m, 1H), 2.26-2.38 (m, 1H), 0.87-0.92 (m, 2H), −0.01 (s, 9H); MS (ES): m/z 417.85 [M+H]$^+$.

Step-II: (+/−)-3-(Biphenyl-4-yloxy)-1-(3-methoxy-4-((2-(trimethylsilyl)ethoxy)methoxy)phenyl)pyrrolidin-2-one (intermediate A5-2)

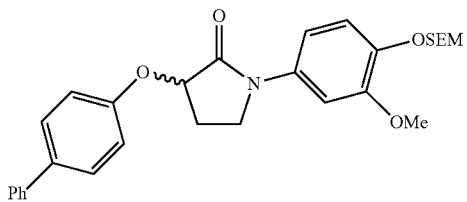

To the solution of (+/−)-3-bromo-1-(3-methoxy-4-((2-(trimethylsilyl)ethoxy)methoxy)phenyl)pyrrolidin-2-one (4.5 g, 10.81 mmol) in acetonitrile (50 mL), were added cesium carbonate (10.56 g, 32.4 mmol) and [1,1'-biphenyl]-4-ol (1.839 g, 10.81 mmol). The reaction mixture was allowed to stir at 60° C. for 16 h. The mixture was partitioned between water and ethyl acetate. The organic layer was washed with water and brine, dried over anhydrous sodium sulfate, and concentrated in vacuo. The crude product was purified using CombiFlash instrument (120 g silica gel column; 20% ethylacetate in petroleum ether) to afford the product as a white solid (2.9 g, 53.1%). $^1$H NMR (400 MHz, DMSO-d$_6$) δ 7.61-7.67 (m, 4H), 7.54-7.58 (m, 1H), 7.42-7.49 (m, 2H), 7.30-7.37 (m, 1H), 7.15-7.20 (m, 2H), 7.08-7.11 (m, 2H), 5.27-5.36 (m, 1H), 5.15-5.22 (m, 2H), 3.79 (s, 7H), 2.66-2.80 (m, 1H), 2.08-2.17 (m, 1H), 0.85-0.95 (m, 2H), 0.01 (s, 9H); MS (ES): m/z 506.5 [M+2H]$^+$.

Step-III: (+/−)-3-(Biphenyl-4-yloxy)-1-(4-hydroxy-3-methoxyphenyl)pyrrolidin-2-one (intermediate A5-3)

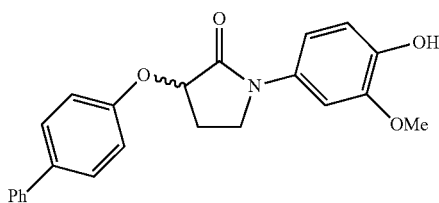 [SMILES: COc1cc(N2CCC(Oc3ccc(-c4ccccc4)cc3)C2=O)ccc1O]

To the compound, (+/−)-3-([1,1'-biphenyl]-4-yloxy)-1-(3-methoxy-4-((2-(trimethylsilyl)ethoxy)methoxy)phenyl)pyrrolidin-2-one (2.9 g, 5.73 mmol), was added 4 N hydrochloric acid in diethyl ether (30 mL, 5.73 mmol) at 0° C. The reaction mixture was allowed to stir at room temperature for 16 h. The precipitated solid was filtered through filter paper. The solid was washed with petroleum ether twice to remove the non-polar impurities and dried under vacuum to afford the title compound as a colorless solid (1.8 g, 84.0%). $^1$H NMR (400 MHz, DMSO-d$_6$) δ 8.86-9.07 (m, 1H), 7.59-7.70 (m, 4H), 7.42-7.52 (m, 3H), 7.28-7.38 (m, 1H), 7.16 (d, J=8.78 Hz, 2H), 6.93-7.04 (m, 1H), 6.81 (s, 1H), 5.20-5.33 (m, 1H), 3.78 (s, 5H), 2.66-2.79 (m, 1H), 2.00-2.17 (m, 1H); MS (ES): m/z 376.5 [M+2H]$^+$.

Step-IV: (+/−)-3-(Biphenyl-4-yloxy)-1-(3-methoxy-4-(2-(pyrrolidin-1-yl)ethoxy)phenyl)pyrrolidin-2-one

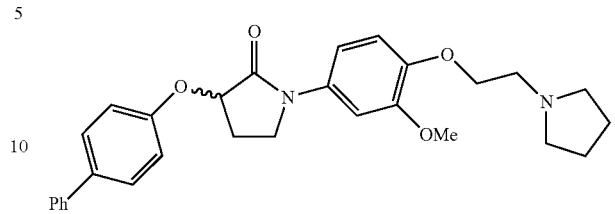

To the solution of (+/−)-3-([1,1'-biphenyl]-4-yloxy)-1-(4-hydroxy-3-methoxyphenyl)pyrrolidin-2-one (0.5 g, 1.332 mmol) in DMF (10 mL), was added potassium carbonate (0.276 g, 1.998 mmol) and 1-(2-chloroethyl)pyrrolidine hydrochloride (0.340 g, 1.998 mmol). The reaction mixture was allowed to stir at 80° C. for 20 h. The reaction mixture was partitioned between water and MTBE. The organic layer was washed with water and brine, dried over anhydrous sodium sulfate, and concentrated in vacuo to afford the crude product. The crude product was purified by reverse phase HPLC (XTERRA® RP 18 column (19×150 mm) 5.0μ; Mobile Phase A: 0.1% trifluoroacetic acid in water; Mobile Phase B: acetonitrile; Flow rate: 14.0 mL/min). The HPLC fractions were concentrated. The residue was treated with saturated sodium bicarbonate solution and then partitioned between DCM and water. The organic layer was dried over sodium sulfate and concentrated in vacuo to afford the pure product as a off-white solid (0.25 g, 40%). $^1$H NMR (400 MHz, DMSO-d$_6$) δ 7.61-7.68 (m, 4H), 7.51-7.55 (m, 1H), 7.42-7.49 (m, 2H), 7.30-7.37 (m, 1H), 7.14-7.21 (m, 2H), 7.06-7.11 (m, 1H), 6.98-7.04 (m, 1H), 5.24-5.35 (m, 1H), 4.02-4.10 (m, 2H), 3.76-3.93 (m, 5H), 2.63-2.84 (m, 3H), 2.53-2.58 (m, 4H), 2.06-2.18 (m, 1H), 1.64-1.74 (m, 4H); MS (ES): m/z 473.2 [M+H]$^+$; HPLC-RT: 7.78 min (Analytical HPLC Method A).

Step-V: Chiral separation of (+/−)-3-(biphenyl-4-yloxy)-1-(3-methoxy-4-(2-(pyrrolidin-1-yl)ethoxy)phenyl)pyrrolidin-2-one Examples 108 and 109

The racemic mixture was separated under chiral HPLC conditions [Column: (CHIRALCEL® OD-H column [250× 20 mm], 5μ; Mobile Phase: 0.2% DEA in n-hexane:ethanol [60:40]; Flow rate: 12.0 mL/min)] to provide Example 108 (S-enantiomer A; 0.12 g, 19.07% yield; chiral purity: 99.97%) and Example 109 (R-enantiomer B; 0.12 g, 19.07% yield; chiral purity: 99.95%)

Procedure-A6

Examples 110 and 111

Enantiomers of 3-(biphenyl-4-yloxy)-1-(3-ethyl-4-(2-(pyrrolidin-1-yl)ethoxy)phenyl)pyrrolidin-2-one

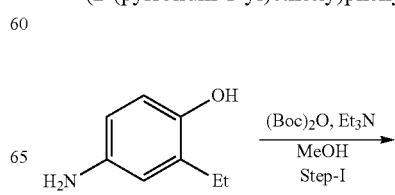

71

-continued

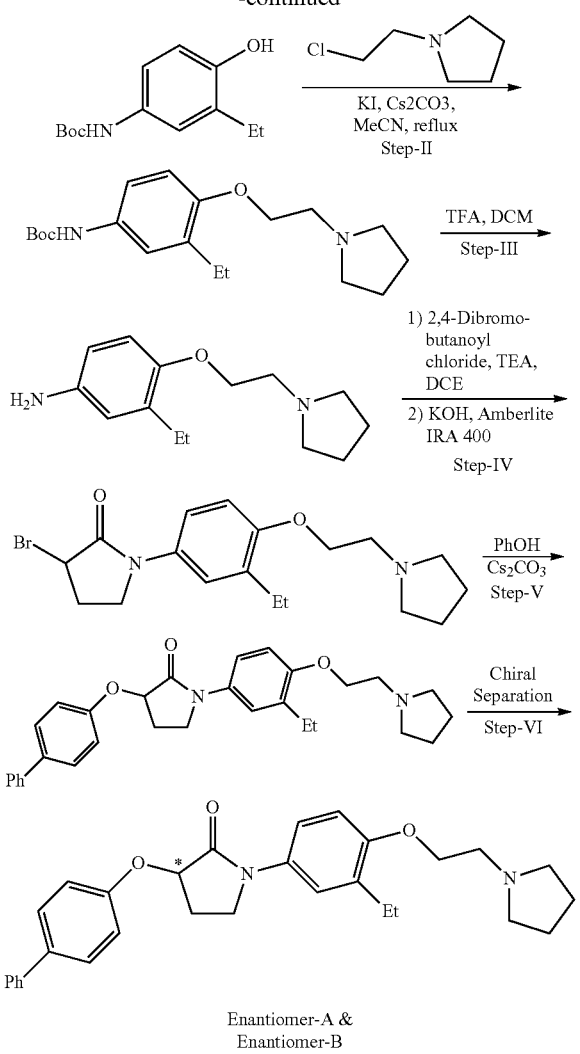

Enantiomer-A & Enantiomer-B

Step-I: tert-Butyl 3-ethyl-4-hydroxyphenylcarbamate (intermediate A6-1)

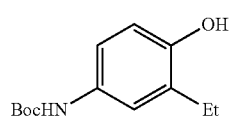

To a solution 4-amino-2-ethylphenol (1 g, 7.29 mmol; intermediate A2-2) and triethylamine (2.213 g, 21.87 mmol) in methanol (15 mL), was added di-tert-butyl dicarbonate (1.750 g, 8.02 mmol). The reaction mixture was allowed to stir at room temperature for 10 h. The excess methanol was evaporated. The residue was washed with 0.25 N hydrochloric acid and extracted thrice with ethyl acetate. The organic layer was washed with water and brine, dried over anhydrous sodium sulfate, and concentrated in vacuo to afford the title compound as a colorless oil (1.3 g, 75%). MS (ES): m/z 236.2 [M−H]⁻.

72

Step-II: t-Butyl 3-ethyl-4-(2-(pyrrolidin-1-yl)ethoxy)phenylcarbamate (intermediate A6-2)

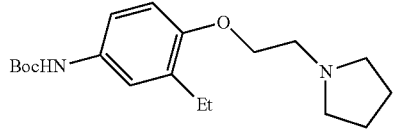 [SMILES: CCc1cc(NC(=O)OC(C)(C)C)ccc1OCCN1CCCC1]

To the solution of tert-butyl 3-ethyl-4-hydroxyphenylcarbamate (1 g, 4.21 mmol) in acetonitrile (20 mL), were added potassium carbonate (1.747 g, 12.64 mmol) and 1-(2-chloroethyl)pyrrolidine hydrochloride (0.788 g, 4.64 mmol). The reaction mixture was allowed to stir at 50° C. for 16 h. The mixture was partitioned between water and ethyl acetate. The organic layer was washed with water and brine, dried over anhydrous sodium sulfate, and concentrated in vacuo. The crude product was purified using CombiFlash instrument (12 g silica gel column; 3% methanol in chloroform) to afford the product as a white solid (0.9 g, 63.9%). ¹H NMR (400 MHz, DMSO-d₆) δ 8.94-9.10 (m, 1H), 7.22-7.31 (m, 1H), 7.13-7.21 (m, 1H), 6.79-6.90 (m, 1H), 4.03 (s, 2H), 2.55-3.02 (m, 8H), 1.71 (br. s., 4H), 1.46 (s, 9H), 1.10 (t, J=7.53 Hz, 3H); MS (ES): m/z 335.2 [M+H]⁺.

Step-III: 3-Ethyl-4-(2-(pyrrolidin-1-yl)ethoxy)aniline (intermediate A6-3)

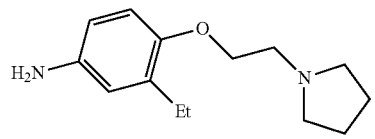 [SMILES: CCc1cc(N)ccc1OCCN1CCCC1]

To a solution of tert-butyl(3-ethyl-4-(2-(pyrrolidin-1-yl)ethoxy)phenyl)carbamate (0.6 g, 1.794 mmol) in dichloromethane (7 mL), was added trifluoroacetic acid (3.00 mL) at 0° C. The reaction mixture was allowed to stir at room temperature for 2 h. Trifluoroacetic acid and dichloromethane were concentrated in vacuo. Then the crude was basified with sodium bicarbonate and extracted with dichloromethane twice. The organic layer was washed with water and brine, dried over anhydrous sodium sulfate, and concentrated in vacuo to afford the product as a blackish oil (0.4 g, 95%). ¹H NMR (400 MHz, DMSO-d₆) δ 6.64 (s, 1H), 6.40 (s, 1H), 6.32-6.39 (m, 1H), 4.33-4.68 (m, 2H), 3.93 (s, 2H), 2.54-2.94 (m, 6H), 2.45 (d, J=7.53 Hz, 2H), 1.72 (br. s., 4H), 1.09 (t, J=7.40 Hz, 3H); MS (ES): m/z 235.8 [M+H]⁺.

Step-IV: 3-Bromo-1-(3-ethyl-4-(2-(pyrrolidin-1-yl)ethoxy)phenyl)pyrrolidin-2-one (intermediate A6-4)

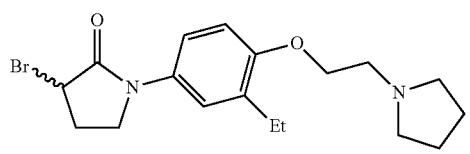 [SMILES: CCc1cc(N2CCC(Br)C2=O)ccc1OCCN1CCCC1]

To a solution of 3-ethyl-4-(2-(pyrrolidin-1-yl)ethoxy)aniline (0.2 g, 0.853 mmol) and triethylamine (0.131 mL, 0.939 mmol) in chloroform (10 mL), was added 2,4-dibromobutanoyl chloride (0.226 g, 0.853 mmol) dropwise over a period of 10 min. The mixture was stirred at room temperature for 30 min. Then 30% aqueous potassium hydroxide (2.66 mL, 4.27 mmol) solution and AMBERLITE® IRA-400 (0.06 g, 0.853 mmol) were added and the reaction was allowed reflux for 12 h. The reaction mixture was diluted with water and extracted with dichloromethane twice. The organic layers were concentrated to afford the title compound as blackish oil. The crude was used for the next step without further purification. $^1$H NMR (400 MHz, DMSO-$d_6$) δ 7.37-7.44 (m, 1H), 6.94-7.01 (m, 2H), 4.79-4.90 (m, 1H), 4.44-4.54 (m, 1H), 4.00-4.12 (m, 3H), 2.78-2.89 (m, 3H), 2.66-2.77 (m, 2H), 2.57 (br. s., 4H), 2.31-2.38 (m, 1H), 1.70 (br. s., 4H), 1.13 (d, J=9.54 Hz, 3H); MS (ES): m/z 381.2 [M+H]$^+$.

Step-VII: (+/−)-3-(Biphenyl-4-yloxy)-1-(3-ethyl-4-(2-(pyrrolidin-1-yl)ethoxy)phenyl)pyrrolidin-2-one

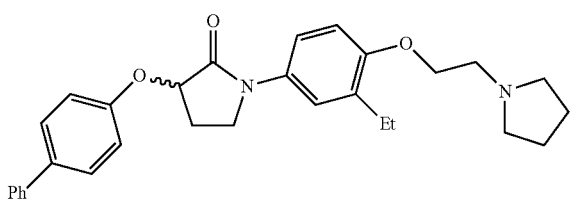 [SMILES: CCc1cc(N2CCC(Oc3ccc(-c4ccccc4)cc3)C2=O)ccc1OCCN1CCCC1]

To a solution of 3-bromo-1-(3-ethyl-4-(2-(pyrrolidin-1-yl)ethoxy)phenyl)pyrrolidin-2-one (0.5 g, 1.311 mmol) in acetonitrile (5 mL), were added cesium carbonate (1.068 g, 3.28 mmol), potassium iodide (0.218 g, 1.311 mmol) and [1,1'-biphenyl]-4-ol (0.246 g, 1.442 mmol). The reaction mixture was allowed to reflux for 12 h. The solid was filtered-off. The organic layer was concentrated, purified by preparative TLC plate with 2% methanol in dichloromethane as eluent system to afford the title compound (0.08 g, 12.9%). MS (ES): m/z 471.2 [M+H]$^+$; HPLC-RT: 9.90 min (Analytical HPLC Method B).

Step-VIII: Chiral separation of 3-(biphenyl-4-yloxy)-1-(3-ethyl-4-(2-(pyrrolidin-1-yl)ethoxy)phenyl)pyrrolidin-2-one

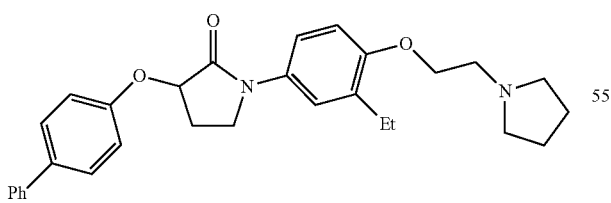

The racemic mixture was separated under chiral HPLC conditions [Column: (CHIRALCEL® OD-H column [250× 20 mm], 5µ; Mobile Phase: 0.2% DEA in n-hexane: ethanol [60:40]; Flow rate: 12.0 mL/min)] to provide Example 110, the S enantiomer; 0.003 g, 0.51% yield; chiral purity: 100%) followed by Example 111, the R enantiomer; 0.011 g, 1.86% yield; chiral purity: 100%).

Procedure-A7

Examples 112 and 113

Enantiomers of 3-(biphenyl-4-yloxy)-1-(3-methyl-4-(2-(pyrrolidin-1-yl)ethoxy)phenyl)pyrrolidin-2-one

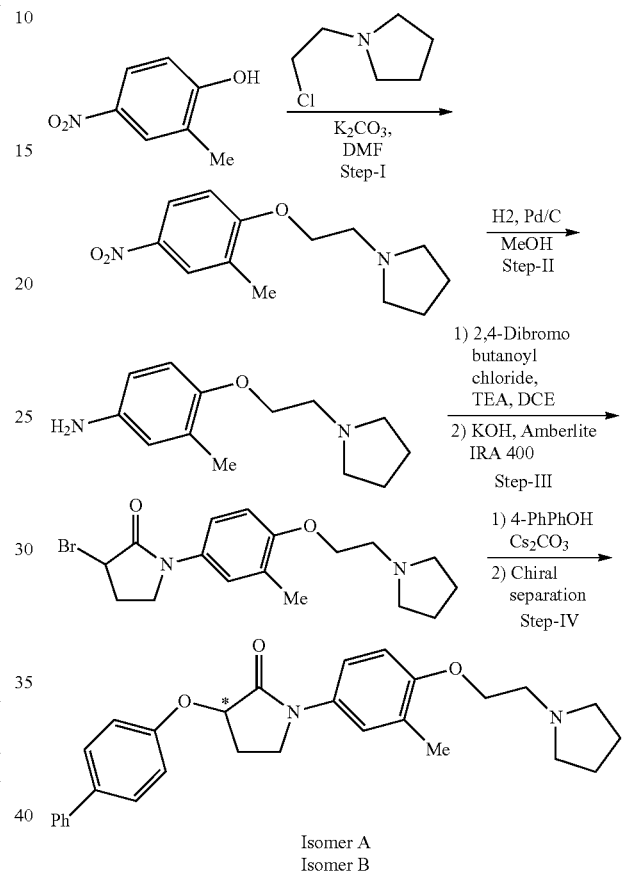

Step-I: 1-(2-(2-Methyl-4-nitrophenoxy)ethyl)pyrrolidine (intermediate A7-1)

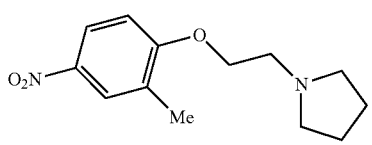

To a solution of 2-methyl-4-nitrophenol (5.0 g, 32.7 mmol) in acetonitrile (50 mL), were added cesium carbonate (37.2 g, 114 mmol), potassium iodide (10.84 g, 65.3 mmol) and 1-(2-chloroethyl)pyrrolidine (8.73 g, 65.3 mmol). The reaction mixture was refluxed for overnight at 70° C. The reaction mixture was concentrated in vacuo. The residue was partitioned between ethyl acetate and water. The organic layer was washed with water, and brine solution, dried over sodium sulfate and concentrated under vacuum. The crude product was purified by CombiFlash instrument (48.0 g silica gel column; 2% chloroform in methanol) to afford the product as light yellowish oil (1.4 g, 17%). $^1$H NMR (400 MHz, chloroform-d) δ 8.01-8.15 (m, 2H), 6.85 (d, J=8.78 Hz, 1H), 4.22 (t, J=5.90 Hz, 2H), 2.99 (t, J=5.77 Hz, 2H), 2.62-2.75 (m, 4H), 2.28 (s, 3H), 1.83 (td, J=3.26, 7.03 Hz, 4H); MS (ES): m/z 251.2 [M+H]$^+$.

Step-II: 3-Methyl-4-(2-(pyrrolidin-1-yl)ethoxy)aniline (intermediate A7-2)

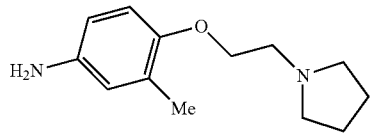 [SMILES: Cc1cc([N+](=O)[O-])ccc1OCCN1CCCC1]

To a solution of 1-(2-(2-methyl-4-nitrophenoxy)ethyl)pyrrolidine (1.4 g, 5.59 mmol) in MeOH (14 mL), was added palladium on carbon (0.595 g, 5.59 mmol). The mixture was flushed with hydrogen and then degassed (three times). After being stirred for 3.0 h, the reaction mixture was filtered through a Celite® pad. The filtrate was concentrated to afford the product as a brownish oil (1.0 g, 81%). $^1$H NMR (400 MHz, DMSO-$d_6$) δ 6.63 (d, J=8.53 Hz, 1H), 6.30-6.44 (m, 2H), 4.50 (br. s., 2H), 3.90 (t, J=6.02 Hz, 2H), 2.74 (t, J=6.02 Hz, 2H), 2.51-2.58 (m, 4H), 2.05 (s, 3H), 1.68 (td, J=3.23, 6.84 Hz, 4H); MS (ES): m/z 220.7 [M+H]$^+$.

Step-III: 3-Bromo-1-(3-methyl-4-(2-(pyrrolidin-1-yl)ethoxy)phenyl)pyrrolidin-2-one (intermediate A7-3)

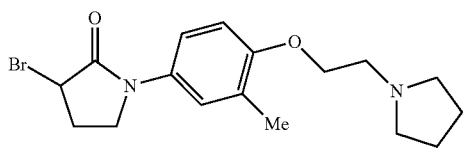

The title compound was prepared from the intermediate A7-2 by following the experimental procedure for the intermediate A6-4 (0.4 g, 48%, yellowish semi-solid). MS (ES): m/z 368.8 [M+H]$^+$.

Step-IV: (+/−)-3-([1,1'-Biphenyl]-4-yloxy)-1-(3-methyl-4-(2-(pyrrolidin-1-yl)ethoxy)phenyl)-pyrrolidin-2-one

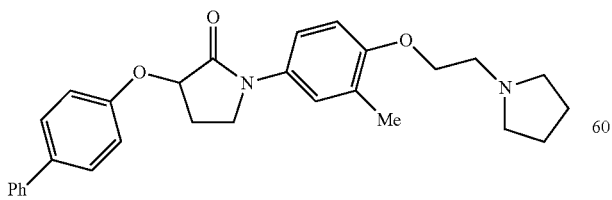

The racemic mixture was prepared from the intermediate A7-3 by following the experimental procedure for the intermediate A6-5.

Step-VIII: Chiral separation of 3-(biphenyl-4-yloxy)-1-(3-methyl-4-(2-(pyrrolidin-1-yl)ethoxy)phenyl)pyrrolidin-2-one The racemic mixture was separated under chiral HPLC conditions [Column: (CHIRALCEL® OD-H column [250× 20 mm], 5μ; Mobile Phase: 0.2% DEA in n-hexane:ethanol [60:40]; Flow rate: 12.0 mL/min)] to provide Example 112 (S enantiomer) and Example 113 (R enantiomer) as colorless solids.

Procedure-A8

Examples 114 and 115

Enantiomers of 3-(biphenyl-4-yloxy)-1-(3-chloro-4-(2-(pyrrolidin-1-yl)ethoxy)phenyl)pyrrolidin-2-one

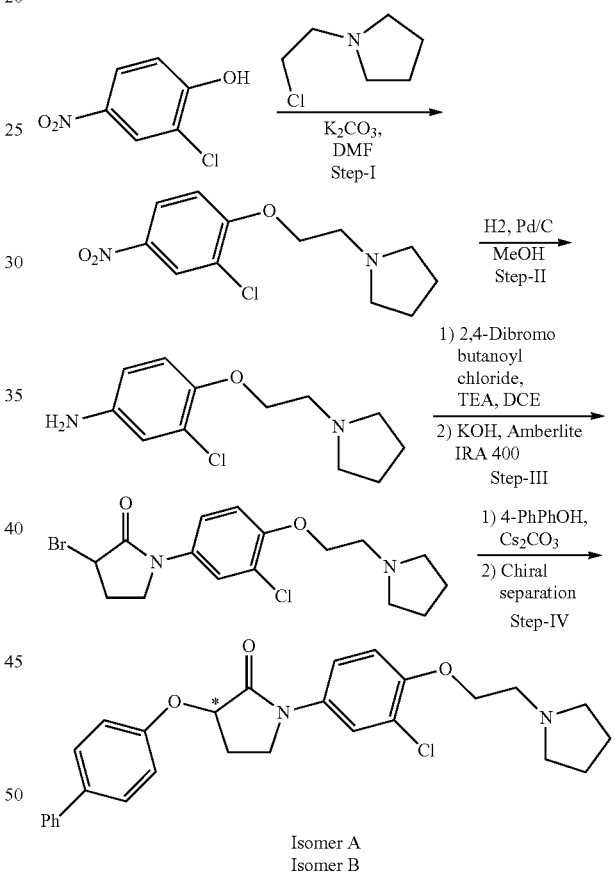

Step-I: 1-(2-(2-Chloro-4-nitrophenoxy)ethyl)pyrrolidine (intermediate A8-1)

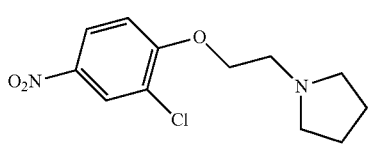 [SMILES: O=[N+]([O-])c1ccc(OCCN2CCCC2)c(Cl)c1]

The title compound was prepared from 2-chloro-4-nitrophenol by following the procedure for the intermediate A7-1 (2.0 g, 12.8%; light-yellowish solid). $^1$H NMR (400 MHz, DMSO-$d_6$) δ 8.32 (d, J=2.51 Hz, 1H), 8.23 (dd, J=2.76, 9.03 Hz, 1H), 7.40 (d, J=9.29 Hz, 1H), 4.33 (t, J=5.65 Hz, 2H), 2.88 (t, J=5.52 Hz, 2H), 2.57 (br. s., 4H), 1.69 (td, J=3.23, 6.84 Hz, 4H); MS (ES): m/z 271.2 [M+H]$^+$.

Step-II: 3-Chloro-4-(2-(pyrrolidin-1-yl)ethoxy)aniline (intermediate A8-2)

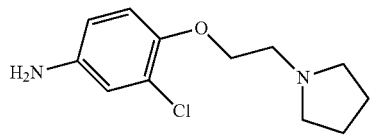

To a stirring solution of 1-(2-(2-chloro-4-nitrophenoxy)ethyl)pyrrolidine (1.7 g, 0.0062 mol) in acetic acid (18 mL) and water (6 mL), Zn powder (3.2 g, 0.050 mol) was added at room temperature. Then it was heated to 55° C. for 2 h. The reaction mixture was filtered through a Celite® pad, and washed with ethyl acetate (100 mL). The filtrate was concentrated under vacuum. The residue was partitioned between ethyl acetate and water. The organic layer was washed with 10% NaHCO$_3$ solution, brine solution (50 mL), dried over anhydrous Na$_2$SO$_4$ and concentrated under vacuum to afford the title product (1.4 g, 93%) as a brownish oil, which was used as such. $^1$H NMR (400 MHz, DMSO-$d_6$) δ 6.85 (d, J=8.78 Hz, 1H), 6.63 (d, J=2.76 Hz, 1H), 6.40-6.50 (m, 1H), 4.89 (s, 2H), 3.96 (t, J=6.02 Hz, 2H), 2.71-2.79 (m, 2H), 2.50-2.58 (m, 4H), 1.67 (td, J=3.23, 6.84 Hz, 4H); MS (ES): m/z 241.0 [M+H]$^+$.

Step-III: 3-Bromo-1-(3-chloro-4-(2-(pyrrolidin-1-yl)ethoxy)phenyl)pyrrolidin-2-one (intermediate A8-3)

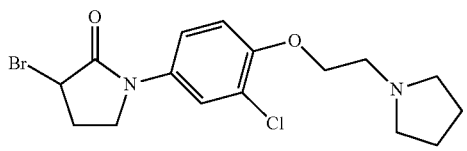 [SMILES: O=C1C(Br)CCN1c1ccc(OCCN2CCCC2)c(Cl)c1]

The title compound was prepared from the intermediate A8-2 by following the experimental procedure for the intermediate A7-3 (blackish liquid). $^1$H NMR (400 MHz, chloroform-d) δ 7.67-7.77 (m, 1H), 7.48-7.58 (m, 1H), 6.93-6.99 (m, 1H), 4.52-4.62 (m, 1H), 4.21-4.30 (m, 2H), 3.93-4.07 (m, 1H), 3.72-3.84 (m, 1H), 3.01-3.14 (m, 2H), 2.67-2.93 (m, 5H), 2.37-2.49 (m, 1H), 1.83-1.95 (m, 4H); MS (ES): m/z 389.0 [M+H]$^+$.

Step-IV: (+/−)-3-([1,1'-Biphenyl]-4-yloxy)-1-(3-chloro-4-(2-(pyrrolidin-1-yl)ethoxy)phenyl)pyrrolidin-2-one

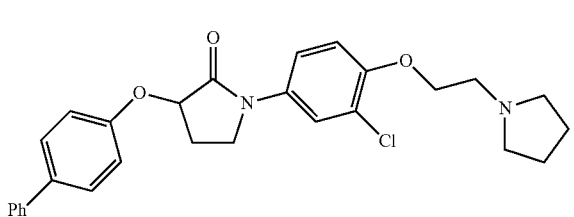 [SMILES: O=C1C(Oc2ccc(-c3ccccc3)cc2)CCN1c1ccc(OCCN2CCCC2)c(Cl)c1]

The racemic mixture was prepared by following the experimental procedure for the intermediate A7-4.

Step-VIII: Chiral separation of 3-([1,1'-biphenyl]-4-yloxy)-1-(3-chloro-4-(2-(pyrrolidin-1-yl)ethoxy)phenyl)pyrrolidin-2-one The racemic mixture was separated under chiral HPLC conditions [Column: (CHIRALCEL® OD-H column [250× 20 mm], 5μ; Mobile Phase: 0.2% DEA in n-hexane:ethanol [70:30]; Flow rate: 12.0 mL/min)] to provide Example 114 (S enantiomer: 22.3 mg) and Example 115 (R enantiomer: 22.2 mg) as colorless solids.

Procedure-A9

Example 116

(S)—N-(2-(4-(3-(4-Cyclopropylphenoxy)-2-oxopyrrolidin-1-yl)-2-methoxyphenoxy)ethyl)-N-methylacetamide

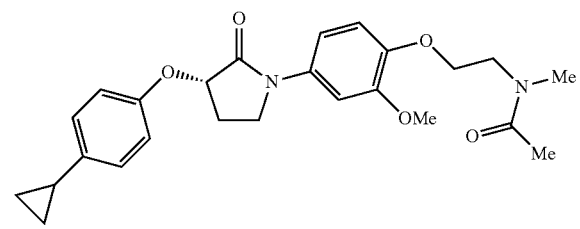 [SMILES: COc1cc(N2CC[C@H](Oc3ccc(C4CC4)cc3)C2=O)ccc1OCCN(C)C(C)=O]

To a solution of 3-(4-cyclopropylphenoxy)-1-(3-methoxy-4-(2-(methylamino)ethoxy)phenyl)pyrrolidin-2-one (0.040 g, 0.101 mmol), Example 15 of Table A, in dichloromethane (2.00 mL), was added triethylamine (0.042 mL, 0.303 mmol) and subsequently acetyl chloride (8.61 μL, 0.121 mmol) at 0° C. The mixture was gradually warmed to ambient temperature and stirred for 3.0 h. The solvent was removed under vacuum. Ice crystals were added to the residue. The precipitated solid was filtered and dried under vacuum to obtain the product as a colorless solid.

Examples 117 to 133 of Table C were prepared by reacting Examples 15, 59 or 60 with the appropriate acid chloride, sulphonyl chloride or chloroformate following Procedure-A9.

Procedure-A10

Examples 134 and 135

Enantiomers of 3-(4-cyclopropylphenoxy)-1-(3-methoxy-4-morpholinophenyl)pyrrolidin-2-one

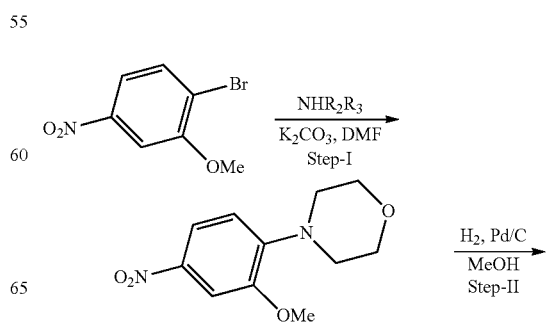

-continued

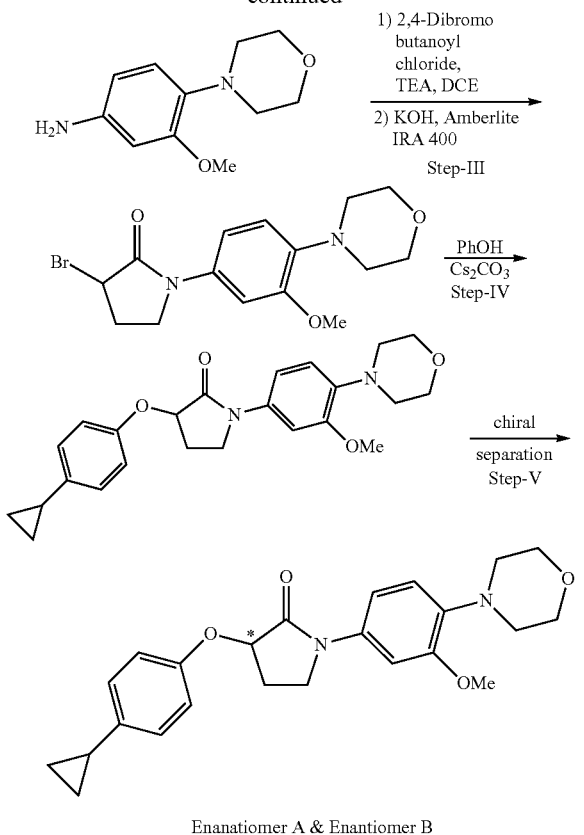

Enantiomer A & Enantiomer B

Step-I: 4-(2-Methoxy-4-nitrophenyl)morpholine (intermediate A10-1)

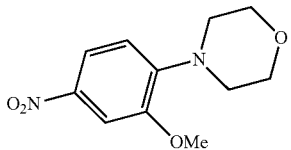 [SMILES: COc1cc([N+](=O)[O-])ccc1N1CCOCC1]

To a solution of 1-bromo-2-methoxy-4-nitrobenzene (1 g, 4.31 mmol) in DMF (10 mL), were added potassium carbonate (1.784 g, 12.93 mmol) and morpholine (0.563 g, 6.46 mmol). The reaction mixture was allowed to stir at 110° C. for 48 h. The mixture was partitioned between water and methyl tert-butyl ether. The organic layer was washed with water and brine, dried over anhydrous sodium sulfate, and concentrated in vacuo to afford yellowish solid. (0.9 g, 88.0%). $^1$H NMR (400 MHz, DMSO-$d_6$) δ 7.96 (s, 1H), 7.85 (dd, J=2.51, 8.78 Hz, 1H), 7.71 (d, J=2.51 Hz, 1H), 3.91 (s, 3H), 3.70-3.78 (m, 4H), 3.15-3.24 (m, 4H); MS (ES): m/z 238.6 [M+H]$^+$.

Step-II: 3-Methoxy-4-morpholinoaniline (intermediate A10-2)

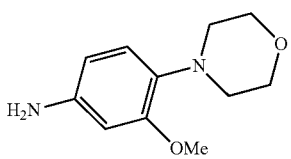

To a solution of 4-(2-methoxy-4-nitrophenyl)morpholine (0.9 g, 3.78 mmol) in methanol (15 mL), was added 5% Pd/C (90 mg, 0.652 mmol). The reaction mixture was degassed and flushed with hydrogen (3×). The reaction mixture was stirred at room temperature under hydrogen pressure (10 Kg/cm$^2$) for 5.0 h in an autoclave. The reaction mixture was filtered through a Celite® bed. The filtrate was concentrated in vacuo to afford the crude product as a brownish oil, which was used as such in the next reaction (0.7 g, 51.5%). $^1$H NMR (400 MHz, DMSO-$d_6$) δ 6.61 (d, J=8.28 Hz, 1H), 6.24 (d, J=2.26 Hz, 1H), 6.05-6.11 (m, 1H), 4.66-4.81 (m, 2H), 3.63-3.72 (m, 7H), 2.76-2.81 (m, 4H); MS (ES): m/z 208.6 [M+H]$^+$.

Step-III: (+/−)-3-Bromo-1-(3-methoxy-4-morpholinophenyl)pyrrolidin-2-one (intermediate A10-3)

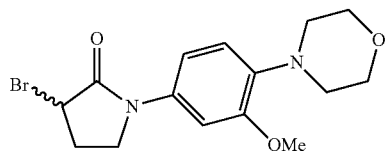 [SMILES: COc1cc(N2CCC(Br)C2=O)ccc1N1CCOCC1]

To a solution of 3-methoxy-4-morpholinoaniline (0.8 g, 3.84 mmol) and triethylamine (1.606 mL, 11.52 mmol) in 1,2-dichloroethane (20 mL), was added 2,4-dibromobutanoyl chloride (0.660 mL, 4.99 mmol) dropwise over a period of 10 min. The mixture was stirred at room temperature for 30 min. Then 30% aqueous potassium hydroxide (1.078 g, 19.21 mmol) solution and AMBERLITE® IR-400 resin (5 g, 3.84 mmol) were added and the reaction was allowed to stir at room temperature for 20 h. The reaction mixture was partitioned between water and dichloromethane. The organic layer was washed with water and brine, dried over anhydrous sodium sulfate, and concentrated in vacuo. The crude product was purified using CombiFlash instrument (12 g silica gel column; 20% ethyl acetate in petroleum ether) to afford the product as a light yellowish solid (0.75 g, 55%). $^1$H NMR (400 MHz, DMSO-$d_6$) δ 7.39-7.46 (m, 1H), 7.06-7.13 (m, 1H), 6.87-6.95 (m, 1H), 4.82-4.93 (m, 1H), 3.85-3.97 (m, 2H), 3.80 (s, 3H), 3.71-3.74 (m, 4H), 2.92-2.98 (m, 4H), 2.73-2.81 (m, 1H), 2.30-2.38 (m, 1H); MS (ES): m/z 356.5 [M+2H]$^+$.

Step-IV: (+/−)-3-(4-Cyclopropylphenoxy)-1-(3-methoxy-4-morpholinophenyl)pyrrolidin-2-one

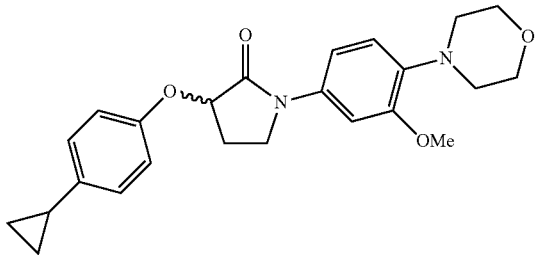

To a solution of (+/−)-3-bromo-1-(3-methoxy-4-morpholinophenyl)pyrrolidin-2-one (1.2 g, 3.38 mmol) in acetonitrile (5.0 mL), were added cesium carbonate (3.30 g, 10.13 mmol) and 4-cyclopropylphenol (0.544 g, 4.05 mmol). The reaction mixture was allowed to stir at 60° C. for 16 h. The mixture was partitioned between water and ethyl acetate. The organic layer was washed with water and brine, dried over anhydrous sodium sulfate, and concentrated in vacuo. The crude product was purified by reverse phase HPLC (X-bridge phenyl column (19×150 mm) 5.0μ; Mobile Phase A: 10 mm ammonium acetate in water; Mobile Phase B: acetonitrile; flow rate: 14.0 mL). The HPLC fractions were concentrated in vacuo to afford the product as an off-white solid. MS (ES): m/z 409.0 [M+H]⁺; HPLC-RT: 9.63 min (Analytical HPLC Method B).

Step-V: Chiral separation of 3-(4-cyclopropylphenoxy)-1-(3-methoxy-4-morpholinophenyl)pyrrolidin-2-one

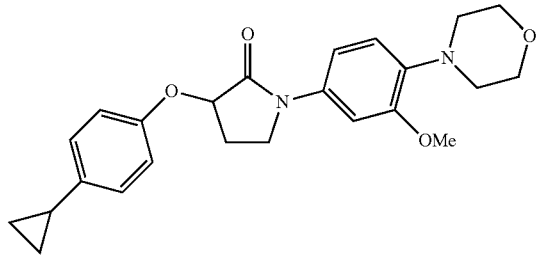

The racemic mixture was separated under chiral HPLC conditions [(CHIRALCEL® OD-H column [250×20 mm], 5μ; Mobile Phase: 0.2% DEA in n-hexane:ethanol[50:50]; Flow rate: 13.0 mL/min)] to provide Example 134 (S enantiomer) (0.1 g, 7.18% yield; chiral purity: 99.03%) followed by Example 135 (R enantiomer B) (0.1 g, 7.18% yield; chiral purity: 99.85%).

Procedure-A11

Examples 136 and 137

Enantiomers of 3-(4-cyclopropylphenoxy)-1-(3-ethyl-4-(pyrrolidin-1-yl)phenyl)pyrrolidin-2-one

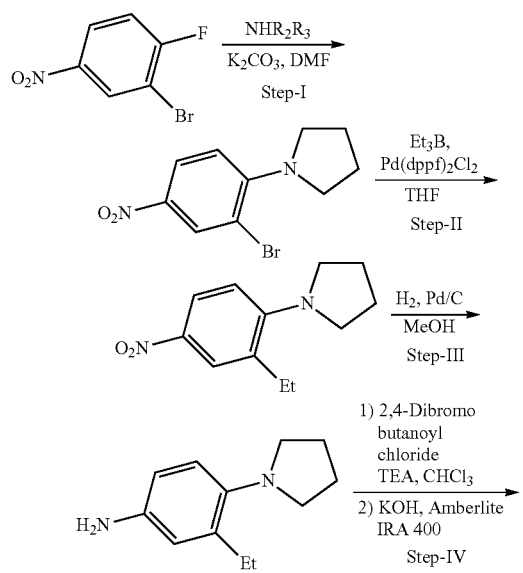

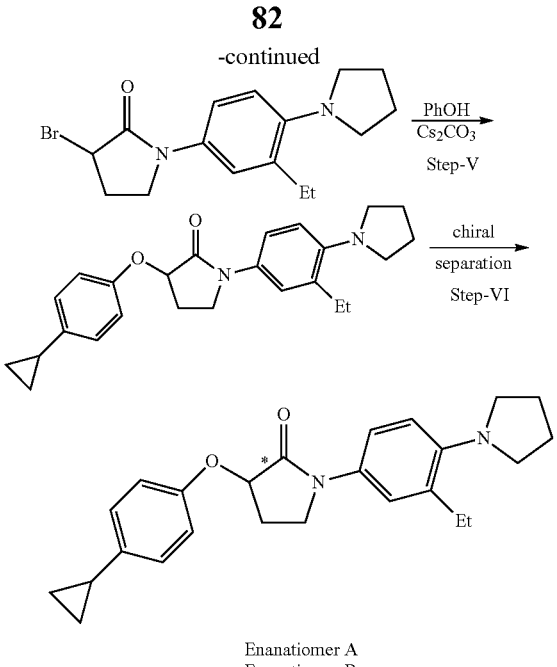

Step-I: 1-(2-Bromo-4-nitrophenyl)pyrrolidine (intermediate A11-1)

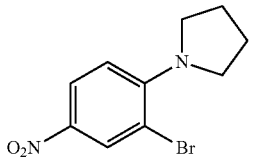

To the stirred solution of 1-bromo-2-fluoro-5-nitrobenzene (0.5 g, 2.272 mmol) in DMF (10 mL), was added pyrrolidine (0.20 g, 2.954 mmol), followed by K₂CO₃ (0.94 g, 6.816 mmol). The reaction mixture was heated to 100° C. for 12 h. The reaction mass was diluted with 30 mL of water. The precipitated solid was filtered, dried under vacuum to afford the title product (0.5 g, 81.3%) as a yellowish solid. ¹H NMR (400 MHz, chloroform-d) δ 8.39 (d, J=2.76 Hz, 1H), 8.01 (dd, J=2.51, 9.29 Hz, 1H), 6.66 (d, J=9.29 Hz, 1H), 3.58-3.74 (m, 4H), 2.00 (td, J=3.48, 6.34 Hz, 4H); MS (ES): m/z 270.9[M+H]⁺.

Step-II: 1-(2-Ethyl-4-nitrophenyl)pyrrolidine (intermediate A11-2)

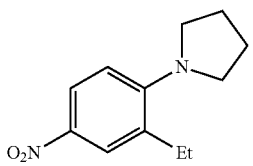

To a stirred solution 1-(2-bromo-4-nitrophenyl)pyrrolidine (1.5 g, 5.53 mmol) in DMF (25 mL), was added 1,1'-bis(diphenylphosphino)ferrocenepalladium (II) dichloride (0.910 g, 1.107 mmol) followed by triethylborane (55.3 mL, 55.3 mmol) and cesium carbonate (7.21 g, 22.13 mmol) at room temperature under argon atmosphere. Then reaction mixture was stirred for 4 h at 60° C. The reaction mass was diluted with 50 mL of chilled water and extracted with 100 mL of ethyl acetate. The separated organic layer was washed with brine solution, dried over anhydrous sodium sulfate and evaporated under reduced pressure. The crude product was purified by CombiFlash instrument (120 g silica gel column; 8% ethyl acetate in petroleum ether) to provide the product as a yellowish liquid (0.6 g, 49.2%). $^1$H NMR (400 MHz, chloroform-d) δ 7.94-8.04 (m, 2H), 6.66-6.73 (m, 1H), 3.45 (s, 4H), 2.73-2.84 (m, 2H), 2.00 (s, 4H), 1.23 (t, J=7.40 Hz, 3H); MS (ES): m/z 391.2 [M+H]$^+$.

Step-III: 3-Ethyl-4-(pyrrolidin-1-yl)aniline (intermediate A11-3)

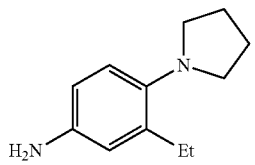 [SMILES: CCc1cc(N)ccc1N1CCCC1]

To a stirred solution 1-(2-ethyl-4-nitrophenyl)pyrrolidine (0.6 g, 2.72 mmol) in methanol (20 mL), was added palladium on carbon (0.058 g, 0.545 mmol) at room temperature. The mixture was degassed and then flushed with hydrogen gas (three times). The mixture was stirred under hydrogen atmosphere (balloon) for 2 h. The reaction mass was filtered through Celite® pad. The filtrate was concentrated to dryness and the brownish residue was used as such in the next reaction (0.4 g, 77%). $^1$H NMR (400 MHz, chloroform-d) δ 6.89 (d, J=8.53 Hz, 1H), 6.59 (d, J=2.76 Hz, 1H), 6.50 (dd, J=2.76, 8.28 Hz, 1H), 3.26-3.54 (m, 2H), 2.93-3.04 (m, 4H), 2.60-2.71 (m, 2H), 1.89 (td, J=3.20, 6.65 Hz, 4H), 1.22 (t, J=7.53 Hz, 3H); MS (ES): m/z 191.2[M+H]$^+$.

Step-IV: Enantiomers of 3-(4-cyclopropylphenoxy)-1-(3-ethyl-4-(pyrrolidin-1-yl)phenyl)pyrrolidin-2-one

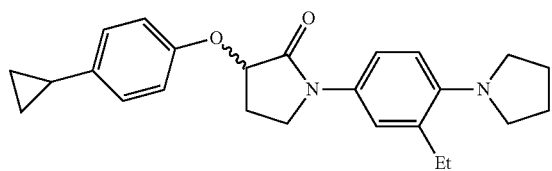 [SMILES: CCc1cc(N2CCC(Oc3ccc(C4CC4)cc3)C2=O)ccc1N1CCCC1]

To a solution of 3-ethyl-4-(pyrrolidin-1-yl)aniline (400 mg, 2.102 mmol) and triethylamine (0.551 mL, 3.95 mmol) in CHCl$_3$ (15 mL), was added 2,4-dibromobutyryl chloride (418 mg, 1.581 mmol) at 0° C. under nitrogen atmosphere. The mixture was stirred for 2 h at ambient temperature. An aqueous solution of potassium hydroxide (296 mg, 5.27 mmol), dissolved in water (15 mL) was added dropwise. AMBERLITE® IRA-400 (CL) ion exchange resin (400 mg, 1.318 mmol) was then added. Subsequently, the mixture was stirred for 5 h. 4-Cyclopropylphenol (354 mg, 2.64 mmol) was then added as one lot. The reaction mixture was heated to 70° C. and stirred for 40 h. The mixture was partitioned between water and DCM. The organic layer was washed with water, dried over anhydrous sodium sulfate and concentrated in vacuo. The crude product was purified using CombiFlash instrument (120 g silica gel column; 23% ethyl acetate in petroleum ether) to afford the product as a colorless solid (80 mg). The racemic product was separated using chiral HPLC (CHIRALCEL® OD-H [250×20 mm]; Mobile Phase A: 0.2% diethylamine in n-hexane; Mobile Phase B: ethanol; Flow rate: 12.0 mL/min] to obtain Example 136 (enantiomer A) (35 mg) and Example 137 (enantiomer B) (45 mg).

Procedure-A12

Examples 138 and 139

R,S and S,R diastereoisomers of 3-(4-cyclopropylphenoxy)-1-(3-methoxy-4-((S)-pyrrolidin-3-yloxy)phenyl)pyrrolidin-2-one

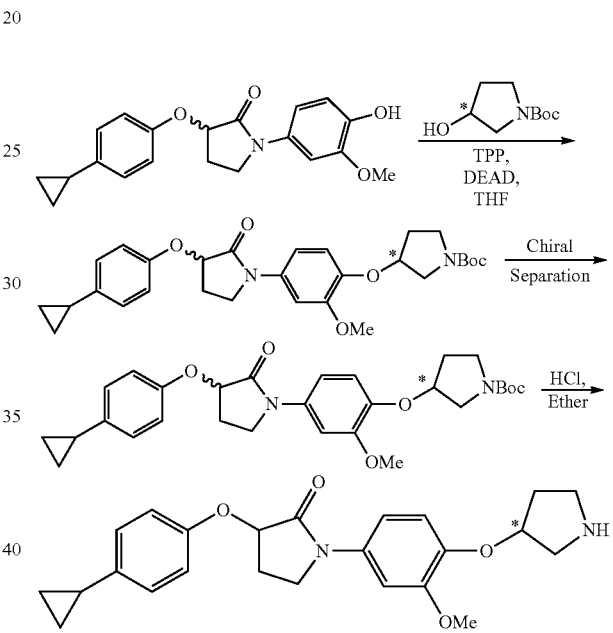

Step-I: (3S)-tert-Butyl 3-(4-(3-(4-cyclopropylphenoxy)-2-oxopyrrolidin-1-yl)-2-methoxyphenoxy)pyrrolidine-1-carboxylate (intermediate A12-1)

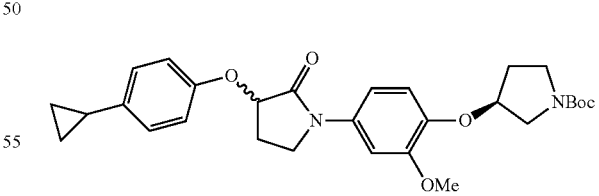

To a stirred solution of 3-(4-cyclopropylphenoxy)-1-(4-hydroxy-3-methoxyphenyl)pyrrolidin-2-one (0.5 g, 1.473 mmol; intermediate A1-4) in tetrahydrofuran (15 mL), was added (R)-tert-butyl 3-hydroxypyrrolidine-1-carboxylate (0.414 g, 2.210 mmol) followed by triphenylphosphine (0.386 g, 1.473 mmol) at room temperature. The reaction mixture was cooled to 0° C. DEAD (0.700 mL, 4.42 mmol) was added. After being stirred for 12.0 h, the solvent was evaporated. The mixture was partitioned between water and ethyl acetate. The separated organic layer was washed with brine solution, dried over anhydrous sodium sulfate and evaporated under reduced pressure. The crude product was purified by CombiFlash instrument (120 g silica gel column; 20% ethyl acetate in petroleum ether) to provide the product as a yellowish liquid. MS (ES): m/z 527.2[M+NH$_4$]$^+$.

Step-II: Chiral separation of (3S)-tert-butyl 3-(4-(3-(4-cyclopropylphenoxy)-2-oxopyrrolidin-1-yl)-2-methoxyphenoxy)pyrrolidine-1-carboxylate (intermediates A12-2a and A12-2b)

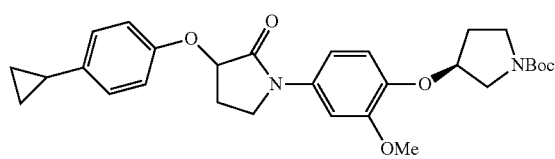 [SMILES: COc1cc(N2CCC(Oc3ccc(C4CC4)cc3)C2=O)ccc1O[C@H]1CCN(C(=O)OC(C)(C)C)C1]

The racemic product was separated using chiral HPLC using SFC [Whelk-01 column (30×250 mm); 5μ; 50% of CO$_2$: 50% of co-solvent: (0.55% diethylamine in methanol); total flow: 1108 mL/min] to give 130 mg of the intermediate A12-2a (isomer-A) and 150 mg of intermediate A12-2b (isomer-B).

Intermediate A12-2a: $^1$H NMR (400 MHz, chloroform-d) δ 7.66-7.76 (m, 1H), 7.00 (q, J=8.92 Hz, 4H), 6.86 (s, 2H), 4.98 (s, 2H), 3.86 (s, 5H), 3.43-3.68 (m, 4H), 3.00-3.09 (m, 1H), 2.58-2.70 (m, 1H), 2.13-2.34 (m, 2H), 1.81-1.90 (m, 1H), 1.46 (br. s., 9H), 0.90 (dd, J=1.88, 8.38 Hz, 2H), 0.54-0.66 (m, 2H); MS (ES): m/z 526.2 [M+NH$_4$+]+; Chiral HPLC-RT: 5.15 min (Whelk-01 column [250×30 mm], 5μ; % CO$_2$: 50%; % of co-solvent: 50% [0.5% diethylamine in methanol]).

Intermediate A12-2b: $^1$H NMR (400 MHz, chloroform-d) δ 7.67-7.78 (m, 1H), 7.00 (d, J=8.75 Hz, 4H), 6.78-6.91 (m, 2H), 4.93-5.03 (m, 1H), 4.78-4.92 (m, 1H), 3.86 (s, 5H), 3.47-3.70 (m, 4H), 2.59-2.71 (m, 1H), 2.13-2.36 (m, 2H), 1.99-2.10 (m, 1H), 1.79-1.90 (m, 1H), 1.47 (br. s., 9H), 0.85-0.95 (m, 2H), 0.57-0.67 (m, 2H); MS (ES): m/z 526.2 [M+NH$_4$+]+; Chiral HPLC-RT: 6.07 min (Whelk-01 column [250×30 mm], 5μ; % CO$_2$: 50%; % of co-solvent: 50% [0.5% diethylamine in methanol]).

Step-III: (R)-3-(4-Cyclopropylphenoxy)-1-(3-methoxy-4-((S)-pyrrolidin-3-yloxy)phenyl)pyrrolidin-2-one Example 138

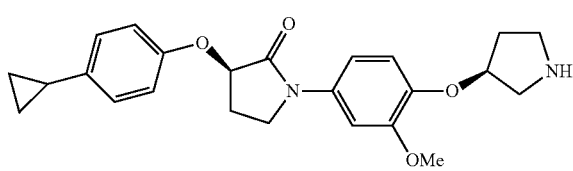

To a stirred solution of (3S)-tert-butyl 3-(4-(3-(4-cyclopropylphenoxy)-2-oxopyrrolidin-1-yl)-2-methoxyphenoxy)pyrrolidine-1-carboxylate (0.13 g, 0.256 mmol; intermediate A12-2a) in anhydrous diethyl ether (5 mL), was added an ethereal solution of hydrogen chloride (2.5 mL, 2.0 M) at 0° C. The mixture was gradually warmed to room temperature. After being stirred for 18.0 h, the reaction mixture was concentrated to dryness. The solvent was concentrated and lyophilized by dissolving in water for 12.0 h to afford Example 138 as a colorless solid (isolated as hydrochloride salt).

Step-III: (S)-3-(4-Cyclopropylphenoxy)-1-(3-methoxy-4-((S)-pyrrolidin-3-yloxy)phenyl)pyrrolidin-2-one Example 139

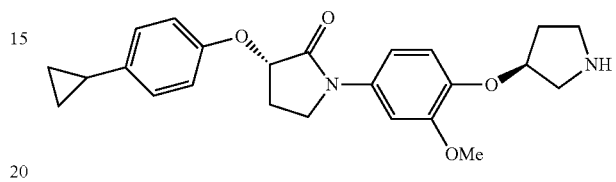

To a stirred solution of (3S)-tert-butyl 3-(4-(3-(4-cyclopropylphenoxy)-2-oxopyrrolidin-1-yl)-2-methoxyphenoxy)pyrrolidine-1-carboxylate (0.13 g, 0.256 mmol; intermediate A12-2b) in anhydrous diethyl ether (5 mL), was added an ethereal solution of hydrogen chloride (2.5 mL, 2.0 M) at 0° C. The mixture was gradually warmed to room temperature. After being stirred for 18.0 h, the reaction mixture was concentrated to dryness. The solvent was concentrated and lyophilized by dissolving in water for 12.0 h to afford Example 139 as a colorless solid (isolated as hydrochloride salt).

The (R,R) and (S,R) diastereoisomers (Examples 140 and 141 respectively) were also prepared by following Procedure-A12 except that (R)-tert-butyl 3-hydroxypyrrolidine-1-carboxylate was used in the first step.

Procedure-B1

Example 142

3-(4-Cyclopropylphenoxy)-1-(3-methoxy-4-(2-(pyrrolidin-1-yl)ethoxy)phenyl)pyrrolidin-2-one

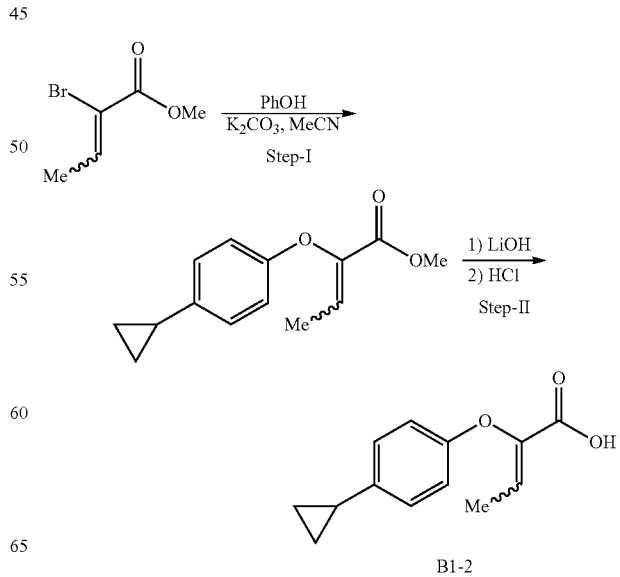

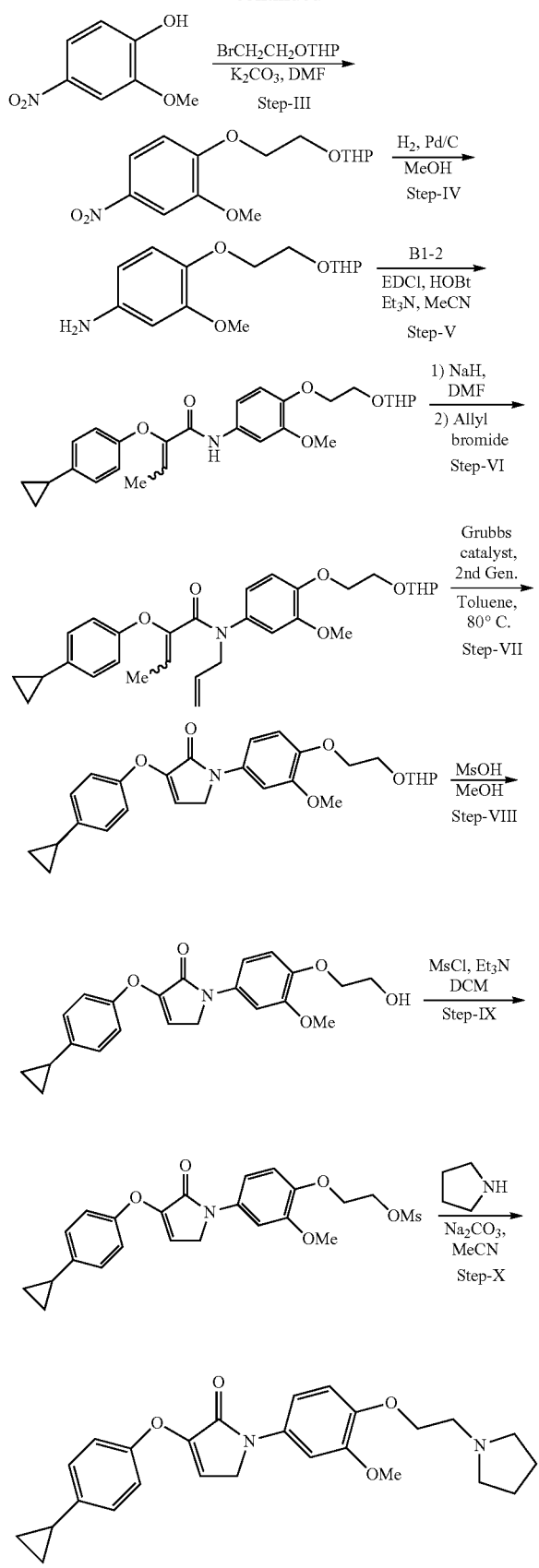

Step-I: Methyl 2-(4-cyclopropylphenoxyl)but-2-enoate (intermediate B1-1)

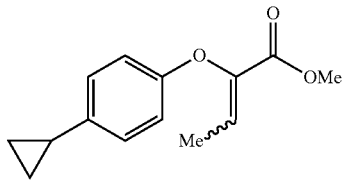

To a stirring solution of 4-cyclopropylphenol (6.81 g, 50.8 mmol) in acetonitrile (150 mL) at 0° C., $K_2CO_3$ (21.06 g, 152 mmol) was added. Methyl 2-bromo-2-butenoate (10 g, 55.9 mmol) was subsequently added dropwise. The reaction was stirred for 16 h at room temperature. The reaction mixture was filtered through Celite®, washed with acetonitrile and concentrated in vacuo to afford the crude product, methyl 2-(4-cyclopropylphenoxyl)but-2-enoate (15 g, 64.6 mmol, ~100% yield), as a light-brownish oil. The crude was taken to the next step without further purification. $^1$H NMR (400 MHz, chloroform-d) δ $^1$H NMR (400 MHz, chloroform-d) δ 7.39 (d, J=6.75 Hz, 0.5H), 6.93-7.04 (m, 2H), 6.75-6.85 (m, 2H), 6.68 (d, J=7.25 Hz, 0.5H), 3.67-3.86 (m, 3H), 1.70-2.00 (m, 4H), 0.81-0.95 (m, 2H), 0.61 (dd, J=1.50, 5.00 Hz, 2H).

Step-II: 2-(4-Cyclopropylphenoxyl)but-2-enoic acid (intermediate B1-2)

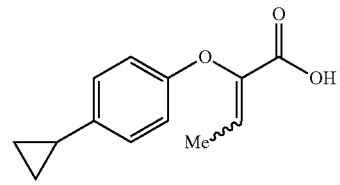

To a stirring solution of methyl 2-(4-cyclopropylphenoxyl)but-2-enoate (16 g, 68.9 mmol) in mixture of THF (120 mL) and water (60 mL), lithium hydroxide hydrate (11.56 g, 276 mmol) was added at 0° C. The reaction mixture was stirred at room temperature for 20 h. The reaction mixture was concentrated in vacuo to remove THF. The aqueous layer was acidified with 1.5 N HCl to pH ~1. The precipitated solid was filtered, washed with cold water (100 mL), and petroleum ether (50 mL) and dried under vacuum to afford 2-(4-cyclopropylphenoxyl)but-2-enoic acid (9.5 g, 43.5 mmol, 63.2% yield) as an off-white solid. $^1$H NMR (400 MHz, DMSO-d$_6$) δ 6.94-7.04 (m, 2H), 6.69-6.78 (m, 2H), 6.54-6.66 (m, 1H), 1.77-1.89 (m, 1H), 1.61-1.70 (m, 3H), 0.78-0.92 (m, 2H), 0.45-0.60 (m, 2H).

Step-III: 2-(2-(2-Methoxy-4-nitrophenoxy)ethoxy) tetrahydro-2H-pyran (intermediate B1-3)

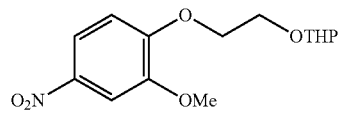

To a solution of 2-methoxy-4-nitrophenol (10.0 g, 59.1 mmol) in DMF (70 mL), were added sequentially potassium iodide (4.91 g, 29.6 mmol), potassium carbonate (20.43 g, 148 mmol) and 2-(2-bromoethoxyl)tetrahydro-2H-pyran (13.60 g, 65.0 mmol). The reaction mixture was stirred for 6.0 h at 80° C. The mixture was partitioned between water and ethyl acetate. The organic layer was washed with water and brine, dried over anhydrous sodium sulfate, and concentrated in vacuo. The crude product was purified using CombiFlash instrument (120 g silica gel column; 5% ethyl acetate in hexane) to afford the product, 2-(2-(2-methoxy-4-nitrophenoxy)ethoxy)tetrahydro-2H-pyran (14.0 g, 80%), as a colorless liquid, which solidified on standing. $^1$H NMR (400 MHz, CDCl$_3$) δ 7.89 (dd, J=2.64, 8.91 Hz, 1H), 7.74 (d, J=2.76 Hz, 1H), 6.99 (d, J=8.78 Hz, 1H), 4.71 (dd, J=3.01, 4.02 Hz, 1H), 4.28-4.39 (m, 2H), 4.06-4.17 (m, 1H), 3.94 (s, 3H), 3.84-3.92 (m, 2H), 3.49-3.57 (m, 1H), 1.68-1.87 (m, 2H), 1.61 (br. s., 1H), 1.53 (dd, J=2.01, 5.02 Hz, 3H).

Step-IV: 3-Methoxy-4-(2-((tetrahydro-2H-pyran-2-yl)oxy)ethoxy)aniline (intermediate B1-4)

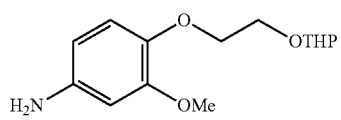

To a solution of 2-(2-(2-methoxy-4-nitrophenoxy)ethoxy)tetrahydro-2H-pyran (12.0 g, 40.4 mmol) in methanol (100.0 mL) in an autoclave, was added palladium on carbon (5%) (1.2 g, 11.28 mmol). The mixture was flushed with nitrogen and degassed (3 times). The mixture was then stirred at ambient temperature in the autoclave under hydrogen atmosphere (28.4 PSI) for 2.0 h. The catalyst was filtered and rinsed with MeOH. The filtrate was concentrated in vacuo. The crude product, 3-methoxy-4-(2-((tetrahydro-2H-pyran-2-yl)oxy)ethoxy)aniline (10.0 g, 93%) was obtained as a dark-brownish oil and used as such in the next reaction. $^1$H NMR (400 MHz, CDCl$_3$) δ 6.80 (d, J=8.53 Hz, 1H), 6.29 (d, J=2.76 Hz, 1H), 6.21 (dd, J=2.51, 8.28 Hz, 1H), 4.66-4.76 (m, 1H), 4.10-4.16 (m, 2H), 3.96-4.04 (m, 1H), 3.89 (s, 1H), 3.75-3.85 (m, 4H), 3.46 (br. s., 3H), 1.80-1.91 (m, 1H), 1.69-1.78 (m, 1H), 1.50-1.67 (m, 4H); MS (ES): m/z 268.2 [M+H]$^+$.

Step-V: 2-(4-Cyclopropylphenoxy)-N-(3-methoxy-4-(2-((tetrahydro-2H-pyran-2-yl)oxy)ethoxy)phenyl)but-2-enamide (intermediate B1-5)

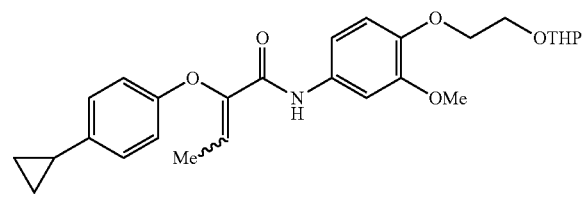

To a solution of 3-methoxy-4-(2-((tetrahydro-2H-pyran-2-yl)oxy)ethoxy)aniline (8.0 g, 29.9 mmol) and 2-(4-cyclopropylphenoxyl)but-2-enoic acid (intermediate B1-2; 6.53 g, 29.9 mmol) in acetonitrile (80.0 mL) at 0° C., was added HOBT (4.58 g, 29.9 mmol) in one lot and subsequently triethylamine (12.51 mL, 90 mmol) dropwise. 1-Ethyl-3-(3-dimethylaminopropyl) carbodiimide) hydrochloride (8.61 g, 44.9 mmol) was then added slowly. The reaction mixture was gradually warmed to ambient temperature and stirred overnight under nitrogen atmosphere. The mixture was partitioned between water and ethyl acetate. The organic layer was washed with water and brine, dried over anhydrous sodium sulfate, and concentrated in vacuo. The crude product was purified using CombiFlash instrument (120 g silica gel column; 30% ethyl acetate in pet. ether) to afford the product, 2-(4-cyclopropylphenoxy)-N-(3-methoxy-4-(2-((tetrahydro-2H-pyran-2-yl)oxy)ethoxy)phenyl)but-2-enamide (12.9 g, 92%), as a colorless liquid. $^1$H NMR (400 MHz, chloroform-d) δ 7.84-7.95 (m, 1H), 7.35-7.44 (m, 1H), 7.02 (s, 2H), 6.93 (s, 2H), 6.85 (s, 1H), 6.74-6.81 (m, 2H), 4.65-4.73 (m, 1H), 4.17 (s, 2H), 3.98-4.06 (m, 1H), 3.84 (s, 5H), 3.45-3.54 (m, 1H), 1.79-1.92 (m, 2H), 1.67 (d, J=7.50 Hz, 5H), 1.58-1.63 (m, 1H), 1.47-1.54 (m, 2H), 0.88-0.98 (m, 2H), 0.59-0.68 (m, 2H); MS (ES): m/z 384.2 [M+H-THP]$^+$.

Step-VI: N-Allyl-2-(4-cyclopropylphenoxy)-N-(3-methoxy-4-(2-((tetrahydro-2H-pyran-2-yl)oxy)ethoxy)phenyl)but-2-enamide (intermediate B1-6)

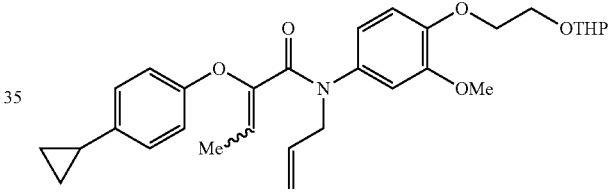

To a solution of 2-(4-cyclopropylphenoxy)-N-(3-methoxy-4-(2-((tetrahydro-2H-pyran-2-yl)oxy)ethoxy)phenyl)but-2-enamide (10 g, 21.39 mmol) in DMF (70.0 mL) at 0° C., was added sodium hydride (1.400 g, 32.1 mmol). The reaction mixture was rigorously stirred at 0° C. for 1.0 h. Allyl bromide (2.221 mL, 25.7 mmol) was then added as a neat liquid. The mixture was stirred for 6.0 h. The mixture was partitioned between water and ethyl acetate. The organic layer was washed with water and brine, dried over anhydrous sodium sulfate, and concentrated in vacuo. The crude product was purified using CombiFlash instrument (120 g silica gel column; 20% ethyl acetate in pet. ether) to afford the product, N-allyl-2-(4-cyclopropylphenoxy)-N-(3-methoxy-4-(2-((tetrahydro-2H-pyran-2-yl)oxy)ethoxy)phenyl)but-2-enamide (9.0 g, 83%), as a light-yellowish solid. $^1$H NMR (400 MHz, chloroform-d) δ 6.80-6.95 (m, 3H), 6.44-6.55 (m, 3H), 6.31-6.37 (m, 1H), 6.19-6.29 (m, 1H), 5.63-5.78 (m, 1H), 4.95-5.04 (m, 1H), 4.84-4.94 (m, 1H), 4.69-4.78 (m, 1H), 4.20-4.28 (m, 2H), 4.04-4.18 (m, 3H), 3.83-3.95 (m, 2H), 3.70 (s, 3H), 3.46-3.58 (m, 1H), 1.69-1.89 (m, 3H), 1.61 (d, J=7.03 Hz, 5H), 1.51-1.55 (m, 2H), 0.85-0.95 (m, 2H), 0.56-0.63 (m, 2H); MS (ES): m/z 508.2 [M+H]$^+$.

Step-VII: 3-(4-Cyclopropylphenoxy)-1-(3-methoxy-4-(2-((tetrahydro-2H-pyran-2-yl)oxy)ethoxy)phenyl)-1H-pyrrol-2(5H)-one (intermediate B1-7)

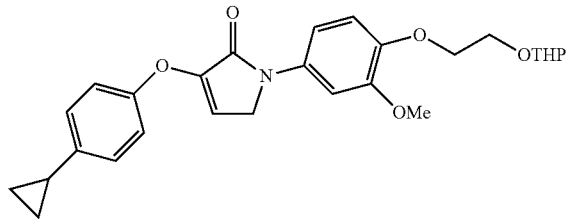

To a solution of N-allyl-2-(4-cyclopropylphenoxy)-N-(3-methoxy-4-(2-((tetrahydro-2H-pyran-2-yl)oxy)ethoxy)phenyl)but-2-enamide (8.5 g, 16.74 mmol) in toluene (200.0 mL), was added tricyclohexylphosphine[1,3-bis(2,4,6-trimethylphenyl)-4,5-dihydroimidazol-2-ylidene][benzylidene]ruthenium (IV)dichloride (0.711 g, 0.837 mmol). The resulting dark-brown colored solution was heated for 12.0 h at 80° C. under nitrogen atmosphere. The solvent was evaporated in vacuo. The residue was purified by CombiFlash instrument (120.0 g silica gel column, 30% ethyl acetate in hexane) to afford the product, 3-(4-cyclopropylphenoxy)-1-(3-methoxy-4-(2-((tetrahydro-2H-pyran-2-yl)oxy)ethoxy)phenyl)-1H-pyrrol-2(5H)-one (6.0 g, 77%), as a light-yellowish solid. $^1$H NMR (400 MHz, chloroform-d) δ 7.66-7.75 (m, 1H), 7.08 (s, 4H), 6.91-6.98 (m, 2H), 5.75 (s, 1H), 4.67-4.74 (m, 1H), 4.18-4.27 (m, 4H), 4.02-4.10 (m, 1H), 3.89 (s, 5H), 3.48-3.56 (m, 1H), 1.81-1.96 (m, 2H), 1.70-1.78 (m, 1H), 1.55-1.68 (m, 4H), 0.93-1.01 (m, 2H), 0.63-0.71 (m, 2H); MS (ES): m/z 382.2 [M+H-THP]$^+$.

Step-VIII: 3-(4-Cyclopropylphenoxy)-1-(4-(2-hydroxyethoxy)-3-methoxyphenyl)-1H-pyrrol-2(5H)-one (intermediate B1-8)

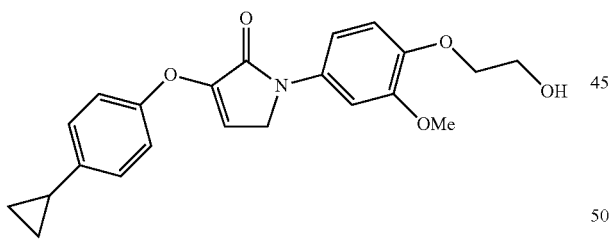

To a solution of 3-(4-cyclopropylphenoxy)-1-(3-methoxy-4-(2-((tetrahydro-2H-pyran-2-yl)oxy)ethoxy)phenyl)-1H-pyrrol-2(5H)-one (0.5 g, 1.074 mmol) in a solvent mixture of dichloromethane (2.0 mL) and methanol (2.0 mL), was added methanesulfonic acid (0.349 mL, 5.37 mmol). The mixture was stirred at ambient temperature for 12.0 h. The solvent was evaporated in vacuo. Saturated sodium bicarbonate solution (5.0 mL) was added to the residue. Ice crystals were added. The precipitated solid was filtered and the solid rinsed with petroleum ether. The solid was dried under vacuum to afford the product as a colorless solid (0.35 g, 85%) and used as such in the next reaction. $^1$H NMR (400 MHz, chloroform-d) δ 7.76 (s, 1H), 7.09 (d, J=0.75 Hz, 4H), 6.87-6.99 (m, 2H), 5.77 (s, 1H), 4.25 (d, J=2.26 Hz, 2H), 4.06-4.17 (m, 2H), 3.85-3.97 (m, 5H), 2.45-2.55 (m, 1H), 1.84-1.97 (m, 1H), 0.97 (dd, J=1.76, 8.53 Hz, 2H), 0.61-0.73 (m, 2H); MS (ES): m/z 382.2 [M+H]$^+$; HPLC RT: a) 9.49 min (Analytical HPLC Method A); b) 9.05 min (Analytical HPLC Method B).

Step-IX: 2-(4-(3-(4-Cyclopropylphenoxy)-2-oxo-2,5-dihydro-1H-pyrrol-1-yl)-2-methoxyphenoxy)ethyl methanesulfonate (intermediate B1-9)

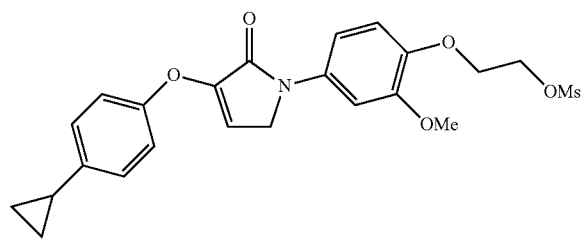 [SMILES: COc1cc(N2CC=C(Oc3ccc(C4CC4)cc3)C2=O)ccc1OCCOS(C)(=O)=O]

To a solution of 3-(4-cyclopropylphenoxy)-1-(4-(2-hydroxyethoxy)-3-methoxyphenyl)-1H-pyrrol-2(5H)-one (0.33 g, 0.865 mmol) in dichloromethane (10.0 mL) at 0° C., was added triethylamine (0.301 mL, 2.163 mmol) and subsequently methanesulfonyl chloride (0.081 mL, 1.038 mmol). The mixture was gradually warmed to room temperature. After being stirred for 6.0 h, the mixture was concentrated and the residue purified by CombiFlash (50% ethyl acetate in hexane; 48 g silica gel column) to afford the product, 2-(4-(3-(4-cyclopropylphenoxy)-2-oxo-2,5-dihydro-1H-pyrrol-1-yl)-2-methoxyphenoxy)ethylmethanesulfonate (0.294 g, 0.640 mmol, 74% yield), as a colorless solid. $^1$H NMR (400 MHz, chloroform-d) δ 7.78 (s, 1H), 7.04-7.13 (m, 4H), 6.88-6.95 (m, 2H), 5.73-5.80 (m, 1H), 4.54-4.63 (m, 2H), 4.20-4.31 (m, 4H), 3.83-3.92 (m, 3H), 3.10-3.18 (m, 3H), 1.86-1.96 (m, 1H), 0.97 (dd, J=1.75, 8.50 Hz, 2H), 0.68 (dd, J=1.75, 5.00 Hz, 2H); MS (ES): m/z 460.2 [M+H]$^+$.

Step-X: 3-(4-Cyclopropylphenoxy)-1-(3-methoxy-4-(2-(pyrrolidin-1-yl)ethoxy)phenyl)-1H-pyrrol-2(5H)-one

Example 142

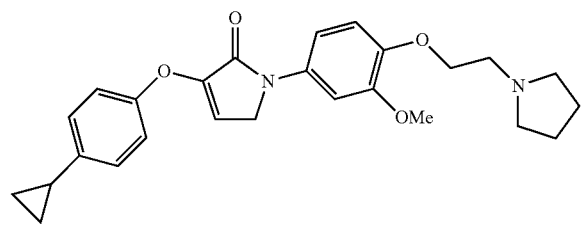 [SMILES: COc1cc(N2CC=C(Oc3ccc(C4CC4)cc3)C2=O)ccc1OCCN1CCCC1]

To a solution of 2-(4-(3-(4-cyclopropylphenoxy)-2-oxo-2,5-dihydro-1H-pyrrol-1-yl)-2-methoxyphenoxy)ethylmethanesulfonate (75 mg, 0.163 mmol; intermediate B1-9) in acetonitrile (2.0 mL), was added pyrrolidine (23.2 mg, 0.326 mmol) and sodium carbonate (51.9 mg, 0.490 mmol). The vial (20.0 mL) was kept in the reaction block (CHEMGLASS®) and stirred at 50° C. for 48.0 h. The mixture was partitioned between DCM and water. The organic layer was washed with water and brine, dried over anhydrous sodium sulfate, and concentrated in vacuo. The crude product was purified by reverse phase HPLC (X-Bridge Phenyl column (19×150 mm) 5.0μ; Mobile Phase A: 10 mM ammonium acetate in water; Mobile Phase B: acetonitrile; Flow rate: 15.0 mL/min). The HPLC fractions were concentrated. The residue was taken in a solvent mixture of acetonitrile and water, frozen and lyophilized for 12.0 h to afford the pure product, Example 142 (49.6 mg, 70%) as a colorless solid. $^1$H NMR (400 MHz, chloroform-d) δ 7.67-7.76 (m, 1H), 7.08 (s, 4H), 6.88-6.96 (m, 2H), 5.72-5.80 (m, 1H), 4.21-4.29 (m, 2H), 4.13-4.20 (m, 2H), 3.89 (s, 3H), 2.90-3.03 (m, 2H), 2.58-2.75 (m, 4H), 1.78-1.96 (m, 5H), 0.93-1.02 (m, 2H), 0.63-0.73 (m, 2H) MS (ES): m/z 435.2 [M+H]$^+$; HPLC RT: a) 7.19 min (Analytical HPLC Method A); b) 8.61 min (Analytical HPLC Method B).

Examples 143 to 163 in Table F were prepared by treating the intermediate B1-9 with an appropriate amine in a similar manner to that employed for the preparation of Example 142.

Procedure-B2

Example 164

3-(4-Cyclopropylphenoxy)-1-(3-ethyl-4-(2-(pyrrolidin-1-yl)ethoxy)phenyl)-1H-pyrrol-2(5H)-one

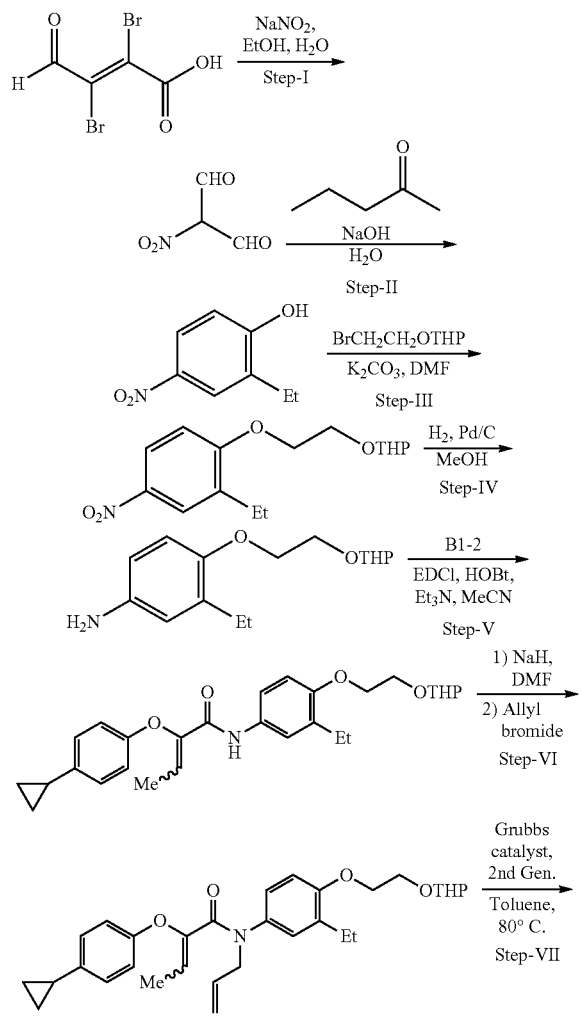

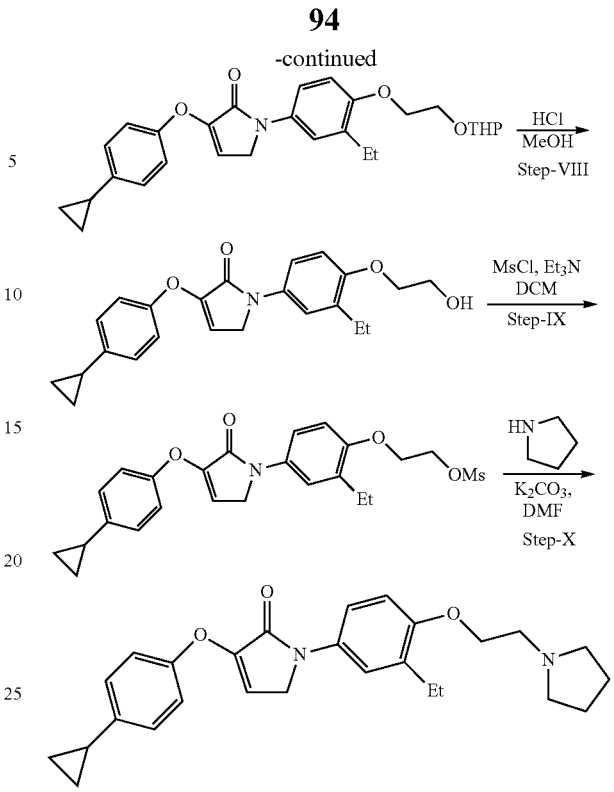

Step-I: 2-Nitromalonaldehyde (intermediate B2-1)

To a solution of 2,3-dibromo-4-oxobut-2-enoic acid (20 g, 78 mmol) in ethanol (30 mL), was added a solution of sodium nitrate (20 g, 235 mmol) in water (30.0 mL) at 0° C. The reaction mixture was allowed to stir at 60° C. for 30 min. Then the reaction mixture was allowed to stir at room temperature for 1 h. The reaction mixture was cooled to 0° C., at which point the solid was precipitated. The precipitated solid was filtered off and dried to afford the title compound as a yellowish solid (9.0 g, 99.0%). MS (ES): m/z 116.2 [M−H]$^-$.

Step-II: 2-Ethyl-4-nitrophenol (intermediate B2-2)

To the solution of pentan-2-one (8.83 g, 103 mmol) in ethanol (180 mL), was added 1.5 N aqueous solution of sodium hydroxide (102.5 mL, 103 mmol). The reaction mixture was allowed to stir for 30 min. Then 2-nitromalonaldehyde (12 g, 103 mmol) in water (180 mL) was added. The reaction mixture was allowed to stir at room temperature for 16 h. The reaction mixture was acidified with aqueous hydrochloric acid (1.5 N) and partitioned between water and ethyl acetate. The organic layer was washed with water and brine, dried over anhydrous sodium sulfate, and concentrated in vacuo. The crude product (brown solid) was directly taken to next step (12.0 g, 70%). ¹H NMR (400 MHz, DMSO-d₆) δ 10.99 (br. s., 1H), 7.93-8.05 (m, 2H), 6.95 (d, J=8.78 Hz, 1H), 2.61 (q, J=7.45 Hz, 2H), 1.16 (t, J=7.53 Hz, 3H); MS (ES): m/z 165.5 [M–H].

Step-III: 2-(2-(2-Ethyl-4-nitrophenoxy)ethoxy)tetrahydro-2H-pyran (intermediate B2-3)

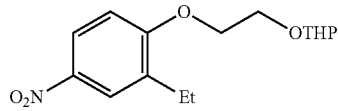

To the solution of 2-ethyl-4-nitrophenol (12 g, 71.8 mmol) in acetonitrile (200 mL), were added potassium carbonate (29.8 g, 215 mmol) and 2-(2-bromoethoxy)tetrahydro-2H-pyran (30.0 g, 144 mmol). The reaction mixture was allowed to reflux for 16 h. The mixture was partitioned between water and ethyl acetate. The organic layer was washed with water and brine, dried over anhydrous sodium sulfate, and concentrated in vacuo. The crude product was purified using CombiFlash instrument (40 g silica gel column; 20% ethyl acetate in petroleum ether) to afford the product as a light yellowish solid (18.0 g, 85%). ¹H NMR (400 MHz, DMSO-d₆) δ 8.04-8.19 (m, 2H), 7.14-7.25 (m, 1H), 4.66-4.75 (m, 1H), 4.26-4.37 (m, 2H), 3.96-4.01 (m, 1H), 3.72-3.83 (m, 2H), 3.41-3.51 (m, 1H), 2.61-2.72 (m, 2H), 1.61-1.74 (m, 2H), 1.44-1.55 (m, 4H), 1.18 (t, J=7.40 Hz, 3H).

Step-IV: 3-Ethyl-4-(2-(tetrahydro-2H-pyran-2-yloxy)ethoxy)aniline (intermediate B2-4)

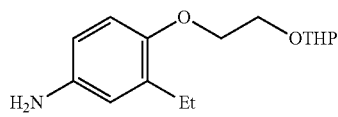

A solution of 2-(2-(2-ethyl-4-nitrophenoxy)ethoxy)tetrahydro-2H-pyran (18 g, 60.9 mmol) in MeOH (100 mL), was flushed with hydrogen and degassed (3 times). Subsequently, 5% Pd/C (0.70 g, 6.09 mmol) was added. Then the reaction mixture was stirred at room temperature under hydrogen pressure (10 Kg/cm²) in an autoclave for 3.0 h. The reaction mixture was filtered through a Celite® bed. The filtrate was concentrated in vacuo to afford the title compound as a brownish solid (13 g, 80.0%), which was used as such. MS (ES): m/z 267.5 [M+2H]⁺.

Step-V: 2-(4-Cyclopropylphenoxy)-N-(3-ethyl-4-(2-(tetrahydro-2H-pyran-2-yloxy)ethoxy)phenyl)but-2-enamide (intermediate B2-5)

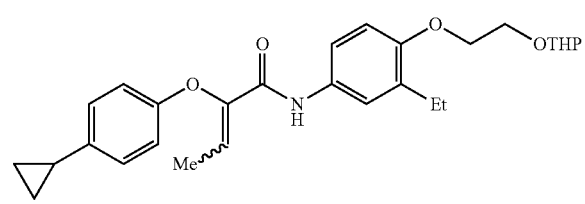

To the solution of 3-ethyl-4-(2-((tetrahydro-2H-pyran-2-yl)oxy)ethoxy)aniline (1.459 g, 5.50 mmol), and 2-(4-cyclopropylphenoxyl)but-2-enoic acid, prepared as B1-2 described in Procedure B1, (1.2 g, 5.50 mmol) in DMF (20 mL), was added 1H-1,2,3-Benzotriazol-1-ol hydrate (1.263 g, 8.25 mmol) and EDCI (1.581 g, 8.25 mmol). The reaction mixture was allowed to stir at room temperature for 16 h. The mixture was partitioned between water and ethyl acetate. The organic layer was washed with water and brine, dried over anhydrous sodium sulfate, and concentrated in vacuo. The crude product was purified using CombiFlash instrument (40 g silica gel column; 10% ethyl acetate in petroleum ether) to afford the product as a brownish solid (1.6 g, 62.5%). ¹H NMR (400 MHz, DMSO-d₆) δ 9.54-9.67 (m, 1H), 7.34-7.48 (m, 2H), 6.98-7.09 (m, 2H), 6.80-6.93 (m, 3H), 6.40-6.50 (m, 1H), 4.63-4.73 (m, 1H), 4.06-4.11 (m, 2H), 3.87-3.94 (m, 1H), 3.64-3.82 (m, 2H), 3.39-3.49 (m, 1H), 2.55-2.62 (m, 2H), 1.79-1.92 (m, 1H), 1.63-1.69 (m, 3H), 1.40-1.54 (m, 6H), 1.09-1.14 (m, 3H), 0.87-0.92 (m, 2H), 0.52-0.62 (m, 2H); MS (ES): m/z 464.1 [M–H]⁻.

Step-VI: N-Allyl-2-(4-cyclopropylphenoxy)-N-(3-ethyl-4-(2-(tetrahydro-2H-pyran-2-yloxy)ethoxy)phenyl)but-2-enamide (intermediate B2-6)

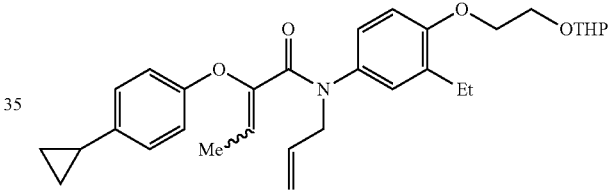

To the solution of 2-(4-cyclopropylphenoxy)-N-(3-ethyl-4-(2-((tetrahydro-2H-pyran-2-yl)oxy)ethoxy)phenyl)but-2-enamide (0.1 g, 0.215 mmol) in DMF (2 mL), was added sodium hydride (8.59 mg, 0.215 mmol) at 0° C. The reaction mixture was allowed to stir at room temperature for 45 min. Then 3-bromoprop-1-ene (0.019 mL, 0.215 mmol) was added to the reaction mixture at 0° C. Then the reaction mixture was allowed to stir at room temperature for 1 h. The mixture was partitioned between water and ethyl acetate. The organic layer was washed with water and brine, dried over anhydrous sodium sulfate, and concentrated in vacuo. The crude product was purified using CombiFlash instrument (40 g silica gel column; 20% ethylacetate in petroleum ether) to afford the product as a light yellowish solid (0.1 g, 92.0%). ¹H NMR (400 MHz, DMSO-d₆) δ ¹H NMR (400 MHz, DMSO-d₆) δ 6.86-7.01 (m, 3H), 6.74-6.82 (m, 1H), 6.66-6.72 (m, 1H), 6.38-6.51 (m, 2H), 5.96-6.05 (m, 1H), 5.58-5.70 (m, 1H), 4.93-5.00 (m, 1H), 4.81-4.90 (m, 1H), 4.68-4.75 (m, 1H), 4.06-4.19 (m, 4H), 3.91-3.99 (m, 1H), 3.72-3.86 (m, 2H), 3.40-3.51 (m, 1H), 2.54-2.58 (m, 2H), 1.81-1.91 (m, 1H), 1.59-1.79 (m, 2H), 1.51 (d, J=7.03 Hz, 7H), 1.11 (s, 3H), 0.86-0.92 (m, 2H), 0.55-0.62 (m, 2H); MS (ES): m/z 506.2 [M+H]⁺.

Step-VII: 3-(4-Cyclopropylphenoxy)-1-(3-ethyl-4-(2-(tetrahydro-2H-pyran-2-yloxy)ethoxy)phenyl)-1H-pyrrol-2(5H)-one (intermediate B2-7)

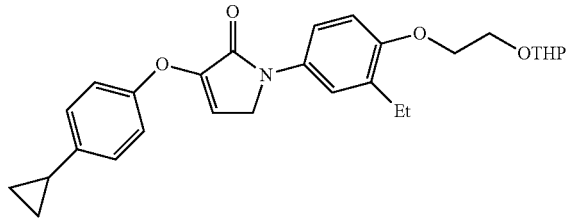

To the solution of N-allyl-2-(4-cyclopropylphenoxy)-N-(3-ethyl-4-(2-(tetrahydro-2H-pyran-2-yloxy)ethoxy)phenyl)but-2-enamide (8 g, 15.82 mmol) in toluene (250 mL), was added tricyclohexylphosphine[1,3-bis(2,4,6-trimethylphenyl)-4,5-dihydroimidazol-2-ylidene][benzylidine]ruthenium (IV)dichloride (0.673 g, 0.791 mmol). The reaction mixture was allowed to stir at 70° C. for 16 h under nitrogen atmosphere. The mixture was partitioned between water and ethyl acetate. The organic layer was washed with water and brine, dried over anhydrous sodium sulfate, and concentrated in vacuo. The crude product was purified using CombiFlash instrument (120 g silica gel column; 15% ethyl acetate in petroleum ether) to afford the product as a brownish solid (3.1 g, 42.3%). MS (ES): m/z 464.2 [M+H]+.

Step-VIII: 3-(4-Cyclopropylphenoxy)-1-(3-ethyl-4-(2-hydroxyethoxyl)phenyl)-1H-pyrrol-2(5H)-one (intermediate B2-8)

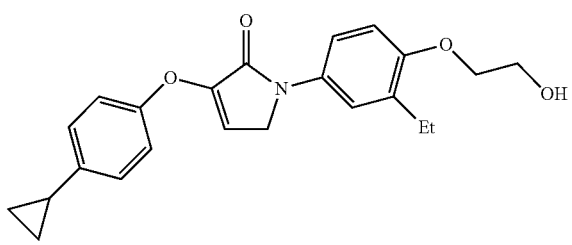 [SMILES: CCc1cc(N2CC=C(Oc3ccc(C4CC4)cc3)C2=O)ccc1OCCO]

To the solution of 3-(4-cyclopropylphenoxy)-1-(3-ethyl-4-(2-((tetrahydro-2H-pyran-2-yl)oxy)ethoxy)phenyl)-1H-pyrrol-2(5H)-one (0.5 g, 1.079 mmol) in methanol (4 mL), was added methanesulfonic acid (0.350 mL, 5.39 mmol) at 0° C. The reaction mixture was allowed to stir at 25° C. for 15 h. The mixture was partitioned between water and ethyl acetate. The organic layer was washed with water and brine, dried over anhydrous sodium sulfate, and concentrated in vacuo. The crude product was purified using CombiFlash instrument (24 g silica gel column; 25% ethyl acetate in petroleum ether) to afford the product as an off-white solid (0.32 g, 78.0%). 1H NMR (400 MHz, DMSO-$d_6$) δ 7.47-7.59 (m, 2H), 7.10 (d, J=14.81 Hz, 4H), 6.92-7.01 (m, 1H), 6.12-6.21 (m, 1H), 4.77-4.85 (m, 1H), 4.28-4.46 (m, 2H), 3.94-4.06 (m, 2H), 3.64-3.81 (m, 2H), 2.56-2.64 (m, 2H), 1.90-1.98 (m, 1H), 1.15 (s, 3H), 0.93-0.98 (m, 2H), 0.63-0.69 (m, 2H); MS (ES): m/z 379.9 [M+H]+.

Step-IX: 2-(4-(3-(4-Cyclopropylphenoxy)-2-oxo-2,5-dihydro-1H-pyrrol-1-yl)-2-ethylphenoxy)ethyl-methanesulfonate (intermediate B2-9)

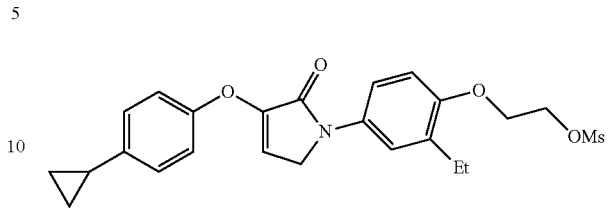

To the solution of 3-(4-cyclopropylphenoxy)-1-(3-ethyl-4-(2-hydroxyethoxyl)phenyl)-1H-pyrrol-2(5H)-one (0.5 g, 1.318 mmol) in dichloromethane (25 mL), was added triethylamine (0.367 mL, 2.64 mmol). The reaction mixture was cooled to 0° C. Then methanesulfonyl chloride (0.123 mL, 1.581 mmol) was added dropwise to the reaction mixture. The reaction mixture was allowed to stir for 1 h. The mixture was partitioned between water and dichloromethane. The organic layer was washed with water and brine, dried over anhydrous sodium sulfate, and concentrated in vacuo to afford the title product as a colorless solid (0.50 g, 83.0%). 1H NMR (400 MHz, DMSO-$d_6$) δ 7.47-7.59 (m, 2H), 7.04-7.20 (m, 4H), 6.94-7.02 (m, 1H), 6.12-6.19 (m, 1H), 4.78-4.85 (m, 1H), 4.33-4.45 (m, 2H), 3.96-4.06 (m, 2H), 3.66-3.79 (m, 2H), 3.32-3.33 (m, 3H), 2.56-2.66 (m, 2H), 1.12-1.19 (m, 3H), 0.93-0.99 (m, 2H), 0.62-0.70 (m, 2H); MS (ES): m/z 458.27 [M+H]+.

Step-X: 3-(4-Cyclopropylphenoxy)-1-(3-ethyl-4-(2-(pyrrolidin-1-yl)ethoxy)phenyl)-1H-pyrrol-2(5H)-one Example 164

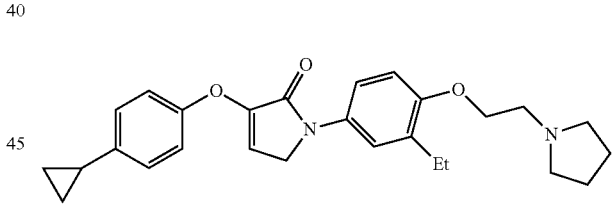

To the solution of 2-(4-(3-(4-cyclopropylphenoxy)-2-oxo-2,5-dihydro-1H-pyrrol-1-yl)-2-ethylphenoxy)ethyl methanesulfonate (0.05 g, 0.109 mmol) in acetonitrile (3 mL), were added potassium iodide (9.07 mg, 0.055 mmol) and pyrrolidine (0.012 g, 0.164 mmol). The reaction mixture was allowed to stir at 50° C. for 16 h. The mixture was partitioned between water and ethyl acetate. The organic layer was washed with water and brine, dried over anhydrous sodium sulfate, and concentrated in vacuo. The crude product was purified by reverse phase HPLC (KROMASIL® C4 column (21×250 mm) 5.0μ; Mobile Phase A: 10 mM ammonium acetate in water; Mobile Phase B: acetonitrile; flow rate: 17.0 mL). The HPLC fractions were concentrated in vacuo to afford the pure product as an off-white solid (0.011 g, 21.72%).

Examples 165 to 183 in Table F were prepared by reaction of intermediate B2-9 with an appropriate amine following a procedure employed for Example 164.

Procedure-B3

Example 184

3-(4-Cyclopropylphenoxy)-1-(3-(difluoromethoxy)-4-(2-(pyrrolidin-1-yl)ethoxy)phenyl)-1H-pyrrol-2(5H)-one

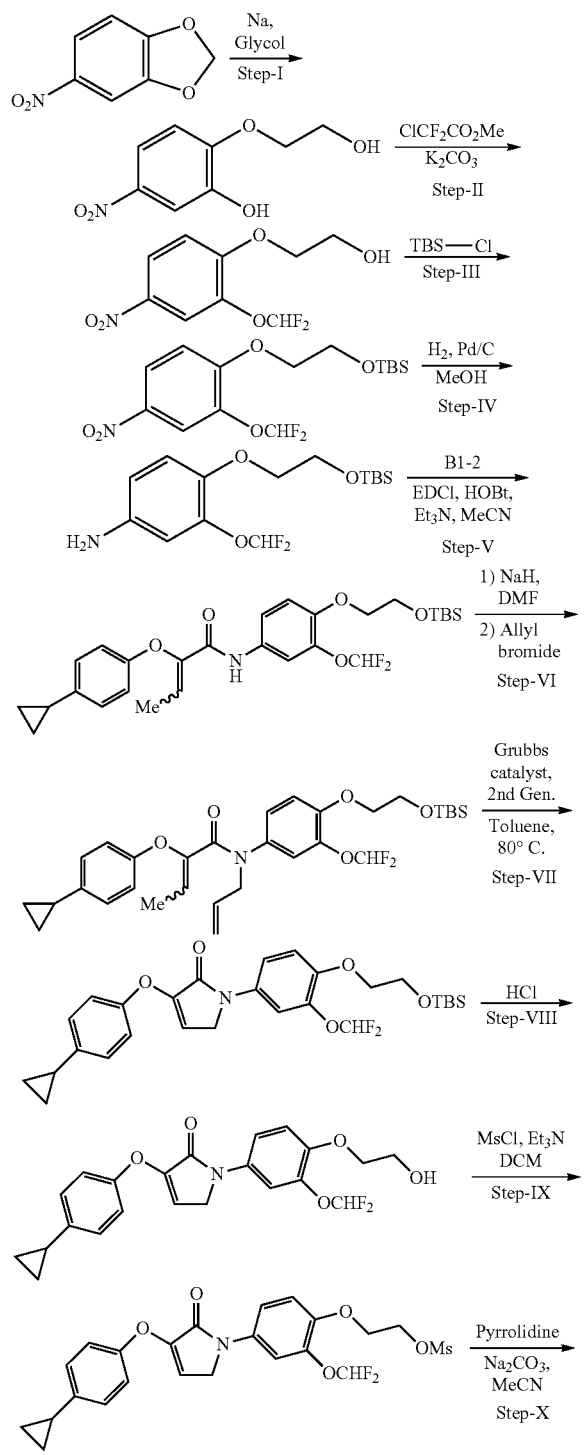

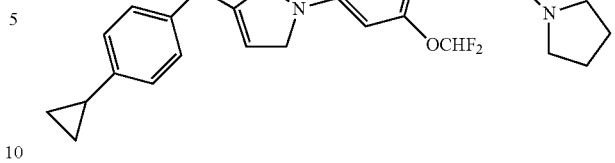

Step-I: 2-(2-Hydroxyethoxy)-5-nitrophenol (intermediate B3-1)

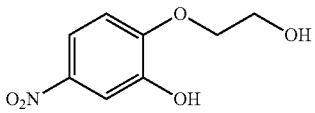 [SMILES: O=[N+]([O-])c1ccc(OCCO)c(O)c1]

To a mixture of sodium (3.30 g, 144 mmol) in ethane-1,2-diol (50 mL, 71.8 mmol), was added 5-nitrobenzo[d][1,3]dioxide (12 g, 71.8 mmol) at room temperature. The reaction mixture was allowed to stir at 120° C. for 3 h. The reaction mixture was cooled to ambient temperature and then slowly diluted with 60 mL of water and subsequently acidified with 1.5N hydrochloric acid solution. The solid, which was precipitated, was filtered and dried in vacuo to afford the title compound as a yellowish solid (12 g, 59.4 mmol, 83%). $^1$H NMR (400 MHz, DMSO) δ 7.73 (d, J=9.03 Hz, 1H), 7.62 (d, J=2.76 Hz, 1H), 7.13 (d, J=9.03 Hz, 1H), 4.12 (t, J=4.89 Hz, 2H), 3.75-3.81 (m, 2H), 3.47-3.69 (m, 1H); MS (ES): m/z 200 [M+H]$^+$.

Step-II: 2-(2-(Difluoromethoxy)-4-nitrophenoxy)ethanol (intermediate B3-2)

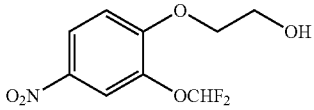

To the stirred solution of 2-(2-hydroxyethoxy)-5-nitrophenol (1.0 g, 5.02 mmol) in N,N-dimethylformamide (10 mL), was added potassium carbonate (2.429 g, 17.57 mmol) followed by methyl chlorodifluroacetate (1.344 mL, 12.55 mmol). The reaction mixture was then allowed to stir at 80° C. for 2 h. The mixture was partitioned between water and ethyl acetate. The organic layer was washed with water, dried over anhydrous sodium sulfate, and concentrated in vacuo to afford the title compound as a yellowish solid (0.7 g, 56.0%). The crude product was used as such in the next step. $^1$H NMR (400 MHz, chloroform-d) δ 8.13-8.18 (m, 1H), 8.09-8.13 (m, 1H), 7.05-7.10 (m, 1H), 6.62 (t, J=73.78 Hz, 1H), 4.22-4.28 (m, 3H), 4.02-4.08 (m, 2H); MS (ES): m/z 248 [M−H]$^+$.

Step-III: tert-Butyl(2-(2-(difluoromethoxy)-4-nitrophenoxy)ethoxy)dimethylsilane (intermediate B3-3)

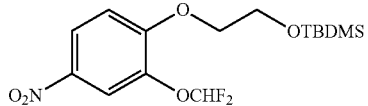

To a solution of 2-(2-(difluoromethoxy)-4-nitrophenoxy)ethanol (0.7 g, 2.81 mmol) in dichloromethane (15 mL), was added imidazole (0.574 g, 8.43 mmol) at 0° C. Then tert-butyldimethylsilyl chloride (0.635 g, 4.21 mmol) was added slowly to the reaction mixture over the period of 10 min. The reaction mixture was allowed to stir at room temperature for 2 h. The mixture was partitioned between water and dichloromethane. The organic layer was washed with water, dried over anhydrous sodium sulfate, and concentrated in vacuo. The crude product was purified using CombiFlash instrument (40 g silica gel column; 16% ethyl acetate in petroleum ether) to afford the title compound as an off-white solid (1.0 g, 97%). $^1$H NMR (400 MHz, chloroform-d) δ 8.11-8.15 (m, 1H), 8.07-8.09 (m, 1H), 7.10 (s, 1H), 6.65 (t, J=74.54 Hz, 1H), 4.22 (d, J=5.00 Hz, 2H), 4.02 (d, J=5.00 Hz, 2H), 0.88-0.90 (m, 9H), 0.09 (s, 6H); MS (ES): m/z 381 [M+NH$_4$]$^+$.

Step-IV: 4-(2-((tert-Butyldimethylsilyl)oxy)ethoxy)-3-(difluoromethoxy)aniline (intermediate B3-4)

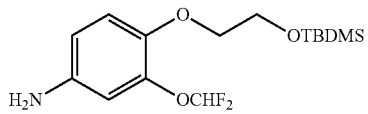 [SMILES: CC(C)(C)[Si](C)(C)OCCOc1ccc([N+](=O)[O-])cc1OC(F)F]

To a solution of tert-butyl(2-(2-(difluoromethoxy)-4-nitrophenoxy)ethoxy)dimethylsilane (6.0 g, 16.51 mmol) in ethanol (60 mL), was added ammonium formate (2.082 g, 33.0 mmol) followed by 5% palladium on carbon (0.703 g, 6.60 mmol). The reaction mixture was allowed to stir for 20 min. Then reaction mixture was filtered through a Celite® bed. The filtrate was concentrated in vacuo to afford the title product as a dark-brownish liquid (4.0 g, 72.7% yield). $^1$H NMR (400 MHz, chloroform-d) δ 6.82 (d, J=8.50 Hz, 1H), 6.53 (d, J=2.25 Hz, 2H), 6.06-6.39 (m, 1H), 4.00 (d, J=5.00 Hz, 2H), 3.93 (d, J=5.00 Hz, 2H), 0.88-0.96 (m, 9H), 0.07-0.14 (m, 6H); MS (ES): m/z 334 [M+H]$^+$.

Step-V: N-(4-(2-((tert-Butyldimethylsilyl)oxy)ethoxy)-3-(difluoromethoxy)phenyl)-2-(4-cyclopropylphenoxyl)but-2-enamide (intermediate B3-5)

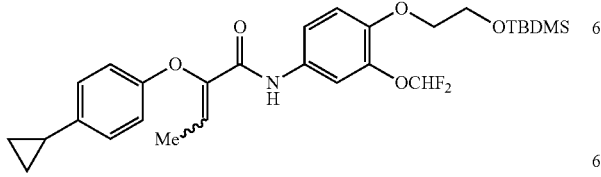

To a solution of 4-(2-((tert-butyldimethylsilyl)oxy)ethoxy)-3-(difluoromethoxy)aniline (4.0 g, 12.00 mmol) in acetonitrile (50 mL), was added 2-(4-cyclopropylphenoxyl)but-2-enoic acid, prepared as B1-2 described in Procedure B1, (2.62 g, 12.00 mmol) followed by triethylamine (5.02 mL, 36.0 mmol), HOBT (1.837 g, 12.00 mmol) and EDCI (3.45 g, 17.99 mmol). The reaction mixture was allowed to stir for 16 h. The reaction mixture was diluted with water and extracted with ethyl acetate (3×). The organic layers were combined, dried over sodium sulfate and concentrated in vacuo. The crude product was purified using CombiFlash instrument (120 g silica gel column; 20% ethyl acetate in petroleum ether) to afford the title compound as a yellow liquid (2.5 g, 39.1%). $^1$H NMR (400 MHz, chloroform-d) δ 7.31-7.53 (m, 2H), 6.99-7.06 (m, 2H), 6.42-6.95 (m, 5H), 4.02-4.09 (m, 2H), 3.90-3.99 (m, 2H), 1.82-1.89 (m, 1H), 1.65-1.71 (m, 3H), 0.89 (s, 11H), 0.59-0.67 (m, 2H), 0.08 (s, 6H); MS (ES): m/z 534 [M+H]$^+$.

Step-VI: N-Allyl-N-(4-(2-((tert-butyldimethylsilyl)oxy)ethoxy)-3-(difluoromethoxy)phenyl)-2-(4-cyclopropylphenoxyl)but-2-enamide (intermediate B3-6)

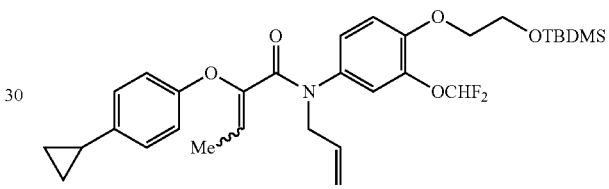

To a solution of N-(4-(2-((tert-butyldimethylsilyl)oxy)ethoxy)-3-(difluoromethoxy)phenyl)-2-(4-cyclopropylphenoxyl)but-2-enamide (2.5 g, 4.68 mmol) in DMF (25 mL) at 0° C., was added sodium hydride (0.375 g, 9.37 mmol) and the mixture stirred for 30 min. Then allyl bromide (0.811 mL, 9.37 mmol) was added. After the completion of the reaction, the reaction mixture was diluted with 100 mL of water and extracted with 200 mL of EtOAc. The organic layer was separated, dried over anhydrous sodium sulfate, and concentrated to dryness in vacuo. The crude product was purified using CombiFlash instrument (120 g silica gel column; 20% ethyl acetate in petroleum ether) to afford the product as a yellowish-liquid (2.5 g, 75% yield). MS (ES): m/z 574 [M+H]$^+$.

Step-VII: 1-(4-(2-((tert-Butyldimethylsilyl)oxy)ethoxy)-3-(difluoromethoxy)phenyl)-3-(4-cyclopropylphenoxy)-1H-pyrrol-2(5H)-one (intermediate B3-7)

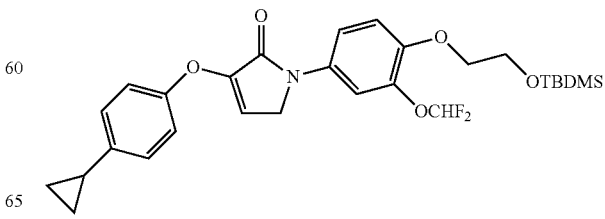

To the stirred solution of N-allyl-N-(4-(2-((tert-butyldimethylsilyl)oxy)ethoxy)-3-(difluoromethoxy)phenyl)-2-(4-cyclopropylphenoxyl)but-2-enamide (2.5 g, 4.36 mmol) in toluene (50 mL), was added Grubbs second generation catalyst (0.370 g, 0.436 mmol). The reaction mixture was heated to 80° C. for 24 h. Then the reaction mixture was evaporated to dryness in vacuo. The crude product was purified using CombiFlash instrument (120 g silica gel column; 25% ethyl acetate in petroleum ether) to afford the product as an off-white solid (1.6 g, 69.1% yield). ¹H NMR (400 MHz, chloroform-d) δ 7.66-7.73 (m, 1H), 7.44-7.50 (m, 1H), 7.08 (d, J=1.76 Hz, 4H), 6.99-7.04 (m, 1H), 6.69 (td, J=1.00, 78.80 Hz, 1H), 5.75 (s, 1H), 4.22 (d, J=2.26 Hz, 2H), 4.11 (s, 2H), 3.97 (s, 2H), 1.86-1.96 (m, 1H), 0.94-1.00 (m, 2H), 0.88-0.92 (m, 9H), 0.65-0.71 (m, 2H), 0.10 (s, 6H); MS (ES): m/z 530 [M−H]⁺.

Step-VIII: 3-(4-Cyclopropylphenoxy)-1-(3-(difluoromethoxy)-4-(2-hydroxyethoxy)phenyl)-1H-pyrrol-2(5H)-one (intermediate B3-8)

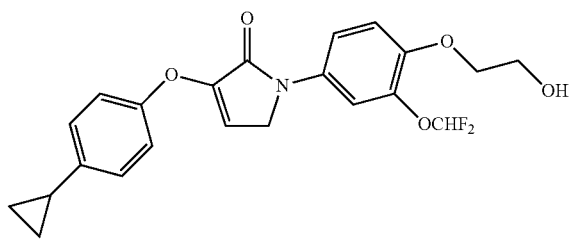 [SMILES: O=C1C(Oc2ccc(C3CC3)cc2)=CCN1c1ccc(OCCO)c(OC(F)F)c1]

To the stirred solution of 1-(4-(2-((tert-butyldimethylsilyl)oxy)ethoxy)-3-(difluoromethoxy)phenyl)-3-(4-cyclopropylphenoxy)-1H-pyrrol-2(5H)-one (0.05 g, 0.094 mmol) in tetrahydrofuran (3 mL), was added 1.5N HCl aqueous solution (0.8 mL, 26.3 mmol). This reaction mixture was stirred at room temperature 3 h. Then the reaction mixture was evaporated to dryness. The off-white solid, obtained after evaporation, was used as such in the next reaction (0.03 g, 73.4% yield). ¹H NMR (400 MHz, DMSO) δ 7.68-7.78 (m, 1H), 7.49-7.59 (m, 1H), 6.91-7.35 (m, 6H), 6.22 (s, 1H), 4.89 (s, 1H), 4.41 (d, J=2.51 Hz, 2H), 4.09 (s, 2H), 3.74 (s, 2H), 1.91-2.00 (m, 1H), 0.95 (s, 2H), 0.58-0.71 (m, 2H); MS (ES): m/z 418 [M+H]⁺.

Step-IX: 2-(4-(3-(4-Cyclopropylphenoxy)-2-oxo-2,5-dihydro-1H-pyrrol-1-yl)-2-(difluoromethoxy)phenoxy)ethylmethanesulfonate (intermediate B3-9)

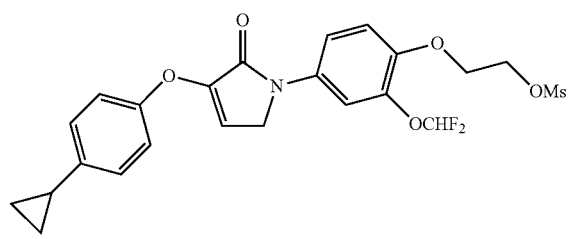 [SMILES: CS(=O)(=O)OCCOc1ccc(N2CC=C(Oc3ccc(C4CC4)cc3)C2=O)cc1OC(F)F]

The title compound was obtained as a grayish semi-solid (0.1 g, 78% yield) from the intermediate B3-8 by following a procedure, similar to that for B1-9. ¹H NMR (400 MHz, chloroform-d) δ 7.62-7.67 (m, 1H), 7.57-7.61 (m, 1H), 7.03-7.12 (m, 4H), 6.98-7.02 (m, 1H), 6.59 (dt, J=74.29, 75.29 Hz, 1H), 5.74-5.79 (m, 1H), 4.55-4.61 (m, 2H), 4.28-4.33 (m, 2H), 4.20-4.25 (m, 2H), 3.12 (s, 3H), 1.86-1.95 (m, 1H), 0.93-1.01 (m, 2H), 0.65-0.71 (m, 2H); MS (ES): m/z 496 [M+H]⁺.

Step-X: 3-(4-Cyclopropylphenoxy)-1-(3-(difluoromethoxy)-4-(2-(pyrrolidin-1-yl)ethoxy)phenyl)-1H-pyrrol-2(5H)-one Example 184

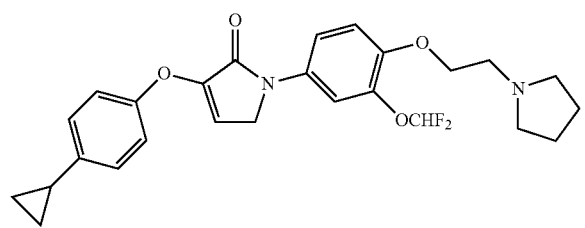 [SMILES: O=C1C(Oc2ccc(C3CC3)cc2)=CCN1c1ccc(OCCN2CCCC2)c(OC(F)F)c1]

To the stirred solution of 2-(4-(3-(4-cyclopropylphenoxy)-2-oxo-2,5-dihydro-1H-pyrrol-1-yl)-2-(difluoromethoxy)phenoxy)ethylmethanesulfonate (0.1 g, 0.202 mmol) in acetonitrile (2 mL) was added pyrrolidine (0.043 g, 0.605 mmol) and Na₂CO₃ (0.064 g, 0.605 mmol) followed by KI (6.70 mg, 0.040 mmol). The mixture was stirred at 80° C. for 24 h. The reaction mass was diluted with 50 mL of water and then extracted with 80 mL of dichloromethane. The organic layer was separated, washed with brine solution and dried over anhydrous sodium sulfate, and evaporated to dryness in vacuo. The residue was purified by reverse phase preparative HPLC (Inertsil ODS (19×250 mm); 5.0μ; Mobile Phase A: 0.1% trifluoroacetic acid in water; Mobile Phase B: methanol; flow: 16.0 mL/min}. The fractions were concentrated in vacuo and partitioned between dichloromethane and aqueous sodium bicarbonate solution. The organic layer was dried over anhydrous sodium sulfate and concentrated in vacuo to afford the product as a off-white solid (0.05 g, 50.5% yield).

Examples 185 to 190 in Table F were prepared by treating the intermediate B3-9 with an appropriate amine in a similar manner to that employed for the preparation of Example 184.

Procedure-B4

Example 191

1-(3-Bromo-4-(2-(pyrrolidin-1-yl)ethoxy)phenyl)-3-(4-cyclopropylphenoxy)-1H-pyrrol-2(5H)-one

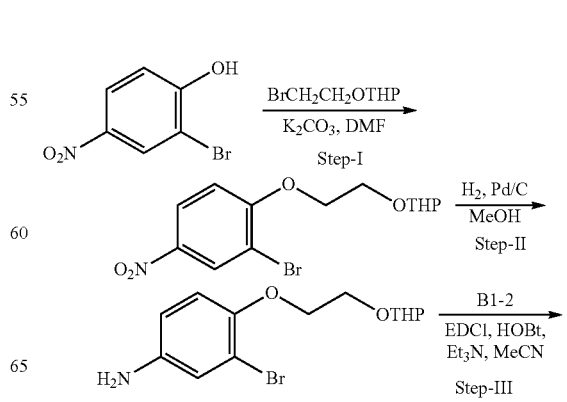

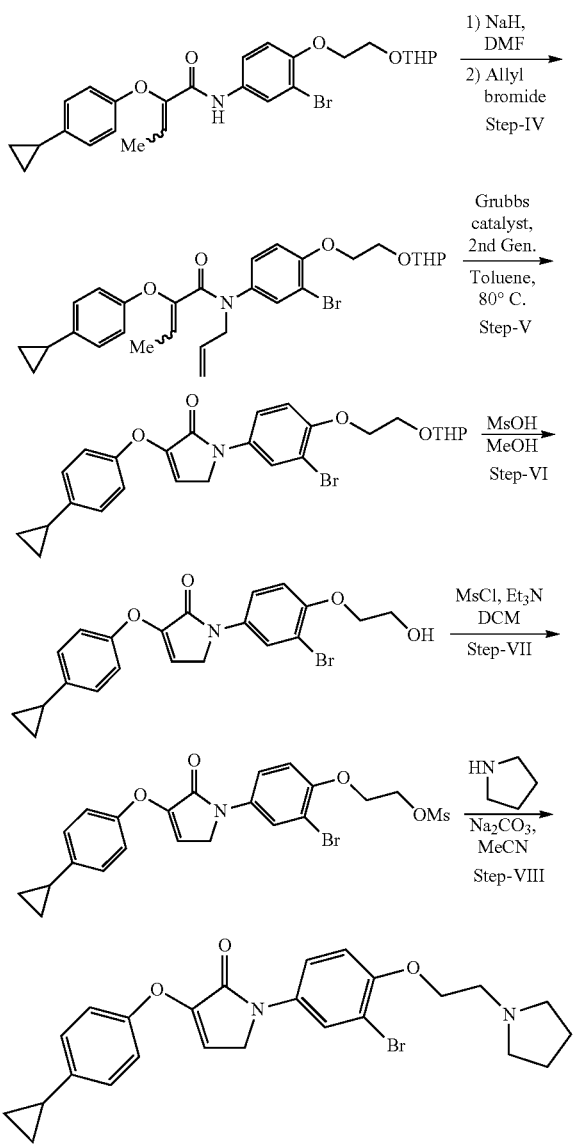

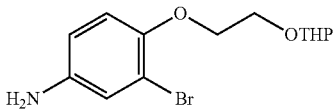

Step-I: 2-(2-(2-Bromo-4-nitrophenoxy)ethoxy)tetrahydro-2H-pyran (intermediate B4-1)

The title compound was obtained as an off-white solid (33 g, 88 mmol, 77% yield) from 2-bromo-4-nitrophenol by following a procedure, similar to that for B1-3. $^1$H NMR (400 MHz, chloroform-d) δ 8.47 (d, J=2.76 Hz, 1H), 8.19 (dd, J=2.76, 9.03 Hz, 1H), 7.02 (d, J=9.03 Hz, 1H), 4.77 (t, J=3.26 Hz, 1H), 4.29-4.38 (m, 2H), 4.08-4.17 (m, 1H), 3.86-3.97 (m, 2H), 3.49-3.61 (m, 1H), 1.74 (s, 2H), 1.62 (d, J=3.51 Hz, 4H).

Step-II: 3-Bromo-4-(2-((tetrahydro-2H-pyran-2-yl)oxy)ethoxy)aniline (intermediate B4-2)

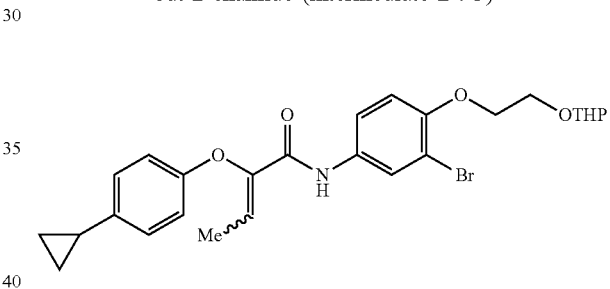

A solution of ammonium chloride (64.9 g, 1213 mmol) in water (390 mL) was added dropwise over 5 minutes to a stirred solution of 2-(2-(2-bromo-4-nitrophenoxy)ethoxy)tetrahydro-2H-pyran (60 g, 173 mmol) in methanol (1200 mL) prior to the addition of iron powder (48.4 g, 867 mmol). The reaction was slowly heated to 95° C. After 3.0 h, the reaction mass was cooled to room temperature, filtered through a Celite® pad and washed with methanol (3×500 mL). The filtrate was concentrated in vacuo. The crude compound was dissolved in ethyl acetate (2000 mL) and washed with water (500 mL), brine (1×250 mL). The organic layer was dried over sodium sulfate and concentrated. The crude compound was purified using CombiFlash instrument (220 g silica gel column; 15% ethyl acetate in hexane) to afford the title product (34 g, 106 mmol, 61.2% yield) as a brown-colored liquid. $^1$H NMR (400 MHz, DMSO-d$_6$) δ 6.85 (d, J=8.53 Hz, 1H), 6.80 (d, J=2.51 Hz, 1H), 6.49-6.56 (m, 1H), 4.91 (s, 2H), 4.66-4.73 (m, 1H), 4.03 (s, 2H), 3.76-3.91 (m, 2H), 3.64-3.73 (m, 1H), 3.41-3.49 (m, 1H), 1.69-1.80 (m, 1H), 1.59-1.67 (m, 1H), 1.40-1.55 (m, 4H); MS (ES): m/z 316 [M+H]$^+$.

Step-III: N-(3-Bromo-4-(2-((tetrahydro-2H-pyran-2-yl)oxy)ethoxy)phenyl)-2-(4-cyclopropylphenoxy)but-2-enamide (intermediate B4-3)

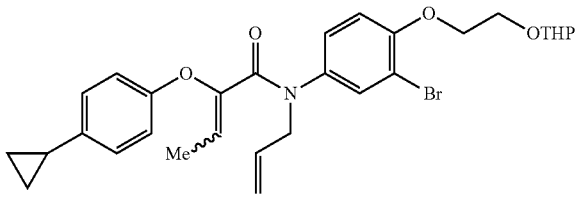

The title compound was obtained as a light-yellowish liquid (23.8 g, 44.7 mmol, 85% yield) upon reaction of the intermediate B4-2 with B1-2 described in Procedure B1 under the conditions employed for the synthesis of B1-5. $^1$H NMR (400 MHz, DMSO-d$_6$) δ 9.83 (s, 1H), 7.92 (d, J=2.51 Hz, 1H), 7.53-7.64 (m, 1H), 6.99-7.12 (m, 3H), 6.88 (d, J=8.78 Hz, 2H), 6.48 (d, J=7.28 Hz, 1H), 4.70 (s, 1H), 4.16 (s, 2H), 3.85-3.95 (m, 1H), 3.67-3.85 (m, 2H), 3.40-3.48 (m, 1H), 1.81-1.91 (m, 1H), 1.66 (d, J=7.03 Hz, 5H), 1.45 (br. s., 4H), 0.88 (dd, J=2.01, 8.28 Hz, 2H), 0.53-0.63 (m, 2H); MS (ES): m/z 514 [M−H]$^+$.

Step-IV: N-Allyl-N-(3-bromo-4-(2-((tetrahydro-2H-pyran-2-yl)oxy)ethoxy)phenyl)-2-(4-cyclopropylphenoxyl)but-2-enamide (intermediate B4-4)

The title compound was obtained as a light-yellow solid (57.9 g, 89% yield) from the intermediate B4-3 by following a procedure, similar to that for B1-6. $^1$H NMR (400 MHz, DMSO-$d_6$) δ 7.05-7.15 (m, 2H), 6.92-7.03 (m, 3H), 6.37-6.49 (m, 2H), 6.02-6.15 (m, 1H), 5.55-5.69 (m, 1H), 4.94-5.03 (m, 1H), 4.81-4.92 (m, 1H), 4.71-4.78 (m, 1H), 4.18-4.30 (m, 2H), 4.06-4.15 (m, 2H), 3.90-4.00 (m, 1H), 3.71-3.87 (m, 2H), 3.40-3.50 (m, 1H), 1.81-1.92 (m, 1H), 1.59-1.79 (m, 2H), 1.40-1.58 (m, 7H), 0.85-0.94 (m, 2H), 0.54-0.65 (m, 2H); MS (ES): m/z 556 [M+H]$^+$.

Step-V: 1-(3-Bromo-4-(2-((tetrahydro-2H-pyran-2-yl)oxy)ethoxy)phenyl)-3-(4-cyclopropylphenoxy)-1H-pyrrol-2(5H)-one (intermediate B4-5)

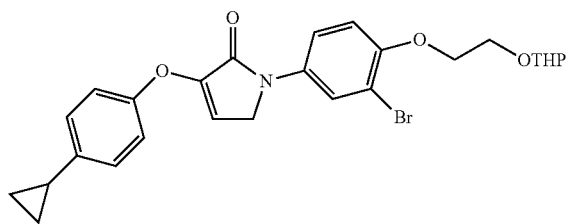

The title compound was obtained as an off-white solid (14.5 g, 28.0 mmol, 78% yield) from the intermediate B4-4 by following a procedure, similar to that for B1-7. $^1$H NMR (400 MHz, DMSO-$d_6$) δ 8.09 (s, 1H), 7.65-7.74 (m, 1H), 7.11 (d, J=13.80 Hz, 5H), 6.22 (s, 1H), 4.68-4.78 (m, 1H), 4.42 (d, J=2.26 Hz, 2H), 4.16-4.29 (m, 2H), 3.88-3.99 (m, 1H), 3.71-3.87 (m, 2H), 3.40-3.52 (m, 1H), 1.90-2.00 (m, 1H), 1.57-1.79 (m, 2H), 1.40-1.54 (m, 4H), 0.89-1.01 (m, 2H), 0.61-0.71 (m, 2H); MS (ES): m/z 512 [M−H]$^+$.

Step-VI: 1-(3-Bromo-4-(2-hydroxyethoxyl)phenyl)-3-(4-cyclopropylphenoxy)-1H-pyrrol-2(5H)-one (intermediate B4-6)

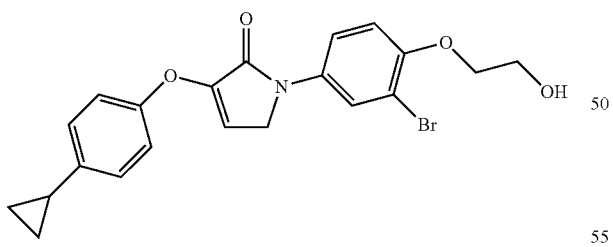

The title compound was obtained as an off-white solid (11.0 g, 25.1 mmol, 74% yield) from the intermediate B4-5 by following a procedure, similar to that for B1-8. $^1$H NMR (400 MHz, DMSO-$d_6$) δ 8.09 (d, J=2.76 Hz, 1H), 7.67 (dd, J=2.64, 8.91 Hz, 1H), 7.04-7.25 (m, 5H), 6.22 (t, J=2.13 Hz, 1H), 4.88 (t, J=5.27 Hz, 1H), 4.41 (d, J=2.01 Hz, 2H), 4.08 (t, J=5.14 Hz, 2H), 3.76 (q, J=5.27 Hz, 2H), 1.89-2.02 (m, 1H), 0.89-1.00 (m, 2H), 0.61-0.73 (m, 2H); MS (ES): m/z 430 [M+H]$^+$; HPLC RT: a) 11.06 min (Analytical HPLC Method A); b) 10.2 min (Analytical HPLC Method B).

Step-VII: 2-(2-Bromo-4-(3-(4-cyclopropylphenoxy)-2-oxo-2,5-dihydro-1H-pyrrol-1-yl)phenoxy)ethyl methanesulfonate (intermediate B4-7)

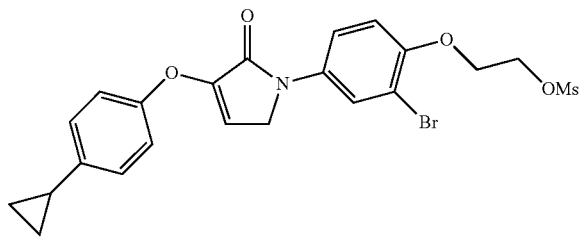 [SMILES: CS(=O)(=O)OCCOc1ccc(N2CC=C(Oc3ccc(C4CC4)cc3)C2=O)cc1Br]

The title compound was obtained as an off-white solid (1.63 g, 3.21 mmol, 92% yield) from the intermediate B4-6 by following a procedure, similar to that for B1-9. $^1$H NMR (400 MHz, chloroform-d) δ 7.88 (d, J=2.76 Hz, 1H), 7.74-7.84 (m, 1H), 7.04-7.14 (m, 4H), 6.94 (d, J=9.03 Hz, 1H), 5.77 (s, 1H), 4.57-4.66 (m, 2H), 4.27-4.34 (m, 2H), 4.22 (d, J=2.26 Hz, 2H), 3.15 (s, 3H), 1.85-1.96 (m, 1H), 0.97 (dd, J=1.76, 8.53 Hz, 2H), 0.63-0.73 (m, 2H); MS (ES): m/z 508 [M+H]$^+$.

Step-VIII: 1-(3-Bromo-4-(2-(pyrrolidin-1-yl)ethoxy)phenyl)-3-(4-cyclopropylphenoxy)-1H-pyrrol-2(5H)-one Example 191

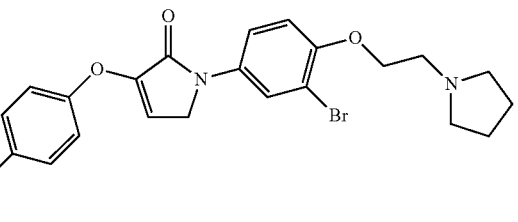

The title compound was obtained as an off-white solid (38 mg, 53% yield) from the intermediate B4-7 by following a procedure, similar to that for B1-10.

Examples 192 to 204 in Table F were prepared by treating the intermediate B4-7 with an appropriate amine in a similar manner to that employed for the preparation of Example 191.

Procedure-B5

Example 205

1-(3-Cyclopropyl-4-(2-(pyrrolidin-1-yl)ethoxy)phenyl)-3-(4-cyclopropylphenoxy)-1H-pyrrol-2(5H)-one

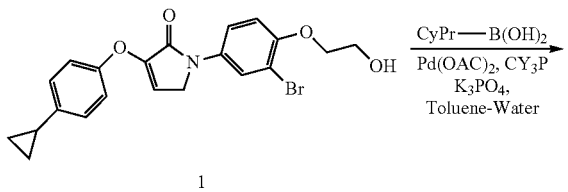

-continued

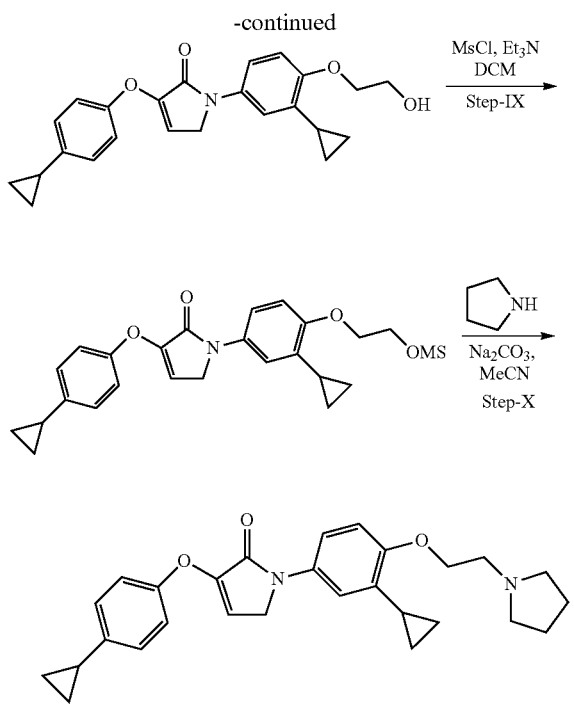

Step-I: 1-(3-Cyclopropyl-4-(2-hydroxyethoxyl)phenyl)-3-(4-cyclopropylphenoxy)-1H-pyrrol-2(5H)-one (intermediate B5-1)

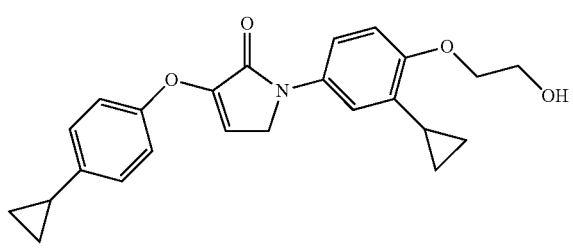 [SMILES: O=C1C(Oc2ccc(C3CC3)cc2)=CCN1c1ccc(OCCO)c(C2CC2)c1]

1-(3-Bromo-4-(2-hydroxyethoxyl)phenyl)-3-(4-cyclopropylphenoxy)-1H-pyrrol-2(5H)-one (0.5 g, 1.162 mmol; intermediate B4-6) was dissolved in a solvent mixture of toluene (9 mL) and water (1 mL). Cyclopropylboronic acid (0.120 g, 1.394 mmol), potassium phosphate, dibasic (0.607 g, 3.49 mmol), and tricyclohexylphosphine (0.098 g, 0.349 mmol) were sequentially added. The mixture was degassed with argon. Palladium (II) acetate (0.052 g, 0.232 mmol) was added. The mixture was heated to 100° C. for 10 h. The reaction mixture was cooled to the ambient temperature, filtered through Celite®, and the filtrate concentrated to dryness. The residue was purified by CombiFlash instrument (24 g silica gel column; 10% ethyl acetate in petroleum ether) to afford the product as a yellowish liquid. (0.4 g, 84%). $^1$H NMR (300 MHz, chloroform-d) δ 7.41-7.50 (m, 1H), 7.20-7.26 (m, 1H), 7.10 (s, 4H), 6.85-6.94 (m, 1H), 5.70-5.78 (m, 1H), 4.20-4.26 (m, 2H), 4.11-4.18 (m, 2H), 3.95-4.05 (m, 2H), 2.15-2.25 (m, 1H), 1.85-1.99 (m, 1H), 0.92-1.05 (m, 4H), 0.65-0.76 (m, 4H); MS (ES): m/z 392.2 [M+H]$^+$.

Step-II: 2-(2-Cyclopropyl-4-(3-(4-cyclopropylphenoxy)-2-oxo-2,5-dihydro-1H-pyrrol-1-yl)phenoxy) ethyl methanesulfonate (intermediate B5-2)

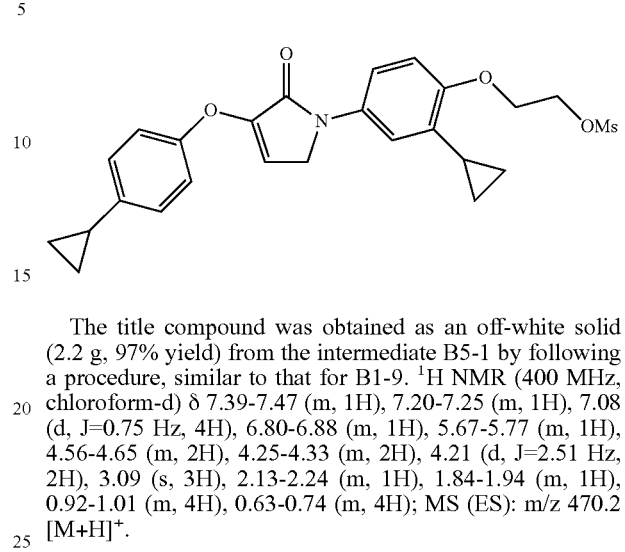

The title compound was obtained as an off-white solid (2.2 g, 97% yield) from the intermediate B5-1 by following a procedure, similar to that for B1-9. $^1$H NMR (400 MHz, chloroform-d) δ 7.39-7.47 (m, 1H), 7.20-7.25 (m, 1H), 7.08 (d, J=0.75 Hz, 4H), 6.80-6.88 (m, 1H), 5.67-5.77 (m, 1H), 4.56-4.65 (m, 2H), 4.25-4.33 (m, 2H), 4.21 (d, J=2.51 Hz, 2H), 3.09 (s, 3H), 2.13-2.24 (m, 1H), 1.84-1.94 (m, 1H), 0.92-1.01 (m, 4H), 0.63-0.74 (m, 4H); MS (ES): m/z 470.2 [M+H]$^+$.

Step-III: 1-(3-Cyclopropyl-4-(2-(pyrrolidin-1-yl)ethoxy)phenyl)-3-(4-cyclopropylphenoxy)-1H-pyrrol-2(5H)-one Example 205

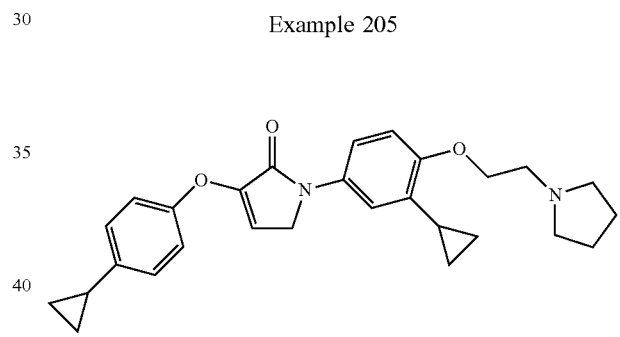

The title compound was obtained as an off-white solid (25 mg, 26% yield) from the intermediate B5-2 by following a procedure, similar to that for B1.

Examples 206 to 211 in Table F were prepared by treating the intermediate B5-2 with an appropriate amine in a similar manner to that employed for the preparation of Example 205.

Procedure-B6

Example 212

3-([1,1'-Biphenyl]-4-yloxy)-1-(4-(2-(3-hydroxyazetidin-1-yl)ethoxy)-3-methoxyphenyl)-1H-pyrrol-2(5H)-one

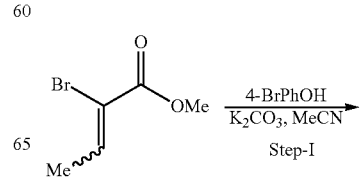

111
-continued

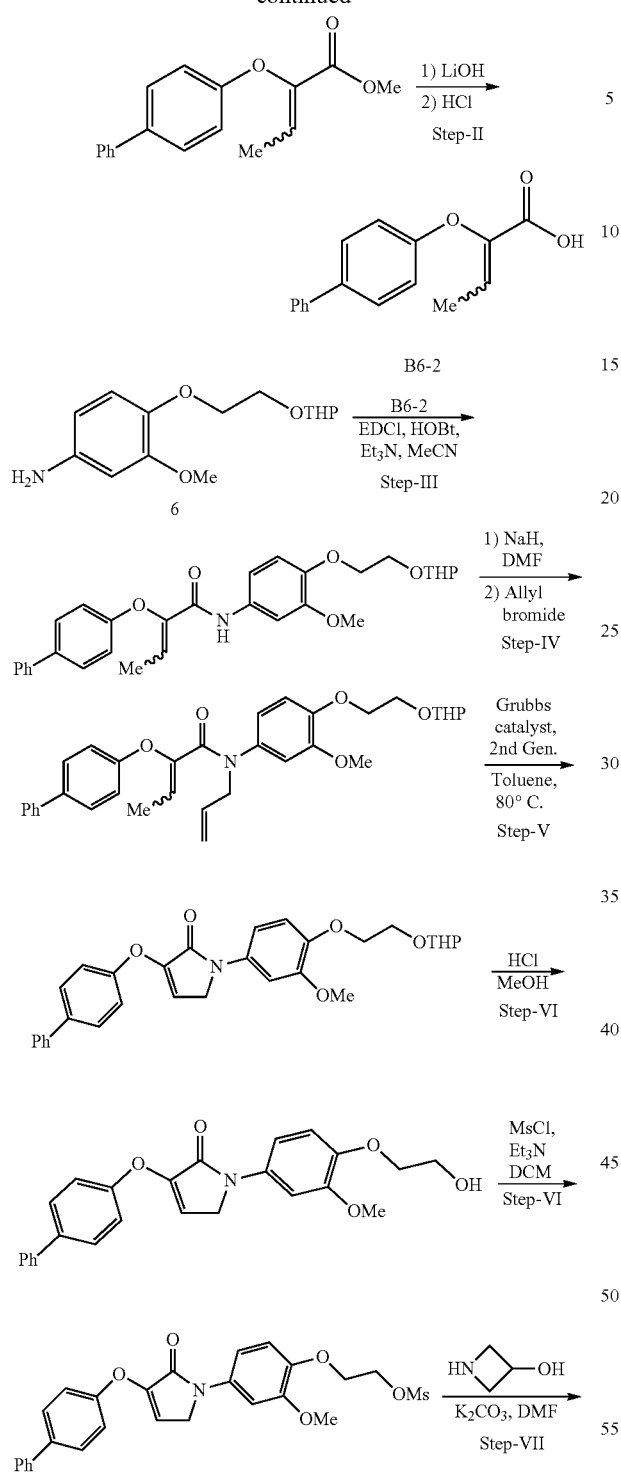

112

Step-I: Methyl 2-(biphenyl-4-yloxy)but-2-enoate (intermediate B6-1)

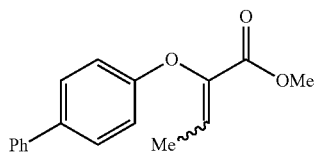

Methyl 2-bromo-2-butenoate (cis/trans) (7.3 g, 40.8 mmol) was added dropwise to a stirring solution of 4-phenylphenol (6.94 g, 40.8 mmol) and $K_2CO_3$ (16.91 g, 122 mmol) in acetonitrile (100 mL) at 0° C. After heating at reflux for 16 h at 80° C., the reaction mixture was filtered through a short pad of Celite®. The Celite® pad was rinsed with acetonitrile prior to concentration of the filtrate under vacuum to afford the title product (11 g, 40.2 mmol, 99% yield) as a light-brownish oil. The crude product was taken to the next step as such. $^1$H NMR (400 MHz, chloroform-d) δ 7.48-7.59 (m, 4H), 7.42 (t, J=7.65 Hz, 2H), 7.32 (d, J=7.28 Hz, 1H), 6.95-7.03 (m, 2H), 6.75 (d, J=7.03 Hz, 1H), 3.74 (s, 3H), 1.82 (d, J=7.03 Hz, 3H); MS (ES): m/z 286.2 $[M+H_2O]^+$.

Step-II: 2-(Biphenyl-4-yloxy)but-2-enoic acid (intermediate B6-2)

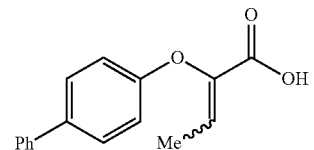

To a stirring solution of methyl 2-([1,1'-biphenyl]-4-yloxy)but-2-enoate (12 g, 44.7 mmol) in a mixture of THF (120 mL) and water (60 mL), lithium hydroxide hydrate (9.38 g, 224 mmol) was added at 0° C. The mixture was gradually warmed to ambient temperature and then heated at 80° C. for 20 h. The reaction mixture was concentrated in vacuo to remove THF. The residual aqueous suspension was acidified with 1.5N aqueous hydrochloric acid to pH=1. The precipitated solid was filtered, washed with cold water (100 mL), petroleum ether (50 mL), and dried to afford the title product (7 g, 27.0 mmol, 60% yield) as an off-white solid. $^1$H NMR (400 MHz, DMSO-$d_6$) δ 7.56-7.64 (m, 4H), 7.40-7.49 (m, 2H), 7.28-7.36 (m, 1H), 6.91-7.01 (m, 2H), 6.63-6.74 (m, 1H), 1.73 (d, J=7.03 Hz, 3H); MS (ES): m/z 253.0 [M−H]$^+$.

Step-III: 2-(Biphenyl-4-yloxy)-N-(3-methoxy-4-(2-(tetrahydro-2H-pyran-2-yloxy)ethoxy)phenyl)but-2-enamide (intermediate B6-3)

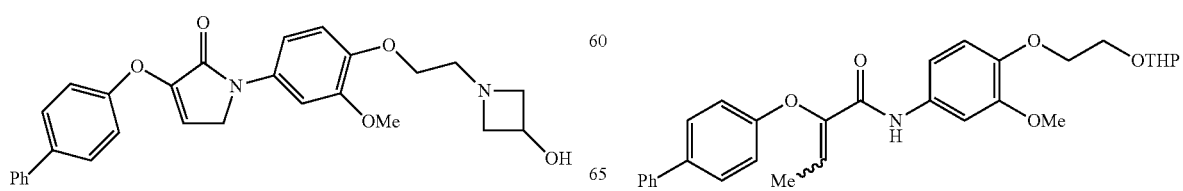

The title compound was obtained as a light-brownish liquid (12.75 g, 24.05 mmol, 92% yield) from the intermediates B1-6 and B6-2 by following a procedure, similar to that for B1-7 (Purification: CombiFlash instrument [20% ethyl acetate in hexane; 120.0 g silica gel column]. $^1$H NMR (400 MHz, chloroform-d) δ 7.86-7.96 (m, 1H), 7.56 (d, J=8.78 Hz, 4H), 7.39-7.48 (m, 3H), 7.28-7.37 (m, 1H), 7.11 (d, J=8.78 Hz, 2H), 6.84 (d, J=14.05 Hz, 3H), 4.63-4.72 (m, 1H), 4.15-4.21 (m, 2H), 3.98-4.06 (m, 1H), 3.85 (s, 5H), 3.44-3.55 (m, 1H), 1.78-1.90 (m, 1H), 1.72 (d, J=7.28 Hz, 4H), 1.56-1.64 (m, 2H), 1.44-1.53 (m, 2H); MS (ES): m/z 502.2 [M–H]$^+$.

Step-IV: 2-([1,1'-Biphenyl]-4-yloxy)-N-allyl-N-(3-methoxy-4-(2-((tetrahydro-2H-pyran-2-yl)oxy)ethoxy)phenyl)but-2-enamide (intermediate B6-4)

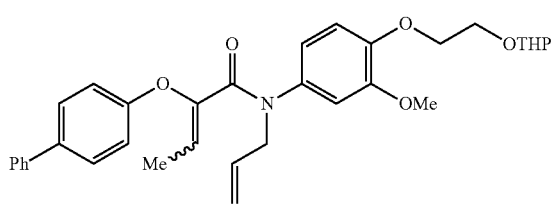

The title compound was obtained as an off-white solid (6.15 g, 10.63 mmol, 94% yield) from the intermediate B6-3 by following a procedure, similar to that for B1-8 (Purification: CombiFlash instrument [15-20% ethyl acetate in hexane; 40.0 g silica gel column]. $^1$H NMR (400 MHz, chloroform-d) δ 7.50-7.57 (m, 2H), 7.39-7.48 (m, 4H), 7.29-7.36 (m, 1H), 6.83-6.90 (m, 1H), 6.61-6.72 (m, 2H), 6.49-6.56 (m, 1H), 6.28-6.40 (m, 2H), 5.68-5.80 (m, 1H), 4.88-5.05 (m, 2H), 4.70-4.76 (m, 1H), 4.22-4.28 (m, 2H), 4.16-4.22 (m, 2H), 4.05-4.14 (m, 1H), 3.81-3.96 (m, 2H), 3.70 (s, 3H), 3.48-3.59 (m, 1H), 1.56-1.92 (m, 9H); MS (ES): m/z 544.4 [M–H]$^+$.

Step-V: 3-(Biphenyl-4-yloxy)-1-(3-methoxy-4-(2-(tetrahydro-2H-pyran-2-yloxy)ethoxy)phenyl)-1H-pyrrol-2(5H)-one (intermediate B6-5)

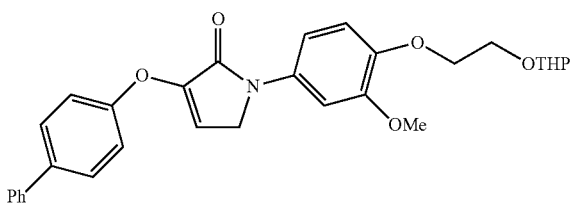

The title compound was obtained as an off-white solid (7.5 g, 14.95 mmol, 56.1% yield) from the intermediate B6-4 by following a procedure, similar to that for B1-9 (Purification: CombiFlash instrument [120 g silica gel column, ethyl acetate:DCM:petroleum ether=1:1:2]. $^1$H NMR (400 MHz, chloroform-d) δ 7.72 (d, J=1.51 Hz, 1H), 7.55-7.65 (m, 4H), 7.41-7.49 (m, 2H), 7.33-7.40 (m, 1H), 7.27 (s, 2H), 6.93-7.00 (m, 2H), 5.92 (s, 1H), 4.67-4.75 (m, 1H), 4.29 (d, J=2.26 Hz, 2H), 4.22 (d, J=4.77 Hz, 2H), 4.02-4.11 (m, 1H), 3.90 (s, 5H), 3.49-3.57 (m, 1H), 1.80-1.89 (m, 1H), 1.69-1.78 (m, 1H), 1.58-1.68 (m, 2H), 1.48-1.55 (m, 2H); MS (ES): m/z 418.2 [M-OTHP]$^+$.

Step-VI: 3-(Biphenyl-4-yloxy)-1-(4-(2-hydroxyethoxy)-3-methoxyphenyl)-1H-pyrrol-2(5H)-one (intermediate B6-6)

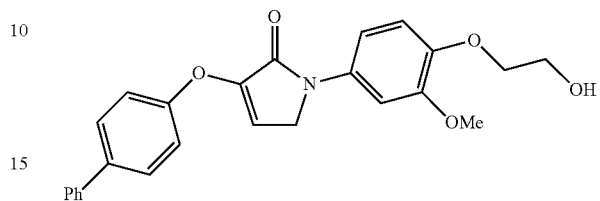

The title compound was obtained as an off-white solid (3.35 g, 7.62 mmol, 96% yield) from the intermediate B6-5 by following a procedure, similar to that for B1-10. $^1$H NMR (400 MHz, DMSO-d$_6$) δ 7.64-7.76 (m, 4H), 7.48 (s, 3H), 7.35-7.42 (m, 1H), 7.29 (d, J=8.78 Hz, 2H), 7.16-7.23 (m, 1H), 6.97-7.05 (m, 1H), 6.46 (s, 1H), 4.80-4.86 (m, 1H), 4.48 (d, J=2.26 Hz, 2H), 3.98 (s, 2H), 3.79 (s, 3H), 3.68-3.76 (m, 2H); MS (ES): m/z 418.2 [M+H]$^+$.

Step-VII: 2-(4-(3-(Biphenyl-4-yloxy)-2-oxo-2,5-dihydro-1H-pyrrol-1-yl)-2-methoxyphenoxy)ethyl methanesulfonate (intermediate B6-7)

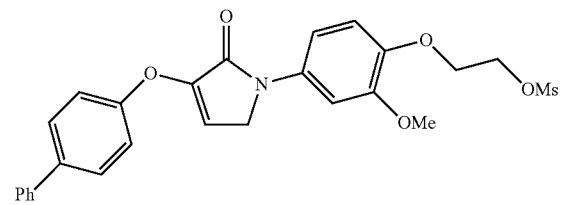 [SMILES: COc1cc(N2CC=C(Oc3ccc(-c4ccccc4)cc3)C2=O)ccc1OCCOS(C)(=O)=O]

The title compound was obtained as a light-pinkish solid (3.6 g, 6.97 mmol, 87% yield) from the intermediate B6-6 by following a procedure, similar to that for B1-11. $^1$H NMR (400 MHz, chloroform-d) δ 7.80 (d, J=1.25 Hz, 1H), 7.53-7.65 (m, 4H), 7.45 (t, J=7.53 Hz, 2H), 7.37 (d, J=7.28 Hz, 1H), 7.22-7.30 (m, 2H), 6.88-6.96 (m, 2H), 5.94 (t, J=2.38 Hz, 1H), 4.56-4.63 (m, 2H), 4.22-4.33 (m, 4H), 3.89 (s, 3H), 3.09-3.17 (m, 3H); MS (ES): m/z 496.2 [M+H]$^+$.

Step-VIII: 3-(Biphenyl-4-yloxy)-1-(4-(2-(3-hydroxyazetidin-1-yl)ethoxy)-3-methoxyphenyl)-1H-pyrrol-2(5H)-one Example 212

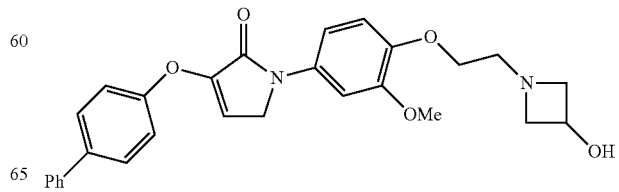

The title compound was obtained as an off-white solid (670 mg, 1.418 mmol, 19.52% yield) from the intermediate B6-7 by following a procedure, similar to that for B1. (Purification: Reverse Phase HPLC [XTERRA® C-18 column [19×300] mm; 5.0µ; Mobile Phase A: 0.1% TFA in water; Mobile Phase B: acetonitrile; Flow Rate: 16.0 mL].

Examples 213 to 231 in Table G were prepared by treating the intermediate B6-7 with an appropriate amine in a similar manner to that employed for the preparation of Example 212.

Procedure-B7

Example 232

3-(4-Cyclopropylphenoxy)-1-(cis-3-(2-(pyrrolidin-1-yl)ethoxy)cyclobutyl)-1H-pyrrol-2(5H)-one

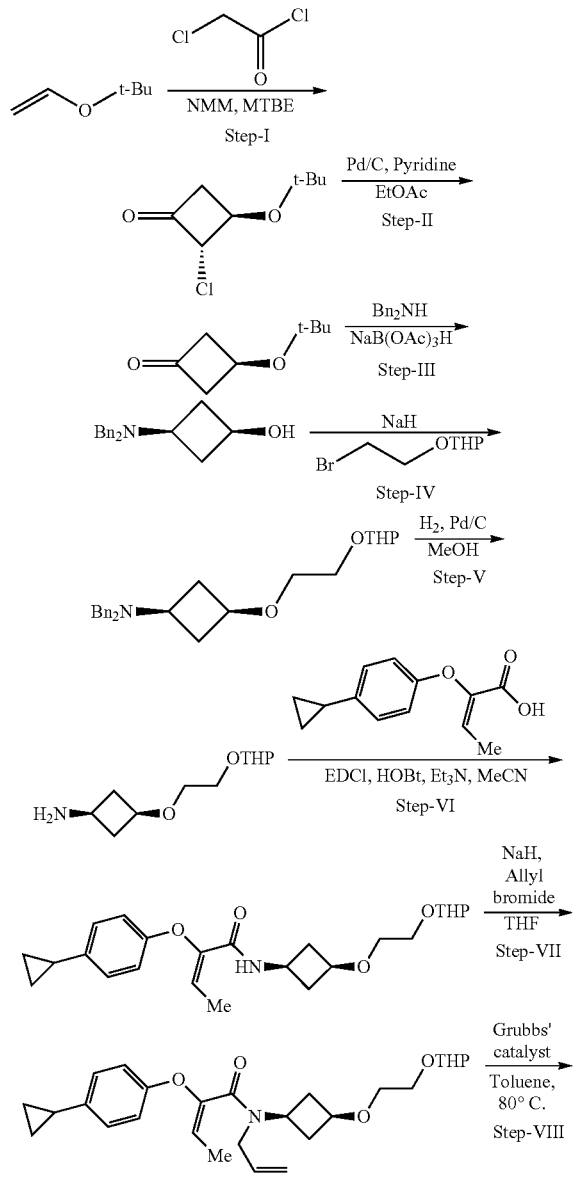

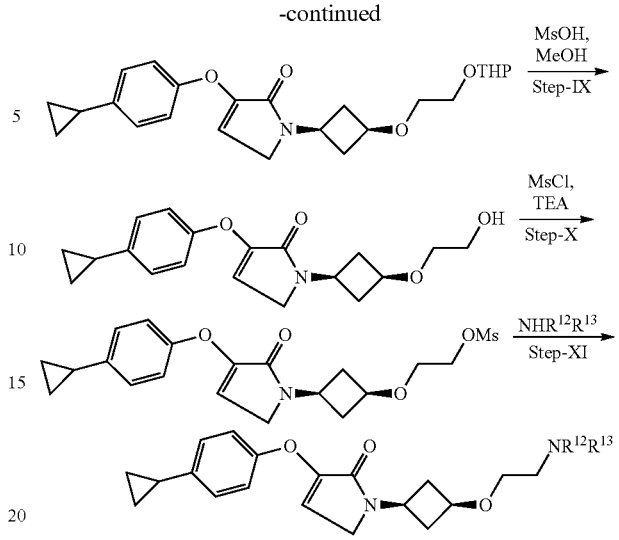

Step-I: (+/−)-3-(tert-Butoxy)-2-chlorocyclobutanone (intermediate B7-1)

A solution of 2-methyl-2-(vinyloxy)propane (100 g, 998 mmol) and 2-chloroacetyl chloride (83.25 mL, 1048 mmol) in methyl t-butyl ether (800 mL) was stirred under nitrogen atmosphere for 30 min prior to being heated to 45° C. After dropwise addition of N-methylmorpholine (132 mL, 1198 mmol), the reaction mixture was stirred at ambient temperature for 1 h before being washed with water and brine, dried over anhydrous sodium sulfate and concentrated to yield the crude product (147 g) as an oil, which was taken for the next step. $^1$H NMR (400 MHz, chloroform-d) δ 4.71-4.77 (m, 1H), 4.24-4.32 (m, 1H), 3.20-3.30 (m, 1H), 3.06-3.16 (m, 1H), 1.27 (s, 9H).

Step-II: 3-(tert-Butoxy)cyclobutanone (intermediate B7-2)

To a solution of (+/−)-3-(tert-Butoxy)-2-chlorocyclobutanone (147 g, 832 mmol) in ethyl acetate (1600 mL), were added with pyridine (236 mL, 2913 mmol), water (1000 mL) and palladium on carbon (10%) (14.7 g, 138 mmol). The mixture was hydrogenated with hydrogen (40 PSI) for overnight. Then the reaction mixture was filtered through Celite® and the organic layer was washed with 6N aqueous hydrogen chloride solution, water, and brine, dried over anhydrous sodium sulfate, and concentrated. The crude obtained was taken for next step. $^1$H NMR (400 MHz, chloroform-d) δ 4.36-4.44 (m, 1H), 3.19 (s, 2H), 3.12 (d, J=5.52 Hz, 2H), 1.23 (s, 9H).

Step-III: cis-3-(Dibenzylamino)cyclobutanol (intermediate B7-3)

To a solution of 3-(tert-butoxy)cyclobutanone (85 g, 598 mmol) in EtOAc (1500 mL), was added dibenzylamine (121 mL, 628 mmol). The reaction was cooled to 0° C. Then sodium triacetoxyborohydride (253 g, 1196 mmol) was added portionwise. The reaction mixture was stirred overnight, and quenched with saturated sodium carbonate solution. The organic layer was then washed with water, and brine, dried over anhydrous sodium sulfate and concentrated in vacuo. The crude product was purified by column chromatography to get the product as a brownish oil (110.5 g), which was taken in hydrochloric acid (250 mL; 6N). The mixture was heated to 50° C. for 3 h. The reaction mass was then cooled with ice bath and made basic (pH ~10) with aqueous sodium hydroxide solution (6N) (500 mL). The reaction mixture was extracted with ethyl acetate. The organic layer was washed with water, brine, dried over anhydrous sodium sulfate and concentrated. The crude product was purified by column chromatography to get product the as yellow oil (68.0 g). $^1$H NMR (400 MHz, chloroform-d) δ 7.20-7.35 (m, 10H), 3.87-3.99 (m, 1H), 3.50 (s, 4H), 2.62-2.73 (m, 1H), 2.43 (s, 2H), 1.71-1.83 (m, 2H); MS (ES): m/z 268.2 [M+H]$^+$; HPLC RT: (a) 5.25 (Analytical HPLC Method A).

Step-IV: cis-N,N-Dibenzyl-3-(2-((tetrahydro-2H-pyran-2-yl)oxy)ethoxy)cyclobutanamine (intermediate B7-4)

To a suspension of sodium hydride (60%) (6.74 g, 281 mmol) in dry DMF (200 mL) under nitrogen atmosphere, cis-3-(dibenzylamino)cyclobutanol (15 g, 56.1 mmol) was added followed by sodium iodide (12.61 g, 84 mmol). The mixture was then stirred at 50° C. for 1 h. Then 2-(2-bromoethoxy)tetrahydro-2H-pyran (16.95 mL, 112 mmol) was added. The reaction mixture was heated to 130° C. overnight. The organic layer was washed with water, brine, dried over anhydrous sodium sulfate and concentrated in vacuo to get the crude product as a brownish oil. The crude was purified by ISCO to get the product as yellowish viscous oil (15.4 g). $^1$H NMR (400 MHz, chloroform-d) δ 7.18-7.35 (m, 10H), 4.58-4.63 (m, 1H), 3.77-3.91 (m, 2H), 3.43-3.70 (m, 9H), 2.73 (s, 1H), 2.29-2.40 (m, 2H), 1.78-1.92 (m, 3H), 1.71 (d, J=3.25 Hz, 1H), 1.46-1.65 (m, 4H); MS (ES): m/z 396.2 [M+H]$^+$; HPLC RT: (a) 6.57 (Analytical HPLC Method A); (b): 8.26 (Analytical HPLC Method B).

Step-V: cis-3-(2-(Tetrahydro-2H-pyran-2-yloxy)ethoxy)cyclobutanamine (intermediate B7-5)

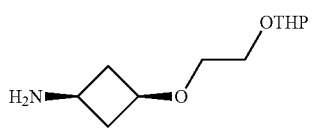

To a stirring solution of N,N-dibenzyl-3-(2-((tetrahydro-2H-pyran-2-yl)oxy)ethoxy)cyclobutan-amine (6.5 g, 16.43 mmol) in MeOH (100 mL), was added Pd/C (1.2 g, 11.28 mmol). After the reaction mixture was degassed, the reaction was stirred for two hours under H$_2$ gas at room temperature. The reaction mixture was filtered through Celite® pad, and washed with methanol (200 mL). The filtrate was concentrated under vacuum to afford 3-(2-((tetrahydro-2H-pyran-2-yl)oxy)ethoxy)cyclobutanamine (3.7 g, 16.46 mmol, ~100% yield) as a light-brownish liquid. $^1$H NMR (400 MHz, DMSO-d$_6$) δ 4.54 (d, J=4.27 Hz, 1H), 3.67 (br. s., 2H), 3.52 (s, 1H), 3.35-3.47 (m, 4H), 2.77 (s, 1H), 2.51 (td, J=1.79, 3.70 Hz, 2H), 2.38-2.49 (m, 2H), 1.55-1.75 (m, 2H), 1.41-1.49 (m, 4H).

Step-VI: 2-(4-Cyclopropylphenoxy)-N-((cis-3-(2-(tetrahydro-2H-pyran-2-yloxy)ethoxy)cyclobutyl)but-2-enamide (intermediate B7-6)

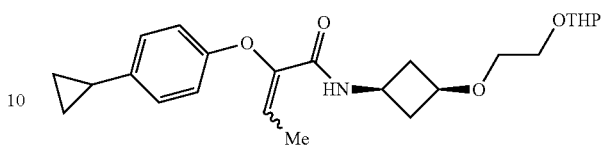

The title compound was obtained as a light-brownish liquid (5.25 g, 11.88 mmol, 63.9% yield) from the reaction of intermediate B7-5 with B1-2 described in Procedure B1 under the conditions employed for the synthesis of B1-5. [Purification: CombiFlash instrument (120 g silica gel column, 20% ethyl acetate in petroleum ether)]. $^1$H NMR (400 MHz, DMSO-d$_6$) δ 8.08-8.20 (m, 1H), 6.96-7.09 (m, 2H), 6.73-6.85 (m, 2H), 6.27-6.39 (m, 1H), 4.50-4.63 (m, 1H), 3.61-3.89 (m, 4H), 3.37-3.51 (m, 4H), 2.39-2.48 (m, 2H), 1.83-1.90 (m, 2H), 1.56 (d, J=7.28 Hz, 10H), 0.82-0.94 (m, 2H), 0.54-0.65 (m, 2H); MS (ES): m/z 414.2 [M–H]$^+$.

Step-VII: N-Allyl-2-(4-cyclopropylphenoxy)-N-(cis-3-(2-(tetrahydro-2H-pyran-2-yloxy)ethoxy)cyclobutyl)but-2-enamide (intermediate B7-7)

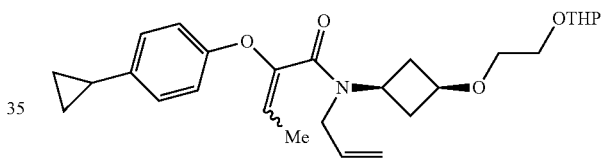

The title compound was obtained as a light-brownish liquid (6 g, 13.17 mmol, 99% yield) from the intermediate B7-6 by following a procedure, similar to that for B1-8 [Purification: CombiFlash instrument (40 g silica gel column, 15-20% ethyl acetate in petroleum ether)]. $^1$H NMR (400 MHz, chloroform-d) δ 6.94-6.99 (m, 2H), 6.84-6.90 (m, 2H), 5.83-5.95 (m, 1H), 5.53-5.71 (m, 1H), 4.76-5.03 (m, 2H), 4.58-4.66 (m, 1H), 3.93-4.03 (m, 2H), 3.78-3.92 (m, 3H), 3.64-3.74 (m, 1H), 3.45-3.54 (m, 4H), 2.47-2.59 (m, 2H), 1.79-1.99 (m, 4H), 1.71 (d, J=7.03 Hz, 4H), 1.55 (s, 4H), 0.88-0.93 (m, 2H), 0.56-0.65 (m, 2H); MS (ES): m/z 372.2 [M-OTHP]$^+$.

Step-VIII: 3-(4-Cyclopropylphenoxy)-1-(cis-3-(2-(tetrahydro-2H-pyran-2-yloxy)ethoxy)cyclobutyl)-1H-pyrrol-2(5H)-one (intermediate B7-8)

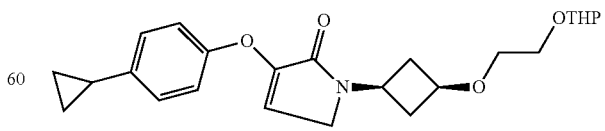

The title compound was obtained as an off-white solid (4 g, 8.61 mmol, 65.4% yield) from the intermediate B7-7 by following a procedure, similar to that for B1-9 [Purification: CombiFlash instrument (120 g silica gel column, 25% ethyl acetate and 25% chloroform in petroleum ether)]. $^1$H NMR (400 MHz, chloroform-d) δ 7.05 (d, J=5.77 Hz, 4H), 5.66 (s, 1H), 4.58-4.68 (m, 1H), 4.38-4.51 (m, 1H), 3.86 (d, J=2.26 Hz, 5H), 3.57 (s, 4H), 2.61-2.72 (m, 2H), 2.06-2.17 (m, 2H), 1.79-1.93 (m, 2H), 1.68-1.78 (m, 1H), 1.57-1.66 (m, 2H), 1.47-1.52 (m, 2H), 0.91-1.00 (m, 2H), 0.63-0.70 (m, 2H); MS (ES): m/z 412.2 [M−H]$^+$.

Step-IX: 3-(4-Cyclopropylphenoxy)-1-(cis-3-(2-hydroxyethoxy)cyclobutyl)-1H-pyrrol-2(5H)-one (intermediate B7-9)

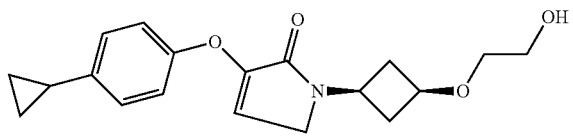 [SMILES: O=C1C(Oc2ccc(C3CC3)cc2)=CCN1[C@H]1C[C@@H](OCCO)C1]

The title compound was obtained as an off-white solid (2.5 g, 7.44 mmol, 76% yield) from the intermediate B7-8 by following a procedure, similar to that for B1-10. $^1$H NMR (400 MHz, DMSO-d$_6$) δ 7.07-7.14 (m, 2H), 6.98-7.05 (m, 2H), 6.03 (s, 1H), 4.10-4.24 (m, 1H), 3.96 (d, J=2.26 Hz, 2H), 3.72-3.82 (m, 1H), 3.47-3.51 (m, 2H), 3.30-3.35 (m, 3H), 2.45-2.50 (m, 2H), 2.02-2.15 (m, 2H), 1.86-1.96 (m, 1H), 0.94 (dd, J=2.13, 8.41 Hz, 2H), 0.60-0.69 (m, 2H); MS (ES): m/z 330.2[M+H]$^+$; HPLC RT: a) 7.86 min (Analytical HPLC Method A); b) 7.5 min (Analytical HPLC Method B).

Step-X: 2-(cis-3-(3-(4-Cyclopropylphenoxy)-2-oxo-2,5-dihydro-1H-pyrrol-1-yl)cyclobutoxy)ethyl methanesulfonate (intermediate B7-10)

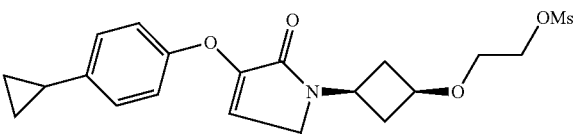 [SMILES: CS(=O)(=O)OCCO[C@H]1C[C@@H](N2CC=C(Oc3ccc(C4CC4)cc3)C2=O)C1]

The title compound was obtained as an light-pink colored solid (2.95 g, 7.02 mmol, 93% yield) from the intermediate B7-9 by following a procedure, similar to that for B1-11. $^1$H NMR (400 MHz, chloroform-d) δ 6.96-7.11 (m, 4H), 5.67 (s, 1H), 4.39-4.50 (m, 1H), 4.30-4.39 (m, 2H), 3.86 (d, J=2.51 Hz, 2H), 3.75-3.82 (m, 1H), 3.60-3.68 (m, 2H), 3.06 (s, 3H), 2.62-2.73 (m, 2H), 2.07-2.18 (m, 2H), 1.84-1.94 (m, 1H), 0.96 (dd, J=1.76, 8.53 Hz, 2H), 0.62-0.71 (m, 2H); MS (ES): m/z 408.2 [M+H]$^+$.

Step-XI: 3-(4-Cyclopropylphenoxy)-1-(cis-3-(2-(pyrrolidin-1-yl)ethoxy)cyclobutyl)-1H-pyrrol-2(5H)-one Example 232

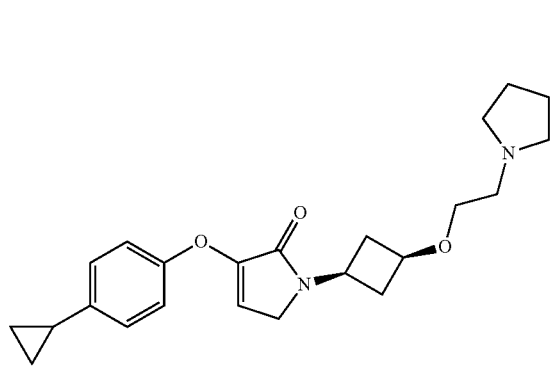 [SMILES: O=C1C(Oc2ccc(C3CC3)cc2)=CCN1[C@H]1C[C@@H](OCCN2CCCC2)C1]

The title compound was obtained as an off-white solid (20 mg, 0.052 mmol, 21.50% yield) from the intermediate B7-10 by following a procedure, similar to that for B1.

Examples 233 to 241 in Table H were prepared by treating the intermediate B7-10 with an appropriate amine in a similar manner to that employed for the preparation of Example 232.

Procedure-B8

Example 242 trans-3-(4-Cyclopropylphenoxy)-1-(-4-(2-morpholinoethoxy)cyclohexyl)-1H-pyrrol-2(5H)-one

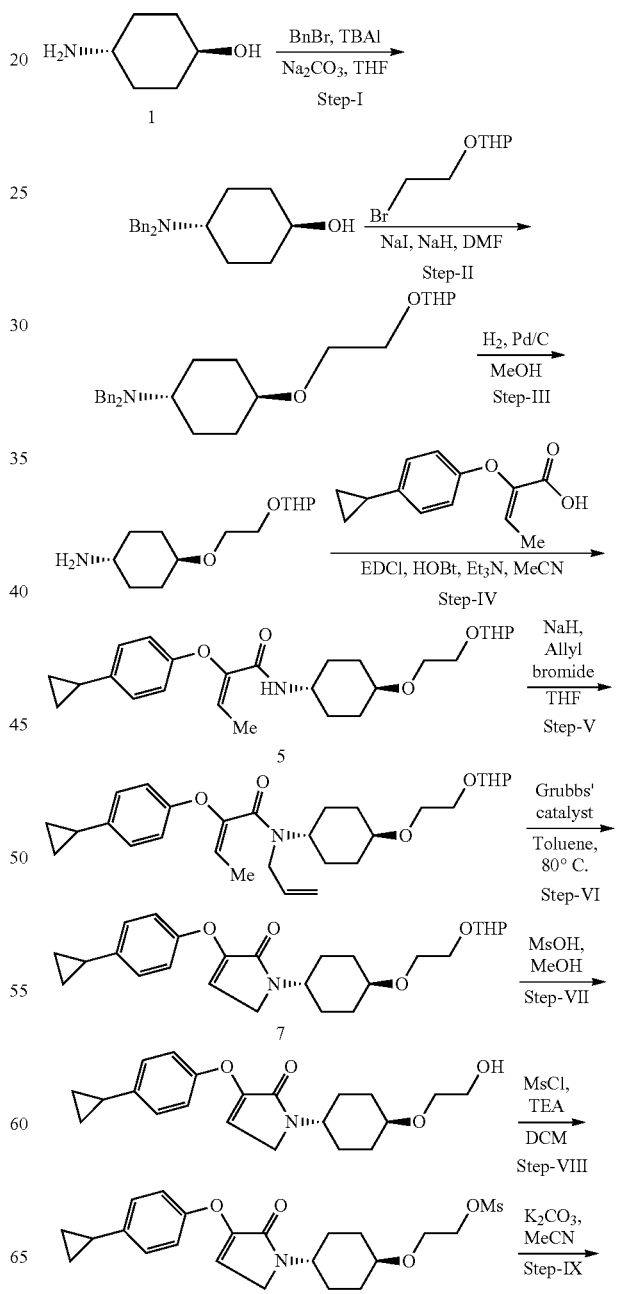

-continued

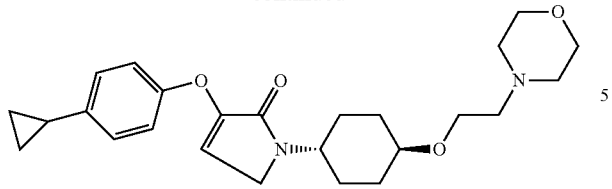

Step-I: trans-4-(Dibenzylamino)cyclohexanol (intermediate B8-1)

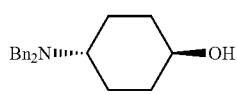

Benzyl bromide (11.36 mL, 96 mmol) was subsequently added dropwise to a stirring solution of trans-4-aminocyclohexanol (5 g, 43.4 mmol) and potassium carbonate (21 g, 152 mmol) in acetonitrile (100 mL). The reaction mixture was stirred at 90° C. for 16 h, cooled to ambient temperature, filtered through a Celite® pad, and washed with ethyl acetate. The filtrate was concentrated in vacuo. The residue was purified using CombiFlash (40.0 g silica gel column; 2% methanol in DCM), to obtain the title product (6 g, 20.31 mmol, 46.8% yield), as an off-white solid. $^1$H NMR (400 MHz, chloroform-d) δ 7.34-7.38 (m, 4H), 7.26-7.31 (m, 4H), 7.15-7.24 (m, 2H), 3.61 (s, 5H), 2.52 (s, 1H), 1.96-2.06 (m, 2H), 1.88 (br. s., 2H), 1.43 (d, J=15.31 Hz, 2H), 1.21 (br. s., 2H); MS (ES): m/z 296.2 [M+H]$^+$.

Step-II: trans-N,N-Dibenzyl-4-(2-(tetrahydro-2H-pyran-2-yloxy)ethoxy)cyclohexanamine (intermediate B8-2)

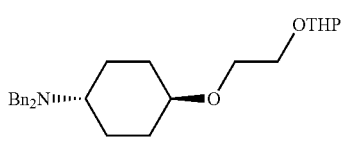

To a stirring solution of trans-4-(dibenzylamino)cyclohexanol (7 g, 23.70 mmol) in DMF (70 mL) at 0° C., NaH (2.84 g, 118 mmol) was added. Then 2-(2-bromoethoxyl) tetrahydro-2H-pyran (10.74 mL, 71.1 mmol) was slowly added. The reaction mixture was then refluxed at 90° C. for 16 h and cooled to room temperature. The reaction mixture was diluted with ethyl acetate and, filtered through Celite® pad. The filtrate was concentrated in vacuo. The residue was dissolved in ethyl acetate (300 mL), and the solution was washed with water and brine, dried over anhydrous sodium sulfate, and concentrated in vacuo. The residue was purified by using CombiFlash instrument (120 g silica gel column, 70% ethyl acetate in petroleum ether) to afford the desired product (5.8 g, 13.69 mmol, 57.8% yield) as a light-yellowish solid. $^1$H NMR (400 MHz, chloroform-d) δ 7.33-7.39 (m, 4H), 7.26-7.31 (m, 4H), 7.16-7.23 (m, 2H), 4.62 (dd, J=3.14, 4.14 Hz, 1H), 3.81 (s, 2H), 3.45-3.65 (m, 8H), 3.15-3.27 (m, 1H), 2.46-2.58 (m, 1H), 2.05 (br. s., 2H), 1.89 (br. s., 2H), 1.75-1.86 (m, 1H), 1.65-1.75 (m, 1H), 1.46-1.57 (m, 4H), 1.31-1.44 (m, 2H), 1.09-1.23 (m, 2H); MS (ES): m/z 424.2 [M+H]$^+$.

Step-III: trans-4-(2-(Tetrahydro-2H-pyran-2-yloxy)ethoxy)cyclohexanamine (intermediate B8-3)

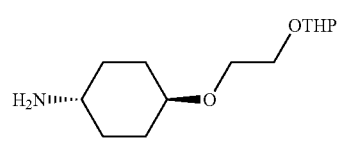

The title product was obtained (1.0 g, 4.11 mmol, 87% yield) as a light-brownish liquid from the intermediate B8-2 by following a procedure, similar to that of B5-5. $^1$H NMR (400 MHz, DMSO-d$_6$) δ 4.55-4.64 (m, 1H), 3.72-3.81 (m, 1H), 3.63-3.71 (m, 1H), 3.51-3.57 (m, 2H), 3.41-3.49 (m, 2H), 3.16-3.25 (m, 2H), 1.87-1.97 (m, 2H), 1.68-1.78 (m, 3H), 1.57-1.65 (m, 1H), 1.42-1.53 (m, 4H), 0.97-1.21 (m, 4H).

Step-IV: 2-(4-Cyclopropylphenoxy)-N-(trans-4-(2-(tetrahydro-2H-pyran-2-yloxy)ethoxy)cyclohexyl)but-2-enamide (intermediate B8-4)

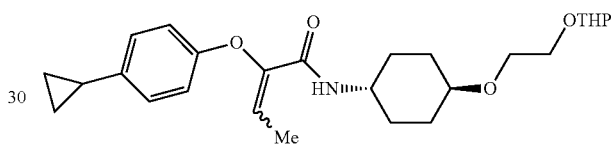

The title compound was obtained as a light-brownish oil (7 g, 14.83 mmol, 80% yield) from the reaction of intermediate B8-3 with B1-2 described in Procedure B1 under the conditions employed for the synthesis of B1-5. (Purification: CombiFlash instrument [120 g silica gel column, 20% ethyl acetate in petroleum ether]). $^1$H NMR (400 MHz, chloroform-d) δ 6.94-7.04 (m, 2H), 6.80-6.88 (m, 2H), 6.59-6.69 (m, 1H), 5.95-6.08 (m, 1H), 4.55-4.67 (m, 1H), 4.06-4.17 (m, 1H), 3.70-3.92 (m, 3H), 3.56-3.63 (m, 2H), 3.45-3.53 (m, 1H), 3.15-3.27 (m, 1H), 1.88-1.98 (m, 4H), 1.66-1.86 (m, 3H), 1.61 (d, J=7.25 Hz, 7H), 1.29-1.42 (m, 2H), 1.01-1.14 (m, 2H), 0.85-0.97 (m, 2H), 0.57-0.68 (m, 2H); MS (ES): m/z 442.2[M−H]$^+$.

Step-V: N-Allyl-2-(4-cyclopropylphenoxy)-N-(trans-4-(2-(tetrahydro-2H-pyran-2-yloxy)ethoxy)cyclohexyl)but-2-enamide (intermediate B8-5)

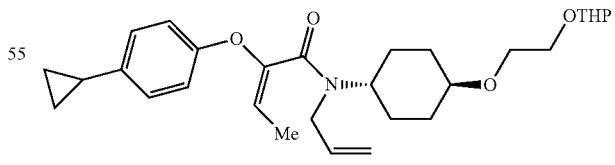

The title compound was obtained as a light-brownish oil (3.5 g, 6.51 mmol, 96% yield) from the intermediate B8-4 by following a procedure, similar to that for B1-8 (Purification: CombiFlash instrument [120 g silica gel column, 15-20% ethyl acetate in petroleum ether]). $^1$H NMR (300 MHz, chloroform-d) δ 6.77-7.04 (m, 4H), 5.81-5.95 (m, 1H), 5.55-5.77 (m, 1H), 4.82-5.33 (m, 2H), 4.59-4.71 (m, 1H), 3.75-4.18 (m, 5H), 3.63 (d, J=3.78 Hz, 4H), 3.11-3.29 (m, 1H), 2.06 (s, 2H), 1.85 (br. s., 2H), 1.68-1.77 (m, 4H), 1.52-1.67 (m, 10H), 0.88-0.92 (m, 2H), 0.62 (dd, J=1.79, 5.00 Hz, 2H); MS (ES): m/z 484.4 [M+H]$^+$.

Step-VI: 3-(4-Cyclopropylphenoxy)-1-(trans-4-(2-(tetrahydro-2H-pyran-2-yloxy)ethoxy)cyclohexyl)-1H-pyrrol-2(5H)-one (intermediate B8-6)

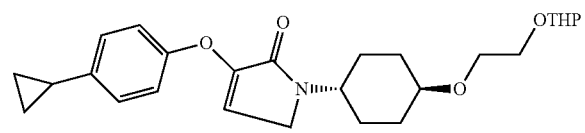

The title compound was obtained as an off-white solid (2.5 g, 5.66 mmol, 78% yield) from the intermediate B8-5 by following a procedure, similar to that for B1-9 (Purification: CombiFlash instrument [120 g silica gel column, 25% ethyl acetate and 25% DCM in petroleum ether]). $^1$H NMR (400 MHz, chloroform-d) δ 7.05 (d, J=2.26 Hz, 4H), 5.60 (s, 1H), 4.59-4.68 (m, 1H), 4.04-4.17 (m, 1H), 3.80-3.93 (m, 2H), 3.74 (d, J=2.26 Hz, 2H), 3.64 (d, J=4.27 Hz, 3H), 3.45-3.54 (m, 1H), 3.22-3.33 (m, 1H), 2.10-2.18 (m, 2H), 1.89 (br. s., 7H), 1.46 (d, J=9.29 Hz, 6H), 0.92-1.00 (m, 2H), 0.66 (d, J=6.78 Hz, 2H); MS (ES): m/z 440.2[M−H]$^+$.

Step-VII: 3-(4-Cyclopropylphenoxy)-1-(trans-4-(2-hydroxyethoxy)cyclohexyl)-1H-pyrrol-2(5H)-one (intermediate B8-7)

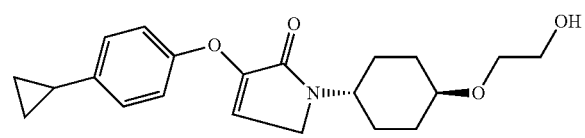 [SMILES: O=C1C(Oc2ccc(C3CC3)cc2)=CCN1[C@H]1CC[C@H](OCCO)CC1]

The title compound was obtained as an off-white solid (1.5 g, 4.15 mmol, 73.4% yield) from the intermediate B8-6 by following a procedure, similar to that for B1-10. $^1$H NMR (400 MHz, chloroform-d) δ 7.05 (d, J=2.26 Hz, 4H), 5.56-5.68 (m, 1H), 4.05-4.18 (m, 1H), 3.67-3.81 (m, 4H), 3.54-3.63 (m, 2H), 3.22-3.33 (m, 1H), 2.10-2.18 (m, 2H), 1.82-2.01 (m, 5H), 1.40-1.48 (m, 3H), 0.90-1.00 (m, 2H), 0.62-0.72 (m, 2H); MS (ES): m/z 358.2[M+H]$^+$.

Step-VIII: 2-(trans-4-(3-(4-Cyclopropylphenoxy)-2-oxo-2,5-dihydro-1H-pyrrol-1-yl)cyclohexyloxy)ethyl methanesulfonate (intermediate B8-8)

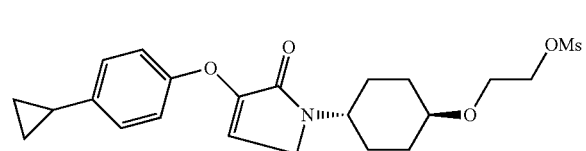

The title compound was obtained as a light-pinkish solid (1.85 g, 4.16 mmol, 99% yield) from the intermediate B8-7 by following a procedure, similar to that for B1-11. $^1$H NMR (400 MHz, chloroform-d) δ 7.05 (d, J=2.50 Hz, 4H), 5.56-5.68 (m, 1H), 4.30-4.42 (m, 2H), 4.05-4.18 (m, 1H), 3.70-3.80 (m, 4H), 3.24-3.35 (m, 1H), 3.06 (s, 3H), 2.07-2.18 (m, 2H), 1.82-1.98 (m, 4H), 1.43-1.49 (m, 3H), 0.93-1.01 (m, 2H), 0.61-0.71 (m, 2H); MS (ES): m/z 436.2 [M+H]$^+$.

Step-IX: 3-(4-Cyclopropylphenoxy)-1-(trans-4-(2-morpholinoethoxyl)cyclohexyl)-1H-pyrrol-2(5M-one Example 242

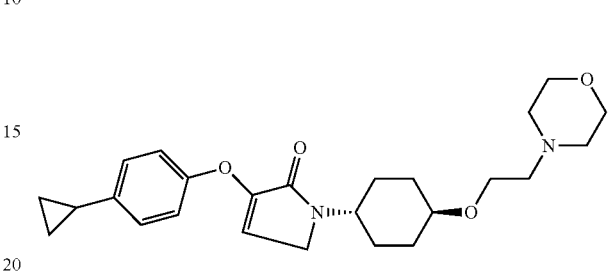

The title compound was obtained as a colorless solid (1.85 g, 4.16 mmol, 99% yield) from the intermediate B8-8 by following a procedure, similar to that for B1.

Examples 243 to 251 in Table I were prepared by treating the intermediate B8-8 with an appropriate amine in a similar manner to that employed for the preparation of Example 242.

Procedure B9

Example 252

3-(4-Cyclopropylphenoxy)-1-(1-(2-(pyrrolidin-1-yl)ethyl)-1H-indazol-5-yl)-1H-pyrrol-2(5H)-one

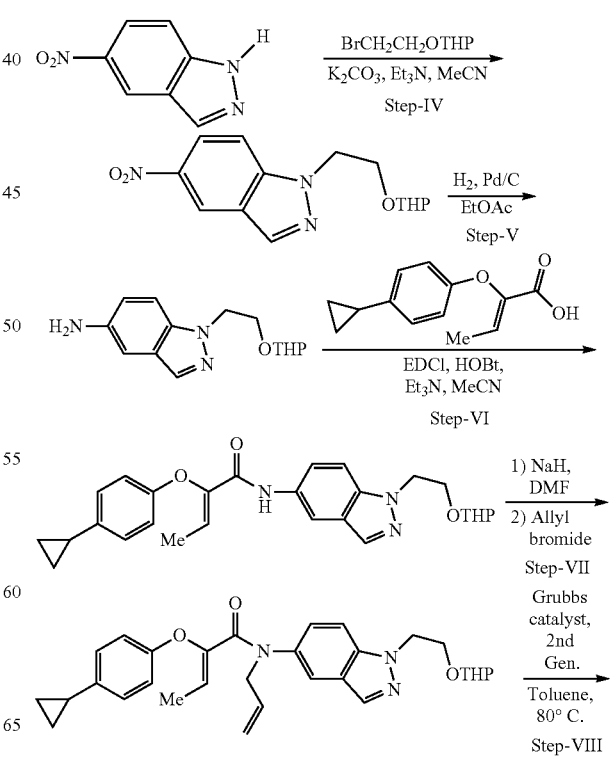

-continued

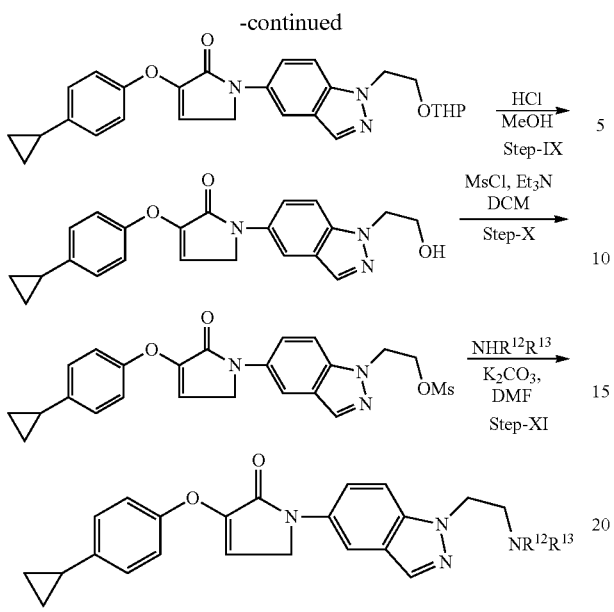

To a stirred solution of 5-nitro-1-(2-((tetrahydro-2H-pyran-2-yl)oxy)ethyl)-1H-indazole (0.2 g, 0.687 mmol) in MeOH (5 mL), was added palladium on carbon (0.073 g, 0.687 mmol). The mixture was stirred under hydrogen atmosphere (balloon) for 2 h. Then reaction mixture was filtered through a Celite® bed. The filtrate was concentrated to dryness and the resulting brownish liquid was used as such (0.15 g, 84%). $^1$H NMR (300 MHz, chloroform-d) δ 7.80 (d, J=0.85 Hz, 1H), 7.32-7.41 (m, 1H), 6.83-6.96 (m, 2H), 4.45-4.59 (m, 3H), 4.06-4.18 (m, 1H), 3.84 (d, J=10.39 Hz, 1H), 3.53-3.61 (m, 1H), 3.32-3.44 (m, 2H), 1.36-1.60 (m, 6H); MS (ES): m/z 178.2 [M-OTHP+H]$^+$.

Step-III: 2-(4-Cyclopropylphenoxy)-N-(1-(2-((tetrahydro-2H-pyran-2-yl)oxy)ethyl)-1H-indazol-5-yl)but-2-enamide (intermediate B9-3)

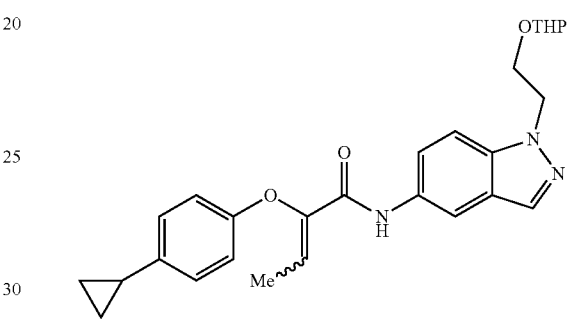

The title compound was obtained as a yellowish liquid (5.3 g, 52% yield) from the reaction of intermediate B9-2 with B1-2 described in Procedure B1 under the conditions employed for the synthesis of B1-5. $^1$H NMR (400 MHz, chloroform-d) δ 7.98-8.07 (m, 2H), 7.93 (d, J=0.75 Hz, 1H), 7.40-7.48 (m, 1H), 7.28-7.36 (m, 1H), 7.04 (s, 2H), 6.96 (s, 2H), 6.76-6.86 (m, 1H), 4.55 (s, 2H), 4.40-4.48 (m, 1H), 4.06-4.19 (m, 1H), 3.75-3.87 (m, 1H), 3.45-3.57 (m, 1H), 3.30-3.41 (m, 1H), 1.81-1.92 (m, 1H), 1.69 (d, J=7.28 Hz, 3H), 1.58-1.65 (m, 1H), 1.34-1.52 (m, 5H), 0.87-0.97 (m, 2H), 0.59-0.68 (m, 2H); MS (ES): m/z 460.1 [M-H]$^+$.

Step-IV: N-Allyl-2-(4-cyclopropylphenoxy)-N-(1-(2-((tetrahydro-2H-pyran-2-yl)oxy)ethyl)-1H-indazol-5-yl)but-2-enamide (intermediate B9-4)

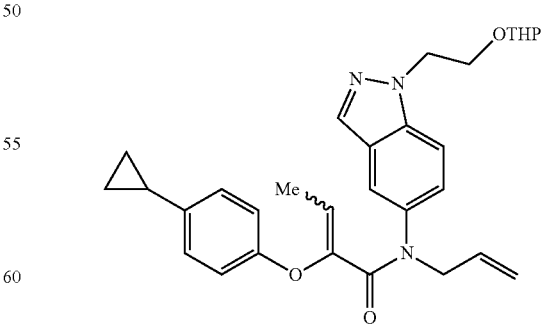

The title compound was obtained as a yellowish liquid (0.32 g, 97% yield) from the intermediate B9-3 by following a procedure, similar to that for B1-8. $^1$H NMR (400 MHz, chloroform-d) δ 7.94 (d, J=0.75 Hz, 1H), 7.42-7.50 (m, 2H), Step-I: 5-Nitro-1-(2-((tetrahydro-2H-pyran-2-yl)oxy)ethyl)-1H-indazole (intermediate B9-1)

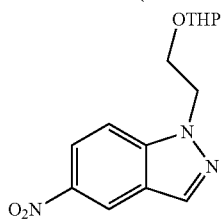

To a stirred solution of 5-nitro-1H-indazole (5.0 g, 30.6 mmol) in DMF (80 mL), was added cesium carbonate (30.0 g, 92 mmol) followed by 2-(2-bromoethoxy)tetrahydro-2H-pyran (12.82 g, 61.3 mmol). The mixture was stirred at room temperature overnight. Then reaction mixture was partitioned between water and ethyl acetate. The organic layer was dried over anhydrous Na$_2$SO$_4$ and concentrated to dryness. The crude product was purified using CombiFlash instrument (120 g silica gel column; 35% ethyl acetate in petroleum ether) to afford the product as a light-yellowish liquid (5.8 g, 65%). $^1$H NMR (400 MHz, chloroform-d) δ 8.71 (dd, J=0.50, 2.25 Hz, 1H), 8.17-8.29 (m, 2H), 7.62 (d, J=9.26 Hz, 1H), 4.61-4.69 (m, 2H), 4.44-4.51 (m, 1H), 4.11-4.21 (m, 1H), 3.85 (ddd, J=5.00, 5.82, 10.69 Hz, 1H), 3.42-3.51 (m, 1H), 3.33-3.42 (m, 1H), 1.31-1.58 (m, 6H); MS (ES): m/z 208.0 [M-OTHP+H]$^+$.

Step-II: 1-(2-((Tetrahydro-2H-pyran-2-yl)oxy)ethyl)-1H-indazol-5-amine (intermediate B9-2)

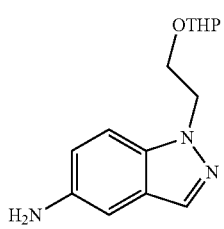

7.11-7.21 (m, 1H), 6.88 (s, 3H), 6.19-6.45 (m, 3H), 5.66-5.80 (m, 1H), 4.94-5.03 (m, 1H), 4.79-4.91 (m, 1H), 4.60 (s, 2H), 4.46-4.53 (m, 1H), 4.11-4.26 (m, 3H), 3.82-3.92 (m, 1H), 3.32-3.54 (m, 2H), 1.77-1.89 (m, 1H), 1.62-1.70 (m, 1H), 1.54-1.60 (m, 3H), 1.34-1.51 (m, 5H), 0.91 (dd, J=1.88, 8.41 Hz, 2H), 0.56-0.65 (m, 2H); MS (ES): m/z 502.2 [M+H]$^+$.

Step-V: 3-(4-Cyclopropylphenoxy)-1-(1-(2-((tetrahydro-2H-pyran-2-yl)oxy)ethyl)-1H-indazol-5-yl)-1H-pyrrol-2(5H)-one (intermediate B9-5)

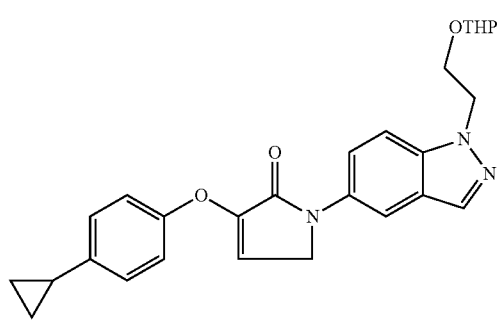

The title compound was obtained as a colorless solid (0.35 g, 76% yield) from the intermediate B9-4 by following a procedure, similar to that for B1-9. $^1$H NMR (400 MHz, chloroform-d) δ 7.91-8.03 (m, 2H), 7.81-7.89 (m, 1H), 7.50-7.60 (m, 1H), 7.10 (s, 4H), 5.77 (s, 1H), 4.60 (s, 2H), 4.45-4.52 (m, 1H), 4.33 (d, J=2.26 Hz, 2H), 4.06-4.19 (m, 1H), 3.80-3.90 (m, 1H), 3.50-3.61 (m, 1H), 3.34-3.43 (m, 1H), 1.86-1.96 (m, 1H), 1.61-1.72 (m, 1H), 1.35-1.54 (m, 5H), 0.92-1.01 (m, 2H), 0.63-0.74 (m, 2H); MS (ES): m/z 458.4 [M−H]$^+$.

Step-VI: 3-(4-Cyclopropylphenoxy)-1-(1-(2-hydroxyethyl)-1H-indazol-5-yl)-1H-pyrrol-2(5H)-one (intermediate B9-6)

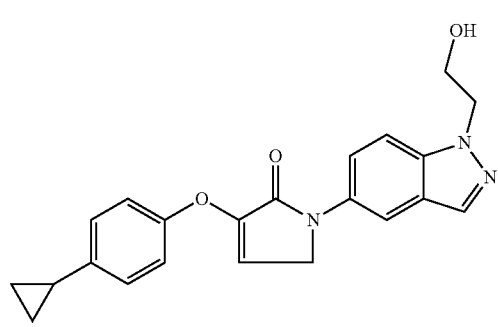 [SMILES: O=C1C(Oc2ccc(C3CC3)cc2)=CCN1c1ccc2c(cnn2CCO)c1]

The title compound was obtained as a colorless solid (2.8 g, 84% yield) from the intermediate B9-5 by following a procedure, similar to that for B1-10. $^1$H NMR (400 MHz, DMSO-d$_6$) δ 8.01-8.13 (m, 2H), 7.77-7.85 (m, 1H), 7.66-7.74 (m, 1H), 7.13 (d, J=7.78 Hz, 4H), 6.16-6.24 (m, 1H), 4.81-4.95 (m, 1H), 4.40-4.53 (m, 4H), 3.75-3.84 (m, 2H), 1.90-2.00 (m, 1H), 0.92-1.00 (m, 2H), 0.62-0.71 (m, 2H); MS (ES): m/z 376.5 [M+H]$^+$; HPLC RT: (a): 9.27 (analytical HPLC Method A); (b): 8.73 (analytical HPLC Method B).

Step-VII: 2-(5-(3-(4-Cyclopropylphenoxy)-2-oxo-2,5-dihydro-1H-pyrrol-1-yl)-1H-indazol-1-yl)ethyl methanesulfonate (intermediate B9-7)

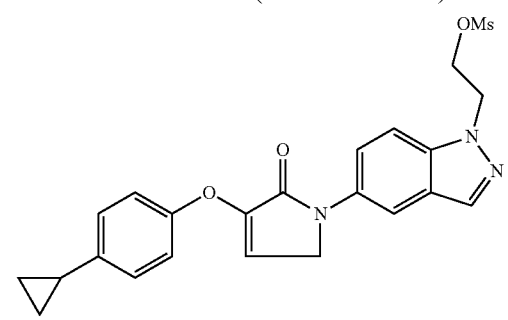

The title compound was obtained as a colorless solid (1.0 g, 81% yield) from the intermediate B9-6 by following a procedure, similar to that for B1-11. $^1$H NMR (400 MHz, chloroform-d) δ 8.01-8.10 (m, 2H), 7.78-7.89 (m, 1H), 7.45-7.55 (m, 1H), 7.10 (s, 4H), 5.75-5.83 (m, 1H), 4.66-4.76 (m, 4H), 4.28-4.39 (m, 2H), 2.71 (s, 3H), 1.86-1.96 (m, 1H), 0.93-1.05 (m, 2H), 0.63-0.74 (m, 2H); MS (ES): m/z 454.2 [M+H]$^+$.

Step-VII: 3-(4-Cyclopropylphenoxy)-1-(1-(2-(pyrrolidin-1-yl)ethyl)-1H-indazol-5-yl)-1H-pyrrol-2(5H)-one Example 252

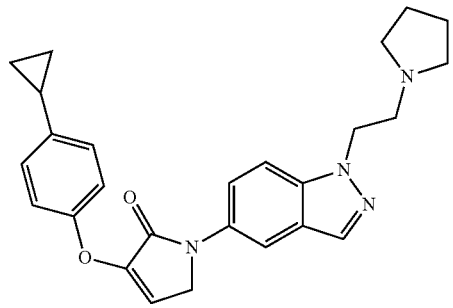 [SMILES: O=C1C(Oc2ccc(C3CC3)cc2)=CCN1c1ccc2c(cnn2CCN2CCCC2)c1]

The title compound was obtained as a colorless solid from the intermediate B9-7 by following a procedure, similar to that for B1 [Purification: reverse phase HPLC [Inertsil ODS (250×19) mm; 5μ; Mobile Phase A: 0.01% TFA in water; Mobile Phase B: acetonitrile; Flow rate: 15.0 mL/min].

Examples 253 to 267 in Table J were prepared by treating the intermediate B9-7 with an appropriate amine in a similar manner to that employed for the preparation of Example 252.

Procedure-B10

Example 268

3-(4-cyclopropylphenoxy)-1-(1-(2-(3-hydroxyazetidin-1-yl)ethyl)-1H-pyrazol-4-yl)-1H-pyrrol-2(5H)-one

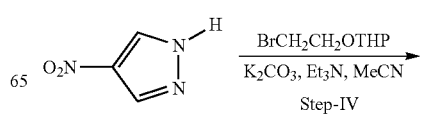

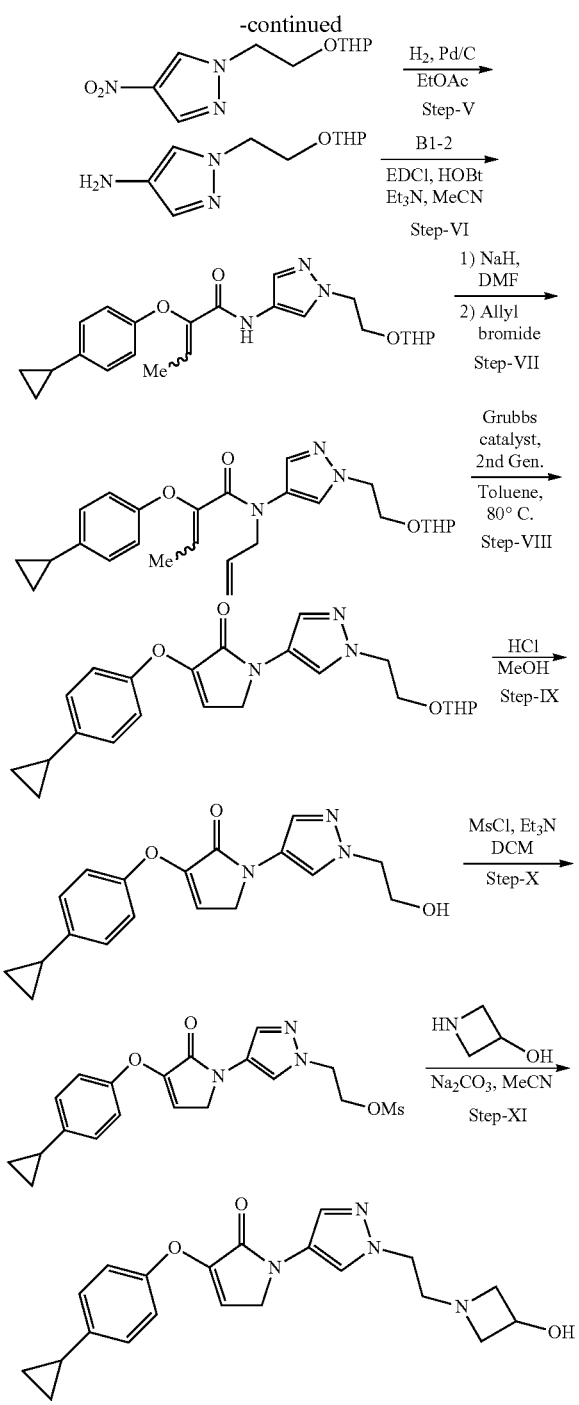

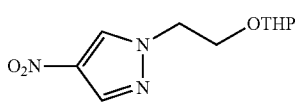

Step-I: 4-Nitro-1-(2-((tetrahydro-2H-pyran-2-yl)oxy)ethyl)-1H-pyrazole (intermediate B10-1)

The title compound was obtained as a yellowish liquid (12.80 g, 60% yield) from 4-nitropyrazole by following a procedure, similar to that for B1-3 [Purification: chromatography on silica (120.0 g column, 5% ethyl acetate in hexane)]. $^1$H NMR (400 MHz, DMSO-d$_6$) δ 8.07 (s, 1H), 7.26 (s, 1H), 4.52-4.60 (s, 1H), 4.32-4.38 (m, 2H), 4.05-4.15 (m, 1H), 3.75-3.82 (m, 1H), 3.70-3.80 (m, 1H), 3.41-3.49 (m, 1H), 1.75-1.95 (m, 2H), 1.40-1.60 (m, 4H).

Step-II: 1-(2-((Tetrahydro-2H-pyran-2-yl)oxy)ethyl)-1H-pyrazol-4-amine (intermediate B10-2)

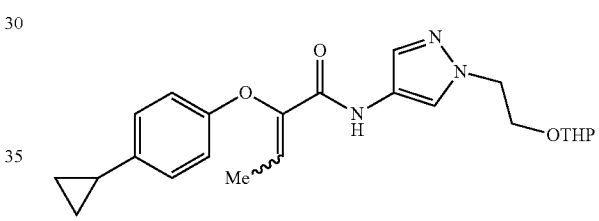

The title compound was obtained as a brown-colored liquid (2.0 g, 9.47 mmol, 91%) from the intermediate B10-1 by following a procedure, similar to that for B1-4. $^1$H NMR (400 MHz, DMSO-d$_6$) δ 7.02-7.08 (m, 1H), 6.87-6.94 (m, 1H), 4.49-4.55 (m, 1H), 4.05-4.13 (m, 2H), 3.74-3.90 (m, 4H), 3.59-3.68 (m, 2H), 1.53-1.75 (m, 2H), 1.32-1.50 (m, 4H).

Step-III: 2-(4-Cyclopropylphenoxy)-N-(1-(2-((tetrahydro-2H-pyran-2-yl)oxy)ethyl)-1H-pyrazol-4-yl)but-2-enamide (intermediate B10-3)

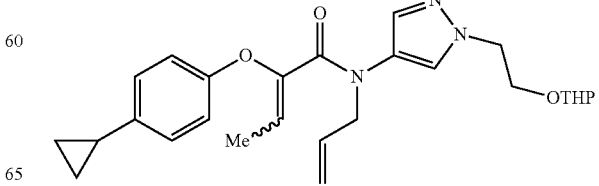

The title compound was obtained as a colorless liquid (3.0 g, 77% yield) from the reaction of intermediate B10-2 with B1-2 described in Procedure B1 under the conditions employed for the synthesis of B1. [Purification: CombiFlash instrument (120 g silica gel column; 25% ethyl acetate in petroleum ether]. $^1$H NMR (400 MHz, DMSO-d$_6$) δ 10.02 (s, 1H), 7.97 (s, 1H), 7.52 (s, 1H), 7.03 (d, J=8.28 Hz, 2H), 6.85 (d, J=8.28 Hz, 2H), 6.46 (d, J=7.28 Hz, 1H), 4.51 (br. s., 1H), 4.21 (br. s., 2H), 3.86 (d, J=5.27 Hz, 1H), 3.67 (d, J=5.27 Hz, 1H), 3.55 (br. s., 1H), 3.33-3.42 (m, 1H), 1.86 (br. s., 1H), 1.51-1.75 (m, 5H), 1.41 (d, J=8.53 Hz, 4H), 0.88 (d, J=7.03 Hz, 2H), 0.59 (d, J=2.51 Hz, 2H); MS (ES): m/z 410.2 [M−H]$^+$.

Step-IV: N-Allyl-2-(4-cyclopropylphenoxy)-N-(1-(2-((tetrahydro-2H-pyran-2-yl)oxy)ethyl)-1H-pyrazol-4-yl)but-2-enamide (intermediate B10-4)

The title compound was obtained as a colorless semi-solid (0.36 g, 65% yield) from the intermediate B10-3 by following a procedure, similar to that for B1-6 [Purification: CombiFlash instrument (24.0 g silica gel column; 40% ethyl acetate in petroleum ether]. $^1$H NMR (400 MHz, DMSO-d$_6$) δ 7.58-7.74 (m, 1H), 7.20-7.36 (m, 1H), 6.78-7.05 (m, 2H), 6.51-6.71 (m, 2H), 5.84-5.99 (m, 1H), 5.51-5.72 (m, 1H), 4.77-5.07 (m, 2H), 4.46-4.59 (m, 1H), 4.16-4.31 (m, 2H), 4.01-4.16 (m, 1H), 3.87-3.98 (m, 1H), 3.65-3.77 (m, 1H), 3.50-3.61 (m, 1H), 3.32-3.43 (m, 2H), 1.79-1.91 (m, 1H), 1.32-1.70 (m, 9H), 0.76-0.93 (m, 2H), 0.47-0.64 (m, 2H).

Step-V: 3-(4-Cyclopropylphenoxy)-1-(1-(2-((tetra-hydro-2H-pyran-2-yl)oxy)ethyl)-1H-pyrazol-4-yl)-1H-pyrrol-2(5H)-one (intermediate B10-5)

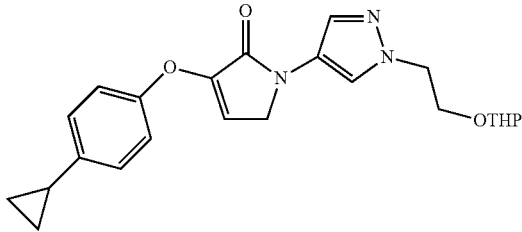

The title compound was obtained as a light-yellowish liquid (1.6 g, 74% yield) from the intermediate B10-4 by following a procedure, similar to that for B1-7 [Purification: CombiFlash instrument (40.0 g silica gel column; 60% ethyl acetate in petroleum ether]. $^1$H NMR (300 MHz, chloroform-d) δ 8.18 (d, J=0.57 Hz, 1H), 7.54 (d, J=0.66 Hz, 1H), 7.09 (s, 4H), 5.73 (t, J=2.36 Hz, 1H), 4.58 (t, J=3.35 Hz, 1H), 4.34 (t, J=5.33 Hz, 2H), 4.02-4.21 (m, 3H), 3.66-3.87 (m, 2H), 3.40-3.57 (m, 1H), 1.85-1.97 (m, 1H), 1.45-1.67 (m, 5H), 1.27 (t, J=7.13 Hz, 1H), 0.92-1.03 (m, 2H), 0.63-0.75 (m, 2H).

Step-VI: 3-(4-Cyclopropylphenoxy)-1-(1-(2-hydroxyethyl)-1H-pyrazol-4-yl)-1H-pyrrol-2(5H)-one (intermediate B10-6)

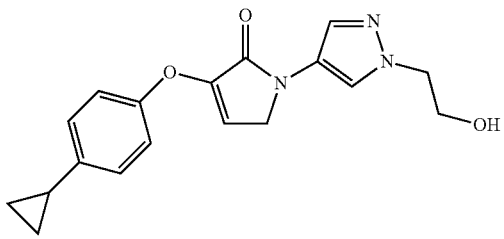 [SMILES: O=C1C(Oc2ccc(C3CC3)cc2)=CCN1c1cnn(CCO)c1]

The title compound was obtained as a gray-colored liquid (0.83 g, 70% yield) from the intermediate B10-5 by following a procedure, similar to that for B1-8. $^1$H NMR (400 MHz, DMSO-d$_6$) δ 8.05 (s, 1H), 7.67 (s, 1H), 7.02-7.18 (m, 4H), 6.15 (t, J=2.26 Hz, 1H), 4.89 (br. s., 1H), 4.27 (d, J=2.26 Hz, 2H), 4.14 (t, J=5.52 Hz, 2H), 3.73 (d, J=3.76 Hz, 2H), 1.88-2.00 (m, 1H), 0.89-1.01 (m, 2H), 0.60-0.71 (m, 2H).

Step-VII: 2-(4-(3-(4-Cyclopropylphenoxy)-2-oxo-2,5-dihydro-1H-pyrrol-1-yl)-1H-pyrazol-1-yl)ethyl methanesulfonate (intermediate B10-7)

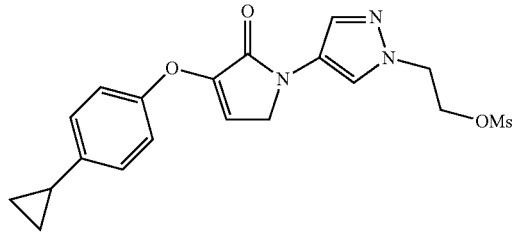 [SMILES: CS(=O)(=O)OCCn1cc(N2CC=C(Oc3ccc(C4CC4)cc3)C2=O)cn1]

The title compound was obtained as a colorless solid (0.11 g, 90% yield) from the intermediate B10-6 by following a procedure, similar to that for B1-9 [Purification by CombiFlash: 50% ethyl acetate in hexane; 12 g silica gel column]. $^1$H NMR (400 MHz, DMSO-d$_6$) δ 8.12-8.20 (m, 1H), 7.71-7.78 (m, 1H), 7.00-7.18 (m, 4H), 6.11-6.21 (m, 1H), 4.51-4.62 (m, 2H), 4.41-4.51 (m, 2H), 4.21-4.33 (m, 2H), 3.10 (s, 3H), 1.88-2.02 (m, 1H), 0.90-1.02 (m, 2H), 0.59-0.70 (m, 2H); MS (ES): m/z 404.2 [M–H]$^+$.

Step-VIII: 3-(4-cyclopropylphenoxy)-1-(1-(2-(3-hydroxyazetidin-1-yl)ethyl)-1H-pyrazol-4-yl)-1H-pyrrol-2(5H)-one Example 268

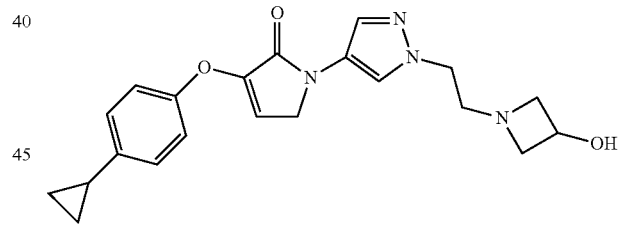

The title compound was obtained as a colorless solid (38.9 mg, 55% yield) from the intermediate B10-7 by following a procedure, similar to that for B1. $^1$H NMR (400 MHz, chloroform-d) δ 8.07-8.15 (m, 1H), 7.44-7.58 (m, 1H), 7.07 (d, J=3.26 Hz, 4H), 5.67-5.77 (m, 1H), 4.34-4.48 (m, 1H), 4.03-4.19 (m, 4H), 3.55-3.67 (m, 2H), 2.93 (s, 4H), 1.83-1.96 (m, 1H), 0.92-1.02 (m, 2H), 0.62-0.72 (m, 2H); MS (ES): m/z 381.2 [M–H]+; HPLC RT: a) 6.07 min (Analytical HPLC Method A); b) 7.17 min (Analytical HPLC Method B).

Examples 269 and 270 in Table K were prepared by treating the intermediate B10-7 with an appropriate amine in a similar manner to that employed for the preparation of Example 268.

Procedure-B11

Example-271

3-(4-Cyclopropylphenoxy)-1-(3-methoxy-4-(pyrrolidin-1-ylmethyl)phenyl)-1H-pyrrol-2(5H)-one

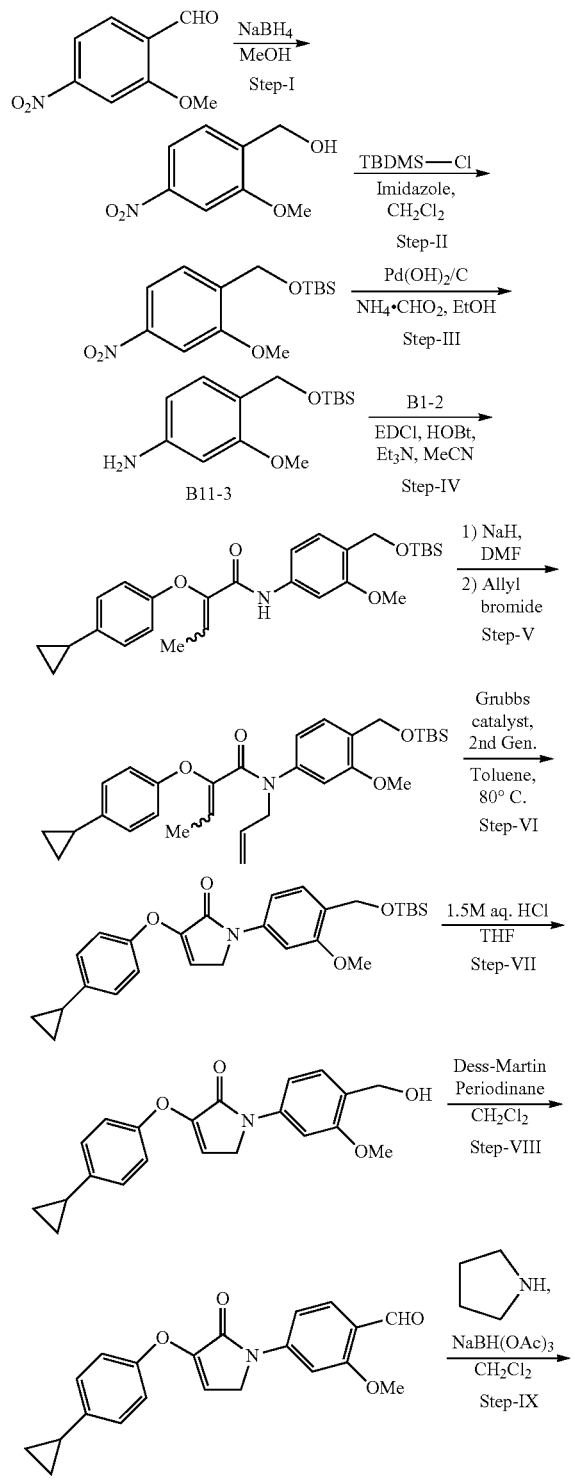

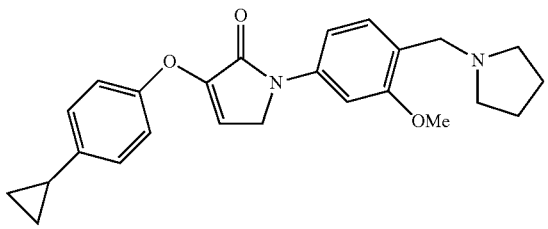

Step-I: (2-Methoxy-4-nitrophenyl)methanol (intermediate B11-1)

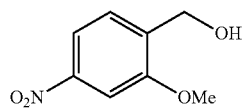

A stirred solution of 2-methoxy-4-nitrobenzaldehyde (10 g, 55.2 mmol) in methanol (100.0 mL) was cooled to 0° C. Sodium borohydride (4.18 g, 110 mmol) was added slowly (caution: effervescence). After being stirred for 12.0 h, the solvent was removed under vacuum. The residue was partitioned between 500 mL of water and 600 mL of ethyl acetate. The organic layer was washed with brine solution (500 mL), dried over anhydrous sodium sulfate, and concentrated to dryness to afford the colorless solid as the title product (10.0 g, 99%). $^1$H NMR (400 MHz, chloroform-d) δ 7.87 (dd, J=2.13, 8.16 Hz, 1H), 7.71 (d, J=2.01 Hz, 1H), 7.52 (d, J=8.28 Hz, 1H), 4.77 (d, J=6.27 Hz, 2H), 3.96 (s, 3H), 2.16 (s, 1H).

Step-II: tert-Butyl((2-methoxy-4-nitrobenzyl)oxy)dimethylsilane (intermediate B11-2)

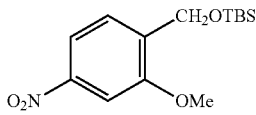

To the stirred solution of (2-methoxy-4-nitrophenyl)methanol (10.0 g, 54.6 mmol) in dichloromethane (100 mL), was added imidazole (11.15 g, 164 mmol) followed by TBDMS-Cl (9.87 g, 65.5 mmol). The mixture was stirred at ambient temperature for 2.0 h. The mixture was diluted with 50 mL of water and 100 mL of dichloromethane. The separated organic layer was dried over anhydrous sodium sulfate, and evaporated to dryness in vacuo. The crude product was purified using CombiFlash instrument (140 g silica gel column; 16% ethyl acetate in petroleum ether) to afford the product as a off-white solid (16.0 g, 99%). $^1$H NMR (400 MHz, chloroform-d) δ 7.81-7.94 (m, 1H), 7.66 (d, J=2.01 Hz, 2H), 4.78 (d, J=0.50 Hz, 2H), 3.91 (s, 3H), 0.94-0.99 (m, 9H), 0.13 (s, 6H).

Step-III: 4-(((tert-Butyldimethylsilyl)oxy)methyl)-3-methoxyaniline (intermediate B11-3)

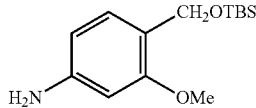

To a stirred solution of tert-butyl((2-methoxy-4-nitrobenzyl)oxy)dimethylsilane (8.0 g, 26.9 mmol) in ethanol (80 mL), was added ammonium formate (3.39 g, 53.8 mmol) followed by palladium hydroxide on carbon (0.755 g, 0.538 mmol). The reaction mixture was stirred for 20 minutes. The reaction mixture was filtered through a short pad of Celite®. The filtrate was concentrated to dryness in vacuo to afford the product as a yellowish liquid (6.5 g, 90%), which was used as such in the next reaction. $^1$H NMR (400 MHz, chloroform-d) δ 7.14-7.21 (m, 1H), 6.26-6.33 (m, 1H), 6.19-6.24 (m, 1H), 4.65 (d, J=0.50 Hz, 2H), 3.76 (s, 3H), 3.55-3.68 (m, 2H), 0.93 (s, 9H), 0.08 (s, 6H); MS (ES): m/z 268.2 [M+H]$^+$.

Step-IV: N-(4-(((tert-Butyldimethylsilyl)oxy)methyl)-3-methoxyphenyl)-2-(4-cyclopropylphenoxyl)but-2-enamide (intermediate B11-4)

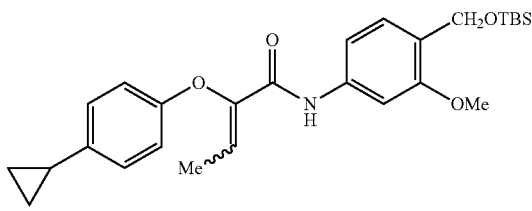

The title compound was obtained as a yellowish liquid (8.0 g, 70% yield) from the reaction of intermediate B11-3 with B1-2 described in Procedure B1 under the conditions employed for the synthesis of B1-5. [Purification: Combi-Flash instrument (120.0 g silica gel column; 20% ethyl acetate in hexane)]. $^1$H NMR (400 MHz, chloroform-d) δ 7.92-8.02 (m, 1H), 7.45-7.51 (m, 1H), 7.30-7.37 (m, 1H), 7.03 (d, J=8.53 Hz, 2H), 6.89-6.97 (m, 2H), 6.69-6.83 (m, 2H), 4.69 (s, 2H), 3.81 (s, 3H), 1.80-1.92 (m, 1H), 1.68 (d, J=7.28 Hz, 3H), 0.84-1.02 (m, 11H), 0.53-0.67 (m, 2H), 0.08 (s, 6H); MS (ES): m/z 466.2 [M−H]$^+$.

Step-V: N-Allyl-N-(4-(((tert-butyldimethylsilyl)oxy)methyl)-3-methoxyphenyl)-2-(4-cyclopropylphenoxyl)but-2-enamide (intermediate B11-5)

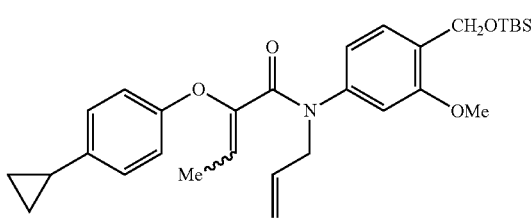

The title compound was obtained as a yellowish liquid (8.0 g, 92% yield) from the intermediate B11-4 by following a procedure, similar to that for B1-8 [Purification: Combi-Flash instrument (120.0 g silica gel column; 23% ethyl acetate in hexane)]. $^1$H NMR (400 MHz, chloroform-d) δ 7.32-7.42 (m, 1H), 6.90 (d, J=8.76 Hz, 2H), 6.53-6.62 (m, 1H), 6.41-6.49 (m, 2H), 6.28 (s, 2H), 5.62-5.79 (m, 1H), 4.84-5.03 (m, 2H), 4.75 (s, 2H), 4.11-4.22 (m, 2H), 3.65 (s, 3H), 1.77-1.88 (m, 1H), 1.61 (d, J=7.00 Hz, 3H), 0.90-0.99 (m, 11H), 0.53-0.65 (m, 2H), 0.13 (s, 6H); MS (ES): m/z 464.2 [M−H]$^+$.

Step-VI: 1-(4-(((tert-Butyldimethylsilyl)oxy)methyl)-3-methoxyphenyl)-3-(4-cyclopropylphenoxy)-1H-pyrrol-2(5H)-one (intermediate B11-6)

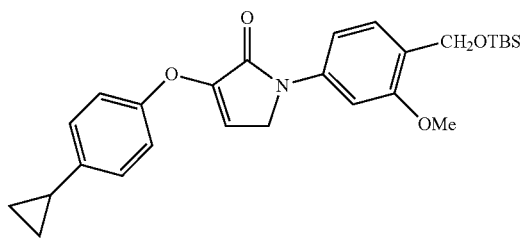

The title compound was obtained as an off-white solid (5.4 g, 74% yield) from the intermediate B11-5 by following a procedure, similar to that for B1-9 [Purification: Combi-Flash instrument (120.0 g silica gel column; 16% ethyl acetate in hexane)]. $^1$H NMR (400 MHz, chloroform-d) δ 7.75-7.84 (m, 1H), 7.40-7.49 (m, 1H), 7.08 (s, 4H), 6.87-6.97 (m, 1H), 5.77 (s, 1H), 4.74 (s, 2H), 4.27 (d, J=2.51 Hz, 2H), 3.86 (s, 3H), 1.85-1.94 (m, 1H), 0.91-1.01 (m, 11H), 0.64-0.73 (m, 2H), 0.11 (s, 6H); MS (ES): m/z 464.2 [M−H]$^+$.

Step-VII: 3-(4-Cyclopropylphenoxy)-1-(4-(hydroxymethyl)-3-methoxyphenyl)-1H-pyrrol-2(5H)-one (intermediate B11-7)

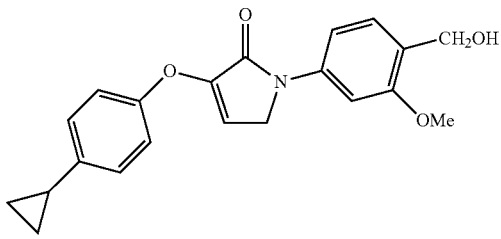 [SMILES: COc1cc(N2CC=C(Oc3ccc(C4CC4)cc3)C2=O)ccc1CO]

To the stirred solution of 1-(4-(((tert-butyldimethylsilyl)oxy)methyl)-3-methoxyphenyl)-3-(4-cyclopropylphenoxy)-1H-pyrrol-2(5H)-one (0.1 g, 0.215 mmol) in tetrahydrofuran (3.0 mL), was added 1.5N aqueous hydrochloric acid solution (2.0 mL, 3.00 mmol). This reaction mixture was stirred at room temperature for 3 h. The solvent was evaporated to dryness in vacuo to afford the product as a colorless solid (0.05 g, 63.6%). $^1$H NMR (400 MHz, methanol-d$_4$) δ 7.61-7.69 (m, 1H), 7.35-7.44 (m, 1H), 7.14 (d, J=13.55 Hz, 5H), 5.93-6.06 (m, 1H), 4.63 (s, 2H), 4.43 (d, J=2.51 Hz, 2H), 3.89 (s, 3H), 1.91-2.01 (m, 1H), 0.94-1.04 (m, 2H), 0.65-0.74 (m, 2H); MS (ES): m/z 352.2 [M+H]$^+$.

Step-VIII: 4-(3-(4-Cyclopropylphenoxy)-2-oxo-2,5-dihydro-1H-pyrrol-1-yl)-2-methoxybenzaldehyde (intermediate B11-8)

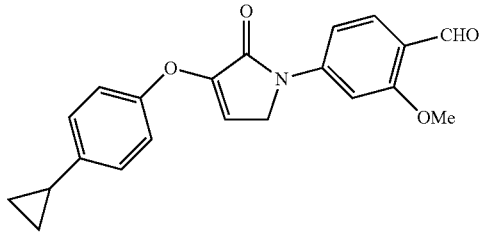 [SMILES: COc1cc(N2CC=C(Oc3ccc(C4CC4)cc3)C2=O)ccc1C=O]

A stirred solution of 3-(4-cyclopropylphenoxy)-1-(4-(hydroxymethyl)-3-methoxyphenyl)-1H-pyrrol-2(5H)-one (0.1 g, 0.142 mmol) in dichloromethane (5 mL) was cooled to 0° C., and then was added Dess-Martin Periodinane (0.121 g, 0.285 mmol). The reaction mixture was stirred in absence of light for 6.0 h. The reaction mixture was diluted with 20 mL of water and made basic with 1N aqueous sodium hydroxide solution. The mixture was extracted with 50 mL of dichloromethane. The organic layer was dried over anhydrous sodium sulfate, and evaporated to dryness in vacuo to afford the title product as a colorless solid (0.046 g, 93%). $^1$H NMR (300 MHz, chloroform-d) δ 10.39 (s, 1H), 8.21 (d, J=1.89 Hz, 1H), 7.87 (d, J=8.59 Hz, 1H), 7.11 (d, J=3.21 Hz, 4H), 6.87-7.00 (m, 1H), 5.87 (s, 1H), 4.34 (d, J=2.45 Hz, 2H), 4.00 (s, 3H), 1.88-2.00 (m, 1H), 0.97-1.08 (m, 2H), 0.69 (s, 2H); MS (ES): m/z 350.2 [M+H]$^+$.

Step-IX: 3-(4-Cyclopropylphenoxy)-1-(3-methoxy-4-(pyrrolidin-1-ylmethyl)phenyl)-1H-pyrrol-2(5H)-one Example 271

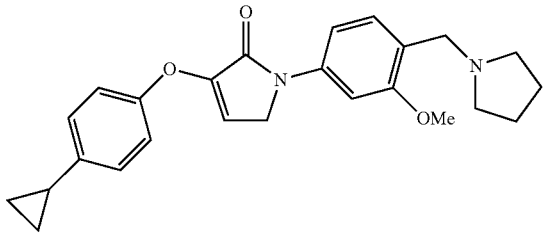 [SMILES: COc1cc(N2CC=C(Oc3ccc(C4CC4)cc3)C2=O)ccc1CN1CCCC1]

To the stirred solution of 4-(3-(4-cyclopropylphenoxy)-2-oxo-2,5-dihydro-1H-pyrrol-1-yl)-2-methoxybenzaldehyde (0.05 g, 0.143 mmol) in 1,2-dichloroethane (5 mL), was added pyrrolidine (0.024 mL, 0.286 mmol) followed by sodium triacetoxyborohydride (0.091 g, 0.429 mmol). Then the reaction mixture was stirred at room temperature for 16 h. The reaction mixture was diluted with 50 mL of water and extracted with 80 mL of dichloromethane. The organic layer was washed with brine solution, dried over anhydrous sodium sulfate, and evaporated to dryness to afford the product as a colorless solid (0.04 g, 63.1%).

Examples 272 to 281 in Table L were prepared by reductive amination of intermediate B11-8 with an appropriate amine in a similar manner to that employed for the preparation of Example 271.

Procedure-B12

Example 282

1-(3-(Difluoromethoxy)-4-(2-(pyrrolidin-1-yl)ethoxy)phenyl)-3-(3,4-difluorophenoxy)-1H-pyrrol-2(5H)-one

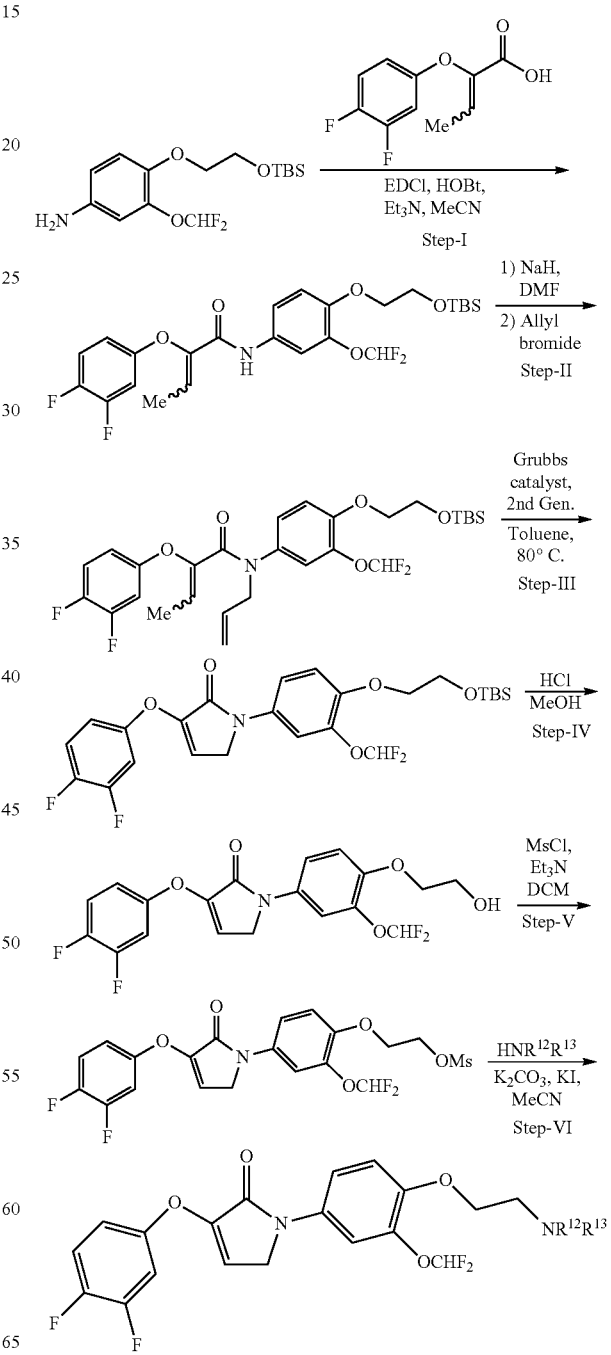

Step-I: N-(4-(2-((tert-Butyldimethylsilyl)oxy) ethoxy)-3-(difluoromethoxy)phenyl)-2-(3,4-difluorophenoxy)but-2-enamide (intermediate B12-1)

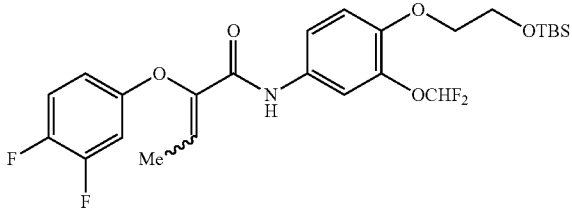

Employing procedures analogous to those described in Procedure B1 for preparation of B1-1 and B1-2, methyl 2-bromo-2-butenoate and 3,4-difluorophenol were condensed to yield, after hydrolysis, 2-(3,4-difluorophenoxyl) but-2-enoic acid. Following the procedure analogous to that described for preparation of B1-5, intermediate B13-4 and the 2-(3,4-difluorophenoxyl)but-2-enoic acid were reacted to generate the title compound as a yellowish liquid (0.75 g, 94% yield). $^1$H NMR (400 MHz, chloroform-d) δ 7.74-7.83 (m, 1H), 7.32-7.40 (m, 2H), 7.08-7.18 (m, 1H), 6.86-6.96 (m, 2H), 6.64 (s, 3H), 4.07 (s, 2H), 3.95 (s, 2H), 1.69 (d, J=7.53 Hz, 3H), 0.83-0.93 (m, 9H), 0.05-0.10 (m, 6H); MS (ES): m/z 530.1 [M+H]$^+$.

Step-II: N-Allyl-N-(4-(2-((tert-butyldimethylsilyl) oxy)ethoxy)-3-(difluoromethoxy)phenyl)-2-(3,4-difluorophenoxyl)but-2-enamide (intermediate B12-2)

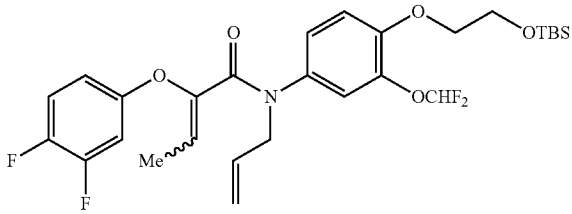

The title compound was obtained as a yellowish liquid (0.5 g, 93% yield) from the intermediate B3-4 by following a procedure, similar to that for preparation of B1-6. $^1$H NMR (400 MHz, chloroform-d) δ 6.83-7.07 (m, 2H), 6.77 (s, 1H), 6.24-6.54 (m, 3H), 5.61-5.77 (m, 1H), 4.85-5.40 (m, 3H), 4.12 (s, 4H), 4.00 (s, 2H), 1.54-1.66 (m, 3H), 0.79-0.97 (m, 9H), 0.05-0.14 (m, 6H); MS (ES): m/z 570.2 [M+H]$^+$.

Step-III: 1-(4-(2-((tert-Butyldimethylsilyl)oxy) ethoxy)-3-(difluoromethoxy)phenyl)-3-(3,4-difluorophenoxy)-1H-pyrrol-2(5H)-one (intermediate B12-3)

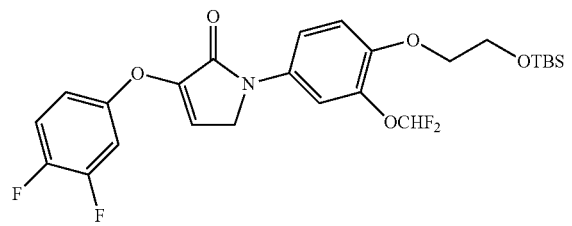 [SMILES: CC(C)(C)[Si](C)(C)OCCOc1ccc(N2CC=C(Oc3ccc(F)c(F)c3)C2=O)cc1OC(F)F]

The title compound was obtained as an off-white liquid (3.7 g, 59% yield) from the intermediate B13-2 by following a procedure, similar to that for B1-9. $^1$H NMR (400 MHz, chloroform-d) δ 7.60-7.71 (m, 1H), 7.43-7.50 (m, 1H), 7.13-7.24 (m, 1H), 6.98-7.10 (m, 2H), 6.90-6.98 (m, 1H), 6.46-6.90 (m, 1H), 5.88-5.99 (m, 1H), 4.28 (d, J=2.25 Hz, 2H), 4.05-4.16 (m, 2H), 3.97 (s, 2H), 0.85-0.96 (m, 9H), 0.09 (s, 6H); MS (ES): m/z 528.2 [M+H]$^+$.

Step-IV: 1-(3-(Difluoromethoxy)-4-(2-hydroxyethoxyl)phenyl)-3-(3,4-difluorophenoxy)-1H-pyrrol-2(5H)-one (intermediate B12-4)

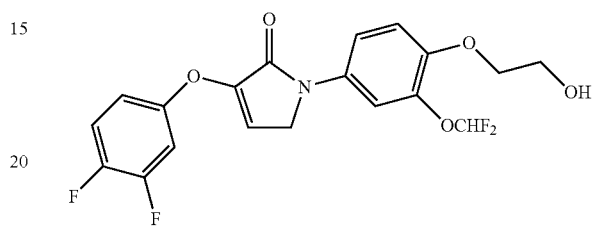

The title compound was obtained as an off-white solid (0.3 g, 77% yield) from the intermediate B13-3 by following a procedure, similar to that for B3-8. $^1$H NMR (400 MHz, DMSO-d$_6$) δ 7.75 (d, J=2.51 Hz, 1H), 7.38-7.59 (m, 3H), 6.91-7.35 (m, 3H), 6.52 (t, J=2.38 Hz, 1H), 4.45 (d, J=2.51 Hz, 2H), 4.08 (t, J=5.02 Hz, 2H), 3.73 (t, J=4.89 Hz, 2H); MS (ES): m/z 414.2 [M+H]$^+$.

Step-V: 2-(2-(Difluoromethoxy)-4-(3-(3,4-difluorophenoxy)-2-oxo-2,5-dihydro-1H-pyrrol-1-yl)phenoxy)ethyl methanesulfonate (intermediate B12-5)

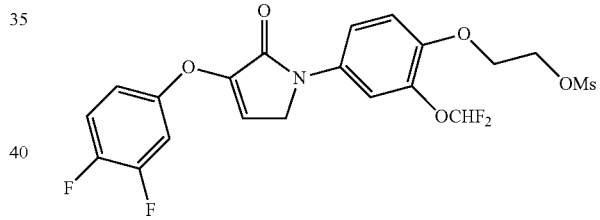

The title compound was obtained as an off-white solid (0.55 g, 90% yield) from the intermediate B13-4 by following a procedure, similar to that for B1-10. $^1$H NMR (400 MHz, chloroform-d) δ 7.58-7.66 (m, 2H), 7.13-7.23 (m, 1H), 6.97-7.08 (m, 2H), 6.89-6.97 (m, 1H), 6.38-6.81 (m, 1H), 5.93-5.98 (m, 1H), 4.54-4.63 (m, 2H), 4.29 (s, 4H), 3.11 (s, 3H); MS (ES): m/z 492.2 [M+H]$^+$.

Step-VI: 1-(3-(Difluoromethoxy)-4-(2-(pyrrolidin-1-yl)ethoxy)phenyl)-3-(3,4-difluorophenoxy)-1H-pyrrol-2(5H)-one Example 282

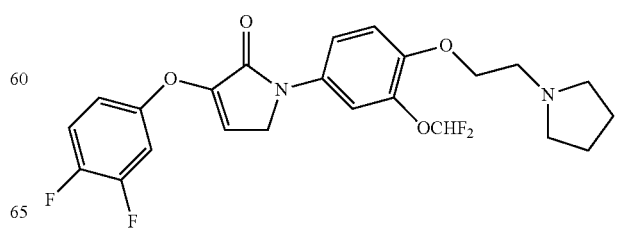

The title compound was obtained as an off-white solid (10 mg, 10% yield) from the intermediate B13-5 by following a procedure, similar to that for B1.

Examples 283 to 297 in Table M were prepared by treating the intermediate B12-5 with an appropriate amine in a similar manner to that employed for the preparation of Example 282

Procedure 13

Example 298

(R)-3-(4-Cyclopropylphenoxy)-1-(3-methoxy-4-(pyrrolidin-3-yloxy)phenyl)-1H-pyrrol-2(5H)-one. hydrochloride

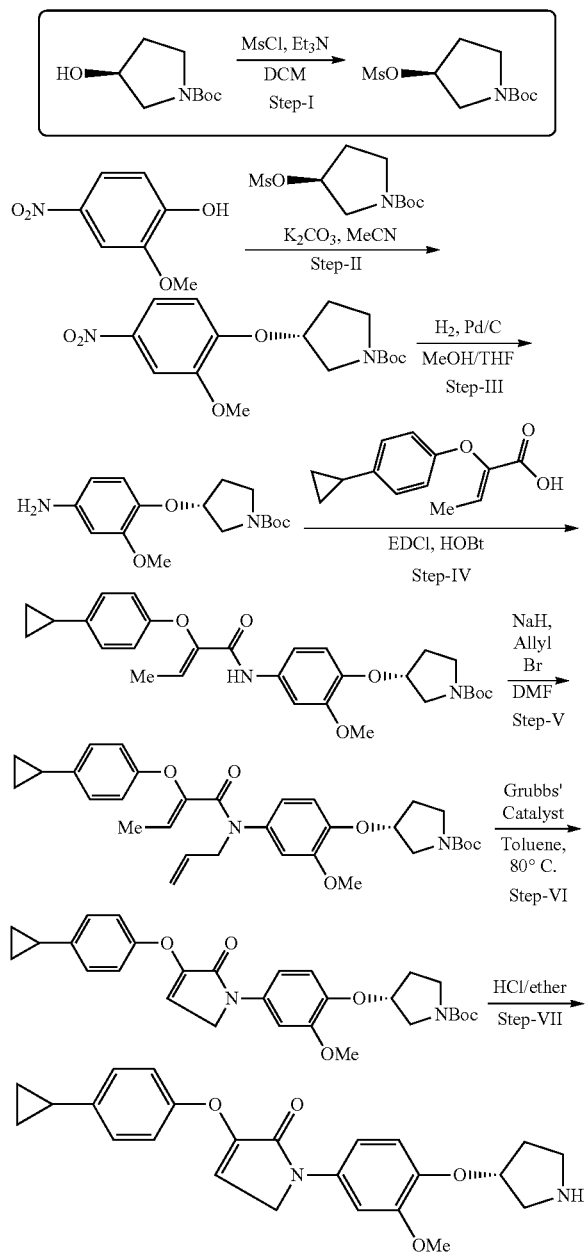

Step-I: (S)-tert-Butyl 3-(methylsulfonyloxy)pyrrolidine-1-carboxylate (intermediate B13-1)

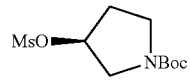 [SMILES: CC(C)(C)OC(=O)N1CC[C@H](OS(C)(=O)=O)C1]

To a solution of (S)-tert-butyl 3-hydroxypyrrolidine-1-carboxylate (1.0 g, 5.34 mmol) in dichloromethane (20.0 mL) at 0° C., was added triethylamine (1.861 mL, 13.35 mmol) and subsequently methanesulfonyl chloride (0.541 mL, 6.94 mmol) as a neat liquid. The temperature of the mixture was gradually raised to room temperature. After being stirred for 6.0 h, the mixture was partitioned between saturated aqueous sodium bicarbonate solution and DCM. The organic layer was dried over anhydrous sodium sulfate and concentrated in vacuo to obtain the crude product as light-yellowish oil, which was used as such in the next reaction. $^1$H NMR (400 MHz, chloroform-d) δ 5.21-5.29 (m, 1H), 3.40-3.73 (m, 4H), 3.04 (s, 3H), 2.05-2.35 (m, 2H), 1.43-1.49 (m, 9H).

Step-II: (R)-tert-Butyl 3-(2-methoxy-4-nitrophenoxy)pyrrolidine-1-carboxylate (intermediate B13-2)

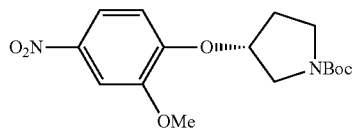

To a solution of 2-methoxy-4-nitrophenol (0.5 g, 2.96 mmol) in DMF (20 mL), were added potassium carbonate (1.226 g, 8.87 mmol) and (S)-tert-butyl 3-((methylsulfonyl)oxy)pyrrolidine-1-carboxylate (0.941 g, 3.55 mmol). The reaction mixture was allowed to reflux for 16 h. The mixture was partitioned between water and ethyl acetate. The organic layer was washed with water and brine, dried over anhydrous sodium sulfate, and concentrated in vacuo. The crude product was purified using CombiFlash instrument (40 g silica gel column; 20% ethyl acetate in petroleum ether) to afford the product as a light yellowish solid (0.70 g, 70.0%). $^1$H NMR (400 MHz, DMSO-d$_6$) δ 7.85-7.95 (m, 1H), 7.75-7.81 (m, 1H), 7.17-7.30 (m, 1H), 5.14-5.23 (m, 1H), 3.89 (s, 3H), 3.57-3.68 (m, 1H), 3.38-3.51 (m, 2H), 3.33-3.37 (m, 1H), 2.02-2.28 (m, 2H), 1.41 (br. s., 9H); MS (ES): m/z 283.11 [M-(t-Bu)]$^+$.

Step-III: (R)-tert-Butyl 3-(4-amino-2-methoxyphenoxy)pyrrolidine-1-carboxylate (intermediate B13-3)

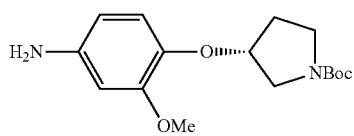 [SMILES: COc1cc([N+](=O)[O-])ccc1O[C@@H]1CCN(C(=O)OC(C)(C)C)C1]

To a solution of (R)-tert-butyl 3-(2-methoxy-4-nitrophenoxy)pyrrolidine-1-carboxylate (900 mg, 2.66 mmol) in degassed MeOH (20 mL), was added 5% Pd/C (0.200 g, 0.266 mmol). Then the reaction mixture was stirred at room temperature under hydrogen pressure (1 Kg/cm²) for 3.0 h. The reaction mixture was filtered through a Celite® bed and washed with MeOH. The filtrate was concentrated in vacuo to afford the crude product as brownish oil, which was used as such in the next reaction (0.6 g, 73.1%). ¹H NMR (400 MHz, DMSO-d₆) δ 6.58-6.65 (m, 1H), 6.23-6.30 (m, 1H), 6.01-6.10 (m, 1H), 4.75-4.82 (m, 2H), 4.59-4.67 (m, 1H), 3.63-3.73 (m, 3H), 3.33-3.41 (m, 4H), 1.84-2.03 (m, 2H), 1.35-1.46 (m, 9H); MS (ES): m/z 309.4 [M+H]⁺.

Step-IV: (R)-tert-Butyl 3-(4-(2-(4-cyclopropylphenoxyl)but-2-enamido)-2-methoxyphenoxy)pyrrolidine-1-carboxylate (intermediate B13-4)

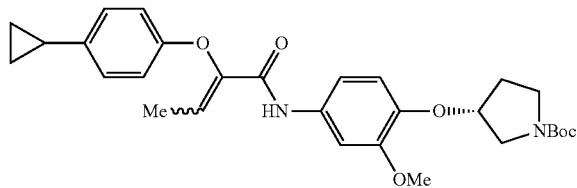

To a solution of (R)-tert-butyl 3-(4-amino-2-methoxyphenoxy)pyrrolidine-1-carboxylate (650 mg, 2.108 mmol), and 2-(4-cyclopropylphenoxyl)but-2-enoic acid prepared as B1-2 described in Procedure B1 (506 mg, 2.319 mmol) in acetonitrile (20 mL), was added triethylamine (1.763 mL, 12.65 mmol), 1H-1,2,3-benzotriazol-1-ol hydrate (484 mg, 3.16 mmol) and EDC (808 mg, 4.22 mmol). After stirring the reaction mixture at room temperature for 16 h, TLC showed the complete consumption of the starting material. The mixture was partitioned between water and ethyl acetate. The organic layer was washed with water and brine, dried over anhydrous sodium sulfate, and concentrated in vacuo. The crude product was purified using CombiFlash instrument (40 g silica gel column; 10% ethyl acetate in petroleum ether) to afford the product as a light yellowish solid (0.75 g, 70.2%). ¹H NMR (400 MHz, DMSO-d₆) δ 8.32 (s, 1H), 7.35-7.46 (m, 1H), 7.15-7.27 (m, 1H), 7.01-7.10 (m, 2H), 6.83-6.94 (m, 3H), 6.40-6.52 (m, 1H), 4.80-4.91 (m, 1H), 3.70 (s, 3H), 3.34-3.48 (m, 4H), 1.93-2.09 (m, 2H), 1.80-1.91 (m, 1H), 1.66 (d, J=7.28 Hz, 3H), 1.40 (d, J=7.28 Hz, 9H), 0.80-0.94 (m, 2H), 0.52-0.65 (m, 2H); MS (ES): m/z 507.46 [M+H]⁺.

Step-V: (R)-tert-Butyl 3-(4-(N-allyl-2-(4-cyclopropylphenoxyl)but-2-enamido)-2-methoxyphenoxy)pyrrolidine-1-carboxylate (intermediate B13-5)

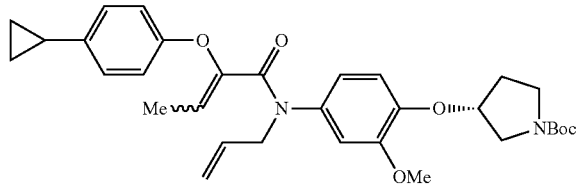

To a solution of (R)-tert-butyl 3-(4-(2-(4-cyclopropylphenoxyl)but-2-enamido)-2-methoxyphenoxy)pyrrolidine-1-carboxylate (600 mg, 1.180 mmol) in tetrahydrofuran (4 mL) was added sodium hydride (51.9 mg, 1.298 mmol) at 0° C. The reaction mixture was allowed to stir at room temperature for 45 min. Then 3-bromoprop-1-ene (0.103 mL, 1.180 mmol) was added to the reaction mixture at 0° C. Then the reaction mixture was allowed to stir at room temperature for 1 h. The reaction mixture was partitioned between water and ethyl acetate. The organic layer was washed with water and brine, dried over anhydrous sodium sulfate, and concentrated in vacuo. The crude product was purified using CombiFlash instrument (40 g silica gel column; 10% ethyl acetate in petroleum ether) to afford the product as a light yellowish solid (0.55 g, 84.9%). ¹H NMR (400 MHz, DMSO-d₆) δ 6.87-7.00 (m, 4H), 6.47-6.53 (m, 2H), 6.37-6.45 (m, 1H), 6.03-6.12 (m, 1H), 5.58-5.73 (m, 1H), 4.84-5.01 (m, 3H), 4.08-4.18 (m, 2H), 3.59-3.66 (m, 3H), 3.37-3.54 (m, 4H), 2.02-2.12 (m, 2H), 1.79-1.89 (m, 1H), 1.51-1.55 (m, 3H), 1.40-1.43 (m, 9H), 0.86-0.89 (m, 2H), 0.56-0.60 (m, 2H); MS (ES): m/z 549.4 [M+H]⁺.

Step-VI: (R)-tert-Butyl 3-(4-(3-(4-cyclopropylphenoxy)-2-oxo-2,5-dihydro-1H-pyrrol-1-yl)-2-methoxyphenoxy)pyrrolidine-1-carboxylate (intermediate B13-6)

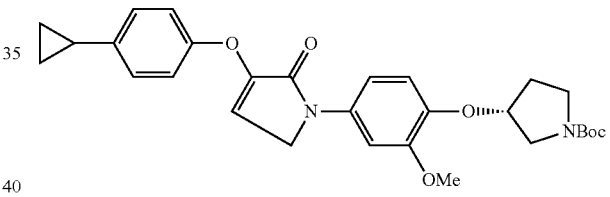

To the solution of (R)-tert-butyl 3-(4-(-2-(4-cyclopropylphenoxy)-N-(prop-1-en-1-yl)but-2-enamido)-2-methoxyphenoxy)pyrrolidine-1-carboxylate (0.200 g, 0.365 mmol) in toluene (30 mL), was added tricyclohexylphosphine[1,3-bis(2,4,6-trimethylphenyl)-4,5-dihydroimidazol-2-ylidene] [benzylidine]ruthenium (IV)dichloride (0.031 g, 0.036 mmol). The reaction mixture was allowed to stir at 70° C. for 16 h under nitrogen atmosphere. TLC showed the complete consumption of the starting material. The mixture was partitioned between water and ethyl acetate. The organic layer was washed with water and brine, dried over anhydrous sodium sulfate, and concentrated in vacuo. The crude product was purified using CombiFlash instrument (24 g silica gel column; 2% methanol in chloroform) to afford the product as a blackish gum. This purified product was washed twice with diethyl ether to remove the non-polar impurities to afford the title compound as off white solid (0.08 g, 43.0%). ¹H NMR (400 MHz, DMSO-d₆) δ 7.48-7.57 (m, 1H), 7.18-7.25 (m, 1H), 7.12-7.17 (m, 2H), 7.06-7.11 (m, 2H), 6.98-7.04 (m, 1H), 6.19-6.24 (m, 1H), 4.88-4.96 (m, 1H), 4.37-4.47 (m, 2H), 3.78 (s, 3H), 3.34-3.55 (m, 4H), 1.88-2.10 (m, 3H), 1.36-1.46 (m, 9H), 0.91-1.00 (m, 2H), 0.60-0.72 (m, 2H); MS (ES): m/z 505.49 [M+H]⁺; HPLC RT: a) 21.44 min (Analytical HPLC Method A); b) 19.27 min (Analytical HPLC Method B).

Step-VII: (R)-3-(4-Cyclopropylphenoxy)-1-(3-methoxy-4-(pyrrolidin-3-yloxy)phenyl)-1H-pyrrol-2(5H)-one. hydrochloride Example 298

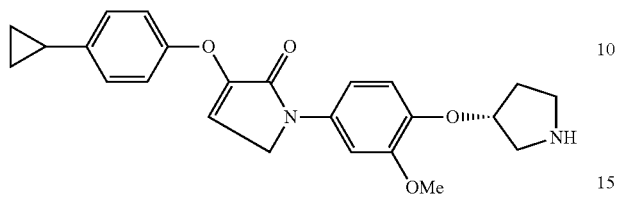

To the solution of tert-butyl 3-(4-(3-(4-cyclopropylphenoxy)-2-oxo-2,5-dihydro-1H-pyrrol-1-yl)-2-methoxyphenoxy)pyrrolidine-1-carboxylate (40 mg, 0.079 mmol) in water (2.0 mL), was added 4N hydrochloric acid in 1,4-dioxane (0.197 mL, 0.790 mmol) at 0° C. After stirring the reaction mixture at room temperature for 2 h, the excess 1,4-dioxane was evaporated. The crude product was lyophilized to afford the title compound as an off white solid (0.013 g, 37.2%).

The present invention is illustrated by but not restricted to the Examples contained in Tables A to N. The Tables also indicate for each Example which of seventeen synthetic methods was employed as well as which of five analytical methods was utilized. Detailed synthetic procedures as well as analytical HPLC conditions, solvent and column are described in the section after the Tables.

TABLE A

| Example No. | Ki (nM) | Structure | Synthetic Procedure Used | HPLC Methods ($t_R$ min) | MS (M + H) | NMR Data |
|---|---|---|---|---|---|---|
| 1 | 2 | (pyrrolidinyl-ethoxy-OMe-phenyl-pyrrolidinone-O-4-cyclopropylphenyl) | A1 | 1 (7.2) 2 (8.73) 3 (6.9) | 437.2 | $^1$H NMR (400 MHz, CDCl$_3$) δ = 7.76 (d, J = 2.5 Hz, 1H), 7.06-6.88 (m, 5H), 6.84-6.75 (m, 1H), 4.98 (s, 1H), 4.33 (s, 2H), 3.87 (s, 5H), 3.21 (s, 2H), 3.04 (br. s., 4H), 2.72-2.58 (m, 1H), 2.35-2.20 (m, 1H), 1.98 (br. s., 4H), 1.92-1.79 (m, 1H), 0.90 (dd, J = 1.9, 8.4 Hz, 2H), 0.62 (dd, J = 1.5, 5.0 Hz, 2H) |
| 2 | 24 | (pyrrolidinyl-ethoxy-OMe-phenyl-pyrrolidinone-O-4-cyclopropylphenyl) | A1 | 1 (7.28) 2 (8.71) 3 (12.1) | 437.2 | $^1$H NMR (400 MHz, CDCl$_3$) δ = 7.75 (d, J = 2.5 Hz, 1H), 7.06-6.95 (m, 4H), 6.91 (d, J = 8.8 Hz, 1H), 6.84-6.76 (m, 1H), 4.98 (t, J = 7.7 Hz, 1H), 4.30 (t, J = 5.6 Hz, 2H), 3.94-3.77 (m, 5H), 3.17 (t, J = 5.5 Hz, 2H), 2.98 (br. s., 4H), 2.66 (dtd, J = 3.5, 7.5, 13.1 Hz, 1H), 2.35-2.20 (m, 1H), 2.03-1.80 (m, 5H), 0.97-0.82 (m, 2H), 0.69-0.56 (m, 2H) |

TABLE A-continued

| Example No. | Structure | Synthetic Procedure Used | HPLC Methods ($t_R$ min) | MS (M + H) | NMR Data | Ki (nM) |
|---|---|---|---|---|---|---|
| 3 | 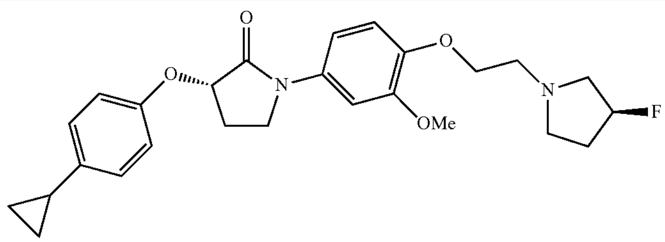 [SMILES: COc1cc(N2CC[C@H](Oc3ccc(C4CC4)cc3)C2=O)ccc1OCCN1CC[C@H](F)C1] | A1 | 1 (7.78) 2 (8.48) | 455.2 | $^1$H NMR (400 MHz, CDCl$_3$) δ 7.70 (d, J = 2.51 Hz, 1H), 7.00 (q, J = 8.78 Hz, 4H), 6.88 (s, 1H), 6.84 (d, J = 2.51 Hz, 1H), 5.08-5.29 (m, 1H), 4.97 (s, 1H), 4.15 (t, J = 6.15 Hz, 2H), 3.87 (s, 5H), 2.97 (t, J = 6.15 Hz, 5H), 2.54-2.71 (m, 2H), 1.98-2.34 (m, 3H), 1.80-1.91 (m, 1H), 0.90 (dd, J = 1.88, 8.41 Hz, 2H), 0.58-0.66 (m, 2H) | 2 |
| 4 | 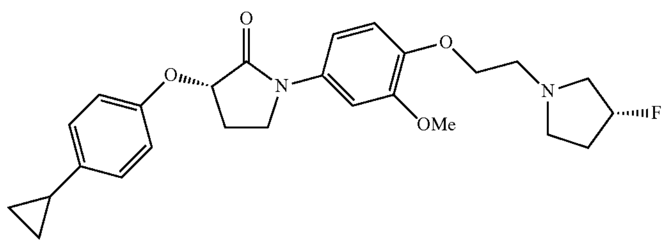 [SMILES: COc1cc(N2CC[C@H](Oc3ccc(C4CC4)cc3)C2=O)ccc1OCCN1CC[C@@H](F)C1] | A1 | 1 (7.89) 2 (8.62) | 455.2 | $^1$H NMR (400 MHz, DMSO-d$_6$) δ 7.51 (d, J = 2.26 Hz, 1H), 6.92-7.10 (m, 6H), 5.10-5.31 (m, 2H), 4.06 (t, J = 5.90 Hz, 2H), 3.78 (s, 5H), 2.61-3.01 (m, 6H), 2.35-2.46 (m, 1H), 1.99-2.21 (m, 2H), 1.88 (s, 2H), 0.89 (dd, J = 2.13, 8.41 Hz, 2H), 0.55-0.64 (m, 2H) | 2 |
| 5 | 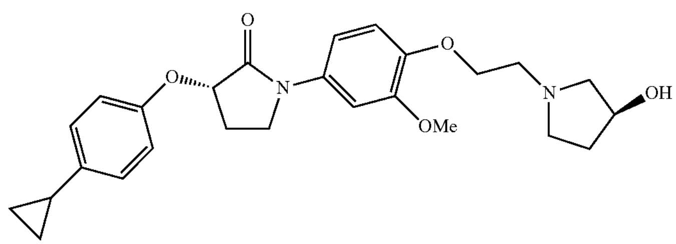 [SMILES: COc1cc(N2CC[C@H](Oc3ccc(C4CC4)cc3)C2=O)ccc1OCCN1CC[C@H](O)C1] | A1 | 1 (6.85) 2 (8.67) | 453 | $^1$H NMR (400 MHz, DMSO-d$_6$) δ 7.50 (d, J = 2.51 Hz, 1H), 6.92-7.10 (m, 6H), 5.15 (s, 1H), 4.68 (d, J = 4.77 Hz, 1H), 4.15-4.23 (m, 1H), 4.03 (t, J = 6.02 Hz, 2H), 3.77 (s, 5H), 2.61-2.82 (m, 5H), 2.38-2.44 (m, 1H), 1.83-2.11 (m, 3H), 1.48-1.58 (m, 1H), 0.85-0.93 (m, 2H), 0.56-0.64 (m, 2H) | 2 |

TABLE A-continued
| Example No. | Ki (nM) | Structure | Synthetic Procedure Used | HPLC Methods ($t_R$ min) | MS (M + H) | $^1$H NMR Data |
|---|---|---|---|---|---|---|
| 6 | 2 | 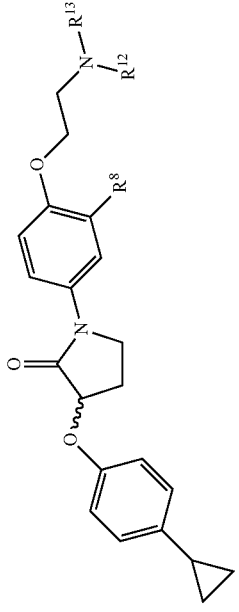 | A1 | 1 (7.01) 2 (8.11) | 453.2 | $^1$H NMR (400 MHz, DMSO-$d_6$) δ 7.50 (d, J = 2.26 Hz, 1H), 6.89–7.11 (m, 6H), 5.14 (s, 1H), 4.62–4.73 (m, 1H), 4.13–4.23 (m, 1H), 4.02 (s, 2H), 3.77 (s, 5H), 2.72–2.82 (m, 3H), 2.60–2.71 (m, 2H), 2.35–2.44 (m, 1H), 1.79–2.11 (m, 3H), 1.46–1.61 (m, 1H), 0.84–0.95 (m, 2H), 0.52–0.66 (m, 2H) |
| 7 | 7 | 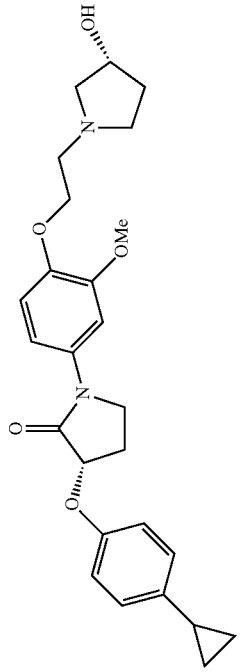 | A1 | 1 (7.43) 2 (8.82) | 473.2 | $^1$H NMR (400 MHz, DMSO-$d_6$) δ 7.50 (d, J = 2.26 Hz, 1H), 6.89–7.11 (m, 6H), 5.14 (s, 1H), 4.62–4.73 (m, 1H), 4.13–4.23 (m, 1H), 4.02 (s, 2H), 3.77 (s, 5H), 2.72–2.82 (m, 3H), 2.60–2.71 (m, 2H), 2.35–2.44 (m, 1H), 1.79–2.11 (m, 3H), 0.84–0.95 (m, 2H), 0.52–0.66 (m, 2H) |
| 8 | 2.5 | 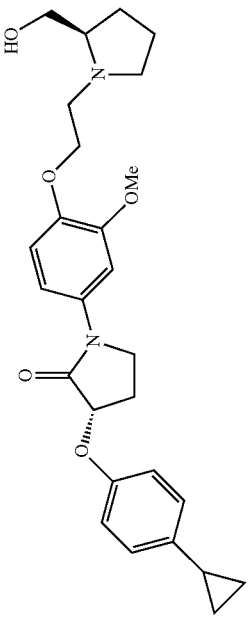 | A1 | 1 (8.48) 2 (8.39) | 467.2 | $^1$H NMR (400 MHz, DMSO-$d_6$) δ 7.49 (d, J = 2.51 Hz, 1H), 6.89–7.11 (m, 6H), 5.14 (s, 1H), 4.28–4.39 (m, 1H), 4.03 (s, 2H), 3.76 (s, 5H), 3.35–3.44 (m, 1H), 3.07–3.29 (m, 3H), 2.59–2.73 (m, 2H), 2.21–2.37 (m, 1H), 1.97–2.12 (m, 1H), 1.73–1.93 (m, 2H), 1.46–1.70 (m, 3H), 0.89 (dd, J = 2.13, 8.41 Hz, 2H), 0.60 (dd, J = 2.01, 5.02 Hz, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 9 | 2 | 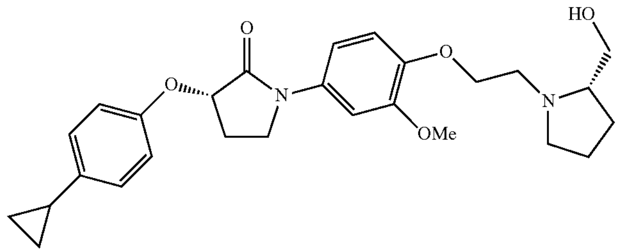 [SMILES: COc1cc(N2CC[C@H](Oc3ccc(C4CC4)cc3)C2=O)ccc1OCCN1CCC[C@H]1CO] | A1 | 1 (7.36) 2 (8.38) | 467.2 | $^1$H NMR (400 MHz, DMSO-d$_6$) δ 7.50 (d, J = 2.51 Hz, 1H), 6.92-7.13 (m, 6H), 5.15 (s, 1H), 4.33 (s, 1H), 4.03 (t, J = 6.40 Hz, 2H), 3.73-3.90 (m, 5H), 3.36-3.44 (m, 1H), 3.22-3.30 (m, 1H), 3.08-3.21 (m, 2H), 2.61-2.72 (m, 2H), 2.24-2.36 (m, 1H), 1.98-2.11 (m, 1H), 1.88 (s, 2H), 1.45-1.72 (m, 3H), 0.85-0.95 (m, 2H), 0.60 (dd, J = 1.76, 5.02 Hz, 2H) |
| 10 | 4 | 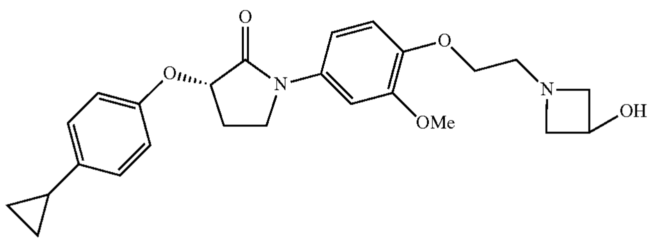 [SMILES: COc1cc(N2CC[C@H](Oc3ccc(C4CC4)cc3)C2=O)ccc1OCCN1CC(O)C1] | A1 | 1 (6.38) 2 (8.4) | 439.2 | $^1$H NMR (400 MHz, DMSO-d$_6$) δ 7.49 (d, J = 2.51 Hz, 1H), 6.90-7.09 (m, 6H), 5.14 (s, 2H), 4.10-4.22 (m, 1H), 3.72-3.93 (m, 7H), 3.51-3.60 (m, 2H), 2.61-2.84 (m, 5H), 2.01, 8.28 Hz, 2H), 1.80-1.94 (m, 1H), 0.89 (dd, J = 2.01, 8.28 Hz, 2H), 0.53-0.66 (m, 2H) |
| 11 | 2 | 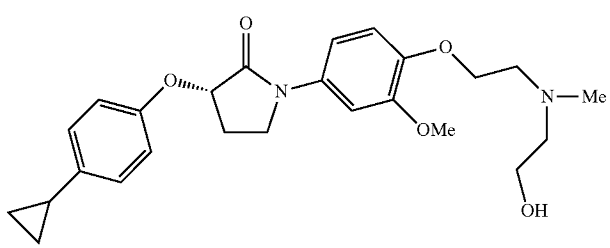 [SMILES: COc1cc(N2CC[C@H](Oc3ccc(C4CC4)cc3)C2=O)ccc1OCCN(C)CCO] | A1 | 1 (6.59) 2 (8.53) | 441.2 | $^1$H NMR (400 MHz, DMSO-d$_6$) δ 7.50 (d, J = 2.51 Hz, 1H), 6.89-7.12 (m, 6H), 5.15 (s, 1H), 4.32 (s, 1H), 4.03 (t, J = 6.02 Hz, 2H), 3.77 (s, 5H), 3.49 (d, J = 5.77 Hz, 2H), 2.75 (t, J = 6.02 Hz, 3H), 2.49 (s, 1H), 2.29 (s, 3H), 1.99-2.14 (m, 1H), 1.82-1.95 (m, 1H), 0.89 (dd, J = 2.13, 8.41 Hz, 2H), 0.60 (dd, J = 1.88, 5.14 Hz, 2H) |

TABLE A-continued

| Example No. | Ki (nM) | Structure | Synthetic Procedure Used | HPLC Methods (t_R min) | MS (M + H) | NMR Data |
|---|---|---|---|---|---|---|
| 12 | 2 | (3-pyrrolinyl-ethoxy, OMe, pyrrolidinone, cyclopropylphenoxy) | A1 | 1 (7.33) 2 (9.02) | 435.2 | $^1$H NMR (400 MHz, DMSO-d$_6$) δ 7.50 (d, J = 2.51 Hz, 1H), 6.89-7.12 (m, 6H), 5.15 (s, 1H), 4.32 (s, 1H), 4.03 (t, J = 6.02 Hz, 2H), 3.77 (s, 5H), 3.49 (d, J = 5.77 Hz, 2H), 2.75 (t, J = 6.02 Hz, 3H), 2.49 (s, 1H), 2.29 (s, 2H), 1.99-2.14 (m, 1H), 1.82-1.95 (m, 1H), 0.89 (dd, J = 2.13, 8.41 Hz, 2H), 0.60 (dd, J = 1.88, 5.14 Hz, 2H) |
| 13 | 11 | (piperazinone-ethoxy, OMe, pyrrolidinone, cyclopropylphenoxy) | A1 | 1 (6.58) 2 (8.44) | 466.2 | $^1$H NMR (400 MHz, DMSO-d$_6$) δ 7.69-7.78 (m, 1H), 7.48-7.56 (m, 1H), 7.02 (d, J = 8.28 Hz, 4H), 6.92-6.98 (m, 2H), 5.09-5.20 (m, 1H), 4.09 (s, 3H), 3.77 (s, 5H), 3.13-3.21 (m, 2H), 3.07 (s, 2H), 2.77 (s, 2H), 2.69 (s, 3H), 1.99-2.12 (m, 1H), 1.82-1.93 (m, 1H), 0.87-0.94 (m, 2H), 0.56-0.65 (m, 2H) |
| 14 | 2 | (N,N-dimethylaminoethoxy, OMe, pyrrolidinone, cyclopropylphenoxy) | A1 | 1 (7.4) 2 (9.02) | 411.2 | $^1$H NMR (400 MHz, CDCl$_3$) δ 7.69 (d, J = 2.51 Hz, 1H), 6.94-7.09 (m, 4H), 6.80-6.93 (m, 2H), 4.97 (s, 1H), 4.11 (t, J = 6.15 Hz, 2H), 3.77-3.94 (m, 5H), 2.79 (t, J = 6.15 Hz, 2H), 2.59-2.71 (m, 1H), 2.36 (s, 6H), 2.20-2.31 (m, 1H), 1.83-1.90 (m, 1H), 0.90 (dd, J = 1.76, 8.53 Hz, 2H), 0.62 (dd, J = 1.63, 5.14 Hz, 2H) |

TABLE A-continued
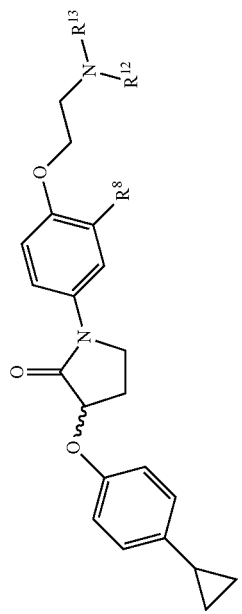
| Example No. | Ki (nM) | Structure | Synthetic Procedure Used | HPLC Methods ($t_R$ min) | MS (M + H) | NMR Data |
|---|---|---|---|---|---|---|
| 15 | 1.6 | 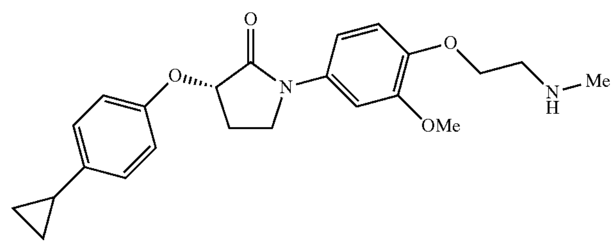 [SMILES: CNCCOc1ccc(N2CC[C@H](Oc3ccc(C4CC4)cc3)C2=O)cc1OC] | A1 | 1 (7.32) 2 (8.82) | 397.2 | $^1$H NMR (400 MHz, CDCl$_3$) δ 7.71 (d, J = 2.51 Hz, 1H), 6.95-7.07 (m, 4H), 6.80-6.93 (m, 2H), 4.97 (s, 1H), 4.12 (t, J = 5.27 Hz, 2H), 3.88 (s, 5H), 2.99 (t, J = 5.27 Hz, 2H), 2.61-2.72 (m, 1H), 2.51 (s, 3H), 2.18-2.36 (m, 1H), 1.78-1.93 (m, 1H), 0.90 (dd, J = 1.76, 8.53 Hz, 2H), 0.56-0.67 (m, 2H) |
| 16 | 5 | 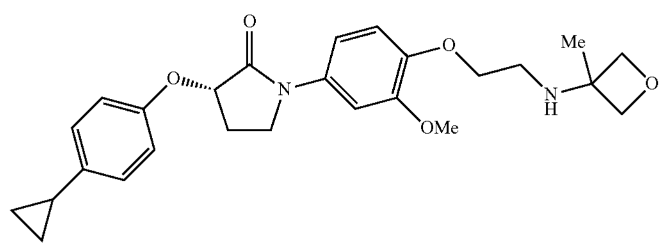 [SMILES: COc1cc(N2CC[C@H](Oc3ccc(C4CC4)cc3)C2=O)ccc1OCCNC1(C)COC1] | A1 | 1 (6.92) 2 (8.83) | 453.2 | $^1$H NMR (400 MHz, CDCl$_3$) δ 7.73-7.79 (m, 1H), 6.91-7.06 (m, 5H), 6.81-6.88 (m, 1H), 4.92-5.02 (m, 1H), 4.64-4.71 (m, 2H), 4.46 (d, J = 6.78 Hz, 2H), 4.13-4.22 (m, 2H), 3.90 (s, 5H), 3.05-3.16 (m, 2H), 2.60-2.73 (m, 1H), 2.22-2.35 (m, 2H), 1.82-1.94 (m, 4H), 0.85-0.94 (m, 2H), 0.58-0.66 (m, 2H) |
| 17 | 3 | 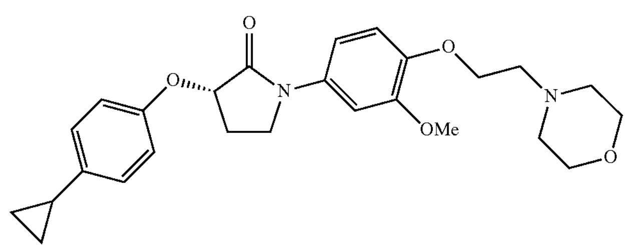 [SMILES: COc1cc(N2CC[C@H](Oc3ccc(C4CC4)cc3)C2=O)ccc1OCCN1CCOCC1] | A1 | 1 (6.68) 2 (8.88) | 453.2 | $^1$H NMR (400 MHz, CDCl$_3$) δ 7.70 (d, J = 2.26 Hz, 1H), 6.94-7.07 (m, 4H), 6.80-6.93 (m, 2H), 4.97 (t, J = 7.65 Hz, 1H), 4.16 (t, J = 6.02 Hz, 2H), 3.71-3.93 (m, 9H), 2.87 (br. s., 2H), 2.56-2.72 (m, 5H), 2.21-2.34 (m, 1H), 1.86 (s, 1H), 0.86-0.97 (m, 2H), 0.54-0.67 (m, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 18 | 3 | [Structure with NMe2 pyrrolidine, OMe phenyl, pyrrolidinone, 4-cyclopropylphenoxy] | A1 | 1 (5.98) 2 (7.85) | 480.4 | $^1$H NMR (400 MHz, CDCl$_3$) δ 7.69 (d, J = 2.51 Hz, 1H), 6.94-7.04 (m, 4H), 6.79-6.91 (m, 2H), 4.97 (s, 1H), 4.11 (t, J = 6.27 Hz, 2H), 3.77-3.92 (m, 5H), 2.82-3.05 (m, 4H), 2.71-2.81 (m, 1H), 2.53-2.70 (m, 2H), 2.37-2.44 (m, 1H), 2.21 (s, 7H), 1.94-2.05 (m, 1H), 1.80-1.90 (m, 1H), 1.73-1.77 (m, 1H), 0.90 (dd, J = 1.88, 8.41 Hz, 2H), 0.56-0.65 (m, 2H) |
| 19 | 1.6 | [Structure with OH piperidine, OMe phenyl, pyrrolidinone, 4-cyclopropylphenoxy] | A1 | 1 (9.29) 2 (8.59) | 467.2 | $^1$H NMR (400 MHz, CDCl$_3$) δ 7.69 (d, J = 2.25 Hz, 1H), 7.00 (d, J = 8.00 Hz, 4H), 6.81-6.92 (m, 2H), 4.97 (s, 1H), 4.12 (s, 2H), 3.88 (s, 6H), 2.76-2.90 (m, 2H), 2.54-2.72 (m, 4H), 2.36-2.53 (m, 2H), 2.21-2.33 (m, 1H), 1.77-1.90 (m, 2H), 1.49-1.57 (m, 3H), 0.86-0.95 (m, 2H), 0.57-0.66 (m, 2H) |
| 20 | 4 | [Structure with 4,4-difluoropiperidine, OMe phenyl, pyrrolidinone, 4-cyclopropylphenoxy] | A1 | 1 (7.67) 2 (9.91) | 487.6 | $^1$H NMR (400 MHz, CDCl$_3$) δ 7.69 (d, J = 2.51 Hz, 1H), 7.00 (d, J = 8.28 Hz, 4H), 6.81-6.94 (m, 2H), 4.97 (s, 1H), 4.13 (s, 2H), 3.87 (s, 5H), 2.84-2.94 (m, 2H), 2.70 (br. s., 5H), 2.21-2.35 (m, 1H), 1.95-2.10 (m, 4H), 1.80-1.90 (m, 1H), 0.90 (d, J = 6.78 Hz, 2H), 0.55-0.66 (m, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 21 | 2 | (adamantyl-OH, NH, OCH2CH2O, OMe, phenyl-pyrrolidinone-O-phenyl-cyclopropyl) | A1 | | 533.2 | $^1$H NMR (400 MHz, CDCl$_3$) δ 7.69-7.77 (m, 1H), 6.95-7.06 (m, 4H), 6.77-6.94 (m, 1H), 4.91-5.03 (m, 1H), 4.08-4.20 (m, 2H), 3.88 (s, 5H), 3.00-3.10 (m, 2H), 2.58-2.72 (m, 1H), 2.23-2.36 (m, 3H), 1.81-1.91 (m, 1H), 1.49-1.57 (m, 13H), 0.86-0.95 (m, 2H), 0.58-0.66 (m, 2H) |
| 22 | 4 | (pyrazinyl-piperazine-ethyl-O, OMe, phenyl-pyrrolidinone-O-phenyl-cyclopropyl) | A1 | | 530.2 | $^1$H NMR (400 MHz, DMSO-d$_6$) δ 8.28-8.37 (m, 1H), 8.06-8.13 (m, 1H), 7.79-7.89 (m, 1H), 7.46-7.55 (m, 1H), 6.92-7.11 (m, 6H), 5.08-5.21 (m, 1H), 4.07-4.18 (m, 2H), 3.73-3.89 (m, 5H), 3.51-3.62 (m, 4H), 2.59-2.80 (m, 7H), 2.01-2.08 (m, 1H), 1.81-1.94 (m, 1H), 0.83-0.93 (m, 2H), 0.53-0.66 (m, 2H) |

TABLE A-continued

| Example No. | Ki (nM) | Structure | Synthetic Procedure Used | HPLC Methods ($t_R$ min) | MS (M + H) | $^1$H NMR Data |
|---|---|---|---|---|---|---|
| 23 | 2 | [structure with pyrrolidine, OMe] | A1 | | 480.2 | $^1$H NMR (400 MHz, DMSO-$d_6$) δ 7.47-7.57 (m, 1H), 6.91-7.10 (m, 6H), 5.10-5.20 (m, 1H), 3.96-4.06 (m, 2H), 3.77 (s, 5H), 2.83-2.91 (m, 2H), 2.65-2.72 (m, 3H), 2.39-2.46 (m, 4H), 2.00-2.10 (m, 1H), 1.91 (s, 4H), 1.63-1.72 (m, 4H), 0.85-0.94 (m, 2H), 0.54-0.64 (m, 2H) |
| 24 | 2 | [structure with NH-t-Bu, OMe] | A1 | | 439.2 | $^1$H NMR (400 MHz, DMSO-$d_6$) δ 7.50-7.57 (m, 1H), 6.89-7.13 (m, 6H), 5.08-5.21 (m, 1H), 4.00-4.13 (m, 2H), 3.78 (s, 5H), 2.91-3.07 (m, 2H), 2.62-2.76 (m, 1H), 2.00-2.10 (m, 1H), 1.83-1.90 (m, 1H), 1.14 (br. s., 9H), 0.83-0.94 (m, 2H), 0.53-0.64 (m, 2H) |
| 25 | 2 | [structure with cyclopentyl-CH2OH, OMe] | A1 | | 481.2 | $^1$H NMR (400 MHz, DMSO-$d_6$) δ 7.48-7.58 (m, 1H), 6.89-7.13 (m, 6H), 5.10-5.21 (m, 1H), 3.98-4.13 (m, 2H), 3.78 (s, 5H), 3.35-3.39 (m, 2H), 2.86-3.06 (m, 2H), 2.62-2.74 (m, 1H), 2.00-2.11 (m, 1H), 1.82-1.90 (m, 1H), 1.45-1.71 (m, 8H), 0.83-0.95 (m, 2H), 0.54-0.65 (m, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 26 | 5 | 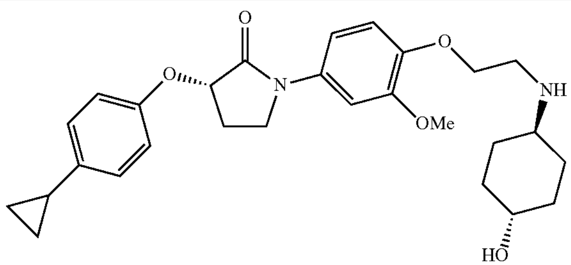 [SMILES: COc1cc(N2CC[C@H](Oc3ccc(C4CC4)cc3)C2=O)ccc1OCCN[C@H]1CC[C@H](O)CC1] | A1 | | 480.2 | $^1$H NMR (400 MHz, DMSO-$d_6$) δ 7.38-7.46 (m, 1H), 6.87-7.04 (m, 6H), 5.01-5.14 (m, 1H), 4.03-4.11 (m, 2H), 3.70-3.83 (m, 5H), 2.85-2.98 (m, 3H), 2.60-2.71 (m, 1H), 1.79-2.05 (m, 7H), 1.25-1.36 (m, 2H), 1.03-1.17 (m, 2H), 0.81-0.93 (m, 2H), 0.48-0.60 (m, 2H) |
| 27 | 5 | 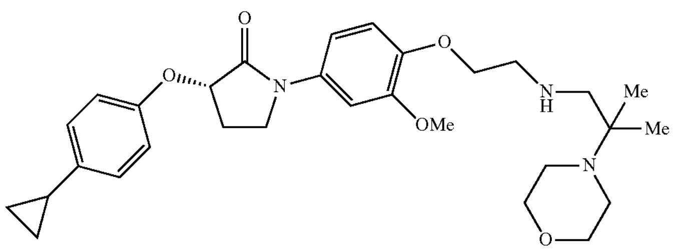 [SMILES: COc1cc(N2CC[C@H](Oc3ccc(C4CC4)cc3)C2=O)ccc1OCCNCC(C)(C)N1CCOCC1] | A1 | | 524.4 | $^1$H NMR (400 MHz, DMSO-$d_6$) δ 7.48-7.55 (m, 1H), 6.91-7.12 (m, 6H), 5.10-5.20 (m, 1H), 4.00-4.16 (m, 2H), 3.78 (s, 5H), 3.55 (br. s., 4H), 2.84-3.05 (m, 2H), 2.57-2.73 (m, 2H), 2.43 (br. s., 5H), 1.99-2.07 (m, 1H), 1.82-1.90 (m, 1H), 0.99 (s, 6H), 0.84-0.94 (m, 2H), 0.55-0.65 (m, 2H) |
| 28 | 2 | 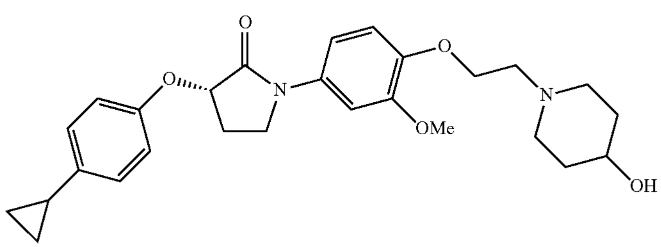 [SMILES: COc1cc(N2CC[C@H](Oc3ccc(C4CC4)cc3)C2=O)ccc1OCCN1CCC(O)CC1] | A1 | | 467.2 | $^1$H NMR (400 MHz, DMSO-$d_6$) δ 7.47-7.56 (m, 1H), 6.90-7.13 (m, 6H), 5.07-5.21 (m, 1H), 4.47-4.67 (m, 1H), 3.98-4.15 (m, 2H), 3.73-3.90 (m, 5H), 3.40-3.57 (m, 2H), 2.61-2.93 (m, 5H), 2.00-2.09 (m, 1H), 1.84-1.89 (m, 1H), 1.63-1.80 (m, 2H), 1.35-1.51 (m, 2H), 0.83-0.94 (m, 2H), 0.53-0.64 (m, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 29 | 6 | (structure: 3-(4-cyclopropylphenoxy)-1-[4-(2-(4-(pyrimidin-2-yl)piperazin-1-yl)ethoxy)-3-methoxyphenyl]pyrrolidin-2-one) | A1 | | 530.2 | $^1$H NMR (400 MHz, DMSO-d$_6$) δ 8.31-8.43 (m, 2H), 7.44-7.57 (m, 1H), 6.89-7.12 (m, 6H), 6.52-6.70 (m, 1H), 5.08-5.20 (m, 1H), 4.06-4.18 (m, 2H), 3.78 (s, 9H), 2.52-2.81 (m, 7H), 1.98-2.12 (m, 1H), 1.83-1.93 (m, 1H), 0.84-0.95 (m, 2H), 0.53-0.64 (m, 2H) |
| 30 | 2 | (structure: 3-(4-cyclopropylphenoxy)-1-[4-(2-(3-morpholinopyrrolidin-1-yl)ethoxy)-3-methoxyphenyl]pyrrolidin-2-one) | A1 | | 522.2 | $^1$H NMR (400 MHz, CDCl$_3$) δ 7.67-7.77 (m, 1H), 7.00 (d, J = 8.53 Hz, 4H), 6.78-6.92 (m, 2H), 4.89-5.03 (m, 1H), 4.09-4.24 (m, 2H), 3.86 (s, 5H), 3.73 (s, 4H), 2.90-3.19 (m, 4H), 2.60-2.71 (m, 2H), 2.41-2.58 (m, 4H), 2.21-2.34 (m, 1H), 1.98-2.08 (m, 1H), 1.75-1.90 (m, 4H), 0.84-0.95 (m, 2H), 0.57-0.67 (m, 2H) |

TABLE A-continued

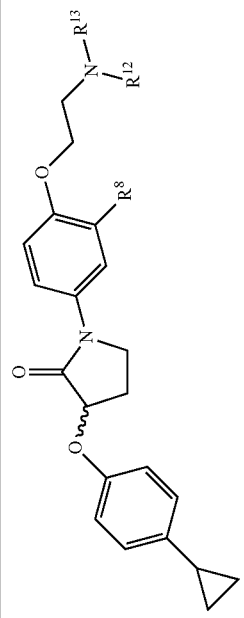

| Example No. | Ki (nM) | Structure | Synthetic Procedure Used | HPLC Methods ($t_R$ min) | MS (M + H) | $^1$H NMR Data |
|---|---|---|---|---|---|---|
| 31 | 1.8 | (structure with (S)-3-methoxypyrrolidine, OMe on phenyl) | A1 | 1 (7.28) 2 (8.71) | 467.2 | $^1$H NMR (400 MHz, CDCl$_3$) δ 7.69 (d, J = 2.51 Hz, 1H), 6.95-7.05 (m, 4H), 6.80-6.90 (m, 2H), 4.97 (t, J = 7.53 Hz, 1H), 4.14 (t, J = 6.27 Hz, 2H), 3.90-3.97 (m, 1H), 3.78-3.89 (m, 5H), 3.29 (s, 3H), 2.93 (t, J = 6.27 Hz, 2H), 2.77-2.86 (m, 2H), 2.54-2.75 (m, 3H), 2.21-2.33 (m, 1H), 2.03-2.14 (m, 1H), 1.85 (s, 2H), 0.90 (dd, J = 2.01, 8.53 Hz, 2H), 0.58-0.65 (m, 2H) |
| 32 | 1.4 | (structure with (R)-3-methoxypyrrolidine, OMe on phenyl) | A1 | 1 (7.28) 2 (8.74) | 467.2 | $^1$H NMR (400 MHz, CDCl$_3$) δ 7.70 (d, J = 2.51 Hz, 1H), 7.00 (d, J = 8.03 Hz, 4H), 6.87 (s, 1H), 6.80-6.85 (m, 1H), 4.97 (s, 1H), 4.15 (s, 2H), 3.91-3.98 (m, 1H), 3.87 (s, 5H), 3.29 (s, 3H), 2.95 (s, 2H), 2.79-2.90 (m, 2H), 2.59-2.77 (m, 3H), 2.22-2.33 (m, 1H), 2.03-2.14 (m, 1H), 1.79-1.89 (m, 2H), 0.90 (d, J = 6.53 Hz, 2H), 0.57-0.65 (m, 2H) |
| 33 | 4 | (structure with N-methylpiperazine, OMe on phenyl) | A1 | 1 (6.28) 2 (7.57) | 466.2 | $^1$H NMR (400 MHz, CDCl$_3$) δ 7.68 (d, J = 2.26 Hz, 1H), 7.00 (d, J = 8.53 Hz, 4H), 6.79-6.92 (m, 2H), 4.97 (s, 1H), 4.13 (t, J = 6.15 Hz, 2H), 3.87 (s, 5H), 2.84 (t, J = 6.02 Hz, 2H), 2.42-2.74 (m, 9H), 2.29 (s, 4H), 1.79-1.90 (m, 1H), 0.90 (d, J = 6.53 Hz, 2H), 0.62 (dd, J = 1.63, 5.14 Hz, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 34 | 4 | 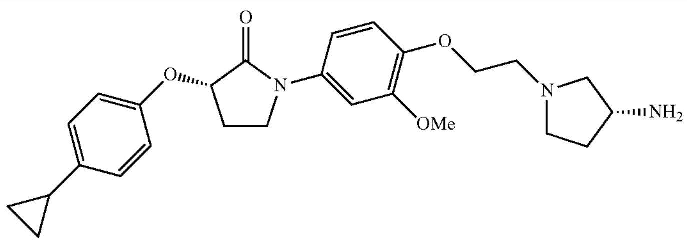 [SMILES: COc1cc(N2CC[C@H](Oc3ccc(C4CC4)cc3)C2=O)ccc1OCCN1CC[C@@H](N)C1] | A1 | 1 (5.91) | 452.2 | $^1$H NMR (400 MHz, DMSO) δ 7.50 (d, J = 2.26 Hz, 1H), 6.91-7.09 (m, 6H), 5.14 (s, 1H), 4.02 (s, 2H), 3.77 (s, 5H), 2.75 (d, J = 6.27 Hz, 3H), 2.52 (br. s., 4H), 2.18-2.24 (m, 1H), 1.82-2.11 (m, 4H), 0.89 (dd, J = 2.13, 8.41 Hz, 2H), 0.54-0.63 (m, 2H) |
| 35 | 3 | 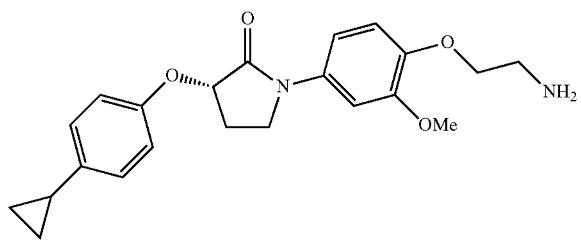 [SMILES: COc1cc(N2CC[C@H](Oc3ccc(C4CC4)cc3)C2=O)ccc1OCCN] | A1 | 1 (6.77) 2 (7.67) | 383.2 | $^1$H NMR (400 MHz, DMSO) δ 7.91-8.04 (m, 2H), 7.54-7.59 (m, 1H), 7.07-7.14 (m, 2H), 7.00-7.06 (m, 2H), 6.92-6.98 (m, 2H), 5.11-5.20 (m, 1H), 4.12-4.18 (m, 2H), 3.81 (s, 5H), 3.17-3.25 (m, 2H), 2.64-2.74 (m, 1H), 2.01-2.11 (m, 1H), 1.84-1.94 (m, 1H), 0.85-0.94 (m, 2H), 0.55-0.65 (m, 2H) |
| 36 | 5 | 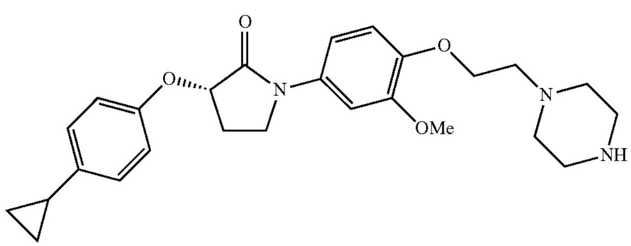 [SMILES: COc1cc(N2CC[C@H](Oc3ccc(C4CC4)cc3)C2=O)ccc1OCCN1CCNCC1] | A1 | 1 (7.93) 2 (8.14) | 452.2 | $^1$H NMR (400 MHz, DMSO-$d_6$) δ 9.44-9.73 (m, 1H), 7.56 (s, 1H), 7.11 (s, 2H), 6.99-7.06 (m, 2H), 6.90-6.98 (m, 2H), 5.16 (s, 1H), 4.32-4.44 (m, 2H), 3.81 (s, 6H), 3.46-3.66 (m, 9H), 2.61-2.75 (m, 1H), 2.00-2.13 (m, 1H), 1.83-1.93 (m, 1H), 0.90 (dd, J = 2.01, 8.28 Hz, 2H), 0.60 (dd, J = 2.01, 5.02 Hz, 2H) |

TABLE A-continued

| Example No. | Ki (nM) | Structure | Synthetic Procedure Used | HPLC Methods ($t_R$ min) | MS (M + H) | $^1$H NMR Data |
|---|---|---|---|---|---|---|
| 37 | 3 | (structure with dihydroxypyrrolidine) | A1 | 1 (6.8)<br>2 (12.5) | 469.2 | $^1$H NMR (400 MHz, CDCl$_3$) δ 7.68-7.72 (m, 1H), 7.00 (d, J = 8.53 Hz, 4H), 6.81-6.91 (m, 2H), 4.94-5.02 (m, 1H), 4.18-4.24 (m, 2H), 4.11 (s, 2H), 3.88 (s, 5H), 2.92 (s, 4H), 2.74-2.82 (m, 2H), 2.60-2.71 (m, 1H), 2.25-2.33 (m, 4H), 1.78-1.91 (m, 3H), 0.86-0.94 (m, 2H), 0.58-0.65 (m, 2H) |
| 38 | 1.1 | (structure with 2-oxa-7-azaspiro[3.5]nonane) | A1 | 1 (6.82)<br>2 (8.03) | 493.2 | $^1$H NMR (400 MHz, CDCl$_3$) δ 7.70 (d, J = 2.01 Hz, 1H), 6.94-7.07 (m, 4H), 6.79-6.92 (m, 2H), 4.97 (s, 1H), 4.42 (s, 4H), 4.16 (br. s., 2H), 3.76-3.93 (m, 5H), 2.80-2.96 (m, 2H), 2.44-2.72 (m, 4H), 2.21-2.35 (m, 1H), 1.73-2.04 (m, 6H), 0.90 (dd, J = 1.88, 8.41 Hz, 2H), 0.57-0.67 (m, 2H) |
| 39 | 1.6 | (structure with azetidinyl-pyrrolidine) | A1 | 1 (6.17)<br>2 (7.46) | 492.3 | $^1$H NMR (400 MHz, CDCl$_3$) δ 7.67-7.72 (m, 1H), 7.00 (d, J = 8.28 Hz, 4H), 6.78-6.89 (m, 2H), 4.93-5.01 (m, 1H), 3.99-4.07 (m, 2H), 3.86 (s, 5H), 3.60-3.71 (m, 2H), 3.14-3.29 (m, 3H), 2.91-3.01 (m, 2H), 2.60-2.72 (m, 1H), 2.44-2.57 (m, 4H), 2.20-2.33 (m, 1H), 1.79-1.89 (m, 4H), 0.88-0.93 (m, 2H), 0.58-0.65 (m, 2H) |

TABLE A-continued

| Example No. | Ki (nM) | Structure | Synthetic Procedure Used | HPLC Methods ($t_R$ min) | MS (M + H) | $^1$H NMR Data |
|---|---|---|---|---|---|---|
| 40 | 3 | (3-OMe phenyl; azetidine with 3-OH, 3-Me substituents) | A1 | 1 (11.29) 2 (12.8) | 453.2 | $^1$H NMR (400 MHz, CDCl$_3$) δ 7.68 (d, J = 2.01 Hz, 1H), 7.00 (d, J = 8.28 Hz, 2H), 6.80-6.90 (m, 2H), 4.97 (s, 1H), 3.99-4.06 (m, 2H), 3.87 (s, 5H), 3.42 (d, J = 8.53 Hz, 2H), 3.21 (s, 2H), 2.93 (s, 2H), 2.60-2.71 (m, 1H), 2.21-2.34 (m, 1H), 1.83-1.90 (m, 1H), 1.50 (s, 3H), 0.89 (s, 2H), 0.59-0.65 (m, 2H) |
| 41 | 1.6 | (3-Et phenyl; pyrrolidine) | A2 | 1 (7.84) 2 (10.1) 4 (6.1) | 435.4 | $^1$H NMR (400 MHz, DMSO-d$_6$) δ 7.47-7.56 (m, 1H), 7.35-7.46 (m, 1H), 6.91-7.07 (m, 5H), 5.05-5.20 (m, 1H), 4.08 (s, 2H), 3.74-3.88 (m, 2H), 2.81 (s, 2H), 2.53-2.72 (m, 7H), 1.98-2.11 (m, 1H), 1.82-1.93 (m, 1H), 1.69 (t, J = 3.51 Hz, 4H), 1.15 (t, J = 7.53 Hz, 3H), 0.84-0.93 (m, 2H), 0.54-0.65 (m, 2H) |
| 42 | 5 | (3-Et phenyl; pyrrolidine) | A2 | 1 (7.85) 2 (10.0) 4 (10.6) | 435.4 | $^1$H NMR (400 MHz, DMSO-d$_6$) δ 7.48-7.55 (m, 1H), 7.38-7.46 (m, 1H), 6.91-7.06 (m, 5H), 5.08-5.18 (m, 1H), 4.03-4.17 (m, 2H), 3.72-3.88 (m, 2H), 2.78-2.95 (m, 2H), 2.55-2.71 (m, 7H), 1.96-2.09 (m, 1H), 1.83-1.93 (m, 1H), 1.65-1.78 (m, 4H), 1.09-1.18 (m, 3H), 0.82-0.94 (m, 2H), 0.53-0.65 (m, 2H) |

TABLE A-continued

| Example No. | Ki (nM) | Structure | Synthetic Procedure Used | HPLC Methods ($t_R$ min) | MS (M + H) | $^1$H NMR Data |
|---|---|---|---|---|---|---|
| 43 | 2 | 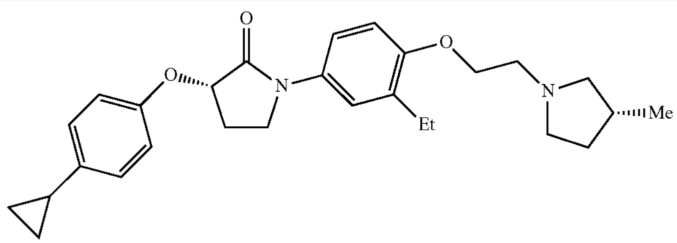 [SMILES: CCc1cc(N2CC[C@H](Oc3ccc(C4CC4)cc3)C2=O)ccc1OCCN1CC[C@@H](C)C1] | A2 | 1 (7.88) 2 (9.35) | 453.3 | $^1$H NMR (400 MHz, DMSO-$d_6$) δ 7.48-7.54 (m, 1H), 7.39-7.46 (m, 1H), 6.87-7.08 (m, 5H), 5.10-5.29 (m, 2H), 4.03-4.15 (m, 2H), 3.75-3.87 (m, 2H), 2.56-3.02 (m, 9H), 1.80-2.15 (m, 4H), 1.10-1.19 (m, 3H), 0.85-0.93 (m, 2H), 0.54-0.64 (m, 2H) |
| 44 | 3 | 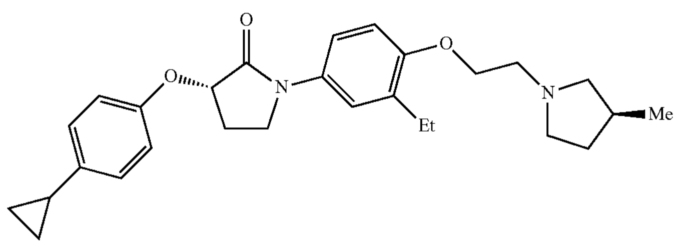 [SMILES: CCc1cc(N2CC[C@H](Oc3ccc(C4CC4)cc3)C2=O)ccc1OCCN1CC[C@H](C)C1] | A2 | 1 (7.86) 2 (9.37) | 453.3 | $^1$H NMR (400 MHz, DMSO-$d_6$) δ 7.48-7.54 (m, 1H), 7.40-7.46 (m, 1H), 6.90-7.07 (m, 5H), 5.10-5.33 (m, 2H), 4.03-4.13 (m, 2H), 3.76-3.87 (m, 2H), 2.81-3.00 (m, 4H), 2.56-2.78 (m, 4H), 2.39-2.47 (m, 1H), 1.99-2.21 (m, 2H), 1.79-1.96 (m, 2H), 1.15 (s, 3H), 0.85-0.95 (m, 2H), 0.56-0.64 (m, 2H) |
| 45 | 3 | 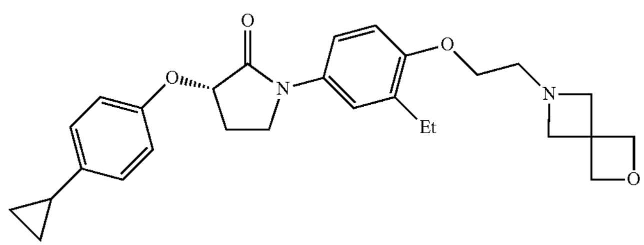 [SMILES: CCc1cc(N2CC[C@H](Oc3ccc(C4CC4)cc3)C2=O)ccc1OCCN1CC2(COC2)C1] | A2 | 1 (7.21) 2 (8.69) | 463.2 | $^1$H NMR (400 MHz, DMSO-$d_6$) δ 7.37-7.46 (m, 1H), 7.48-7.55 (m, 1H), 5.06-5.19 (m, 1H), 4.60 (s, 4H), 3.88-3.97 (m, 2H), 3.74-3.85 (m, 2H), 3.38 (s, 4H), 2.70 (s, 5H), 1.98-2.11 (m, 1H), 1.81-1.94 (m, 1H), 1.15 (t, J = 7.40 Hz, 3H), 0.82-0.94 (m, 2H), 0.53-0.65 (m, 2H) |

TABLE A-continued

| Example No. | Ki (nM) | Structure | Synthetic Procedure Used | HPLC Methods ($t_R$ min) | MS (M + H) | $^1$H NMR Data |
|---|---|---|---|---|---|---|
| 46 | 15 | 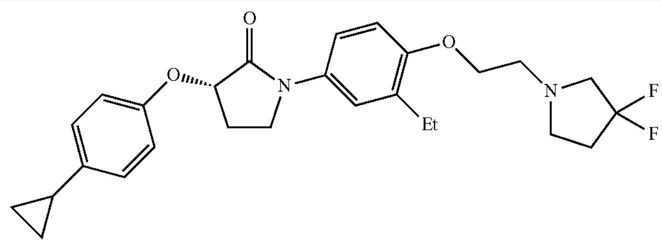 | A2 | 1 (8.44) 2 (9.64) | 471.1 | $^1$H NMR (400 MHz, DMSO-$d_6$) δ 7.48-7.55 (m, 1H), 7.39-7.46 (m, 1H), 6.91-7.08 (m, 5H), 5.06-5.17 (m, 1H), 4.03-4.14 (m, 2H), 3.73-3.89 (m, 2H), 2.96-3.07 (m, 2H), 2.79-2.91 (m, 4H), 2.59-2.70 (m, 3H), 2.18-2.31 (m, 2H), 1.98-2.12 (m, 1H), 1.81-1.93 (m, 1H), 1.09-1.21 (m, 3H), 0.84-0.94 (m, 2H), 0.53-0.66 (m, 2H) |
| 47 | 4 | 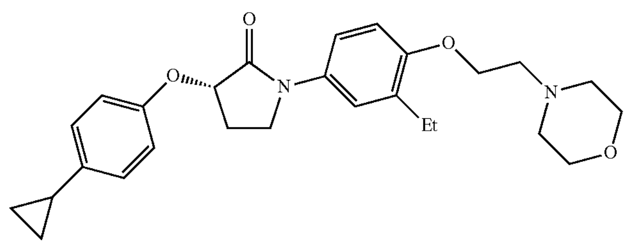 | A2 | 1 (7.3) 2 (9.01) | 451 | $^1$H NMR (400 MHz, DMSO-$d_6$) δ 7.47-7.54 (m, 1H), 7.37-7.45 (m, 1H), 6.90-7.07 (m, 5H), 5.07-5.18 (m, 1H), 4.05-4.16 (m, 2H), 3.74-3.87 (m, 2H), 3.54-3.64 (m, 4H), 2.52-2.75 (m, 9H), 1.99-2.10 (m, 1H), 1.82-1.92 (m, 1H), 1.14 (s, 3H), 0.84-0.94 (m, 2H), 0.53-0.65 (m, 2H) |
| 48 | 1.2 | 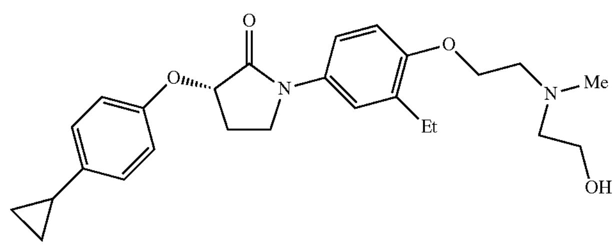 [SMILES: CCc1cc(N2CC[C@H](Oc3ccc(C4CC4)cc3)C2=O)ccc1OCCN(C)CCO] | A2 | 1 (7.36) 2 (8.71) | 439.1 | $^1$H NMR (400 MHz, DMSO-$d_6$) δ 7.51 (d, J = 2.51 Hz, 1H), 7.42 (s, 1H), 6.91-7.06 (m, 5H), 5.13 (s, 1H), 4.33 (s, 1H), 4.06 (t, J = 5.77 Hz, 2H), 3.75-3.87 (m, 2H), 3.49 (d, J = 5.52 Hz, 2H), 2.79 (t, J = 5.77 Hz, 2H), 2.53-2.72 (m, 5H), 2.31 (s, 3H), 1.98-2.11 (m, 1H), 1.81-1.92 (m, 1H), 1.15 (t, J = 7.53 Hz, 3H), 0.89 (dd, J = 2.01, 8.53 Hz, 2H), 0.60 (dd, J = 1.88, 5.14 Hz, 2H) |

TABLE A-continued

| Example No. | Ki (nM) | Structure | Synthetic Procedure Used | HPLC Methods ($t_R$ min) | MS (M + H) | $^1$H NMR Data |
|---|---|---|---|---|---|---|
| 49 | 1.5 | (3-hydroxypyrrolidine ethoxy, Et-phenyl-pyrrolidinone, 4-cyclopropylphenoxy) | A2 | 1 (7.38) 2 (8.74) | 451.1 | $^1$H NMR (400 MHz, DMSO-d$_6$) δ 7.49-7.55 (m, 1H), 7.39-7.46 (m, 1H), 6.92-7.06 (m, 5H), 5.06-5.18 (m, 1H), 4.62-4.71 (m, 1H), 4.16-4.24 (m, 1H), 4.02-4.10 (m, 2H), 3.75-3.87 (m, 2H), 2.76-2.86 (m, 3H), 2.56-2.72 (m, 5H), 2.39-2.47 (m, 1H), 1.94-2.10 (m, 2H), 1.83-1.93 (m, 1H), 1.50-1.59 (m, 1H), 1.15 (s, 3H), 0.82-0.93 (m, 2H), 0.55-0.64 (m, 2H) |
| 50 | 1.3 | (3-hydroxypyrrolidine ethoxy, Et-phenyl-pyrrolidinone, 4-cyclopropylphenoxy) | A2 | 1 (7.42) 2 (8.74) | 451 | $^1$H NMR (400 MHz, DMSO-d$_6$) δ 7.49-7.56 (m, 1H), 7.38-7.46 (m, 1H), 6.91-7.06 (m, 5H), 5.09-5.18 (m, 1H), 4.64-4.71 (m, 1H), 4.15-4.24 (m, 1H), 4.06 (s, 2H), 2.80 (s, 3H), 2.54-2.72 (m, 5H), 2.38-2.47 (m, 1H), 1.93-2.10 (m, 2H), 1.83-1.92 (m, 1H), 1.48-1.59 (m, 1H), 1.15 (t, J = 7.53 Hz, 3H), 0.84-0.93 (m, 2H), 0.55-0.63 (m, 2H) |
| 51 | 1.0 | (2-hydroxymethylpyrrolidine ethoxy, Et-phenyl-pyrrolidinone, 4-cyclopropylphenoxy) | A2 | 1 (7.65) 2 (9.07) | 465 | $^1$H NMR (400 MHz, DMSO-d$_6$) δ 7.50 (s, 1H), 7.39-7.46 (m, 1H), 6.91-7.07 (m, 5H), 5.13 (s, 1H), 4.29-4.41 (m, 1H), 4.00-4.12 (m, 2H), 3.76-3.87 (m, 2H), 3.37-3.45 (m, 1H), 3.09-3.29 (m, 3H), 2.59 (d, J = 7.53 Hz, 5H), 2.28-2.40 (m, 1H), 1.97-2.11 (m, 1H), 1.74-1.94 (m, 2H), 1.61-1.72 (m, 2H), 1.47-1.58 (m, 1H), 1.14 (t, J = 7.40 Hz, 3H), 0.90 (s, 2H), 0.60 (dd, J = 2.01, 5.02 Hz, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 52 | 7 | 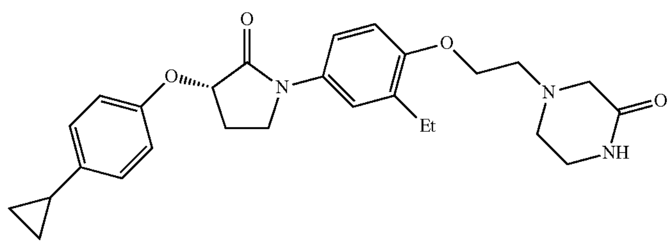 | A2 | 1 (7.3) 2 (8.45) | 464.9 | $^1$H NMR (400 MHz, DMSO-d$_6$) δ 7.67-7.77 (m, 1H), 7.47-7.55 (m, 1H), 7.40-7.46 (m, 1H), 6.91-7.07 (m, 5H), 5.05-5.18 (m, 1H), 4.11 (s, 2H), 3.74-3.87 (m, 2H), 3.13-3.21 (m, 2H), 3.07 (s, 2H), 2.81 (s, 2H), 2.70 (s, 2H), 2.55-2.62 (m, 2H), 1.98-2.11 (m, 1H), 1.82-1.93 (m, 1H), 1.14 (t, J = 7.53 Hz, 3H), 0.85-0.94 (m, 2H), 0.54-0.64 (m, 2H) |
| 53 | 3 | 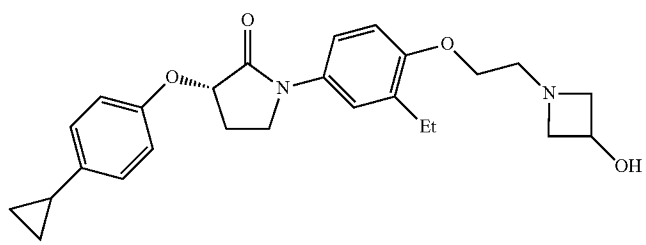 | A2 | 1 (7.44) 2 (8.78) | 437.1 | $^1$H NMR (400 MHz, DMSO-d$_6$) δ 7.47-7.56 (m, 1H), 7.35-7.46 (m, 1H), 6.95 (s, 5H), 5.29-5.45 (m, 1H), 5.06-5.17 (m, 1H), 4.16-4.29 (m, 1H), 3.93-4.04 (m, 2H), 3.75-3.86 (m, 2H), 3.63-3.74 (m, 2H), 2.81-3.09 (m, 4H), 2.56-2.66 (m, 3H), 1.98-2.10 (m, 1H), 1.82-1.95 (m, 1H), 1.15 (s, 3H), 0.86-0.94 (m, 2H), 0.54-0.65 (m, 2H) |

TABLE A-continued
| Example No. | Ki (nM) | Structure | Synthetic Procedure Used | HPLC Methods ($t_R$ min) | MS (M + H) | NMR Data |
|---|---|---|---|---|---|---|
| 54 | 1.5 | 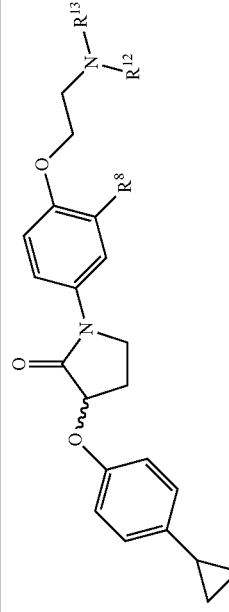 | A2 | 1 (7.65) 2 (9.08) | 465.1 | $^1$H NMR (400 MHz, DMSO-d$_6$) δ 7.48-7.54 (m, 1H), 7.38-7.47 (m, 1H), 6.96 (s, 5H), 5.07-5.17 (m, 1H), 4.29-4.39 (m, 1H), 4.01-4.10 (m, 2H), 3.74-3.88 (m, 2H), 3.35-3.45 (m, 2H), 3.09-3.28 (m, 3H), 2.59-2.75 (m, 4H), 2.27-2.37 (m, 1H), 1.98-2.10 (m, 1H), 1.76-1.91 (m, 2H), 1.61-1.72 (m, 2H), 1.47-1.58 (m, 1H), 1.14 (s, 3H), 0.82-0.93 (m, 2H), 0.54-0.64 (m, 2H) |
| 55 | 5 | 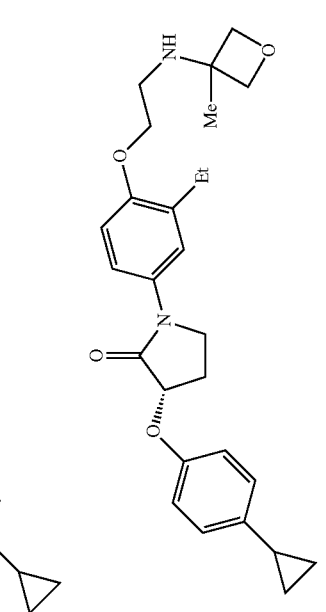 | A2 | 1 (7.61) 2 (8.9) | 451.2 | $^1$H NMR (400 MHz, DMSO-d$_6$) δ 7.47-7.53 (m, 1H), 7.35-7.44 (m, 1H), 6.89-7.04 (m, 5H), 6.21-6.29 (m, 1H), 5.05-5.14 (m, 1H), 4.40-4.47 (m, 2H), 4.18-4.27 (m, 2H), 3.95-4.04 (m, 2H), 3.73-3.86 (m, 2H), 2.86-2.98 (m, 2H), 2.58-2.65 (m, 3H), 1.95-2.08 (m, 1H), 1.80-1.91 (m, 1H), 1.38 (s, 3H), 1.13 (s, 3H), 0.79-0.92 (m, 2H), 0.51-0.63 (m, 2H) |
| 56 | 3 | 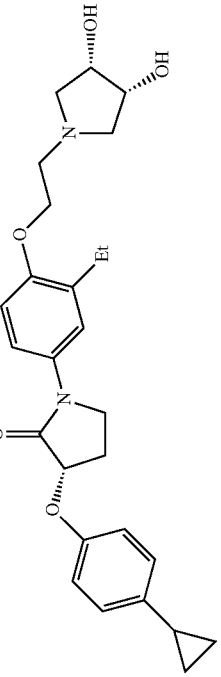 | A2 | 1 (7.28) 2 (8.58) | 467.1 | $^1$H NMR (400 MHz, CD$_3$OD) δ 7.47-7.53 (m, 1H), 7.38-7.46 (m, 1H), 7.01 (d, J = 17.32 Hz, 5H), 5.05-5.16 (m, 1H), 4.18-4.30 (m, 4H), 3.84-3.95 (m, 2H), 3.34-3.38 (m, 2H), 3.03-3.14 (m, 2H), 2.68-2.80 (m, 3H), 2.14-2.25 (m, 1H), 1.83-1.93 (m, 1H), 1.24 (s, 4H), 0.89-0.96 (m, 3H), 0.56-0.66 (m, 2H) |

TABLE A-continued
| Example No. | Ki (nM) | Structure | Synthetic Procedure Used | HPLC Methods ($t_R$ min) | MS (M + H) | NMR Data |
|---|---|---|---|---|---|---|
| 57 | 0.8 | 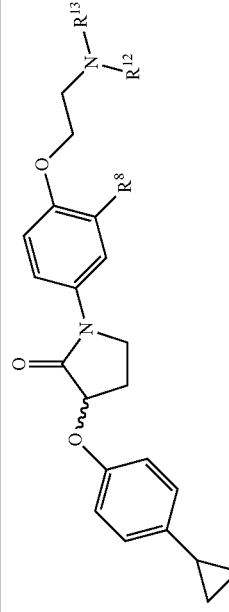 | A2 | 1 (7.59) 2 (9.99) | 465.1 | $^1$H NMR (400 MHz, DMSO-d$_6$) δ 7.51 (d, J = 2.76 Hz, 1H), 7.39-7.46 (m, 1H), 6.90-7.08 (m, 5H), 5.13 (s, 1H), 4.07 (s, 2H), 3.76-3.93 (m, 3H), 3.17 (s, 3H), 2.75-2.85 (m, 3H), 2.59 (d, J = 7.53 Hz, 6H), 1.94-2.09 (m, 2H), 1.84-1.93 (m, 1H), 1.60-1.70 (m, 1H), 1.15 (t, J = 7.53 Hz, 3H), 0.89 (dd, J = 2.13, 8.41 Hz, 2H), 0.53-0.65 (m, 2H) |
| 58 | 1.6 | 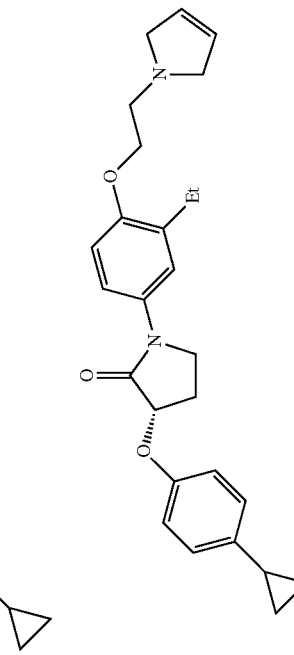 | A2 | 1 (11.44) 2 (14.7) | 433 | $^1$H NMR (400 MHz, DMSO-d$_6$) δ 7.48-7.55 (m, 1H), 7.40-7.46 (m, 1H), 6.92-7.06 (m, 5H), 5.77-5.87 (m, 2H), 5.06-5.18 (m, 1H), 4.03-4.14 (m, 2H), 3.77-3.86 (m, 2H), 3.51-3.63 (m, 4H), 2.95-3.12 (m, 2H), 2.57-2.70 (m, 3H), 2.01-2.10 (m, 1H), 1.83-1.94 (m, 1H), 1.11-1.20 (m, 3H), 0.83-0.94 (m, 2H), 0.55-0.65 (m, 2H) |
| 59 | 3 | 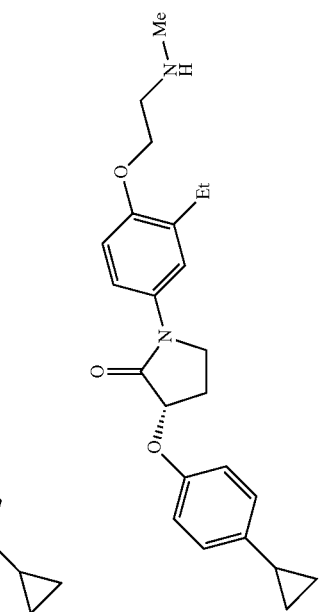 | A2 | 1 (11.61) 2 (13.72) | 395 | $^1$H NMR (400 MHz, CD$_3$OD) δ 7.47-7.53 (m, 1H), 7.38-7.45 (m, 1H), 6.94-7.09 (m, 5H), 5.05-5.16 (m, 1H), 4.15-4.24 (m, 1H), 3.84-3.95 (m, 2H), 3.11-3.20 (m, 2H), 2.66-2.81 (m, 4H), 2.56-2.66 (m, 3H), 2.14-2.26 (m, 1H), 1.83-1.95 (m, 1H), 1.22-1.28 (m, 3H), 0.90-0.95 (m, 2H), 0.57-0.67 (m, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 60 | 4 | (structure with Et, OCH₂CH₂NH₂, pyrrolidinone, 4-cyclopropylphenoxy) | A2 | 1 (10.63) 2 (13.25) | 381 | ¹H NMR (400 MHz, DMSO-d₆) δ 7.48-7.55 (m, 1H), 7.38-7.46 (m, 1H), 6.96 (s, 5H), 5.07-5.18 (m, 1H), 3.93-4.02 (m, 2H), 3.75-3.87 (m, 2H), 2.92-3.01 (m, 2H), 2.56-2.70 (m, 4H), 1.98-2.10 (m, 1H), 1.82-1.92 (m, 1H), 1.15 (s, 3H), 0.85-0.94 (m, 2H), 0.54-0.65 (m, 2H) |
| 61 | 1.4 | (structure with Et, OCH₂CH₂-N-pyrrolidinyl-OMe, pyrrolidinone, 4-cyclopropylphenoxy) | A2 | 1 (11.81) 2 (15.3) | 464.9 | ¹H NMR (400 MHz, CD₃OD) δ 7.45-7.52 (m, 1H), 7.37-7.43 (m, 1H), 6.93-7.09 (m, 5H), 5.04-5.15 (m, 1H), 4.13-4.23 (m, 2H), 3.97-4.05 (m, 1H), 3.85-3.94 (m, 2H), 3.31 (s, 3H), 2.81-3.03 (m, 5H), 2.63-2.80 (m, 4H), 2.05-2.25 (m, 2H), 1.80-1.92 (m, 2H), 1.22 (s, 3H), 0.87-0.96 (m, 2H), 0.57-0.67 (m, 2H) |
| 62 | 2 | (structure with Et, OCH₂CH₂NMe₂, pyrrolidinone, 4-cyclopropylphenoxy) | A2 | 1 (8.17) 2 (9.14) | 409 | ¹H NMR (400 MHz, DMSO-d₆) δ 7.49-7.57 (m, 1H), 7.40-7.48 (m, 1H), 6.91-7.06 (m, 5H), 5.08-5.18 (m, 1H), 4.12-4.24 (m, 2H), 3.75-3.87 (m, 2H), 2.99-3.14 (m, 2H), 2.59-2.69 (m, 3H), 2.50 (s, 6H), 1.98-2.10 (m, 1H), 1.82-1.93 (m, 1H), 1.15 (t, J = 7.40 Hz, 3H), 0.83-0.94 (m, 2H), 0.53-0.64 (m, 2H) |

TABLE A-continued
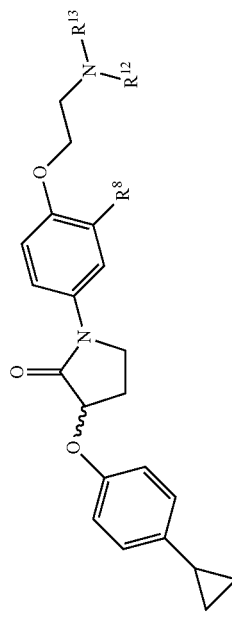
| Example No. | Ki (nM) | Structure | Synthetic Procedure Used | HPLC Methods ($t_R$ min) | MS (M + H) | NMR Data |
|---|---|---|---|---|---|---|
| 63 | 1.2 | 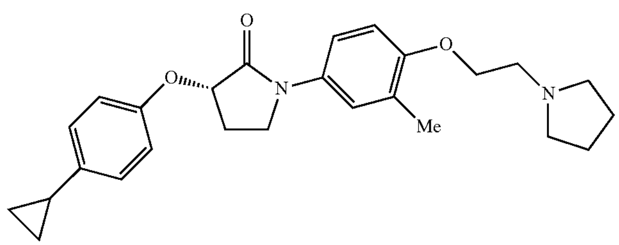 | A3 | 1 (7.56) 2 (9.56) 4 (6.6) | 421.0 | $^1$H NMR (400 MHz, DMSO-d$_6$) δ 7.36-7.52 (m, 2H), 6.86-7.07 (m, 5H), 5.05-5.18 (m, 1H), 4.02-4.12 (m, 2H), 3.72-3.86 (m, 2H), 2.77-2.86 (m, 2H), 2.53-2.71 (m, 5H), 2.14-2.21 (m, 3H), 1.97-2.09 (m, 1H), 1.82-1.92 (m, 1H), 1.62-1.74 (m, 4H), 0.83-0.95 (m, 2H), 0.52-0.65 (m, 2H) |
| 64 | 13 | 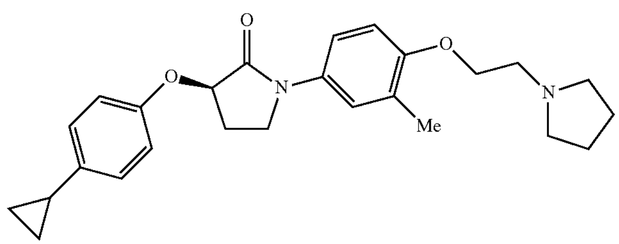 | A3 | 1 (7.56) 2 (9.58) 4 (12.5) | 421.0 | $^1$H NMR (400 MHz, DMSO-d$_6$) δ 7.39-7.53 (m, 2H), 6.87-7.07 (m, 5H), 5.06-5.18 (m, 1H), 4.08 (s, 2H), 3.71-3.86 (m, 2H), 2.79-2.89 (m, 2H), 2.54-2.71 (m, 5H), 2.17 (s, 3H), 1.97-2.10 (m, 1H), 1.80-1.92 (m, 1H), 1.69 (br. s., 4H), 0.83-0.95 (m, 2H), 0.52-0.66 (m, 2H) |
| 65 | 0.8 | 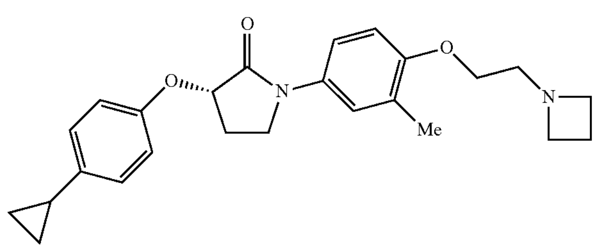 | A3 | | 421.2 | $^1$H NMR (400 MHz, DMSO-d$_6$) δ 7.40-7.51 (m, 2H), 6.88-7.07 (m, 5H), 5.05-5.17 (m, 1H), 3.93-4.03 (m, 2H), 3.72-3.86 (m, 2H), 2.81-2.89 (m, 2H), 2.61-2.71 (m, 2H), 2.19 (s, 3H), 2.00-2.16 (m, 3H), 1.84-1.93 (m, 1H), 1.53-1.76 (m, 4H), 0.85-0.95 (m, 2H), 0.56-0.64 (m, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 66 | 1.1 | (structure with NH-CH2CH2-OMe, Me on phenyl) | A3 | | 425.2 | $^1$H NMR (400 MHz, DMSO-d$_6$) δ 7.39-7.52 (m, 2H), 6.95 (s, 5H), 5.07-5.18 (m, 1H), 4.00-4.11 (m, 2H), 3.74-3.86 (m, 2H), 3.40-3.49 (m, 2H), 3.26 (s, 3H), 2.93-3.01 (m, 2H), 2.77-2.84 (m, 2H), 2.62-2.71 (m, 1H), 2.18 (s, 3H), 1.98-2.08 (m, 1H), 1.84-1.91 (m, 1H), 0.83-0.94 (m, 2H), 0.55-0.64 (m, 2H) |
| 67 | 2 | (structure with piperazine-C(O)Me) | A3 | | 478.2 | $^1$H NMR (400 MHz, DMSO-d$_6$) δ 7.39-7.51 (m, 2H), 6.89-7.07 (m, 5H), 5.07-5.17 (m, 1H), 4.05-4.16 (m, 2H), 3.74-3.86 (m, 2H), 3.39-3.48 (m, 4H), 2.72-2.82 (m, 2H), 2.60-2.70 (m, 2H), 2.42-2.48 (m, 3H), 2.14-2.21 (m, 3H), 1.96-2.08 (m, 4H), 1.82-1.93 (m, 1H), 0.83-0.95 (m, 2H), 0.54-0.64 (m, 2H) |
| 68 | 1.2 | (structure with pyrrolidine-NHC(O)Me) | A3 | | 478.2 | $^1$H NMR (400 MHz, DMSO-d$_6$) δ 7.88-8.05 (m, 1H), 7.38-7.54 (m, 2H), 6.95 (s, 5H), 5.03-5.20 (m, 1H), 4.02-4.20 (m, 3H), 3.71-3.88 (m, 2H), 2.61-2.90 (m, 5H), 2.50 (br. s., 3H), 2.17 (s, 3H), 1.98-2.12 (m, 2H), 1.84-1.91 (m, 1H), 1.78 (s, 3H), 0.83-0.93 (m, 2H), 0.54-0.64 (m, 2H) |

TABLE A-continued
| Example No. | Ki (nM) | Structure | Synthetic Procedure Used | HPLC Methods ($t_R$ min) | MS (M + H) | NMR Data |
|---|---|---|---|---|---|---|
| 69 | 1.1 | 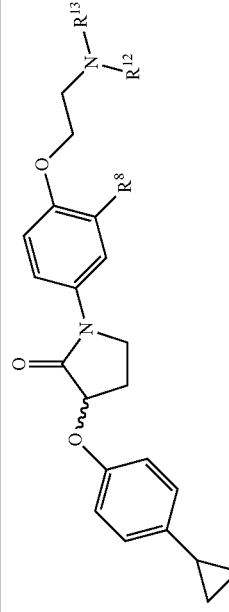 | A3 | | 437.2 | $^1$H NMR (400 MHz, DMSO-d$_6$) δ 7.38-7.52 (m, 2H), 6.90-7.09 (m, 5H), 5.07-5.18 (m, 1H), 4.62-4.71 (m, 1H), 4.15-4.26 (m, 1H), 4.00-4.11 (m, 2H), 3.71-3.85 (m, 2H), 2.77-2.85 (m, 2H), 2.62-2.72 (m, 2H), 2.41-2.46 (m, 1H), 2.18 (s, 3H), 1.95-2.09 (m, 2H), 1.84-1.92 (m, 2H), 1.49-1.59 (m, 1H), 0.83-0.94 (m, 2H), 0.55-0.65 (m, 2H) |
| 70 | 1.0 | 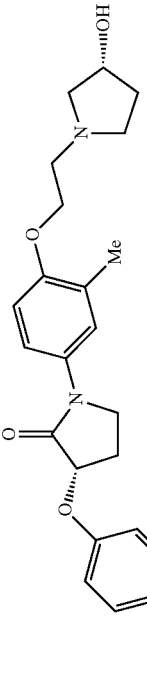 | A3 | | 439.2 | $^1$H NMR (400 MHz, DMSO-d$_6$) δ 7.40-7.53 (m, 2H), 6.90-7.07 (m, 5H), 5.06-5.32 (m, 2H), 4.03-4.16 (m, 2H), 3.74-3.87 (m, 2H), 2.81-3.01 (m, 4H), 2.63-2.79 (m, 2H), 2.39-2.48 (m, 2H), 2.18 (s, 3H), 2.01-2.10 (m, 1H), 1.79-1.94 (m, 2H), 0.84-0.95 (m, 2H), 0.56-0.63 (m, 2H) |
| 71 | 7 | 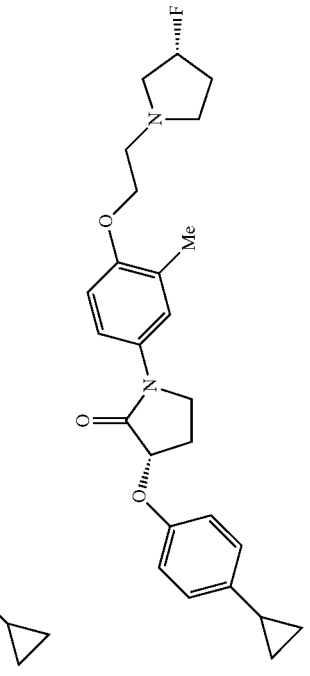 | A3 | | 457.2 | $^1$H NMR (400 MHz, DMSO-d$_6$) δ 7.36-7.50 (m, 2H), 6.86-7.04 (m, 5H), 5.03-5.15 (m, 1H), 4.52-4.64 (m, 4H), 3.85-3.98 (m, 2H), 3.71-3.83 (m, 2H), 3.33-3.43 (m, 3H), 2.88-3.04 (m, 1H), 2.66-2.72 (m, 1H), 2.14-2.20 (m, 3H), 1.97-2.06 (m, 1H), 1.82-1.88 (m, 1H), 0.78-0.92 (m, 2H), 0.50-0.61 (m, 2H) |

TABLE A-continued
| Example No. | Ki (nM) | Structure | Synthetic Procedure Used | HPLC Methods ($t_R$ min) | MS (M + H) | NMR Data |
|---|---|---|---|---|---|---|
| 72 | 0.8 | 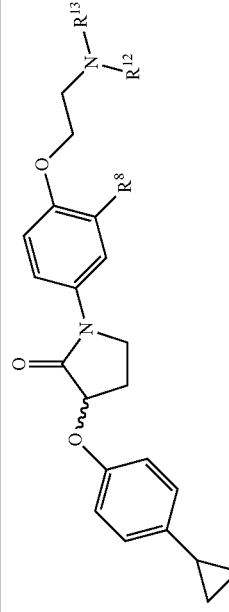 | A3 | | 451.2 | $^1$H NMR (400 MHz, DMSO-d$_6$) δ 7.39-7.54 (m, 2H), 6.91-7.09 (m, 4H), 5.04-5.19 (m, 1H), 4.26-4.41 (m, 1H), 4.00-4.11 (m, 2H), 3.73-3.86 (m, 2H), 3.37-3.46 (m, 1H), 3.09-3.27 (m, 3H), 2.63-2.77 (m, 2H), 2.55-2.60 (m, 1H), 2.27-2.38 (m, 1H), 2.18 (s, 3H), 1.98-2.09 (m, 1H), 1.80-1.92 (m, 2H), 1.61-1.71 (m, 2H), 1.48-1.57 (m, 1H), 0.85-0.93 (m, 2H), 0.54-0.65 (m, 2H) |
| 73 | 1.4 | 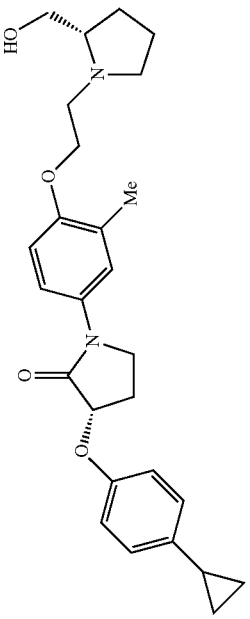 | A3 | | 449.2 | $^1$H NMR (400 MHz, DMSO-d$_6$) δ 7.38-7.51 (m, 2H), 6.86-7.07 (m, 5H), 4.99-5.17 (m, 1H), 4.01-4.11 (m, 2H), 3.73-3.82 (m, 2H), 2.93-3.06 (m, 2H), 2.76-2.87 (m, 4H), 2.55-2.70 (m, 2H), 2.51-2.54 (m, 1H), 2.15 (s, 5H), 1.95-2.07 (m, 1H), 1.80-1.90 (m, 1H), 0.82-0.92 (m, 2H), 0.52-0.61 (m, 2H) |
| 74 | 5 | 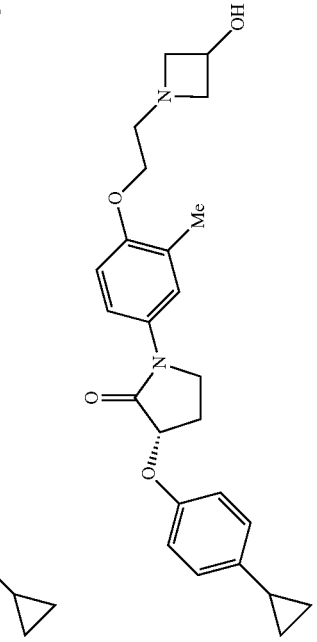 | A3 | | 423.2 | $^1$H NMR (400 MHz, DMSO-d$_6$) δ 7.40-7.52 (m, 2H), 6.87-7.08 (m, 5H), 5.26-5.39 (m, 1H), 5.08-5.17 (m, 1H), 4.15-4.26 (m, 1H), 3.92-4.00 (m, 2H), 3.74-3.83 (m, 2H), 3.58-3.73 (m, 2H), 2.78-3.00 (m, 3H), 2.62-2.69 (m, 1H), 2.17 (s, 3H), 1.98-2.05 (m, 1H), 1.81-1.90 (m, 1H), 0.82-0.93 (m, 2H), 0.52-0.64 (m, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 75 | 2 | (morpholine-ethoxy, Me-substituted aryl pyrrolidinone, 4-cyclopropylphenoxy) | A3 | | 437.2 | $^1$H NMR (400 MHz, DMSO-d$_6$) δ 7.40-7.52 (m, 2H), 6.91-7.07 (m, 5H), 5.03-5.19 (m, 1H), 4.05-4.17 (m, 2H), 3.76-3.85 (m, 2H), 3.55-3.64 (m, 4H), 2.61-2.76 (m, 3H), 2.52-2.59 (m, 4H), 2.17 (s, 3H), 1.98-2.09 (m, 1H), 1.83-1.92 (m, 1H), 0.85-0.95 (m, 2H), 0.58-0.64 (m, 2H) |
| 76 | 5 | (3-oxopiperazine-ethoxy, Me-substituted aryl pyrrolidinone, 4-cyclopropylphenoxy) | A3 | | 450.2 | $^1$H NMR (400 MHz, DMSO-d$_6$) δ 7.68-7.78 (m, 1H), 7.41-7.52 (m, 2H), 6.90-7.07 (m, 5H), 5.05-5.20 (m, 1H), 4.07-4.17 (m, 2H), 3.75-3.86 (m, 2H), 3.14-3.21 (m, 2H), 3.09 (s, 2H), 2.78-2.86 (m, 2H), 2.61-2.75 (m, 3H), 2.18 (s, 3H), 1.98-2.08 (m, 1H), 1.83-1.92 (m, 1H), 0.84-0.94 (m, 2H), 0.53-0.64 (m, 2H) |
| 77 | 1.3 | (N-Me-N-(2-hydroxyethyl)amino-ethoxy, Me-substituted aryl pyrrolidinone, 4-cyclopropylphenoxy) | A3 | | 425.2 | $^1$H NMR (400 MHz, DMSO-d$_6$) δ 7.40-7.52 (m, 2H), 6.91-7.06 (m, 5H), 5.06-5.20 (m, 1H), 4.29-4.39 (m, 1H), 4.00-4.11 (m, 2H), 3.75-3.86 (m, 2H), 3.44-3.56 (m, 2H), 2.75-2.84 (m, 2H), 2.61-2.71 (m, 1H), 2.54-2.58 (m, 1H), 2.31 (s, 3H), 2.18 (s, 3H), 1.97-2.08 (m, 1H), 1.83-1.93 (m, 1H), 0.83-0.95 (m, 2H), 0.53-0.65 (m, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 78 | 1.4 | 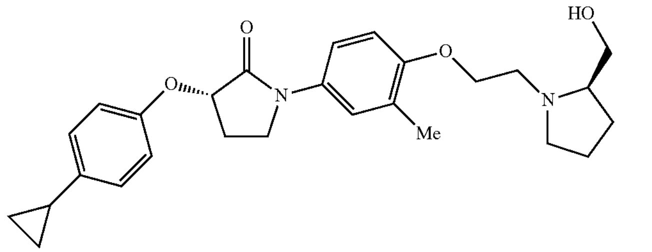 [SMILES: CCc1cc(N2CC[C@H](Oc3ccc(C4CC4)cc3)C2=O)ccc1OCCN1CCC[C@@H]1CO] | A3 | | 451.2 | $^1$H NMR (400 MHz, DMSO-$d_6$) δ 7.40-7.52 (m, 1H), 6.91-7.08 (m, 5H), 5.07-5.19 (m, 1H), 4.00-4.10 (m, 2H), 3.74-3.85 (m, 2H), 3.37-3.44 (m, 3H), 3.10-3.25 (m, 3H), 2.59-2.77 (m, 2H), 2.30-2.38 (m, 1H), 2.18 (s, 3H), 2.00-2.07 (m, 1H), 1.75-1.85 (m, 1H), 1.45-1.72 (m, 3H), 0.84-0.93 (m, 2H), 0.52-0.64 (m, 2H) |
| 79 | 1.0 | 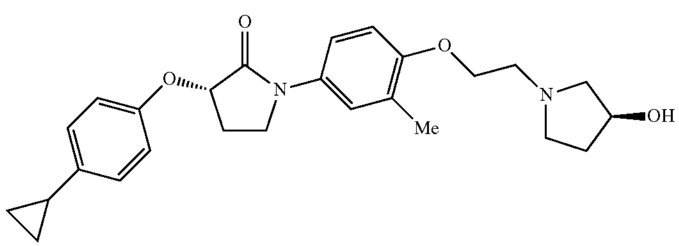 [SMILES: Cc1cc(N2CC[C@H](Oc3ccc(C4CC4)cc3)C2=O)ccc1OCCN1CC[C@H](O)C1] | A3 | | 437.2 | $^1$H NMR (400 MHz, DMSO-$d_6$) δ 7.39-7.53 (m, 2H), 6.92-7.07 (m, 5H), 5.06-5.18 (m, 1H), 4.61-4.72 (m, 1H), 4.14-4.24 (m, 1H), 4.02-4.11 (m, 2H), 3.76-3.86 (m, 2H), 2.76-2.85 (m, 3H), 2.63-2.72 (m, 2H), 2.55-2.59 (m, 1H), 2.38-2.47 (m, 1H), 2.18 (s, 3H), 1.96-2.09 (m, 2H), 1.84-1.89 (m, 1H), 1.46-1.59 (m, 1H), 0.84-0.94 (m, 2H), 0.56-0.64 (m, 2H) |
| 80 | 1.1 | 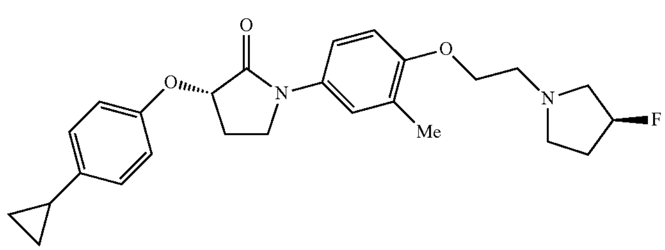 [SMILES: Cc1cc(N2CC[C@H](Oc3ccc(C4CC4)cc3)C2=O)ccc1OCCN1CC[C@H](F)C1] | A3 | | 439.2 | $^1$H NMR (400 MHz, DMSO-$d_6$) δ 7.41-7.52 (m, 2H), 6.89-7.08 (m, 5H), 5.07-5.32 (m, 2H), 4.04-4.14 (m, 2H), 3.75-3.85 (m, 2H), 2.82-3.01 (m, 4H), 2.61-2.71 (m, 2H), 2.41-2.47 (m, 1H), 2.18 (s, 3H), 1.97-2.15 (m, 2H), 1.81-1.95 (m, 2H), 0.84-0.94 (m, 2H), 0.54-0.64 (m, 2H) |

TABLE A-continued

| Example No. | Ki (nM) | Structure | Synthetic Procedure Used | HPLC Methods ($t_R$ min) | MS (M + H) | $^1$H NMR Data |
|---|---|---|---|---|---|---|
| 81 | 1.2 | (structure with MeO-pyrrolidine, Me, cyclopropyl phenyl) | A3 | | 465.4 | $^1$H NMR (400 MHz, DMSO-$d_6$) δ 7.40-7.57 (m, 2H), 6.89-7.09 (m, 5H), 5.00-5.18 (m, 1H), 3.97-4.15 (m, 2H), 3.74-3.87 (m, 2H), 3.38-3.45 (m, 1H), 3.07-3.29 (m, 6H), 2.61-2.78 (m, 3H), 2.56-2.59 (m, 1H), 2.14-2.25 (m, 3H), 1.98-2.10 (m, 1H), 1.77-1.93 (m, 2H), 1.59-1.75 (m, 2H), 1.40-1.53 (m, 1H), 0.84-0.93 (m, 2H), 0.56-0.63 (m, 2H) |
| 82 | 2 | (structure with H$_2$N-C(O)-pyrrolidine, Me, cyclopropyl phenyl) | A3 | | 464.2 | $^1$H NMR (400 MHz, DMSO-$d_6$) δ 7.42-7.54 (m, 2H), 7.09-7.30 (m, 2H), 6.89-7.07 (m, 5H), 5.06-5.19 (m, 1H), 4.02-4.18 (m, 2H), 3.73-3.86 (m, 2H), 3.18-3.26 (m, 1H), 2.94-3.06 (m, 2H), 2.75-2.85 (m, 1H), 2.60-2.70 (m, 2H), 2.38-2.45 (m, 1H), 2.17 (s, 3H), 1.99-2.10 (m, 2H), 1.83-1.93 (m, 1H), 1.63-1.78 (m, 3H), 0.84-0.94 (m, 2H), 0.54-0.65 (m, 2H) |
| 83 | 1.2 | (structure with HO-ethyl-NH linker, Me, cyclopropyl phenyl) | A3 | | 411.2 | $^1$H NMR (400 MHz, DMSO-$d_6$) δ 7.40-7.55 (m, 2H), 6.89-7.09 (m, 6H), 5.07-5.18 (m, 1H), 4.66-4.83 (m, 1H), 4.06-4.16 (m, 2H), 3.72-3.86 (m, 2H), 3.50-3.60 (m, 2H), 3.02-3.14 (m, 2H), 2.77-2.89 (m, 2H), 2.64-2.72 (m, 1H), 2.20 (s, 3H), 1.98-2.10 (m, 1H), 1.83-1.90 (m, 2H), 0.85-0.94 (m, 2H), 0.55-0.65 (m, 2H) |

TABLE A-continued

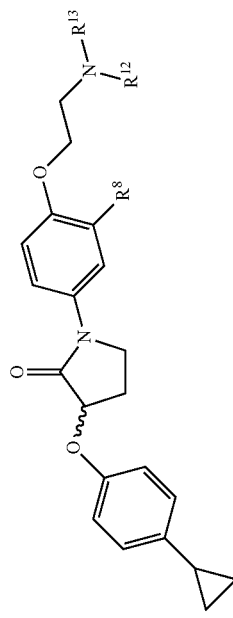

| Example No. | Ki (nM) | Structure | Synthetic Procedure Used | HPLC Methods (t_R min) | MS (M + H) | NMR Data |
|---|---|---|---|---|---|---|
| 84 | 0.9 | (structure with cyclopentyl-CH2OH amine, Me on ring) | A3 | | 465.2 | $^1$H NMR (400 MHz, DMSO-d$_6$) δ 7.40-7.52 (m, 2H), 6.90-7.07 (m, 5H), 5.06-5.17 (m, 1H), 4.40-4.64 (m, 1H), 3.93-4.09 (m, 2H), 3.72-3.86 (m, 2H), 2.77-2.96 (m, 2H), 2.61-2.71 (m, 1H), 2.41-2.47 (m, 1H), 2.18 (s, 3H), 1.99-2.09 (m, 1H), 1.84-1.93 (m, 1H), 1.59-1.71 (m, 2H), 1.38-1.57 (m, 6H), 0.82-0.94 (m, 2H), 0.54-0.65 (m, 2H) |
| 85 | 7 | (structure with CH2CN amine, Me on ring) | A3 | | 406.2 | $^1$H NMR (400 MHz, DMSO-d$_6$) δ 7.41-7.54 (m, 2H), 6.90-7.08 (m, 5H), 5.06-5.18 (m, 1H), 4.01-4.10 (m, 2H), 3.68-3.86 (m, 4H), 2.92-3.03 (m, 2H), 2.61-2.79 (m, 2H), 2.19 (s, 3H), 2.00-2.09 (m, 1H), 1.83-1.92 (m, 1H), 0.84-0.94 (m, 2H), 0.55-0.65 (m, 2H) |
| 86 | 1.1 | (structure with NHMe amine, Me on ring) | A3 | | 381.2 | $^1$H NMR (400 MHz, DMSO-d$_6$) δ 7.39-7.56 (m, 2H), 6.88-7.07 (m, 5H), 5.08-5.19 (m, 1H), 4.08 (s, 2H), 3.74-3.86 (m, 2H), 2.98-3.07 (m, 2H), 2.61-2.71 (m, 1H), 2.47 (s, 3H), 2.20 (s, 3H), 1.99-2.09 (m, 1H), 1.81-1.90 (m, 1H), 0.83-0.93 (m, 2H), 0.53-0.65 (m, 2H) |

TABLE A-continued
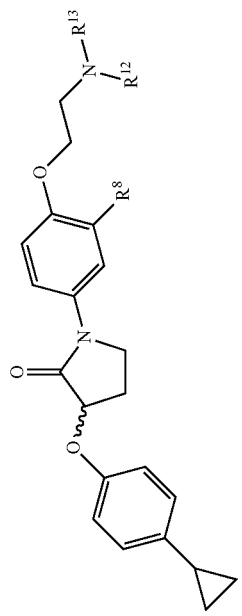
| Example No. | Ki (nM) | Structure | Synthetic Procedure Used | HPLC Methods ($t_R$ min) | MS (M + H) | NMR Data |
|---|---|---|---|---|---|---|
| 87 | 1.0 | 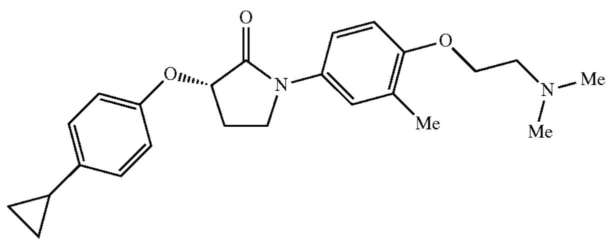 [SMILES: Cc1cc(N2CC[C@H](Oc3ccc(C4CC4)cc3)C2=O)ccc1OCCN(C)C] | A3 | | 395.2 | $^1$H NMR (400 MHz, DMSO-d$_6$) δ 7.39-7.55 (m, 3H), 6.89-7.09 (m, 5H), 5.03-5.21 (m, 1H), 4.07 (s, 2H), 3.71-3.87 (m, 2H), 2.62-2.75 (m, 3H), 2.27 (s, 6H), 2.17 (s, 3H), 1.99-2.08 (m, 1H), 1.83-1.93 (m, 1H), 0.82-0.94 (m, 2H), 0.54-0.64 (m, 2H) |
| 88 | 18 | 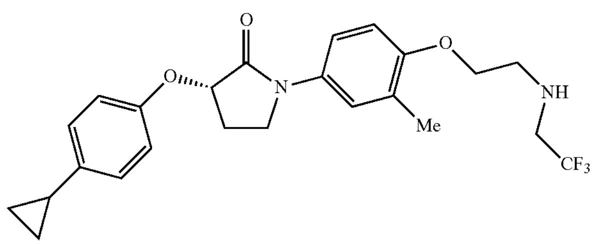 [SMILES: Cc1cc(N2CC[C@H](Oc3ccc(C4CC4)cc3)C2=O)ccc1OCCNCC(F)(F)F] | A3 | | 449.2 | $^1$H NMR (400 MHz, DMSO-d$_6$) δ 7.39-7.53 (m, 2H), 6.91-7.09 (m, 5H), 5.06-5.19 (m, 1H), 3.97-4.07 (m, 2H), 3.72-3.86 (m, 2H), 3.34-3.43 (m, 2H), 2.96-3.05 (m, 2H), 2.61-2.72 (m, 1H), 2.18 (s, 3H), 1.99-2.09 (m, 1H), 1.82-1.92 (m, 1H), 0.83-0.94 (m, 2H), 0.54-0.64 (m, 2H) |
| 89 | 1.0 | 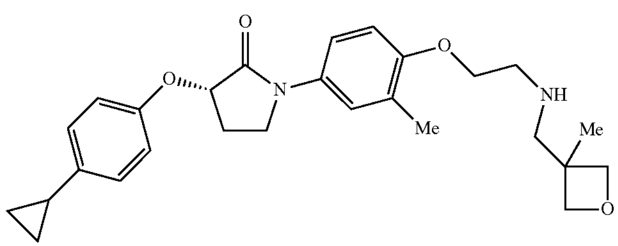 [SMILES: Cc1cc(N2CC[C@H](Oc3ccc(C4CC4)cc3)C2=O)ccc1OCCNCC1(C)COC1] | A3 | | 451.2 | $^1$H NMR (400 MHz, DMSO-d$_6$) δ 7.41-7.53 (m, 2H), 6.92-7.06 (m, 5H), 5.06-5.17 (m, 1H), 4.32-4.39 (m, 2H), 4.14-4.23 (m, 2H), 3.98-4.09 (m, 2H), 3.74-3.85 (m, 1H), 2.89-2.98 (m, 2H), 2.74-2.82 (m, 2H), 2.63-2.72 (m, 1H), 2.15-2.23 (m, 3H), 1.99-2.10 (m, 1H), 1.83-1.91 (m, 1H), 1.20-1.31 (m, 3H), 0.81-0.94 (m, 2H), 0.54-0.65 (m, 2H) |

TABLE A-continued
| Example No. | Ki (nM) | Structure | Synthetic Procedure Used | HPLC Methods ($t_R$ min) | MS (M + H) | NMR Data |
|---|---|---|---|---|---|---|
| 90 | 1.0 | 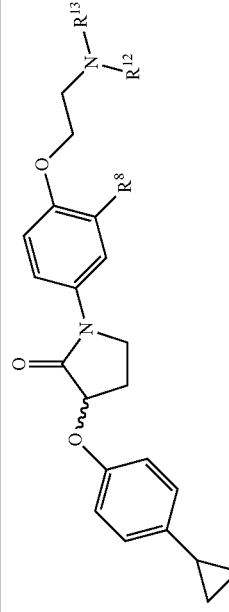 | A3 | | 477.2 | $^1$H NMR (400 MHz, DMSO-d$_6$) δ 7.39-7.55 (m, 2H), 6.87-7.08 (m, 5H), 5.08-5.18 (m, 1H), 4.24-4.46 (m, 4H), 4.03-4.11 (m, 1H), 3.73-3.85 (m, 2H), 3.44-3.58 (m, 1H), 3.36-3.43 (m, 1H), 2.93-3.16 (m, 1H), 2.58-2.72 (m, 3H), 2.30-2.45 (m, 3H), 2.13-2.25 (m, 3H), 1.99-2.11 (m, 1H), 1.69-1.93 (m, 4H), 0.82-0.94 (m, 2H), 0.53-0.65 (m, 2H) |
| 91 | 1.8 | 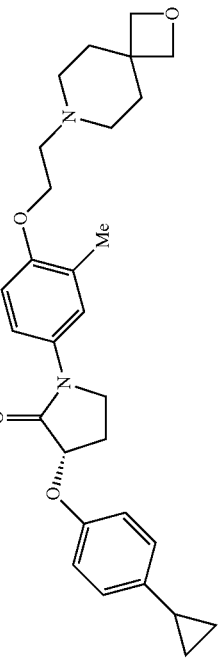 | A3 | | 467.2 | $^1$H NMR (400 MHz, DMSO-d$_6$) δ 7.38-7.53 (m, 2H), 6.88-7.08 (m, 5H), 5.06-5.18 (m, 1H), 4.23-4.34 (m, 4H), 4.00-4.13 (m, 2H), 3.75-3.86 (m, 2H), 3.58-3.68 (m, 2H), 2.85-3.05 (m, 4H), 2.63-2.72 (m, 2H), 2.15-2.22 (m, 3H), 1.99-2.08 (m, 1H), 1.82-1.90 (m, 1H), 0.83-0.96 (m, 2H), 0.51-0.65 (m, 2H) |
| 92 | 0.75 | 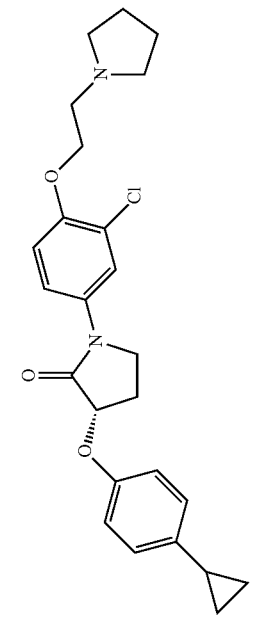 | A4 | 1 (7.76) 2 (9.22) 4 (9.8) | 461.0 | $^1$H NMR (400 MHz, DMSO-d$_6$) δ 7.88 (d, J = 2.76 Hz, 1H), 7.54 (d, J = 2.76 Hz, 1H), 7.21 (d, J = 9.03 Hz, 1H), 6.99-7.06 (m, 2H), 6.89-6.98 (m, 2H), 5.15 (s, 1H), 4.16 (t, J = 5.90 Hz, 2H), 3.73-3.92 (m, 2H), 2.82 (t, J = 5.77 Hz, 2H), 2.61-2.72 (m, 1H), 2.53-2.58 (m, 4H), 1.99-2.13 (m, 1H), 1.81-1.92 (m, 1H), 1.68 (td, J = 3.23, 6.84 Hz, 4H), 0.89 (dd, J = 2.13, 8.41 Hz, 2H), 0.52-0.65 (m, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 93 | 28 | 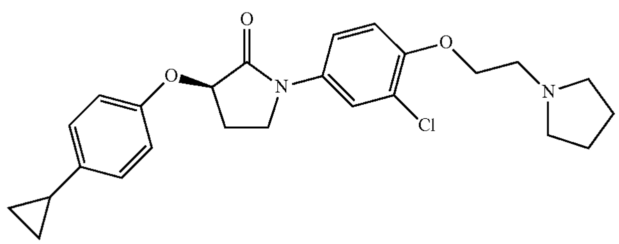 | A4 | 1 (7.75) 2 (9.23) 4 (14.7) | 461.0 | $^1$H NMR (400 MHz, DMSO-$d_6$) δ 7.83-7.93 (m, 1H), 7.50-7.63 (m, 1H), 7.19-7.29 (m, 1H), 6.92-7.06 (m, 4H), 5.05-5.21 (m, 1H), 4.14-4.27 (m, 2H), 3.70-3.90 (m, 2H), 2.53-3.09 (m, 7H), 1.97-2.11 (m, 1H), 1.83-1.92 (m, 1H), 1.64-1.81 (m, 4H), 0.82-0.94 (m, 2H), 0.54-0.64 (m, 2H) |
| 94 | 0.9 | 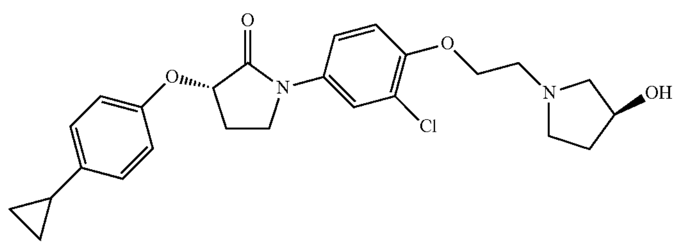 [SMILES: O=C1[C@@H](Oc2ccc(C3CC3)cc2)CCN1c1ccc(OCCN2CC[C@H](O)C2)c(Cl)c1] | A4 | 1 (7.66) 2 (8.78) | 457.2 | $^1$H NMR (400 MHz, DMSO-$d_6$) δ 7.83-7.92 (m, 1H), 7.52-7.61 (m, 1H), 7.17-7.27 (m, 1H), 7.01 (s, 2H), 6.95 (s, 2H), 5.10-5.20 (m, 1H), 4.63-4.72 (m, 1H), 4.10-4.23 (m, 3H), 3.73-3.89 (m, 2H), 2.76-2.85 (m, 3H), 2.61-2.74 (m, 2H), 2.53-2.58 (m, 1H), 2.41-2.46 (m, 1H), 1.93-2.11 (m, 2H), 1.81-1.91 (m, 1H), 1.45-1.58 (m, 1H), 0.83-0.94 (m, 2H), 0.56-0.65 (m, 2H) |
| 95 | 1.1 | 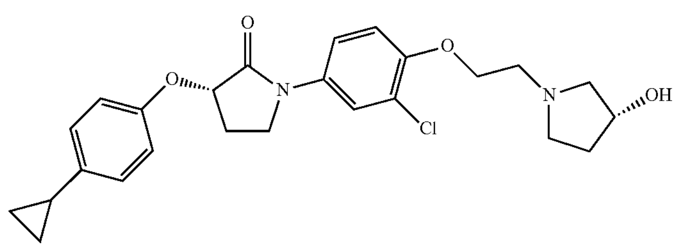 [SMILES: O=C1[C@@H](Oc2ccc(C3CC3)cc2)CCN1c1ccc(OCCN2CC[C@@H](O)C2)c(Cl)c1] | A4 | 1 (7.67) 2 (8.74) | 457.2 | $^1$H NMR (400 MHz, DMSO-$d_6$) δ 7.83-7.94 (m, 1H), 7.50-7.60 (m, 1H), 7.17-7.26 (m, 1H), 7.01 (s, 2H), 6.95 (s, 2H), 5.09-5.21 (m, 1H), 4.62-4.71 (m, 1H), 4.14 (s, 3H), 3.70-3.89 (m, 2H), 2.80 (s, 3H), 2.60-2.73 (m, 2H), 2.52-2.59 (m, 1H), 2.39-2.47 (m, 1H), 1.92-2.12 (m, 2H), 1.80-1.91 (m, 1H), 1.47-1.58 (m, 1H), 0.84-0.94 (m, 2H), 0.54-0.64 (m, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 96 | 1.3 | 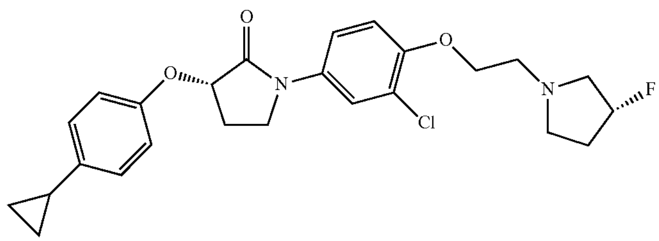 [SMILES: O=C1[C@@H](Oc2ccc(C3CC3)cc2)CCN1c1ccc(OCCN2CC[C@@H](F)C2)c(Cl)c1] | A4 | 1 (7.6) 2 (9.1) | 459.2 | $^1$H NMR (400 MHz, DMSO-d$_6$) δ 7.85-7.96 (m, 1H), 7.49-7.63 (m, 1H), 7.17-7.28 (m, 2H), 7.01 (s, 2H), 6.96 (s, 2H), 5.11-5.32 (m, 2H), 4.11-4.23 (m, 1H), 3.72-3.91 (m, 2H), 2.82-3.04 (m, 4H), 2.62-2.80 (m, 2H), 2.39-2.48 (m, 2H), 1.99-2.23 (m, 3H), 1.79-1.95 (m, 2H), 0.80-0.94 (m, 2H), 0.53-0.66 (m, 2H) |
| 97 | 3 | 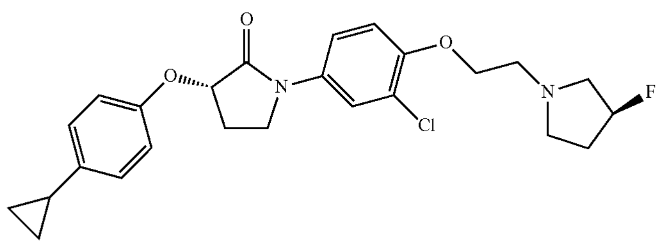 [SMILES: O=C1[C@@H](Oc2ccc(C3CC3)cc2)CCN1c1ccc(OCCN2CC[C@H](F)C2)c(Cl)c1] | A4 | 1 (7.6) 2 (9.1) | 459.2 | $^1$H NMR (400 MHz, DMSO-d$_6$) δ 7.84-7.93 (m, 1H), 7.53-7.64 (m, 1H), 7.19-7.28 (m, 2H), 6.99-7.07 (m, 2H), 6.89-6.99 (m, 2H), 5.07-5.32 (m, 2H), 4.17 (s, 2H), 3.74-3.89 (m, 2H), 2.83-3.04 (m, 4H), 2.61-2.81 (m, 2H), 2.40-2.48 (m, 1H), 2.01-2.22 (m, 2H), 1.78-1.95 (m, 2H), 0.84-0.94 (m, 2H), 0.55-0.64 (m, 2H) |
| 98 | 3 | 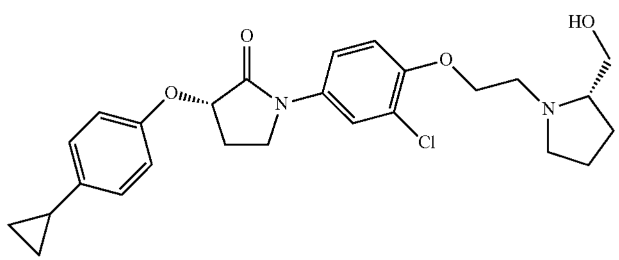 [SMILES: O=C1[C@@H](Oc2ccc(C3CC3)cc2)CCN1c1ccc(OCCN2CCC[C@H]2CO)c(Cl)c1] | A4 | 1 (7.53) 2 (8.98) | 471.2 | $^1$H NMR (400 MHz, DMSO-d$_6$) δ 7.84-7.92 (m, 1H), 7.49-7.60 (m, 1H), 7.15-7.25 (m, 1H), 6.99-7.07 (m, 2H), 6.89-6.99 (m, 2H), 5.09-5.21 (m, 1H), 4.05-4.41 (m, 3H), 3.73-3.90 (m, 2H), 3.37-3.47 (m, 1H), 3.12-3.27 (m, 2H), 2.55-2.80 (m, 3H), 2.28-2.40 (m, 1H), 1.99-2.12 (m, 1H), 1.45-1.93 (m, 5H), 0.84-0.95 (m, 2H), 0.53-0.64 (m, 2H) |

TABLE A-continued
| Example No. | Ki (nM) | Structure | Synthetic Procedure Used | HPLC Methods ($t_R$ min) | MS (M + H) | NMR Data |
|---|---|---|---|---|---|---|
| 99 | 1.2 | 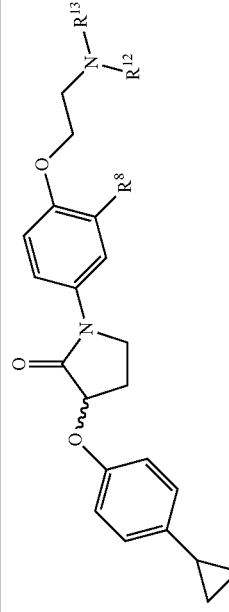 | A4 | 1 (7.37) 2 (8.59) | 445.2 | $^1$H NMR (400 MHz, DMSO-d$_6$) δ 7.83-7.97 (m, 1H), 7.50-7.62 (m, 1H), 7.15-7.27 (m, 1H), 6.98-7.08 (m, 2H), 6.90-6.98 (m, 2H), 5.06-5.21 (m, 1H), 4.27-4.40 (m, 1H), 4.08-4.20 (m, 2H), 3.74-3.92 (m, 2H), 3.43-3.55 (m, 2H), 2.77-2.88 (m, 2H), 2.61-2.73 (m, 1H), 2.54-2.59 (m, 3H), 2.28-2.36 (m, 2H), 1.97-2.13 (m, 1H), 1.79-1.92 (m, 1H), 0.83-0.94 (m, 2H), 0.54-0.66 (m, 2H) |
| 100 | 30 | 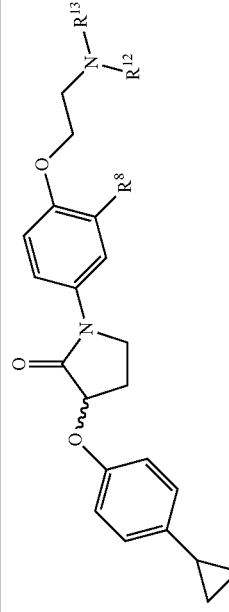 | A4 | 1 (8.33) 2 (9.35) | 477.2 | $^1$H NMR (400 MHz, DMSO-d$_6$) δ 7.89 (d, J = 2.51 Hz, 1H), 7.51-7.62 (m, 1H), 7.17-7.25 (m, 1H), 6.98-7.08 (m, 2H), 6.90-6.98 (m, 2H), 5.08-5.21 (m, 1H), 4.17 (s, 2H), 3.73-3.90 (m, 2H), 3.04 (s, 2H), 2.86 (d, J = 14.05 Hz, 4H), 2.62-2.72 (m, 1H), 2.54-2.60 (m, 1H), 2.16-2.31 (m, 2H), 1.99-2.11 (m, 1H), 1.82-1.92 (m, 1H), 0.81-0.96 (m, 2H), 0.54-0.64 (m, 2H) |
| 101 | 1.0 | 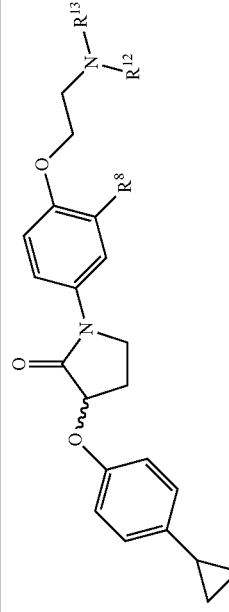 | A4 | 1 (7.32) 2 (8.98) | 471.2 | $^1$H NMR (400 MHz, DMSO-d$_6$) δ 7.85-7.93 (m, 1H), 7.50-7.62 (m, 1H), 7.16-7.26 (m, 1H), 7.01 (s, 2H), 6.95 (s, 2H), 5.09-5.22 (m, 1H), 4.28-4.37 (m, 1H), 4.05-4.19 (m, 2H), 3.74-3.91 (m, 2H), 3.36-3.45 (m, 1H), 3.12-3.29 (m, 3H), 2.62-2.78 (m, 2H), 2.28-2.40 (m, 1H), 1.97-2.11 (m, 1H), 1.75-1.93 (m, 2H), 1.57-1.73 (m, 2H), 1.44-1.55 (m, 1H), 0.80-0.95 (m, 2H), 0.53-0.65 (m, 2H) |

TABLE A-continued

| Example No. | Ki (nM) | Structure | Synthetic Procedure Used | HPLC Methods ($t_R$ min) | MS (M + H) | NMR Data |
|---|---|---|---|---|---|---|
| 102 | 2 | (structure: 3-[(4-cyclopropylphenyl)oxy]-1-{3-chloro-4-[2-(morpholin-4-yl)ethoxy]phenyl}pyrrolidin-2-one) | A4 | 1 (7.53) 2 (8.76) | 457.2 | $^1$H NMR (400 MHz, DMSO-d$_6$) δ 7.84-7.92 (m, 1H), 7.50-7.60 (m, 1H), 7.19-7.29 (m, 1H), 7.01 (s, 2H), 6.95 (s, 2H), 5.09-5.21 (m, 1H), 4.18 (s, 2H), 3.74-3.92 (m, 2H), 3.53-3.63 (m, 4H), 2.73 (s, 7H), 1.98-2.10 (m, 1H), 1.82-1.93 (m, 1H), 0.84-0.94 (m, 2H), 0.55-0.64 (m, 2H) |
| 103 | 12 | (structure: 3-[(4-cyclopropylphenyl)oxy]-1-{3-chloro-4-[2-(3-oxopiperazin-1-yl)ethoxy]phenyl}pyrrolidin-2-one) | A4 | 1 (7.23) 2 (8.33) | 470.2 | $^1$H NMR (400 MHz, DMSO-d$_6$) δ 7.83-7.92 (m, 1H), 7.67-7.76 (m, 1H), 7.53-7.61 (m, 1H), 7.17-7.28 (m, 1H), 6.90-7.06 (m, 4H), 5.11-5.21 (m, 1H), 4.15-4.25 (m, 2H), 3.75-3.91 (m, 2H), 3.13-3.20 (m, 2H), 2.79-2.87 (m, 2H), 2.63-2.76 (m, 3H), 2.56-2.60 (m, 1H), 1.99-2.10 (m, 1H), 1.80-1.94 (m, 1H), 0.84-0.95 (m, 2H), 0.50-0.65 (m, 2H) |
| 104 | 8 | (structure: prolinamide-linked) | A4 | 1 (7.41) 2 (8.72) | 484.2 | $^1$H NMR (400 MHz, DMSO-d$_6$) δ 7.86-7.93 (m, 1H), 7.53-7.63 (m, 1H), 7.26-7.35 (m, 1H), 7.14-7.25 (m, 2H), 6.90-7.07 (m, 4H), 5.09-5.22 (m, 1H), 4.11-4.25 (m, 2H), 3.73-3.90 (m, 2H), 3.20-3.28 (m, 1H), 2.96-3.10 (m, 2H), 2.61-2.85 (m, 2H), 2.33-2.45 (m, 1H), 2.00-2.13 (m, 2H), 1.83-1.94 (m, 1H), 1.64-1.80 (m, 3H), 0.85-0.94 (m, 2H), 0.55-0.67 (m, 2H) |

TABLE A-continued

| Example No. | Ki (nM) | Structure | Synthetic Procedure Used | HPLC Methods ($t_R$ min) | MS (M + H) | $^1$H NMR Data |
|---|---|---|---|---|---|---|
| 105 | 1.5 | 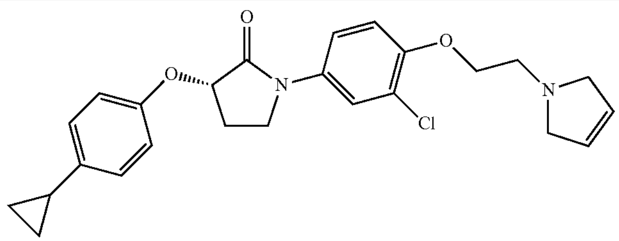 | A4 | 1 (7.56) 2 (9.88) | 439.2 | $^1$H NMR (400 MHz, DMSO-d$_6$) δ 7.83-7.94 (m, 1H), 7.51-7.62 (m, 1H), 7.18-7.27 (m, 1H), 6.85-7.09 (m, 4H), 5.80 (s, 2H), 5.04-5.20 (m, 1H), 4.14 (s, 2H), 3.73-3.93 (m, 2H), 3.54 (s, 4H), 3.01 (s, 2H), 2.61-2.74 (m, 2H), 1.99-2.11 (m, 1H), 1.83-1.93 (m, 1H), 0.85-0.96 (m, 2H), 0.55-0.66 (m, 2H) |
| 106 | 1.3 | 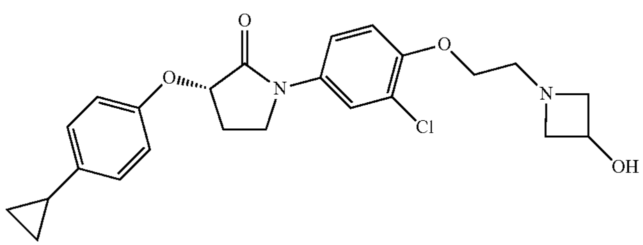 [SMILES: O=C1[C@@H](Oc2ccc(C3CC3)cc2)CCN1c1ccc(OCCN2CC(O)C2)c(Cl)c1] | A4 | 1 (7.26) 2 (8.6) | 443.2 | $^1$H NMR (400 MHz, DMSO-d$_6$) δ 7.83-7.94 (m, 1H), 7.52-7.60 (m, 1H), 7.12-7.22 (m, 1H), 6.89-7.08 (m, 4H), 5.09-5.29 (m, 2H), 4.11-4.22 (m, 1H), 3.99-4.09 (m, 2H), 3.74-3.91 (m, 2H), 3.55-3.65 (m, 2H), 2.81-2.91 (m, 2H), 2.74-2.81 (m, 2H), 2.62-2.71 (m, 1H), 1.98-2.12 (m, 1H), 1.82-1.93 (m, 1H), 0.85-0.95 (m, 2H), 0.55-0.65 (m, 2H) |
| 107 | 1.4 | 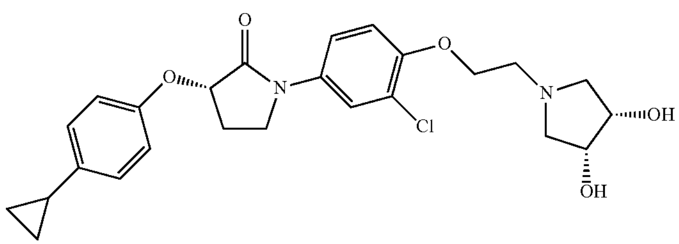 [SMILES: O=C1[C@@H](Oc2ccc(C3CC3)cc2)CCN1c1ccc(OCCN2C[C@@H](O)[C@@H](O)C2)c(Cl)c1] | A4 | 1 (7.09) 2 (8.36) | 473.2 | $^1$H NMR (400 MHz, DMSO-d$_6$) δ 7.84-7.93 (m, 1H), 7.51-7.61 (m, 1H), 7.17-7.25 (m, 1H), 6.88-7.08 (m, 4H), 5.03-5.20 (m, 1H), 4.45-4.58 (m, 2H), 4.07-4.16 (m, 2H), 3.72-3.98 (m, 4H), 2.93-3.02 (m, 2H), 2.77-2.87 (m, 2H), 2.65-2.71 (m, 1H), 2.42-2.45 (m, 2H), 1.98-2.10 (m, 1H), 1.81-1.91 (m, 1H), 0.84-0.94 (m, 2H), 0.53-0.64 (m, 2H) |

TABLE B

| Example No. | Ki (nM) | Structure | Synthetic Procedure Used | HPLC Methods ($t_R$ min) | MS (M+H) | NMR Data |
|---|---|---|---|---|---|---|
| 108 | 0.5 | (OMe) | A5 | 1 (7.39) 2 (9.77) 4 (10.5) | 473.2 | $^1$H NMR (400 MHz, DMSO-$d_6$) δ 7.63 (d, J = 9.04 Hz, 4H), 7.50-7.55 (m, 1H), 7.42-7.50 (m, 2H), 7.29-7.37 (m, 1H), 7.18 (s, 2H), 6.98-7.12 (m, 2H), 5.24-5.35 (m, 1H), 4.05 (s, 2H), 3.78 (s, 5H), 2.79 (s, 3H), 2.52 (br. s., 4H), 2.04-2.18 (m, 1H), 1.69 (s, 4H) |
| 109 | 14 | (OMe) | A5 | 1 (7.39) 2 (9.77) 4 (18.4) | 473.2 | $^1$H NMR (400 MHz, DMSO-$d_6$) δ 7.62 (s, 4H), 7.50-7.56 (m, 1H), 7.42-7.50 (m, 2H), 7.30-7.38 (m, 1H), 7.14-7.23 (m, 2H), 7.06-7.11 (m, 1H), 6.98-7.04 (m, 1H), 5.25-5.35 (m, 1H), 4.01-4.12 (m, 2H), 3.78 (s, 5H), 2.66-2.84 (m, 3H), 2.53-2.58 (m, 4H), 2.05-2.17 (m, 1H), 1.69 (s, 4H) |
| 110 | 0.5 | (Et) | A6 | 1 (8.3) 2 (9.95) 4 (6.7) | 471.2 | (400 MHz, CDCl$_3$) δ 7.53 (d, J = 8.78 Hz, 5H), 7.35-7.44 (m, 3H), 7.30-7.33 (m, 1H), 7.14-7.19 (m, 2H), 6.80-6.89 (m, 1H), 5.02-5.11 (m, 1H), 4.11-4.22 (m, 2H), 3.80-3.96 (m, 2H), 2.97-3.10 (m, 2H), 2.60-2.88 (m, 7H), 2.25-2.39 (m, 1H), 1.81-1.94 (m, 4H), 1.20 (s, 3H) |
| 111 | 12 | (Et) | A6 | 1 (8.32) 2 (9.91) 4 (17.2) | 471.2 | $^1$H NMR (400 MHz, CDCl$_3$) δ 7.50-7.61 (m, 5H), 7.28-7.45 (m, 4H), 7.16 (d, J = 9.03 Hz, 2H), 6.79-6.90 (m, 1H), 5.00-5.12 (m, 1H), 4.10-4.23 (m, 2H), 3.79-3.97 (m, 2H), 3.01-3.12 (m, 2H), 2.62-2.91 (m, 7H), 2.28-2.39 (m, 1H), 1.83-1.93 (m, 4H), 1.20 (t, J = 7.53 Hz, 3H) |
| 112 | 0.5 | (Me) | A7 | 1 (7.46) 2 (9.82) 4 (7.6) | 457.2 | $^1$H NMR (400 MHz, CD$_3$OD) δ 7.57-7.64 (m, 4H), 7.38-7.51 (m, 4H), 7.28-7.35 (m, 1H), 7.15-7.22 (m, 2H), 6.94-7.02 (m, 1H), 5.18-5.27 (m, 1H), 4.17-4.26 (m, 2H), 3.89-3.97 (m, 2H), 3.07-3.16 (m, 2H), 2.75-2.92 (m, 5H), 2.25-2.32 (m, 3H), 2.16-2.27 (m, 1H), 1.85-1.95 (m, 4H) |

TABLE B-continued

| Example No. | Ki (nM) | Structure | Synthetic Procedure Used | HPLC Methods ($t_R$ min) | MS (M + H) | NMR Data |
|---|---|---|---|---|---|---|
| 113 | 15 | (3-(biphenyl-4-yloxy)-1-(4-(2-(pyrrolidin-1-yl)ethoxy)-3-methylphenyl)pyrrolidin-2-one) | A7 | 1 (7.48)<br>2 (9.82)<br>4 (20.5) | 457.2 | $^1$H NMR (400 MHz, CD$_3$OD) δ 7.57-7.64 (m, 4H), 7.38-7.51 (m, 4H), 7.28-7.35 (m, 1H), 7.15-7.22 (m, 2H), 6.94-7.02 (m, 1H), 5.18-5.27 (m, 1H), 4.17-4.26 (m, 2H), 3.89-3.97 (m, 2H), 3.07-3.16 (m, 2H), 2.75-2.92 (m, 5H), 2.25-2.32 (m, 3H), 2.16-2.27 (m, 1H), 1.85-1.95 (m, 4H) |
| 114 | 0.5 | (3-(biphenyl-4-yloxy)-1-(3-chloro-4-(2-(pyrrolidin-1-yl)ethoxy)phenyl)pyrrolidin-2-one) | A8 | 1 (13.2)<br>2 (9.81)<br>4 (11.7) | 477.2 | $^1$H NMR (400 MHz, DMSO-d$_6$) δ 7.86-7.96 (m, 1H), 7.53-7.69 (m, 5H), 7.42-7.50 (m, 2H), 7.29-7.39 (m, 1H), 7.09-7.26 (m, 3H), 5.21-5.36 (m, 1H), 4.13-4.25 (m, 2H), 3.77-3.94 (m, 2H), 2.81-2.96 (m, 2H), 2.69-2.78 (m, 1H), 2.57-2.66 (m, 4H), 2.04-2.19 (m, 1H), 1.62-1.75 (m, 4H) |
| 115 | 12 | (3-(biphenyl-4-yloxy)-1-(3-chloro-4-(2-(pyrrolidin-1-yl)ethoxy)phenyl)pyrrolidin-2-one) | A8 | 1 (13.2)<br>2 (9.81)<br>4 (21.9) | 477.2 | $^1$H NMR (400 MHz, DMSO-d$_6$) δ 7.85-7.95 (m, 1H), 7.55-7.68 (m, 5H), 7.40-7.49 (m, 2H), 7.30-7.37 (m, 1H), 7.13-7.27 (m, 3H), 5.25-5.35 (m, 1H), 4.12-4.25 (m, 2H), 3.76-3.95 (m, 2H), 2.57-2.99 (m, 7H), 2.05-2.18 (m, 1H), 1.65-1.78 (m, 4H) |

TABLE C

| Example No. | Ki (nM) | Structure | Synthetic Procedure Used | HPLC Methods ($t_R$ min) | MS (M + H) | NMR Data |
|---|---|---|---|---|---|---|
| 116 | 6 | 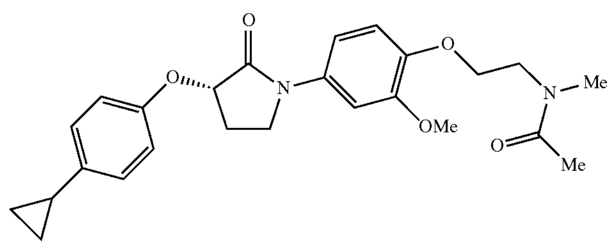 [SMILES: COc1cc(N2CC[C@H](Oc3ccc(C4CC4)cc3)C2=O)ccc1OCCN(C)C(C)=O] | A9 | 1 (16.1) 2 (14.9) | 439.2 | $^1$H NMR (400 MHz, CDCl$_3$) δ 7.67-7.82 (m, 1H), 6.94-7.06 (m, 4H), 6.87 (s, 2H), 4.97 (s, 1H), 4.18 (s, 2H), 3.69-3.94 (m, 7H), 2.96-3.23 (m, 3H), 2.60-2.72 (m, 1H), 2.24-2.35 (m, 1H), 2.06-2.23 (s, 3H), 1.82-1.91 (m, 1H), 0.90 (dd, J = 1.88, 8.41 Hz, 2H), 0.62 (dd, J = 1.63, 5.14 Hz, 2H) |
| 117 | 6 | 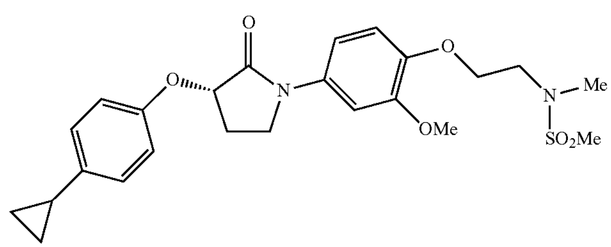 [SMILES: COc1cc(N2CC[C@H](Oc3ccc(C4CC4)cc3)C2=O)ccc1OCCN(C)S(C)(=O)=O] | A9 | 1 (18.1) 2 (16.8) | 475.2 | $^1$H NMR (400 MHz, CDCl$_3$) δ 7.75 (d, J = 2.51 Hz, 1H), 7.00 (q, J = 8.78 Hz, 4H), 6.77-6.93 (m, 2H), 4.98 (s, 1H), 4.16 (t, J = 5.40 Hz, 2H), 3.78-3.93 (m, 5H), 3.64 (t, J = 5.40 Hz, 2H), 3.03 (s, 3H), 2.93 (s, 3H), 2.61-2.71 (m, 1H), 2.22-2.35 (m, 1H), 1.79-1.92 (m, 1H), 0.90 (dd, J = 1.88, 8.41 Hz, 2H), 0.62 (dd, J = 1.63, 5.14 Hz, 2H) |

TABLE C-continued
| Example No. | Ki (nM) | Structure | Synthetic Procedure Used | HPLC Methods ($t_R$ min) | MS (M + H) | NMR Data |
|---|---|---|---|---|---|---|
| 118 | 85 | 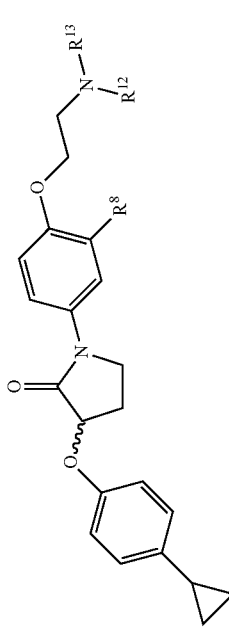 | A9 | | 615.2 | $^1$H NMR (400 MHz, DMSO-$d_6$) δ 7.43-7.56 (m, 1H), 6.90-7.09 (m, 6H), 5.08-5.22 (m, 1H), 4.07-4.18 (m, 2H), 3.74-3.88 (m, 5H), 3.40-3.48 (m, 2H), 2.88-2.96 (m, 3H), 2.62-2.72 (m, 1H), 2.51-2.55 (m, 3H), 2.14-2.21 (m, 3H), 1.97-2.10 (m, 1H), 1.81-1.93 (m, 1H), 0.82-0.95 (m, 2H), 0.52-0.66 (m, 2H) |
| 119 | 16 | 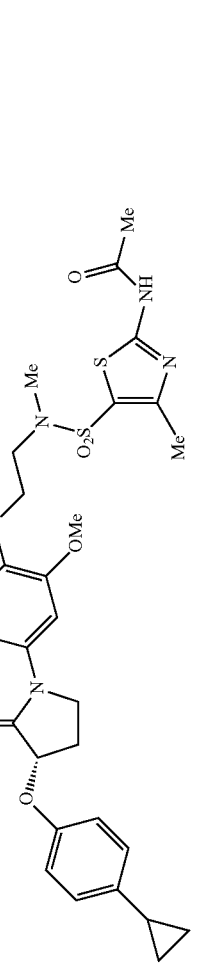 | A9 | | 537.2 | $^1$H NMR (400 MHz, DMSO-$d_6$) δ 7.79-7.89 (m, 2H), 7.59-7.76 (m, 3H), 7.47-7.55 (m, 1H), 6.87-7.12 (m, 6H), 5.07-5.22 (m, 1H), 4.03-4.17 (m, 2H), 3.73-3.91 (m, 5H), 3.36-3.42 (m, 2H), 2.77-2.90 (m, 3H), 2.62-2.73 (m, 1H), 1.98-2.13 (m, 1H), 1.81-1.94 (m, 1H), 0.83-0.94 (m, 2H), 0.51-0.64 (m, 2H) |
| 120 | 8 | 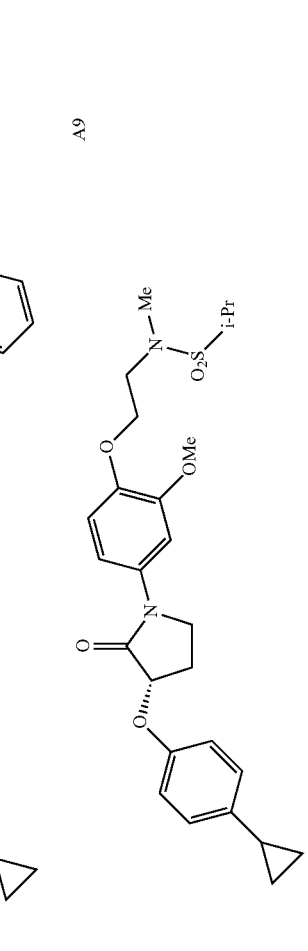 | A9 | | 503.2 | $^1$H NMR (400 MHz, DMSO-$d_6$) δ 7.46-7.59 (m, 1H), 6.90-7.14 (m, 6H), 5.08-5.20 (m, 1H), 4.05-4.16 (m, 2H), 3.78 (s, 5H), 3.49-3.61 (m, 3H), 2.97 (s, 3H), 2.62-2.73 (m, 1H), 1.96-2.13 (m, 1H), 1.83-1.92 (m, 1H), 1.23 (d, J = 6.78 Hz, 6H), 0.83-0.93 (m, 2H), 0.55-0.65 (m, 2H) |

TABLE C-continued
| Example No. | Ki (nM) | Structure | Synthetic Procedure Used | HPLC Methods ($t_R$ min) | MS (M + H) | NMR Data |
|---|---|---|---|---|---|---|
| 121 | 21 | 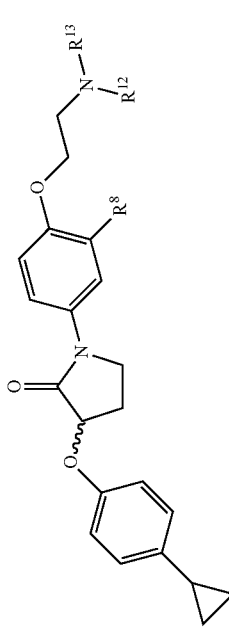 | A9 | | 543.2 | $^1$H NMR (400 MHz, DMSO-$d_6$) δ 7.48-7.56 (m, 1H), 6.90-7.14 (m, 6H), 5.08-5.21 (m, 1H), 4.56-4.73 (m, 2H), 4.08-4.18 (m, 2H), 3.73-3.90 (m, 5H), 3.59-3.70 (m, 2H), 2.92-3.02 (m, 3H), 2.60-2.74 (m, 1H), 1.98-2.11 (m, 1H), 1.84-1.93 (m, 1H), 0.83-0.94 (m, 2H), 0.56-0.64 (m, 2H) |
| 122 | 6 | 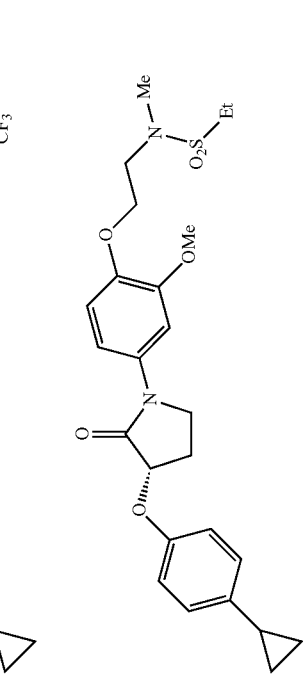 | A9 | | 489.2 | $^1$H NMR (400 MHz, DMSO-$d_6$) δ 7.49-7.59 (m, 1H), 6.89-7.12 (m, 6H), 5.07-5.21 (m, 1H), 4.05-4.17 (m, 2H), 3.78 (s, 5H), 3.49-3.58 (m, 2H), 3.13-3.22 (m, 2H), 2.93 (s, 3H), 2.62-2.73 (m, 1H), 2.00-2.11 (m, 1H), 1.83-1.92 (m, 1H), 1.16-1.24 (m, 3H), 0.83-0.94 (m, 2H), 0.55-0.64 (m, 2H) |

TABLE C-continued

| Example No. | Ki (nM) | Structure | Synthetic Procedure Used | HPLC Methods (t_R min) | MS (M + H) | NMR Data |
|---|---|---|---|---|---|---|
| 123 | 8 | 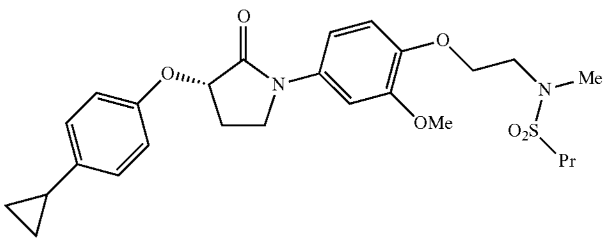 | A9 | | 503.2 | ¹H NMR (400 MHz, DMSO-d₆) δ 7.46-7.57 (m, 1H), 6.91-7.12 (m, 6H), 5.09-5.23 (m, 1H), 4.06-4.16 (m, 2H), 3.78 (s, 5H), 3.50-3.59 (m, 2H), 3.08-3.18 (m, 2H), 2.92 (s, 3H), 2.62-2.73 (m, 1H), 1.99-2.11 (m, 1H), 1.83-1.93 (m, 1H), 1.65-1.76 (m, 2H), 0.94-1.03 (m, 3H), 0.82-0.92 (m, 2H), 0.57-0.66 (m, 2H) |
| 124 | 19 | 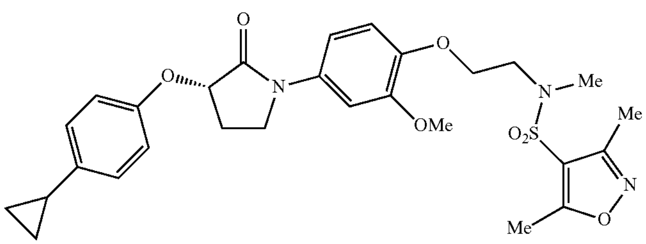 [SMILES: COc1cc(N2CC[C@H](Oc3ccc(C4CC4)cc3)C2=O)ccc1OCCN(C)S(=O)(=O)c1c(C)noc1C] | A9 | | 556.2 | ¹H NMR (400 MHz, DMSO-d₆) δ 7.47-7.57 (m, 1H), 6.91-7.12 (m, 6H), 5.10-5.22 (m, 1H), 4.07-4.18 (m, 2H), 3.77 (s, 5H), 3.46-3.54 (m, 2H), 2.92 (s, 3H), 2.63 (s, 4H), 2.35 (s, 3H), 2.00-2.11 (m, 1H), 1.84-1.93 (m, 1H), 0.86-0.94 (m, 2H), 0.56-0.64 (m, 2H) |
| 125 | 6 | 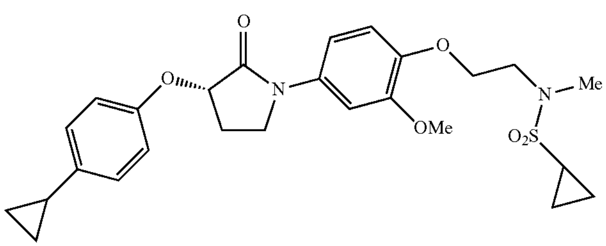 [SMILES: COc1cc(N2CC[C@H](Oc3ccc(C4CC4)cc3)C2=O)ccc1OCCN(C)S(=O)(=O)C1CC1] | A9 | | 501.2 | ¹H NMR (400 MHz, DMSO-d₆) δ 7.47-7.59 (m, 1H), 6.89-7.13 (m, 6H), 5.11-5.20 (m, 1H), 4.09-4.19 (m, 2H), 3.77 (s, 5H), 3.50-3.61 (m, 2H), 2.94 (s, 3H), 2.75-2.83 (m, 1H), 2.63-2.72 (m, 1H), 1.99-2.11 (m, 1H), 1.82-1.93 (m, 1H), 0.83-1.00 (m, 6H), 0.54-0.63 (m, 2H) |

TABLE C-continued
| Example No. | Ki (nM) | Structure | Synthetic Procedure Used | HPLC Methods ($t_R$ min) | MS (M + H) | NMR Data |
|---|---|---|---|---|---|---|
| 126 | 35 | 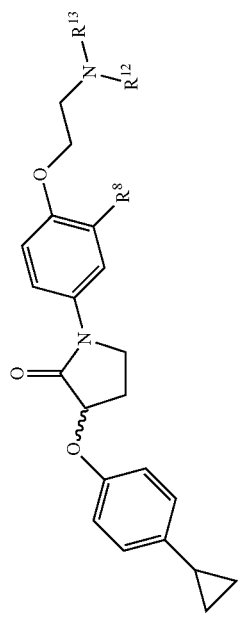 | A9 | | 542.2 | $^1$H NMR (400 MHz, DMSO-$d_6$) δ 7.47-7.58 (m, 1H), 6.88-7.06 (m, 7H), 5.09-5.20 (m, 1H), 3.98-4.10 (m, 2H), 3.74-3.89 (m, 5H), 3.39-3.47 (m, 2H), 2.66-2.73 (m, 4H), 1.96-2.11 (m, 2H), 1.84-1.91 (m, 3H), 0.83-0.95 (m, 2H), 0.52-0.66 (m, 2H) |
| 127 | 5 | 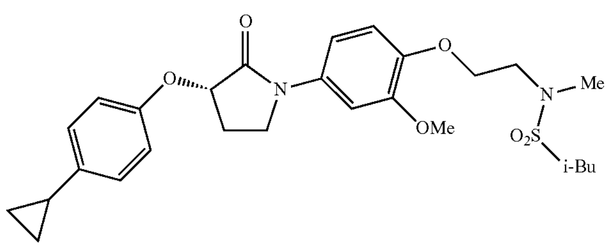 | A9 | | 517.2 | $^1$H NMR (400 MHz, DMSO-$d_6$) δ 7.46-7.56 (m, 1H), 6.89-7.13 (m, 6H), 5.08-5.26 (m, 1H), 4.05-4.16 (m, 2H), 3.73-3.91 (m, 5H), 3.48-3.55 (m, 2H), 2.98-3.06 (m, 2H), 2.87-2.95 (m, 3H), 2.62-2.74 (m, 1H), 2.01-2.16 (m, 2H), 1.82-1.92 (m, 1H), 1.03 (d, J = 6.78 Hz, 5H), 0.85-0.94 (m, 2H), 0.52-0.64 (m, 2H) |

TABLE C-continued

| Example No. | Ki (nM) | Structure | Synthetic Procedure Used | HPLC Methods ($t_R$ min) | MS (M + H) | NMR Data |
|---|---|---|---|---|---|---|
| 128 | 6 | [structure with N-Me, OMe, C(O)CH2OMe group] | A9 | 1 (8.0) 2 (7.66) | 469.62 | $^1$H NMR (400 MHz, CDCl$_3$) δ 7.66-7.81 (m, 1H), 7.00 (d, J = 8.76 Hz, 4H), 6.74-6.91 (m, 2H), 4.97 (s, 1H), 4.07-4.33 (m, 4H), 3.70-3.92 (m, 7H), 3.44 (s, 3H), 3.00-3.18 (m, 3H), 2.60-2.73 (m, 1H), 2.21-2.35 (m, 1H), 1.81-1.91 (m, 1H), 0.90 (d, J = 6.75 Hz, 2H), 0.55-0.67 (m, 2H) |
| 129 | 14 | [structure with N-Me, OMe, C(O)OEt group] | A9 | 1 (10) 2 (9.13) | 469.65 | $^1$H NMR (400 MHz, CDCl$_3$) δ 7.65-7.80 (m, 1H), 7.00 (d, J = 8.03 Hz, 4H), 6.77-6.93 (m, 2H), 4.91-5.04 (m, 1H), 4.10-4.25 (m, 4H), 3.87 (s, 5H), 3.60-3.72 (m, 2H), 3.04 (s, 3H), 2.60-2.72 (m, 1H), 2.21-2.34 (m, 1H), 1.79-1.91 (m, 1H), 1.26 (s, 3H), 0.84-0.95 (m, 2H), 0.62 (d, J = 6.78 Hz, 2H) |
| 130 | 4 | [structure with N-Me, OMe, C(O)OMe group] | A9 | 1 (9.53) 2 (8.85) | 455.2 | $^1$H NMR (400 MHz, CDCl$_3$) δ 7.66-7.79 (m, 1H), 7.00 (d, J = 8.26 Hz, 4H), 6.76-6.93 (m, 2H), 4.90-5.03 (m, 1H), 4.07-4.26 (m, 2H), 3.87 (s, 5H), 3.70 (s, 5H), 3.05 (s, 3H), 2.60-2.72 (m, 1H), 2.24-2.35 (m, 3H), 1.80-1.92 (m, 1H), 0.83-0.95 (m, 2H), 0.55-0.67 (m, 2H) |

TABLE C-continued

| Example No. | Ki (nM) | Structure | Synthetic Procedure Used | HPLC Methods ($t_R$ min) | MS (M + H) | NMR Data |
|---|---|---|---|---|---|---|
| 131 | 14 | 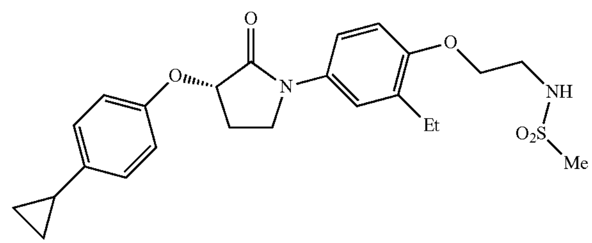 [SMILES: CCc1cc(N2CC[C@H](Oc3ccc(C4CC4)cc3)C2=O)ccc1OCCNS(C)(=O)=O] | A9 | 1 (18.8) 2 (17.2) | 459.1 | $^1$H NMR (400 MHz, DMSO-$d_6$) δ 8.29-8.34 (m, 1H), 7.50-7.55 (m, 1H), 7.39-7.46 (m, 1H), 7.24-7.32 (m, 1H), 6.91-7.06 (m, 4H), 5.09-5.16 (m, 1H), 4.00-4.07 (m, 2H), 3.77-3.85 (m, 2H), 3.35-3.39 (m, 1H), 2.95 (s, 3H), 2.58-2.70 (m, 4H), 2.00-2.07 (m, 1H), 1.83-1.92 (m, 1H), 1.11-1.19 (m, 3H), 0.85-0.93 (m, 2H), 0.56-0.63 (m, 2H) |
| 132 | 13 | 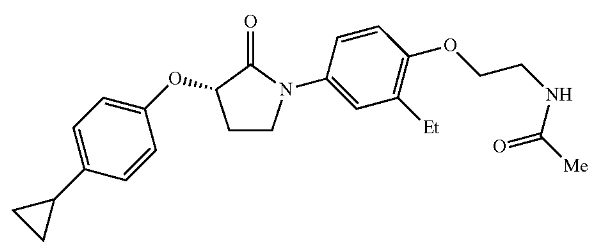 [SMILES: CCc1cc(N2CC[C@H](Oc3ccc(C4CC4)cc3)C2=O)ccc1OCCNC(C)=O] | A9 | 1 (17.4) 2 (15.8) | 422.8 | $^1$H NMR (400 MHz, DMSO-$d_6$) δ 7.99-8.09 (m, 1H), 7.48-7.54 (m, 1H), 7.38-7.45 (m, 1H), 6.93-7.04 (m, 5H), 5.07-5.17 (m, 1H), 3.91-4.03 (m, 2H), 3.74-3.87 (m, 2H), 3.37-3.48 (m, 2H), 2.57-2.72 (m, 3H), 1.99-2.10 (m, 1H), 1.83 (s, 4H), 1.14 (s, 3H), 0.83-0.94 (m, 2H), 0.53-0.64 (m, 2H) |

TABLE C-continued

| Example No. | Ki (nM) | Structure | Synthetic Procedure Used | HPLC Methods ($t_R$ min) | MS (M + H) | NMR Data |
|---|---|---|---|---|---|---|
| 133 | 5 | (structure with R8, R12, R13, cyclopropyl-phenyl-pyrrolidinone; specific substituent: Et, CH2CH2-N(Me)(SO2Me)) | A9 | 1 (20.1) 2 (16.8) | 472.9 | $^1$H NMR (400 MHz, DMSO-$d_6$) δ 7.51-7.57 (m, 1H), 7.40-7.48 (m, 1H), 6.92-7.06 (m, 5H), 5.08-5.19 (m, 1H), 4.09-4.20 (m, 2H), 3.72-3.88 (m, 2H), 3.44-3.55 (m, 2H), 2.92 (d, J = 8.78 Hz, 6H), 2.57-2.72 (m, 3H), 1.98-2.12 (m, 1H), 1.82-1.93 (m, 1H), 1.15 (t, J = 7.53 Hz, 3H), 0.83-0.94 (m, 2H), 0.55-0.64 (m, 2H) |

TABLE D

| Example No. | Ki (nM) | Structure | Synthetic Procedure Used | HPLC Methods ($t_R$ min) | MS (M + H) | NMR Data |
|---|---|---|---|---|---|---|
| 134 | 13 | 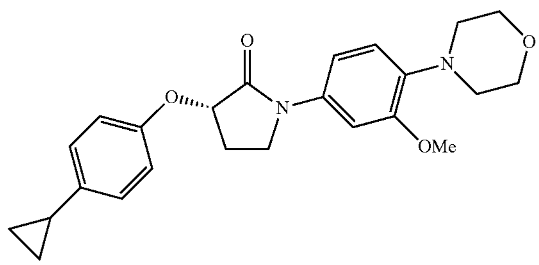 [SMILES: COc1cc(N2CC[C@H](Oc3ccc(C4CC4)cc3)C2=O)ccc1N1CCOCC1] | A10 | 1 (9.81) 2 (9.14) 4 (8.2) | 409.1 | $^1$H NMR (400 MHz, DMSO-d$_6$) δ 7.43-7.58 (m, 1H), 7.05-7.10 (m, 1H), 7.01 (s, 2H), 6.88-6.97 (m, 3H), 5.09-5.22 (m, 1H), 3.79 (s, 5H), 3.69-3.75 (m, 4H), 2.95 (d, J = 4.52 Hz, 4H), 2.61-2.73 (m, 1H), 1.99-2.13 (m, 1H), 1.83-1.94 (m, 1H), 0.83-0.95 (m, 2H), 0.56-0.64 (m, 2H) |
| 135 | 534 | 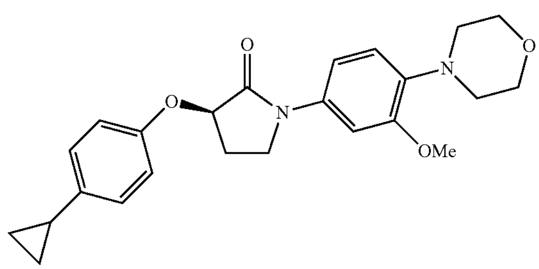 [SMILES: COc1cc(N2CC[C@@H](Oc3ccc(C4CC4)cc3)C2=O)ccc1N1CCOCC1] | A10 | 1 (9.80) 2 (9.13) 4 (10.9) | 409.1 | $^1$H NMR (400 MHz, DMSO-d$_6$) δ 7.46-7.51 (m, 1H), 7.05-7.10 (m, 1H), 6.99-7.04 (m, 2H), 6.88-6.97 (m, 3H), 5.10-5.19 (m, 1H), 3.79 (s, 5H), 3.69-3.75 (m, 4H), 2.91-2.98 (m, 4H), 2.60-2.71 (m, 1H), 2.00-2.10 (m, 1H), 1.84-1.93 (m, 1H), 0.87-0.91 (m, 2H), 0.57-0.64 (m, 2H) |
| 136 | 167 | 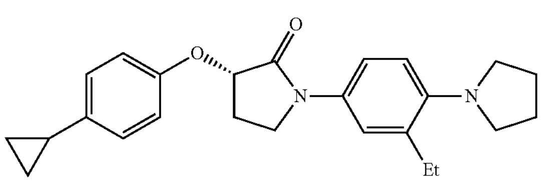 [SMILES: CCc1cc(N2CC[C@H](Oc3ccc(C4CC4)cc3)C2=O)ccc1N1CCCC1] | A11 | 1 (5.89) 2 (7.13) 4 (8.5) | 391.2 | $^1$H NMR (400 MHz, CDCl$_3$) δ 7.48-7.56 (m, 1H), 7.32-7.40 (m, 1H), 7.01 (d, J = 4.52 Hz, 5H), 4.91-5.02 (m, 1H), 3.78-3.96 (m, 2H), 3.14 (br. s., 4H), 2.59-2.78 (m, 3H), 2.21-2.34 (m, 1H), 1.94 (s, 5H), 1.26 (t, J = 7.53 Hz, 3H), 0.86-0.96 (m, 2H), 0.59-0.67 (m, 2H) |
| 137 | 1358 | 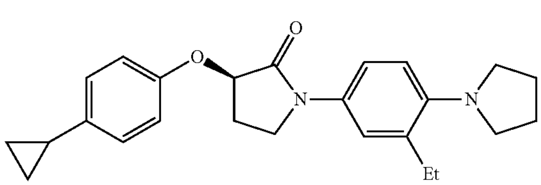 [SMILES: CCc1cc(N2CC[C@@H](Oc3ccc(C4CC4)cc3)C2=O)ccc1N1CCCC1] | A11 | 1 (5.88) 2 (7.1) 4 (13.8) | 391.2 | $^1$H NMR (400 MHz, CDCl$_3$) δ 7.52 (d, J = 2.51 Hz, 1H), 7.33-7.40 (m, 1H), 7.01 (d, J = 5.02 Hz, 5H), 4.97 (s, 1H), 3.77-3.94 (m, 2H), 3.18 (br. s., 4H), 2.59-2.81 (m, 3H), 2.19-2.35 (m, 1H), 1.96 (br. s., 5H), 1.26 (t, J = 7.53 Hz, 3H), 0.91 (dd, J = 2.01, 8.53 Hz, 2H), 0.56-0.67 (m, 2H) |

TABLE E
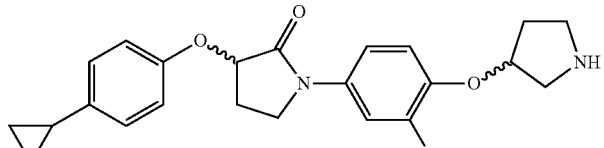
| Example No. | Ki (nM) | Structure | Synthetic Procedure Used | HPLC Methods ($t_R$ min) | MS (M + H) | NMR Data |
|---|---|---|---|---|---|---|
| 138 | 684 | 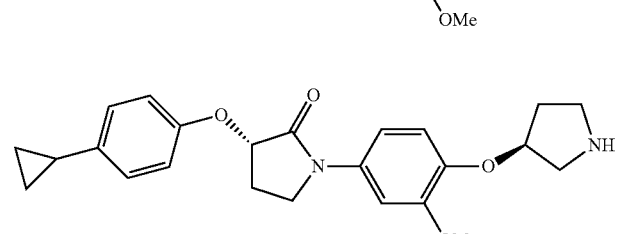 | A12 | 1 (6.72)<br>2 (8.39) | 409.2 | $^1$H NMR (400 MHz, CD$_3$OD) δ 7.55-7.65 (m, 1H), 6.94-7.14 (m, 6H), 5.08-5.19 (m, 2H), 3.90 (s, 5H), 3.38-3.60 (m, 4H), 2.70-2.83 (m, 1H), 2.14-2.36 (m, 3H), 1.83-1.92 (m, 1H), 0.88-0.99 (m, 2H), 0.57-0.67 (m, 2H) |
| 139 | 5 | 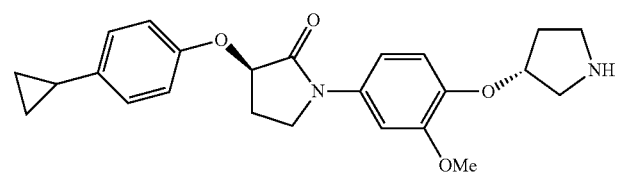 [SMILES: COc1cc(N2CC[C@@H](Oc3ccc(C4CC4)cc3)C2=O)ccc1O[C@@H]1CCNC1] | A12 | 1 (6.65)<br>2 (8.38) | 409.2 | $^1$H NMR (400 MHz, CD$_3$OD) δ 7.52-7.66 (m, 1H), 6.94-7.15 (m, 6H), 5.08-5.20 (m, 2H), 3.90 (s, 5H), 3.43-3.68 (m, 4H), 2.72-2.81 (m, 1H), 2.32-2.41 (m, 1H), 2.13-2.27 (m, 2H), 1.85-1.93 (m, 1H), 0.87-0.97 (m, 2H), 0.58-0.67 (m, 2H) |
| 140 | 130 | 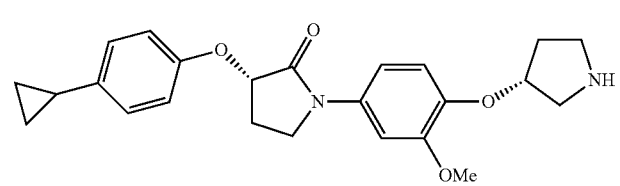 | A12 | 1 (6.71)<br>2 (8.37) | 409.2 | $^1$H NMR (400 MHz, CD$_3$OD) d 7.59 (s, 1H), 6.92-7.17 (m, 6H), 5.06-5.25 (m, 2H), 3.90 (s, 5H), 3.41-3.68 (m, 4H), 2.70-2.84 (m, 1H), 2.29-2.41 (m, 1H), 2.13-2.28 (m, 2H), 1.82-1.95 (m, 1H), 0.87-0.99 (m, 2H), 0.62 (d, J = 5.27 Hz, 2H) |
| 141 | 2 | 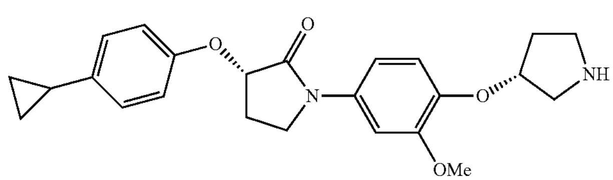 [SMILES: COc1cc(N2CC[C@H](Oc3ccc(C4CC4)cc3)C2=O)ccc1O[C@@H]1CCNC1] | A12 | 1 (6.73)<br>2 (8.39) | 409.2 | $^1$H NMR (400 MHz, CD$_3$OD) d 7.52-7.66 (m, 1H), 6.94-7.13 (m, 6H), 5.05-5.19 (m, 2H), 3.90 (s, 5H), 3.35-3.57 (m, 4H), 2.71-2.83 (m, 1H), 2.13-2.35 (m, 3H), 1.84-1.92 (m, 1H), 0.86-0.96 (m, 2H), 0.58-0.68 (m, 2H) |

TABLE F

[Structure header showing pyrrolinone with phenoxy-cyclopropylphenyl and aryloxy-ethylamine N-R12/R13 substituents, with R8 on the central phenyl]

| Example No. | Ki (nM) | Structure | Synthetic Procedure Used | HPLC Methods ($t_R$ min) | MS (M + H) | NMR Data |
|---|---|---|---|---|---|---|
| 142 | 0.7 | [Structure: 3-(4-cyclopropylphenoxy)-1-[4-(2-pyrrolidin-1-yl-ethoxy)-3-methoxyphenyl]-1,5-dihydro-pyrrol-2-one] | Method B1 | 1 (7.19) 2 (8.61) | 435.2 | $^1$H NMR (400 MHz, CDCl$_3$) δ 7.67-7.76 (m, 1H), 7.08 (s, 4H), 6.88-6.96 (m, 2H), 5.72-5.80 (m, 1H), 4.21-4.29 (m, 2H), 4.13-4.20 (m, 2H), 3.89 (s, 3H), 2.90-3.03 (m, 2H), 2.58-2.75 (m, 4H), 1.78-1.96 (m, 5H), 0.93-1.02 (m, 2H), 0.63-0.73 (m, 2H) |
| 143 | 0.8 | [Structure: as above with (3-hydroxy)pyrrolidine] | Method B1 | 1 (6.84) 2 (8.13) | 451.2 | $^1$H NMR (400 MHz, DMSO-d$_6$) δ 7.51-7.55 (m, 1H), 7.01-7.25 (m, 6H), 6.18-6.24 (m, 1H), 4.38-4.45 (m, 2H), 3.99-4.36 (m, 3H), 3.77-3.84 (m, 3H), 2.76-3.21 (m, 4H), 2.65-2.71 (m, 1H), 2.30-2.36 (m, 1H), 2.02-2.16 (m, 1H), 1.90-1.99 (m, 1H), 1.58-1.76 (m, 1H), 0.90-1.00 (m, 2H), 0.62-0.71 (m, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 144 | 0.9 | (3-OH pyrrolidine, OMe, cyclopropylphenyl pyrrolinone) | Method B1 | 1 (6.85) 2 (8.13) | 451.2 | $^1$H NMR (400 MHz, DMSO-d$_6$) δ 7.50-7.54 (m, 1H), 7.18-7.23 (m, 1H), 7.12-7.17 (m, 2H), 7.06-7.11 (m, 2H), 7.00-7.05 (m, 1H), 6.17-6.23 (m, 1H), 4.39-4.46 (m, 2H), 4.21-4.32 (m, 1H), 4.04-4.17 (m, 2H), 3.79 (s, 3H), 2.77-3.16 (m, 4H), 2.65-2.70 (m, 1H), 2.31-2.38 (m, 1H), 2.00-2.11 (m, 1H), 1.89-1.99 (m, 1H), 1.57-1.72 (m, 1H), 0.91-1.00 (m, 2H), 0.62-0.70 (m, 2H) |
| 145 | 0.8 | (3-F pyrrolidine, OMe, cyclopropylphenyl pyrrolinone) | Method B1 | 1 (6.84) 2 (8.62) | 453.2 | $^1$H NMR (400 MHz, DMSO-d$_6$) δ 7.48-7.55 (m, 1H), 7.18-7.24 (m, 1H), 7.12-7.17 (m, 2H), 7.06-7.11 (m, 2H), 6.99-7.05 (m, 1H), 6.16-6.24 (m, 1H), 5.08-5.35 (m, 1H), 4.36-4.47 (m, 2H), 4.00-4.13 (m, 2H), 3.79 (s, 3H), 2.72-3.03 (m, 4H), 2.63-2.70 (m, 1H), 2.31-2.37 (m, 1H), 2.05-2.25 (m, 1H), 1.77-2.00 (m, 2H), 0.91-1.01 (m, 2H), 0.61-0.71 (m, 2H) |
| 146 | 0.6 | (3-F pyrrolidine, OMe, cyclopropylphenyl pyrrolinone) | Method B1 | 1 (6.79) 2 (8.98) | 453.2 | $^1$H NMR (400 MHz, DMSO-d$_6$) δ 7.55-7.59 (m, 1H), 7.22-7.27 (m, 1H), 7.04-7.17 (m, 5H), 6.20-6.25 (m, 1H), 5.37-5.63 (m, 1H), 4.38-4.48 (m, 2H), 4.25-4.36 (m, 2H), 3.82 (s, 9H), 2.07-2.32 (m, 2H), 1.90-2.00 (m, 1H), 0.90-1.00 (m, 2H), 0.61-0.71 (m, 2H) |

TABLE F-continued
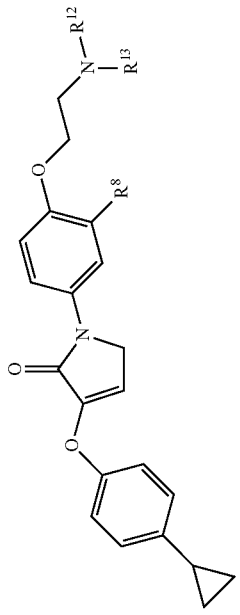
| Example No. | Ki (nM) | Structure | Synthetic Procedure Used | HPLC Methods ($t_R$ min) | MS (M + H) | NMR Data |
|---|---|---|---|---|---|---|
| 147 | 1.3 | 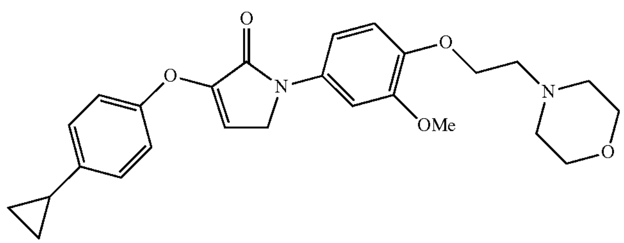 [SMILES: COc1cc(N2CC=C(Oc3ccc(C4CC4)cc3)C2=O)ccc1OCCN1CCOCC1] | Method B1 | 1 (6.61) 2 (8.66) | 451.2 | $^1$H NMR (400 MHz, DMSO-$d_6$) δ 7.47-7.52 (m, 1H), 6.98-7.22 (m, 6H), 6.17-6.23 (m, 1H), 4.36-4.44 (m, 2H), 4.02-4.11 (m, 2H), 3.78 (s, 3H), 3.53-3.65 (m, 4H), 2.57-2.75 (m, 6H), 1.88-2.00 (m, 1H), 0.89-1.00 (m, 2H), 0.60-0.70 (m, 2H) |
| 148 | 0.8 | 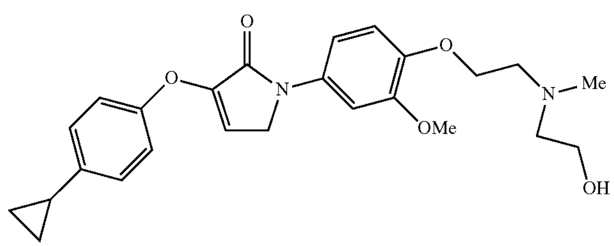 [SMILES: COc1cc(N2CC=C(Oc3ccc(C4CC4)cc3)C2=O)ccc1OCCN(C)CCO] | Method B1 | 1 (6.45) 2 (8.31) | 439.2 | $^1$H NMR (400 MHz, DMSO-$d_6$) δ 7.47-7.52 (m, 1H), 7.17-7.22 (m, 1H), 7.11-7.17 (m, 2H), 7.04-7.10 (m, 2H), 6.99-7.03 (m, 1H), 6.17-6.22 (m, 1H), 4.38-4.43 (m, 2H), 3.99-4.10 (m, 2H), 3.78 (s, 3H), 3.46-3.56 (m, 2H), 2.73-2.88 (m, 2H), 2.60-2.69 (m, 2H), 2.24-2.39 (m, 3H), 1.87-1.98 (m, 1H), 0.90-0.99 (m, 2H), 0.61-0.70 (m, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 149 | 0.8 | [Structure with pyrrolinone, 4-cyclopropylphenoxy, OMe, and azetidin-3-ol side chain] | Method B1 | 1 (6.56) 2 (7.87) | 437.2 | $^1$H NMR (400 MHz, CDCl$_3$) δ 7.68 (d, J = 2.51 Hz, 1H), 7.08 (d, J = 0.50 Hz, 4H), 6.87 (s, 2H), 5.75 (s, 1H), 4.41-4.52 (m, 1H), 4.23 (d, J = 2.26 Hz, 2H), 4.01 (t, J = 5.77 Hz, 2H), 3.89 (s, 3H), 3.77 (d, J = 2.76 Hz, 2H), 3.07 (s, 2H), 2.91 (t, J = 5.90 Hz, 2H), 1.85-1.95 (m, 1H), 0.91-1.02 (m, 2H), 0.62-0.72 (m, 2H) |
| 150 | 0.7 | [Structure with pyrrolinone, 4-cyclopropylphenoxy, OMe, and (S)-prolinol side chain] | Method B1 | 1 (7.15) 2 (8.3) | 465.2 | $^1$H NMR (400 MHz, DMSO-d$_6$) δ 7.49 (d, J = 2.51 Hz, 1H), 7.18 (d, J = 2.50 Hz, 1H), 7.12-7.16 (m, 2H), 7.06-7.10 (m, 2H), 7.00 (d, J = 9.03 Hz, 1H), 6.18-6.22 (m, 1H), 4.41 (d, J = 2.26 Hz, 2H), 4.31-4.36 (m, 1H), 4.03 (d, J = 1.00 Hz, 2H), 3.78 (s, 3H), 3.36-3.43 (m, 1H), 3.22-3.29 (m, 1H), 3.08-3.21 (m, 2H), 2.62-2.72 (m, 1H), 2.26-2.36 (m, 1H), 1.90-2.00 (m, 1H), 1.74-1.85 (m, 1H), 1.47-1.71 (m, 3H), 0.95 (dd, J = 2.13, 8.41 Hz, 2H), 0.66 (dd, J = 2.01, 5.01 Hz, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 151 | 0.5 | (structure with pyrrolidine-CH2OH, OMe, cyclopropylphenyl) | Method B1 | 1 (6.7) 2 (8.5) | 465.2 | $^1$H NMR (400 MHz, DMSO-d$_6$) δ 7.49 (d, J = 2.51 Hz, 1H), 7.17-7.22 (m, 1H), 7.12-7.16 (m, 2H), 7.06-7.11 (m, 2H), 7.00 (d, J = 8.78 Hz, 1H), 6.20 (s, 1H), 4.41 (d, J = 2.51 Hz, 2H), 4.31-4.36 (m, 1H), 4.03 (d, J = 1.00 Hz, 2H), 3.78 (s, 3H), 3.35-3.43 (m, 1H), 3.22-3.29 (m, 1H), 3.09-3.21 (m, 2H), 2.62-2.72 (m, 1H), 2.26-2.36 (m, 1H), 1.91-1.99 (m, 1H), 1.75-1.86 (m, 1H), 1.46-1.72 (m, 3H), 0.95 (dd, J = 2.13, 8.41 Hz, 2H), 0.66 (dd, J = 2.01, 5.02 Hz, 2H) |
| 152 | 2.7 | (structure with 3,3-difluoropyrrolidine, OMe, cyclopropylphenyl) | Method B1 | 1 (7.38) 2 (9.39) | 471.2 | $^1$H NMR (400 MHz, CDCl$_3$) δ 7.70-7.74 (m, 1H), 7.08 (s, 4H), 6.88-6.95 (m, 2H), 5.72-5.78 (m, 1H), 4.22-4.27 (m, 2H), 4.13-4.21 (m, 2H), 3.90 (s, 3H), 2.96-3.05 (m, 2H), 2.26-2.41 (m, 2H), 1.86-1.95 (m, 1H), 1.58-1.66 (m, 4H), 0.93-1.01 (m, 2H), 0.64-0.72 (m, 2H) |
| 153 | 0.4 | (structure with trifluoroacetamido pyrrolidine, OMe, cyclopropylphenyl) | Method B1 | 1 (7.49) 2 (9.25) | 546.2 | $^1$H NMR (400 MHz, CDCl$_3$) δ 7.69 (d, J = 2.51 Hz, 1H), 7.08 (s, 4H), 6.93-6.98 (m, 1H), 6.89 (s, 1H), 5.75 (s, 1H), 4.49-4.58 (m, 1H), 4.24 (d, J = 2.51 Hz, 2H), 4.07-4.16 (m, 2H), 3.90 (s, 3H), 3.11-3.20 (m, 1H), 2.89-3.00 (m, 3H), 2.53-2.61 (m, 1H), 2.26-2.41 (m, 2H), 1.89-1.95 (m, 1H), 1.69-1.79 (m, 1H), 0.97 (d, J = 6.78 Hz, 2H), 0.64-0.71 (m, 2H) |

TABLE F-continued
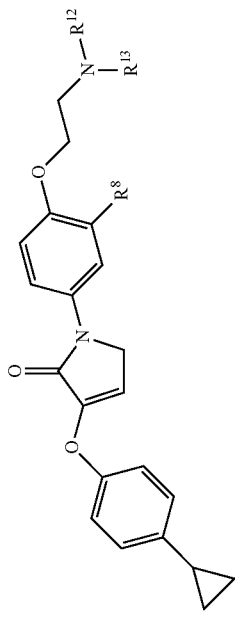
| Example No. | Ki (nM) | Structure | Synthetic Procedure Used | HPLC Methods (t_R min) | MS (M + H) | NMR Data |
|---|---|---|---|---|---|---|
| 154 | 0.5 | 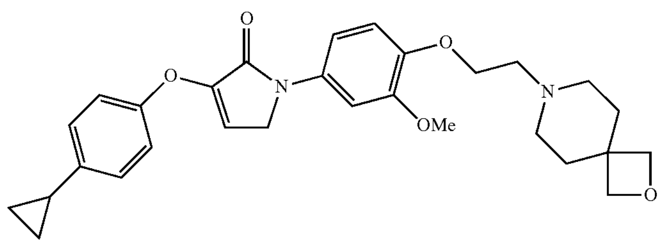 [SMILES: COc1cc(N2CC=C(Oc3ccc(C4CC4)cc3)C2=O)ccc1OCCN1CCC2(CC1)COC2] | Method B1 | 1 (7.24) 2 (8.44) | 491.2 | $^1$H NMR (400 MHz, CDCl$_3$) δ 7.66-7.71 (m, 1H), 7.08 (d, J = 0.50 Hz, 4H), 6.92-6.97 (m, 1H), 6.89 (s, 1H), 5.75 (s, 1H), 4.42 (s, 4H), 4.24 (d, J = 2.51 Hz, 2H), 4.13 (s, 2H), 3.89 (s, 3H), 2.76-2.85 (m, 2H), 2.41-2.57 (m, 3H), 1.91 (d, J = 5.27 Hz, 5H), 1.70-1.71 (m, 1H), 0.93-1.01 (m, 2H), 0.63-0.71 (m, 2H) |
| 155 | 0.5 | 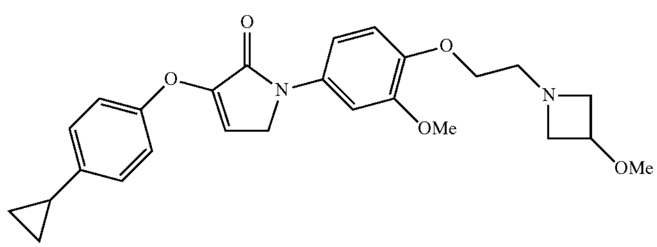 [SMILES: COc1cc(N2CC=C(Oc3ccc(C4CC4)cc3)C2=O)ccc1OCCN1CC(OC)C1] | Method B1 | 1 (7.32) 2 (8.71) | 451.2 | $^1$H NMR (400 MHz, CDCl$_3$) δ 7.69 (d, J = 2.51 Hz, 1H), 7.08 (s, 4H), 6.82-6.95 (m, 2H), 5.75 (s, 1H), 4.23 (d, J = 2.26 Hz, 2H), 4.05-4.12 (m, 1H), 4.02 (s, 2H), 3.88 (s, 3H), 3.73-3.81 (m, 2H), 3.27 (s, 3H), 3.04-3.13 (m, 2H), 2.93 (s, 2H), 1.86-1.95 (m, 1H), 0.97 (dd, J = 1.76, 8.53 Hz, 2H), 0.64-0.71 (m, 2H) |

TABLE F-continued
| Example No. | Ki (nM) | Structure | Synthetic Procedure Used | HPLC Methods ($t_R$ min) | MS (M + H) | NMR Data |
|---|---|---|---|---|---|---|
| 156 | 0.7 | 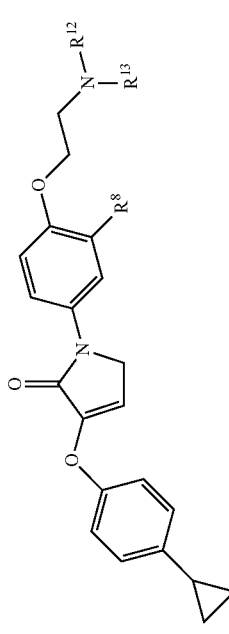 | Method B1 | 1 (7.04) 2 (8.09) | 451.2 | $^1$H NMR (400 MHz, CDCl$_3$) δ 7.68-7.71 (m, 1H), 7.04-7.13 (m, 4H), 6.91-6.96 (m, 1H), 6.85-6.90 (m, 1H), 5.73-5.77 (m, 1H), 4.22-4.27 (m, 2H), 4.01-4.08 (m, 2H), 3.89 (s, 3H), 3.42-3.49 (m, 2H), 3.20-3.29 (m, 2H), 2.89-2.98 (m, 2H), 1.85-1.96 (m, 1H), 1.50-1.52 (m, 3H), 0.93-1.00 (m, 2H), 0.64-0.72 (m, 2H) |
| 157 | 0.4 | 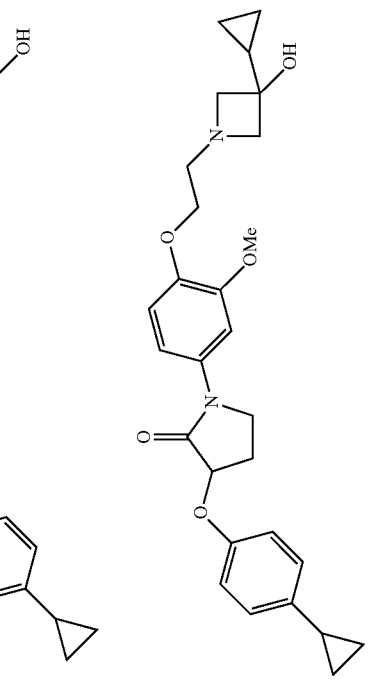 | Method B1 | 1 (8.27) 2 (8.84) | 477.2 | $^1$H NMR (400 MHz, CDCl$_3$) δ 7.68 (d, J = 2.26 Hz, 1H), 7.08 (s, 4H), 6.91-6.95 (m, 1H), 6.88 (s, 1H), 5.75 (s, 1H), 4.23 (d, J = 2.26 Hz, 2H), 4.01 (s, 2H), 3.89 (s, 3H), 3.33 (d, J = 8.78 Hz, 2H), 3.16 (d, J = 8.78 Hz, 2H), 2.91 (s, 2H), 1.87-1.95 (m, 1H), 1.14-1.23 (m, 1H), 0.92-1.01 (m, 2H), 0.67 (s, 2H), 0.49-0.58 (m, 2H), 0.39-0.47 (m, 2H) |
| 158 | 2.9 | 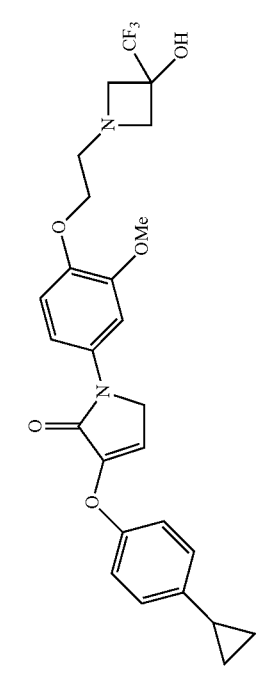 | Method B1 | 1 (7.5) 2 (9.1) | 505.2 | $^1$H NMR (400 MHz, CDCl$_3$) δ 7.68-7.73 (m, 1H), 7.08 (d, J = 0.75 Hz, 4H), 6.90-6.96 (m, 1H), 6.87 (s, 1H), 5.76 (s, 1H), 4.24 (d, J = 2.51 Hz, 2H), 4.06 (s, 2H), 3.88 (s, 3H), 3.74 (s, 2H), 3.45-3.51 (m, 2H), 2.98 (s, 2H), 1.85-1.95 (m, 1H), 0.93-1.01 (m, 2H), 0.62-0.71 (m, 2H) |

TABLE F-continued
| Example No. | Ki (nM) | Structure | Synthetic Procedure Used | HPLC Methods ($t_R$ min) | MS (M + H) | NMR Data |
|---|---|---|---|---|---|---|
| 159 | 2.7 | 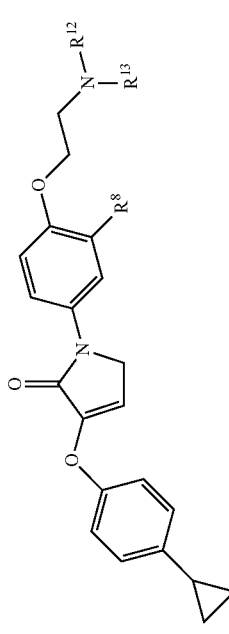 | Method B1 | 1 (6.82) 2 (8.16) | 446.2 | $^1$H NMR(400 MHz, CDCl3) δ 7.67-7.71 (m, 1H), 7.06-7.13 (m, 3H), 6.91-6.96 (m, 1H), 6.82-6.88 (m, 1H), 5.73-5.78 (m, 1H), 4.20-4.27 (m, 2H), 3.99-4.05 (m, 2H), 3.86-3.91 (m, 3H), 3.75-3.82 (m, 2H), 3.47-3.55 (m, 2H), 3.29-3.41 (m, 1H), 2.88-2.96 (m, 2H), 1.86-1.95 (m, 1H), 0.93-1.01 (m, 2H), 0.64-0.71 (m, 2H) |
| 160 | 2.3 | 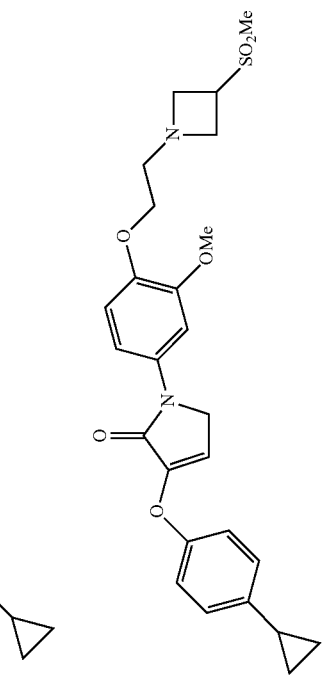 | Method B1 | 1 (6.77) 2 (8.08) | 499.2 | $^1$H NMR (400 MHz, CDCl$_3$) δ 7.68-7.73 (m, 1H), 7.04-7.13 (m, 4H), 6.90-6.96 (m, 1H), 6.84-6.89 (m, 1H), 5.73-5.79 (m, 1H), 4.21-4.27 (m, 2H), 3.68-4.10 (m, 10H), 2.96-3.10 (m, 2H), 2.90-2.94 (m, 3H), 1.86-1.95 (m, 1H), 0.93-1.01 (m, 2H), 0.63-0.72 (m, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 161 | 0.5 | 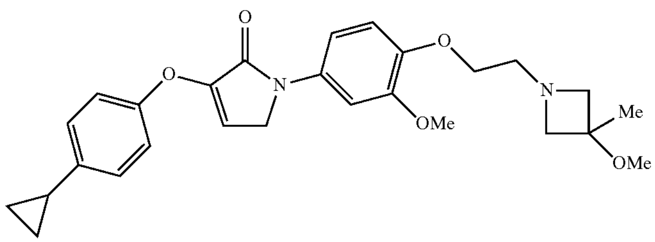 [SMILES: COc1cc(N2CC=C(Oc3ccc(C4CC4)cc3)C2=O)ccc1OCCN1CC(C)(OC)C1] | Method B1 | 1 (7.19) 2 (8.63) | 465.2 | $^1$H NMR (400 MHz, CDCl$_3$) δ 7.68-7.73 (m, 1H), 7.08 (s, 4H), 6.90-6.94 (m, 1H), 6.85-6.89 (m, 1H), 5.73-5.78 (m, 1H), 4.23 (d, J = 2.51 Hz, 2H), 4.01-4.10 (m, 2H), 3.89 (s, 3H), 3.36-3.45 (m, 2H), 3.23-3.30 (m, 2H), 3.21 (s, 3H), 2.94-3.03 (m, 2H), 1.86-1.95 (m, 1H), 1.49 (s, 3H), 0.91-1.01 (m, 2H), 0.62-0.71 (m, 2H) |
| 162 | | 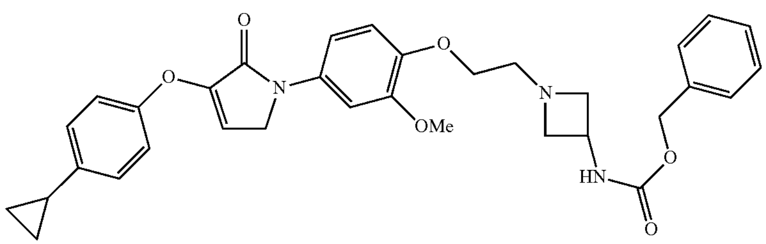 [SMILES: COc1cc(N2CC=C(Oc3ccc(C4CC4)cc3)C2=O)ccc1OCCN1CC(NC(=O)OCc2ccccc2)C1] | Method B1 | 1 (7.87) 2 (9.46) | 570.2 | $^1$H NMR (400 MHz, CDCl$_3$) δ 7.69-7.75 (m, 1H), 7.35 (s, 5H), 7.08 (s, 4H), 6.89-6.93 (m, 1H), 6.83-6.88 (m, 1H), 5.73-5.78 (m, 1H), 5.03-5.18 (m, 3H), 4.38-4.56 (m, 1H), 4.19-4.27 (m, 2H), 3.97-4.12 (m, 2H), 3.87 (s, 5H), 3.17-3.38 (m, 1H), 2.82-3.09 (m, 2H), 1.84-1.96 (m, 1H), 0.92-1.03 (m, 2H), 0.61-0.72 (m, 2H) |
| 163 | 0.4 | 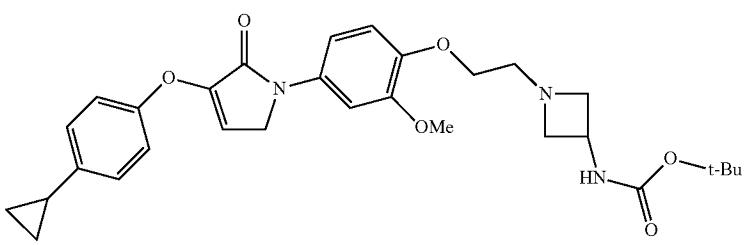 [SMILES: COc1cc(N2CC=C(Oc3ccc(C4CC4)cc3)C2=O)ccc1OCCN1CC(NC(=O)OC(C)(C)C)C1] | Method B1 | 1 (7.89) 2 (8.9) | 536.4 | $^1$H NMR (400 MHz, DMSO-d$_6$) δ 7.46-7.53 (m, 1H), 7.27-7.38 (m, 1h), 7.11 (d, J = 14.56 Hz, 5H), 6.87-7.01 (m, 1H), 6.19 (s, 1H), 4.40 (d, J = 2.51 Hz, 2H), 3.97-4.09 (m, 1H), 3.88 (s, 2H), 3.77 (s, 3H), 3.49-3.57 (m, 2H), 2.83-2.92 (m, 2H), 2.65-2.76 (m, 2H), 1.90-1.99 (m, 1H), 1.37 (s, 9H), 0.89-1.00 (m, 2H), 0.62-0.70 (m, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 164 | 0.5 | 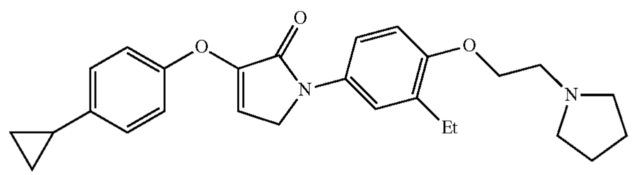 [SMILES: CCc1cc(N2CC=C(Oc3ccc(C4CC4)cc3)C2=O)ccc1OCCN1CCCC1] | Method B2 | 1 (7.81) 2 (9.29) | 433.2 | $^1$H NMR(400 MHz, DMSO-$d_6$) δ 7.47-7.59 (m, 2H), 7.09 (s, 4H), 6.95-7.03 (m, 1H), 6.13-6.21 (m, 1H), 4.31-4.41 (m, 2H), 4.03-4.12 (m, 2H), 2.78-2.86 (m, 2H), 2.52-2.64 (m, 6H), 1.90-1.99 (m, 1H), 1.65-1.74 (m, 4H), 1.15 (s, 3H), 0.92-1.00 (m, 2H), 0.61-0.70 (m, 2H) |
| 165 | 0.7 | 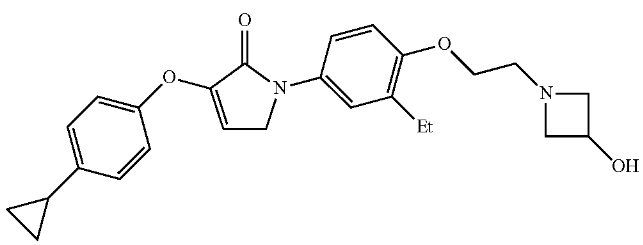 [SMILES: CCc1cc(N2CC=C(Oc3ccc(C4CC4)cc3)C2=O)ccc1OCCN1CC(O)C1] | Method B2 | 1 (7.32) 2 (8.47) | 435.2 | $^1$H NMR (400 MHz, chloroform-d) δ 7.44-7.54 (m, 2H), 7.08 (s, 4H), 6.78-6.85 (m, 1H), 5.72-5.79 (m, 1H), 4.56-4.67 (m, 1H), 4.23 (d, J = 2.51 Hz, 2H), 4.10-4.19 (m, 4H), 3.73-3.85 (m, 2H), 3.23-3.32 (m, 2H), 2.59-2.70 (m, 2H), 1.86-1.95 (m, 2H), 1.17-1.22 (m, 3H), 0.93-1.01 (m, 2H), 0.64-0.71 (m, 2H) |
| 166 | 0.4 | 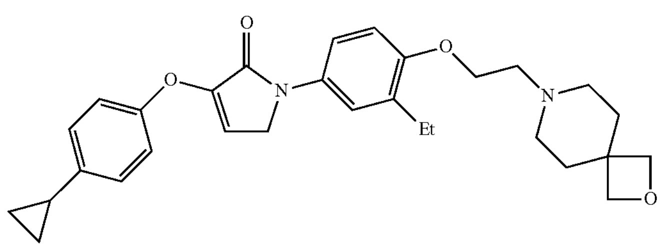 [SMILES: CCc1cc(N2CC=C(Oc3ccc(C4CC4)cc3)C2=O)ccc1OCCN1CCC2(CC1)COC2] | Method B2 | 1 (7.59) 2 (8.79) | 489.3 | $^1$H NMR (400 MHz, DMSO-$d_6$) δ 7.47-7.58 (m, 2H), 6.94-7.17 (m, 5H), 6.12-6.22 (m, 1H), 4.34-4.43 (m, 2H), 4.26-4.30 (m, 4H), 4.02-4.14 (m, 2H), 2.53-2.72 (m, 4H), 2.31-2.49 (m, 4H), 1.89-2.00 (m, 1H), 1.72-1.83 (m, 4H), 1.10-1.19 (m, 3H), 0.91-1.00 (m, 2H), 0.61-0.71 (m, 2H) |

TABLE F-continued
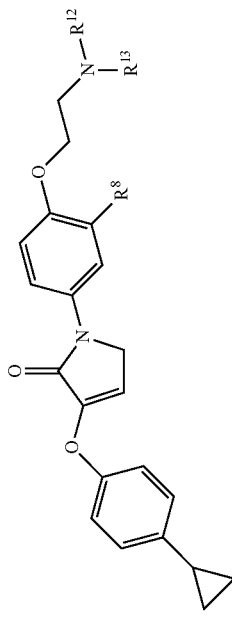
| Example No. | Ki (nM) | Structure | Synthetic Procedure Used | HPLC Methods ($t_R$ min) | MS (M + H) | NMR Data |
|---|---|---|---|---|---|---|
| 167 | 0.4 | 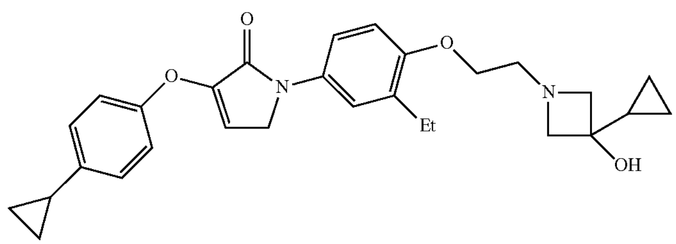 [SMILES: CCc1cc(N2CC=C(Oc3ccc(C4CC4)cc3)C2=O)ccc1OCCN1CC(O)(C2CC2)C1] | Method B2 | 1 (7.9) 2 (9.37) | 475.5 | $^1$H NMR (400 MHz, DMSO-d$_6$) δ 7.54 (s, 2H), 7.04-7.19 (m, 4H), 6.88-7.00 (m, 1H), 6.16 (s, 1H), 4.99-5.19 (m, 1H), 4.38 (d, J = 2.51 Hz, 2H), 3.88-4.03 (m, 2H), 3.24-3.31 (m, 2H), 2.74-3.09 (m, 4H), 2.58 (s, 2H), 1.93-1.97 (m, 1H), 1.16 (t, J = 7.53 Hz, 4H), 0.91-1.00 (m, 2H), 0.66 (s, 2H), 0.34 (d, J = 6.78 Hz, 4H) |
| 168 | 0.9 | 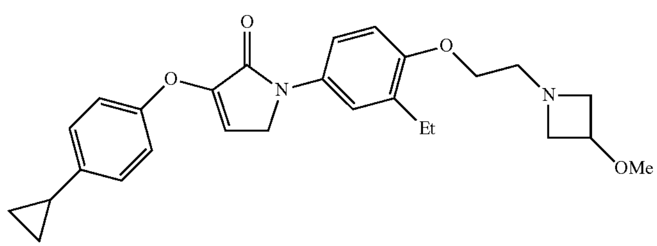 [SMILES: CCc1cc(N2CC=C(Oc3ccc(C4CC4)cc3)C2=O)ccc1OCCN1CC(OC)C1] | Method B2 | 1 (12.88) 2 (13.98) | 449.2 | $^1$H NMR (400 MHz, DMSO-d$_6$) δ 7.48-7.58 (m, 2H), 7.10 (d, J = 14.81 Hz, 4H), 6.90-6.98 (m, 1H), 6.11-6.21 (m, 1H), 4.31-4.44 (m, 2H), 3.90-4.03 (m, 3H), 3.56-3.67 (m, 2H), 3.15 (s, 3H), 2.92-3.02 (m, 2H), 2.77-2.86 (m, 2H), 2.55-2.64 (m, 2H), 1.90-1.99 (m, 1H), 1.15 (s, 3H), 0.91-0.99 (m, 2H), 0.63-0.70 (m, 2H) |
| 169 | 0.5 | 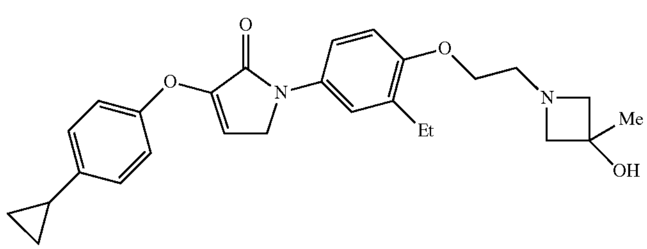 | Method B2 | 1 (11.64) 2 (13.92) | 449.2 | $^1$H NMR (400 MHz, DMSO-d$_6$) δ 7.57-7.59 (m, 2H), 7.11 (d, J = 14.56 Hz, 4H), 6.90-7.00 (m, 1H), 6.13-6.21 (m, 1H), 5.10-5.28 (m, 1H), 4.32-4.44 (m, 2H), 3.90-4.05 (m, 2H), 2.97-3.12 (m, 2H), 2.76-2.90 (m, 2H), 2.53-2.64 (m, 4H), 1.91-1.99 (m, 1H), 1.16 (s, 3H), 0.92-0.99 (m, 2H), 0.62-0.72 (m, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 170 | 5.9 | (structure with 3-hydroxy-3-trifluoromethyl azetidine, Et substituent) | Method B2 | 1 (12.7) 2 (9.42) | 503.2 | $^1$H NMR (400 MHz, chloroform-d) δ 7.43-7.53 (m, 2H), 7.08 (s, 4H), 6.78-6.86 (m, 1H), 5.71-5.78 (m, 1H), 4.23 (d, J = 2.51 Hz, 2H), 3.98-4.08 (m, 2H), 3.74-3.82 (m, 2H), 3.41-3.51 (m, 2H), 2.94-3.02 (m, 2H), 2.57-2.68 (m, 2H), 1.85-1.95 (m, 1H), 1.17-1.24 (m, 3H), 0.93-1.01 (m, 2H), 0.65-0.72 (m, 2H) |
| 171 | 0.6 | (structure with Boc-amino azetidine, Et substituent) | Method B2 | 1 (13.55) 2 (15.51) | 534.4 | $^1$H NMR (400 MHz, DMSO-d$_6$) δ 7.47-7.57 (m, 2H), 7.27-7.37 (m, 1H), 7.05-7.16 (m, 4H), 6.89-6.98 (m, 1H), 6.11-6.21 (m, 1H), 4.34-4.42 (m, 2H), 4.00-4.10 (m, 1H), 3.89-3.97 (m, 2H), 3.52-3.63 (m, 2H), 2.87-2.96 (m, 2H), 2.71-2.78 (m, 2H), 2.54-2.62 (m, 2H), 1.87-1.99 (m, 1H), 1.37 (s, 9H), 1.15 (s, 3H), 0.91-1.00 (m, 2H), 0.62-0.71 (m, 2H) |

TABLE F-continued

| Example No. | Ki (nM) | Structure | Synthetic Procedure Used | HPLC Methods ($t_R$ min) | MS (M + H) | $^1$H NMR Data |
|---|---|---|---|---|---|---|
| 172 | 1.4 | 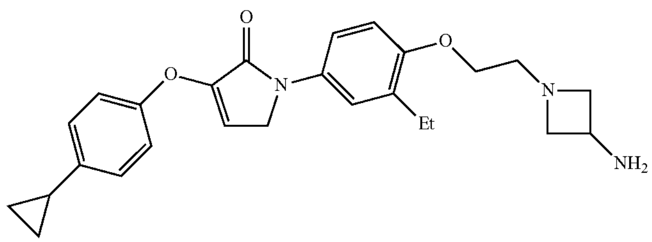 [SMILES: CCc1cc(N2CC=C(Oc3ccc(C4CC4)cc3)C2=O)ccc1OCCN1CC(N)C1] | Method B2 | 1 (6.01)<br>2 (7.09) | 434.3 | $^1$H NMR (400 MHz, DMSO-$d_6$) δ 8.53-8.84 (m, 2H), 7.60 (s, 1H), 7.52-7.57 (m, 1H), 7.11-7.16 (m, 2H), 7.05-7.10 (m, 2H), 6.98-7.03 (m, 1H), 6.18 (s, 1H), 4.39 (d, J = 2.51 Hz, 6H), 4.22-4.30 (m, 2H), 4.11-4.21 (m, 1H), 3.70-3.85 (m, 2H), 2.63 (d, J = 7.53 Hz, 2H), 1.89-2.00 (m, 1H), 1.17 (t, J = 7.53 Hz, 3H), 0.95 (dd, J = 2.01, 8.53 Hz, 2H), 0.62-0.70 (m, 2H) |
| 173 | 0.9 | 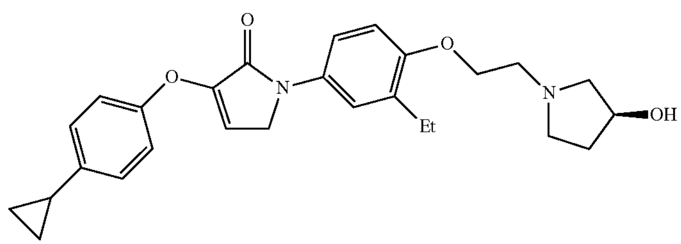 [SMILES: CCc1cc(N2CC=C(Oc3ccc(C4CC4)cc3)C2=O)ccc1OCCN1CC[C@H](O)C1] | Method B2 | 1 (7.74)<br>2 (8.08) | 449.4 | $^1$H NMR (400 MHz, DMSO-$d_6$) δ 7.46-7.59 (m, 2H), 7.12 (s, 2H), 7.09 (s, 2H), 6.93-7.02 (m, 1H), 6.16 (s, 1H), 4.38 (d, J = 2.26 Hz, 2H), 4.16-4.25 (m, 1H), 4.06 (s, 2H), 2.75-2.85 (m, 3H), 2.64-2.72 (m, 1H), 2.53-2.63 (m, 3H), 2.39-2.46 (m, 1H), 1.89-2.03 (m, 2H), 1.47-1.59 (m, 1H), 1.15 (t, J = 7.53 Hz, 3H), 0.89-1.00 (m, 2H), 0.61-0.71 (m, 2H) |
| 174 | 1.3 | 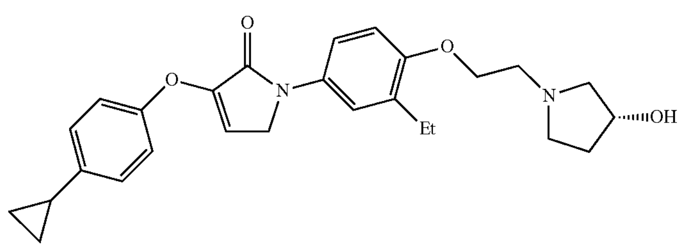 [SMILES: CCc1cc(N2CC=C(Oc3ccc(C4CC4)cc3)C2=O)ccc1OCCN1CC[C@@H](O)C1] | Method B2 | 1 (7.74)<br>2 (8.08) | 449.3 | $^1$H NMR (400 MHz, DMSO-$d_6$) δ 7.46-7.58 (m, 2H), 7.12 (s, 2H), 7.09 (s, 2H), 6.94-7.01 (m, 1H), 6.14-6.21 (m, 1H), 4.38 (d, J = 2.51 Hz, 2H), 4.15-4.24 (m, 1H), 4.00-4.10 (m, 2H), 2.76-2.85 (m, 3H), 2.65-2.73 (m, 1H), 2.54-2.65 (m, 3H), 2.37-2.46 (m, 1H), 1.90-2.04 (m, 2H), 1.48-1.59 (m, 1H), 1.10-1.21 (m, 3H), 0.88-0.99 (m, 2H), 0.61-0.72 (m, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 175 | 2.2 | 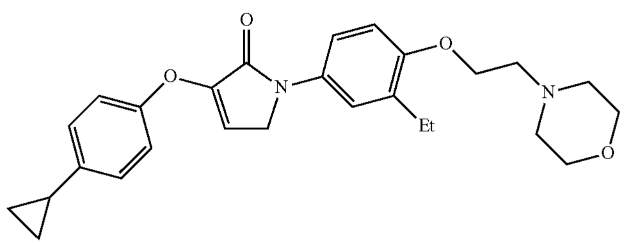 [SMILES: CCc1cc(N2CC=C(Oc3ccc(C4CC4)cc3)C2=O)ccc1OCCN1CCOCC1] | Method B2 | 1 (7.60) 2 (8.67) | 449.4 | $^1$H NMR (400 MHz, DMSO-d$_6$) δ 7.46-7.57 (m, 2H), 7.10-7.17 (m, 2H), 7.04-7.10 (m, 2H), 6.94-7.03 (m, 1H), 6.12-6.21 (m, 1H), 4.34-4.42 (m, 2H), 4.05-4.14 (m, 2H), 3.54-3.62 (m, 3H), 2.68-2.77 (m, 2H), 2.52 (br. s., 6H), 1.90-1.99 (m, 1H), 1.15 (s, 3H), 0.89-0.99 (m, 2H), 0.61-0.70 (m, 2H) |
| 176 | 0.7 | 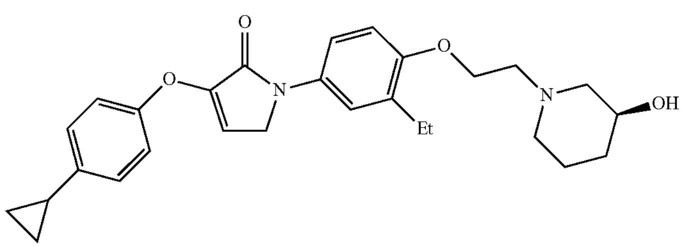 [SMILES: CCc1cc(N2CC=C(Oc3ccc(C4CC4)cc3)C2=O)ccc1OCCN1CCC[C@H](O)C1] | Method B2 | 1 (7.53) 2 (8.59) | 463.4 | $^1$H NMR (400 MHz, DMSO-d$_6$) δ 7.46-7.57 (m, 2H), 7.12 (s, 2H), 7.09 (s, 2H), 6.96-7.03 (m, 1H), 6.13-6.22 (m, 1H), 4.52-4.61 (m, 1H), 4.38 (d, J = 2.26 Hz, 2H), 4.01-4.12 (m, 2H), 3.38-3.51 (m, 1H), 2.88-2.98 (m, 1H), 2.68-2.80 (m, 3H), 2.55-2.63 (m, 2H), 1.74-2.04 (m, 4H), 1.57-1.66 (m, 1H), 1.35-1.47 (m, 1H), 1.11-1.19 (m, 3H), 0.89-0.99 (m, 2H), 0.62-0.69 (m, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 177 | 0.9 | (structure: 3-(4-cyclopropylphenoxy)-1-[4-(2-piperidin-1-ylethoxy)-3-ethylphenyl]-1,5-dihydro-2H-pyrrol-2-one) | Method B2 | 1 (8.01) 2 (9.10) | 447.4 | $^1$H NMR (400 MHz, DMSO-$d_6$) δ 7.50-7.62 (m, 2H), 7.13 (s, 2H), 7.09 (s, 2H), 6.95-7.04 (m, 1H), 6.13-6.22 (m, 1H), 4.38 (s, 2H), 4.09-4.28 (m, 2H), 2.51-2.64 (m, 8H), 1.92-2.00 (m, 1H), 1.35-1.71 (m, 6H), 1.15 (s, 3H), 0.90-0.99 (m, 2H), 0.62-0.70 (m, 2H) |
| 178 |  | (structure: with 4-methylpiperazinyl ethoxy) | Method B2 | 1 (6.82) 2 (7.88) | 462.2 | $^1$H NMR (400 MHz, DMSO-$d_6$) δ 7.56 (s, 2H), 7.12-7.19 (m, 2H), 7.05-7.12 (m, 2H), 7.01 (d, J = 8.78 Hz, 1H), 6.18 (s, 1H), 4.38 (d, J = 2.26 Hz, 2H), 4.17 (s, 2H), 2.96-3.55 (m, 8H), 2.80 (s, 3H), 2.60 (d, J = 7.53 Hz, 2H), 2.52-2.55 (m, 2H), 1.90-1.99 (m, 1H), 1.16 (t, J = 7.40 Hz, 3H), 0.95 (dd, J = 2.13, 8.41 Hz, 2H), 0.62-0.72 (m, 2H) |
| 179 |  | (structure: with 4-chlorobenzylamino ethoxy) | Method B2 | 1 (14.35) 2 (16.56) | 503.2 | $^1$H NMR (400 MHz, DMSO-$d_6$) δ 9.01-9.17 (m, 1H), 7.52-7.64 (m, 5H), 6.99-7.19 (m, 5H), 6.19 (s, 1H), 4.39 (d, J = 2.26 Hz, 2H), 4.19-4.34 (m, 4H), 3.37-3.46 (m, 2H), 2.60-2.73 (m, 2H), 1.90-2.00 (m, 1H), 1.16 (t, J = 7.53 Hz, 3H), 0.90-1.00 (m, 2H), 0.62-0.71 (m, 2H) |

TABLE F-continued
| Example No. | Ki (nM) | Structure | Synthetic Procedure Used | HPLC Methods ($t_R$ min) | MS (M + H) | NMR Data |
|---|---|---|---|---|---|---|
| 180 | | 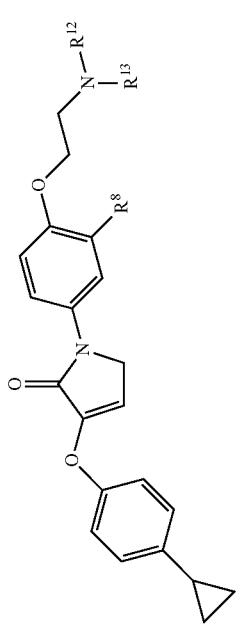 | Method B2 | 1 (8.21) 2 (9.53) | 483.2 | $^1$H NMR (400 MHz, DMSO-d$_6$) δ 7.48-7.58 (m, 2H), 7.11 (d, J = 15.06 Hz, 5H), 6.10-6.21 (m, 1H), 4.34-4.44 (m, 2H), 4.05-4.17 (m, 2H), 2.78-2.87 (m, 2H), 2.54-2.71 (m, 6H), 1.87-2.03 (m, 5H), 1.15 (s, 3H), 0.89-1.00 (m, 2H), 0.61-0.70 (m, 2H) |
| 181 | | 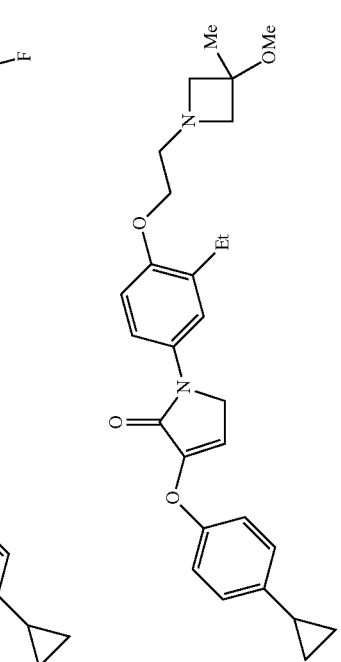 | Method B2 | 1 (7.99) 2 (9.26) | 463.2 | $^1$H NMR (400 MHz, DMSO-d$_6$) δ 7.47-7.58 (m, 2H), 7.12-7.18 (m, 2H), 7.04-7.12 (m, 2H), 6.90-7.00 (m, 1H), 6.13-6.21 (m, 1H), 4.33-4.44 (m, 2H), 3.93-4.02 (m, 2H), 3.20-3.29 (m, 2H), 3.11 (s, 4H), 2.78-2.89 (m, 1H), 2.54-2.65 (m, 2H), 2.43-2.50 (m, 2H), 1.88-1.99 (m, 1H), 1.38 (s, 3H), 1.16 (s, 3H), 0.89-1.00 (m, 2H), 0.59-0.71 (m, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 182 | | 3-(4-cyclopropylphenoxy)-1-{4-[2-(3,3-difluoroazetidin-1-yl)ethoxy]-3-ethylphenyl}-1,5-dihydro-2H-pyrrol-2-one | Method B2 | 1 (7.96) 2 (7.75) | 455.2 | $^1$H NMR (400 MHz, DMSO-$d_6$) δ 7.46-7.60 (m, 2H), 7.11 (d, J = 14.81 Hz, 4H), 6.93-7.01 (m, 1H), 6.13-6.21 (m, 1H), 4.34-4.42 (m, 2H), 3.96-4.05 (m, 2H), 3.64-3.78 (m, 4H), 2.90-3.01 (m, 2H), 2.53-2.64 (m, 2H), 1.89-2.00 (m, 1H), 1.15 (s, 3H), 0.89-1.00 (m, 2H), 0.62-0.71 (m, 2H) |
| 183 | | 1-{4-[2-(azetidin-1-yl)ethoxy]-3-ethylphenyl}-3-(4-cyclopropylphenoxy)-1,5-dihydro-2H-pyrrol-2-one | Method B2 | 1 (7.36) 2 (7.54) | 419.2 | $^1$H NMR (400 MHz, DMSO-$d_6$) δ 7.47-7.59 (m, 2H), 7.10 (d, J = 15.56 Hz, 4H), 6.90-7.00 (m, 1H), 6.12-6.22 (m, 1H), 4.30-4.45 (m, 2H), 3.91-4.05 (m, 2H), 3.43-3.63 (m, 4H), 2.94-3.11 (m, 2H), 2.56-2.65 (m, 2H), 2.06-2.20 (m, 2H), 1.89-1.99 (m, 1H), 1.16 (s, 3H), 0.92-1.00 (m, 2H), 0.61-0.71 (m, 2H) |
| 184 | 0.4 | 3-(4-cyclopropylphenoxy)-1-{3-(difluoromethoxy)-4-[2-(pyrrolidin-1-yl)ethoxy]phenyl}-1,5-dihydro-2H-pyrrol-2-one | Method B3 | 1 (7.28) 2 (8.71) | 471.2 | $^1$H NMR (400 MHz, DMSO-$d_6$) δ 7.71-7.81 (m, 1H), 7.50-7.61 (m, 1H), 6.94-7.38 (m, 6H), 6.23 (s, 1H), 4.41 (d, J = 2.26 Hz, 2H), 4.11-4.24 (m, 2H), 2.55-3.10 (m, 6H), 1.88-2.01 (m, 1H), 1.65-1.84 (m, 4H), 0.95 (dd, J = 2.13, 8.41 Hz, 2H), 0.66 (dd, J = 2.13, 5.14 Hz, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 185 | 0.6 | (structure with OCHF$_2$, azetidine-OH) | Method B3 | 1 (6.98) 2 (8.78) | 471.2 | $^1$H NMR (400 MHz, DMSO-d$_6$) δ 7.72-7.79 (m, 1H), 7.49-7.56 (m, 1H), 6.90-7.32 (m, 6H), 6.15-6.26 (m, 1H), 5.21-5.40 (m, 1H), 4.35-4.46 (m, 2H), 4.10-4.25 (m, 1H), 3.97-4.08 (m, 2H), 3.56-3.69 (m, 2H), 2.70-3.00 (m, 4H), 1.88-2.00 (m, 2H), 0.91-0.99 (m, 2H), 0.62-0.71 (m, 2H) |
| 186 | 5.2 | (structure with OCHF$_2$, azetidine-SO$_2$Me) | Method B3 | 1 (7.43) 2 (8.77) | 535.2 | $^1$H NMR (400 MHz, DMSO-d$_6$) δ 7.75 (d, J = 2.51 Hz, 1H), 7.50-7.60 (m, 1H), 6.87-7.30 (m, 6H), 6.22 (s, 1H), 4.41 (d, J = 2.26 Hz, 2H), 4.11-4.22 (m, 1H), 4.03 (s, 2H), 3.56-3.67 (m, 2H), 3.43-3.53 (m, 2H), 2.94 (s, 3H), 2.82 (s, 2H), 1.88-1.99 (m, 1H), 0.95 (dd, J = 2.13, 8.41 Hz, 2H), 0.66 (dd, J = 2.01, 5.02 Hz, 2H) |

TABLE F-continued

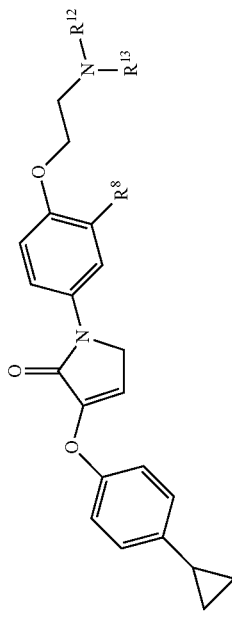

| Example No. | Ki (nM) | Structure | Synthetic Procedure Used | HPLC Methods ($t_R$ min) | MS (M + H) | NMR Data |
|---|---|---|---|---|---|---|
| 187 | 5.4 | (structure with CF₃, OH azetidine; OCHF₂; cyclopropyl phenyl) | Method B3 | 1 (7.82) 2 (9.14) | 541.2 | ¹H NMR (400 MHz, DMSO-d₆) δ 7.71-7.80 (m, 1H), 7.48-7.59 (m, 1H), 7.11 (d, J = 15.06 Hz, 6H), 6.86 (s, 1H), 6.13-6.27 (m, 1H), 4.35-4.49 (m, 2H), 4.00-4.10 (m, 2H), 3.58-3.69 (m, 2H), 3.20-3.29 (m, 2H), 2.79-2.92 (m, 2H), 1.88-2.01 (m, 1H), 0.90-1.01 (m, 2H), 0.61-0.72 (m, 2H) |
| 188 | 2.7 | (structure with CN azetidine; OCHF₂; cyclopropyl phenyl) | Method B3 | 1 (7.50) 2 (8.82) | 482.2 | ¹H NMR (400 MHz, DMSO-d₆) δ 7.73-7.79 (m, 1H), 7.49-7.60 (m, 1H), 6.88-7.34 (m, 6H), 6.17-6.27 (m, 1H), 4.36-4.45 (m, 2H), 3.97-4.09 (m, 2H), 3.43-3.57 (m, 3H), 3.34-3.40 (m, 2H), 2.73-2.83 (m, 2H), 1.87-2.00 (m, 1H), 0.90-1.00 (m, 2H), 0.60-0.71 (m, 2H) |
| 189 | 0.6 | (structure with OMe azetidine; OCHF₂; cyclopropyl phenyl) | Method B3 | 1 (7.85) 2 (9.02) | 487.2 | ¹H NMR (400 MHz, DMSO-d₆) δ 7.70-7.79 (m, 1H), 7.47-7.58 (m, 1H), 7.10 (d, J = 14.81 Hz, 6H), 6.13-6.28 (m, 1H), 4.36-4.47 (m, 2H), 3.99-4.07 (m, 2H), 3.89-3.98 (m, 1H), 3.50-3.61 (m, 2H), 3.15 (s, 3H), 2.87-2.97 (m, 2H), 2.74-2.82 (m, 2H), 1.90-1.99 (m, 1H), 0.89-1.01 (m, 2H), 0.60-0.71 (m, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 190 | 0.6 | (3-methyl-3-hydroxyazetidinyl-ethoxy, OCHF₂-phenyl, pyrrolinone, 4-cyclopropylphenoxy) | Method B3 | 1 (7.47) 2 (8.36) | 487.2 | ¹H NMR (400 MHz, DMSO-d₆) δ 7.70-7.78 (m, 1H), 7.48-7.58 (m, 1H), 6.95-7.39 (m, 6H), 6.16-6.26 (m, 1H), 5.06-5.16 (m, 1H), 4.38-4.46 (m, 2H), 3.97-4.07 (m, 2H), 3.20-3.27 (m, 2H), 2.90-2.98 (m, 2H), 2.73-2.81 (m, 2H), 1.90-2.00 (m, 1H), 1.33 (s, 3H), 0.91-1.00 (m, 2H), 0.59-0.71 (m, 2H) |
| 191 | | (pyrrolidinyl-ethoxy, Br-phenyl, pyrrolinone, 4-cyclopropylphenoxy) | Method B4 | 1 (7.5) 2 (9.0) | 485.2 | ¹H NMR (400 MHz, CDCl₃) δ 7.80-7.88 (m, 1H), 7.69-7.78 (m, 1H), 7.03-7.14 (m, 4H), 6.89-6.97 (m, 1H), 5.70-5.81 (m, 1H), 4.13-4.24 (m, 4H), 2.96-3.05 (m, 2H), 2.67-2.79 (m, 4H), 1.86-1.95 (m, 1H), 1.78-1.85 (m, 4H), 0.91-1.02 (m, 2H), 0.63-0.73 (m, 2H) |

TABLE F-continued

| Example No. | Ki (nM) | Structure | Synthetic Procedure Used | HPLC Methods ($t_R$ min) | MS (M + H) | ¹H NMR Data |
|---|---|---|---|---|---|---|
| 192 | 0.9 | (3-hydroxyazetidine derivative, Br, cyclopropyl) | Method B4 | 1 (7.05)  2 (8.34) | 485.0 | ¹H NMR (400 MHz, CDCl₃) δ 7.81-7.88 (m, 1H), 7.74-7.81 (m, 1H), 7.08 (d, J = 1.76 Hz, 1H), 6.84-6.93 (m, 4H), 5.69-5.80 (m, 1H), 4.44-4.55 (m, 1H), 4.22 (d, J = 2.26 Hz, 2H), 4.11-4.19 (m, 2H), 3.94-4.02 (m, 2H), 3.63-3.71 (m, 3H), 3.09-3.17 (m, 2H), 1.84-1.97 (m, 1H), 0.93-1.03 (m, 2H), 0.62-0.73 (m, 2H) |
| 193 | 0.6 | (3-methyl-3-hydroxyazetidine derivative, Br, cyclopropyl) | Method B4 | 1 (8.2)  2 (8.5) | 499.0 | ¹H NMR (400 MHz, CDCl₃) δ 7.81-7.90 (m, 1H), 7.71-7.79 (m, 1H), 7.08 (d, J = 1.76 Hz, 1H), 6.84-6.93 (m, 4H), 5.69-5.80 (m, 1H), 4.22 (d, J = 2.26 Hz, 2H), 4.11-4.19 (m, 2H), 3.63-3.78 (m, 4H), 3.09-3.19 (m, 2H), 1.84-1.94 (m, 1H), 1.51 (s, 3H), 0.93-1.02 (m, 2H), 0.63-0.72 (m, 2H) |
| 194 | | (3-hydroxypyrrolidine derivative, Br, cyclopropyl) | Method B4 | 1 (7.2)  2 (8.4) | 499.0 | ¹H NMR (400 MHz, CDCl₃) δ 7.83-7.89 (m, 1H), 7.71-7.80 (m, 1H), 7.04-7.14 (m, 4H), 6.87-6.97 (m, 1H), 5.70-5.79 (m, 1H), 4.39-4.48 (m, 1H), 4.22 (s, 4H), 3.31-3.41 (m, 1H), 3.12-3.23 (m, 2H), 2.95-3.07 (m, 1H), 2.77-2.88 (m, 2H), 2.61-2.72 (m, 1H), 2.22-2.35 (m, 1H), 1.84-1.96 (m, 1H), 0.93-1.02 (m, 4H), 0.63-0.71 (m, 2H) |

TABLE F-continued

| Example No. Ki (nM) | Structure | Synthetic Procedure Used | HPLC Methods ($t_R$ min) | MS (M + H) | NMR Data |
|---|---|---|---|---|---|
| 195 | (structure with 3-hydroxypiperidine, Br, cyclopropylphenoxy pyrrolinone) | Method B4 | 1 (7.3) 2 (8.8) | 513.2 | $^1$H NMR (400 MHz, CDCl$_3$) δ 7.74-7.85 (m, 2H), 7.08 (d, J = 1.76 Hz, 4H), 6.89-6.97 (m, 1H), 5.70-5.80 (m, 1H), 4.19-4.27 (m, 2H), 4.10-4.17 (m, 2H), 3.78-3.88 (m, 1H), 3.49 (s, 1H), 2.85-2.92 (m, 2H), 2.61-2.72 (m, 3H), 2.38-2.50 (m, 1H), 1.76-1.95 (m, 2H), 1.47-1.64 (m, 3H), 0.92-1.02 (m, 2H), 0.64-0.73 (m, 2H) |
| 196 | (structure with piperidine, Br, cyclopropylphenoxy pyrrolinone) | Method B4 | 1 (7.6) 2 (9.2) | 497.2 | $^1$H NMR (400 MHz, CDCl$_3$) δ 8.06 (s, 1H), 7.58 (d, J = 7.03 Hz, 1H), 7.01-7.13 (m, 4H), 6.93 (d, J = 8.53 Hz, 1H), 5.77 (s, 1H), 4.51 (br. s., 2H), 4.22 (d, J = 1.76 Hz, 2H), 3.75 (d, J = 11.04 Hz, 2H), 3.51 (br. s., 2H), 2.93 (t, J = 11.17 Hz, 2H), 2.12 (d, J = 12.05 Hz, 2H), 1.80-1.99 (m, 4H), 1.37-1.54 (m, 1H), 0.90-1.03 (m, 2H), 0.60-0.74 (m, 2H) |
| 197 | (structure with morpholine, Br, cyclopropylphenoxy pyrrolinone) | Method B4 | 1 (7.3) 2 (8.7) | 499.0 | $^1$H NMR (400 MHz, CDCl$_3$) δ 7.80 (s, 2H), 7.08 (d, J = 1.76 Hz, 4H), 6.88-6.97 (m, 1H), 5.75 (s, 1H), 4.13-4.25 (m, 4H), 3.67-3.79 (m, 4H), 2.86 (s, 2H), 2.64 (br. s., 4H), 1.82-1.96 (m, 1H), 0.90-1.02 (m, 2H), 0.63-0.71 (m, 2H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 198 | | 2-bromo-4-[3-(4-cyclopropylphenoxy)-2-oxo-2,5-dihydro-1H-pyrrol-1-yl]phenyl ether with (S)-prolinol-ethyl linker | Method B4 | 1 (7.4) 2 (8.8) | 513.0 | $^1$H NMR (400 MHz, CDCl$_3$) δ 7.72-7.87 (m, 3H), 7.08 (d, J = 1.76 Hz, 4H), 6.85-6.98 (m, 1H), 5.65-5.83 (m, 1H), 4.18-4.27 (m, 2H), 4.03-4.16 (m, 2H), 3.63-3.73 (m, 1H), 3.37-3.47 (m, 1H), 3.18-3.35 (m, 2H), 2.74-2.89 (m, 2H), 2.42-2.55 (m, 1H), 1.85-1.96 (m, 2H), 1.73-1.84 (m, 3H), 0.93-1.04 (m, 2H), 0.63-0.71 (m, 2H) |
| 199 | | 2-bromo-4-[3-(4-cyclopropylphenoxy)-2-oxo-2,5-dihydro-1H-pyrrol-1-yl]phenyl ether with 4,4-difluoropiperidine-ethyl linker | Method B4 | 1 (8.03) 2 (9.7) | 533.2 | $^1$H NMR (400 MHz, CDCl$_3$) δ 8.01 (d, J = 2.75 Hz, 1H), 7.63-7.72 (m, 1H), 7.08 (d, J = 3.50 Hz, 4H), 6.91 (d, J = 9.01 Hz, 1H), 5.77 (s, 1H), 4.40-4.50 (m, 2H), 4.22 (d, J = 2.50 Hz, 2H), 3.56 (d, J = 4.25 Hz, 6H), 2.33-2.53 (m, 4H), 1.82-1.96 (m, 1H), 0.97 (dd, J = 1.75, 8.50 Hz, 2H), 0.62-0.73 (m, 2H) |

TABLE F-continued

| Example No. | Ki (nM) | Structure | Synthetic Procedure Used | HPLC Methods ($t_R$ min) | MS (M + H) | $^1$H NMR Data |
|---|---|---|---|---|---|---|
| 200 | | azetidine-ethoxy-Br-phenyl-pyrrolinone-cyclopropylphenoxy | Method B4 | 1 (7.4) 2 (8.9) | 469.2 | $^1$H NMR (400 MHz, CDCl$_3$) δ 8.02-8.10 (m, 1H), 7.57-7.66 (m, 1H), 7.04-7.14 (m, 4H), 6.85-6.94 (m, 1H), 5.72-5.82 (m, 1H), 4.41-4.55 (m, 2H), 4.27-4.38 (m, 2H), 4.09-4.25 (m, 4H), 3.53-3.61 (m, 2H), 2.75-2.90 (m, 1H), 2.33-2.47 (m, 1H), 1.85-1.97 (m, 1H), 0.94-1.03 (m, 2H), 0.62-0.72 (m, 2H) |
| 201 | | 3-cyanoazetidine-ethoxy-Br-phenyl-pyrrolinone-cyclopropylphenoxy | Method B4 | 1 (7.47) 2 (8.9) | 496.0 | $^1$H NMR (400 MHz, CDCl$_3$) δ 7.87-7.99 (m, 1H), 7.69-7.81 (m, 1H), 7.04-7.13 (m, 4H), 6.81-6.94 (m, 1H), 5.71-5.81 (m, 1H), 4.40-4.53 (m, 2H), 4.19-4.31 (m, 4H), 4.09-4.18 (m, 2H), 3.80-3.98 (m, 1H), 3.36-3.47 (m, 2H), 1.95-2.00 (m, 1H), 0.93-1.02 (m, 2H), 0.62-0.71 (m, 2H) |
| 202 | | (2-hydroxymethyl)pyrrolidine-ethoxy-Br-phenyl-pyrrolinone-cyclopropylphenoxy | Method B4 | 1 (7.5) 2 (8.9) | 513.2 | $^1$H NMR (400 MHz, CDCl$_3$) δ 7.80 (s, 2H), 7.08 (d, J = 1.76 Hz, 4H), 6.85-6.94 (m, 1H), 5.75 (s, 1H), 4.21 (d, J = 2.26 Hz, 2H), 4.07-4.17 (m, 2H), 3.63-3.73 (m, 1H), 3.39-3.47 (m, 1H), 3.18-3.37 (m, 2H), 2.73-2.89 (m, 2H), 2.44-2.54 (m, 1H), 1.85-1.97 (m, 2H), 1.73-1.83 (m, 3H), 0.91-1.01 (m, 2H), 0.62-0.73 (m, 2H) |

TABLE F-continued

| Example No. Ki (nM) | Structure | Synthetic Procedure Used | HPLC Methods ($t_R$ min) | MS (M + H) | NMR Data |
|---|---|---|---|---|---|
| 203 | [structure with F-pyrrolidine, Br, cyclopropyl] | Method B4 | 1 (7.5) 2 (8.98) | 501.2 | $^1$H NMR (400 MHz, CDCl$_3$) δ 7.99-8.09 (m, 1H), 7.60-7.72 (m, 1H), 7.08 (d, J = 3.01 Hz, 4H), 6.86-6.96 (m, 1H), 5.72-5.82 (m, 1H), 5.29-5.52 (m, 1H), 4.37-4.51 (m, 2H), 4.23 (d, J = 2.26 Hz, 3H), 3.95-4.11 (m, 1H), 3.55-3.74 (m, 3H), 3.36-3.53 (m, 1H), 2.25-2.51 (m, 2H), 1.86-1.95 (m, 1H), 0.91-1.03 (m, 2H), 0.63-0.73 (m, 2H) |
| 204 | [structure with OH-pyrrolidine, Br, cyclopropyl] | Method B4 | 1 (7.1) 2 (8.4) | 499.0 | $^1$H NMR (400 MHz, CDCl$_3$) δ 7.80-7.91 (m, 1H), 7.72-7.79 (m, 1H), 7.08 (d, J = 2.00 Hz, 4H), 6.87-6.97 (m, 1H), 5.69-5.79 (m, 1H), 4.38-4.47 (m, 1H), 4.22 (d, J = 2.50 Hz, 4H), 3.23-3.34 (m, 1H), 3.05-3.16 (m, 3H), 2.80-2.92 (m, 1H), 2.61-2.73 (m, 1H), 2.22-2.33 (m, 2H), 1.83-1.94 (m, 1H), 0.92-1.00 (m, 2H), 0.62-0.73 (m, 2H) |

TABLE F-continued
| Example No. | Ki (nM) | Structure | Synthetic Procedure Used | HPLC Methods ($t_R$ min) | MS (M + H) | NMR Data |
|---|---|---|---|---|---|---|
| 205 | 0.6 | 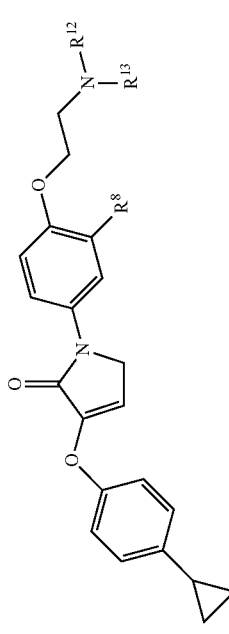 | Method B5 | 1 (7.67) 2 (9.4) | 445.2 | $^1$H NMR (400 MHz, DMSO-d$_6$) δ 7.42-7.50 (m, 1H), 7.03-7.21 (m, 5H), 6.93-7.01 (m, 1H), 6.11-6.19 (m, 1H), 4.33-4.39 (m, 2H), 4.06-4.13 (m, 2H), 2.80-2.89 (m, 2H), 2.54-2.61 (m, 4H), 2.10-2.21 (m, 1H), 1.89-1.99 (m, 1H), 1.65-1.75 (m, 4H), 0.86-0.98 (m, 4H), 0.60-0.71 (m, 4H) |
| 206 | 5.5 | 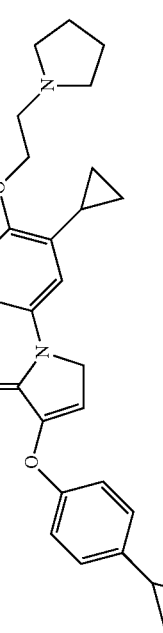 | Method B5 | 1 (7.51) 2 (9.08) | 461.4 | $^1$H NMR (400 MHz, DMSO-d$_6$) δ 7.43-7.51 (m, 1H), 7.19 (d, J = 2.76 Hz, 1H), 7.11-7.15 (m, 2H), 7.05-7.09 (m, 2H), 7.00 (s, 1H), 6.15 (s, 1H), 4.36 (d, J = 2.26 Hz, 2H), 4.12 (s, 2H), 3.54-3.63 (m, 4H), 2.74 (s, 2H), 2.52-2.57 (m, 4H), 2.10-2.19 (m, 1H), 1.88-2.00 (m, 1H), 0.87-0.98 (m, 4H), 0.61-0.71 (m, 4H) |
| 207 | 0.9 | 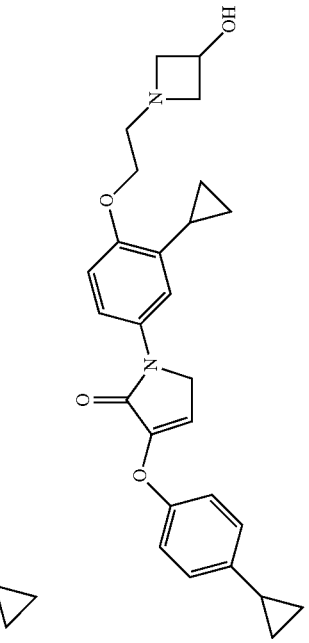 | Method B5 | 1 (7.28) 2 (8.74) | 447.3 | $^1$H NMR (400 MHz, DMSO-d$_6$) δ 7.42-7.48 (m, 1H), 7.16-7.19 (m, 1H), 7.11-7.15 (m, 2H), 7.03-7.09 (m, 2H), 6.91-6.96 (m, 1H), 6.12-6.18 (m, 1H), 5.19-5.29 (m, 1H), 4.33-4.41 (m, 2H), 4.10-4.22 (m, 1H), 3.92-4.00 (m, 2H), 3.55-3.65 (m, 2H), 2.82-2.88 (m, 1H), 2.74-2.82 (m, 2H), 2.11-2.21 (m, 1H), 1.87-1.98 (m, 1H), 0.88-0.99 (m, 4H), 0.61-0.70 (m, 4H) |

TABLE F-continued

| Example No. | Ki (nM) | Structure | Synthetic Procedure Used | HPLC Methods ($t_R$ min) | MS (M + H) | NMR Data |
|---|---|---|---|---|---|---|
| 208 | 1.7 | (3-cyclopropyl-4-(2-((S)-3-hydroxypyrrolidin-1-yl)ethoxy)phenyl pyrrolinone with 4-cyclopropylphenoxy) | Method B5 | 1 (7.10) | 461.3 | $^1$H NMR (400 MHz, DMSO-$d_6$) d 7.43-7.50 (m, 1H), 7.16-7.20 (m, 1H), 7.12 (s, 2H), 7.08 (s, 2H), 6.95-7.00 (m, 1H), 6.12-6.19 (m, 1H), 4.65-4.73 (m, 1H), 4.37 (d, J = 2.51 Hz, 2H), 4.15-4.25 (m, 1H), 4.03-4.13 (m, 2H), 2.77-2.89 (m, 3H), 2.67-2.76 (m, 1H), 2.53-2.61 (m, 1H), 2.44-2.48 (m, 1H), 2.11-2.21 (m, 1H), 1.89-2.03 (m, 2H), 1.49-1.60 (m, 1H), 0.86-0.99 (m, 4H), 0.59-0.70 (m, 4H) |
| 209 | 1.2 | (3-cyclopropyl-4-(2-(3-hydroxy-3-methylazetidin-1-yl)ethoxy)phenyl pyrrolinone with 4-cyclopropylphenoxy) | Method B5 | 1 (7.51) | 461.2 | $^1$H NMR (400 MHz, DMSO-$d_6$) d 7.43-7.49 (m, 1H), 7.17-7.20 (m, 1H), 7.13 (s, 2H), 7.08 (s, 2H), 6.91-6.97 (m, 1H), 6.16 (s, 1H), 5.10 (s, 1H), 4.37 (d, J = 2.26 Hz, 2H), 3.92-4.01 (m, 2H), 3.27 (s, 2H), 2.94-3.02 (m, 2H), 2.74-2.84 (m, 2H), 2.10-2.20 (m, 1H), 1.88-1.99 (m, 1H), 1.35 (s, 3H), 0.87-0.99 (m, 4H), 0.60-0.71 (m, 4H) |

TABLE F-continued
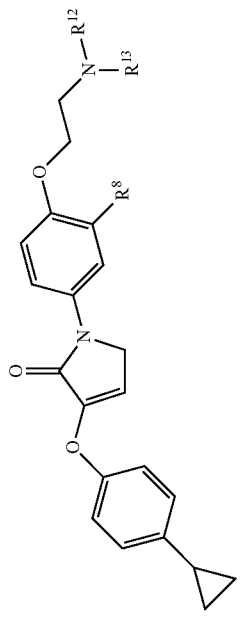
| Example No. | Ki (nM) | Structure | Synthetic Procedure Used | HPLC Methods ($t_R$ min) | MS (M + H) | NMR Data |
|---|---|---|---|---|---|---|
| 210 | 0.9 | 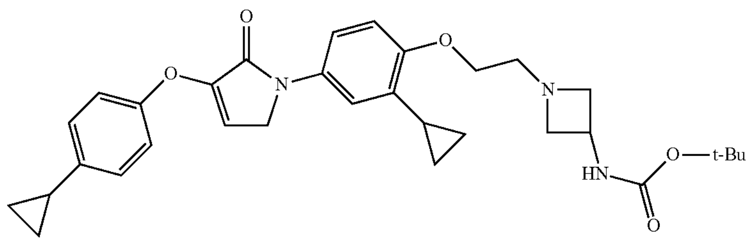 [SMILES: CC(C)(C)OC(=O)NC1CN(CCOc2ccc(N3CC=C(Oc4ccc(C5CC5)cc4)C3=O)cc2C2CC2)C1] | Method B5 | 1 (13.73) 2 (8.45) | 546.2 | $^1$H NMR (400 MHz, DMSO-d$_6$) δ 7.41-7.50 (m, 1H), 7.24-7.36 (m, 1H), 7.04-7.21 (m, 5H), 6.89-6.98 (m, 2H), 6.13-6.21 (m, 1H), 4.31-4.41 (m, 2H), 4.01-4.12 (m, 1H), 3.91-4.00 (m, 2H), 3.54-3.65 (m, 2H), 2.89-3.00 (m, 2H), 2.74-2.82 (m, 2H), 2.08-2.20 (m, 1H), 1.90-1.99 (m, 1H), 1.38 (s, 9H), 0.88-0.99 (m, 4H), 0.57-0.72 (m, 4H) |
| 211 | | 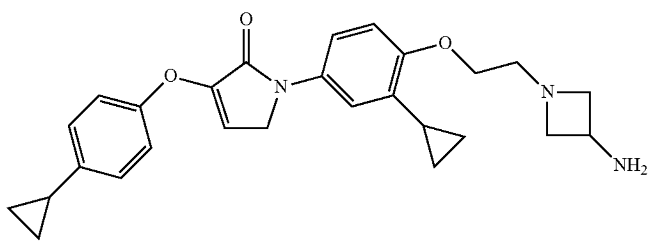 [SMILES: NC1CN(CCOc2ccc(N3CC=C(Oc4ccc(C5CC5)cc4)C3=O)cc2C2CC2)C1] | Method B5 | 1 (6.0) 2 (7.2) | 446.2 | $^1$H NMR (400 MHz, CD$_3$OD) δ 7.40-7.49 (m, 1H), 7.29-7.36 (m, 1H), 7.14-7.21 (m, 2H), 7.05-7.13 (m, 2H), 6.95-7.04 (m, 1H), 5.91-6.04 (m, 1H), 4.43-4.56 (m, 2H), 4.20-4.38 (m, 7H), 3.59-3.71 (m, 2H), 2.15-2.27 (m, 1H), 1.89-2.01 (m, 1H), 0.93-1.04 (m, 4H), 0.64-0.77 (m, 4H) |

TABLE G

| Example No. | Ki (nM) | Structure | Synthetic Procedure Used | HPLC methods (t_R min) | MS (M + H) | NMR Data |
|---|---|---|---|---|---|---|
| 212 | 0.50 | 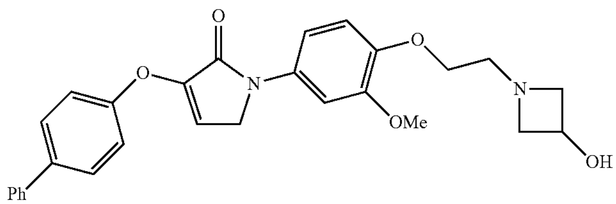 [SMILES: COc1cc(N2CC=C(Oc3ccc(-c4ccccc4)cc3)C2=O)ccc1OCCN1CC(O)C1] | Method B6 | 1 (7.28) 2 (8.71) | 473.2 | $^1$H NMR (400 MHz, DMSO-d$_6$) δ 7.64-7.76 (m, 4H), 7.44-7.55 (m, 3H), 7.34-7.41 (m, 1H), 7.25-7.32 (m, 2H), 7.15-7.23 (m, 1H), 6.92-7.02 (m, 1H), 6.41-6.48 (m, 1H), 5.20-5.28 (m, 1H), 4.42-4.50 (m, 2H), 4.10-4.21 (m, 1H), 3.85-3.95 (m, 2H), 3.73-3.81 (m, 3H), 3.51-3.61 (m, 2H), 2.70-2.84 (m, 4H) |
| 213 | 0.3 | 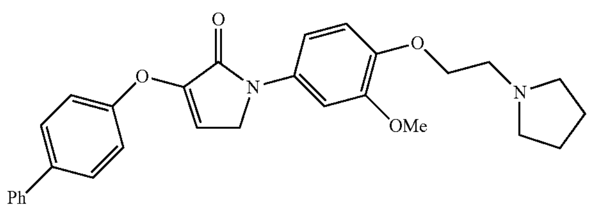 [SMILES: COc1cc(N2CC=C(Oc3ccc(-c4ccccc4)cc3)C2=O)ccc1OCCN1CCCC1] | Method B6 | 1 (12.2) 2 (14.7) | 471.2 | $^1$H NMR (400 MHz, CDCl$_3$) δ 7.50-7.78 (m, 6H), 7.33-7.49 (m, 4H), 6.88-6.95 (m, 2H), 5.89-5.95 (m, 1H), 4.26-4.32 (m, 2H), 4.15-4.25 (m, 2H), 3.88-3.94 (m, 3H), 2.99-3.13 (m, 2H), 2.66-2.89 (m, 4H), 1.81-1.94 (m, 4H) |
| 214 | 0.4 | 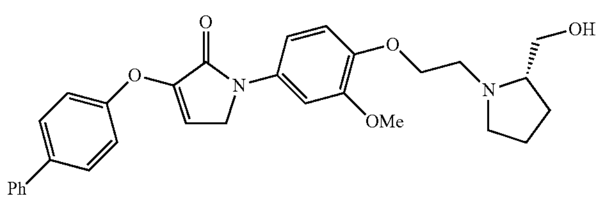 [SMILES: COc1cc(N2CC=C(Oc3ccc(-c4ccccc4)cc3)C2=O)ccc1OCCN1CCC[C@H]1CO] | Method B6 | 1 (7.75) 2 (8.96) | 501.4 | $^1$H NMR (400 MHz, DMSO-d$_6$) δ 7.70-7.77 (m, 2H), 7.64-7.70 (m, 2H), 7.56-7.60 (m, 1H), 7.45-7.52 (m, 2H), 7.34-7.41 (m, 1H), 7.20-7.32 (m, 3H), 7.08-7.13 (m, 1H), 6.47-6.51 (m, 1H), 5.46-5.54 (m, 1H), 4.44-4.54 (m, 2H), 4.24-4.39 (m, 2H), 3.82 (s, 5H), 3.61-3.74 (m, 3H), 3.45-3.59 (m, 1H), 1.98-2.18 (m, 2H), 1.81-1.97 (m, 1H), 1.69-1.80 (m, 1H) |
| 215 | 1.0 | 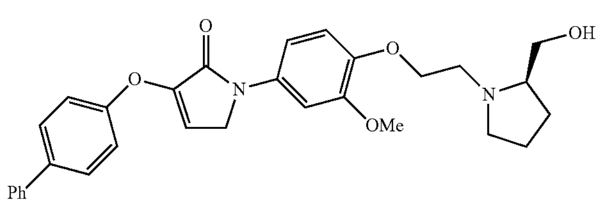 [SMILES: COc1cc(N2CC=C(Oc3ccc(-c4ccccc4)cc3)C2=O)ccc1OCCN1CCC[C@@H]1CO] | Method B6 | 1 (7.73) 2 (8.98) | 501.4 | $^1$H NMR (400 MHz, DMSO-d$_6$) δ 7.73 (d, J = 8.78 Hz, 2H), 7.65-7.70 (m, 2H), 7.55-7.60 (m, 1H), 7.48 (s, 2H), 7.34-7.41 (m, 1H), 7.29 (d, J = 8.53 Hz, 3H), 7.07-7.14 (m, 1H), 6.46-6.50 (m, 1H), 5.46-5.53 (m, 1H), 4.49 (d, J = 2.26 Hz, 2H), 4.24-4.38 (m, |

TABLE G-continued

| Example No. | Ki (nM) | Structure | Synthetic Procedure Used | HPLC methods (t$_R$ min) | MS (M + H) | NMR Data |
|---|---|---|---|---|---|---|
| | | | | | | 2H), 3.82 (s, 5H), 3.62-3.74 (m, 3H), 3.47-3.58 (m, 1H), 1.97-2.18 (m, 2H), 1.81-1.95 (m, 1H), 1.68-1.79 (m, 1H) |
| 216 | 0.4 | 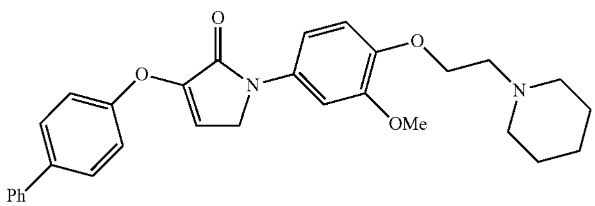 [SMILES: COc1cc(N2CC=C(Oc3ccc(-c4ccccc4)cc3)C2=O)ccc1OCCN1CCCCC1] | B6 | Method 1 (7.80) 2 (9.47) | 485.4 | $^1$H NMR (400 MHz, DMSO-d$_6$) δ 7.71-7.76 (m, 2H), 7.65-7.69 (m, 2H), 7.57-7.60 (m, 1H), 7.45-7.51 (m, 2H), 7.35-7.40 (m, 1H), 7.27 (s, 3H), 7.08-7.14 (m, 1H), 6.46-6.51 (m, 1H), 4.44-4.56 (m, 2H), 4.25-4.36 (m, 2H), 3.82 (s, 3H), 3.47-3.62 (m, 4H), 2.96-3.12 (m, 2H), 1.80-1.91 (m, 2H), 1.62-1.78 (m, 3H), 1.35-1.47 (m, 1H) |
| 217 | 0.7 | 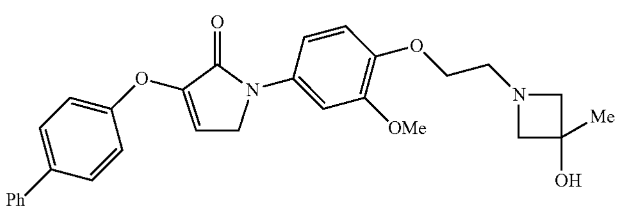 [SMILES: COc1cc(N2CC=C(Oc3ccc(-c4ccccc4)cc3)C2=O)ccc1OCCN1CC(C)(O)C1] | B6 | Method 1 (7.39) 2 (8.83) | 485.2 | $^1$H NMR (400 MHz, DMSO-d$_6$) δ 7.70-7.76 (m, 2H), 7.65-7.70 (m, 2H), 7.55-7.59 (m, 1H), 7.45-7.52 (m, 2H), 7.35-7.41 (m, 1H), 7.22-7.31 (m, 3H), 7.03-7.09 (m, 1H), 6.46-6.50 (m, 1H), 4.42-4.55 (m, 2H), 3.89-4.23 (m, 6H), 3.82 (s, 3H), 3.50-3.66 (m, 2H), 1.39-1.51 (m, 3H) |
| 218 | 0.7 | 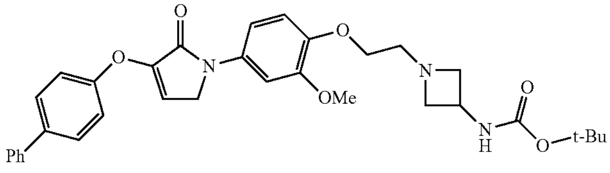 [SMILES: COc1cc(N2CC=C(Oc3ccc(-c4ccccc4)cc3)C2=O)ccc1OCCN1CC(NC(=O)OC(C)(C)C)C1] | B6 | Method 1 (13.33) 2 (10.04) | 572.4 | $^1$H NMR (400 MHz, DMSO-d$_6$) δ 7.70-7.76 (m, 2H), 7.65-7.70 (m, 2H), 7.45-7.53 (m, 3H), 7.34-7.40 (m, 1H), 7.25-7.31 (m, 2H), 7.16-7.23 (m, 1H), 6.95-7.00 (m, 1H), 6.43-6.48 (m, 1H), 4.42-4.51 (m, 1H), 3.98-4.14 (m, 1H), 3.86-3.95 (m, 2H), 3.73-3.82 (m, 3H), 3.48-3.64 (m, 2H), 2.83-3.00 (m, 2H), 2.68-2.79 (m, 2H), 1.38 (s, 9H) |

US 9,499,482 B2

TABLE G-continued

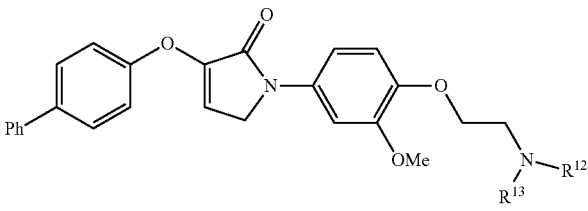

| Example No. | Ki (nM) | Structure | Synthetic Procedure Used | HPLC methods ($t_R$ min) | MS (M + H) | NMR Data |
|---|---|---|---|---|---|---|
| 219 | 0.7 | 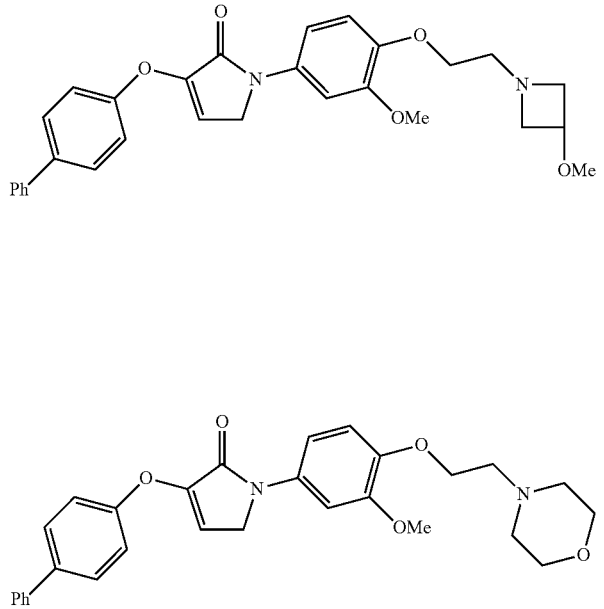 | Method B6 | 1 (7.57)<br>2 (9.20) | 487.3 | $^1$H NMR (400 MHz, DMSO-d$_6$) δ 7.71-7.75 (m, 2H), 7.65-7.70 (m, 2H), 7.56-7.59 (m, 1H), 7.45-7.51 (m, 2H), 7.35-7.40 (m, 1H), 7.23-7.31 (m, 3H), 7.04-7.09 (m, 1H), 6.46-6.50 (m, 1H), 4.47-4.52 (m, 2H), 4.35-4.47 (m, 2H), 4.23-4.29 (m, 1H), 4.14-4.21 (m, 2H), 4.00-4.13 (m, 2H), 3.83 (s, 3H), 3.58-3.66 (m, 2H), 3.28 (s, 3H) |
| 220 | | 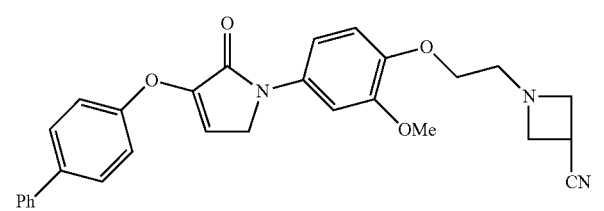 [SMILES: COc1cc(N2CC=C(Oc3ccc(-c4ccccc4)cc3)C2=O)ccc1OCCN1CC(C#N)C1] | Method B6 | 1 (7.70)<br>2 (8.97) | 487.4 | $^1$H NMR (400 MHz, CD$_3$OD) δ 7.69-7.72 (m, 2H), 7.61-7.66 (m, 2H), 7.58-7.60 (m, 1H), 7.43-7.49 (m, 2H), 7.29-7.38 (m, 3H), 7.12-7.17 (m, 1H), 7.02-7.07 (m, 1H), 6.18-6.22 (m, 1H), 4.41-4.48 (m, 2H), 4.15-4.22 (m, 2H), 3.89 (s, 3H), 3.69-3.78 (m, 4H), 2.80-2.87 (m, 2H), 2.61-2.70 (m, 4H) |
| 221 | | 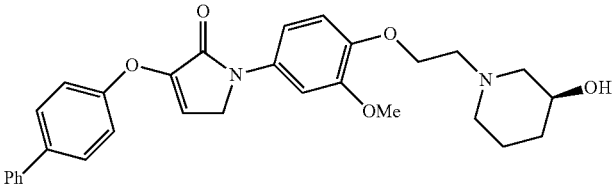 [SMILES: COc1cc(N2CC=C(Oc3ccc(-c4ccccc4)cc3)C2=O)ccc1OCCN1CCC[C@H](O)C1] | Method B6 | 1 (7.59)<br>2 (9.16) | 482.2 | $^1$H NMR (400 MHz, DMSO-d$_6$) δ 5.37-5.44 (m, 2H), 5.26-5.36 (m, 3H), 5.12-5.19 (m, 2H), 4.98-5.09 (m, 3H), 4.79-4.86 (m, 1H), 4.66-4.73 (m, 1H), 3.86-3.93 (m, 1H), 2.09-2.17 (m, 2H), 1.71-1.79 (m, 2H), 1.59 (s, 3H), 1.42-1.49 (m, 2H), 1.23-1.30 (m, 2H), 1.12-1.21 (m, 1H), 0.58-0.66 (m, 2H) |
| 222 | | 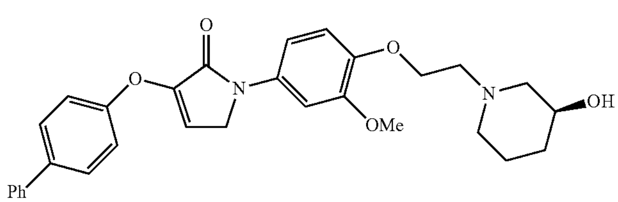 | Method B6 | 1 (7.63)<br>2 (8.82) | 501.4 | $^1$H NMR (400 MHz, DMSO-d$_6$) δ 7.73 (d, J = 8.78 Hz, 2H), 7.65-7.70 (m, 2H), 7.56-7.60 (m, 1H), 7.45-7.52 (m, 2H), 7.35-7.41 (m, 1H), 7.29 (d, J = 8.78 Hz, 3H), 7.07-7.15 (m, 1H), 6.46-6.51 (m, |

TABLE G-continued

| Example No. | Ki (nM) | Structure | Synthetic Procedure Used | HPLC methods ($t_R$ min) | MS (M + H) | NMR Data |
|---|---|---|---|---|---|---|
| | | | | | | 1H), 5.36-5.54 (m, 1H), 4.44-4.55 (m, 2H), 4.24-4.41 (m, 2H), 3.82 (d, J = 2.51 Hz, 3H), 3.66-3.80 (m, 1H), 3.51-3.63 (m, 2H), 3.42-3.50 (m, 3H), 3.16-3.28 (m, 1H), 1.86-2.11 (m, 2H), 1.54-1.77 (m, 2H) |
| 223 | | 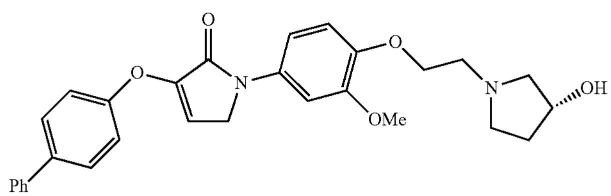 [SMILES: COc1cc(N2CC=C(Oc3ccc(-c4ccccc4)cc3)C2=O)ccc1OCCN1CC[C@@H](O)C1] | B6 | Method 1 (7.60) 2 (8.73) | 487.4 | $^1$H NMR (400 MHz, CD$_3$OD) δ 7.68-7.74 (m, 2H), 7.60-7.66 (m, 3H), 7.43-7.49 (m, 2H), 7.29-7.39 (m, 3H), 7.13-7.19 (m, 1H), 7.05-7.10 (m, 1H), 6.18-6.23 (m, 1H), 4.41-4.53 (m, 3H), 4.20-4.29 (m, 2H), 3.92 (s, 3H), 3.20-3.31 (m, 5H), 3.05-3.17 (m, 2H), 2.17-2.31 (m, 1H), 1.87-1.95 (m, 1H) |
| 224 | | 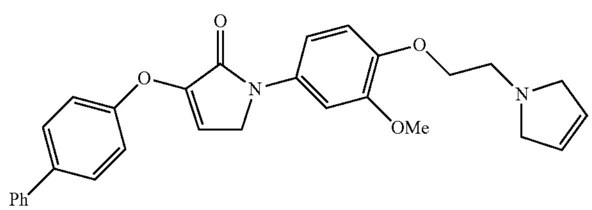 [SMILES: COc1cc(N2CC=C(Oc3ccc(-c4ccccc4)cc3)C2=O)ccc1OCCN1CC=CC1] | B6 | Method 1 (7.66) 2 (8.96) | 469.4 | $^1$H NMR (400 MHz, DMSO-d$_6$) δ 7.73 (d, J = 8.78 Hz, 2H), 7.64-7.71 (m, 2H), 7.58-7.62 (m, 1H), 7.45-7.53 (m, 2H), 7.35-7.42 (m, 1H), 7.29 (d, J = 8.78 Hz, 3H), 7.07-7.15 (m, 1H), 6.46-6.53 (m, 1H), 5.99 (s, 2H), 4.49 (d, J = 2.26 Hz, 2H), 4.24-4.39 (m, 4H), 4.05-4.17 (m, 2H), 3.84 (s, 3H), 3.69-3.76 (m, 2H) |
| 225 | | 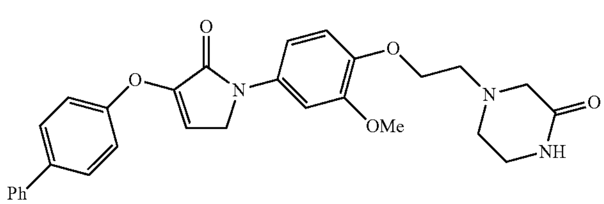 [SMILES: COc1cc(N2CC=C(Oc3ccc(-c4ccccc4)cc3)C2=O)ccc1OCCN1CCNC(=O)C1] | B6 | Method 1 (9.03) 2 (8.38) | 500.4 | $^1$H NMR (400 MHz, CD$_3$OD) δ 7.68-7.75 (m, 2H), 7.58-7.67 (m, 3H), 7.42-7.50 (m, 2H), 7.28-7.40 (m, 3H), 7.12-7.19 (m, 1H), 7.02-7.09 (m, 1H), 6.17-6.24 (m, 1H), 4.42-4.49 (m, 2H), 4.16-4.23 (m, 2H), 3.85-3.94 (m, 3H), 3.35-3.40 (m, 4H), 2.85-2.97 (m, 4H) |

TABLE G-continued

| Example No. | Ki (nM) | Structure | Synthetic Procedure Used | HPLC methods ($t_R$ min) | MS (M + H) | NMR Data |
|---|---|---|---|---|---|---|
| 226 | | 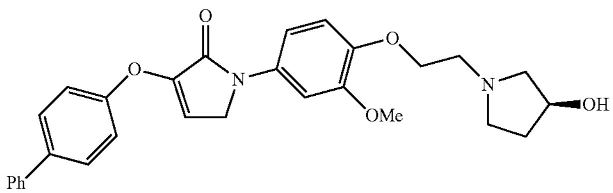 [SMILES: COc1cc(N2CC=C(Oc3ccc(-c4ccccc4)cc3)C2=O)ccc1OCCN1CC[C@H](O)C1] | B6 | Method 1 (7.61)<br>2 (8.72) | 487.4 | $^1$H NMR (400 MHz, CD$_3$OD) δ 7.68-7.75 (m, 2H), 7.60-7.67 (m, 3H), 7.43-7.50 (m, 2H), 7.28-7.39 (m, 3H), 7.13-7.20 (m, 1H), 7.03-7.12 (m, 1H), 6.13-6.27 (m, 1H), 4.49-4.55 (m, 1H), 4.43-4.48 (m, 2H), 4.21-4.31 (m, 2H), 3.92 (s, 3H), 3.24-3.32 (m, 5H), 3.10-3.23 (m, 2H), 2.20-2.33 (m, 1H), 1.88-1.95 (m, 1H) |
| 227 | | 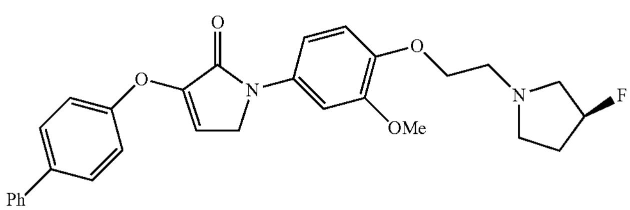 [SMILES: COc1cc(N2CC=C(Oc3ccc(-c4ccccc4)cc3)C2=O)ccc1OCCN1CC[C@H](F)C1] | B6 | Method 1 (7.69)<br>2 (9.26) | 489.3 | $^1$H NMR (400 MHz, DMSO-d$_6$) δ 7.73 (d, J = 9.03 Hz, 2H), 7.65-7.69 (m, 2H), 7.56-7.62 (m, 1H), 7.48 (s, 2H), 7.36-7.42 (m, 1H), 7.29 (d, J = 8.78 Hz, 3H), 7.07-7.16 (m, 1H), 6.49 (s, 1H), 5.38-5.64 (m, 1H), 4.49 (d, J = 2.51 Hz, 2H), 4.22-4.35 (m, 2H), 3.91-4.09 (m, 1H), 3.58-3.73 (m, 4H), 3.28-3.47 (m, 4H), 2.07-2.44 (m, 2H) |
| 228 | | 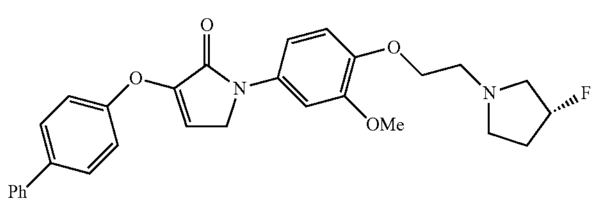 [SMILES: COc1cc(N2CC=C(Oc3ccc(-c4ccccc4)cc3)C2=O)ccc1OCCN1CC[C@@H](F)C1] | B6 | Method 1 (7.69)<br>2 (9.24) | 489.3 | $^1$H NMR (400 MHz, DMSO-d$_6$) δ 7.73 (d, J = 9.03 Hz, 2H), 7.67 (dd, J = 1.13, 8.41 Hz, 2H), 7.59 (d, J = 2.26 Hz, 1H), 7.48 (t, J = 7.65 Hz, 2H), 7.37 (s, 1H), 7.29 (d, J = 8.78 Hz, 3H), 7.13 (s, 1H), 6.49 (s, 1H), 5.39-5.62 (m, 1H), 4.49 (d, J = 2.26 Hz, 2H), 4.29 (br. s., 2H), 3.91-4.07 (m, 1H), 3.83 (s, 5H), 3.29-3.58 (m, 3H), 2.08-2.40 (m, 2H) |

TABLE G-continued

| Example No. | Ki (nM) | Structure | Synthetic Procedure Used | HPLC methods (t_R min) | MS (M + H) | NMR Data |
|---|---|---|---|---|---|---|
| 229 | | 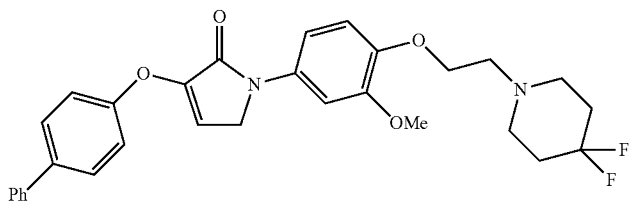 [SMILES: COc1cc(N2CC=C(Oc3ccc(-c4ccccc4)cc3)C2=O)ccc1OCCN1CCC(F)(F)CC1] | Method B6 | 1 (8.25) 2 (9.67) | 521.4 | $^1$H NMR (400 MHz, CD$_3$OD) δ 7.67-7.76 (m, 2H), 7.56-7.66 (m, 3H), 7.43-7.51 (m, 2H), 7.29-7.39 (m, 3H), 7.12-7.19 (m, 1H), 7.00-7.09 (m, 1H), 6.17-6.23 (m, 1H), 4.42-4.50 (m, 2H), 4.13-4.22 (m, 2H), 3.89 (s, 3H), 2.86-2.94 (m, 2H), 2.73-2.82 (m, 4H), 1.96-2.10 (m, 4H) |
| 230 | | 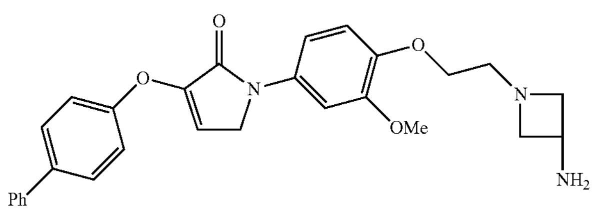 [SMILES: COc1cc(N2CC=C(Oc3ccc(-c4ccccc4)cc3)C2=O)ccc1OCCN1CC(N)C1] | Method B6 | 1 (6.27) 2 (7.42) | 472.2 | $^1$H NMR (400 MHz, DMSO-d$_6$) d 7.70-7.78 (m, 2H), 7.64-7.70 (m, 2H), 7.56-7.62 (m, 1H), 7.44-7.53 (m, 2H), 7.34-7.42 (m, 1H), 7.21-7.33 (m, 3H), 7.04-7.11 (m, 1H), 6.44-6.52 (m, 1H), 4.46-4.52 (m, 2H), 4.27-4.45 (m, 3H), 4.06-4.26 (m, 3H), 3.83 (s, 3H), 3.58-3.75 (m, 2H), 2.52-2.56 (m, 3H) |
| 231 | | 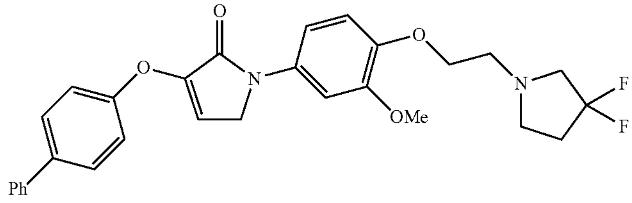 [SMILES: COc1cc(N2CC=C(Oc3ccc(-c4ccccc4)cc3)C2=O)ccc1OCCN1CCC(F)(F)C1] | Method B6 | 1 (12.7) 2 (9.5) | 507.4 | $^1$H NMR (400 MHz, DMSO-d$_6$) δ 7.64-7.77 (m, 4H), 7.54-7.60 (m, 1H), 7.44-7.52 (m, 2H), 7.34-7.41 (m, 1H), 7.22-7.32 (m, 3H), 7.03-7.12 (m, 1H), 6.45-6.52 (m, 1H), 4.46-4.54 (m, 2H), 4.13-4.27 (m, 2H), 3.82 (s, 3H), 3.37-3.55 (m, 6H), 2.37-2.45 (m, 2H) |

TABLE H

| Example No. | Ki (nM) | Structure | Synthetic Procedure Used | HPLC methods ($t_R$ min) | MS (M + H) | NMR data |
|---|---|---|---|---|---|---|
| 232 | 939 | 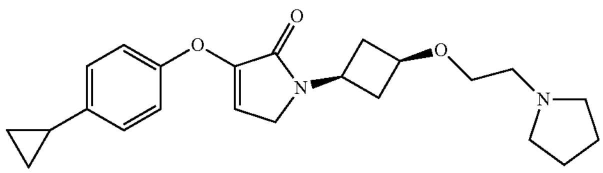 [SMILES: O=C1C(Oc2ccc(C3CC3)cc2)=CCN1[C@H]1C[C@@H](OCCN2CCCC2)C1] | Method B7 | 1 (5.96) 2 (7.06) | 383.2 | $^1$H NMR (400 MHz, DMSO-d$_6$) δ 7.08-7.16 (m, 2H), 6.97-7.05 (m, 2H), 5.97-6.06 (m, 1H), 4.11-4.21 (m, 1H), 3.93-3.99 (m, 2H), 3.68-3.79 (m, 1H), 3.40-3.43 (m, 2H), 2.54-2.61 (m, 4H), 2.45-2.48 (m, 4H), 2.04-2.15 (m, 2H), 1.92-1.97 (m, 1H), 1.63-1.72 (m, 4H), 0.89-0.98 (m, 2H), 0.57-0.69 (m, 2H) |
| 233 | 1778 | 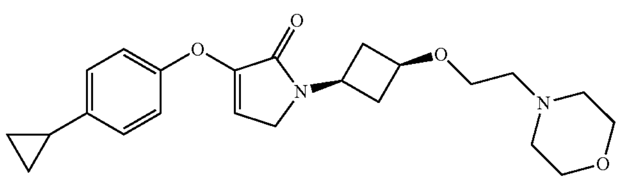 [SMILES: O=C1C(Oc2ccc(C3CC3)cc2)=CCN1[C@H]1C[C@@H](OCCN2CCOCC2)C1] | Method B7 | 1 (5.94) 2 (6.73) | 399.2 | $^1$H NMR (400 MHz, DMSO-d$_6$) δ 7.10 (s, 2H), 7.02 (s, 2H), 5.99-6.07 (m, 1H), 4.09-4.24 (m, 1H), 3.90-4.00 (m, 2H), 3.69-3.81 (m, 1H), 3.52-3.62 (m, 4H), 3.39-3.48 (m, 2H), 2.31-2.49 (m, 8H), 2.03-2.13 (m, 2H), 1.91-1.97 (m, 1H), 0.89-0.99 (m, 2H), 0.60-0.68 (m, 2H) |
| 234 | 654 | 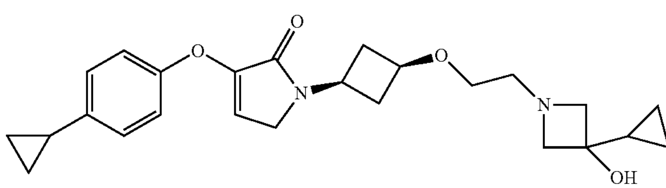 [SMILES: O=C1C(Oc2ccc(C3CC3)cc2)=CCN1[C@H]1C[C@@H](OCCN2CC(O)(C3CC3)C2)C1] | Method B7 | 1 (6.25) 2 (7.35) | 425.2 | $^1$H NMR (400 MHz, DMSO-d$_6$) δ 7.07-7.15 (m, 2H), 6.98-7.05 (m, 2H), 5.96-6.08 (m, 1H), 4.88-5.09 (m, 1H), 4.09-4.21 (m, 1H), 3.93-4.01 (m, 2H), 3.65-3.79 (m, 1H), 3.23-3.27 (m, 2H), 3.09-3.21 (m, 2H), 2.82-2.94 (m, 2H), 2.53-2.59 (m, 2H), 2.44-2.49 (m, 2H), 2.02-2.11 (m, 2H), 1.86-1.97 (m, 1H), 1.08-1.17 (m, 1H), 0.89-0.98 (m, 2H), 0.61-0.69 (m, 2H), 0.30-0.36 (m, 4H) |
| 235 | | 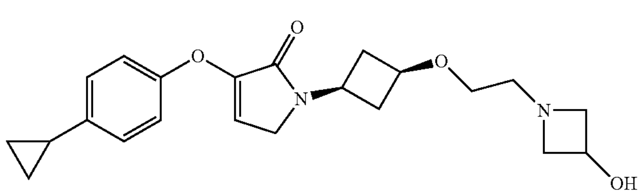 [SMILES: O=C1C(Oc2ccc(C3CC3)cc2)=CCN1[C@H]1C[C@@H](OCCN2CC(O)C2)C1] | Method B7 | 1 (5.81) 2 (6.76) | 385.2 | $^1$H NMR (400 MHz, CD$_3$OD) δ 7.10-7.19 (m, 2H), 7.00-7.09 (m, 2H), 5.86-5.98 (m, 1H), 4.22-4.42 (m, 2H), 3.96-4.06 (m, 2H), 3.68-3.87 (m, 3H), 3.39-3.46 (m, 2H), 2.95-3.05 (m, 2H), 2.58-2.75 (m, 4H), 2.12-2.23 (m, 2H), 1.90- |

TABLE H-continued

| Example No. | Ki (nM) | Structure | Synthetic Procedure Used | HPLC methods ($t_R$ min) | MS (M + H) | NMR data |
|---|---|---|---|---|---|---|
| | | | | | | 1.98 (m, 1H), 0.93-1.02 (m, 2H), 0.63-0.71 (m, 2H) |
| 236 | | (4-cyclopropylphenoxy-pyrrolinone-cyclobutyl-O-ethyl-azetidine-SO₂Me) | Method B7 | 1 (6.06) 2 (7.15) | 447.2 | ¹H NMR (400 MHz, CD₃OD) δ 7.11-7.18 (m, 2H), 7.03-7.09 (m, 2H), 5.86-5.95 (m, 1H), 4.25-4.34 (m, 1H), 4.14-4.23 (m, 1H), 4.00-4.06 (m, 2H), 3.78-3.86 (m, 1H), 3.68-3.76 (m, 2H), 3.58-3.65 (m, 2H), 3.41-3.47 (m, 2H), 2.90-2.96 (m, 3H), 2.61-2.75 (m, 4H), 2.15-2.25 (m, 2H), 1.86-1.98 (m, 1H), 0.92-1.01 (m, 2H), 0.62-0.71 (m, 2H) |
| 237 | 339 | (4-cyclopropylphenoxy-pyrrolinone-cyclobutyl-O-ethyl-azetidine-OMe) | Method B7 | 1 (6.67) 2 (6.62) | 399.2 | ¹H NMR (400 MHz, CD₃OD) δ 7.11-7.18 (m, 2H), 7.03-7.08 (m, 2H), 5.89-5.96 (m, 1H), 4.23-4.35 (m, 1H), 4.06-4.16 (m, 1H), 4.00-4.05 (m, 2H), 3.76-3.87 (m, 2H), 3.59-3.69 (m, 2H), 3.43-3.48 (m, 2H), 3.22-3.25 (m, 1H), 2.74-2.89 (m, 3H), 2.61-2.70 (m, 3H), 2.16-2.26 (m, 2H), 1.89-1.99 (m, 2H), 0.96-1.01 (m, 2H), 0.63-0.70 (m, 2H) |
| 238 | 128 | (4-cyclopropylphenoxy-pyrrolinone-cyclobutyl-O-ethyl-pyrrolidine-OH) | Method B7 | 1 (5.81) 2 (6.81) | 399.2 | ¹H NMR (400 MHz, DMSO-d₆) d 7.07-7.15 (m, 2H), 6.97-7.05 (m, 2H), 6.00-6.06 (m, 1H), 4.59-4.70 (m, 1H), 4.10-4.22 (m, 2H), 3.93-3.99 (m, 2H), 3.68-3.79 (m, 1H), 3.35-3.43 (m, 2H), 2.66-2.76 (m, 1H), 2.53-2.62 (m, 3H), 2.41-2.48 (m, 2H), 2.29-2.39 (m, 1H), 2.02-2.14 (m, 2H), 1.86-2.00 (m, 2H), 1.46-1.58 (m, 1H), 0.89-0.98 (m, 2H), 0.61-0.69 (m, 2H) |

TABLE H-continued

| Example No. | Ki (nM) | Structure | Synthetic Procedure Used | HPLC methods ($t_R$ min) | MS (M + H) | NMR data |
|---|---|---|---|---|---|---|
| 239 | | 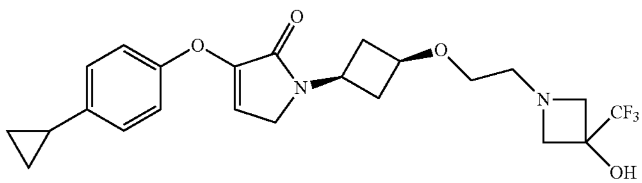 [SMILES: O=C1C(Oc2ccc(C3CC3)cc2)=CCN1[C@H]1C[C@@H](OCCN2CC(O)(C(F)(F)F)C2)C1] | Method B7 | 1 (6.54) 2 (7.42) | 453.2 | $^1$H NMR (400 MHz, CD$_3$OD) δ 7.10-7.18 (m, 2H), 7.00-7.09 (m, 2H), 5.84-5.94 (m, 1H), 4.22-4.34 (m, 1H), 3.99-4.07 (m, 2H), 3.78-3.86 (m, 1H), 3.64-3.73 (m, 2H), 3.42-3.49 (m, 2H), 3.34-3.37 (m, 2H), 2.72-2.78 (m, 2H), 2.59-2.70 (m, 2H), 2.12-2.24 (m, 2H), 1.87-1.98 (m, 1H), 0.93-1.02 (m, 2H), 0.64-0.71 (m, 2H) |
| 240 | 3000 | 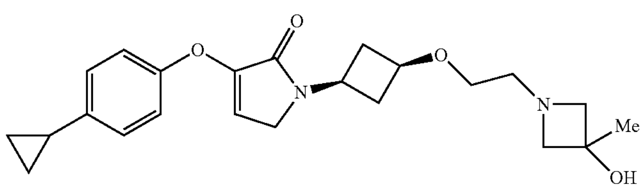 [SMILES: CC1(O)CN(CCO[C@H]2C[C@@H](N3CC=C(Oc4ccc(C5CC5)cc4)C3=O)C2)C1] | Method B7 | 1 (6.01) 2 (6.77) | 399.2 | $^1$H NMR (400 MHz, CD$_3$OD) δ 7.11-7.17 (m, 2H), 7.01-7.09 (m, 2H), 5.85-5.94 (m, 1H), 4.23-4.36 (m, 1H), 3.98-4.06 (m, 2H), 3.77-3.87 (m, 1H), 3.38-3.47 (m, 4H), 3.09-3.18 (m, 3H), 2.61-2.78 (m, 4H), 2.13-2.24 (m, 2H), 1.86-1.98 (m, 1H), 1.42-1.52 (m, 3H), 0.95-1.01 (m, 2H), 0.62-0.72 (m, 2H) |
| 241 | 2364 | 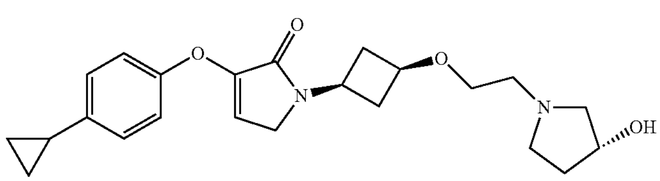 [SMILES: O=C1C(Oc2ccc(C3CC3)cc2)=CCN1[C@H]1C[C@@H](OCCN2CC[C@@H](O)C2)C1] | Method B7 | 1 (5.93) 2 (6.66) | 399.2 | $^1$H NMR (400 MHz, CD$_3$OD) δ 7.10-7.18 (m, 2H), 7.01-7.09 (m, 2H), 5.87-5.95 (m, 1H), 4.52-4.60 (m, 1H), 4.23-4.42 (m, 2H), 3.99-4.06 (m, 2H), 3.81-3.90 (m, 1H), 3.52-3.60 (m, 2H), 2.57-3.02 (m, 9H), 2.09-2.28 (m, 3H), 1.89-1.99 (m, 1H), 0.94-1.02 (m, 2H), 0.62-0.71 (m, 2H) |

TABLE I

| Example No. | Ki (nM) | Structure | Synthetic Procedure Used | HPLC Methods (t_R min) | MS (M + H) | NMR Data |
|---|---|---|---|---|---|---|
| 242 | 43 | 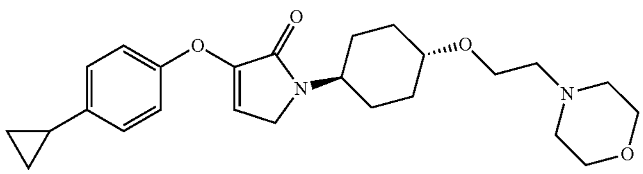 [SMILES: O=C1C(Oc2ccc(C3CC3)cc2)=CCN1[C@H]1CC[C@H](OCCN2CCOCC2)CC1] | Method B8 | 1 (6.68) 2 (7.62) | 427.2 | $^1$H NMR (400 MHz, DMSO-d$_6$) δ 7.07-7.16 (m, 2H), 6.97-7.05 (m, 2H), 5.91-6.03 (m, 1H), 3.72-3.89 (m, 3H), 3.48-3.61 (m, 5H), 3.17-3.26 (m, 2H), 2.36-2.48 (m, 6H), 2.00-2.13 (m, 2H), 1.87-1.98 (m, 1H), 1.67-1.80 (m, 2H), 1.43-1.62 (m, 2H), 1.19-1.35 (m, 2H), 0.90-0.99 (m, 2H), 0.58-0.69 (m, 2H) |
| 243 | 36 | 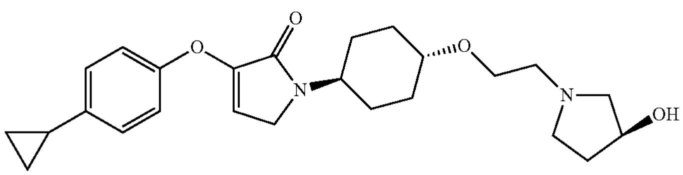 [SMILES: O=C1C(Oc2ccc(C3CC3)cc2)=CCN1[C@H]1CC[C@H](OCCN2CC[C@H](O)C2)CC1] | Method B8 | 1 (6.69) 2 (6.89) | 427.2 | $^1$H NMR (400 MHz, DMSO-d$_6$) δ 7.06-7.16 (m, 2H), 6.97-7.05 (m, 2H), 5.92-6.01 (m, 1H), 4.57-4.68 (m, 1H), 4.10-4.21 (m, 1H), 3.73-3.88 (m, 3H), 3.44-3.55 (m, 2H), 3.16-3.27 (m, 1H), 2.54-2.75 (m, 3H), 2.26-2.47 (m, 3H), 2.00-2.08 (m, 2H), 1.87-1.98 (m, 2H), 1.67-1.76 (m, 2H), 1.46-1.61 (m, 2H), 1.18-1.32 (m, 3H), 0.90-0.99 (m, 2H), 0.59-0.69 (m, 2H) |
| 244 | 41 | 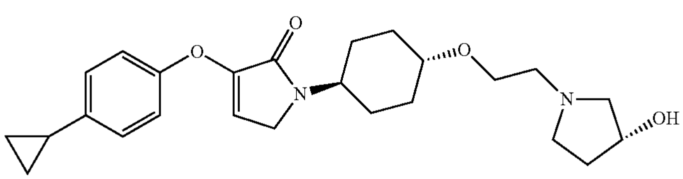 [SMILES: O=C1C(Oc2ccc(C3CC3)cc2)=CCN1[C@H]1CC[C@H](OCCN2CC[C@@H](O)C2)CC1] | Method B8 | 1 (6.56) 2 (7.44) | 427.2 | $^1$H NMR (400 MHz, DMSO-d$_6$) δ 7.08-7.15 (m, 2H), 6.96-7.05 (m, 2H), 5.93-6.02 (m, 1H), 4.91-5.28 (m, 1H), 4.20-4.39 (m, 1H), 3.74-3.89 (m, 3H), 3.56-3.67 (m, 2H), 3.20-3.30 (m, 3H), 2.71-3.16 (m, 4H), 1.99-2.13 (m, 3H), 1.87-1.97 (m, 1H), 1.65-1.79 (m, 3H), 1.47-1.63 (m, 2H), 1.25-1.35 (m, 2H), 0.89-0.98 (m, 2H), 0.59-0.68 (m, 2H) |
| 245 | 40 | 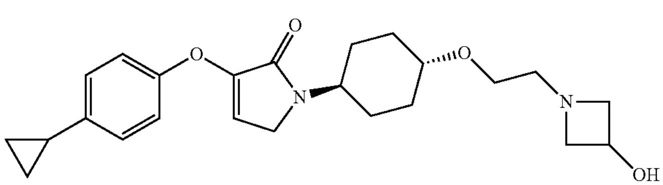 [SMILES: O=C1C(Oc2ccc(C3CC3)cc2)=CCN1[C@H]1CC[C@H](OCCN2CC(O)C2)CC1] | Method B8 | 1 (6.36) 2 (7.25) | 413.4 | $^1$H NMR (400 MHz, CD$_3$OD) δ 7.02-7.17 (m, 4H), 5.84-5.89 (m, 1H), 4.49-4.60 (m, 1H), 4.08-4.18 (m, 2H), 3.88-4.02 (m, 4H), 3.54-3.71 (m, 4H), 3.08-3.20 (m, 2H), 2.14- |

TABLE I-continued

| Example No. | Ki (nM) | Structure | Synthetic Procedure Used | HPLC Methods ($t_R$ min) | MS (M + H) | NMR Data |
|---|---|---|---|---|---|---|
| | | | | | | 2.26 (m, 2H), 1.84-1.98 (m, 3H), 1.58-1.73 (m, 2H), 1.34-1.48 (m, 2H), 0.91-1.02 (m, 2H), 0.63-0.72 (m, 2H) |
| 246 | 43 | 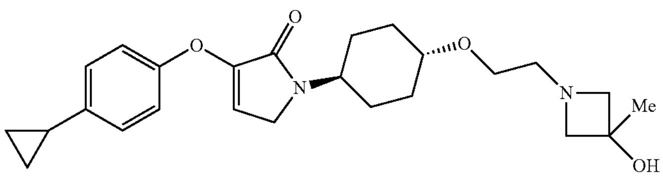 [SMILES: CC1(O)CN(CCO[C@H]2CC[C@H](N3CC=C(Oc4ccc(C5CC5)cc4)C3=O)CC2)C1] | B8 | Method 1 (6.49) 2 (7.42) | 427.4 | $^1$H NMR (400 MHz, DMSO-d$_6$) δ 6.97-7.16 (m, 4H), 5.92-6.02 (m, 1H), 3.73-4.16 (m, 6H), 3.63 (br. s., 2H), 3.21-3.32 (m, 4H), 2.06 (d, J = 10.79 Hz, 2H), 1.93 (s, 1H), 1.73 (br. s., 2H), 1.57 (br. s., 2H), 1.44 (br. s., 2H), 1.21-1.35 (m, 2H), 0.88-0.99 (m, 2H), 0.64 (dd, J = 1.76, 5.02 Hz, 2H) |
| 247 | 23 | 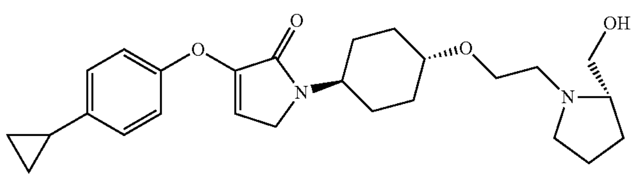 [SMILES: O=C1C(Oc2ccc(C3CC3)cc2)=CCN1[C@H]1CC[C@H](OCCN2CCC[C@H]2CO)CC1] | B8 | Method 1 (6.54) 2 (7.57) | 441.4 | $^1$H NMR (400 MHz, CD$_3$OD) δ 7.10-7.18 (m, 2H), 7.01-7.10 (m, 2H), 5.83-5.92 (m, 1H), 3.81-4.04 (m, 6H), 3.63-3.80 (m, 4H), 3.37-3.48 (m, 1H), 3.23-3.31 (m, 2H), 2.17-2.30 (m, 4H), 1.99-2.17 (m, 2H), 1.84-1.99 (m, 4H), 1.60-1.75 (m, 2H), 1.38-1.53 (m, 2H), 0.93-1.02 (m, 2H), 0.62-0.72 (m, 2H) |
| 248 | 22 | 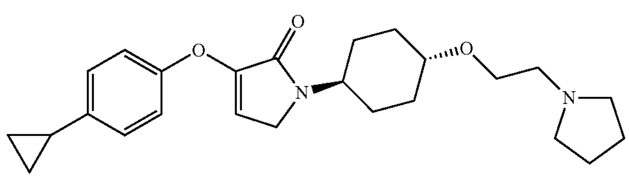 [SMILES: O=C1C(Oc2ccc(C3CC3)cc2)=CCN1[C@H]1CC[C@H](OCCN2CCCC2)CC1] | B8 | Method 1 (7.06) 2 (7.26) | 411.4 | $^1$H NMR (400 MHz, CD$_3$OD) δ 7.09-7.18 (m, 2H), 7.00-7.08 (m, 2H), 5.82-5.92 (m, 1H), 3.89-4.05 (m, 2H), 3.61-3.71 (m, 2H), 3.35-3.40 (m, 1H), 2.61-2.80 (m, 6H), 2.14-2.24 (m, 2H), 1.80-1.99 (m, 7H), 1.57-1.72 (m, 2H), 1.34-1.48 (m, 2H), 0.92-1.02 (m, 2H), 0.61-0.71 (m, 2H) |
| 249 | 790 | 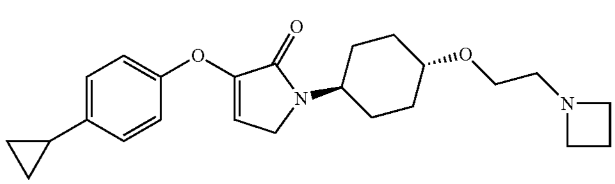 [SMILES: O=C1C(Oc2ccc(C3CC3)cc2)=CCN1[C@H]1CC[C@H](OCCN2CCC2)CC1] | B8 | Method 1 (6.93) 2 (7.08) | 397.4 | $^1$H NMR (400 MHz, CD$_3$OD) δ 7.01-7.16 (m, 4H), 5.83-5.91 (m, 1H), 3.86-4.04 (m, 5H), 3.65-3.78 (m, 4H), 3.54-3.63 (m, 1H), 2.87-3.01 (m, 2H), 2.09- |

TABLE I-continued

| Example No. | Ki (nM) | Structure | Synthetic Procedure Used | HPLC Methods ($t_R$ min) | MS (M + H) | NMR Data |
|---|---|---|---|---|---|---|
| | | | | | | 2.33 (m, 2H), 1.82-1.92 (m, 4H), 1.59-1.72 (m, 2H), 1.31-1.48 (m, 3H), 0.92-1.00 (m, 2H), 0.59-0.72 (m, 2H) |
| 250 | 51 | 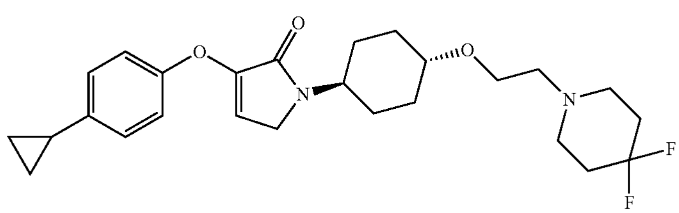 [SMILES: O=C1C(Oc2ccc(C3CC3)cc2)=CCN1[C@H]1CC[C@H](OCCN2CCC(F)(F)CC2)CC1] | Method B8 | 1 (7.43) 2 (7.75) | 461.2 | $^1$H NMR (400 MHz, DMSO-$d_6$) δ 6.99-7.15 (m, 4H), 5.93-6.02 (m, 1H), 3.69-3.90 (m, 5H), 3.57-3.66 (m, 3H), 3.12-3.34 (m, 4H), 2.21-2.42 (m, 4H), 2.06-2.15 (m, 2H), 1.87-1.97 (m, 1H), 1.68-1.81 (m, 2H), 1.49-1.63 (m, 2H), 1.27-1.41 (m, 2H), 0.88-0.97 (m, 2H), 0.60-0.69 (m, 2H) |
| 251 | | 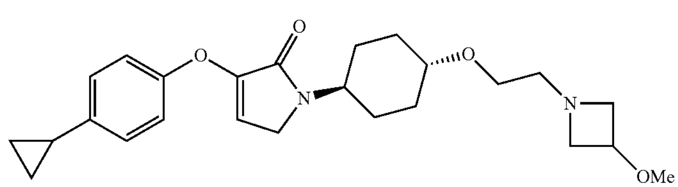 [SMILES: COC1CN(CCO[C@H]2CC[C@H](N3CC=C(Oc4ccc(C5CC5)cc4)C3=O)CC2)C1] | Method B8 | 1 (7.04) 2 (7.22) | 427.4 | $^1$H NMR (400 MHz, CD$_3$OD) δ 7.10-7.18 (m, 2H), 7.06 (s, 2H), 5.81-5.91 (m, 1H), 4.06-4.16 (m, 1H), 3.89-4.03 (m, 4H), 3.79-3.87 (m, 2H), 3.54-3.62 (m, 2H), 3.29 (s, 3H), 2.82-2.90 (m, 2H), 2.12-2.23 (m, 2H), 1.83-1.99 (m, 5H), 1.57-1.71 (m, 3H), 1.30-1.45 (m, 2H), 0.91-1.02 (m, 2H), 0.62-0.71 (m, 2H) |

TABLE J

[Structure: core compound with R12, R13 substituents on terminal amine]

| Example No. | Ki (nM) | Structure | Synthetic Procedure Used | HPLC Methods (t_R min) | MS (M + H) | NMR Data |
|---|---|---|---|---|---|---|
| 252 | 0.4 | [pyrrolidine] | Method B9 | 1 (7.03) 2 (7.97) | 427.2 | $^1$H NMR (400 MHz, DMSO-d$_6$) δ 8.04-8.12 (m, 2H), 7.79-7.91 (m, 1H), 7.71-7.79 (m, 1H), 7.13 (d, J = 8.78 Hz, 4H), 6.17-6.25 (m, 1H), 4.49 (d, J = 2.26 Hz, 4H), 2.83-2.98 (m, 2H), 2.41-2.50 (m, 4H), 1.90-2.02 (m, 1H), 1.56-1.71 (m, 4H), 0.89-1.03 (m, 2H), 0.59-0.74 (m, 2H) |
| 253 | 3.8 | [3-methyl-3-hydroxyazetidine] | Method B9 | 1 (6.7) 2 (11.52) | 445.3 | $^1$H NMR (400 MHz, DMSO-d$_6$) δ 8.07 (d, J = 0.75 Hz, 2H), 7.81-7.90 (m, 1H), 7.66-7.75 (m, 1H), 7.12 (d, J = 8.28 Hz, 4H), 6.21 (s, 1H), 5.05 (s, 1H), 4.49 (d, J = 2.51 Hz, 2H), 4.37 (s, 2H), 3.04 (d, J = 7.78 Hz, 2H), 2.85 (s, 2H), 2.69-2.78 (m, 2H), 1.88-2.00 (m, 1H), 1.23 (s, 3H), 0.91-0.99 (m, 2H), 0.61-0.70 (m, 2H) |
| 254 | 1.0 | [3-hydroxypyrrolidine] | Method B9 | 1 (6.65) 2 (7.72) | 445.3 | $^1$H NMR (400 MHz, DMSO-d$_6$) δ 8.04-8.11 (m, 2H), 7.79-7.87 (m, 1H), 7.69-7.78 (m, 1H), 7.05-7.19 (m, 4H), 6.17-6.25 (m, 1H), 4.62-4.71 (m, 1H), 4.44-4.54 (m, 4H), 4.07-4.19 (m, 1H), 2.83-2.93 (m, 2H), 2.65-2.78 (m, 1H), 2.54-2.63 (m, 2H), 2.25-2.36 (m, 1H), 1.85-2.01 (m, 2H), 1.43-1.54 (m, 1H), 0.90-1.00 (m, 2H), 0.61-0.71 (m, 2H) |
| 255 | 2.8 | [3-methoxyazetidine] | Method B9 | 1 (6.89) 2 (8.08) | 445.2 | $^1$H NMR (400 MHz, DMSO-d$_6$) δ 8.00-8.11 (m, 2H), 7.78-7.89 (m, 1H), 7.67-7.74 (m, 1H), 7.13 (d, J = 8.28 Hz, 4H), 6.17-6.25 (m, 1H), 4.45-4.55 (m, 2H), 4.31-4.42 (m, 2H), 3.78-3.89 (m, 1H), 3.34-3.39 (m, 2H), 3.08 (s, 3H), 2.82-2.92 (m, 2H), 2.67-2.76 (m, 2H), 1.90-2.02 (m, 1H), 0.89-1.01 (m, 2H), 0.63-0.71 (m, 2H) |
| 256 | 1.9 | [3-hydroxyazetidine] | Method B9 | 1 (6.75) 2 (7.67) | 431.2 | $^1$H NMR (400 MHz, DMSO-d$_6$) δ 8.03-8.12 (m, 2H), 7.80-7.88 (m, 1H), 7.66-7.75 (m, 1H), 7.04-7.21 (m, 4H), 6.16-6.25 (m, 1H), 5.14-5.22 (m, 1H), 4.44-4.54 (m, 2H), 4.31-4.41 (m, 2H), 3.96-4.08 (m, 1H), 3.34-3.38 (m, 1H), 2.80-2.88 (m, 2H), 2.58-2.65 (m, 2H), 1.90-2.00 (m, 1H), 0.90-1.00 (m, 2H), 0.61-0.72 (m, 2H) |
| 257 | 0.8 | [3-hydroxypiperidine] | Method B9 | 1 (6.94) 2 (7.94) | 459.4 | $^1$H NMR (400 MHz, DMSO-d$_6$) δ 8.03-8.14 (m, 2H), 7.80-7.88 (m, 1H), 7.69-7.78 (m, 1H), 7.13 (d, J = 8.53 Hz, 4H), 6.16-6.26 (m, 1H), 4.44-4.59 (m, 5H), 2.65-2.93 (m, 4H), 1.86-2.00 (m, 2H), 1.69-1.83 (m, 2H), 1.51-1.60 (m, 1H), 1.26-1.36 (m, 1H), 0.99-1.08 (m, 1H), 0.91-0.98 (m, 2H), 0.60-0.70 (m, 2H) |

TABLE J-continued

| Example No. | Ki (nM) | Structure | Synthetic Procedure Used | HPLC Methods (t_R min) | MS (M + H) | NMR Data |
|---|---|---|---|---|---|---|
| 258 | 9.5 | 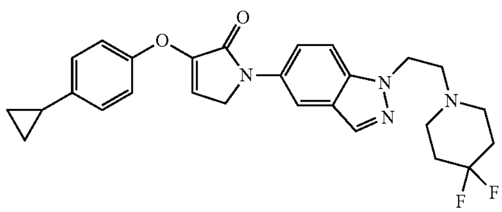 [SMILES: O=C1C(Oc2ccc(C3CC3)cc2)=CCN1c1ccc2c(cnn2CCN2CCC(F)(F)CC2)c1] | Method B9 | 1 (7.53) 2 (8.72) | 479.4 | $^1$H NMR (400 MHz, DMSO-d$_6$) δ 8.04-8.15 (m, 2H), 7.82-7.90 (m, 1H), 7.72-7.81 (m, 1H), 7.13 (d, J = 9.03 Hz, 4H), 6.21 (s, 1H), 4.49 (d, J = 2.26 Hz, 4H), 2.81-2.91 (m, 2H), 2.52-2.62 (m, 4H), 1.78-1.99 (m, 5H), 0.91-1.00 (m, 2H), 0.62-0.71 (m, 2H) |
| 259 | 1.2 | 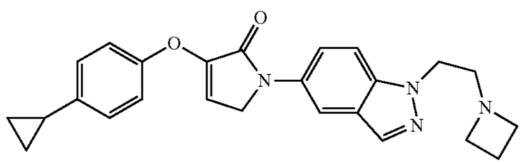 [SMILES: O=C1C(Oc2ccc(C3CC3)cc2)=CCN1c1ccc2c(cnn2CCN2CCC2)c1] | Method B9 | 1 (6.50) 2 (7.99) | 415.3 | $^1$H NMR (400 MHz, DMSO-d$_6$) δ 8.18-8.23 (m, 1H), 8.10-8.15 (m, 1H), 7.88-7.97 (m, 1H), 7.76-7.85 (m, 1H), 7.04-7.19 (m, 4H), 6.18-6.26 (m, 1H), 4.64-4.72 (m, 2H), 4.44-4.53 (m, 2H), 3.83-3.98 (m, 4H), 3.62-3.73 (m, 2H), 2.14-2.37 (m, 2H), 1.90-2.01 (m, 1H), 0.90-1.01 (m, 2H), 0.61-0.71 (m, 2H) |
| 260 | 0.6 | 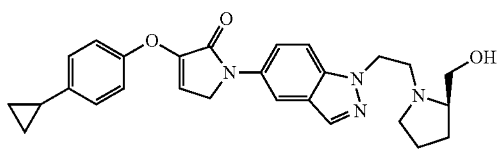 [SMILES: O=C1C(Oc2ccc(C3CC3)cc2)=CCN1c1ccc2c(cnn2CCN2CCC[C@@H]2CO)c1] | Method B9 | 1 (6.56) 2 (8.04) | 459.4 | $^1$H NMR (400 MHz, DMSO-d$_6$) δ 8.02-8.21 (m, 2H), 7.68-7.96 (m, 2H), 7.05-7.20 (m, 4H), 6.17-6.27 (m, 1H), 4.38-4.58 (m, 4H), 4.18-4.32 (m, 1H), 3.20-3.30 (m, 2H), 2.96-3.12 (m, 2H), 2.71-2.81 (m, 1H), 2.17-2.29 (m, 1H), 1.91-2.01 (m, 1H), 1.38-1.85 (m, 4H), 0.91-1.01 (m, 2H), 0.62-0.71 (m, 2H) |
| 261 | 1.7 | 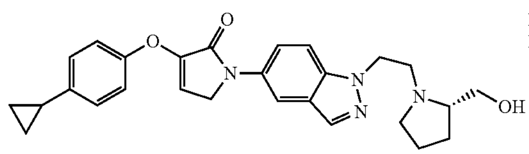 [SMILES: O=C1C(Oc2ccc(C3CC3)cc2)=CCN1c1ccc2c(cnn2CCN2CCC[C@H]2CO)c1] | Method B9 | 1 (6.56) 2 (8.01) | 459.4 | $^1$H NMR (400 MHz, DMSO-d$_6$) δ 8.03-8.14 (m, 2H), 7.81-7.90 (m, 1H), 7.68-7.79 (m, 1H), 7.02-7.20 (m, 4H), 6.14-6.26 (m, 1H), 4.41-4.58 (m, 4H), 4.21-4.35 (m, 1H), 3.17-3.30 (m, 2H), 2.95-3.12 (m, 2H), 2.69-2.81 (m, 1H), 2.14-2.29 (m, 1H), 1.88-2.00 (m, 1H), 1.68-1.81 (m, 1H), 1.48-1.68 (m, 2H), 1.37-1.48 (m, 1H), 0.89-1.01 (m, 2H), 0.61-0.71 (m, 2H) |
| 262 | 1.1 | 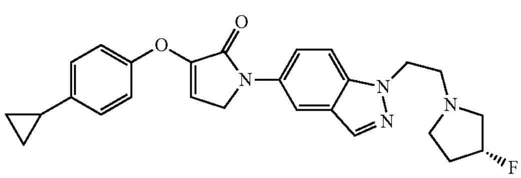 [SMILES: O=C1C(Oc2ccc(C3CC3)cc2)=CCN1c1ccc2c(cnn2CCN2CC[C@@H](F)C2)c1] | Method B9 | 1 (6.95) 2 (8.19) | 447.2 | $^1$H NMR (400 MHz, DMSO-d$_6$) δ 8.02-8.09 (m, 2H), 7.79-7.86 (m, 1H), 7.71-7.77 (m, 1H), 7.02-7.18 (m, 4H), 6.13-6.23 (m, 1H), 5.01-5.24 (m, 1H), 4.41-4.54 (m, 4H), 2.84-2.94 (m, 2H), 2.72-2.81 (m, 1H), 2.51-2.68 (m, 2H), 2.25-2.37 (m, 1H), 1.69-2.12 (m, 3H), 0.86-0.99 (m, 2H), 0.57-0.69 (m, 2H) |
| 263 | 1.5 | 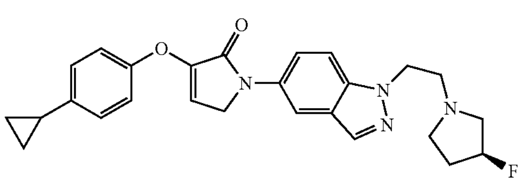 [SMILES: O=C1C(Oc2ccc(C3CC3)cc2)=CCN1c1ccc2c(cnn2CCN2CC[C@H](F)C2)c1] | Method B9 | 1 (6.90) 2 (8.45) | 447.2 | $^1$H NMR (400 MHz, DMSO-d$_6$) δ 8.02-8.12 (m, 2H), 7.81-7.87 (m, 1H), 7.69-7.78 (m, 1H), 7.04-7.18 (m, 4H), 6.14-6.28 (m, 1H), 5.04-5.28 (m, 1H), 4.44-4.55 (m, 4H), 2.89-2.95 (m, 2H), 2.75-2.82 (m, 1H), 2.53-2.70 (m, 2H), 2.29-2.40 (m, 1H), 1.70-2.15 (m, 3H), 0.91-1.01 (m, 2H), 0.62-0.71 (m, 2H) |
| 264 | 0.8 | 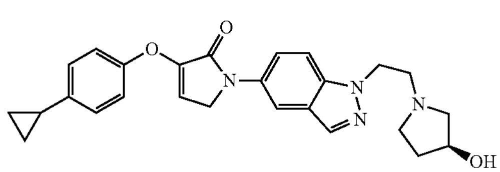 [SMILES: O=C1C(Oc2ccc(C3CC3)cc2)=CCN1c1ccc2c(cnn2CCN2CC[C@H](O)C2)c1] | Method B9 | 1 (6.61) 2 (7.96) | 445.3 | $^1$H NMR (400 MHz, DMSO-d$_6$) δ 8.02-8.13 (m, 2H), 7.79-7.88 (m, 1H), 7.68-7.78 (m, 1H), 7.06-7.19 (m, 4H), 6.16-6.26 (m, 1H), 4.60-4.69 (m, 1H), 4.45-4.55 (m, 4H), 4.07-4.19 (m, 1H), 2.83-2.93 (m, 2H), 2.65-2.78 (m, 1H), 2.53-2.63 (m, 1H), 2.28-2.37 (m, 1H), |

TABLE J-continued

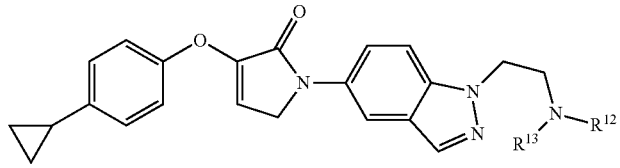

| Example No. | Ki (nM) | Structure | Synthetic Procedure Used | HPLC Methods ($t_R$ min) | MS (M + H) | NMR Data |
|---|---|---|---|---|---|---|
| | | | | | | 1.85-2.00 (m, 2H), 1.44-1.55 (m, 1H), 0.91-1.01 (m, 2H), 0.62-0.72 (m, 2H) |
| 265 | 59 | 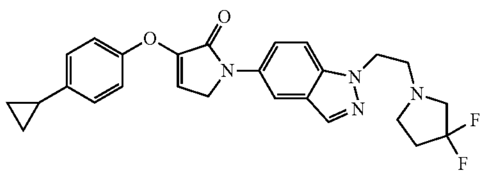 [SMILES: O=C1C(Oc2ccc(C3CC3)cc2)=CCN1c1ccc2c(cnn2CCN2CCC(F)(F)C2)c1] | Method B9 | 1 (7.70) 2 (8.27) | 465.4 | $^1$H NMR (400 MHz, DMSO-d$_6$) δ 8.05-8.14 (m, 2H), 7.81-7.89 (m, 1H), 7.72-7.80 (m, 1H), 7.06-7.19 (m, 4H), 6.16-6.26 (m, 1H), 4.45-4.59 (m, 5H), 2.88-2.98 (m, 4H), 2.67-2.77 (m, 3H), 2.10-2.25 (m, 2H), 1.89-2.01 (m, 1H), 0.91-1.00 (m, 2H), 0.62-0.71 (m, 2H) |
| 266 | 0.7 | 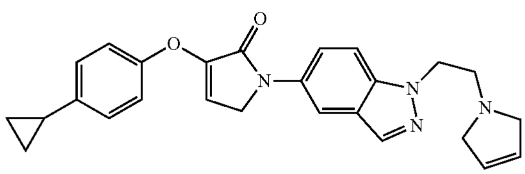 [SMILES: O=C1C(Oc2ccc(C3CC3)cc2)=CCN1c1ccc2c(cnn2CCN2CC=CC2)c1] | Method B9 | 1 (7.04) 2 (7.77) | 427.3 | $^1$H NMR (400 MHz, DMSO-d$_6$) δ 8.03-8.12 (m, 2H), 7.79-7.88 (m, 1H), 7.70-7.79 (m, 1H), 7.04-7.19 (m, 4H), 6.15-6.27 (m, 1H), 5.69-5.79 (m, 2H), 4.44-4.56 (m, 4H), 3.37-3.46 (m, 4H), 3.03-3.12 (m, 2H), 1.88-2.02 (m, 1H), 0.92-1.00 (m, 2H), 0.61-0.71 (m, 2H) |
| 267 | 118 | 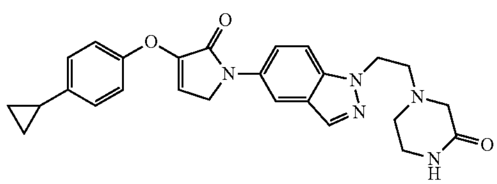 [SMILES: O=C1CN(CCn2ncc3cc(N4CC=C(Oc5ccc(C6CC6)cc5)C4=O)ccc32)CCN1] | Method B9 | 1 (6.83) 2 (7.27) | 458.3 | $^1$H NMR (400 MHz, DMSO-d$_6$) δ 8.08 (d, J = 0.75 Hz, 2H), 7.74-7.89 (m, 2H), 7.61-7.71 (m, 1H), 7.13 (d, J = 8.78 Hz, 4H), 6.17-6.25 (m, 1H), 4.49 (d, J = 2.26 Hz, 4H), 3.03-3.11 (m, 2H), 2.98 (s, 2H), 2.81-2.90 (m, 2H), 2.56-2.65 (m, 2H), 1.89-2.00 (m, 1H), 0.91-1.00 (m, 2H), 0.60-0.71 (m, 2H) |

TABLE K

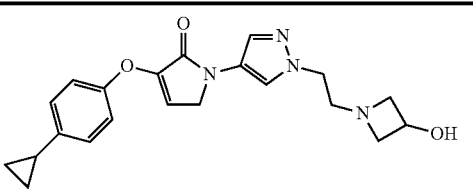

| Example No. | Ki (nM) | Structure | Synthetic Procedure Used | HPLC Methods ($t_R$ min) | MS (M + H) | NMR Data |
|---|---|---|---|---|---|---|
| 268 | 923 | 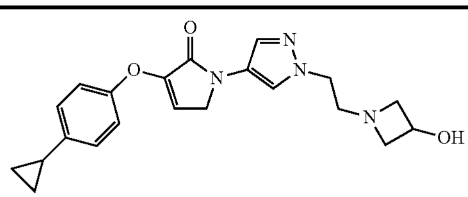 | Method B10 | 1 (6.07) 2 (7.17) | 381.2 | $^1$H NMR (400 MHz, CDCl$_3$) δ 8.07-8.15 (m, 1H), 7.44-7.58 (m, 1H), 7.07 (d, J = 3.26 Hz, 4H), 5.67-5.77 (m, 1H), 4.34-4.48 (m, 1H), 4.03-4.19 (m, 4H), 3.55-3.67 (m, 2H), 2.93 (s, 4H), 1.83-1.96 (m, 1H), 0.92-1.02 (m, 2H), 0.62-0.72 (m, 2H) |

TABLE K-continued

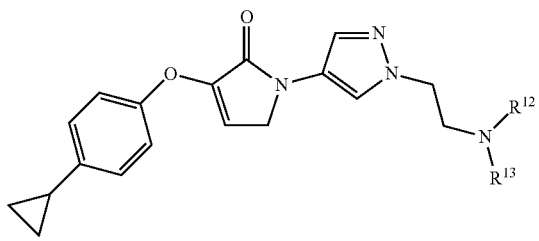

| Example No. | Ki (nM) | Structure | Synthetic Procedure Used | HPLC Methods ($t_R$ min) | MS (M + H) | NMR Data |
|---|---|---|---|---|---|---|
| 269 | 1410 | 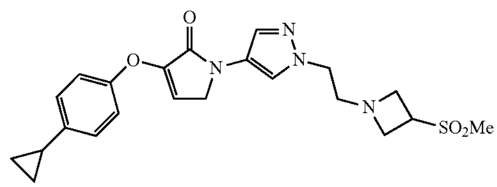 [SMILES: CS(=O)(=O)C1CN(CCn2cc(N3CC=C(Oc4ccc(C5CC5)cc4)C3=O)cn2)C1] | Method B10 | 1 (6.28) 2 (7.58) | 443.2 | $^1$H NMR (400 MHz, CDCl$_3$) δ 8.06-8.15 (m, 1H), 7.44-7.53 (m, 1H), 7.02-7.13 (m, 4H), 5.68-5.78 (m, 1H), 4.07-4.19 (m, 4H), 3.74-3.88 (m, 1H), 3.43-3.60 (m, 4H), 2.90 (s, 5H), 1.84-1.96 (m, 1H), 0.93-1.04 (m, 2H), 0.62-0.74 (m, 2H) |
| 270 | 400 | 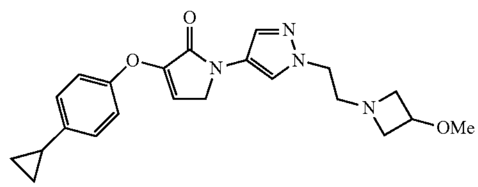 [SMILES: COC1CN(CCn2cc(N3CC=C(Oc4ccc(C5CC5)cc4)C3=O)cn2)C1] | Method B10 | 1 (6.06) 2 (7.99) | 395.2 | $^1$H NMR (400 MHz, CDCl$_3$) δ 8.07 (s, 1H), 7.50 (d, J = 0.50 Hz, 1H), 7.02-7.12 (m, 4H), 5.72 (t, J = 2.38 Hz, 1H), 4.06-4.21 (m, 4H), 3.99 (t, J = 5.88 Hz, 1H), 3.51-3.63 (m, 2H), 3.22 (s, 3H), 2.83-2.99 (m, 4H), 1.88 (d, J = 8.50 Hz, 1H), 0.88-1.04 (m, 2H), 0.64-0.71 (m, 2H) |

TABLE L

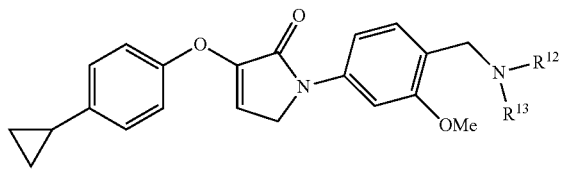

| Example No. | Ki (nM) | Structure | Synthetic Procedure Used | HPLC Methods ($t_R$ min) | MS (M + H) | NMR Data |
|---|---|---|---|---|---|---|
| 271 | 99 | 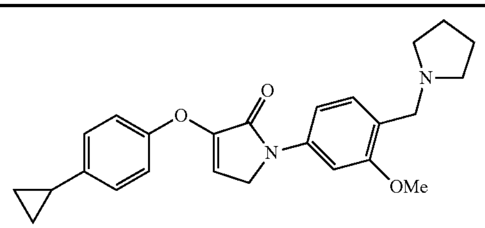 | Method B11 | 1 (7.1) 2 (8.32) | 405.2 | $^1$H NMR (400 MHz, DMSO-d$_6$) δ 7.51-7.60 (m, 1H), 7.23-7.39 (m, 2H), 7.03-7.19 (m, 4H), 6.14-6.29 (m, 1H), 4.41-4.51 (m, 2H), 3.76-3.85 (m, 3H), 3.51-3.68 (m, 2H), 2.40-2.50 (m, 4H), 1.91-2.01 (m, 1H), 1.63-1.80 (m, 4H), 0.92-1.00 (m, 2H), 0.62-0.70 (m, 2H) |
| 272 | 520 | 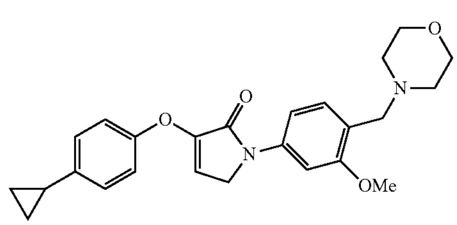 [SMILES: COc1cc(N2CC=C(Oc3ccc(C4CC4)cc3)C2=O)ccc1CN1CCOCC1] | Method B11 | 1 (6.86) 2 (8.25) | 421.2 | $^1$H NMR (400 MHz, DMSO-d$_6$) δ 7.50-7.57 (m, 1H), 7.24-7.34 (m, 2H), 7.04-7.18 (m, 4H), 6.16-6.29 (m, 1H), 4.39-4.51 (m, 2H), 3.80 (s, 3H), 3.53-3.63 (m, 4H), 3.40-3.47 (m, 2H), 2.32-2.42 (m, 4H), 1.89-1.99 (m, 1H), 0.89-0.99 (m, 2H), 0.60-0.70 (m, 2H) |

TABLE L-continued

| Example No. | Ki (nM) | Structure | Synthetic Procedure Used | HPLC Methods ($t_R$ min) | MS (M + H) | NMR Data |
|---|---|---|---|---|---|---|
| 273 | 189 | 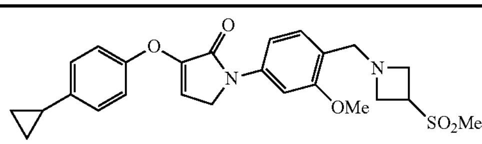 | Method B11 | 1 (6.95) 2 (8.57) | 469.2 | $^1$H NMR (400 MHz, DMSO-d$_6$) δ 7.47-7.56 (m, 1H), 7.20-7.31 (m, 2H), 7.04-7.18 (m, 4H), 6.14-6.31 (m, 1H), 4.40-4.51 (m, 2H), 4.07-4.21 (m, 1H), 3.80 (s, 3H), 3.49-3.62 (m, 4H), 3.38-3.46 (m, 2H), 2.96 (s, 3H), 1.89-2.01 (m, 1H), 0.92-1.00 (m, 2H), 0.60-0.69 (m, 2H) |
| 274 | 370 | 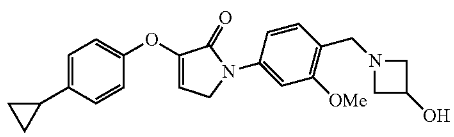 [SMILES: COc1cc(N2CC=C(Oc3ccc(C4CC4)cc3)C2=O)ccc1CN1CC(O)C1] | Method B11 | 1 (6.72) 2 (7.98) | 405.2 | $^1$H NMR (400 MHz, DMSO-d$_6$) δ 7.44-7.55 (m, 1H), 7.18-7.30 (m, 2H), 7.03-7.17 (m, 4H), 6.17-6.29 (m, 1H), 5.16-5.29 (m, 1H), 4.39-4.48 (m, 1H), 4.08-4.25 (m, 1H), 3.76-3.82 (m, 2H), 3.45-3.53 (m, 3H), 2.70-2.79 (m, 2H), 2.52-2.60 (m, 2H), 1.89-1.99 (m, 1H), 0.91-1.00 (m, 2H), 0.61-0.71 (m, 2H) |
| 275 | 191 | 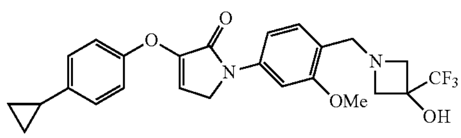 [SMILES: COc1cc(N2CC=C(Oc3ccc(C4CC4)cc3)C2=O)ccc1CN1CC(O)(C(F)(F)F)C1] | Method B11 | 1 (7.36) 2 (8.73) | 475.2 | $^1$H NMR (400 MHz, DMSO-d$_6$) δ 7.53 (d, J = 1.76 Hz, 1H), 7.19-7.31 (m, 2H), 7.04-7.17 (m, 4H), 6.85 (s, 1H), 6.24 (s, 1H), 4.44 (d, J = 2.26 Hz, 2H), 3.80 (s, 3H), 3.50-3.65 (m, 4H), 3.18 (d, J = 8.53 Hz, 2H), 1.90-2.01 (m, 1H), 0.95 (dd, J = 2.01, 8.53 Hz, 2H), 0.59-0.72 (m, 2H) |
| 276 | 396 | 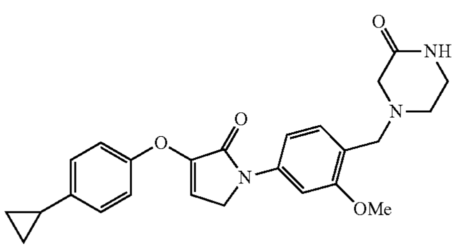 [SMILES: COc1cc(N2CC=C(Oc3ccc(C4CC4)cc3)C2=O)ccc1CN1CCNC(=O)C1] | Method B11 | 1 (6.48) 2 (7.79) | 434.2 | $^1$H NMR (400 MHz, DMSO-d$_6$) δ 7.66-7.75 (m, 1H), 7.55 (d, J = 1.51 Hz, 1H), 7.27-7.36 (m, 2H), 7.04-7.18 (m, 4H), 6.25 (s, 1H), 4.45 (d, J = 2.26 Hz, 2H), 3.81 (s, 3H), 3.52 (s, 2H), 3.14 (br. s., 2H), 2.92 (s, 2H), 2.55 (s, 2H), 1.88-2.02 (m, 1H), 0.95 (dd, J = 2.01, 8.53 Hz, 2H), 0.61-0.71 (m, 2H) |
| 277 | 154 | 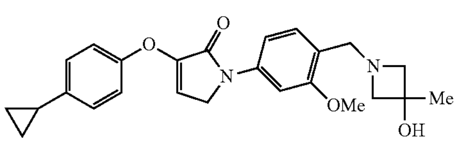 [SMILES: COc1cc(N2CC=C(Oc3ccc(C4CC4)cc3)C2=O)ccc1CN1CC(C)(O)C1] | Method B11 | 1 (7.36) 2 (8.73) | 421.2 | $^1$H NMR (400 MHz, DMSO-d$_6$) δ 7.47-7.56 (m, 1H), 7.21-7.29 (m, 2H), 7.01-7.18 (m, 5H), 6.20-6.28 (m, 1H), 5.07-5.19 (m, 1H), 4.39-4.50 (m, 2H), 3.79 (s, 3H), 3.49-3.57 (m, 2H), 3.13-3.23 (m, 2H), 2.83-2.93 (m, 2H), 1.87-2.00 (m, 1H), 1.31-1.43 (m, 3H), 0.92-1.01 (m, 2H), 0.63-0.72 (m, 2H) |
| 278 | 40 | 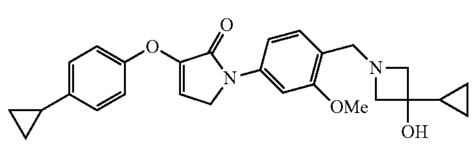 [SMILES: COc1cc(N2CC=C(Oc3ccc(C4CC4)cc3)C2=O)ccc1CN1CC(O)(C2CC2)C1] | Method B11 | 1 (7.06) 2 (8.54) | 447.2 | $^1$H NMR (400 MHz, DMSO-d$_6$) δ 7.45-7.57 (m, 1H), 7.19-7.29 (m, 2H), 7.05-7.18 (m, 4H), 6.17-6.29 (m, 1H), 5.00-5.11 (m, 1H), 4.38-4.49 (m, 2H), 3.79 (s, 3H), 3.49-3.59 (m, 2H), 3.14-3.25 (m, 2H), 2.86-2.96 (m, 2H), 1.90-2.01 (m, 1H), 1.11-1.22 (m, 1H), 0.89-1.00 (m, 2H), 0.60-0.71 (m, 2H), 0.36 (d, J = 6.78 Hz, 4H) |
| 279 | 234 | 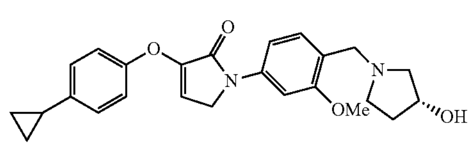 [SMILES: COc1cc(N2CC=C(Oc3ccc(C4CC4)cc3)C2=O)ccc1CN1CC[C@@H](O)C1] | Method B11 | 1 (6.67) 2 (7.97) | 421.2 | $^1$H NMR (400 MHz, DMSO-d$_6$) δ 7.48-7.55 (m, 1H), 7.23-7.34 (m, 2H), 7.04-7.18 (m, 4H), 6.13-6.29 (m, 1H), 4.60-4.71 (m, 1H), 4.39-4.49 (m, 2H), 4.12-4.24 (m, 1H), 3.79 (s, 3H), 3.48-3.59 (m, 2H), 2.63-2.74 (m, 1H), 2.54-2.61 (m, 1H), 2.28-2.46 (m, 2H), 1.92-2.04 (m, 2H), 1.48-1.59 (m, 1H), 0.91-1.00 (m, 2H), 0.62-0.71 (m, 2H) |

TABLE L-continued

| Example No. | Ki (nM) | Structure | Synthetic Procedure Used | HPLC Methods ($t_R$ min) | MS (M + H) | NMR Data |
|---|---|---|---|---|---|---|
| 280 | 335 | 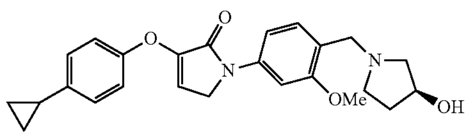 [SMILES: COc1cc(N2CC=C(Oc3ccc(C4CC4)cc3)C2=O)ccc1CN1CC[C@H](O)C1] | Method B11 | 1 (6.67) 2 (7.97) | 421.2 | $^1$H NMR (400 MHz, DMSO-d$_6$) δ 7.47-7.55 (m, 1H), 7.21-7.34 (m, 2H), 7.04-7.18 (m, 4H), 6.19-6.29 (m, 1H), 4.61-4.71 (m, 1H), 4.41-4.50 (m, 2H), 4.10-4.24 (m, 1H), 3.79 (s, 3H), 3.47-3.60 (m, 2H), 2.54-2.73 (m, 2H), 2.28-2.46 (m, 2H), 1.90-2.05 (m, 2H), 1.46-1.60 (m, 1H), 0.91-0.99 (m, 2H), 0.62-0.71 (m, 2H) |
| 281 | 258 | 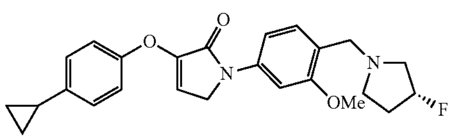 [SMILES: COc1cc(N2CC=C(Oc3ccc(C4CC4)cc3)C2=O)ccc1CN1CC[C@@H](F)C1] | Method B11 | 1 (7.64) 2 (7.99) | 423.2 | $^1$H NMR (400 MHz, DMSO-d$_6$) δ 7.54 (d, J = 1.76 Hz, 1H), 7.23-7.35 (m, 2H), 7.04-7.19 (m, 4H), 6.24 (t, J = 2.38 Hz, 1H), 5.08-5.47 (m, 1H), 4.45 (d, J = 2.26 Hz, 2H), 3.80 (s, 3H), 3.56-3.65 (m, 3H), 2.56-2.87 (m, 3H), 2.29-2.42 (m, 1H), 2.02-2.23 (m, 2H), 0.89-1.00 (m, 2H), 0.60-0.71 (m, 2H) |

TABLE M

| Example No. | Ki (nM) | Structure | Synthetic Procedure Used | HPLC Methods ($t_R$ min) | MS (M + H) | NMR Data |
|---|---|---|---|---|---|---|
| 282 | | 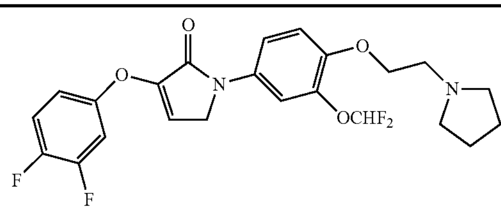 | Method B12 | 1 (7.28) 2 (7.98) | 467.2 | $^1$H NMR (400 MHz, DMSO-d$_6$) δ 7.73-7.82 (m, 1H), 7.40-7.62 (m, 3H), 6.95-7.38 (m, 3H), 6.50-6.57 (m, 1H), 4.38-4.51 (m, 2H), 4.18-4.32 (m, 2H), 3.32-3.39 (m, 4H), 2.52-2.57 (m, 2H), 1.64-1.90 (m, 4H) |
| 283 | | 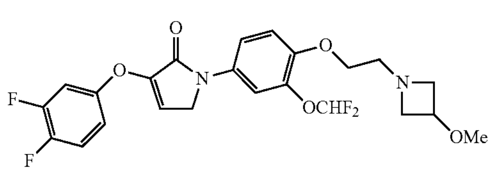 [SMILES: COC1CN(CCOc2ccc(N3CC=C(Oc4ccc(F)c(F)c4)C3=O)cc2OC(F)F)C1] | Method B13 | 1 (7.27) 2 (7.99) | 483.2 | $^1$H NMR (400 MHz, DMSO-d$_6$) δ 7.76 (d, J = 2.01 Hz, 1H), 7.39-7.59 (m, 3H), 6.89-7.34 (m, 3H), 6.53 (s, 1H), 4.45 (d, J = 1.51 Hz, 2H), 4.06 (t, J = 4.89 Hz, 3H), 3.71 (br. s., 2H), 3.52 (br. s., 1H), 3.17 (s, 4H), 2.93 (br. s., 2H) |

TABLE M-continued

![Structure: 3-(3,4-difluorophenoxy)-1-[4-(2-NR12R13-ethoxy)-3-(OCHF2)phenyl]-pyrrol-2(5H)-one common core]

| Example No. | Ki (nM) | Structure | Synthetic Procedure Used | HPLC Methods ($t_R$ min) | MS (M + H) | NMR Data |
|---|---|---|---|---|---|---|
| 284 | | ![structure with azetidine-OH, OMe] | Method B13 | 1 (6.71) 2 (8.12) | 483.2 | $^1$H NMR (400 MHz, DMSO-d$_6$) δ 7.75 (d, J = 2.51 Hz, 1H), 7.40-7.59 (m, 3H), 6.95-7.38 (m, 3H), 6.52 (t, J = 2.26 Hz, 1H), 5.19-5.42 (m, 1H), 4.45 (d, J = 2.26 Hz, 2H), 4.09 (t, J = 5.02 Hz, 2H), 3.10-3.50 (m, 5H), 2.95 (br. s., 1H), 1.36 (s, 3H) |
| 285 | | ![structure with (S)-3-fluoropyrrolidine] | Method B13 | 1 (7.27) 2 (8.04) | 485.2 | $^1$H NMR (400 MHz, DMSO-d$_6$) δ 7.71-7.80 (m, 1H), 7.39-7.59 (m, 3H), 6.90-7.34 (m, 3H), 6.47-6.58 (m, 1H), 5.07-5.31 (m, 1H), 4.40-4.52 (m, 2H), 4.11-4.22 (m, 2H), 2.78-3.02 (m, 4H), 2.59-2.75 (m, 1H), 2.31-2.44 (m, 1H), 2.03-2.23 (m, 1H), 1.74-1.96 (m, 1H) |
| 286 | | ![structure with (R)-3-fluoropyrrolidine] | Method B13 | 1 (7.28) 2 (8.03) | 485.2 | $^1$H NMR (400 MHz, DMSO-d$_6$) δ 7.72-7.78 (m, 1H), 7.39-7.60 (m, 3H), 6.90-7.34 (m, 3H), 6.46-6.57 (m, 1H), 5.06-5.31 (m, 1H), 4.40-4.52 (m, 2H), 4.10-4.23 (m, 2H), 2.78-3.00 (m, 4H), 2.59-2.76 (m, 1H), 2.35-2.43 (m, 1H), 2.04-2.23 (m, 1H), 1.78-1.95 (m, 1H) |
| 287 | | ![structure with 3,3-difluoropyrrolidine] | Method B12 | 1 (7.72) 2 (8.35) | 503.0 | $^1$H NMR (400 MHz, DMSO-d$_6$) δ 7.72-7.80 (m, 1H), 7.39-7.59 (m, 3H), 6.91-7.33 (m, 3H), 6.49-6.55 (m, 1H), 4.40-4.51 (m, 2H), 4.09-4.21 (m, 2H), 2.94-3.07 (m, 2H), 2.76-2.89 (m, 4H), 2.15-2.30 (m, 2H) |
| 288 | | ![structure with 2,5-dihydropyrrole] | Method B12 | 1 (7.23) 2 (7.97) | 465.2 | $^1$H NMR (400 MHz, DMSO-d$_6$) δ 7.73-7.80 (m, 1H), 7.39-7.59 (m, 3H), 7.05-7.34 (m, 3H), 6.49-6.56 (m, 1H), 5.77-5.83 (m, 1H), 4.42-4.49 (m, 2H), 4.11-4.18 (m, 2H), 3.51 (s, 4H), 2.93-3.02 (m, 2H) |
| 289 | | ![structure with 4,4-difluoropiperidine] | Method B12 | 1 (7.41) 2 (9.01) | 517.2 | $^1$H NMR (400 MHz, DMSO-d$_6$) δ 7.71-7.84 (m, 1H), 7.40-7.62 (m, 3H), 6.93-7.36 (m, 3H), 6.50-6.56 (m, 1H), 4.46 (d, J = 2.01 Hz, 2H), 4.06-4.25 (m, 2H), 2.58-2.89 (m, 6H), 1.85-2.04 (m, 4H) |
| 290 | | ![structure with 3-hydroxypiperidine] | Method B12 | 1 (6.71) 2 (8.16) | 497.2 | $^1$H NMR (400 MHz, DMSO-d$_6$) δ 7.75 (br. s., 1H), 7.50 (d, J = 10.29 Hz, 3H), 6.92-7.39 (m, 3H), 6.53 (t, J = 2.26 Hz, 1H), 4.52-4.72 (m, 1H), 4.46 (d, J = 2.26 Hz, 2H), 4.10-4.33 (m, 2H), 3.41-3.60 (m, 1H), 2.60-3.04 (m, 3H), 1.57-2.08 (m, 4H), 1.32-1.54 (m, 1H), 0.96-1.19 (m, 1H) |

TABLE M-continued

General structure: 3-(3,4-difluorophenoxy)-1-[4-(2-NR¹²R¹³-ethoxy)-3-(OCHF₂)phenyl]-1H-pyrrol-2(5H)-one

| Example No. | Ki (nM) | Structure | Synthetic Procedure Used | HPLC Methods (t_R min) | MS (M+H) | NMR Data |
|---|---|---|---|---|---|---|
| 291 | | morpholine | Method B12 | 1 (6.79), 2 (8.29) | 483 | $^1$H NMR (400 MHz, DMSO-d$_6$) δ 7.70-7.84 (m, 1H), 7.39-7.60 (m, 3H), 6.97-7.38 (m, 3H), 6.49-6.57 (m, 1H), 4.46 (d, J = 2.01 Hz, 2H), 4.12-4.25 (m, 2H), 3.49-3.67 (m, 4H), 2.63-2.78 (m, 2H), 2.53-2.60 (m, 2H), 2.41-2.49 (m, 2H) |
| 292 | | piperazinone | Method B12 | 1 (6.52), 2 (7.71) | 496.0 | $^1$H NMR (400 MHz, DMSO-d$_6$) δ 7.75 (d, J = 2.51 Hz, 2H), 7.39-7.60 (m, 3H), 7.13 (s, 3H), 6.53 (s, 1H), 4.46 (d, J = 2.26 Hz, 2H), 4.13-4.27 (m, 2H), 3.01-3.22 (m, 4H), 2.65-2.86 (m, 4H) |
| 293 | | (R)-3-hydroxypyrrolidine | Method B12 | 1 (6.94), 2 (7.76) | 483.2 | $^1$H NMR (400 MHz, DMSO-d$_6$) δ 7.75 (d, J = 2.51 Hz, 1H), 7.53 (d, J = 2.51 Hz, 3H), 6.93-7.35 (m, 3H), 6.52 (s, 1H), 4.68-4.78 (m, 1H), 4.45 (d, J = 2.26 Hz, 2H), 4.15 (s, 3H), 2.64-2.91 (m, 4H), 2.55-2.60 (m, 1H), 2.41-2.48 (m, 1H), 1.90-2.04 (m, 1H), 1.48-1.62 (m, 1H) |
| 294 | | (S)-3-hydroxypyrrolidine | Method B12 | 1 (6.62), 2 (7.84) | 483.2 | $^1$H NMR (400 MHz, DMSO-d$_6$) δ 7.69-7.78 (m, 1H), 7.38-7.59 (m, 3H), 6.91-7.34 (m, 3H), 6.46-6.57 (m, 1H), 4.69-4.78 (m, 1H), 4.40-4.49 (m, 2H), 4.10-4.24 (m, 3H), 2.65-2.93 (m, 4H), 2.55-2.61 (m, 1H), 2.40-2.47 (m, 1H), 1.91-2.05 (m, 1H), 1.46-1.61 (m, 1H) |
| 295 | | (S)-2-(hydroxymethyl)pyrrolidine | Method B12 | 1 (6.69), 2 (7.95) | 497.2 | $^1$H NMR (400 MHz, DMSO-d$_6$) d 7.70-7.77 (m, 1H), 7.40-7.58 (m, 3H), 6.94-7.38 (m, 3H), 6.48-6.55 (m, 1H), 4.41-4.52 (m, 1H), 4.07-4.18 (m, 1H), 3.05-3.20 (m, 2H), 2.61-2.71 (m, 2H), 2.54-2.58 (m, 1H), 2.19-2.37 (m, 2H), 1.75-1.85 (m, 1H), 1.44-1.73 (m, 3H) |
| 296 | | (R)-2-(hydroxymethyl)pyrrolidine | Method B12 | 1 (6.69), 2 (7.93) | 497.2 | $^1$H NMR (400 MHz, DMSO-d$_6$) δ 7.71-7.78 (m, 1H), 7.39-7.58 (m, 3H), 6.92-7.38 (m, 3H), 6.47-6.55 (m, 1H), 4.41-4.51 (m, 2H), 4.08-4.18 (m, 3H), 3.04-3.25 (m, 3H), 2.60-2.72 (m, 2H), 2.24-2.36 (m, 2H), 1.75-1.84 (m, 1H), 1.57-1.71 (m, 3H) |
| 297 | | 3,3-difluoroazetidine | Method B12 | 1 (7.24), 2 (8.39) | 489.0 | $^1$H NMR (400 MHz, DMSO-d$_6$) δ 7.72-7.80 (m, 1H), 7.38-7.59 (m, 3H), 6.90-7.32 (m, 3H), 6.49-6.57 (m, 1H), 4.42-4.51 (m, 2H), 4.01-4.12 (m, 2H), 3.69 (s, 4H), 2.88-2.98 (m, 2H) |

TABLE N

| Example No. | Ki (nM) | Structure | Synthetic Procedure Used | HPLC Methods ($t_R$ min) | MS (M + H) | NMR Data |
|---|---|---|---|---|---|---|
| 298 | 6 | 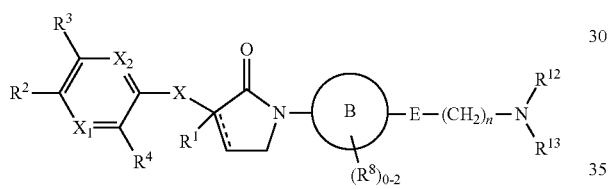 | Method B13 | 1 (6.96) 2 (8.22) | 407.4 | NMR (400 MHz, DMSO-$d_6$) δ 7.44-7.54 (m, 1H), 7.15-7.20 (m, 1H), 7.09-7.14 (m, 2H), 7.02-7.08 (m, 3H), 6.08-6.21 (m, 1H), 4.94-5.07 (m, 1H), 4.32-4.45 (m, 2H), 3.78 (s, 4H), 3.27-3.44 (m, 4H), 2.07-2.19 (m, 2H), 1.83-1.97 (m, 1H), 0.89-0.99 (m, 2H), 0.58-0.67 (m, 2H) |
| 299 | 239 | 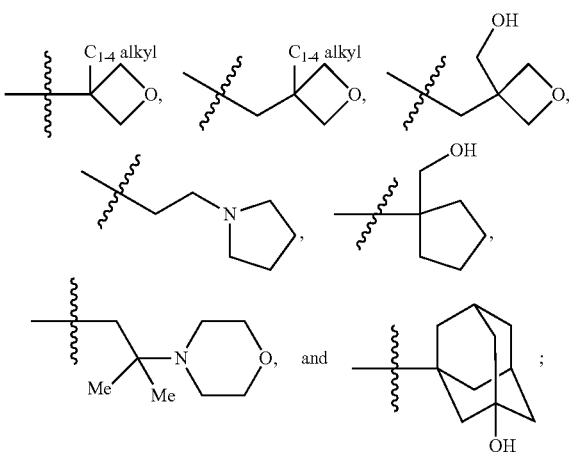 | A7 except alkylated with N-(2-chloroethyl) imidazole | 1 3.56 | 440 | $^1$H NMR (CDCl$_3$, 400 MHz) δ 9.10 (1H, br s), 7.67 (1H, s), 7.47 (1H, s), 7.39 (1H, s), 7.16 (2H, d, J = 9.0 Hz), 7.09 (2H, d, J = 9.2 Hz), 6.85 (2H, s), 5.02 (1H, t, J = 7.7 Hz), 4.60 (2H, br s), 4.34 (2H, br s), 3.86 (3H, s), 3.78-3.95 (2H, m), 2.64-2.76 (1H, m), 2.27-2.38 (1H, m). |

What is claimed is:

1. A compound of Formula II:

(II)

[structure of Formula II]

or a stereoisomer, a tautomer, or a pharmaceutically acceptable salt thereof, wherein:

= = = is independently a single or double bond; provided that when = = = is a single bond, $R^1$ is H or $C_{1-4}$ alkyl; and when = = = is a double bond $R^1$ is absent;

X is independently O or S;

$X_1$ is independently N or $CR^5$;

$X_2$ is independently N or $CR^6$;

ring B is independently $C_{3-6}$ carbocycle or a 5- to 10-membered heterocycle containing carbon atoms and 1-4 heteroatoms selected from the group consisting of N, $NR^e$, O, and $S(O)_p$;

E is independently selected from: a bond, O and $CH_2$;

$R^2$, at each occurrence, is independently at selected from: H, halogen, OH, CN, $NO_2$, $C_{1-6}$ alkyl, $C_{1-6}$ alkoxy, $C_{1-6}$ alkylthio, $C_{1-6}$ haloalkyl, $C_{1-6}$ haloalkoxy, $C_{1-6}$ haloalkylthio, $R^9$, and —O—$R^9$;

$R^3$, $R^4$, $R^5$ and $R^6$, at each occurrence, are independently selected from: H, halogen, OH, CN, $NO_2$, $C_{1-6}$ alkyl, $C_{1-6}$ alkoxy, $C_{1-6}$ alkylthio, $C_{1-6}$ haloalkyl, $C_{1-6}$ haloalkoxy, and $C_{1-6}$ haloalkylthio;

$R^8$, at each occurrence, is independently selected from: H, $C_{1-6}$ alkyl, $C_{1-6}$ alkoxy, halogen, $C_{1-6}$ alkylthio, $C_{1-6}$ haloalkyl, $C_{1-6}$ haloalkoxy, $C_{1-6}$ haloalkylthio, CN, $C_{3-6}$ cycloalkyl, and —O—$C_{3-6}$ cycloalkyl;

$R^9$, at each occurrence, is independently a $C_{3-6}$ carbocycle or a 3- to 6-membered heterocycle containing carbon and 1-4 heteroatoms selected from the group consisting of N, $NR^e$, O, and $S(O)_p$; wherein said carbocycle and heterocycle are each substituted with 0-3 $R^b$;

$R^{12}$ is independently selected from: H, $C_{1-8}$ alkyl substituted with 0-3 $R^a$, $C_{1-4}$ haloalkyl, $CO(C_{1-4}$ alkyl), $COCH_2O(C_{1-4}$ alkyl), $CO_2(C_{1-4}$ alkyl), $SO_2R^f$, —$(CH_2)_s$—($C_{3-6}$ carbocycle substituted with 0-2 $R^b$),

[structures: $C_{1-4}$ alkyl-oxetane, $C_{1-4}$ alkyl-oxetane, oxetane-CH$_2$OH, pyrrolidinylmethyl, cyclopentyl-CH$_2$OH, Me$_2$C-morpholine, and adamantyl-OH];

$R^{13}$ is independently H or $C_{1-4}$ alkyl;

alternatively, $R^{12}$ and $R^{13}$ are combined, together with the nitrogen atom they are attached to, form a 4- to 10-membered heterocycle containing carbon atoms and additional 1-2 heteroatoms selected from the group consisting of N, $NR^e$, O, and $S(O)_p$; wherein said heterocycle is substituted with 0-3 $R^c$ and may form a spiro ring;

$R^a$, at each occurrence, is independently selected from: halogen, $OR^d$, $CH_2OR^d$, CN, $C_{1-4}$ alkyl, $C_{1-4}$ alkoxy, $C_{1-4}$ haloalkyl, $C_{3-6}$ cycloalkyl, —O—$C_{3-6}$ cycloalkyl, $C(O)C_{1-4}$ alkyl, $CO_2H$, $CO_2C_{1-4}$ alkyl, $SO(C_{1-4}$ alkyl), and $SO_2(C_{1-4}$ alkyl);

$R^b$, at each occurrence, is independently selected from: halogen, OH, CN, $CH_2OH$, $C_{1-4}$ alkyl, $C_{1-4}$ alkoxy, $C_{1-4}$ haloalkyl, $C_{1-4}$ haloalkoxy, $C_{3-6}$ cycloalkyl, and —O—$C_{3-6}$ cycloalkyl;

$R^c$, at each occurrence, is independently selected from: =O, halogen, $OR^d$, $CH_2OR^d$, CN, $C_{1-4}$ alkyl, $C_{1-4}$ alkoxy, $C_{1-4}$ haloalkyl, $NH_2$, $N(C_{1-4}$ alkyl$)_2$, $CH_2C_{1-4}$ alkoxy, $C_{1-4}$ haloalkoxy, $CONH_2$, $CO_2(C_{1-4}$ alkyl), $CO_2Bn$, $SO_2C_{1-4}$ alkyl, $NHCOC_{1-4}$ alkyl, $NHCOC_{1-4}$ haloalkyl, $NHCO_2C_{1-4}$ alkyl, $NHCO_2Ph$, $NHCO_2Bn$, $C_{3-6}$ cycloalkyl, pyrrolidinyl, and morpholinyl; and $R^d$, at each occurrence, is independently selected from: H, $C(O)C_{1-4}$ alkyl, $C(O)(Ph)$, $C(O)CH_2NH_2$, —$C(O)CH(C_{1-4}$ alkyl)$NH_2$, —$C(O)CH_2CO_2H$, —$C(O)(CH_2)_2CO_2H$, and $P(O)(OH)_2$;

$R^e$, at each occurrence, is independently H, $C_{1-4}$ alkyl, $C(O)C_{1-4}$ alkyl, $CO_2(C_{1-4}$ alkyl), $CO_2Bn$, pyrimidinyl and pyrazinyl;

$R^f$ is independently selected from: $C_{1-4}$ alkyl, $C_{1-4}$ haloalkyl, $C_{3-6}$ cycloalkyl, Ph,

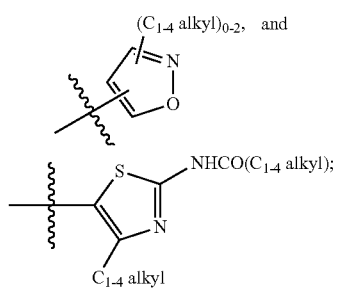

n, at each occurrence, is independently 1, 2, and 3;
p, at each occurrence, is independently 0, 1 or 2; and
s, at each occurrence, is independently 0, 1, or 2.

2. A compound according to claim 1, wherein the compound is of Formula (III):

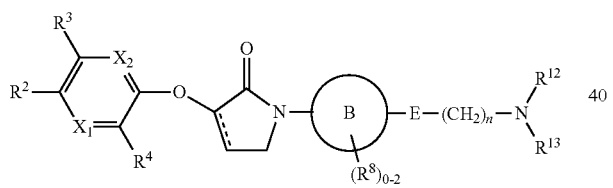

or a stereoisomer, a tautomer, or a pharmaceutically acceptable salt thereof.

3. A compound according to claim 1, wherein the compound is of Formula (IIIa):

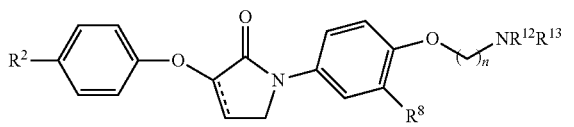

or a stereoisomer, a tautomer, or a pharmaceutically acceptable salt thereof, wherein:
--- is a single or double bond;
$R^2$ is independently $C_{3-6}$ cycloalkyl or phenyl substituted with 0-2 $R^b$;
$R^8$ is independently selected from: halogen, $C_{1-4}$ alkyl, $C_{1-4}$ alkoxy, $C_{1-4}$ haloalkoxy, and $C_{3-6}$ cycloalkyl;
$R^{12}$ is independently at selected from: H, $C_{1-6}$ alkyl, $CH_2CH_2OH$, $CH_2CH_2(C_{1-4}$ alkoxy), $CH_2CN$, $C_{1-4}$ haloalkyl, $CO(C_{1-4}$ alkyl, $COCH_2O(C_{1-4}$ alkyl), $CO_2(C_{1-4}$ alkyl), $SO_2(C_{1-4}$ alkyl), $SO_2CH_2CF_3$, $SO_2(C_{3-6}$ cycloalkyl), $SO_2Ph$, $C_{3-6}$ cycloalkyl,

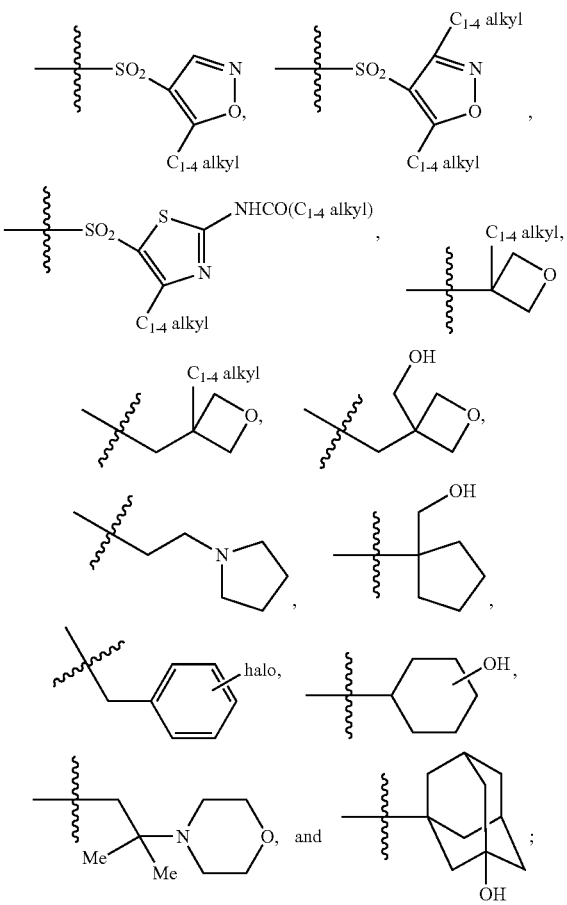

$R^{13}$ is independently H or $C_{1-4}$ alkyl;
alternatively, $R^{12}$ and $R^{13}$ are combined, together with the nitrogen atom they are attached to, form a heterocycle substituted with 0-3 $R^c$; wherein said heterocycle is independently at selected from:

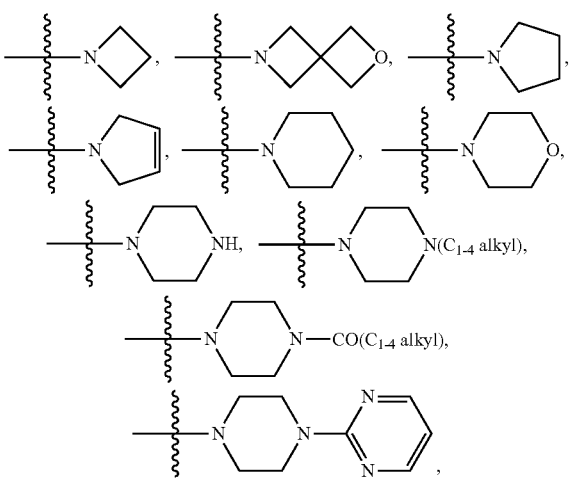

-continued

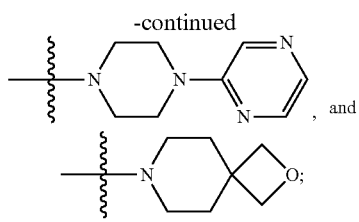
, and

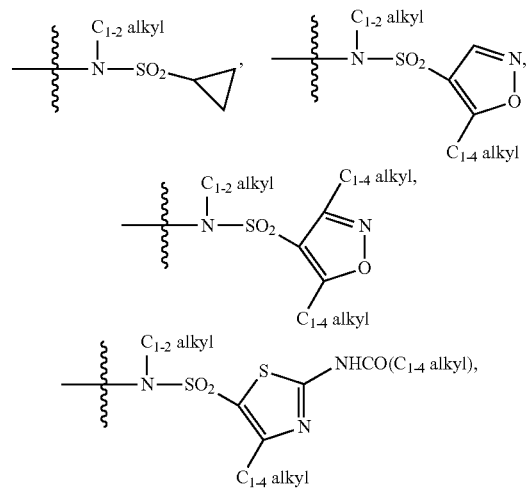
;

$R^b$, at each occurrence, is independently selected from: halogen, $C_{1-4}$ alkyl, $C_{1-4}$ alkoxy, $C_{1-4}$ haloalkyl, and $C_{1-4}$ haloalkoxy;

$R^c$, at each occurrence, is independently selected from: =O, halogen, OH, $CH_2OH$, CN, $NH_2$, $N(C_{1-4}$ alkyl$)_2$, $C_{1-4}$ alkyl, $C_{1-4}$ alkoxy, $CH_2C_{1-4}$ alkoxy, $C_{1-4}$ haloalkyl, $C_{1-4}$ haloalkoxy, $CONH_2$, $SO_2C_{1-4}$ alkyl, $NHCOC_{1-4}$ alkyl, $NHCOC_{1-4}$ haloalkyl, $NHCO_2C_{1-4}$ alkyl, $NHCO_2Bn$, $C_{3-6}$ cycloalkyl, pyrrolidinyl, and morpholinyl; and n, at each occurrence, is independently 1, or 2.

4. A compound according to claim 1, wherein the compound is of Formula (IIIb):

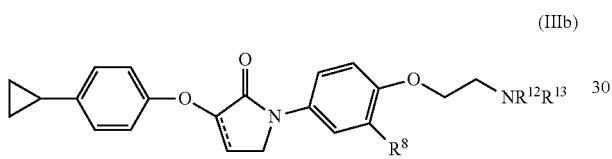
(IIIb)

or a stereoisomer, a tautomer, or a pharmaceutically acceptable salt thereof, wherein:

--- is a single or double bond;

$NR^{12}R^{13}$ is independently at selected from: $NH_2$, $NH(C_{1-6}$ alkyl), $N(C_{1-4}$ alkyl$)_2$, $NH(CH_2CH_2OH)$, $NH(CH_2CH_2(C_{1-4}$ alkoxy)), $NH(CH_2CN)$, $NH(C_{1-4}$ haloalkyl), $N(C_{1-2}$ alkyl)$(CH_2CH_2OH)$, $NH(CO(C_{1-4}$ alkyl)), $N(C_{1-2}$ alkyl)$(CO(C_{1-4}$ alkyl)), $N(C_{1-2}$ alkyl)$(COCH_2O(C_{1-4}$ alkyl)), $N(C_{1-2}$ alkyl)$(CO_2(C_{1-4}$ alkyl)), $NH(SO_2(C_{1-4}$ alkyl)), $N(C_{1-2}$ alkyl)$(SO_2(C_{1-4}$ alkyl)), $N(C_{1-2}$ alkyl)$(SO_2CH_2CF_3)$, $N(C_{1-2}$ alkyl)$(SO_2Ph)$,

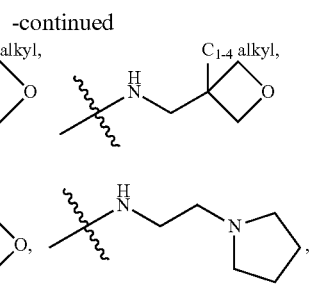
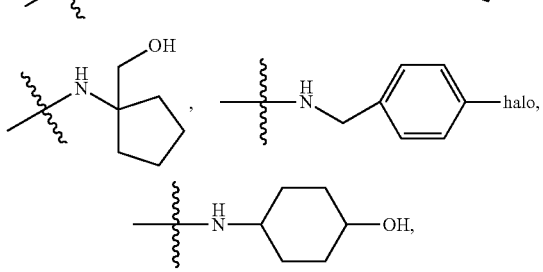
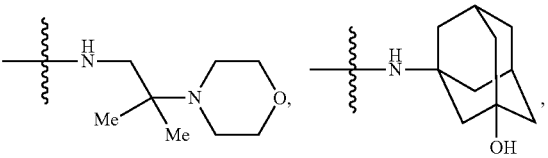
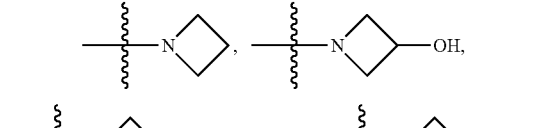
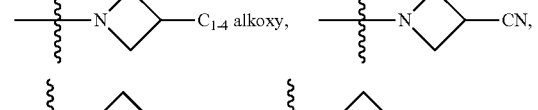
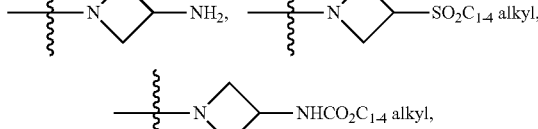
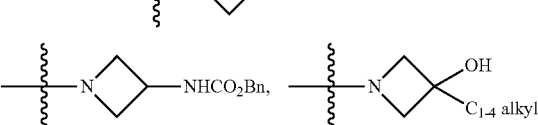
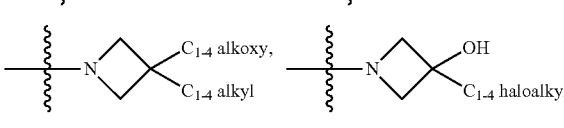
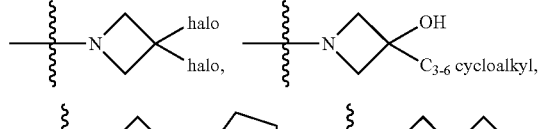
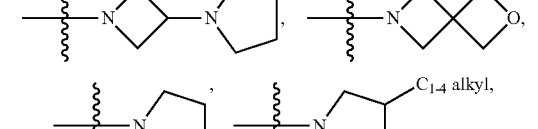
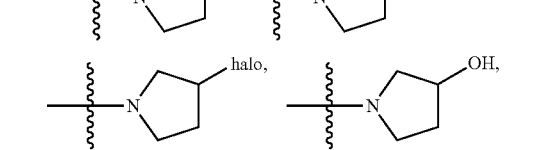

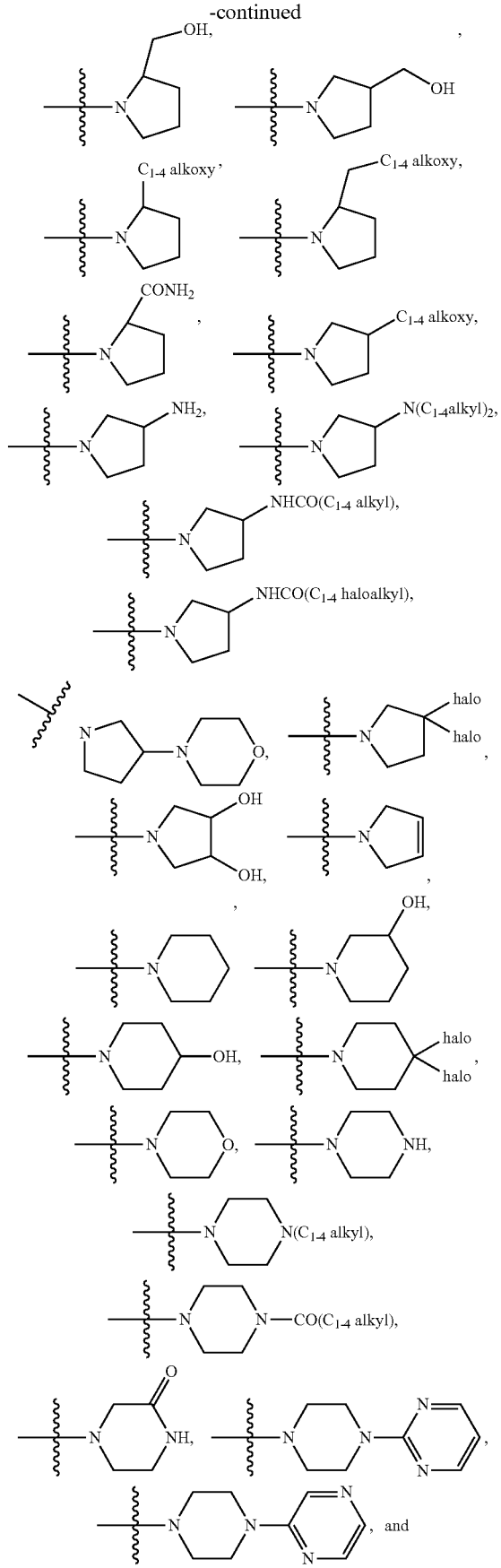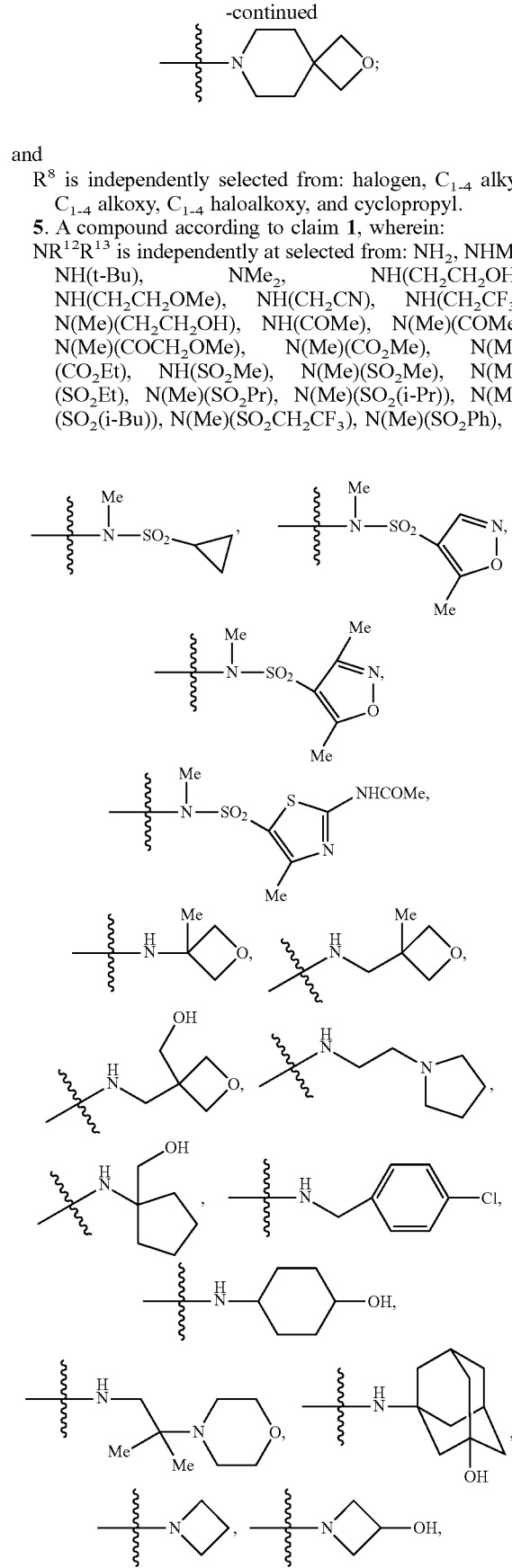

and

R[8] is independently selected from: halogen, $C_{1-4}$ alkyl, $C_{1-4}$ alkoxy, $C_{1-4}$ haloalkoxy, and cyclopropyl.

5. A compound according to claim 1, wherein:

$NR^{12}R^{13}$ is independently at selected from: $NH_2$, NHMe, NH(t-Bu), $NMe_2$, $NH(CH_2CH_2OH)$, $NH(CH_2CH_2OMe)$, $NH(CH_2CN)$, $NH(CH_2CF_3)$, $N(Me)(CH_2CH_2OH)$, NH(COMe), N(Me)(COMe), $N(Me)(COCH_2OMe)$, $N(Me)(CO_2Me)$, $N(Me)(CO_2Et)$, $NH(SO_2Me)$, $N(Me)(SO_2Me)$, $N(Me)(SO_2Et)$, $N(Me)(SO_2Pr)$, $N(Me)(SO_2(i\text{-}Pr))$, $N(Me)(SO_2(i\text{-}Bu))$, $N(Me)(SO_2CH_2CF_3)$, $N(Me)(SO_2Ph)$, -continued

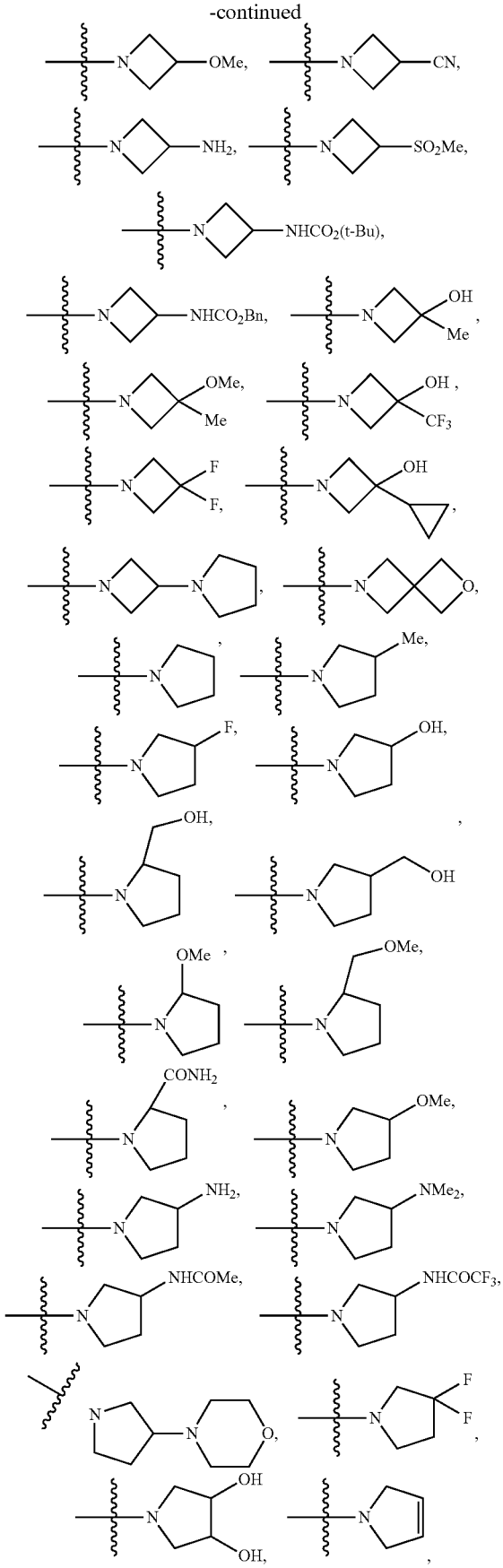

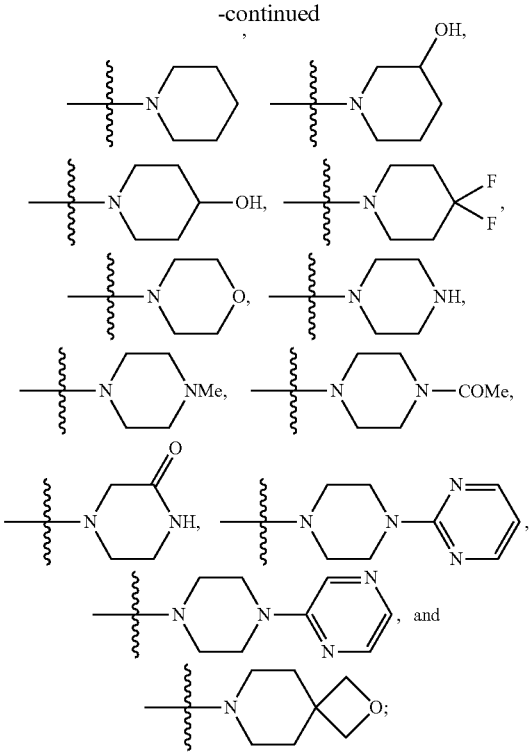

and

R[8] is independently selected from: Cl, Br, Me, Et, OMe, OCF$_2$, and cyclopropyl.

6. A compound according to claim 1, wherein the compound is of Formula (IIIc):

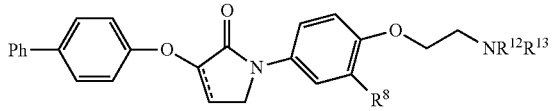

(IIIc)

or a stereoisomer, a tautomer, a pharmaceutically acceptable salt, or a solvate thereof, within the scope of any of the first to fifth aspects, wherein:

≡≡≡ is a single or double bond;

NR$^{12}$R$^{13}$ is independently at selected from:

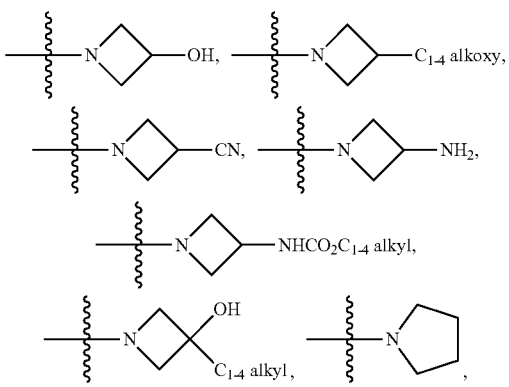

-continued

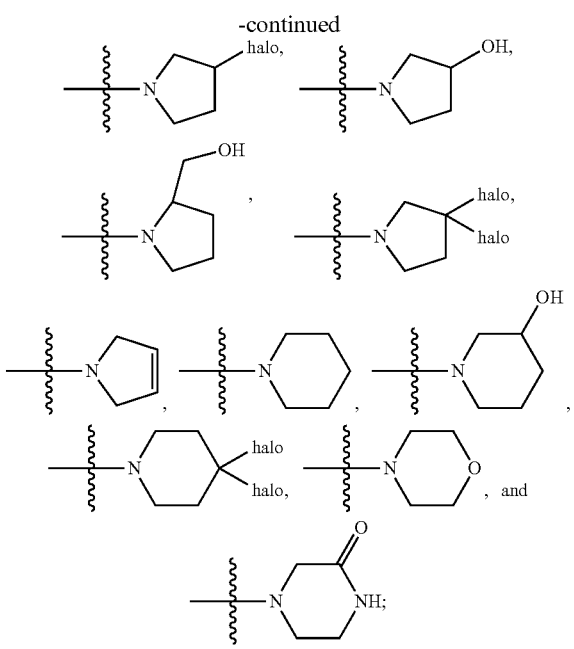

and

R[8] is independently selected from: halogen, $C_{1-4}$ alkyl and $C_{1-4}$ alkoxy.

7. A compound according to claim 1, wherein:
NR[12]R[13] is independently at selected from:

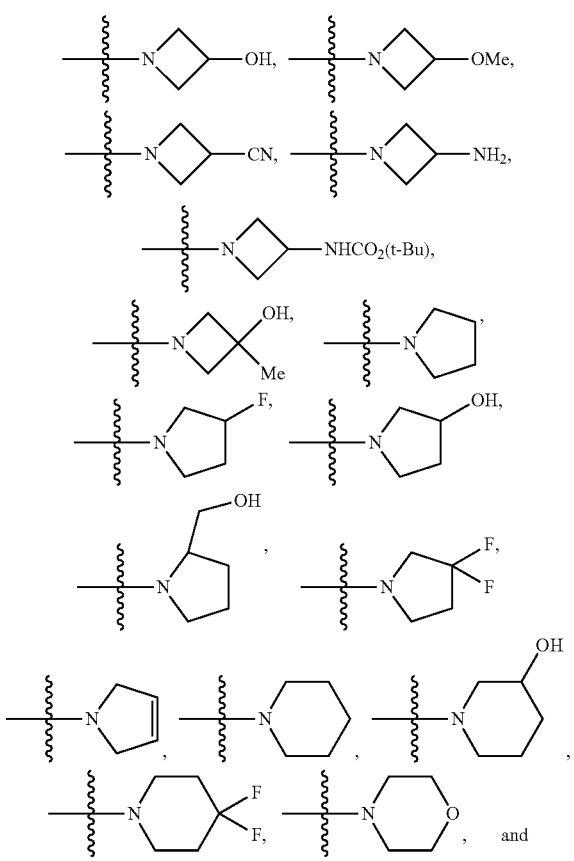

-continued

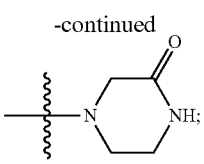

and

R[8] is independently selected from: Cl, Me, Et, and OMe.

8. A compound according to claim 1, wherein the compound is of Formula (IIId):

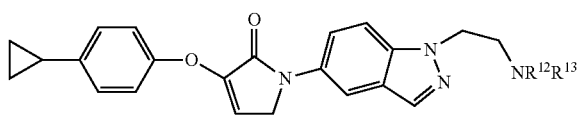
(IIId)

or a stereoisomer, a tautomer, or a pharmaceutically acceptable salt thereof, wherein:
NR[12]R[13] is independently at selected from:

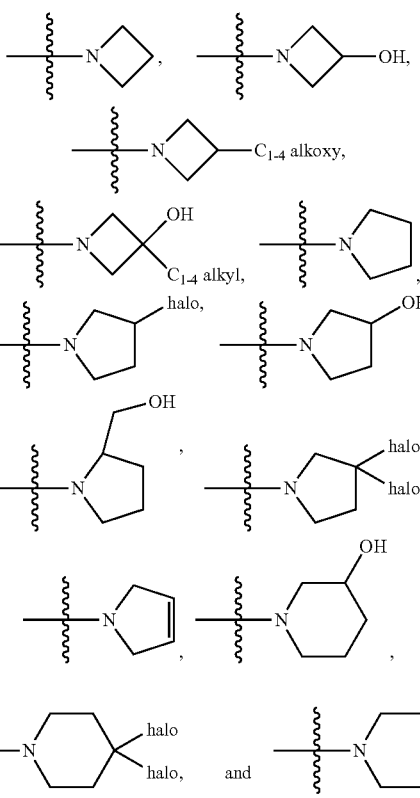

9. A compound according to claim 1, wherein:
NR[12]R[13] is independently at selected from:

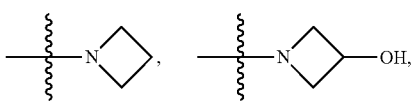

353
-continued
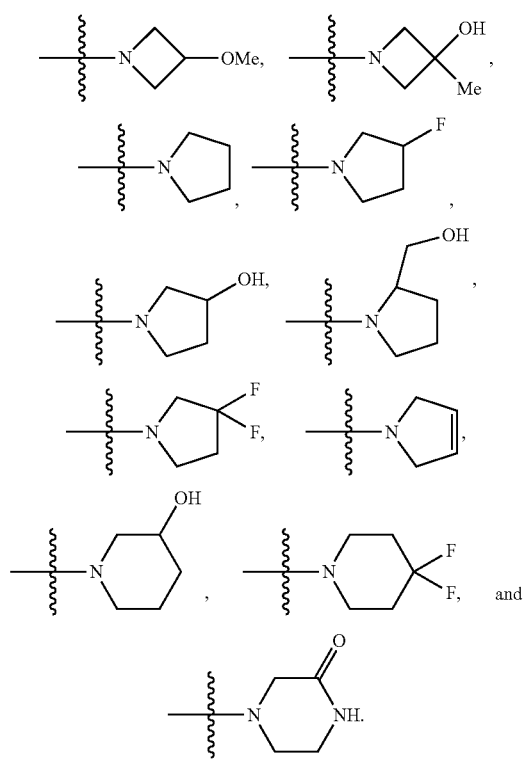
10. A compound according to claim 1, wherein the compound is selected from the group consisting of
354
-continued
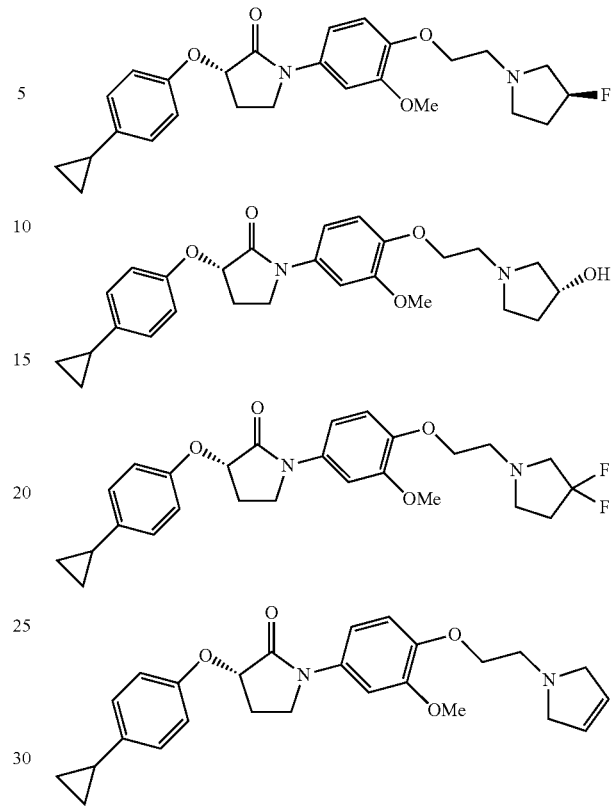
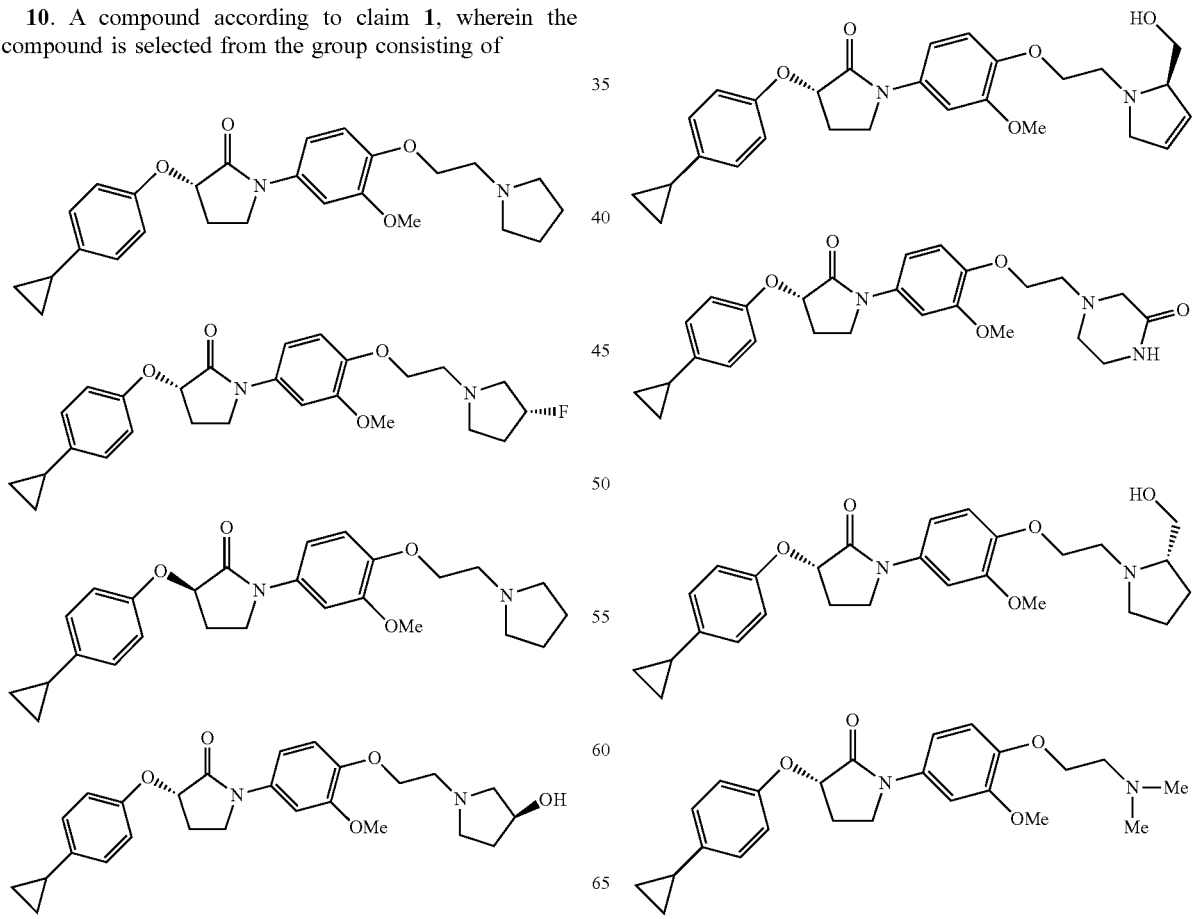

355
-continued
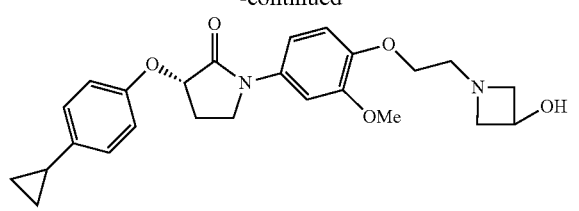
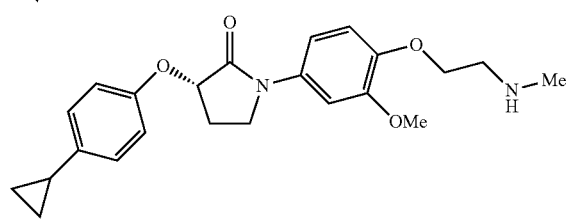
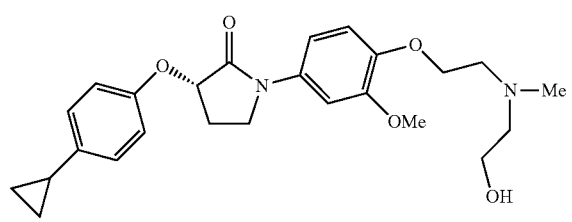
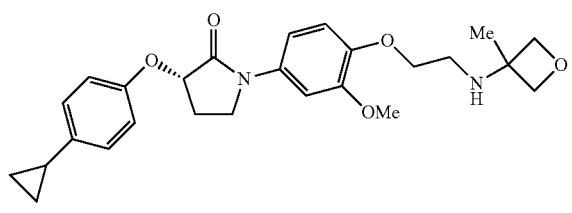
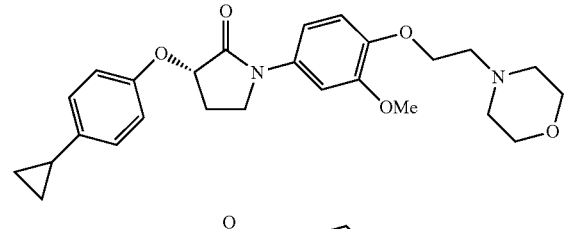
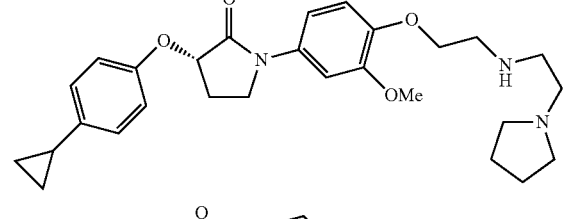
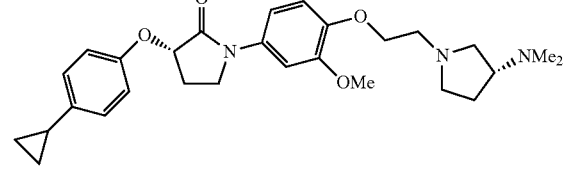
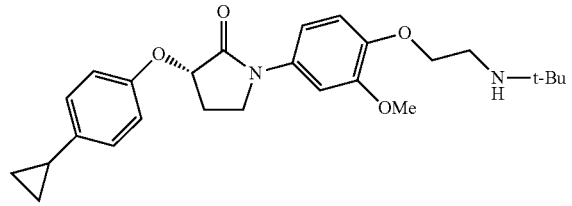
356
-continued
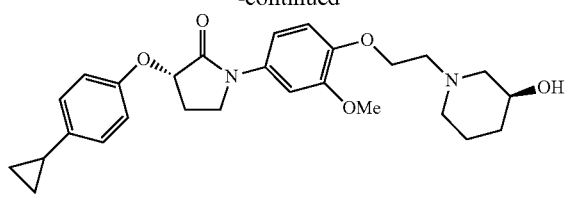
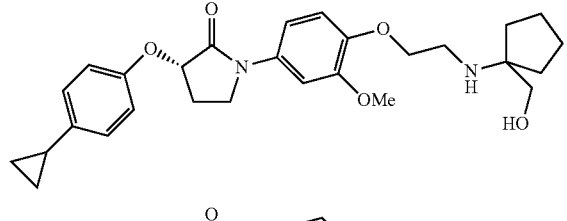
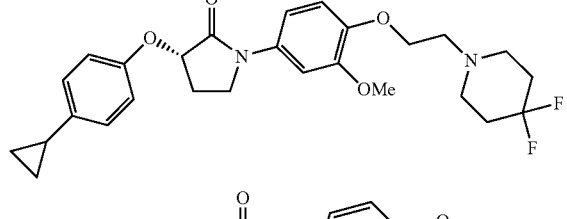
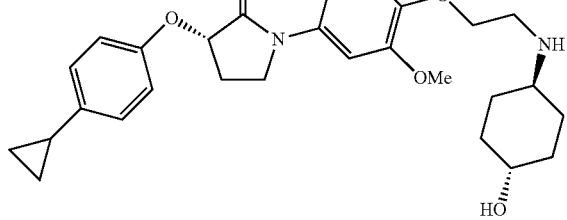
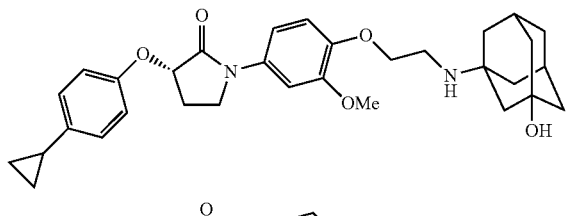
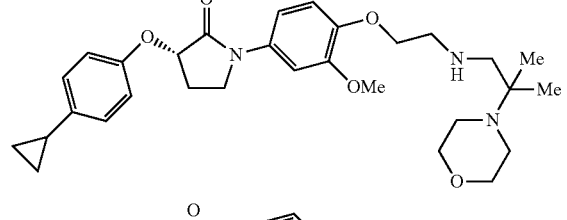
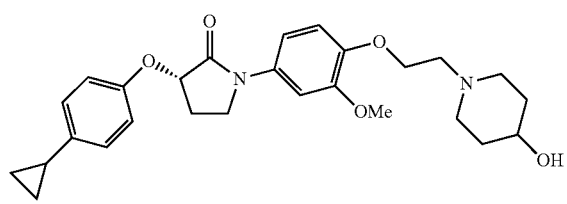

357
-continued
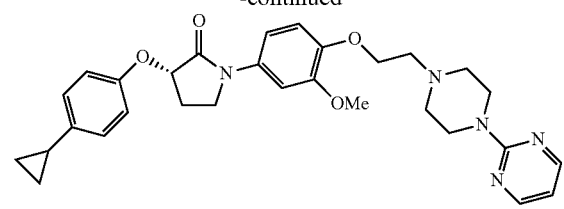
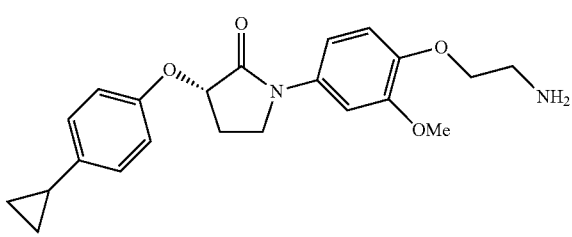
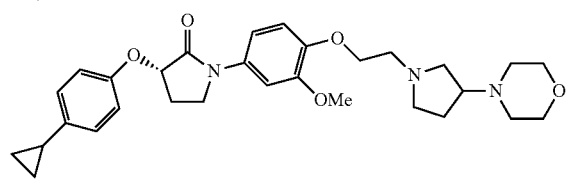
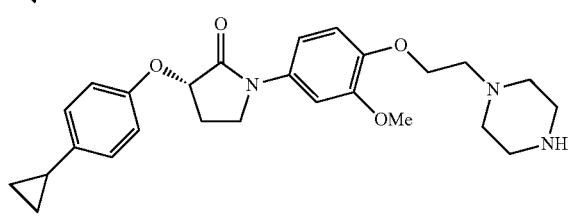
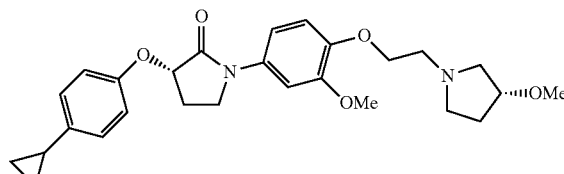
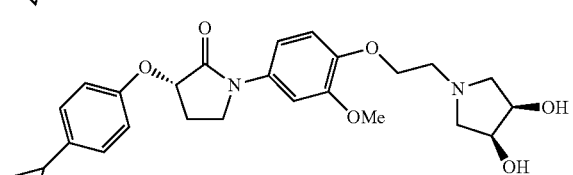
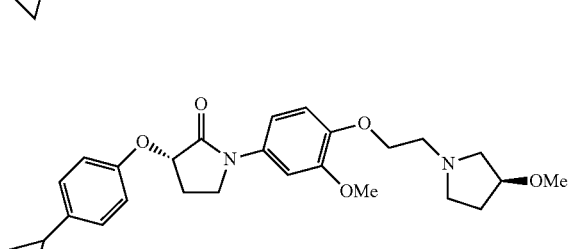
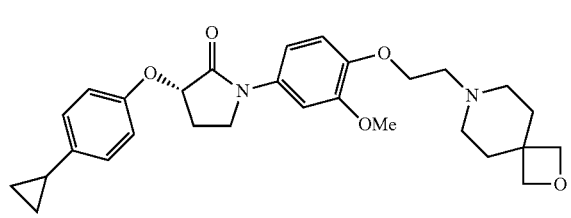
358
-continued
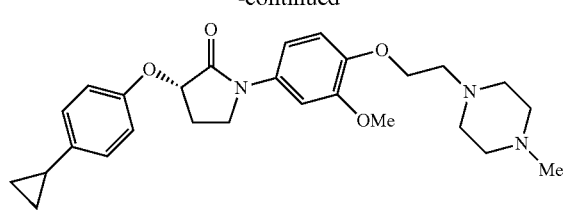
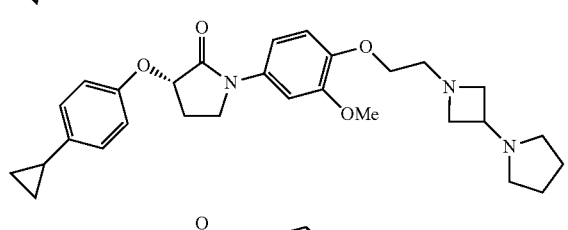
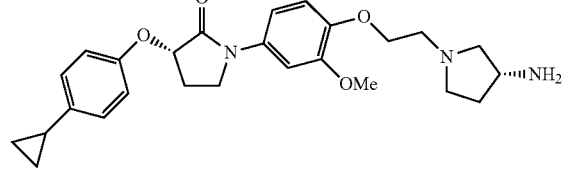
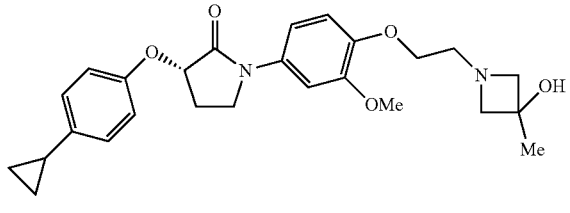
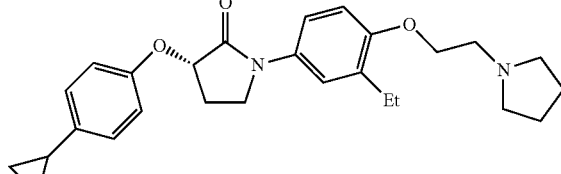
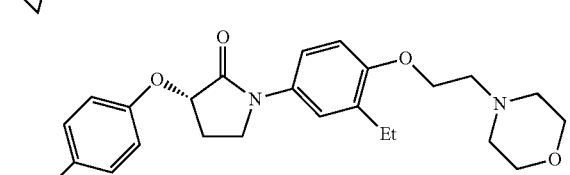
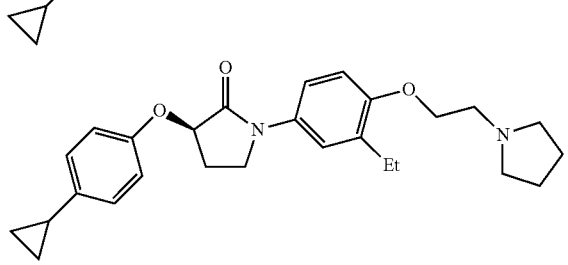
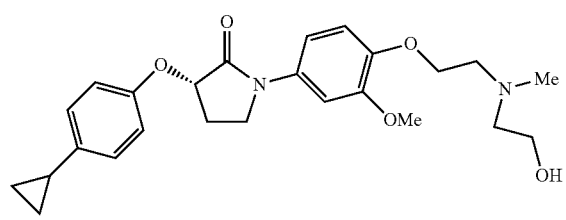

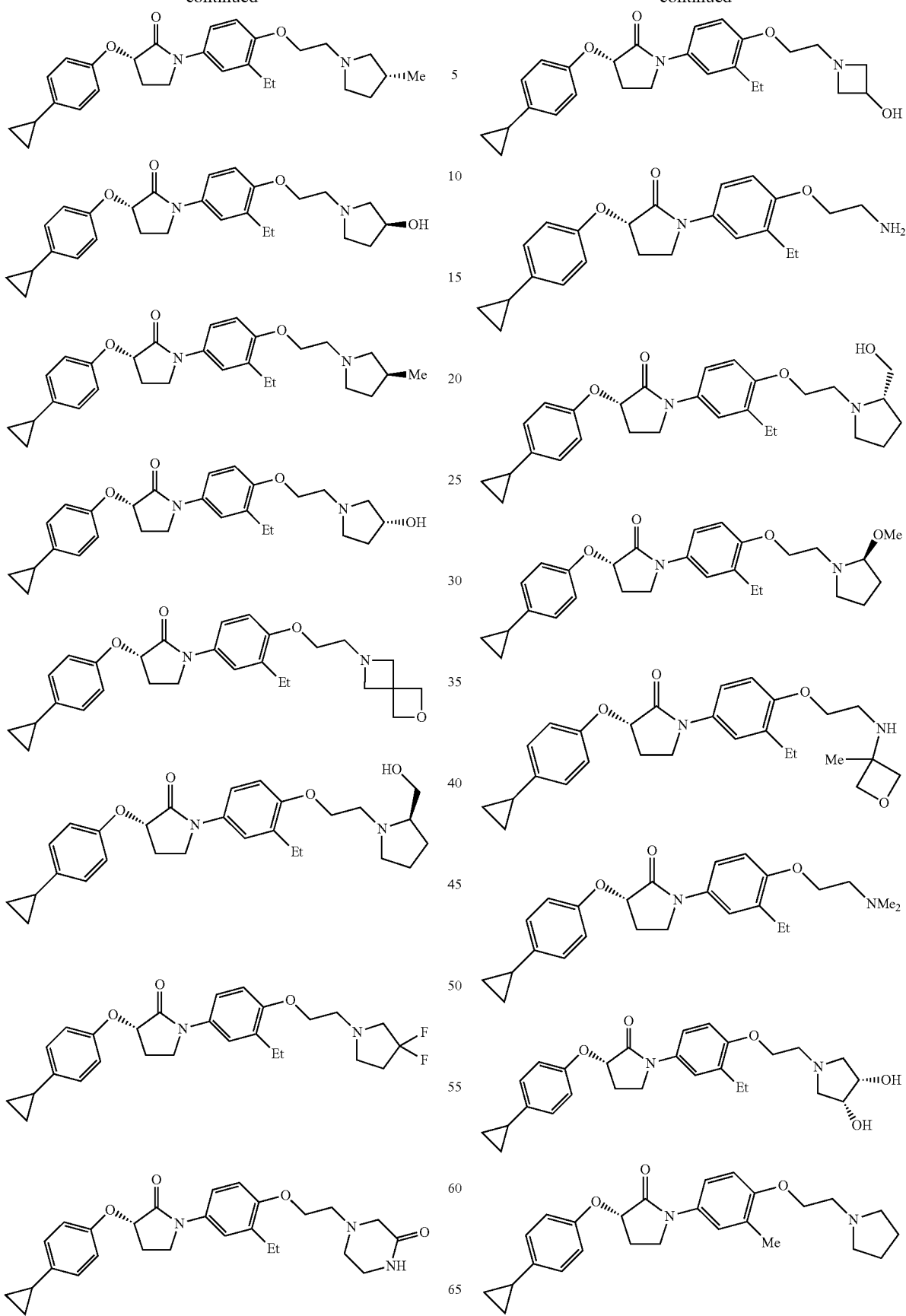

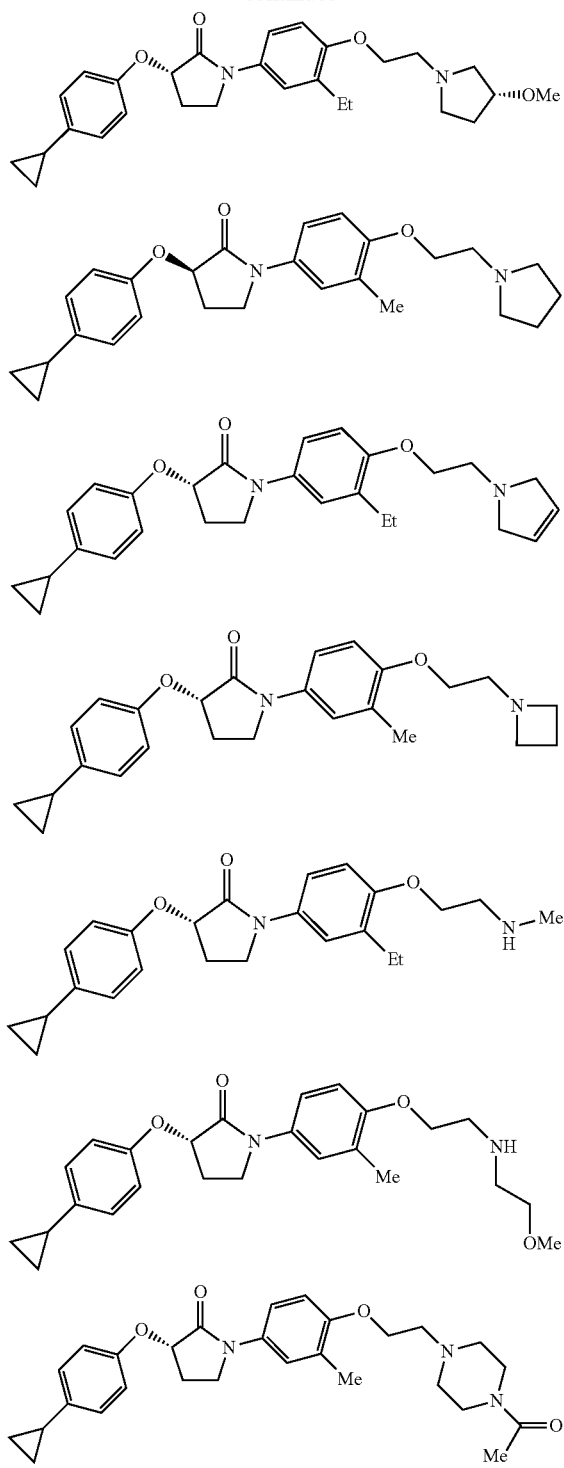
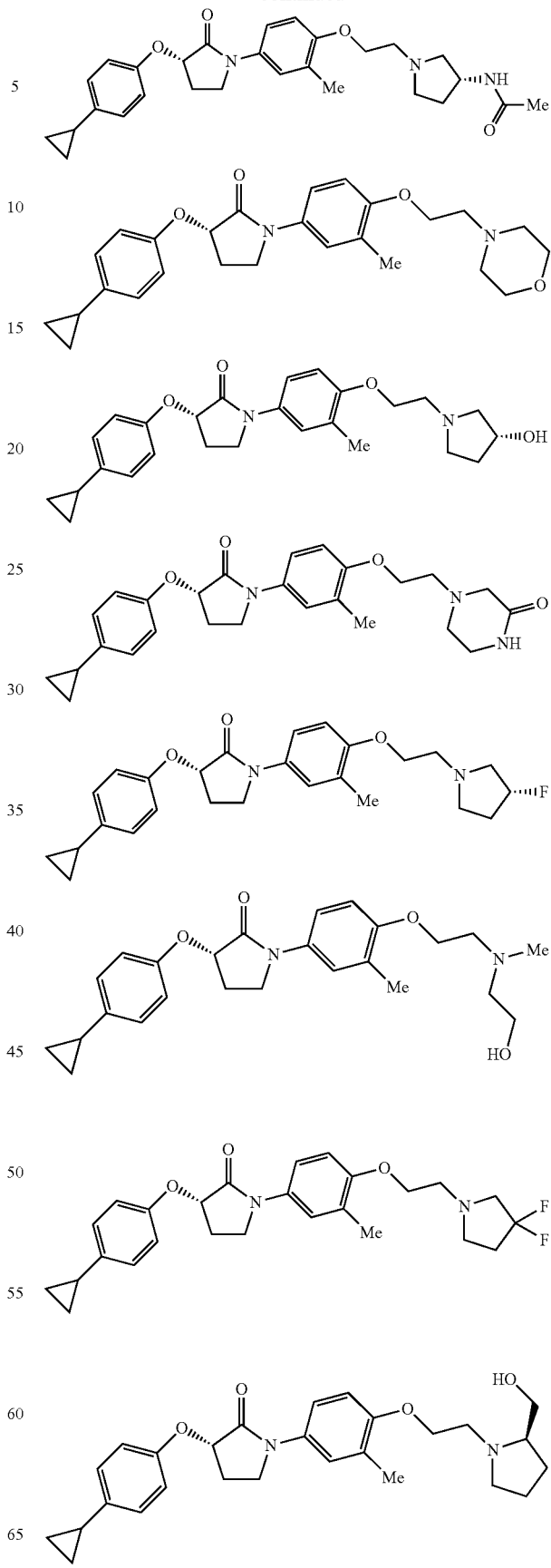

363
-continued
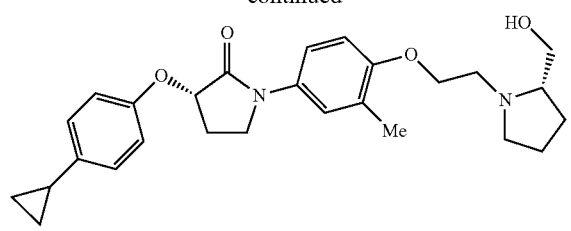
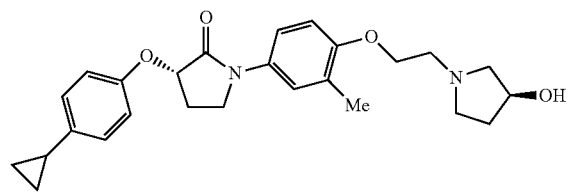
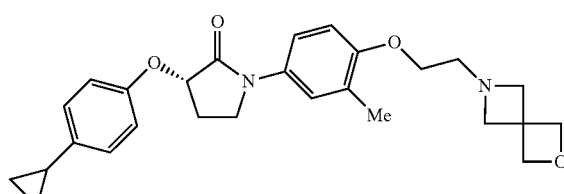
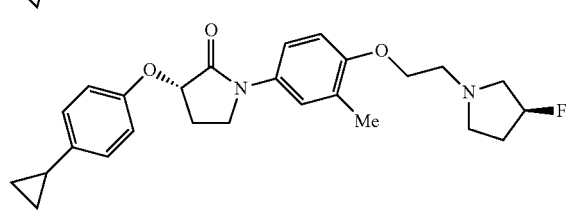
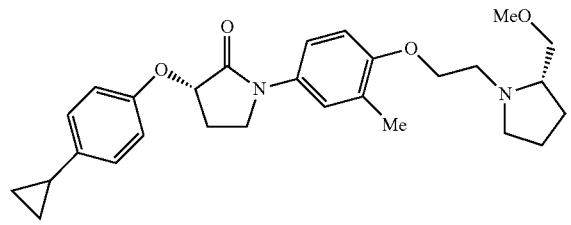
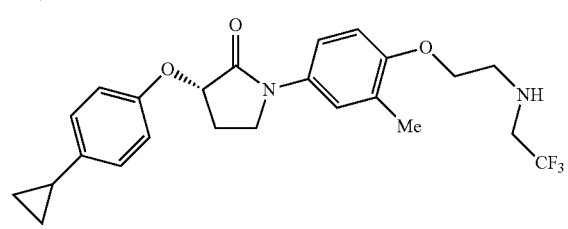
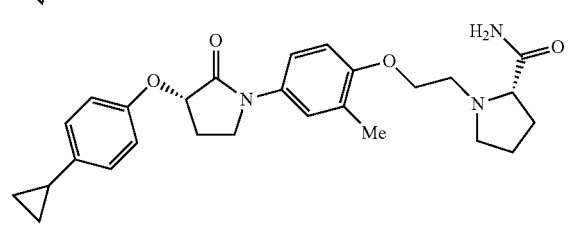
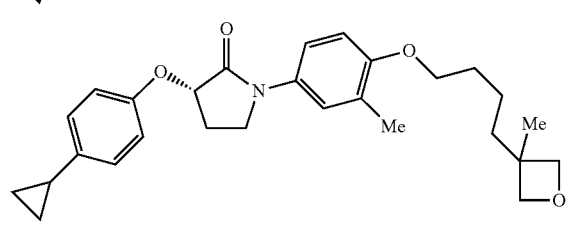
364
-continued
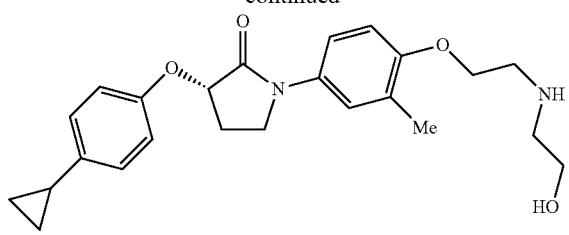
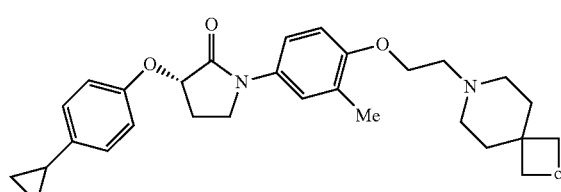
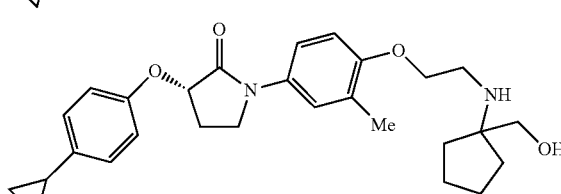
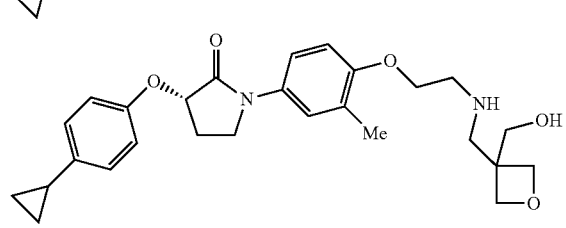
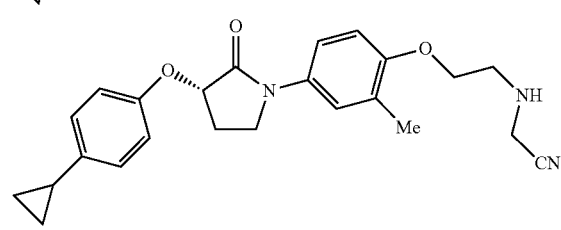
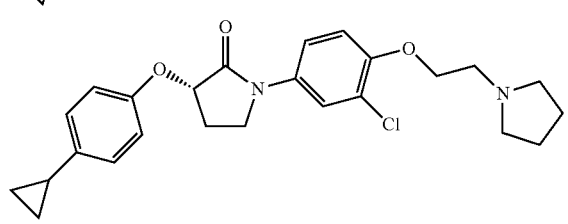
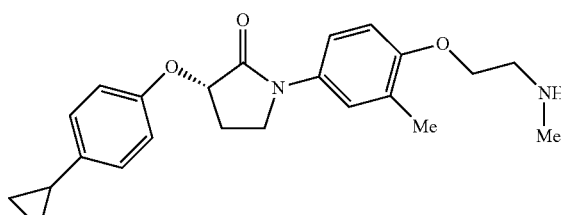
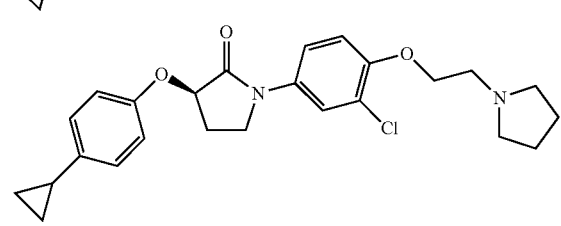

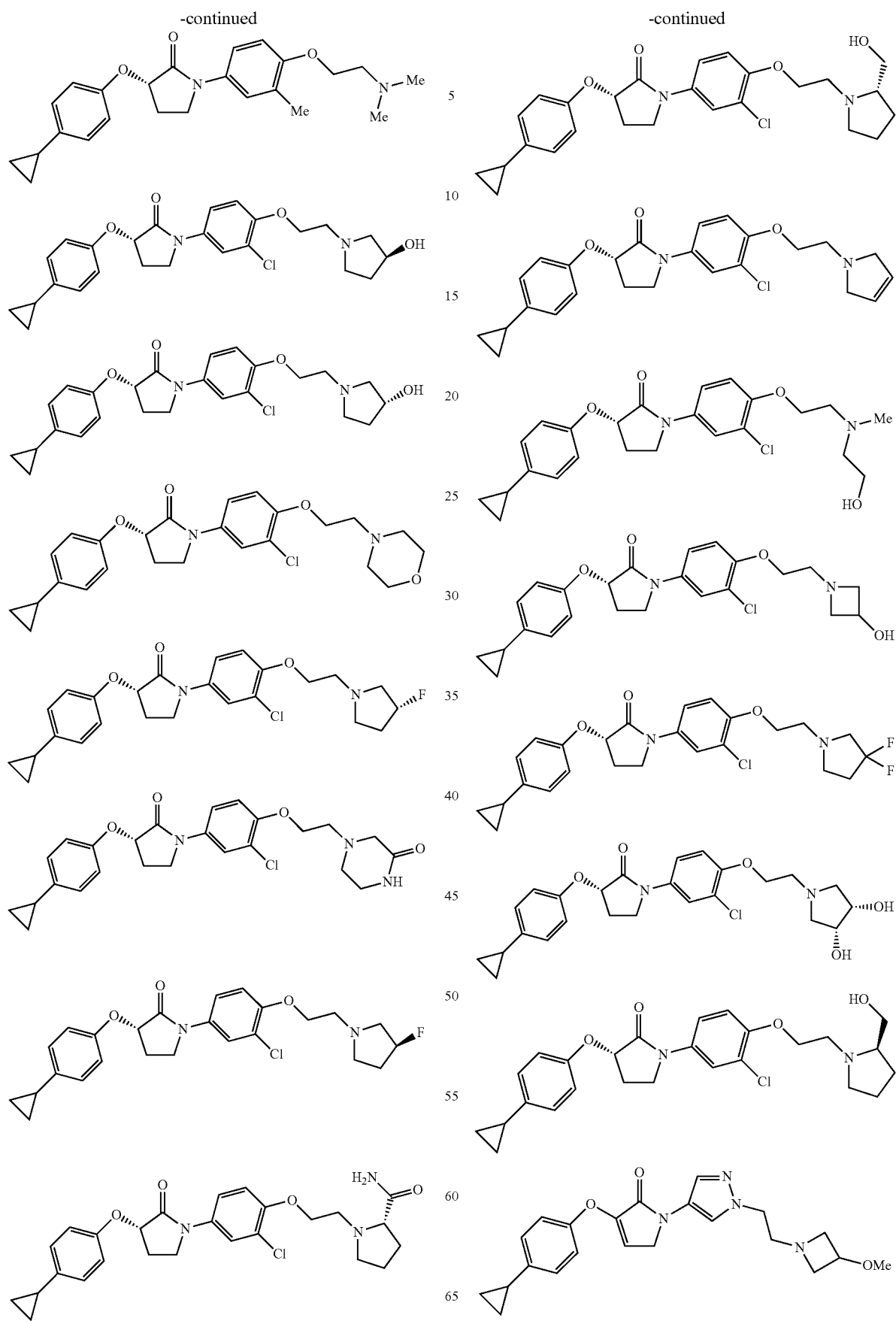

-continued
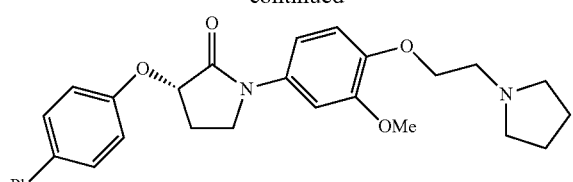
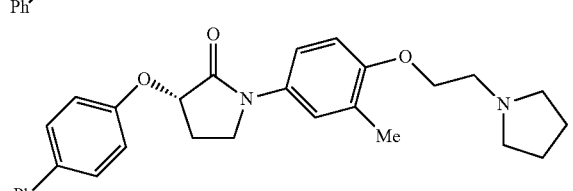
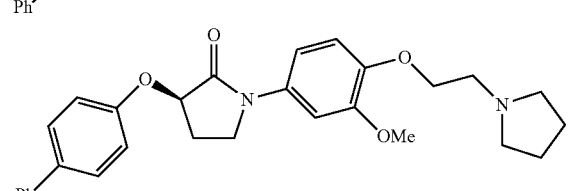
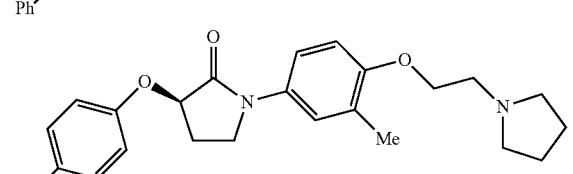
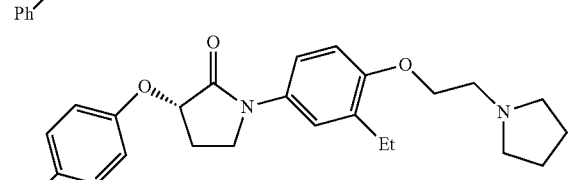
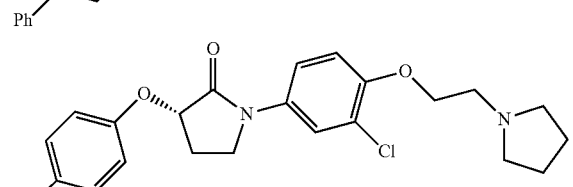
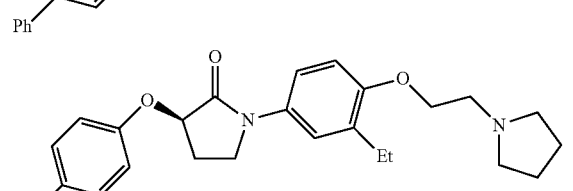
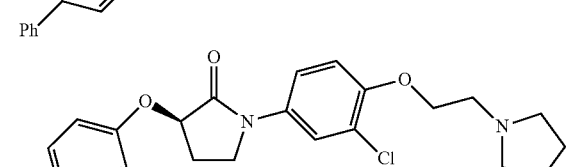
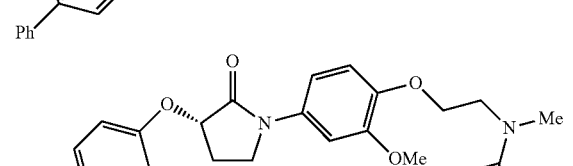
-continued
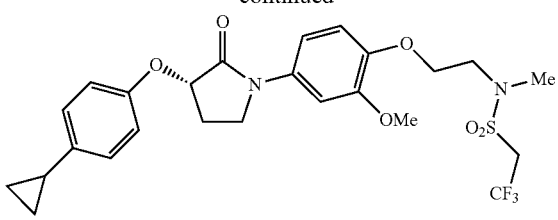
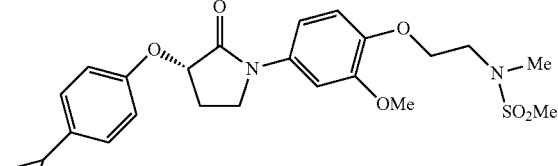
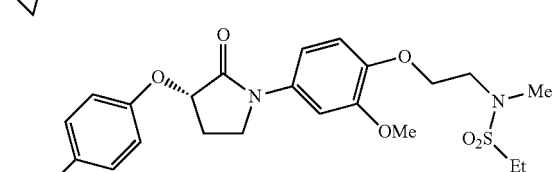
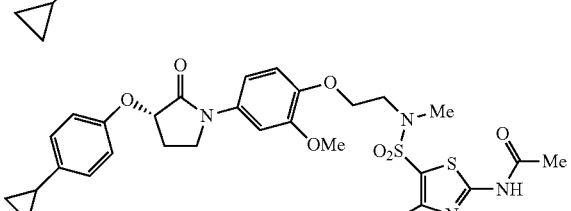
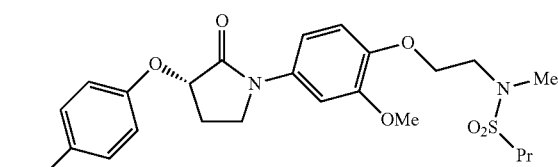
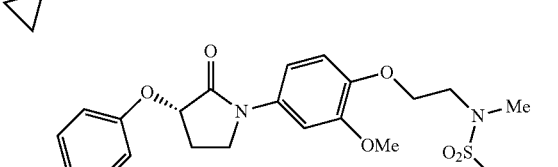
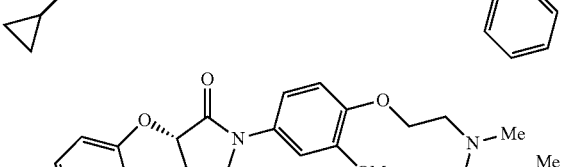
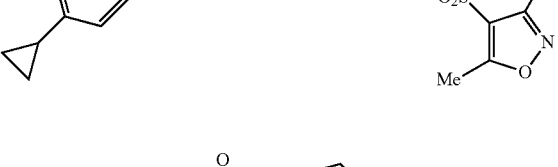
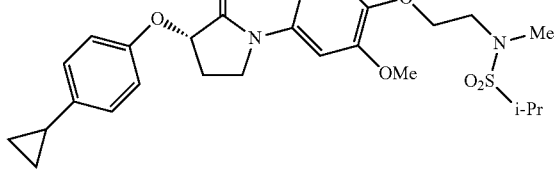

369
-continued
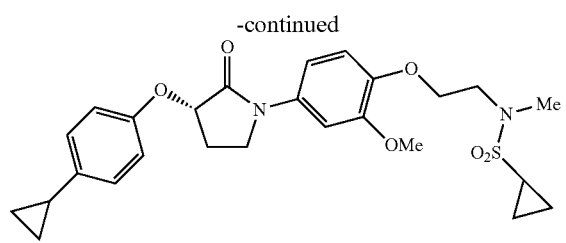
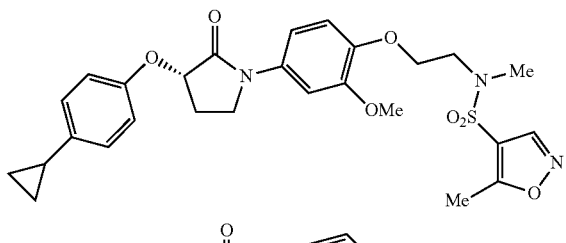
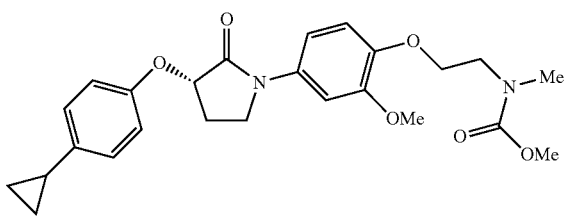
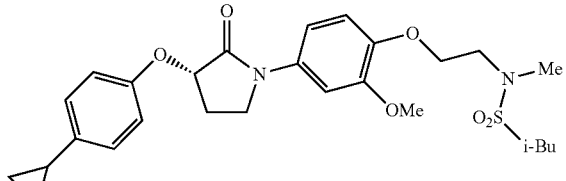
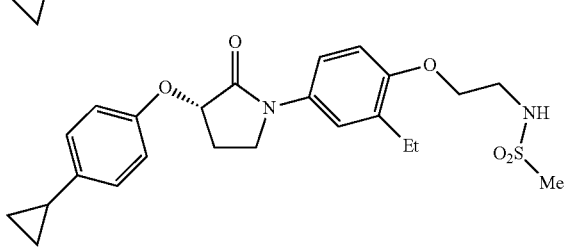
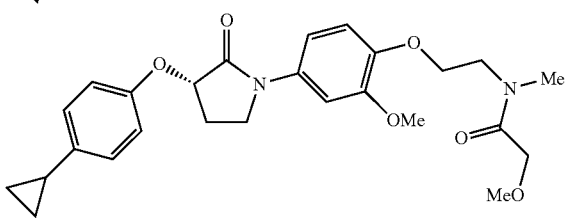
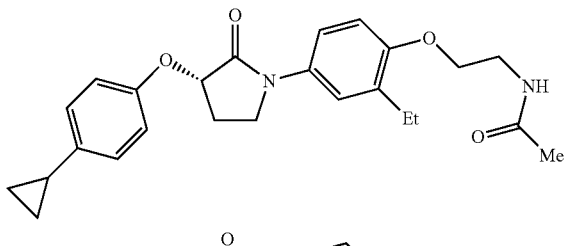
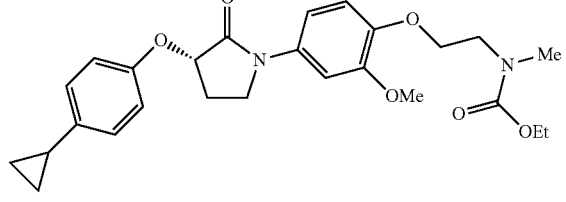
370
-continued
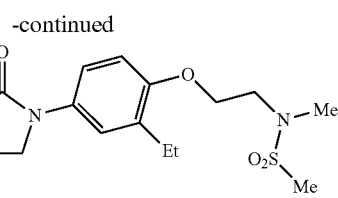
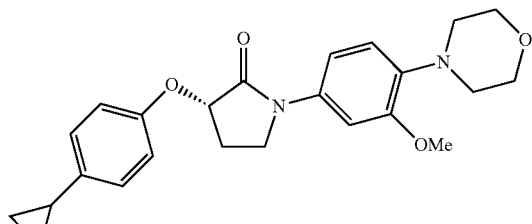
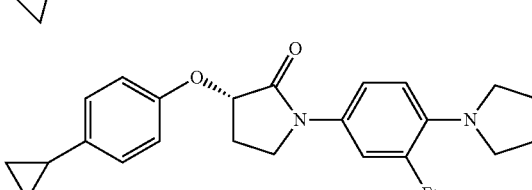
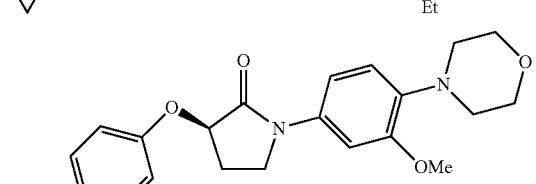
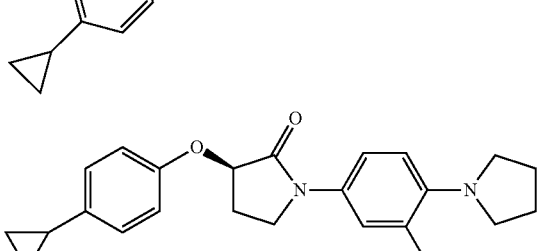
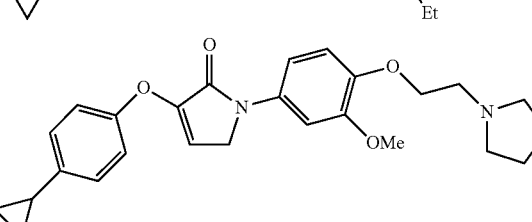
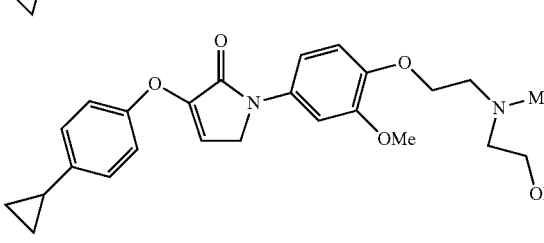
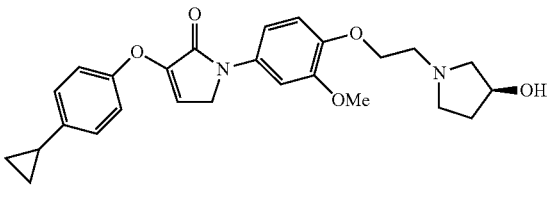

371
-continued
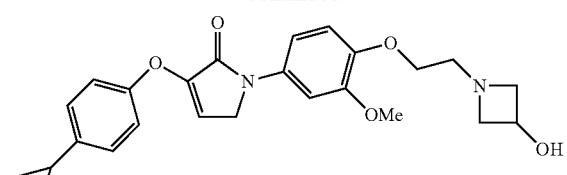
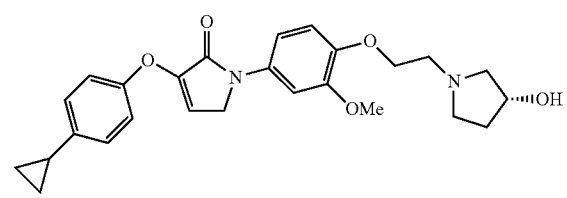
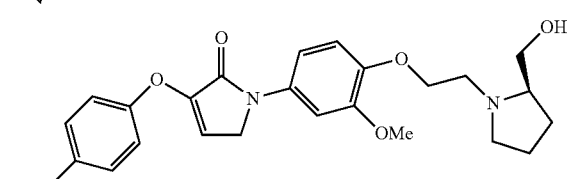
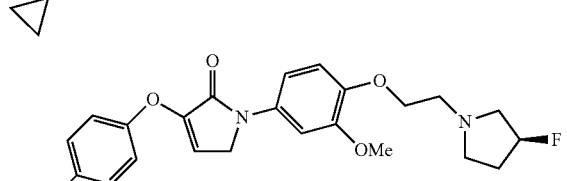
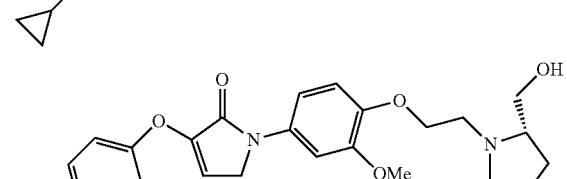
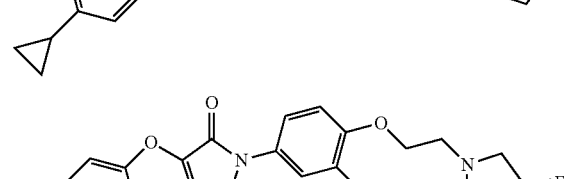
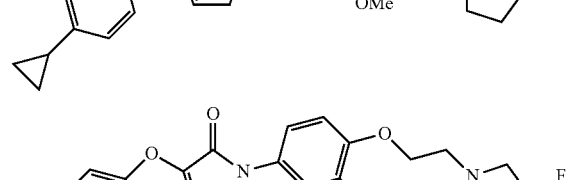
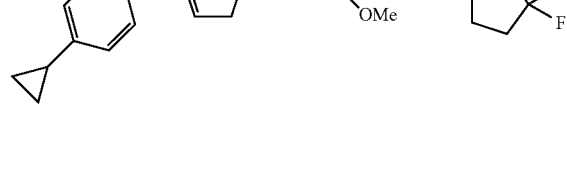
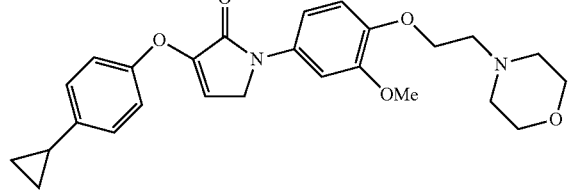
372
-continued
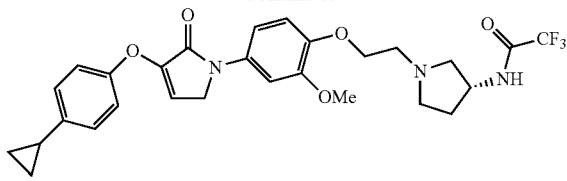
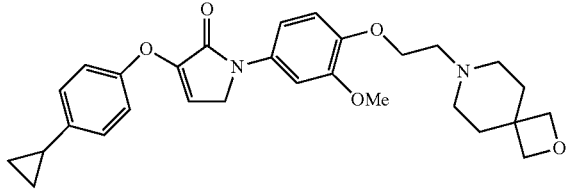
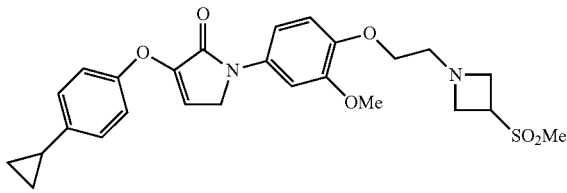
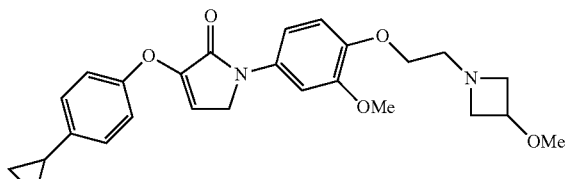
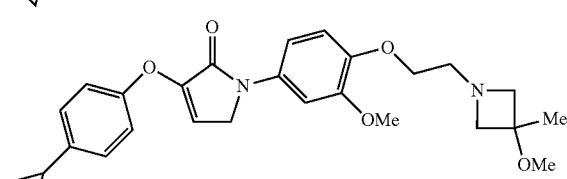
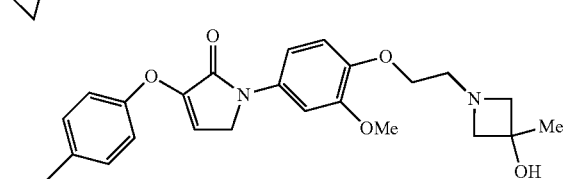
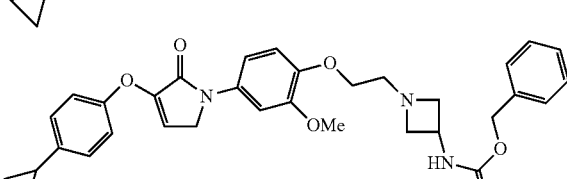
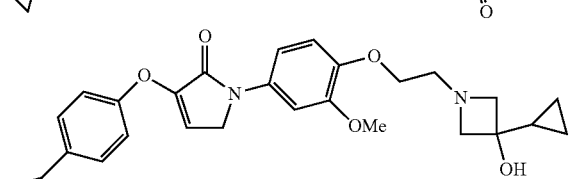
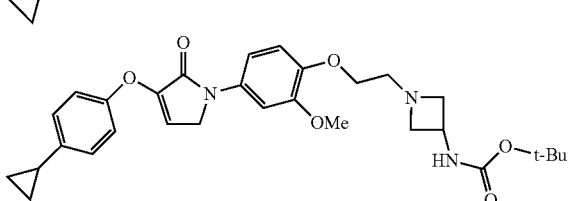

373
-continued
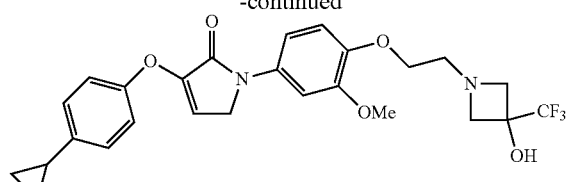
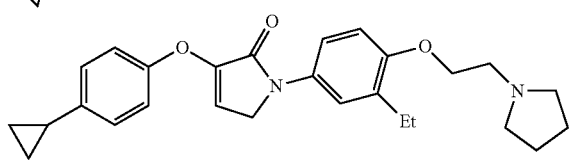
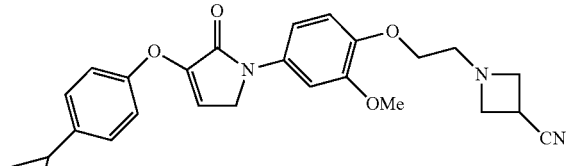
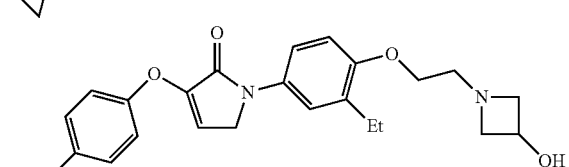
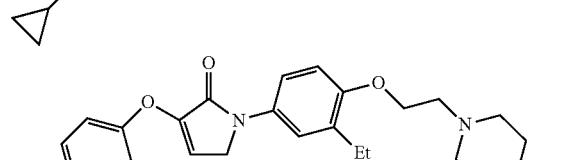
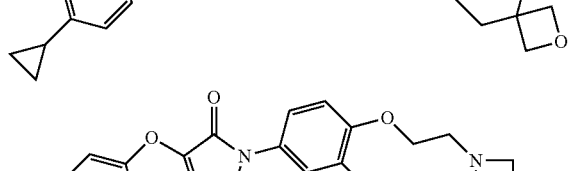
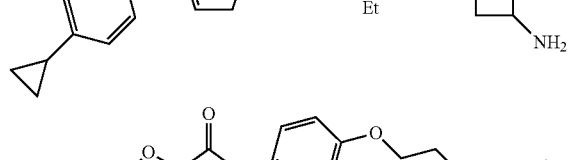
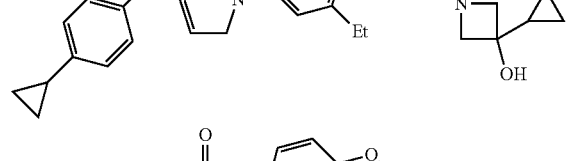
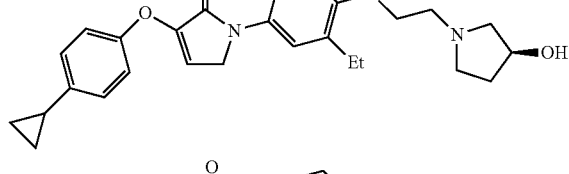
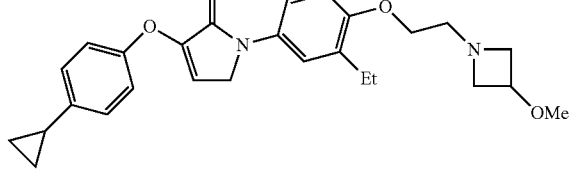
374
-continued
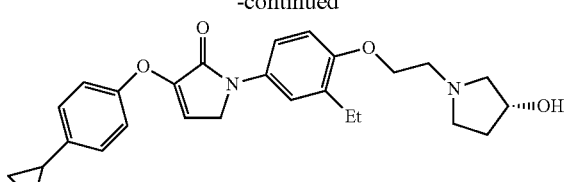
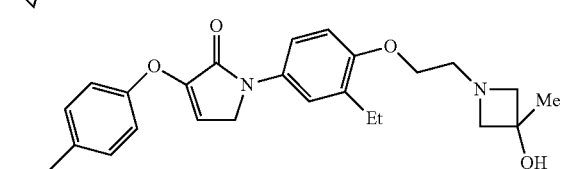
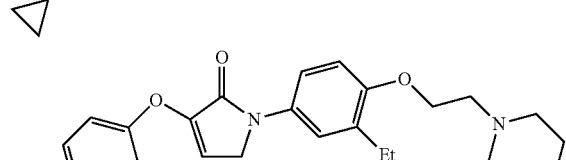
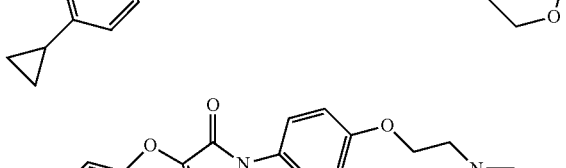
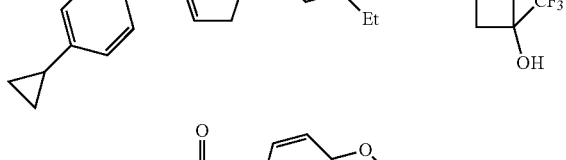
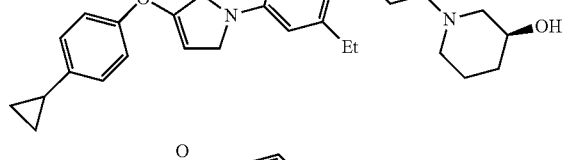
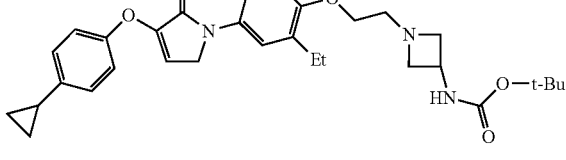
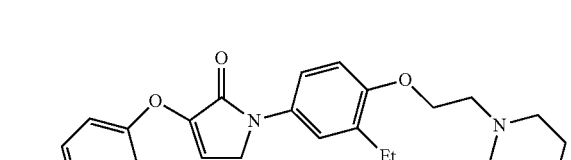
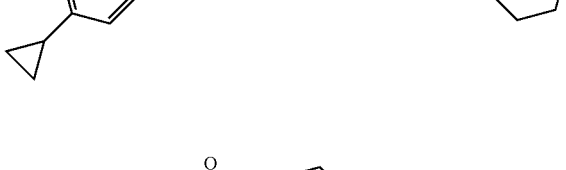
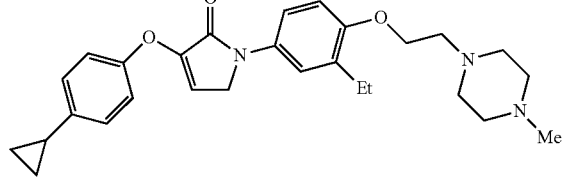

-continued

377
-continued
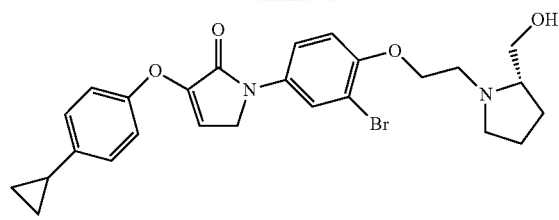
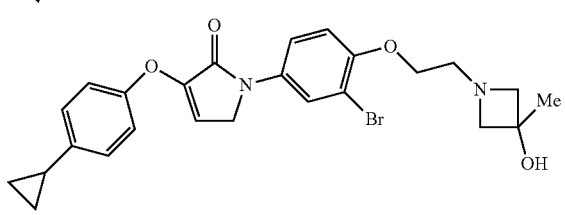
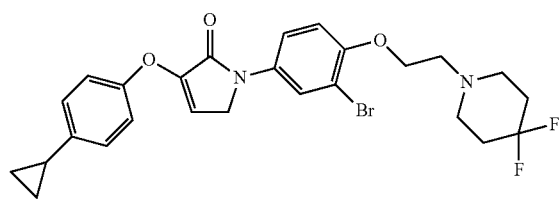
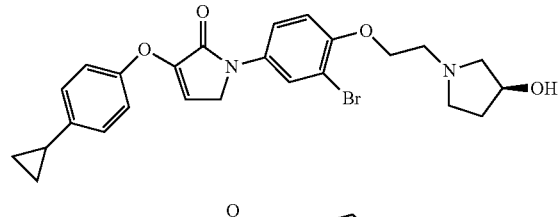
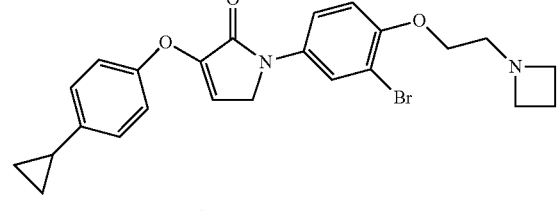
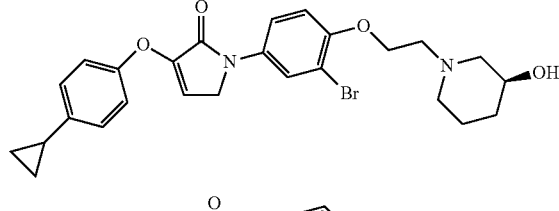
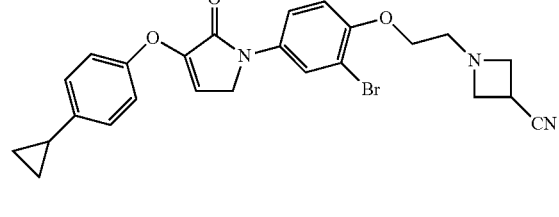
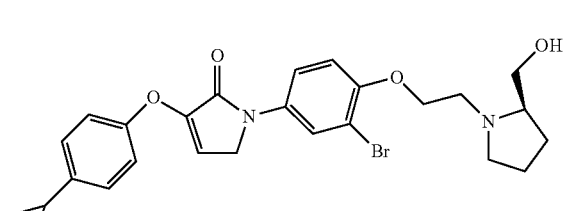
378
-continued
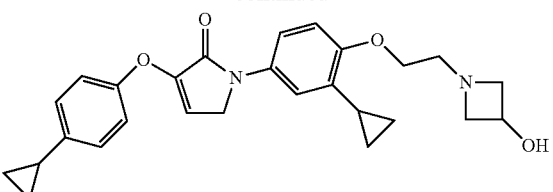
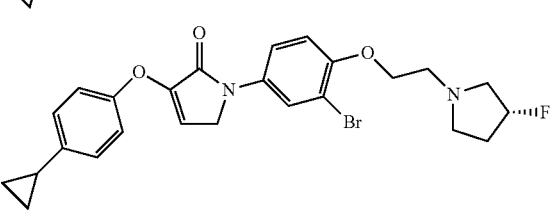
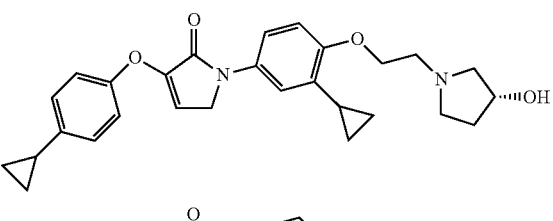
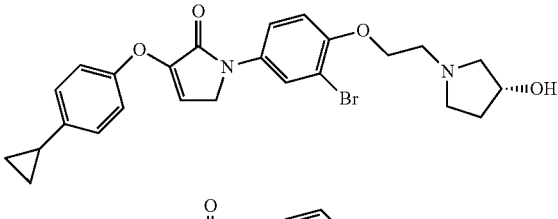
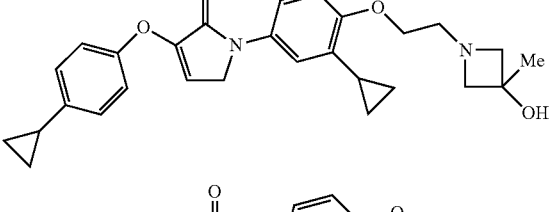
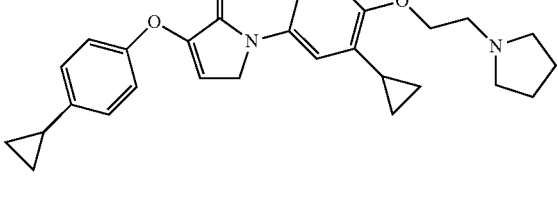
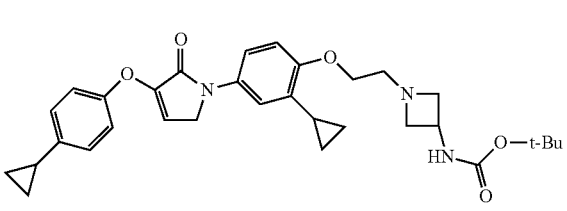
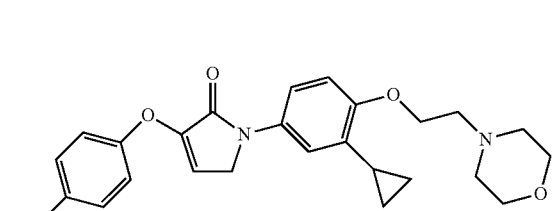

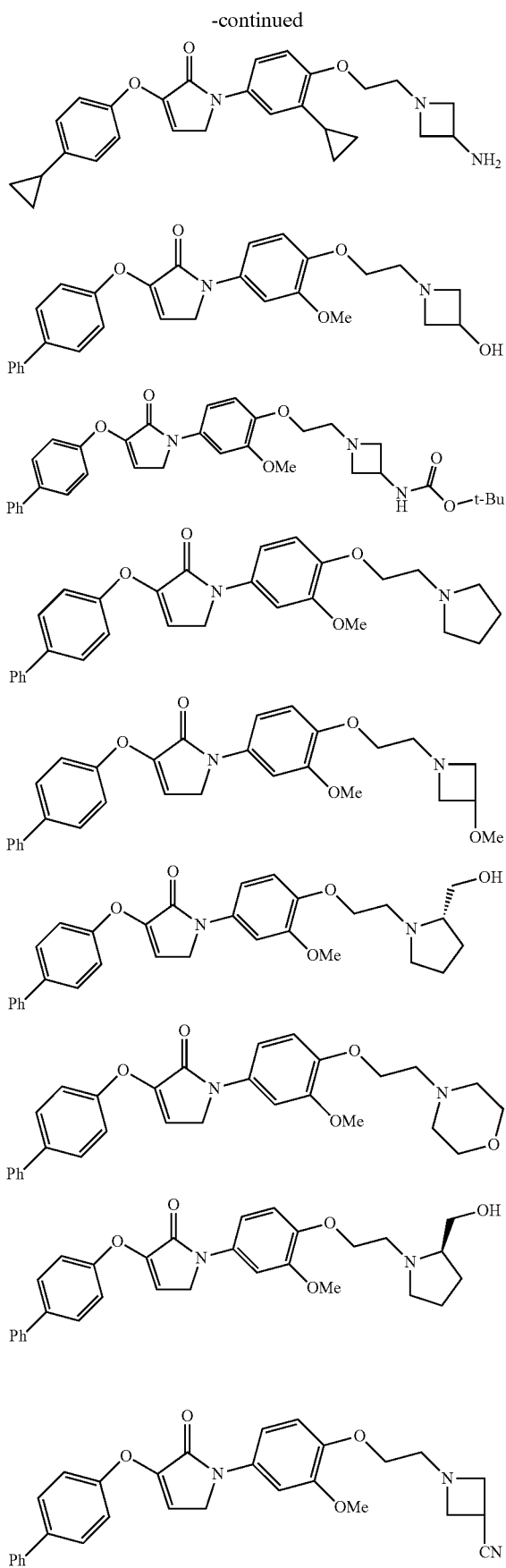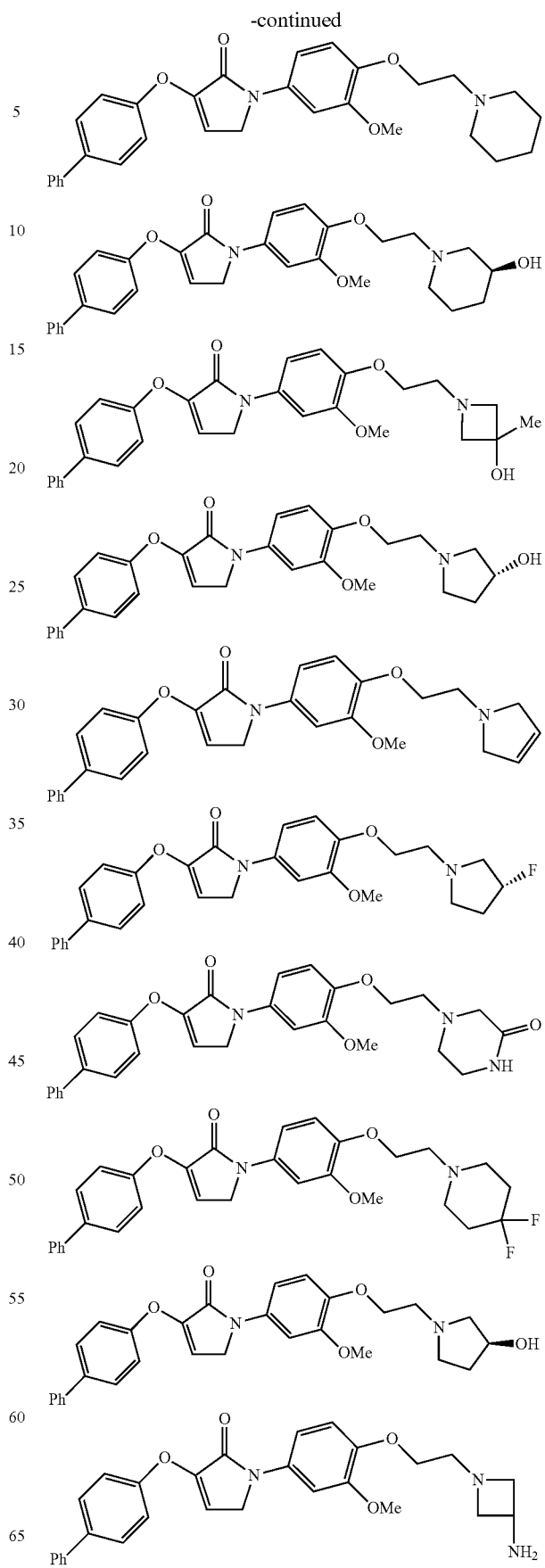

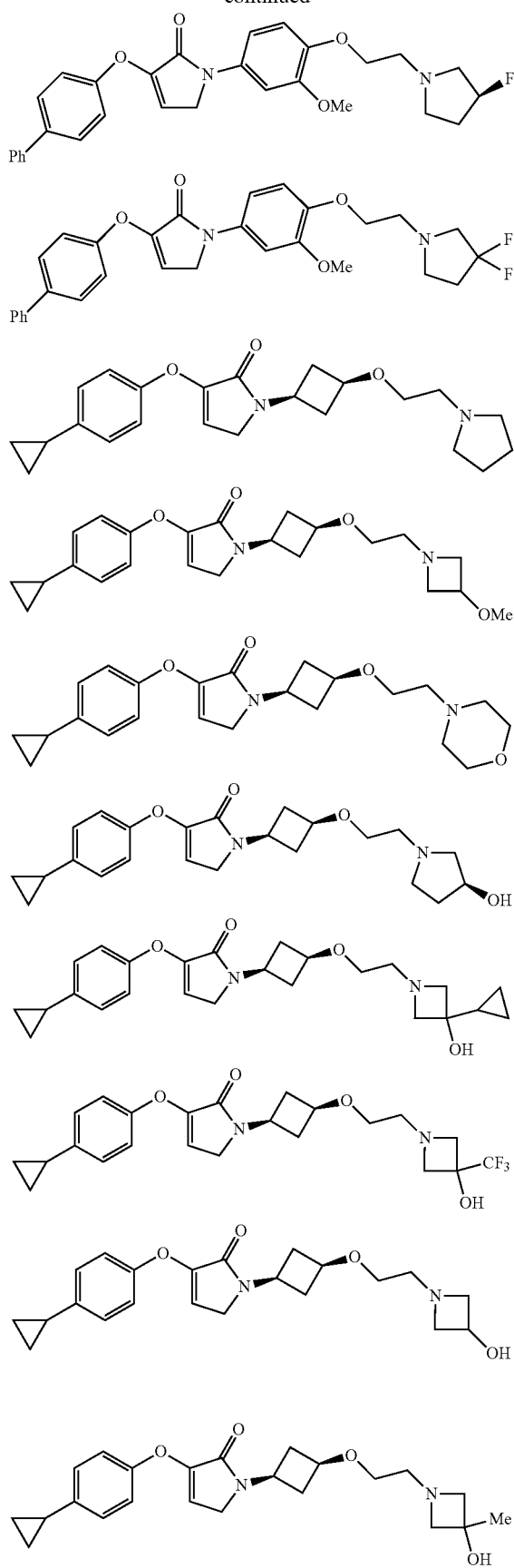
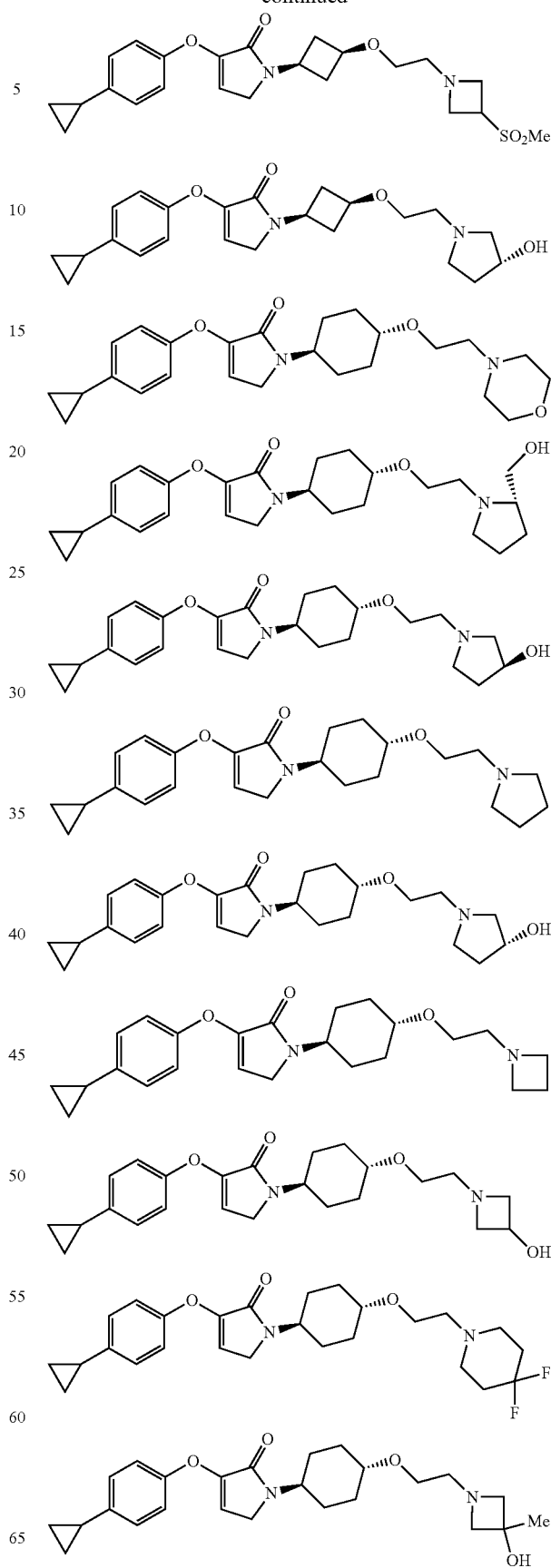

383
-continued
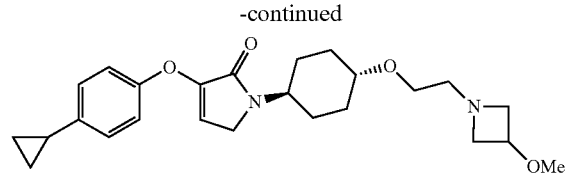
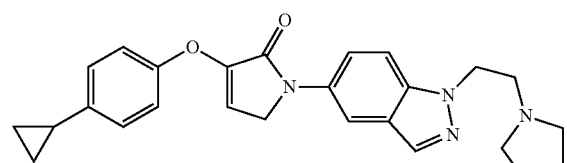
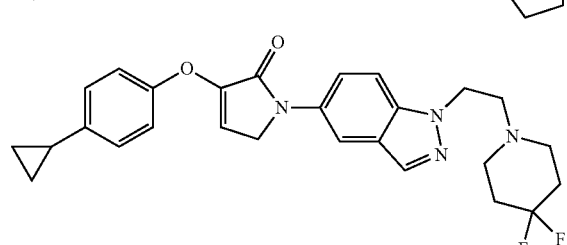
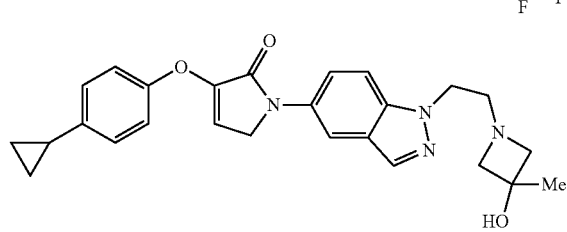
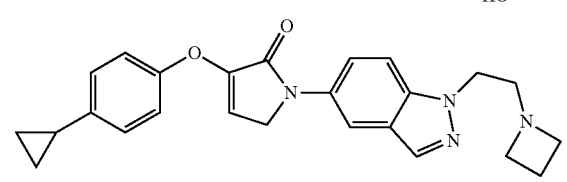
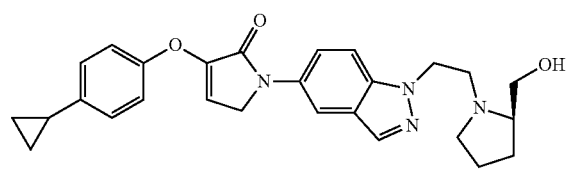
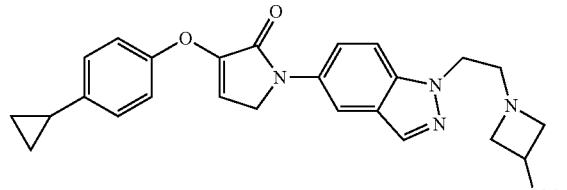
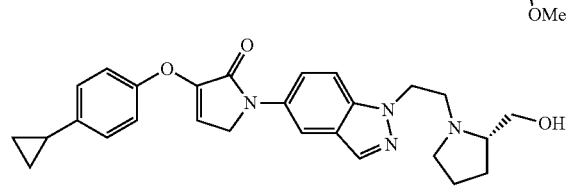
384
-continued
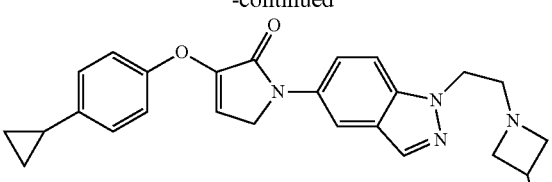
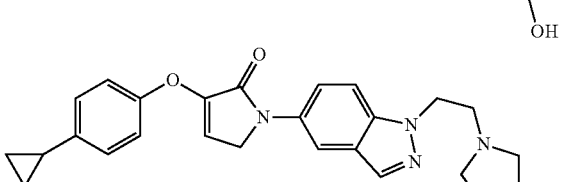
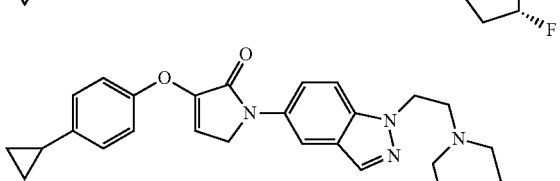
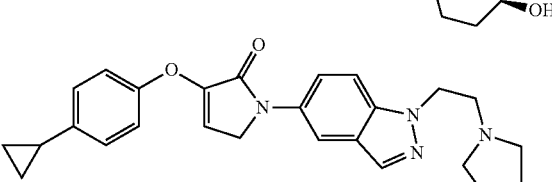
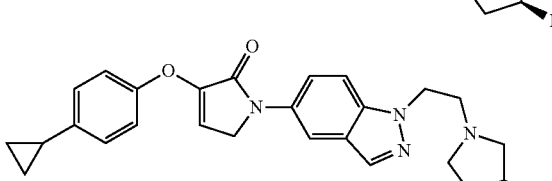
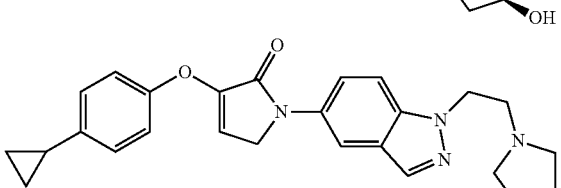
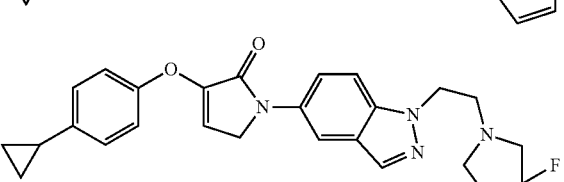
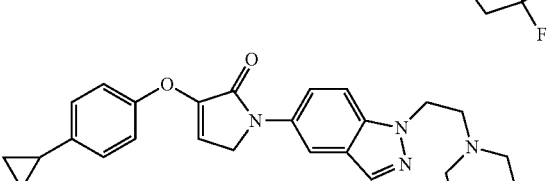
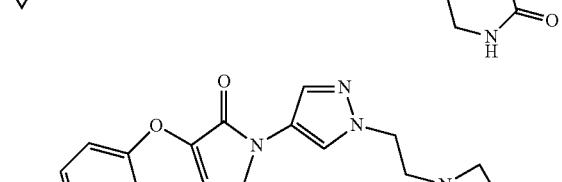

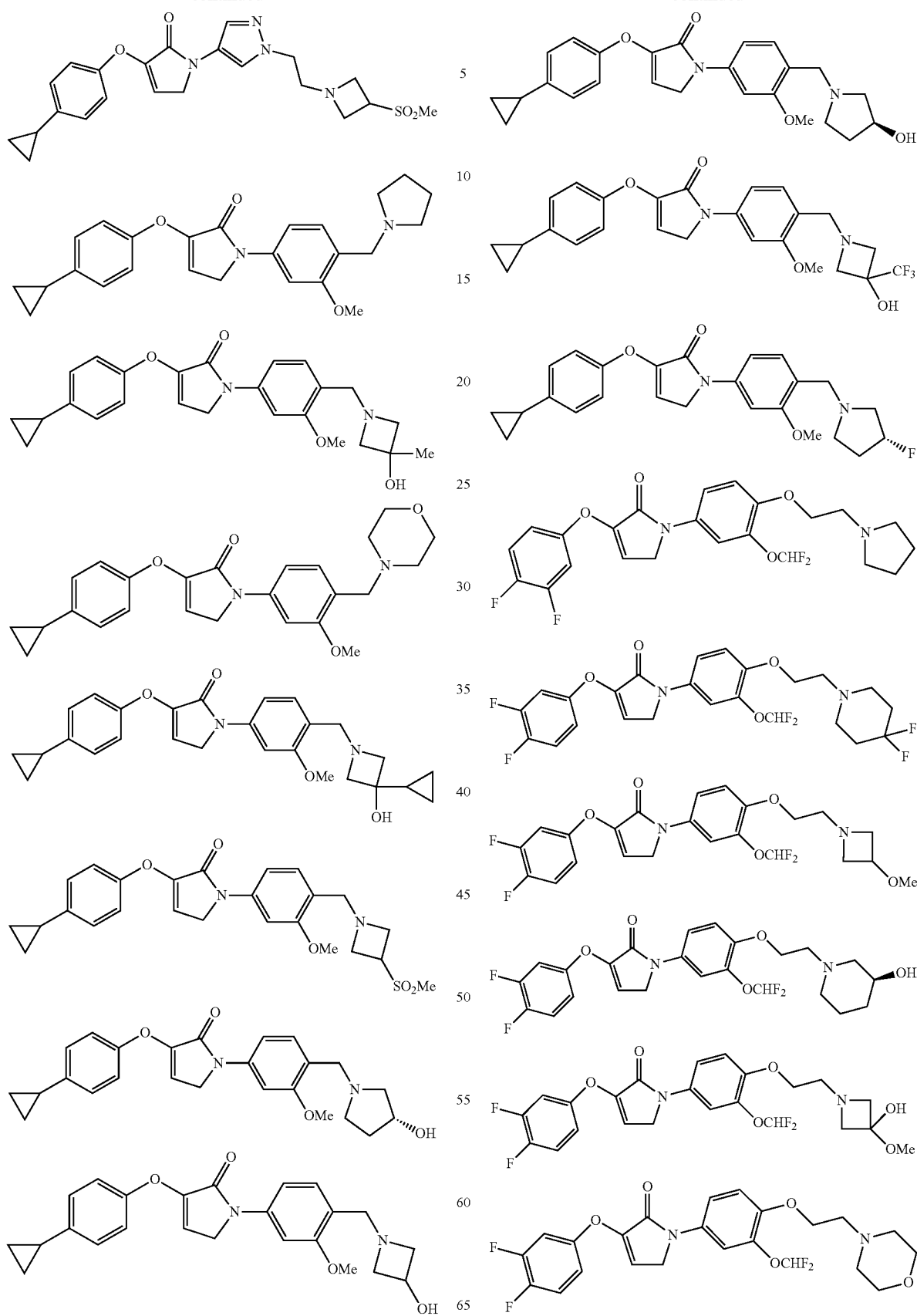

-continued

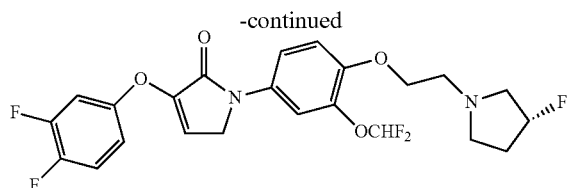
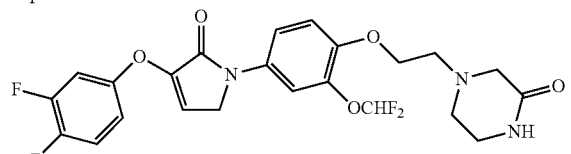
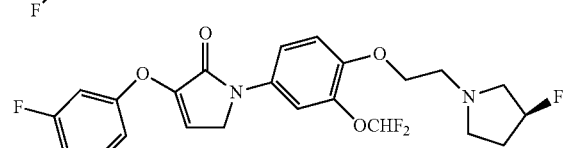
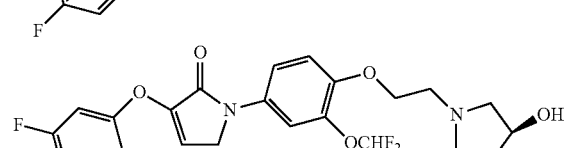
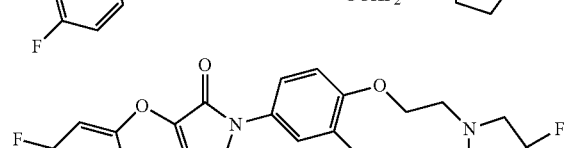
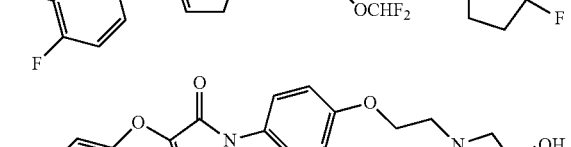
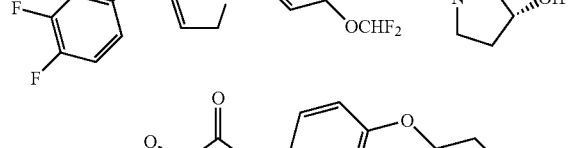
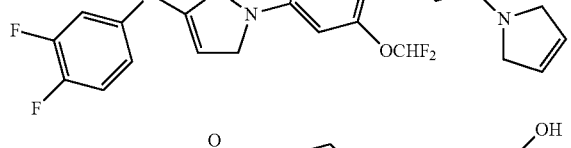
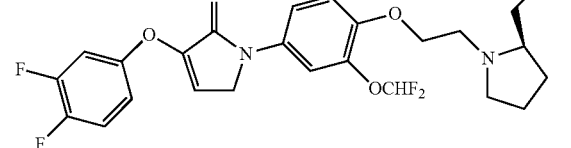
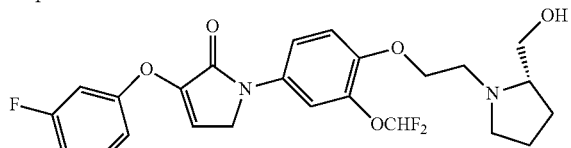
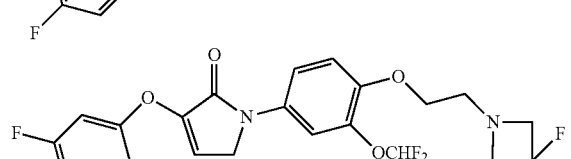

-continued

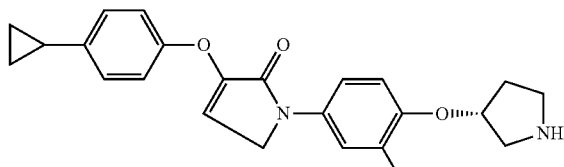
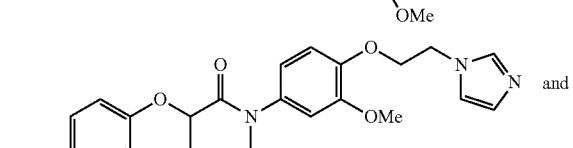
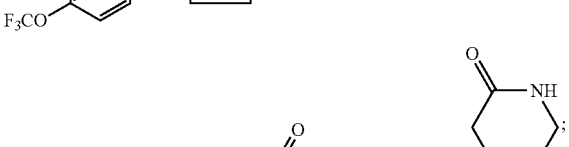

or a stereoisomer, a tautomer, or a pharmaceutically acceptable salt thereof.

11. A pharmaceutical composition, comprising: a pharmaceutically acceptable carrier and a compound of claim 1.

12. A compound selected from the group consisting of:

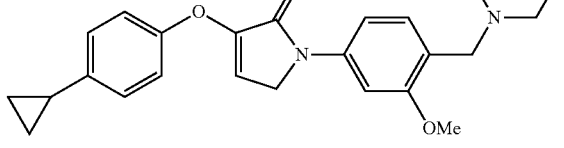
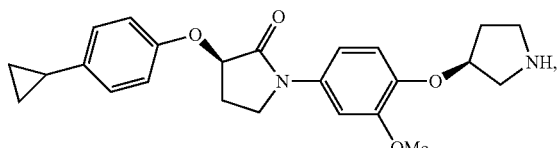
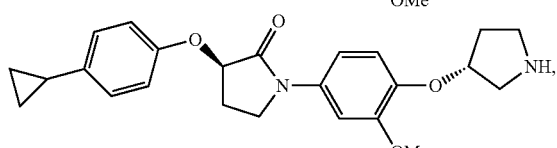
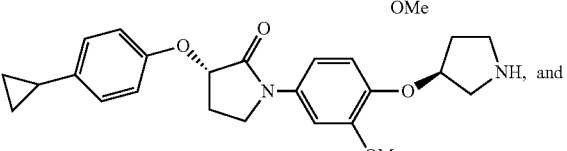
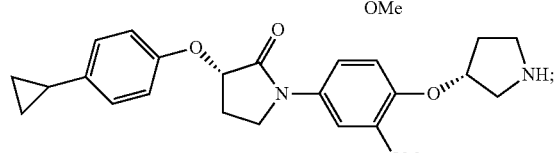

or a stereoisomer, a tautomer, or a pharmaceutically acceptable salt thereof.

13. A pharmaceutical composition, comprising: a pharmaceutically acceptable carrier and a compound of claim 12.

* * * * *

UNITED STATES PATENT AND TRADEMARK OFFICE
CERTIFICATE OF CORRECTION

PATENT NO. : 9,499,482 B2
APPLICATION NO. : 14/425165
DATED : November 22, 2016
INVENTOR(S) : William N. Washburn et al.

Page 1 of 2

It is certified that error appears in the above-identified patent and that said Letters Patent is hereby corrected as shown below:

In the Claims

Claim 10, Column 354, Lines 32-40 (Approx.) delete

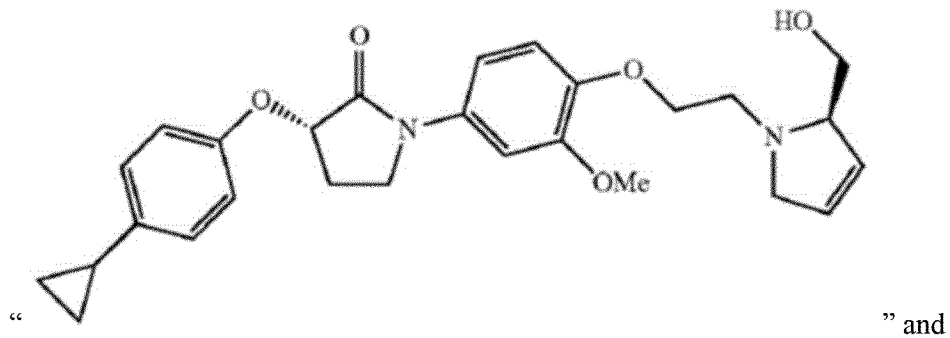

" and

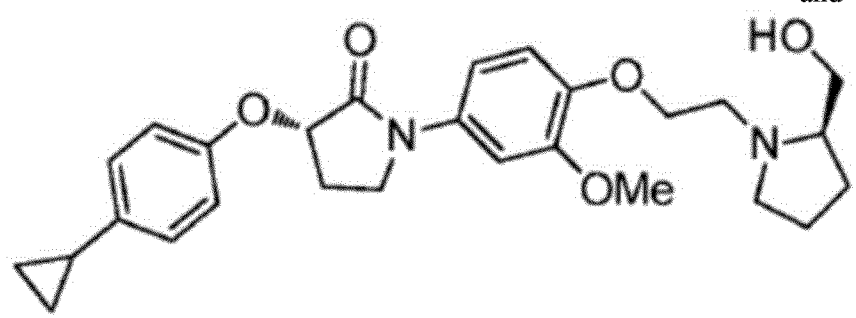

insert -- --, therefor.

Signed and Sealed this
Twenty-eighth Day of August, 2018

Andrei Iancu
*Director of the United States Patent and Trademark Office*

CERTIFICATE OF CORRECTION (continued)
U.S. Pat. No. 9,499,482 B2

Claim 10, Column 363, Lines 58-65 (Approx.) delete

" 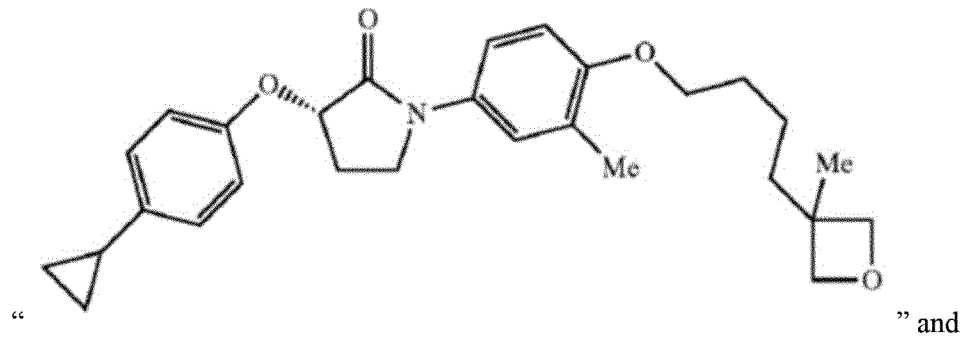 " and insert -- 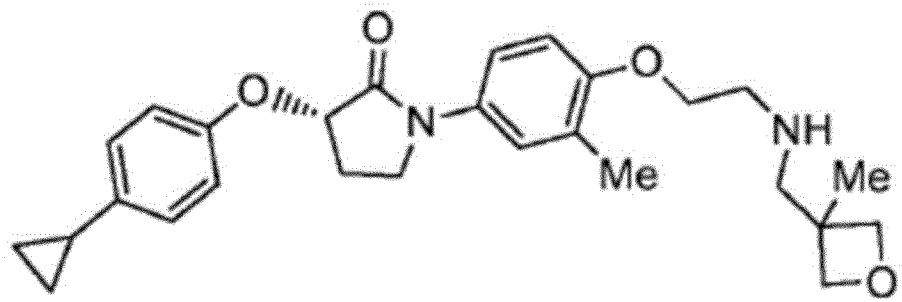 --, therefor.